(12) United States Patent
Lindenthal et al.

(10) Patent No.: US 9,655,887 B2
(45) Date of Patent: May 23, 2017

(54) PHARMACEUTICAL COMPOSITION AND THE USE THEREOF, AND APPLICATION REGIME OF SAID PHARMACEUTICAL COMPOSITION FOR ON-DEMAND CONTRACEPTION

(71) Applicant: BAYER PHARMA AKTIENGESELLSCHAFT, Berlin (DE)

(72) Inventors: Bernhard Lindenthal, Berlin (DE); Nico Bräuer, Falkensee (DE); Peter Serno, Bergisch Gladbach (DE); Andrea Rotgeri, Berlin (DE); Ulrike Fuhrmann, Berlin (DE); Bernd Buchmann, Hohen Neuendorf (DE); Anne Mengel, Berlin (DE); Ulrike Röhn, Berlin (DE); Antonius Ter Laak, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/893,508

(22) PCT Filed: May 16, 2014

(86) PCT No.: PCT/EP2014/060103
§ 371 (c)(1),
(2) Date: Nov. 23, 2015

(87) PCT Pub. No.: WO2014/187744
PCT Pub. Date: Nov. 27, 2014

(65) Prior Publication Data
US 2016/0089364 A1 Mar. 31, 2016

(30) Foreign Application Priority Data
May 23, 2013 (EP) .................... 13169029

(51) Int. Cl.
| | | |
|---|---|---|
| C07D 401/06 | (2006.01) |
| C07D 401/14 | (2006.01) |
| C07D 403/06 | (2006.01) |
| C07D 403/14 | (2006.01) |
| A61K 31/416 | (2006.01) |
| A61K 31/4439 | (2006.01) |
| A61K 31/454 | (2006.01) |
| A61K 31/196 | (2006.01) |
| A61K 31/405 | (2006.01) |
| A61K 31/5415 | (2006.01) |
| A61K 31/18 | (2006.01) |
| A61K 31/192 | (2006.01) |
| A61K 31/365 | (2006.01) |
| A61K 31/407 | (2006.01) |
| A61K 31/42 | (2006.01) |
| A61K 31/444 | (2006.01) |
| A61K 31/4545 | (2006.01) |
| A61K 31/5377 | (2006.01) |
| A61K 31/542 | (2006.01) |
| A61K 31/635 | (2006.01) |

(52) U.S. Cl.
CPC ............ *A61K 31/454* (2013.01); *A61K 31/18* (2013.01); *A61K 31/192* (2013.01); *A61K 31/196* (2013.01); *A61K 31/365* (2013.01); *A61K 31/405* (2013.01); *A61K 31/407* (2013.01); *A61K 31/416* (2013.01); *A61K 31/42* (2013.01); *A61K 31/444* (2013.01); *A61K 31/4545* (2013.01); *A61K 31/5377* (2013.01); *A61K 31/542* (2013.01); *A61K 31/5415* (2013.01); *A61K 31/635* (2013.01)

(58) Field of Classification Search
CPC .. C07D 401/06; C07D 401/14; C07D 403/06; C07D 403/14; A61K 31/416; A61K 31/506; A61K 31/4439; A61K 31/4545
See application file for complete search history.

(56) References Cited

U.S. PATENT DOCUMENTS

| | | |
|---|---|---|
| 2012/0172343 A1 | 7/2012 | Lindenthal et al. |
| 2013/0089574 A1 | 4/2013 | Schmidt-Gollwitzer et al. |

FOREIGN PATENT DOCUMENTS

| | | |
|---|---|---|
| DE | 102009049662 | 10/2009 |
| EP | 1448207 | 4/2005 |
| WO | 2007/045513 | 4/2007 |
| WO | 2007/091107 | 8/2007 |
| WO | WO2008/070599 | 6/2008 |
| WO | 2010/119029 | 10/2010 |

(Continued)

OTHER PUBLICATIONS

Jensen et al., "Evaluation of the phosphodiesterase 3 inhibitor ORG 9935 as a contraceptive in female macaques: initial trials," Contraception (2010) 81:165-171.

(Continued)

*Primary Examiner* — San-Ming Hui
(74) *Attorney, Agent, or Firm* — Nixon & Vanderhye P.C.

(57) ABSTRACT

The invention relates to a pharmaceutical composition for non-hormonal, on-demand contraception and to processes for preparing this pharmaceutical composition. The latter comprises 2H-indazole as novel EP2 receptor antagonists in combination with COX inhibitors. The invention furthermore provides a method for non-hormonal female-controlled on-demand contraception where a pharmaceutical composition comprising EP2 receptor antagonists in combination with COX inhibitors is taken on demand prior to expected sexual intercourse.

19 Claims, No Drawings

(56) References Cited

FOREIGN PATENT DOCUMENTS

| WO | 2010/119030 | 10/2010 |
| WO | 2010/124102 | 10/2010 |
| WO | 2010/149273 | 12/2010 |
| WO | 2011/091892 | 4/2011 |
| WO | 2011/069871 | 6/2011 |
| WO | 2013079425 | 6/2013 |

OTHER PUBLICATIONS

Aitken et al., "Bridging the gap between male and female fertility control; contraception-on-demand Contraception," (2008) 78: S28-S35.
Opare-Addo et al., A Study of the Use of Primolut N Tablet as a Contraceptive in the Kumasi Metropolis of Ghana, Afr. J. Reprod. Health (2011), 15(1):65-7.
Raymond et al. Pericoital Oral Contraception With Levonorgestrel, Obstet Gynecol.; (Mar. 2011); 117(3):673-81.
Matsumoto et al., Diversification of Cyclooxygenase-2-Derived Prostaglandins in Ovulation and Implantation, Biology of Reproduction (2001), 64:1557-1565.
Hizaki et al., Abortive expansion of the cumulus and impaired fertility in mice lacking the prostaglandin E receptor subtype EP2 Proc Natl Acad Sci U.S.A. (Aug. 1999), 96:10501-10506.
Peluffo et al., Contraceptive trial testing a prostaglandin E2 receptor (EP2) antagonist in female monkeys, Fertility and Sterility (Sep. 2012), 98(3):S34.
Pall et al., "Induciton of delayed follicular rupture in the human by the selective COX-2 inhibitor refecoxib: a randomized double-blind study," Human Reproduction (2001), 16(7):1323-1328.
Edelmann et al., "Impact of the prostaglandin synthase-2 inhibitor celecoxib on ovulation and luteal events in women," Contraception. (2013), 87:352-357.
Edelmann et al., "A nonhormonal model for emergency contraception: prostaglandin synthesis inhibitor effects on luteal function and lifespan, a pilot study," Contraception; (2010); 81(6):496-500.
Athanasious et al., "Effects of indomethacin on follicular structure, vascularity, and function over the periovulatory period in women," Fertil Steril.; (Mar. 1996); 65(3): 556-60.
Lim et al., "Multiple Female Reproductive Failures in Cyclooxygenase 2-Deficient Mice," Cell (Oct. 17, 1997), 91 (2):197-208.
Bata et al., "Delay of Ovulation by Meloxicam in Healthy Cycling Volunteers: A Placebo-Controlled, Double-blind, Crossover Study," J Clin Pharmacol (2006); 46:925-932.
Jesam et al., "Suppression of follicular rupture with meloxicam, a cyclooxygenase-2 inhibitor: potential for emergency contraception," Hum Reprod. (2010), 25(2):368-73.
Castellsague et al., "Individual NSAIDs and Upper Gastrointestinal Complications," Drug Saf., (2012), 35(12):1127-46.
Varas-Lorenzo et al., "Myocardial infarction and individual nonsteroidal anti-inflammatory drugs meta-analysis of observational studies," Pharmacoepidemiol Drug Saf. (2013), 22:559-570.
Massai et el., "Does meloxicam increase the incidence of anovulation induced by single administration of levonorgestrel in emergency contraception? A pilot study," Human Reproduction (2007) 22(2):434-439.
Vanderhyden et al., "Developmental Pattern of the Secretion of Cumulus Expansion-Enabling Factor by Mouse Oocytes and the Role of Oocytes in Promoting Granulosa Cell Differentiation," Dev Biol. (1990), 140(2):307-317.
Hizaki et al., "Abortive expansion of the cumulus and impaired fertility in mice lacking the prostaglandin E receptor subtype EP2," Proc Natl Acad Sci U. S. A;. (1999) 96(18):10501-10506.
Cheng et al., "Loss of Cyclooxygenase-2 Retards Decidual Growth but Does Not Inhibit Embryo Implantation or Development to Term," Biol Reprod. (2003), 68(2):401-4.
Huntjens et al., "Pharmacokinetic—pharmacodynamic correlations and biomarkers in the development of COX-2 Inhibitors Rheumatology," (2005); 44:846-859.
Vanderhyden et al., "Developmental Pattern of the Secretion of Cumulus Expansion-Enabling Factor by Mouse Oocytes and the Role of Oocytes in Promoting Granulosa Cell Differentiation," Dev Biol.; (1990); 140(2):307-317.
Hizaki et al., "Abortive expansion of the cumulus and impaired fertility in mice lacking the prostaglandin E receptor subtype EP2," Proc Natl Acad Sci USA (1999) 96(18):10501-10506.
Killick et al., Pharmacologic production of lutenized unruptured follicles by prostaglandin synthetase inhibitors, Fertil Steril (1987), 47(5):773-7.

PHARMACEUTICAL COMPOSITION AND THE USE THEREOF, AND APPLICATION REGIME OF SAID PHARMACEUTICAL COMPOSITION FOR ON-DEMAND CONTRACEPTION

The present invention relates to the subject matter stated in the patent claims, i.e.:

(a) the use of a pharmaceutical composition comprising at least one 2H-indazole as novel EP2 receptor antagonist according to general formula I and at least one cyclooxygenase inhibitor (COX inhibitor) for non-hormonal on-demand contraception and contraception, (b) a pharmaceutical composition comprising at least one 2H-indazole as novel EP2 receptor antagonist according to general formula Ia and at least one (COX inhibitor) and (c) the use of at least one EP2 receptor antagonist according to general formula Ia in combination with at least one COX inhibitor for preparing a pharmaceutical composition, and also processes for preparing this pharmaceutical composition and its use for non-hormonal on-demand contraception and fertility control.

DESCRIPTION OF THE INVENTION

Hormonal contraception with daily orally administered low dosages of synthetic gestagens and oestrogens is, in addition to administration of a gestagen via an intrauterine system (IUS) such as Mirena®, currently the method showing best pharmacological efficacy in the prevention of pregnancies in clinical studies. Oral contraception requires continuous regular intake of hormone-containing pills, independent of the frequency of sexual intercourse and thus the necessity of contraceptive protection. Women having infrequent sexual intercourse are thus exposed to hormones for an unnecessarily long period of time. Especially for this group of users, there is therefore a need for a preparation which can be taken only when required shortly before or optionally also immediately after intercourse but, at the same time, offers a (contraceptive) protection similar to that of the classic oral contraceptives.

Although there has been such a need for decades (Canzler et al. Zbl. Gynäkol.; (1984); 106:1182-1191), there is hitherto no preparation allowing contraception on demand (alternatively also referred to in the literature as on-demand contraception, fertility control on demand or precoital contraception) (Aitken et al. Contraception; (2008); 78: p.28-p.35). In a study carried out in Ghana, it has been reported that woman use Primolut-N tablets comprising 5 mg of norethisterone, which are approved for the treatment of various gynaecological disorders as on-demand contraceptive in 94% of cases and for the treatment of menstrual disorders in only 6% of cases (Opare-Addo et al. Afr. J. Reprod. Health.; (2011); 15(1):65-7). Anecdotal reports and data collected by Family Health International confirm that women in many emerging countries and South American and Africa, but also in countries such as Great Britain, deliberately use preparations developed for emergency contraception also for on-demand contraception.

Products approved for emergency contraception are Postinor®, Plan B® and Levonelle® (single administration of 1.5 mg of levonorgestrel (LNG) within 72 hours) and ellaOne® (single administration of 30 mg of ulipristal acetate (UPA) within 120 h after sexual intercourse). These preparations are described, for example, in the application EP 1448207 (LNG) and in the applications WO2011/069871 and WO2011/091892 (UPA). Levonorgestrel is a progesterone derivative, and ulipristal acetate is a selective progesterone receptor modulator. Thus, both are hormonal methods employed in very high doses compared to a hormone-comprising oral contraceptive taken regularly. Thus, for example, administration of a single dose of 1.5 mg of LNG corresponds to 10 times the amount that is administered daily when an LNG-containing pill (such as Microgynon®) is taken regularly. In Europe, the mini pill Microlut®, which contains 0.03 mg of LNG and is taken for a period of 28 days, which corresponds to a dose of only 0.84 mg of LNG per cycle, has been approved. Here, the single dose of 1.5 mg of LNG for emergency contraception corresponds to more than two monthly doses of Microlut®. If a pill developed for emergency contraception is used several times a month, the dose is, correspondingly, even higher. Raymond et al. have shown that even single administration may have effects on the cycle (Raymond et al. Obstet Gynecol.; (2011); 117(3):673-81). In addition, these preparations for emergency contraception do not have the same contraceptive reliability as a hormone-containing oral contraceptive taken regularly; however, this would be desirable for on-demand contraception. Evaluation of different studies for pre- and postcoital use of 0.75 mg of LNG showed a Pearl Index of 5.1 [pregnancies per 100 woman years] (95% confidence interval [CI] 3.8-6.7), which represents moderate efficacy (Raymond et al. Obstet Gynecol.; (2011); 117(3): 673-81).

Hitherto, for on-demand contraception, only hormonal methods have been described; however, none of these has yet been approved:

WO 2010/119030 describes an on-demand preparation where, as gestagen, levonorgestrel or norgestrel is used in a dose range of from 0.5 to 1.5 mg, with the preparation to be used 24 hours prior to intercourse. However, the dose of LNG corresponds to the dose used for emergency contraception.

WO2007/045513 describes a method for on-demand contraception where a gestagen is, if required, administered transdermally using a patch.

WO96/12494 uses competitive progesterone antagonists for on-demand contraception.

WO2010/119029 describes progesterone or progesterone receptor modulators for on-demand contraception which are administered within 72 hours prior to expected sexual intercourse. Here, 30 mg of UPA are employed once prior to sexual intercourse, which corresponds to the dose used for emergency contraception.

Non-hormonal methods for on-demand contraception have not yet been described. However, there is a need for non-hormonal pharmacological methods for women who, for medicinal or personal reasons, do not want to use or cannot use hormonal contraceptives. A further advantage of a non-hormonal approach is the fact that the menstrual cycle is not affected.

It has already long been known that prostaglandins are key molecules in the processes of female reproductive biology, such as for example the regulation of ovulation and fertilization. The effects of the prostaglandins are mediated through their G protein coupled receptors, which are located in the cell membrane. Of particular interest is prostaglandin E2 (PGE2), which effects a great variety of cellular actions by binding to functionally different receptor subtypes, namely the $EP_1$, $EP_2$, $EP_3$ and $EP_4$ receptors. The receptor subtypes to which prostaglandin $E_2$ binds are of particular importance for the receptor-mediated actions which are involved in the regulation of fertility. Thus it could be shown that the reproductive functions are impaired in EP2 knockout mice (EP2$^{-/-}$), e.g. in mice which no longer have a functional PGE$_2$ receptor subtype EP2, and that these animals have a smaller number of offspring per pregnancy (Matsumoto et al. Biology of Reproduction; (2001); 64: 1557-1565). Likewise it could be shown that these EP2 knockout mice (Hizaki et al. Proc Natl Acad Sci U.S.A.; (1999); 96(18):10501-10506) display markedly decreased cumulus expansion and severe subfertility, which is to be regarded as being causally linked with decreased reproductive processes such as ovulation and fertilization. Accordingly, the EP2 receptor is an important target for the development of drugs for the regulation of female fertility.

The application DE 10 2009 049 662 A1 describes 2-5-disubstituted 2H-indazoles which, with high binding affinity, selectively antagonize the EP2 receptor. These EP2 receptor antagonists are disclosed inter alia for use as contraceptive, but not for on-demand contraception.

In a pairing study with cynomolgus monkey, it was shown that an EP2 receptor antagonist administered continuously has a subfertile effect (Peluffo et al. 2012, Annual Meeting of the American Society for Reproductive Medicine). However, continuous administration does not correspond to use for on-demand contraception.

The applications of Summit Corporation Plc. (WO2007/091107), C M Sun et al. (WO2008/070599) and Janssen Pharmaceutica NV (WO2010/124102) describe 2H-indazoles. The compounds disclosed in WO2007/091107 interact with the utropine A promoter and are claimed for the treatment of Duchenne muscular dystrophy, Becker muscular dystrophy or cachexia. WO2008/070599 describes compounds binding to the VGEFR-3 receptor. They are claimed for the treatment of cancer. The compounds described in the application WO2010/124102 inhibit monoacylglycerol lipase (MGL) and are claimed for the treatment of inflammatory pain. None of the three applications mentioned discloses whether the compounds bind to the EP2 receptor and are suitable for fertility control.

The effect of COX inhibitors on female ovulation has been investigated by several research groups. Thus, Pall et al. examined the effect of rofecoxib on ovulation (Pall et al.; Human Reproduction; (2001); 16(7):1323-1328). In this study, 25 mg of the active compound were used on 9 successive days. In 4 of 6 patients, ovulation was delayed by more than 48 hours.

Edelmann et al. 2013 examined the effect of the daily oral administration of 400 mg of celecoxib on ovulation. Depending on time and duration of administration, an increase in ovulatory dysfunction of 25-30% was observed. The ovulatory dysfunction was characterized by a flattened LH (luteinizing hormone) peak and/or by anovulation (Edelmann et al. Contraception. (2013); 87(3):352-357). In 2010, Edelmann et al. had already shown that daily administration of 400 mg of celecoxib over the entire cycle increased the cycle length from 27.2+/−2.4 days to 28.5+/−2.5 days and changed time and height of the LH peak (Edelmann et al. Contraception; (2010); 81(6):496-500). Both results showed that the benefit of celecoxib for emergency contraception is limited.

In a pilot study with 6 women treated with 3×50 mg of indomethacin per day for at least 3 days, it was shown that administration of indomethacin delayed ovulation by 2-12 days in 5 cases. The treatment was initiated when the dominant follicle had reached a maximum size of >16 mm or LH was detected in the urine (Athanasious et al. Fertil Steril.; (1996); 65(3): 556-60). This study also confirmed the results by Killick S and Elstein M. 1987 where indomethacin administered in a dose of 2×100 mg per day over 5 days led to inhibition of ovulation (Killick S and Elstein M. Fertil Steril.; (1987); 47(5):773-7).

A clinical study by Bata et al. 2006 showed that administration of meloxicam reversibly delayed ovulation by 5 days (Bata et al., J Clin Pharmacol (2006); 46:925-932). This result was confirmed by Jesam et al. 2010 (Jesam et al. Hum Reprod.; (2010); 25(2):368-73). In this clinical study, 30 mg or 15 mg of meloxicam were administered daily over a period of 5 days during the late follicular phase. In 90.9% (30 mg meloxicam group) or 50.0% (15 mg meloxicam group), ovulation was abnormal, which shows that meloxicam may be suitable for emergency contraception.

In principle, COX inhibitors are known to be relatively well tolerated; however, Castellsague et al. 2012 and Varas-Lorenzo et al. 2013 indicated that there is an increased risk of cardiovascular and gastrointestinal events for this class of substances. It is therefore recommended to use a relatively low dosage (Castellsague et al. Drug Saf.; (2012); 35(12): 1127-46; Varas-Lorenzo et al. Pharmacoepidemiol Drug Saf.; (2013); doi: 10.1002/pds. 3437. [Epub ahead of print]).

In a pilot study, Massai et al. 2007 examined the use of meloxicam in combination with levonorgestrel (LNG) on the time of ovulation in connection with emergency contraception (Massai et el. Human Reproduction; (2007) 22(2): 434-439). In this study, 2 tablets of in each case 0.75 mg of LNG (known inter alia by the trade name Postinor-2) were administered on their own or together with 15 mg of meloxicam. In the treatment group which received the combination of meloxicam and LNG, there was a trend to reduced frequency of ovulation compared to the group treated exclusively with LNG. This effect was increasingly pronounced the later the tablets were taken relative to the time of ovulation.

In WO2010/149273 (Bayer Pharma AG), it was shown that a low dose of levonorgestrel which, on its own, does not inhibit ovulation, may achieve virtually complete suppression of ovulation in the rat when combined with piroxicam. However, this approach comprises, in addition to the non-hormonally acting COX inhibitor, a hormonal component in the form of levonorgestrel and does therefore not represent a non-hormonal alternative to purely hormonal approaches.

Accordingly, it is an object of the present invention to provide a method and a pharmaceutical composition for on-demand contraception based on a pharmacological non-hormonal approach and thus providing an alternative to hormonal methods.

In accordance with the invention, this object is achieved by using a non-hormonal pharmaceutical composition comprising at least one EP2 receptor antagonist according to formula I and at least one COX inhibitor. In addition, this object is achieved by the pharmaceutical composition itself which comprises at least one EP2 receptor antagonist according to formula Ia and at least one COX inhibitor.

The EP2 receptor antagonists according to formula I or Ia according to the invention have already been described in the patent application PCT/EP2012/073556, unpublished at the priority date of the present application. There, they are claimed inter alia for use for contraception and emergency contraception. In addition, a pharmaceutical composition comprising at least one EP2 receptor antagonist of formula I and at least one COX inhibitor and its use for contraception are described.

In the patent application PCT/EP2012/073556, it was shown that the EP2 receptor antagonists according to formula I or Ia have an antagonistic action at the EP2 receptor (see biological examples; Table 1) and are thus suitable for fertility control (see biological examples; Tables 2, 3 and 4). In the present application, in accordance with the invention, it was possible, by combining the EP2 receptor antagonists according to formula I or Ia with a COX inhibitor, to achieve the contraceptive action of the EP2 receptor antagonists or the COX inhibitors surprisingly even at a still ineffective dose of the individual active compounds (see biological examples; Tables 6.1-6.5 and 7.1). Thus, the combination of EP2 receptor antagonists according to general formula I or Ia with COX inhibitors allows both the dose of the COX inhibitor and the dose of the EP2 receptor antagonists to be reduced, which in turn reduces possible side effects and thus increases acceptance and safety of the method.

In addition, the contraceptive action was, surprisingly, achieved even after single administration of an EP2 receptor antagonist according to general formula I or Ia in combination with a COX inhibitor shortly before sexual intercourse (see biological examples; Tables 6.1-6.5 and 7.1). This shows that EP2 receptor antagonists in combination with COX inhibitors constitute an effective pharmaceutical composition for on-demand contraception which can be administered before or shortly after expected sexual intercourse. Since this pharmaceutical composition is non-hormonal, it represents an alternative to hormonal approaches.

In the pre-ovulatory antral follicle, the oocyte is surrounded by cumulus cells which form a dense cell crown around the oocyte. After the LH peak (luteinizing hormone), a series of processes is activated, which results in a marked morphological change in this cell crown of cumulus cells. During this, the cumulus cells form an extracellular matrix, which leads to the so-called cumulus expansion (Vanderhyden et al. Dev Biol.; (1990); 140(2):307-317). This cumulus expansion is an important component of the ovulatory process and the subsequent possibility of fertilization.

During the cumulus expansion, prostaglandins and here prostaglandin $E_2$, synthesis whereof is induced by the LH peak, are of decisive importance. Prostanoid EP2 knockout mice (Hizaki et al. Proc Natl Acad Sci USA.; (1999) 96(18):10501-10506.) show a markedly decreased cumulus expansion and severe subfertility, which demonstrates the importance of the prostanoid EP2 receptor for this process.

The anti-ovulatory action of COX inhibitors in humans has been demonstrated in clinical studies (as described above). COX inhibitors lead to reduced prostaglandin synthesis. In COX-2 knockout mice, it was shown that prostaglandins play a role in particular in processes of ovulation, cumulus expansion and fertilization (Cheng J G and Stewart C L. Biol Reprod.; (2003); 68(2):401-4; Lim et al. Cell; (1997) 91(2):197-208).

Since, within the prostaglandin pathway, the EP2 receptor is inhibited directly by the EP2 receptor antagonists, the onset of action by this class of substances is earlier than the onset of action of COX inhibitors, where the action is triggered by lowering of prostaglandin concentrations.

On-Demand Contraception or Contraception on Demand

On-demand contraception, fertility control on demand, precoital contraception or contraception on demand all refer to the on-demand use of one or more substances for preventing unwanted pregnancy. The administration can be before or shortly after expected sexual intercourse. Here, on-demand does not mean optional. Rather, the substance/substances has/have to be administered to prevent unwanted pregnancy.

The invention provides the use of a pharmaceutical composition comprising (a) at least one EP2 receptor antagonist according to formula (I)

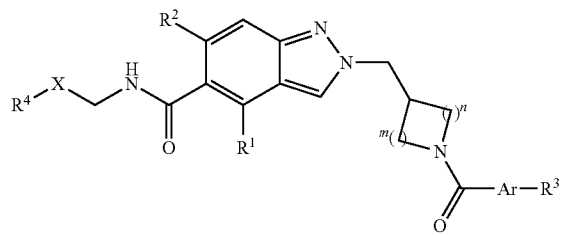

(formula I)

wherein
$R^1$: means H, $C_1$-$C_2$ alkyl or $C_1$-$C_2$ alkyloxy;
$R^2$: H or methyl;
subject to the proviso that one of the two residues $R^1$ or $R^2$ equals H;
X: —$(CH_2)_l$—, —$(CH_2)_k$—O—, —$CH_2$—S—, $CH_2$—S$(O)_2$—, —$CH(CH_3)$—, —$CH(CH_3)$—O— or —$C(CH_3)_2$—O—;
k: 1 or 2;
l: 0, 1 or 2;
$R^4$: H, $C_1$-$C_4$ alkyl, $C_3$-$C_4$ cycloalkyl, or $CH_2$—$C_3$-$C_4$ cycloalkyl;
and in the case that X means $(CH_2)_l$— with l meaning 0 or 1 or —$CH(CH_3)$—
$R^4$: additionally a 4-6-membered heterocyclyl residue;
and in the case that X means —$(CH_2)_l$— or —$CH(CH_3)$—
$R^4$: additionally CN;
m: 1 or 2;
n: 1 or 2;
Ar: a 6-10-membered aryl or 5-10-membered hetaryl residue,
$R^3$: halogen, CN, $SF_5$, $C_1$-$C_4$ alkyl, $C_3$-$C_6$ cycloalkyl, $C_4$-$C_6$ heterocyclyl, O—$C_1$-$C_4$ alkyl, O—$C_3$-$C_6$ cycloalkyl, O—$C_4$-$C_6$ heterocyclyl, S—$C_1$-$C_4$ alkyl, S$(O)_2$—$C_1$-$C_4$ alkyl, Ar', O—Ar', $C(CH_3)_2$—CN or $C(CH_3)_2$—OH;
Ar': an optionally singly or doubly substituted 6-membered aryl or 5-6-membered heteroaryl residue;
wherein the substituents are selected from F, Cl, CN, $C_1$-$C_4$ alkyl, O—$C_1$-$C_4$ alkyl, $C(CH_3)_2$—CN, $C(CH_3)_2$—OH and $C(O)NH_2$;
and comprising (b) at least one COX inhibitor selected from the list below:
C1 indomethacin;
C2 diclofenac;
C4 naproxen;
C5 ibuprofen;
C6 meloxicam;
C7 piroxicam;
C8 nimesulide;
C9 ketoprofen;
C10 tenoxicam;
C11 mefanemic acid;
C12 ketoralac;
C13 celecoxib(4-[5-(4-methylphenyl)-3-(trifluoromethyl)-1H-pyrazol-1-yl]benzenesulphonamide);
C14 parecoxib(N-[4-(5-methyl-3-phenyl-4-isoxazolyl)phenyl]sulphonylpropionamide);
C15 rofecoxib (4-(4-mesylphenyl)-3-phenylfuran-2(5H)-one);
C16 valdecoxib (4-[5-methyl-3-phenyl-4-isoxazoyl)benzenesulphonamide);
C17 etoricoxib
for on-demand contraception.

The invention furthermore provides the use of a pharmaceutical composition comprising (a) at least one EP2 receptor antagonist according to formula (I), where $R^1$: means H, $C_1$-$C_2$ alkyl or $C_1$-$C_2$ alkyloxy;
$R^2$: H or methyl;
subject to the proviso that one of the two residues $R^1$ or $R^2$ equals H;
X: —(CH$_2$)$_l$—, —(CH$_2$)$_k$—O—, —CH$_2$—S—, CH$_2$—S(O)$_2$—, —CH(CH$_3$)—, —CH(CH$_3$)—O— or —C(CH$_3$)$_2$—O—;
k: 1 or 2;
l: 0, 1 or 2;
$R^4$: H, $C_1$-$C_4$ alkyl, $C_3$-$C_4$ cycloalkyl, or CH$_2$—$C_3$-$C_4$ cycloalkyl;
and in the case that X means (CH$_2$)$_l$— with l meaning 0
$R^4$: additionally a 4-6-membered heterocyclyl residue linked via a ring carbon atom;
m: 1 or 2;
n: 1 or 2;
Ar: a 6-10-membered aryl or 5-10-membered hetaryl residue,
$R^3$: halogen, CN, SF$_5$, $C_1$-$C_4$ alkyl, $C_3$-$C_6$ cycloalkyl, $C_4$-$C_6$ heterocyclyl, O—$C_1$-$C_4$ alkyl, O—$C_3$-$C_6$ cycloalkyl, O—$C_4$-$C_6$ heterocyclyl, S—$C_1$-$C_4$ alkyl, S(O)$_2$—$C_1$-$C_4$ alkyl, Ar', O—Ar', C(CH$_3$)$_2$—CN or C(CH$_3$)$_2$—OH;
Ar': an optionally singly or doubly substituted 6-membered aryl or 5-6-membered heteroaryl residue;
wherein the substituents are selected from F, Cl, CN, $C_1$-$C_4$ alkyl, O—$C_1$-$C_4$ alkyl, C(CH$_3$)$_2$—CN, C(CH$_3$)$_2$—OH and C(O)NH$_2$;
and comprising (b) at least one COX inhibitor selected from the list above (COX inhibitors $C_1$-$C_{17}$) for on-demand contraception.

The 2H-indazoles according to the invention have an antagonistic action on the EP2 receptor.

$C_1$-$C_2$ alkyl or $C_1$-$C_4$ alkyl should each be understood to mean a linear or branched alkyl residue, such as for example methyl, ethyl, propyl, isopropyl, butyl, isobutyl, sec-butyl or tert-butyl.

The alkyl residues can optionally be singly or multiply substituted with fluorine.

The hydrogen atoms can optionally be replaced by deuterium.

$C_1$-$C_2$ alkoxy or $C_1$-$C_4$ alkoxy should be understood to mean a linear or branched residue of the formula alkyl-O—, such as for example methoxy, ethoxy, n-propoxy, isopropoxy, n-butoxy, sec-butoxy, isobutoxy or tert-butyloxy.

The alkoxy residues can optionally be singly or multiply substituted with fluorine.

$C_3$-$C_6$ cycloalkyl should be understood to mean monocyclic alkyl rings such as cyclopropyl, cyclobutyl, cyclopentyl and cyclohexyl.

The cycloalkyl residues can optionally be singly or multiply substituted with fluorine.

4-6-membered heterocyclyl should be understood to mean monocyclic rings which instead of the carbon atoms contain one or more hetero atoms, such as oxygen, sulphur and/or nitrogen or a hetero group such as —S(O)— or —SO$_2$—. The linking bond can be at any carbon atom or at a nitrogen atom.

For example, azetidinyl, pyrrolidinyl, piperidinyl, piperazinyl, 1,4-diazepanyl, morpholinyl, thiomorpholinyl, oxetanyl, tetrahydrofuranyl, tetrahydropyranyl, 1,4-dioxanyl and 2-oxo-oxazolidinyl may be mentioned.

The heterocyclyl residues can optionally be singly or multiply substituted with fluorine, hydroxy, methoxy or with oxo.

Halogen should in each case be understood to mean fluorine, chlorine, bromine or iodine.

The $C_6$-$C_{10}$-membered aryl residue in each case comprises 6-10 carbon atoms and can be benzo-condensed. Phenyl and naphthyl may be mentioned.

The $C_6$-$C_{10}$-membered aryl residue can optionally be singly substituted with fluorine, chlorine or a methyl group.

The $C_5$-$C_{10}$ heteroaryl residue should be understood to mean mono- or bicyclic ring systems which each contain 5-10 ring atoms and which instead of the carbon can contain one or more identical or different hetero atoms, such as oxygen, sulphur or nitrogen. The linking bond can be at any carbon atom or at a nitrogen atom.

For example, thienyl, thiazolyl, furyl, pyrrolyl, oxazolyl, imidazolyl, pyrazolyl, isoxazolyl, isothiazolyl, oxadiazolyl, triazolyl, thiadiazolyl, tetrazolyl, pyridyl, pyridazinyl, pyrimidinyl, pyrazinyl, triazinyl, phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, isoquinolinyl, quinolinyl, quinolizinyl, quinazolinyl, quinoxalinyl, cinnolinyl, phthalazinyl, 1,7- or 1,8-naphthyridinyl and pteridinyl may be mentioned.

The $C_5$-$C_{10}$-membered heteroaryl residue can optionally be singly substituted by fluorine, chlorine or a methyl group.

If radicals in the compounds according to the invention are substituted, the radicals can, unless specified otherwise, be mono- or polysubstituted. In the context of the present invention it applies that for all radicals which occur multiple times, their meanings are independent of one another. Substitution with one, two or three identical or different substituents is preferred. Substitution with one substituent is very particularly preferred.

If a basic functional group is contained, the physiologically compatible salts of organic and inorganic acids, such as inter alia hydrochloric acid, sulphuric acid, phosphoric acid, citric acid and tartaric acid, are suitable.

Pharmaceutical Composition Comprising at Least One EP2 Receptor Antagonist According to General Formula Ia and at Least One COX Inhibitor The present invention provides a pharmaceutical composition comprising (a) at least one EP2 receptor antagonist according to the formula (Ia) and (b) at least one COX inhibitor.

The present invention furthermore provides the use of at least one EP2 receptor antagonist of the general formula Ia together with at least one COX inhibitor for preparing a medicament or a pharmaceutical composition comprising suitable formulation auxiliaries and carriers.

EP2 Receptor Antagonists which, According to the Invention, are Comprised in the Pharmaceutical Composition EP2 receptor antagonists according to the invention which are comprised in the pharmaceutical composition according to the invention are 2H-indazoles of the general formula Ia, where

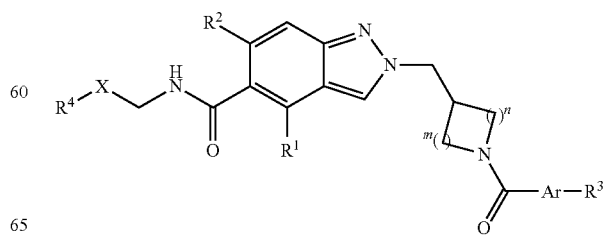

(Ia)

R¹, R²: mean H or methyl;
subject to the proviso that one of the two residues R¹ or R² equals H;
X: —(CH$_2$)$_l$— or —(CH$_2$)$_k$—O—;
k: 1 or 2;
l: 0, 1 or 2;
R⁴: H, C$_1$-C$_4$ alkyl, C$_3$-C$_4$ cycloalkyl or CH$_2$—C$_3$-C$_4$ cycloalkyl;
m: 1 or 2;
n: 1 or 2;
Ar: a 6-10-membered aryl or 5-10-membered hetaryl residue,
R³: halogen, CN, SF$_5$, C$_1$-C$_4$ alkyl, C$_3$-C$_6$ cycloalkyl, C$_4$-C$_6$ heterocyclyl, O—C$_1$-C$_4$ alkyl, O—C$_3$-C$_6$ cycloalkyl, O—C$_4$-C$_6$ heterocyclyl, S—C$_1$-C$_4$ alkyl, S(O)$_2$—C$_1$-C$_4$ alkyl, Ar', O—Ar', C(CH$_3$)$_2$—CN or C(CH$_3$)$_2$—OH; and
Ar': an optionally singly or doubly substituted 6-membered aryl or 5-6-membered heteroaryl residue;
wherein the substituents are selected from F, Cl, CN, C$_1$-C$_4$ alkyl, O—C$_1$-C$_4$ alkyl, C(CH$_3$)$_2$—CN, C(CH$_3$)$_2$—OH and C(O)NH$_2$;
and salts, solvates or solvates of the salts thereof, and isomers, diastereomers, enantiomers and salts or cyclodextrin clathrates thereof, for producing medicaments which overcome the known disadvantages and have improved properties such as good in-vivo efficacy, good solubility and stability.

The compounds according to the invention have an antagonistic action at the EP2 receptor.

The radicals and substituents have the same meaning as described above for the EP2 receptor antagonists of the general formula I.

Preferred are compounds of the formula Ia, wherein
R¹: means a methyl group;
R²: H;
X: —(CH$_2$)$_l$— or —(CH$_2$)$_k$—O—;
k: 1;
l: 0 or 1;
R⁴: C$_1$-C$_4$ alkyl, C$_3$-C$_4$ cycloalkyl or CH$_2$—C$_3$-C$_4$ cycloalkyl;
m, n: 2;
Ar: a phenyl residue;
and salts, solvates or solvates of the salts thereof, and isomers, diastereomers, enantiomers and salts or cyclodextrin clathrates thereof, for producing medicaments which overcome the known disadvantages and have improved properties such as good in-vivo efficacy, good solubility and stability.

Also preferred are compounds of the formula Ia, wherein
R¹: means a methyl group;
R²: H;
X: —(CH$_2$)$_l$— or —(CH$_2$)$_k$—O—;
k: 1;
l: 0 or 1;
R⁴: C$_1$-C$_4$ alkyl, C$_3$-C$_4$ cycloalkyl or CH$_2$—C$_3$-C$_4$ cycloalkyl;
m, n: 1;
Ar: a phenyl residue;
and salts, solvates or solvates of the salts thereof, and isomers, diastereomers, enantiomers and salts or cyclodextrin clathrates thereof, for producing medicaments which overcome the known disadvantages and have improved properties such as good in-vivo efficacy, good solubility and stability.

The following EP2 receptor antagonists according to the invention are particularly preferred:

E1 2-{[1-(4-cyano-2-fluorobenzoyl)piperidin-4-yl]methyl}-N-(2-methoxyethyl)-4-methyl-2H-indazole-5-carboxamide
E2 2-{[1-(4-tert-butoxybenzoyl)piperidin-4-yl]methyl}-N-(2-methoxyethyl)-4-methyl-2H-indazole-5-carboxamide
E3 2-({1-[4-(4-fluorophenoxy)benzoyl]piperidin-4-yl}methyl)-N-(2-methoxyethyl)-4-methyl-2H-indazole-5-carboxamide
E4 N-(2-methoxyethyl)-4-methyl-2-{[1-(4-morpholinobenzoyl)piperidin-4-yl]methyl}-2H-indazole-5-carboxamide
E5 2-({1-[(4'-fluorobiphenyl-4-yl)carbonyl]piperidin-4-yl}methyl)-N-(2-methoxyethyl)-4-methyl-2H-indazole-5-carboxamide
E6 2-{[1-(2-fluoro-4-mesylbenzoyl)piperidin-4-yl]methyl}-N-(2-methoxyethyl)-4-methyl-2H-indazole-5-carboxamide
E7 2-{[1-(2-fluoro-4-methoxybenzo yl)piperidin-4-yl]methyl}-N-(2-methoxyethyl)-4-methyl-2H-indazole-5-carboxamide
E8 2-{[1-(4-bromo-2-fluorobenzoyl)piperidin-4-yl]methyl}-N-(2-methoxyethyl)-4-methyl-2H-indazole-5-carboxamide
E9 2-{[1-(2-fluoro-4-methylbenzoyl)piperidin-4-yl]methyl}-N-(2-methoxyethyl)-4-methyl-2H-indazole-5-carboxamide
E10 2-({1-[2-fluoro-4-(trifluoromethyl)benzoyl]piperidin-4-yl}methyl)-N-(2-methoxyethyl)-4-methyl-2H-indazole-5-carboxamide
E11 N-(2-methoxyethyl)-4-methyl-2-({1-[4-(pentafluoro-λ$^6$-sulphanyl)benzoyl]piperidin-4-yl}methyl)-2H-indazole-5-carboxamide
E12 N-(2-methoxyethyl)-4-methyl-2-{[1-(4-methylbenzoyl)piperidin-4-yl]methyl}-2H-indazole-5-carboxamide
E13 2-({1-[4-(4-chlorophenoxy)benzoyl]piperidin-4-yl}methyl)-N-(2-methoxyethyl)-4-methyl-2H-indazole-5-carboxamide
E14 N-(2-methoxyethyl)-4-methyl-2-({1-[4-(4-methylphenoxy)benzoyl]piperidin-4-yl}-methyl)-2H-indazole-5-carboxamide
E15 2-({1-[4-(4-tert-butylphenoxy)benzoyl]piperidin-4-yl}methyl)-N-(2-methoxyethyl)-4-methyl-2H-indazole-5-carboxamide
E16 N-(2-methoxyethyl)-4-methyl-2-[(1-{4-[4-(trifluoromethyl)phenoxy]benzoyl}piperidin-4-yl)methyl]-2H-indazole-5-carboxamide
E17 N-(2-methoxyethyl)-2-({1-[4-(4-methoxyphenoxy)benzoyl]piperidin-4-yl}methyl)-4-methyl-2H-indazole-5-carboxamide
E18 N-(2-methoxyethyl)-4-methyl-2-{[1-(4-phenoxybenzoyl)piperidin-4-yl]methyl}-2H-indazole-5-carboxamide
E19 2-{[1-(4-cyclopropylbenzoyl)piperidin-4-yl]methyl}-N-(2-methoxyethyl)-4-methyl-2H-indazole-5-carboxamide
E20 2-{[1-(4-methoxybenzoyl)piperidin-4-yl]methyl}-N-(2-methoxyethyl)-4-methyl-2H-indazole-5-carboxamide
E21 2-{[1-(4-fluorobenzoyl)piperidin-4-yl]methyl}-N-(2-methoxyethyl)-4-methyl-2H-indazole-5-carboxamide
E22 N-(2-methoxyethyl)-4-methyl-2-({1-[4-(trifluoromethyl)benzoyl]piperidin-4-yl}-methyl)-2H-indazole-5-carboxamide
E23 2-{[1-(2-methoxybenzoyl)piperidin-4-yl]methyl}-N-(2-methoxyethyl)-4-methyl-2H-indazole-5-carboxamide
E24 N-(2-methoxyethyl)-4-methyl-2-[(1-{4-[(trifluoromethyl)sulphonyl]benzoyl}piperidin-4-yl)methyl]-2H-indazole-5-carboxamide E25 N-(2-methoxyethyl)-4-methyl-2-{1-[3-(trifluoromethyl)benzoyl]piperidin-4-yl}-methyl)-2H-indazole-5-carboxamide E26 N-(2-methoxyethyl)-4-methyl-2-{[1-(3-methylbenzoyl)piperidin-4-yl]methyl}-2H-indazole-5-carboxamide E27 2-{[1-(3-chlorobenzoyl)piperidin-4-yl]methyl}-N-(2-methoxyethyl)-4-methyl-2H-indazole-5-carboxamide E28 2-({1-[4-(4-carbamoylphenoxy)benzoyl]piperidin-4-yl}methyl)-N-(2-methoxyethyl)-4-methyl-2H-indazole-5-carboxamide E29 2-({1-[4-(cyclopentyloxy)benzoyl]piperidin-4-yl}methyl)-N-(2-methoxyethyl)-4-methyl-2H-indazole-5-carboxamide E30 2-({1-[4-(difluoromethyl)benzoyl]piperidin-4-yl}methyl)-N-(2-methoxyethyl)-4-methyl-2H-indazole-5-carboxamide E31 2-{[1-(4-cyanobenzoyl)piperidin-4-yl]methyl}-N-(2-methoxyethyl)-4-methyl-2H-indazole-5-carboxamide E32 2-({1-[4-(1H-imidazol-1-yl)benzoyl]piperidin-4-yl}methyl)-N-(2-methoxyethyl)-4-methyl-2H-indazole-5-carboxamide E33 N-(2-methoxyethyl)-4-methyl-2-({1-[4-(oxazol-2-yl)benzoyl]piperidin-4-yl}methyl)-2H-indazole-5-carboxamide E34 N-(2-methoxyethyl)-4-methyl-2-({1-[4-(oxazol-5-yl)benzoyl]piperidin-4-yl}methyl)-2H-indazole-5-carboxamide E35 N-(2-methoxyethyl)-4-methyl-2-({1-[4-(isoxazol-5-yl)benzoyl]piperidin-4-yl}methyl)-2H-indazole-5-carboxamide E36 N-(2-methoxyethyl)-4-methyl-2-({1-[4-(1H-pyrazol-1-yl)benzoyl]piperidin-4-yl}-methyl)-2H-indazole-5-carboxamide E37 N-(2-methoxyethyl)-4-methyl-2-({1-[4-(1H-1,2,4-triazol-1-yl)benzoyl]piperidin-4-yl}-methyl)-2H-indazole-5-carboxamide E38 2-({1-[4-(difluoromethoxy)-2-fluorobenzoyl]piperidin-4-yl}methyl)-N-(2-methoxy-ethyl)-4-methyl-2H-indazole-5-carboxamide E39 2-({1-[2-fluoro-4-(pyrrolidin-1-yl)benzoyl]piperidin-4-yl}methyl)-N-(2-methoxyethyl)-4-methyl-2H-indazole-5-carboxamide E40 2-({1-[(3,4'-difluorobiphenyl-4-yl)carbonyl]piperidin-4-yl}methyl)-N-(2-methoxyethyl)-4-methyl-2H-indazole-5-carboxamide E41 2-({1-[(3-fluoro-4'-methoxybiphenyl-4-yl)carbonyl]piperidin-4-yl}methyl)-N-(2-methoxyethyl)-4-methyl-2H-indazole-5-carboxamide E42 2-({1-[(3-fluoro-4'-methylbiphenyl-4-yl)carbonyl]piperidin-4-yl}methyl)-N-(2-methoxyethyl)-4-methyl-2H-indazole-5-carboxamide E43 2-[(1-{[3-fluoro-3'-(trifluoromethyl)biphenyl-4-yl]carbonyl}piperidin-4-yl)methyl]-N-(2-methoxyethyl)-4-methyl-2H-indazole-5-carboxamide E44 2-[(1-{[3-fluoro-2'-(trifluoromethoxy)biphenyl-4-yl]carbonyl}piperidin-4-yl)methyl]-N-(2-methoxyethyl)-4-methyl-2H-indazole-5-carboxamide E45 2-({1-[(2'-fluorobiphenyl-4-yl)carbonyl]piperidin-4-yl}methyl)-N-(2-methoxyethyl)-4-methyl-2H-indazole-5-carboxamide E46 2-({1-[(2',4'-difluorobiphenyl-4-yl)carbonyl]piperidin-4-yl}methyl)-N-(2-methoxy-ethyl)-4-methyl-2H-indazole-5-carboxamide E47 2-({1-[(2-fluorobiphenyl-4-yl)carbonyl]piperidin-4-yl}methyl)-N-(2-methoxyethyl)-4-methyl-2H-indazole-5-carboxamide E48 N-(2-methoxyethyl)-4-methyl-2-({1-[(2'-methylbiphenyl-4-yl)carbonyl]piperidin-4-yl}-methyl)-2H-indazole-5-carboxamide E49 N-(2-methoxyethyl)-4-methyl-2-({1-[4-(4-pyridyloxy)benzoyl]piperidin-4-yl}methyl)-2H-indazole-5-carboxamide E50 N-(2-methoxyethyl)-4-methyl-2-({1-[4-(4H-1,2,4-triazol-4-yl)benzoyl]piperidin-4-yl}-methyl)-2H-indazole-5-carboxamide E51 2-({1-[2-fluoro-4-[morpholin-4-yl)benzoyl]piperidin-4-yl}methyl)-N-(2-methoxyethyl)-4-methyl-2H-indazole-5-carboxamide E52 2-{[1-(4-bromobenzoyl)piperidin-4-yl]methyl}-N-(2-methoxyethyl)-4-methyl-2H-indazole-5-carboxamide E53 N-(2-methoxyethyl)-4-methyl-2-({1-[4-(trifluoromethoxy)benzoyl]piperidin-4-yl}-methyl)-2H-indazole-5-carboxamide E54 2-{[1-(4-chlorobenzoyl)piperidin-4-yl]methyl}-N-(2-methoxyethyl)-4-methyl-2H-indazole-5-carboxamide E55 N-(2-methoxyethyl)-4-methyl-2-[(1-{4-[(trifluoromethyl)sulphanyl]benzoyl}piperidin-4-yl)methyl]-2H-indazole-5-carboxamide E56 4-methyl-2-({1-[4-(pentafluoro-$\lambda^6$-sulphanyl)benzoyl]piperidin-4-yl}methyl)-N-(2,2,2-trifluoroethyl)-2H-indazole-5-carboxamide E57 2-{[1-(4-chlorobenzoyl)piperidin-4-yl]methyl}-4-methyl-N-(2,2,2-trifluoroethyl)-2H-indazole-5-carboxamide E58 4-methyl-N-(2,2,2-trifluoroethyl)-2-({1-[4-(trifluoromethoxy)benzoyl]piperidin-4-yl}methyl)-2H-indazole-5-carboxamide E59 2-{[1-(4-chlorobenzoyl)piperidin-4-yl]methyl}-N-[2-(cyclopropylmethoxy)ethyl]-4-methyl-2H-indazole-5-carboxamide E60 N-[2-(cyclopropylmethoxy)ethyl]-4-methyl-2-{[1-(4-methylbenzoyl)piperidin-4-yl]-methyl}-2H-indazole-5-carboxamide E61 N-[2-(cyclopropylmethoxy)ethyl]-2-({1-[4-(4-fluorophenoxy)benzoyl]piperidin-4-yl}-methyl)-4-methyl-2H-indazole-5-carboxamide E62 N-[2-(cyclopropylmethoxy)ethyl]-4-methyl-2-({1-[4-(trifluoromethyl)benzoyl]piperidin-4-yl}methyl)-2H-indazole-5-carboxamide E63 N-[2-(cyclopropylmethoxy)ethyl]-2-({1-[(4'-fluorobiphenyl-4-yl)carbonyl]piperidin-4-yl}methyl)-4-methyl-2H-indazole-5-carboxamide E64 2-{[1-(4-cyclopropylbenzoyl)piperidin-4-yl]methyl}-N-[2-(cyclopropylmethoxy)ethyl]-4-methyl-2H-indazole-5-carboxamide E65 2-{[1-(4-chlorobenzoyl)piperidin-4-yl]methyl}-4-methyl-N-[2-(2,2,2-trifluoroethoxy)-ethyl]-2H-indazole-5-carboxamide E66 4-methyl-2-{[1-(4-methylbenzoyl)piperidin-4-yl]methyl}-N-[2-(2,2,2-trifluoroethoxy)-ethyl]-2H-indazole-5-carboxamide E67 2-({1-[4-(4-fluorophenoxy)benzoyl]piperidin-4-yl}methyl)-4-methyl-N-[2-(2,2,2-trifluoroethoxyethyl]-2H-indazole-5-carboxamide E68 4-methyl-N-[2-(2,2,2-trifluoroethoxy)ethyl]-2-({1-[4-(trifluoromethyl)benzoyl]-piperidin-4-yl}methyl)-2H-indazole-5-carboxamide E69 2-({1-[(4'-fluorobiphenyl-4-yl)carbonyl]piperidin-4-yl}methyl)-4-methyl-N-[2-(2,2,2-trifluoroethoxy)ethyl]-2H-indazole-5-carboxamide E70 2-{[1-(4-cyclopropylbenzoyl)piperidin-4-yl]methyl}-4-methyl-N-[2-(2,2,2-trifluoro-ethoxy)ethyl]-2H-indazole-5-carboxamide E71 2-{[1-(4-chlorobenzoyl)piperidin-4-yl]methyl}-N-(2-isopropoxyethyl)-4-methyl-2H-indazole-5-carboxamide E72 N-(2-isopropoxyethyl)-4-methyl-2-{[1-(4-methylbenzoyl)piperidin-4-yl]methyl}-2H-indazole-5-carboxamide E73 2-({1-[4-(4-fluorophenoxy)benzoyl]piperidin-4-yl}methyl)-N-(2-isopropoxyethyl)-4-methyl-2H-indazole-5-carboxamide E74 N-(2-isopropoxyethyl)-4-methyl-2-({1-[4-(trifluoromethyl)benzoyl]piperidin-4-yl}-methyl)-2H-indazole-5-carboxamide E75 2-({1-[(4'-fluorobiphenyl-4-yl)carbonyl]piperidin-4-yl}methyl)-N-(2-isopropoxyethyl)-4-methyl-2H-indazole-5-carboxamide E76 2-{[1-(4-cyclopropylbenzoyl)piperidin-4-yl]methyl}-N-(2-isopropoxyethyl)-4-methyl-2H-indazole-5-carboxamide E77 2-{[1-(4-chlorobenzoyl)piperidin-4-yl]methyl}-4-methyl-N-[2-(trifluoromethoxy)ethyl]-2H-indazole-5-carboxamide E78 2-({1-[4-(4-fluorophenoxy)benzoyl]piperidin-4-yl}methyl)-4-methyl-N-[2-(trifluoro-methoxy)ethyl]-2H-indazole-5-carboxamide E79 2-({1-[(4'-fluorobiphenyl-4-yl)carbonyl]piperidin-4-yl}methyl)-4-methyl-N-[2-(trifluoromethoxy)ethyl]-2H-indazole-5-carboxamide E80 4-methyl-N-[2-(trifluoromethoxy)ethyl]-2-[(1-{4-[4-(trifluoromethyl)phenoxy]-benzoyl}piperidin-4-yl)methyl]-2H-indazole-5-carboxamide E81 N-(2-tert-butoxyethyl)-2-{[1-(4-chlorobenzoyl)piperidin-4-yl]methyl}-4-methyl-2H-indazole-5-carboxamide E82 N-(2-tert-butoxyethyl)-2-({1-[4-(4-fluorophenoxy)benzoyl]piperidin-4-yl}methyl)-4-methyl-2H-indazole-5-carboxamide E83 N-(2-tert-butoxyethyl)-2-({1-[(4'-fluorobiphenyl-4-yl)carbonyl]piperidin-4-yl}methyl)-4-methyl-2H-indazole-5-carboxamide E84 N-(2-tert-butoxyethyl)-4-methyl-2-[(1-{4-[4-(trifluoromethyl)phenoxy]benzoyl}-piperidin-4-yl)methyl]-2H-indazole-5-carboxamide E85 2-{[1-(4-chlorobenzoyl)piperidin-4-yl]methyl}-4-methyl-N-{2-[($^{2}$H3)methyloxy]-($^{2}$H4)ethyl}-2H-indazole-5-carboxamide E86 2-({1-[4-(4-fluorophenoxy)benzoyl]piperidin-4-yl}methyl)-4-methyl-N-{2-[($^{2}$H3)methyloxy]($^{2}$H4)ethyl}-2H-indazole-5-carboxamide E87 2-{[1-(4-chlorobenzoyl)azetidin-3-yl]methyl}-N-(2-methoxyethyl)-4-methyl-2H-indazole-5-carboxamide E88 N-(2-methoxyethyl)-4-methyl-2-[(1-{4-[(trifluoromethyl)sulphanyl]benzoyl}azetidin-3-yl)methyl]-2H-indazole-5-carboxamide E89 N-(2-methoxyethyl)-4-methyl-2-({1-[4-(trifluoromethoxy)benzoyl]azetidin-3-yl}-methyl)-2H-indazole-5-carboxamide E90 2-({1-[2-fluoro-4-(trifluoromethyl)benzoyl]azetidin-3-yl}methyl)-N-(2-methoxyethyl)-4-methyl-2H-indazole-5-carboxamide E91 2-{[1-(4-chloro-2-fluorobenzoyl)azetidin-3-yl]methyl}-N-(2-methoxyethyl)-4-methyl-2H-indazole-5-carboxamide E92 2-({1-[3-fluoro-4-(trifluoromethyl)benzoyl]azetidin-3-yl}methyl)-N-(2-methoxyethyl)-4-methyl-2H-indazole-5-carboxamide E93 2-({1-[4-chloro-3-(trifluoromethyl)benzoyl]azetidin-3-yl}methyl)-N-(2-methoxyethyl)-4-methyl-2H-indazole-5-carboxamide E94 2-{[1-(4-cyclopropylbenzoyl)azetidin-3-yl]methyl}-N-(2-methoxyethyl)-4-methyl-2H-indazole-5-carboxamide E95 N-(2-methoxyethyl)-4-methyl-2-[(1-{4-[4-(trifluoromethyl)phenoxy]benzoyl}azetidin-3-yl)methyl]-2H-indazole-5-carboxamide E96 2-{[1-(4-chlorobenzoyl)azetidin-3-yl]methyl}-4-methyl-N-(2,2,2-trifluoroethyl)-2H-indazole-5-carboxamide E97 4-methyl-N-(2,2,2-trifluoroethyl)-2-({1-[4-(trifluoromethoxy)benzoyl]azetidin-3-yl}-methyl)-2H-indazole-5-carboxamide E98 2-({1-[2-fluoro-4-(trifluoromethyl)benzoyl]azetidin-3-yl}methyl)-4-methyl-N-(2,2,2-trifluoroethyl)-2H-indazole-5-carboxamide E99 4-methyl-2-({1-[4-(pentafluoro-$\lambda^{6}$-sulphanyl)benzoyl]azetidin-3-yl}methyl)-N-(2,2,2-trifluoroethyl)-2H-indazole-5-carboxamide E100 N-[2-(cyclopropyloxy)ethyl]-4-methyl-2-({1-[4-(trifluoromethoxy)benzoyl]azetidin-3-yl}methyl)-2H-indazole-5-carboxamide E101 N-[2-(cyclobutyloxy)ethyl]-4-methyl-2-({1-[4-(trifluoromethoxy)benzoyl]azetidin-3-yl}methyl)-2H-indazole-5-carboxamide E102 2-{[1-(4-chlorobenzoyl)azetidin-3-yl]methyl}-N-[2-(cyclopropylmethoxy)ethyl]-4-methyl-2H-indazole-5-carboxamide E103 N-[2-(cyclopropylmethoxy)ethyl]-2-({1-[4-(4-fluorophenoxy)benzoyl]azetidin-3-yl}-methyl)-4-methyl-2H-indazole-5-carboxamide E104 N-[2-(cyclopropylmethoxy)ethyl]-4-methyl-2-{[1-(4-methylbenzoyl)azetidin-3-yl]-methyl}-2H-indazole-5-carboxamide E105 2-{[1-(4-chlorobenzoyl)azetidin-3-yl]methyl}-4-methyl-N-[2-(trifluoromethoxy)ethyl]-2H-indazole-5-carboxamide E106 N-(2-tert-butoxyethyl)-2-{[1-(4-chlorobenzoyl)azetidin-3-yl]methyl}-4-methyl-2H-indazole-5-carboxamide E107 N-[2-(cyclopropylmethoxy)ethyl]-2-({1-[(4'-fluorobiphenyl-4-yl)carbonyl]azetidin-3-yl}methyl)-4-methyl-2H-indazole-5-carboxamide E108 2-({1-[(4'-fluorobiphenyl-4-yl)carbonyl]azetidin-3-yl}methyl)-N-(2-methoxyethyl)-4-methyl-2H-indazole-5-carboxamide E109 2-({1-[4-(4-fluorophenoxy)benzoyl]azetidin-3-yl}methyl)-N-(2-methoxyethyl)-4-methyl-2H-indazole-5-carboxamide E110 2-({1-[4-(4-fluorophenoxy)benzoyl]azetidin-3-yl}methyl)-4-methyl-N-(2,2,2-trifluoroethyl)-2H-indazole-5-carboxamide E111 2-({1-[(4'-fluorobiphenyl-4-yl)carbonyl]azetidin-3-yl}methyl)-4-methyl-N-(2,2,2-trifluoroethyl)-2H-indazole-5-carboxamide E112 2-{[1-(4-chlorobenzoyl)azetidin-3-yl]methyl}-4-methyl-N-[2-(2,2,2-trifluoroethoxy)-ethyl]-2H-indazole-5-carboxamide E113 4-methyl-N-[2-(2,2,2-trifluoroethoxy)ethyl]-2-[(1-{4-[4-(trifluoromethyl)phenoxy]-benzoyl}azetidin-3-yl)methyl]-2H-indazole-5-carboxamide E114 4-methyl-N-(2,2,2-trifluoroethyl)-2-[(1-{4-[4-(trifluoromethyl)phenoxy]benzoyl}-azetidin-3-yl)methyl]-2H-indazole-5-carboxamide E115 2-({1-[4-(4-chlorophenoxy)benzoyl]azetidin-3-yl}methyl)-4-methyl-N-(2,2,2-trifluoro-ethyl)-2H-indazole-5-carboxamide E116 2-({1-[4-(4-chlorophenoxy)benzoyl]azetidin-3-yl}methyl)-N-(2-methoxyethyl)-4-methyl-2H-indazole-5-carboxamide E117 N-(2-methoxyethyl)-4-methyl-2-{[1-(4-{[5-(trifluoromethyl)pyridin-2-yl]oxy}benzoyl)-azetidin-3-yl]methyl}-2H-indazole-5-carboxamide E118 4-methyl-N-(2,2,2-trifluoroethyl)-2-{[1-(4-{[5-(trifluoromethyl)pyridin-2-yl]oxy}benzoyl)azetidin-3-yl]methyl}-2H-indazole-5-carboxamide E119 2-{[1-(4-chlorobenzoyl)piperidin-4-yl]methyl}-N-ethyl-4-methyl-2H-indazole-5-carboxamide E120 2-({1-[4-(4-fluorophenoxy)benzoyl]piperidin-4-yl}methyl)-4-methyl-N-(2,2,2-trifluoro-ethyl)-2H-indazole-5-carboxamide E121 2-({1-[4-(4-chlorophenoxy)benzoyl]piperidin-4-yl}methyl)-4-methyl-N-(2,2,2-trifluoro-ethyl)-2H-indazole-5-carboxamide E122 4-methyl-2-({1-[4-(4-methylphenoxy)benzoyl]piperidin-4-yl}methyl)-N-(2,2,2-trifluoroethyl)-2H-indazole-5-carboxamide E123 2-({1-[(4'-fluorobiphenyl-4-yl)carbonyl]piperidin-4-yl}methyl)-4-methyl-N-(2,2,2-trifluoroethyl)-2H-indazole-5-carboxamide E124 4-methyl-2-{[1-(4-morpholinobenzoyl)piperidin-4-yl]methyl}-N-(2,2,2-trifluoroethyl)-2H-indazole-5-carboxamide E125 4-methyl-N-(2,2,2-trifluoroethyl)-2-[(1-{4-[(trifluoromethyl)sulphanyl]benzoyl}-piperidin-4-yl)methyl]-2H-indazole-5-carboxamide E126 4-methyl-N-(2,2,2-trifluoroethyl)-2-[(1-{4-[4-(trifluoromethyl)phenoxy]benzoyl}-piperidin-4-yl)methyl]-2H-indazole-5-carboxamide E127 4-methyl-N-(2,2,2-trifluoroethyl)-2-{[1-(4-{[5-(trifluoromethyl)pyridin-2-yl]oxy}-benzoyl)piperidin-4-yl]methyl}-2H-indazole-5-carboxamide E128 4-methyl-N-(2,2,2-trifluoroethyl)-2-{[1-(4-{[6-(trifluoromethyl)pyridin-3-yl]oxy}-benzoyl)piperidin-4-yl]methyl}-2H-indazole-5-carboxamide E129 4-methyl-N-(2,2,2-trifluoroethyl)-2-{[1-(4-{[6-(trifluoromethyl)pyridin-2-yl]oxy}-benzoyl)piperidin-4-yl]methyl}-2H-indazole-5-carboxamide E130 2-({1-[4-(4-cyanophenoxy)benzoyl]piperidin-4-yl}methyl)-4-methyl-N-(2,2,2-trifluoro-ethyl)-2H-indazole-5-carboxamide E131 2-({1-[4-(3-fluorophenoxy)benzoyl]piperidin-4-yl}methyl)-4-methyl-N-(2,2,2-trifluoro-ethyl)-2H-indazole-5-carboxamide E132 4-methyl-N-(2,2,2-trifluoroethyl)-2-[(1-{4-[3-(trifluoromethyl)phenoxy]benzoyl}-piperidin-4-yl)methyl]-2H-indazole-5-carboxamide E133 2-[(1-{4-[(5-cyanopyridin-2-yl)oxy]benzoyl}piperidin-4-yl)methyl]-4-methyl-N-(2,2,2-trifluoroethyl)-2H-indazole-5-carboxamide E134 2-[(1-{4-[(5-chloropyridin-2-yl)oxy]benzoyl}piperidin-4-yl)methyl]-4-methyl-N-(2,2,2-trifluoroethyl)-2H-indazole-5-carboxamide E135 4-methyl-N-(2,2,2-trifluoroethyl)-2-[(1-{4-[5-(trifluoromethyl)pyridin-2-yl]benzoyl}-piperidin-4-yl)methyl]-2H-indazole-5-carboxamide E136 2-({1-[4-(2,4-difluorophenoxy)benzoyl]piperidin-4-yl}methyl)-4-methyl-N-(2,2,2-trifluoroethyl)-2H-indazole-5-carboxamide E137 2-({1-[4-(3,4-difluorophenoxy)benzoyl]piperidin-4-yl}methyl)-4-methyl-N-(2,2,2-trifluoroethyl)-2H-indazole-5-carboxamide E138 4-methyl-N-(2,2,2-trifluoroethyl)-2-[(1-{[4'-(trifluoromethyl)biphenyl-4-yl]carbonyl}-piperidin-4-yl)methyl]-2H-indazole-5-carboxamide E139 2-{[1-(4-bromobenzoyl)piperidin-4-yl]methyl}-4-methyl-N-(2,2,2-trifluoroethyl)-2H-indazole-5-carboxamide E140 2-({1-[4-(5-chloropyridin-2-yl)benzoyl]piperidin-4-yl}methyl)-4-methyl-N-(2,2,2-trifluoroethyl)-2H-indazole-5-carboxamide E141 2-({1-[(4'-methoxy-2'-methylbiphenyl-4-yl)carbonyl]piperidin-4-yl}methyl)-4-methyl-N-(2,2,2-trifluoroethyl)-2H-indazole-5-carboxamide E142 4-methyl-2-({1-[4-(6-methylpyridin-3-yl)benzoyl]piperidin-4-yl}methyl)-N-(2,2,2-trifluoroethyl)-2H-indazole-5-carboxamide E143 2-({1-[(4'-fluoro-2'-methoxybiphenyl-4-yl)carbonyl]piperidin-4-yl}methyl)-4-methyl-N-(2,2,2-trifluoroethyl)-2H-indazole-5-carboxamide E144 4-methyl-N-(2,2,2-trifluoroethyl)-2-[(1-{4-[6-(trifluoromethyl)pyridin-3-yl]benzoyl}-piperidin-4-yl)methyl]-2H-indazole-5-carboxamide E145 2-({1-[4-(6-methoxypyridin-3-yl)benzoyl]piperidin-4-yl}methyl)-4-methyl-N-(2,2,2-trifluoroethyl)-2H-indazole-5-carboxamide E146 2-({1-[4-(6-methoxypyridin-2-yl)benzoyl]piperidin-4-yl}methyl)-4-methyl-N-(2,2,2-trifluoroethyl)-2H-indazole-5-carboxamide E147 4-methyl-2-({1-[4-(5-methylpyridin-2-yl)benzoyl]piperidin-4-yl}methyl)-N-(2,2,2-trifluoroethyl)-2H-indazole-5-carboxamide E148 2-({1-[4-(5-fluoropyridin-2-yl)benzoyl]piperidin-4-yl}methyl)-4-methyl-N-(2,2,2-trifluoroethyl)-2H-indazole-5-carboxamide E149 2-({1-[4-(5-methoxypyridin-2-yl)benzoyl]piperidin-4-yl}methyl)-4-methyl-N-(2,2,2-trifluoroethyl)-2H-indazole-5-carboxamide E150 4-methyl-2-({1-[4-(2-methylpyrimidin-5-yl)benzoyl]piperidin-4-yl}methyl)-N-(2,2,2-trifluoroethyl)-2H-indazole-5-carboxamide E151 4-methyl-N-(2,2,2-trifluoroethyl)-2-[(1-{4-[2-(trifluoromethyl)pyrimidin-5-yl]benzoyl}-piperidin-4-yl)methyl]-2H-indazole-5-carboxamide E152 4-methyl-N-(2,2,2-trifluoroethyl)-2-[(1-{4-[6-(trifluoromethyl)pyridin-2-yl]benzoyl}-piperidin-4-yl)methyl]-2H-indazole-5-carboxamide E153 2-({1-[4-(4-cyanophenoxy)benzoyl]piperidin-4-yl}methyl)-N-(2-methoxyethyl)-4-methyl-2H-indazole-5-carboxamide E154 2-{[1-(4-bromo-3-methylbenzoyl)piperidin-4-yl]methyl}-N-(2-methoxyethyl)-4-methyl-2H-indazole-5-carboxamide E155 2-{[1-(4-tert-butylbenzoyl)piperidin-4-yl]methyl}-N-(2-methoxyethyl)-4-methyl-2H-indazole-5-carboxamide E156 2-({1-[4-(1-hydroxy-1-methylethyl)benzoyl]piperidin-4-yl}methyl)-N-(2-methoxy-ethyl)-4-methyl-2H-indazole-5-carboxamide E157 2-{[1-(4-cyclohexylbenzoyl)piperidin-4-yl]methyl}-N-(2-methoxyethyl)-4-methyl-2H-indazole-5-carboxamide E158 2-({1-[4-(1-cyano-1-methylethyl)benzoyl]piperidin-4-yl}methyl)-N-(2-methoxyethyl)-4-methyl-2H-indazole-5-carboxamide E159 N-(2-methoxyethyl)-4-methyl-2-({1-[4-(pyrimidin-2-yloxy)benzoyl]piperidin-4-yl}-methyl)-2H-indazole-5-carboxamide E160 N-(2-methoxyethyl)-4-methyl-2-({1-[4-(pyridin-3-yloxy)benzoyl]piperidin-4-yl}methyl)-2H-indazole-5-carboxamide E161 N-(2-methoxyethyl)-4-methyl-2-{[1-(4-{[5-(trifluoromethyl)pyridin-2-yl]oxy}benzoyl)-piperidin-4-yl]methyl}-2H-indazole-5-carboxamide E162 N-(2-methoxyethyl)-4-methyl-2-({1-[4-(pyridin-2-yloxy)benzoyl]piperidin-4-yl}methyl)-2H-indazole-5-carboxamide E163 N-(2-methoxyethyl)-4-methyl-2-{[1-(4-{[4-(trifluoromethyl)pyrimidin-2-yl]oxy}-benzoyl)piperidin-4-yl]methyl}-2H-indazole-5-carboxamide E164 N-(2-methoxyethyl)-4-methyl-2-{[1-(4-{[6-(trifluoromethyl)pyridin-3-yl]oxy}benzoyl)-piperidin-4-yl]methyl}-2H-indazole-5-carboxamide E165 N-(2-methoxyethyl)-4-methyl-2-{[1-(4-{[6-(trifluoromethyl)pyridin-2-yl]oxy}benzoyl)-piperidin-4-yl]methyl}-2H-indazole-5-carboxamide E166 2-({1-[(4'-methoxybiphenyl-4-yl)carbonyl]piperidin-4-yl}methyl)-N-(2-methoxyethyl)-4-methyl-2H-indazole-5-carboxamide E167 N-(2-methoxyethyl)-4-methyl-2-({1-[4-(3,4,5,6-tetrahydro-2H-pyran-4-yloxy)benzoyl]-piperidin-4-yl}methyl)-2H-indazole-5-carboxamide E168 N-(2-methoxyethyl)-4-methyl-2-[(1-{4-[3-(trifluoromethyl)phenoxy]benzoyl}piperidin-4-yl)methyl]-2H-indazole-5-carboxamide E169 2-[(1-{4-[(5-cyanopyridin-2-yl)oxy]benzoyl}piperidin-4-yl)methyl]-N-(2-methoxy-ethyl)-4-methyl-2H-indazole-5-carboxamide E170 2-[(1-{4-[(5-chloropyridin-2-yl)oxy]benzoyl}piperidin-4-yl)methyl]-N-(2-methoxy-ethyl)-4-methyl-2H-indazole-5-carboxamide E171 2-({1-[4-(2,4-difluorophenoxy)benzoyl]piperidin-4-yl}methyl)-N-(2-methoxyethyl)-4-methyl-2H-indazole-5-carboxamide E172 2-({1-[4-(3,4-difluorophenoxy)benzoyl]piperidin-4-yl}methyl)-N-(2-methoxyethyl)-4-methyl-2H-indazole-5-carboxamide E173 N-(2-methoxyethyl)-4-methyl-2-[(1-{[4'-(trifluoromethyl)biphenyl-4-yl]carbonyl}-piperidin-4-yl)methyl]-2H-indazole-5-carboxamide E174 2-({1-[4-(3-fluorophenoxy)benzoyl]piperidin-4-yl}methyl)-N-(2-methoxyethyl)-4-methyl-2H-indazole-5-carboxamide E175 2-{[1-(2-fluoro-4-isopropoxybenzoyl)piperidin-4-yl]methyl}-N-(2-methoxyethyl)-4-methyl-2H-indazole-5-carboxamide E176 2-({1-[(3-fluoro-3',4'-dimethylbiphenyl-4-yl)carbonyl]piperidin-4-yl}methyl)-N-(2-methoxyethyl)-4-methyl-2H-indazole-5-carboxamide E177 2-({1-[(2',3-difluoro-4'-methoxybiphenyl-4-yl)carbonyl]piperidin-4-yl}methyl)-N-(2-methoxyethyl)-4-methyl-2H-indazole-5-carboxamide E178 2-({1-[4-(difluoromethoxy)benzoyl]piperidin-4-yl}methyl)-N-(2-methoxyethyl)-4-methyl-2H-indazole-5-carboxamide E179 2-({1-[4-(2-fluorophenoxy)benzoyl]piperidin-4-yl}methyl)-N-(2-methoxyethyl)-4-methyl-2H-indazole-5-carboxamide E180 2-({1-[(4'-cyano-2'-methylbiphenyl-4-yl)carbonyl]piperidin-4-yl}methyl)-N-(2-methoxyethyl)-4-methyl-2H-indazole-5-carboxamide E181 2-({1-[4-(5-chloropyridin-2-yl)benzoyl]piperidin-4-yl}methyl)-N-(2-methoxyethyl)-4-methyl-2H-indazole-5-carboxamide E182 N-(2-methoxyethyl)-4-methyl-2-[(1-{4-[6-(trifluoromethyl)pyridin-2-yl]benzoyl}-piperidin-4-yl)methyl]-2H-indazole-5-carboxamide E183 N-(2-methoxyethyl)-2-({1-[(4'-methoxy-2'-methylbiphenyl-4-yl)carbonyl]piperidin-4-yl}methyl)-4-methyl-2H-indazole-5-carboxamide E184 2-({1-[(4'-chloro-2'-methylbiphenyl-4-yl)carbonyl]piperidin-4-yl}methyl)-N-(2-methoxyethyl)-4-methyl-2H-indazole-5-carboxamide E185 2-[(1-{[4'-(2-cyanopropan-2-yl)biphenyl-4-yl]carbonyl}piperidin-4-yl)methyl]-N-(2-methoxyethyl)-4-methyl-2H-indazole-5-carboxamide E186 N-(2-methoxyethyl)-2-({1-[4-(5-methoxypyridin-2-yl)benzoyl]piperidin-4-yl}methyl)-4-methyl-2H-indazole-5-carboxamide E187 N-(2-methoxyethyl)-2-[(1-{4-[6-(trifluoromethyl)pyridin-3-yl]benzoyl}-piperidin-4-yl)methyl]-2H-indazole-5-carboxamide E188 N-(2-methoxyethyl)-2-({1-[4-(6-methoxypyridin-3-yl)benzoyl]piperidin-4-yl}methyl)-4-methyl-2H-indazole-5-carboxamide E189 2-({1-[(4'-fluoro-2'-methylbiphenyl-4-yl)carbonyl]piperidin-4-yl}methyl)-N-(2-methoxyethyl)-4-methyl-2H-indazole-5-carboxamide E190 N-(2-methoxyethyl)-4-methyl-2-({1-[4-(6-methylpyridin-3-yl)benzoyl]piperidin-4-yl}methyl)-2H-indazole-5-carboxamide E191 N-(2-methoxyethyl)-2-({1-[4-(6-methoxypyridin-2-yl)benzoyl]piperidin-4-yl}methyl)-4-methyl-2H-indazole-5-carboxamide E192 N-(2-methoxyethyl)-4-methyl-2-({1-[4-(2-methylpyrimidin-5-yl)benzoyl]piperidin-4-yl}methyl)-2H-indazole-5-carboxamide E193 2-({1-[(4'-fluoro-2'-methoxybiphenyl-4-yl)carbonyl]piperidin-4-yl}methyl)-N-(2-methoxyethyl)-4-methyl-2H-indazole-5-carboxamide E194 2-({1-[(4'-chloro-2'-methoxybiphenyl-4-yl)carbonyl]piperidin-4-yl}methyl)-N-(2-methoxyethyl)-4-methyl-2H-indazole-5-carboxamide E195 N-(2-methoxyethyl)-4-methyl-2-[(1-{4-[2-(trifluoromethyl)pyrimidin-5-yl]benzoyl}-piperidin-4-yl)methyl]-2H-indazole-5-carboxamide E196 2-({1-[(4'-chloro-2'-fluorobiphenyl-4-yl)carbonyl]piperidin-4-yl}methyl)-N-(2-methoxy-ethyl)-4-methyl-2H-indazole-5-carboxamide E197 2-({1-[(2'-chloro-4'-fluorobiphenyl-4-yl)carbonyl]piperidin-4-yl}methyl)-N-(2-methoxy-ethyl)-4-methyl-2H-indazole-5-carboxamide E198 2-({1-[4-(5-chloropyridin-3-yl)benzoyl]piperidin-4-yl}methyl)-N-(2-methoxyethyl)-4-methyl-2H-indazole-5-carboxamide E199 2-({1-[4-(5-fluoropyridin-3-yl)benzoyl]piperidin-4-yl}methyl)-N-(2-methoxyethyl)-4-methyl-2H-indazole-5-carboxamide E200 N-(2-methoxyethyl)-4-methyl-2-[(1-{4-[5-(trifluoromethyl)pyridin-3-yl]benzoyl}-piperidin-4-yl)methyl]-2H-indazole-5-carboxamide E201 2-[(1-{[4'-(2-hydroxypropan-2-yl)biphenyl-4-yl]carbonyl}piperidin-4-yl)methyl]-N-(2-methoxyethyl)-4-methyl-2H-indazole-5-carboxamide E202 2-({1-[(3',5'-difluorobiphenyl-4-yl)carbonyl]piperidin-4-yl}methyl)-N-(2-methoxy-ethyl)-4-methyl-2H-indazole-5-carboxamide E203 2-({1-[(4'-fluoro-2-methylbiphenyl-4-yl)carbonyl]piperidin-4-yl}methyl)-N-(2-methoxyethyl)-4-methyl-2H-indazole-5-carboxamide E204 2-({1-[(3',5'-difluoro-2-methylbiphenyl-4-yl)carbonyl]piperidin-4-yl}methyl)-N-(2-methoxyethyl)-4-methyl-2H-indazole-5-carboxamide E205 N-(2-methoxyethyl)-4-methyl-2-({1-[3-methyl-4-(3-pyridyl)benzoyl]piperidin-4-yl}-methyl)-2H-indazole-5-carboxamide E206 N-(2-methoxyethyl)-4-methyl-2-({1-[3-methyl-4-(4-pyridyl)benzoyl]piperidin-4-yl}-methyl)-2H-indazole-5-carboxamide E207 N-(2-methoxyethyl)-4-methyl-2-({1-[(2-methylbiphenyl-4-yl)carbonyl]piperidin-4-yl}-methyl)-2H-indazole-5-carboxamide From the 207 compounds, particular preference is given to the compounds having an EP2 receptor antagonism of >50 nM:

E2 2-{[1-(4-tert-butoxybenzoyl)piperidin-4-yl]methyl}-N-(2-methoxyethyl)-4-methyl-2H-indazole-5-carboxamide E3 2-({1-[4-(4-fluorophenoxy)benzoyl]piperidin-4-yl}methyl)-N-(2-methoxyethyl)-4-methyl-2H-indazole-5-carboxamide E5 2-({1-[(4'-fluorobiphenyl-4-yl)carbonyl]piperidin-4-yl}methyl)-N-(2-methoxyethyl)-4-methyl-2H-indazole-5-carboxamide E7 2-{[1-(2-fluoro-4-methoxybenzo yl)piperidin-4-yl]methyl}-N-(2-methoxyethyl)-4-methyl-2H-indazole-5-carboxamide E8 2-{[1-(4-bromo-2-fluorobenzoyl)piperidin-4-yl]methyl}-N-(2-methoxyethyl)-4-methyl-2H-indazole-5-carboxamide E9 2-{[1-(2-fluoro-4-methylbenzoyl)piperidin-4-yl]methyl}-N-(2-methoxyethyl)-4-methyl-2H-indazole-5-carboxamide E10 2-({1-[2-fluoro-4-(trifluoromethyl)benzoyl]piperidin-4-yl}methyl)-N-(2-methoxyethyl)-4-methyl-2H-indazole-5-carboxamide E11 N-(2-methoxyethyl)-4-methyl-2-({1-[4-(pentafluoro-λ⁶-sulphanyl)benzoyl]piperidin-4-yl}methyl)-2H-indazole-5-carboxamide E12 N-(2-methoxyethyl)-4-methyl-2-{[1-(4-methylbenzoyl)piperidin-4-yl]methyl}-2H-indazole-5-carboxamide E13 2-({1-[4-(4-chlorophenoxy)benzoyl]piperidin-4-yl}methyl)-N-(2-methoxyethyl)-4-methyl-2H-indazole-5-carboxamide E14 N-(2-methoxyethyl)-4-methyl-2-({1-[4-(4-methylphenoxy)benzoyl]piperidin-4-yl}-methyl)-2H-indazole-5-carboxamide E15 2-({1-[4-(4-tert-butylphenoxy)benzoyl]piperidin-4-yl}methyl)-N-(2-methoxyethyl)-4-methyl-2H-indazole-5-carboxamide E16 N-(2-methoxyethyl)-4-methyl-2-[(1-{4-[4-(trifluoromethyl)phenoxy]benzoyl}piperidin-4-yl)methyl]-2H-indazole-5-carboxamide E17 N-(2-methoxyethyl)-2-({1-[4-(4-methoxyphenoxy)benzoyl]piperidin-4-yl}methyl)-4-methyl-2H-indazole-5-carboxamide E18 N-(2-methoxyethyl)-4-methyl-2-{[1-(4-phenoxybenzoyl)piperidin-4-yl]methyl}-2H-indazole-5-carboxamide E19 2-{[1-(4-cyclopropylbenzoyl)piperidin-4-yl]methyl}-N-(2-methoxyethyl)-4-methyl-2H-indazole-5-carboxamide E20 2-{[1-(4-methoxybenzoyl)piperidin-4-yl]methyl}-N-(2-methoxyethyl)-4-methyl-2H-indazole-5-carboxamide E21 2-{[1-(4-fluorobenzoyl)piperidin-4-yl]methyl}-N-(2-methoxyethyl)-4-methyl-2H-indazole-5-carboxamide E22 N-(2-methoxyethyl)-4-methyl-2-({1-[4-(trifluoromethyl)benzoyl]piperidin-4-yl}-methyl)-2H-indazole-5-carboxamide E24 N-(2-methoxyethyl)-4-methyl-2-[(1-{4-[(trifluoromethyl)sulfonyl]benzoyl}piperidin-4-yl)methyl]-2H-indazole-5-carboxamide E25 N-(2-methoxyethyl)-4-methyl-2-{1-[3-(trifluoromethyl)benzoyl]piperidin-4-yl}-methyl)-2H-indazole-5-carboxamide E26 N-(2-methoxyethyl)-4-methyl-2-{[1-(3-methylbenzoyl)piperidin-4-yl]methyl}-2H-indazole-5-carboxamide E27 2-{[1-(3-chlorobenzoyl)piperidin-4-yl]methyl}-N-(2-methoxyethyl)-4-methyl-2H-indazole-5-carboxamide E29 2-({1-[4-(cyclopentyloxy)benzoyl]piperidin-4-yl}methyl)-N-(2-methoxyethyl)-4-methyl-2H-indazole-5-carboxamide E30 2-({1-[4-(difluoromethyl)benzoyl]piperidin-4-yl}methyl)-N-(2-methoxyethyl)-4-methyl-2H-indazole-5-carboxamide E31 2-{[1-(4-cyanobenzoyl)piperidin-4-yl]methyl}-N-(2-methoxyethyl)-4-methyl-2H-indazole-5-carboxamide E36 N-(2-methoxyethyl)-4-methyl-2-({1-[4-(1H-pyrazol-1-yl)benzoyl]piperidin-4-yl}-methyl)-2H-indazole-5-carboxamide E38 2-({1-[4-(difluoromethoxy)-2-fluorobenzoyl]piperidin-4-yl}methyl)-N-(2-methoxy-ethyl)-4-methyl-2H-indazole-5-carboxamide E39 2-({1-[2-fluoro-4-(pyrrolidin-1-yl)benzoyl]piperidin-4-yl}methyl)-N-(2-methoxyethyl)-4-methyl-2H-indazole-5-carboxamide E40 2-({1-[(3,4'-difluorobiphenyl-4-yl)carbonyl]piperidin-4-yl}methyl)-N-(2-methoxyethyl)-4-methyl-2H-indazole-5-carboxamide E41 2-({1-[(3-fluoro-4'-methoxybiphenyl-4-yl)carbonyl]piperidin-4-yl}methyl)-N-(2-methoxyethyl)-4-methyl-2H-indazole-5-carboxamide E44 2-[(1-{[3-fluoro-2'-(trifluoromethoxy)biphenyl-4-yl]carbonyl}piperidin-4-yl)methyl]-N-(2-methoxyethyl)-4-methyl-2H-indazole-5-carboxamide E45 2-({1-[(2'-fluorobiphenyl-4-yl)carbonyl]piperidin-4-yl}methyl)-N-(2-methoxyethyl)-4-methyl-2H-indazole-5-carboxamide E46 2-({1-[(2',4'-difluorobiphenyl-4-yl)carbonyl]piperidin-4-yl}methyl)-N-(2-methoxy-ethyl)-4-methyl-2H-indazole-5-carboxamide E47 2-({1-[(2-fluorobiphenyl-4-yl)carbonyl]piperidin-4-yl}methyl)-N-(2-methoxyethyl)-4-methyl-2H-indazole-5-carboxamide E48 N-(2-methoxyethyl)-4-methyl-2-({1-[(2'-methylbiphenyl-4-yl)carbonyl]piperidin-4-yl}-methyl)-2H-indazole-5-carboxamide E51 2-({1-[2-fluoro-4-(morpholin-4-yl)benzoyl]piperidin-4-yl}methyl)-N-(2-methoxyethyl)-4-methyl-2H-indazole-5-carboxamide E52 2-{[1-(4-bromobenzoyl)piperidin-4-yl]methyl}-N-(2-methoxyethyl)-4-methyl-2H-indazole-5-carboxamide E53 N-(2-methoxyethyl)-4-methyl-2-({1-[4-(trifluoromethoxy)benzoyl]piperidin-4-yl}-methyl)-2H-indazole-5-carboxamide E54 2-{[1-(4-chlorobenzoyl)piperidin-4-yl]methyl}-N-(2-methoxyethyl)-4-methyl-2H-indazole-5-carboxamide E55 N-(2-methoxyethyl)-4-methyl-2-[(1-{4-[(trifluoromethyl)sulphanyl]benzoyl}piperidin-4-yl)methyl]-2H-indazole-5-carboxamide E59 2-{[1-(4-chlorobenzoyl)piperidin-4-yl]methyl}-N-[2-(cyclopropylmethoxy)ethyl]-4-methyl-2H-indazole-5-carboxamide E60 N-[2-(cyclopropylmethoxy)ethyl]-4-methyl-2-{[1-(4-methylbenzoyl)piperidin-4-yl]-methyl}-2H-indazole-5-carboxamide E61 N-[2-(cyclopropylmethoxy)ethyl]-2-({1-[4-(4-fluorophenoxy)benzoyl]piperidin-4-yl}-methyl)-4-methyl-2H-indazole-5-carboxamide E62 N-[2-(cyclopropylmethoxy)ethyl]-4-methyl-2-({1-[4-(trifluoromethyl)benzoyl]piperidin-4-yl}methyl)-2H-indazole-5-carboxamide E63 N-[2-(cyclopropylmethoxy)ethyl]-2-({1-[(4'-fluorobiphenyl-4-yl)carbonyl]piperidin-4-yl}methyl)-4-methyl-2H-indazole-5-carboxamide E64 2-{[1-(4-cyclopropylbenzoyl)piperidin-4-yl]methyl}-N-[2-(cyclopropylmethoxy)ethyl]-4-methyl-2H-indazole-5-carboxamide E65 2-{[1-(4-chlorobenzoyl)piperidin-4-yl]methyl}-4-methyl-N-[2-(2,2,2-trifluoroethoxy)-ethyl]-2H-indazole-5-carboxamide E66 4-methyl-2-{[1-(4-methylbenzoyl)piperidin-4-yl]methyl}-N-[2-(2,2,2-trifluoroethoxy)-ethyl]-2H-indazole-5-carboxamide E67 2-({1-[4-(4-fluorophenoxy)benzoyl]piperidin-4-yl}methyl)-4-methyl-N-[2-(2,2,2-trifluoroethoxyletyl]-2H-indazole-5-carboxamide E68 4-methyl-N-[2-(2,2,2-trifluoroethoxy)ethyl]-2-({1-[4-(trifluoromethyl)benzoyl]-piperidin-4-yl}methyl)-2H-indazole-5-carboxamide E69 2-({1-[(4'-fluorobiphenyl-4-yl)carbonyl]piperidin-4-yl}methyl)-4-methyl-N-[2-(2,2,2-trifluoroethoxy)ethyl]-2H-indazole-5-carboxamide E70 2-{[1-(4-cyclopropylbenzoyl)piperidin-4-yl]methyl}-4-methyl-N-[2-(2,2,2-trifluoro-ethoxy)ethyl]-2H-indazole-5-carboxamide E71 2-{[1-(4-chlorobenzoyl)piperidin-4-yl]methyl}-N-(2-isopropoxyethyl)-4-methyl-2H-indazole-5-carboxamide E72 N-(2-isopropoxyethyl)-4-methyl-2-{[1-(4-methylbenzoyl)piperidin-4-yl]methyl}-2H-indazole-5-carboxamide E73 2-({1-[4-(4-fluorophenoxy)benzoyl]piperidin-4-yl}methyl)-N-(2-isopropoxyethyl)-4-methyl-2H-indazole-5-carboxamide E74 N-(2-isopropoxyethyl)-4-methyl-2-({1-[4-(trifluoromethyl)benzoyl]piperidin-4-yl}-methyl)-2H-indazole-5-carboxamide E75 2-({1-[(4'-fluorobiphenyl-4-yl)carbonyl]piperidin-4-yl}methyl)-N-(2-isopropoxyethyl)-4-methyl-2H-indazole-5-carboxamide E76 2-{[1-(4-cyclopropylbenzoyl)piperidin-4-yl]methyl}-N-(2-isopropoxyethyl)-4-methyl-2H-indazole-5-carboxamide E77 2-{[1-(4-chlorobenzoyl)piperidin-4-yl]methyl}-4-methyl-N-[2-(trifluoromethoxy)ethyl]-2H-indazole-5-carboxamide E78 2-({1-[4-(4-fluorophenoxy)benzoyl]piperidin-4-yl}methyl)-4-methyl-N-[2-(trifluoro-methoxy)ethyl]-2H-indazole-5-carboxamide E79 2-({1-[(4'-fluorobiphenyl-4-yl)carbonyl]piperidin-4-yl}methyl)-4-methyl-N-[2-(trifluoromethoxy)ethyl]-2H-indazole-5-carboxamide E80 4-methyl-N-[2-(trifluoromethoxy)ethyl]-2-[(1-{4-[4-(trifluoromethyl)phenoxy]-benzoyl}piperidin-4-yl)methyl]-2H-indazole-5-carboxamide E81 N-(2-tert-butoxyethyl)-2-{[1-(4-chlorobenzoyl)piperidin-4-yl]methyl}-4-methyl-2H-indazole-5-carboxamide E82 N-(2-tert-butoxyethyl)-2-({1-[4-(4-fluorophenoxy)benzoyl]piperidin-4-yl}methyl)-4-methyl-2H-indazole-5-carboxamide E83 N-(2-tert-butoxyethyl)-2-({1-[(4'-fluorobiphenyl-4-yl)carbonyl]piperidin-4-yl}methyl)-4-methyl-2H-indazole-5-carboxamide E84 N-(2-tert-butoxyethyl)-4-methyl-2-[(1-{4-[4-(trifluoromethyl)phenoxy]benzoyl}-piperidin-4-yl)methyl]-2H-indazole-5-carboxamide E85 2-{[1-(4-chlorobenzoyl)piperidin-4-yl]methyl}-4-methyl-N-{2-[(2H3)methyloxy]-(2H4)ethyl}-2H-indazole-5-carboxamide E86 2-({1-[4-(4-fluorophenoxy)benzoyl]piperidin-4-yl}methyl)-4-methyl-N-{2-[(2H3)methyloxy](2H4)ethyl}-2H-indazole-5-carboxamide E87 2-{[1-(4-chlorobenzoyl)azetidin-3-yl]methyl}-N-(2-methoxyethyl)-4-methyl-2H-indazole-5-carboxamide E88 N-(2-methoxyethyl)-4-methyl-2-[(1-{4-[(trifluoromethyl)sulphanyl]benzoyl}azetidin-3-yl)methyl]-2H-indazole-5-carboxamide E89 N-(2-methoxyethyl)-4-methyl-2-({1-[4-(trifluoromethoxy)benzoyl]azetidin-3-yl}-methyl)-2H-indazole-5-carboxamide E90 2-({1-[2-fluoro-4-(trifluoromethyl)benzoyl]azetidin-3-yl}methyl)-N-(2-methoxyethyl)-4-methyl-2H-indazole-5-carboxamide E91 2-{[1-(4-chloro-2-fluorobenzoyl)azetidin-3-yl]methyl}-N-(2-methoxyethyl)-4-methyl-2H-indazole-5-carboxamide E92 2-({1-[3-fluoro-4-(trifluoromethyl)benzoyl]azetidin-3-yl}methyl)-N-(2-methoxyethyl)-4-methyl-2H-indazole-5-carboxamide E93 2-({1-[4-chloro-3-(trifluoromethyl)benzoyl]azetidin-3-yl}methyl)-N-(2-methoxyethyl)-4-methyl-2H-indazole-5-carboxamide E94 2-{[1-(4-cyclopropylbenzoyl)azetidin-3-yl]methyl}-N-(2-methoxyethyl)-4-methyl-2H-indazole-5-carboxamide E95 N-(2-methoxyethyl)-4-methyl-2-[(1-{4-[4-(trifluoromethyl)phenoxy]benzoyl}azetidin-3-yl)methyl]-2H-indazole-5-carboxamide E100 N-[2-(cyclopropyloxy)ethyl]-4-methyl-2-({1-[4-(trifluoromethoxy)benzoyl]azetidin-3-yl}methyl)-2H-indazole-5-carboxamide E101 N-[2-(cyclobutyloxy)ethyl]-4-methyl-2-({1-[4-(trifluoromethoxy)benzoyl]azetidin-3-yl}methyl)-2H-indazole-5-carboxamide E102 2-{[1-(4-chlorobenzoyl)azetidin-3-yl]methyl}-N-[2-(cyclopropylmethoxy)ethyl]-4-methyl-2H-indazole-5-carboxamide E103 N-[2-(cyclopropylmethoxy)ethyl]-2-({1-[4-(4-fluorophenoxy)benzoyl]azetidin-3-yl}-methyl)-4-methyl-2H-indazole-5-carboxamide E104 N-[2-(cyclopropylmethoxy)ethyl]-4-methyl-2-{[1-(4-methylbenzoyl)azetidin-3-yl]-methyl}-2H-indazole-5-carboxamide E105 2-{[1-(4-chlorobenzoyl)azetidin-3-yl]methyl}-4-methyl-N-[2-(trifluoromethoxy)ethyl]-2H-indazole-5-carboxamide E107 N-[2-(cyclopropylmethoxy)ethyl]-2-({1-[(4'-fluorobiphenyl-4-yl)carbonyl]azetidin-3-yl}methyl)-4-methyl-2H-indazole-5-carboxamide E108 2-({1-[(4'-fluorobiphenyl-4-yl)carbonyl]azetidin-3-yl}methyl)-N-(2-methoxyethyl)-4-methyl-2H-indazole-5-carboxamide E109 2-({1-[4-(4-fluorophenoxy)benzoyl]azetidin-3-yl}methyl)-N-(2-methoxyethyl)-4-methyl-2H-indazole-5-carboxamide E112 2-{[1-(4-chlorobenzoyl)azetidin-3-yl]methyl}-4-methyl-N-[2-(2,2,2-trifluoroethoxy)-ethyl]-2H-indazole-5-carboxamide E113 4-methyl-N-[2-(2,2,2-trifluoroethoxy)ethyl]-2-[(1-{4-[4-(trifluoromethyl)phenoxy]-benzoyl}azetidin-3-yl)methyl]-2H-indazole-5-carboxamide E114 4-methyl-N-(2,2,2-trifluoroethyl)-2-[(1-{4-[4-(trifluoromethyl)phenoxy]benzoyl}-azetidin-3-yl)methyl]-2H-indazole-5-carboxamide E115 2-({1-[4-(4-chlorophenoxy)benzoyl]azetidin-3-yl}methyl)-4-methyl-N-(2,2,2-trifluoro-ethyl)-2H-indazole-5-carboxamide E116 2-({1-[4-(4-chlorophenoxy)benzoyl]azetidin-3-yl}methyl)-N-(2-methoxyethyl)-4-methyl-2H-indazole-5-carboxamide E117 N-(2-methoxyethyl)-4-methyl-2-{[1-(4-{[5-(trifluoromethyl)pyridin-2-yl]oxy}benzoyl)-azetidin-3-yl]methyl}-2H-indazole-5-carboxamide E125 4-methyl-N-(2,2,2-trifluoroethyl)-2-[(1-{4-[(trifluoromethyl)sulphanyl]benzoyl}-piperidin-4-yl)methyl]-2H-indazole-5-carboxamide E126 4-methyl-N-(2,2,2-trifluoroethyl)-2-[(1-{4-[4-(trifluoromethyl)phenoxy]benzoyl}-piperidin-4-yl)methyl]-2H-indazole-5-carboxamide E127 4-methyl-N-(2,2,2-trifluoroethyl)-2-{[1-(4-{[5-(trifluoromethyl)pyridin-2-yl]oxy}-benzoyl)piperidin-4-yl]methyl}-2H-indazole-5-carboxamide E128 4-methyl-N-(2,2,2-trifluoroethyl)-2-{[1-(4-{[6-(trifluoromethyl)pyridin-3-yl]oxy}-benzoyl)piperidin-4-yl]methyl}-2H-indazole-5-carboxamide E131 2-({1-[4-(3-fluorophenoxy)benzoyl]piperidin-4-yl}methyl)-4-methyl-N-(2,2,2-trifluoro-ethyl)-2H-indazole-5-carboxamide E132 4-methyl-N-(2,2,2-trifluoroethyl)-2-[(1-{4-[3-(trifluoromethyl)phenoxy]benzoyl}-piperidin-4-yl)methyl]-2H-indazole-5-carboxamide E137 2-({1-[4-(3,4-difluorophenoxy)benzoyl]piperidin-4-yl}methyl)-4-methyl-N-(2,2,2-trifluoroethyl)-2H-indazole-5-carboxamide E138 4-methyl-N-(2,2,2-trifluoroethyl)-2-[(1-{[4'-(trifluoromethyl)biphenyl-4-yl]carbonyl}-piperidin-4-yl)methyl]-2H-indazole-5-carboxamide E141 2-({1-[(4'-methoxy-2'-methylbiphenyl-4-yl)carbonyl]piperidin-4-yl}methyl)-4-methyl-N-(2,2,2-trifluoro-ethyl)-2H-indazole-5-carboxamide E143 2-({1-[(4'-fluoro-2'-methoxybiphenyl-4-yl)carbonyl]piperidin-4-yl}methyl)-4-methyl-N-(2,2,2-trifluoro-ethyl)-2H-indazole-5-carboxamide E153 2-({1-[4-(4-cyanophenoxy)benzoyl]piperidin-4-yl}methyl)-N-(2-methoxyethyl)-4-methyl-2H-indazole-5-carboxamide E154 2-{[1-(4-bromo-3-methylbenzoyl)piperidin-4-yl]methyl}-N-(2-methoxyethyl)-4-methyl-2H-indazole-5-carboxamide E155 2-{[1-(4-tert-butylbenzoyl)piperidin-4-yl]methyl}-N-(2-methoxyethyl)-4-methyl-2H-indazole-5-carboxamide E157 2-{[1-(4-cyclohexylbenzoyl)piperidin-4-yl]methyl}-N-(2-methoxyethyl)-4-methyl-2H-indazole-5-carboxamide E160 N-(2-methoxyethyl)-4-methyl-2-({1-[4-(pyridin-3-yloxy)benzoyl]piperidin-4-yl}methyl)-2H-indazole-5-carboxamide E161 N-(2-methoxyethyl)-4-methyl-2-{[1-(4-{[5-(trifluoromethyl)pyridin-2-yl]oxy}benzoyl)-piperidin-4-yl]methyl}-2H-indazole-5-carboxamide E162 N-(2-methoxyethyl)-4-methyl-2-({1-[4-(pyridin-2-yloxy)benzoyl]piperidin-4-yl}methyl)-2H-indazole-5-carboxamide E163 N-(2-methoxyethyl)-4-methyl-2-{[1-(4-{[4-(trifluoromethyl)pyrimidin-2-yl]oxy}-benzoyl)piperidin-4-yl]methyl}-2H-indazole-5-carboxamide E164 N-(2-methoxyethyl)-4-methyl-2-{[1-(4-{[6-(trifluoromethyl)pyridin-3-yl]oxy}benzoyl)-piperidin-4-yl]methyl}-2H-indazole-5-carboxamide E165 N-(2-methoxyethyl)-4-methyl-2-{[1-(4-{[6-(trifluoromethyl)pyridin-2-yl]oxy}benzoyl)-piperidin-4-yl]methyl}-2H-indazole-5-carboxamide E166 2-({1-[(4'-methoxybiphenyl-4-yl)carbonyl]piperidin-4-yl}methyl)-N-(2-methoxyethyl)-4-methyl-2H-indazole-5-carboxamide E168 N-(2-methoxyethyl)-4-methyl-2-[(1-{4-[3-(trifluoromethyl)phenoxy]benzoyl}piperidin-4-yl)methyl]-2H-indazole-5-carboxamide E170 2-[(1-{4-[(5-chloropyridin-2-yl)oxy]benzoyl}piperidin-4-yl)methyl]-N-(2-methoxy-ethyl)-4-methyl-2H-indazole-5-carboxamide E171 2-({1-[4-(2,4-difluorophenoxy)benzoyl]piperidin-4-yl}methyl)-N-(2-methoxyethyl)-4-methyl-2H-indazole-5-carboxamide E172 2-({1-[4-(3,4-difluorophenoxy)benzoyl]piperidin-4-yl}methyl)-N-(2-methoxyethyl)-4-methyl-2H-indazole-5-carboxamide E173 N-(2-methoxyethyl)-4-methyl-2-[(1-{[4'-(trifluoromethyl)biphenyl-4-yl]carbonyl}-piperidin-4-yl)methyl]-2H-indazole-5-carboxamide E174 2-({1-[4-(3-fluorophenoxy)benzoyl]piperidin-4-yl}methyl)-N-(2-methoxyethyl)-4-methyl-2H-indazole-5-carboxamide E175 2-{[1-(2-fluoro-4-isopropoxybenzoyl)piperidin-4-yl]methyl}-N-(2-methoxyethyl)-4-methyl-2H-indazole-5-carboxamide E176 2-({1-[(3-fluoro-3',4'-dimethylbiphenyl-4-yl)carbonyl]piperidin-4-yl}methyl)-N-(2-methoxyethyl)-4-methyl-2H-indazole-5-carboxamide E177 2-({1-[(2',3-difluoro-4'-methoxybiphenyl-4-yl)carbonyl]piperidin-4-yl}methyl)-N-(2-methoxyethyl)-4-methyl-2H-indazole-5-carboxamide E178 2-({1-[4-(difluoromethoxy)benzoyl]piperidin-4-yl}methyl)-N-(2-methoxyethyl)-4-methyl-2H-indazole-5-carboxamide E179 2-({1-[4-(2-fluorophenoxy)benzoyl]piperidin-4-yl}methyl)-N-(2-methoxyethyl)-4-methyl-2H-indazole-5-carboxamide E180 2-({1-[(4'-cyano-2'-methylbiphenyl-4-yl)carbonyl]piperidin-4-yl}methyl)-N-(2-methoxyethyl)-4-methyl-2H-indazole-5-carboxamide E181 2-({1-[4-(5-chloropyridin-2-yl)benzoyl]piperidin-4-yl}methyl)-N-(2-methoxyethyl)-4-methyl-2H-indazole-5-carboxamide E182 N-(2-methoxyethyl)-4-methyl-2-[(1-{4-[6-(trifluoromethyl)pyridin-2-yl]benzoyl}-piperidin-4-yl)methyl]-2H-indazole-5-carboxamide E183 N-(2-methoxyethyl)-2-({1-[(4'-methoxy-2'-methylbiphenyl-4-yl)carbonyl]piperidin-4-yl}methyl)-4-methyl-2H-indazole-5-carboxamide E184 2-({1-[(4'-chloro-2'-methylbiphenyl-4-yl)carbonyl]piperidin-4-yl}methyl)-N-(2-methoxyethyl)-4-methyl-2H-indazole-5-carboxamide E185 2-[(1-{[4'-(2-cyanopropan-2-yl)biphenyl-4-yl]carbonyl}piperidin-4-yl)methyl]-N-(2-methoxyethyl)-4-methyl-2H-indazole-5-carboxamide E186 N-(2-methoxyethyl)-2-({1-[4-(5-methoxypyridin-2-yl)benzoyl]piperidin-4-yl}methyl)-4-methyl-2H-indazole-5-carboxamide E187 N-(2-methoxyethyl)-4-methyl-2-[(1-{4-[6-(trifluoromethyl)pyridin-3-yl]benzoyl}-piperidin-4-yl)methyl]-2H-indazole-5-carboxamide E188 N-(2-methoxyethyl)-2-({1-[4-(6-methoxypyridin-3-yl)benzoyl]piperidin-4-yl}methyl)-4-methyl-2H-indazole-5-carboxamide E189 2-({1-[(4'-fluoro-2'-methylbiphenyl-4-yl)carbonyl]piperidin-4-yl}methyl)-N-(2-methoxyethyl)-4-methyl-2H-indazole-5-carboxamide E190 N-(2-methoxyethyl)-4-methyl-2-({1-[4-(6-methylpyridin-3-yl)benzoyl]piperidin-4-yl}methyl)-2H-indazole-5-carboxamide E191 N-(2-methoxyethyl)-2-({1-[4-(6-methoxypyridin-2-yl)benzoyl]piperidin-4-yl}methyl)-4-methyl-2H-indazole-5-carboxamide E193 2-({1-[(4'-fluoro-2'-methoxybiphenyl-4-yl)carbonyl]piperidin-4-yl}methyl)-N-(2-methoxyethyl)-4-methyl-2H-indazole-5-carboxamide E194 2-({1-[(4'-chloro-2'-methoxybiphenyl-4-yl)carbonyl]piperidin-4-yl}methyl)-N-(2-methoxyethyl)-4-methyl-2H-indazole-5-carboxamide E195 N-(2-methoxyethyl)-4-methyl-2-[(1-{4-[2-(trifluoromethyl)pyrimidin-5-yl]benzoyl}-piperidin-4-yl)methyl]-2H-indazole-5-carboxamide E196 2-({1-[(4'-chloro-2'-fluorobiphenyl-4-yl)carbonyl]piperidin-4-yl}methyl)-N-(2-methoxy-ethyl)-4-methyl-2H-indazole-5-carboxamide E197 2-({1-[(2'-chloro-4'-fluorobiphenyl-4-yl)carbonyl]piperidin-4-yl}methyl)-N-(2-methoxy-ethyl)-4-methyl-2H-indazole-5-carboxamide E198 2-({1-[4-(5-chloropyridin-3-yl)benzoyl]piperidin-4-yl}methyl)-N-(2-methoxyethyl)-4-methyl-2H-indazole-5-carboxamide E199 2-({1-[4-(5-fluoropyridin-3-yl)benzoyl]piperidin-4-yl}methyl)-N-(2-methoxyethyl)-4-methyl-2H-indazole-5-carboxamide E200 N-(2-methoxyethyl)-4-methyl-2-[(1-{4-[5-(trifluoromethyl)pyridin-3-yl]benzoyl}-piperidin-4-yl)methyl]-2H-indazole-5-carboxamide E201 2-[(1-{[4'-(2-hydroxypropan-2-yl)biphenyl-4-yl]carbonyl}piperidin-4-yl)methyl]-N-(2-methoxyethyl)-4-methyl-2H-indazole-5-carboxamide E202 2-({1-[(3',5'-difluorobiphenyl-4-yl)carbonyl]piperidin-4-yl}methyl)-N-(2-methoxy-ethyl)-4-methyl-2H-indazole-5-carboxamide E203 2-({1-[(4'-fluoro-2-methylbiphenyl-4-yl)carbonyl]piperidin-4-yl}methyl)-N-(2-methoxyethyl)-4-methyl-2H-indazole-5-carboxamide E204 2-({1-[(3',5'-difluoro-2-methylbiphenyl-4-yl)carbonyl]piperidin-4-yl}methyl)-N-(2-methoxyethyl)-4-methyl-2H-indazole-5-carboxamide E205 N-(2-methoxyethyl)-4-methyl-2-({1-[3-methyl-4-(3-pyridyl)benzoyl]piperidin-4-yl}-methyl)-2H-indazole-5-carboxamide E206 N-(2-methoxyethyl)-4-methyl-2-({1-[3-methyl-4-(4-pyridyl)benzoyl]piperidin-4-yl}-methyl)-2H-indazole-5-carboxamide E207 N-(2-methoxyethyl)-4-methyl-2-({1-[(2-methylbiphenyl-4-yl)carbonyl]piperidin-4-yl}-methyl)-2H-indazole-5-carboxamide Particular preference is furthermore given to the following compounds:

E16 N-(2-methoxyethyl)-4-methyl-2-[(1-{4-[4-(trifluoromethyl)phenoxy]benzoyl}piperidin-4-yl)methyl]-2H-indazole-5-carboxamide E126 4-methyl-N-(2,2,2-trifluoroethyl)-2-[(1-{4-[4-(trifluoromethyl)phenoxy]benzoyl}piperidin-4-yl)methyl]-2H-indazole-5-carboxamide E161 N-(2-methoxyethyl)-4-methyl-2-{[1-(4-{[5-(trifluoromethyl)pyridin-2-yl]oxy}benzoyl)piperidin-4-yl]methyl}-2H-indazole-5-carboxamide Administration of the EP2 receptor antagonist according to general formula I or Ia can take place as a single dose or as two doses. The daily dose is 0.1-1000 mg, preferably 50-600 mg, where the dose may be administered as a single dose to be administered once or divided into 2 or more partial doses.

It may be necessary to deviate from the amounts mentioned of EP2 receptor antagonist of the general formula I or Ia, depending on body weight, administration route, individual response to the active compound, type of preparation and time or interval at which administration takes place. Thus, in some cases it may be sufficient to use less than the minimum amount mentioned above, whereas in other cases the upper limit mentioned must be exceeded.

COX Inhibitors which, According to the Invention, are Contained in the Pharmaceutical Composition In principle, COX inhibitors suitable for use according to the invention are all COX inhibitors available for other indications. This means both selective and non-selective COX inhibitors. According to the invention, those suitable include:

C1 indomethacin;
C2 diclofenac;
C4 naproxen;
C5 ibuprofen;
C6 meloxicam;
C7 piroxicam;
C8 nimesulide;
C9 ketoprofen;
C10 tenoxicam;
C11 mefanemic acid;
C12 ketoralac;
C13 celecoxib (4-[5-(4-methylphenyl)-3-(trifluoromethyl)-1H-pyrazol-1-yl]benzenesulphonamide);
C14 parecoxib (N-[4-(5-methyl-3-phenyl-4-isoxazolyl)phenyl]sulphonylpropionamide);
C15 rofecoxib (4-(4-mesylphenyl)-3-phenylfuran-2(5H)-one);
C16 valdecoxib (4-[5-methyl-3-phenyl-4-isoxazoyl)benzenesulphonamide);
C17 etoricoxib.

Particular preference is given to:
C1 indomethacin;
C2 diclofenac;
C4 naproxen;
C5 ibuprofen;
C6 meloxicam;
C7 piroxicam;
C8 nimesulide.

Very particular preference is given to:
C1 indomethacin;
C2 diclofenac;
C6 meloxicam;
C7 piroxicam.

In the case of the COX inhibitors, too, administration of the COX inhibitors may be by administration of single doses or by administration of two doses. In the case of the COX inhibitors, too, different dosages are used, depending on the COX inhibitor employed. The amount of COX inhibitor present in the pharmaceutical composition varies, depending on the chosen inhibitor. Dose ranges for the COX inhibitors used according to the invention result from the therapeutic doses per day for the COX inhibitor in question. These therapeutic doses refer to relatively long-term treatments and continuous therapies, so that for the present indication of on-demand contraception, it is also possible to use four times the recommended therapeutic dose. The lower limit is considered to be a quarter of the recommended therapeutic dose. In the case of the COX inhibitors, too, the dose can be administered as a single dose to be administered once or divided into 2 or more partial doses.

According to the invention, the following dose ranges are suitable for on-demand use:
C1 indomethacin: 19-800 mg/day (daily therapeutic dose: 75-200 mg/day*)
C2 diclofenac: 37.5-800 mg/day (daily therapeutic dose: 150-200 mg/day*)
C4 naproxen: 125-4000 mg/day (daily therapeutic dose: 500-1000 mg/day*)
C5 ibuprofen: 200-4800 mg/day (daily therapeutic dose: 800-1200 mg/day*)
C6 meloxicam: 2-60 mg/day (daily therapeutic dose: 7.5-15 mg/day)
C7 piroxicam: 5-80 mg/day (daily therapeutic dose: 20 mg/day*)
C8 nimesulide: 25-800 mg/day (daily therapeutic dose: 100-200 mg/day*)
C9 ketoprofen: 25-1200 mg/day (daily therapeutic dose: 100-300 mg/day*)
C10 tenoxicam: 10-160 mg/day (daily therapeutic dose: 40 mg/day*)
C11 mefanemic acid: 125-2000 mg/day (daily therapeutic dose: 500 mg/day*)
C12 ketoralac: 2.5-160 mg/day (daily therapeutic dose: 10-40 mg/day*)
C13 celecoxib: 25-800 mg/day (daily therapeutic dose: 100-200 mg/day*)
C14 parecoxib: 12.5-200 mg/day (daily therapeutic dose: 50 mg/day*)
C15 rofecoxib: 6-200 mg/day (daily therapeutic dose: 25-50 mg/day*)
C16 valdecoxib: 10-160 mg/day (daily therapeutic dose: 40 mg/day)
C17 etoricoxib: 15-360 mg/day (daily therapeutic dose: 60-90 mg/day)
*Huntjens et al. Rheumatology; (2005); 44:846-859

In the case of the COX inhibitors, too, it may, if required, be necessary to deviate from the above-mentioned amounts of COX inhibitors, namely depending on body weight, administration route, individual response to the reactive compound, type of preparation and time or interval at which the administration takes place. Thus, in some cases it may be sufficient to use less than the minimum amount mentioned above, whereas in other cases the upper limit mentioned must be exceeded.

The details given for the COX inhibitors refer to their combination with EP2 receptor antagonists according to the general formula I or Ia.

Combinations which are preferred in accordance with the invention comprise an EP2 receptor antagonist according to general formula Ia from the list
E16 N-(2-methoxyethyl)-4-methyl-2-[(1-{4-[4-(trifluoromethyl)phenoxy]benzoyl}piperidin-4-yl)methyl]-2H-indazole-5-carboxamide
E126 4-methyl-N-(2,2,2-trifluoroethyl)-2-[(1-{4-[4-(trifluoromethyl)phenoxy]benzoyl}piperidin-4-yl)methyl]-2H-indazole-5-carboxamide
E161 N-(2-methoxyethyl)-4-methyl-2-{[1-(4-{[5-(trifluoromethyl)pyridin-2-yl]oxy}benzoyl)piperidin-4-yl]methyl}-2H-indazole-5-carboxamide
and a COX inhibitor from the list
C1 indomethacin;
C2 diclofenac;
C4 naproxen;
C5 ibuprofen;
C6 meloxicam;
C7 piroxicam;
C8 nimesulide;
or COX inhibitors which are preferably used in accordance with the invention, from the following list:
C1 indomethacin;
C2 diclofenac;
C6 meloxicam;
C7 piroxicam.

Use of the Pharmaceutical Composition for on-Demand Contraception and Fertility Control The invention furthermore provides the use of the pharmaceutical composition comprising at least one EP2 receptor antagonist of formula Ia and at least one COX inhibitor for on-demand contraception and for fertility control.

On-demand contraception, fertility control on demand, precoital contraception or contraception on demand all refer to the on-demand use of one or more substances for preventing unwanted pregnancy. The administration can be before or shortly after expected sexual intercourse. Here, on-demand does not mean optional. Rather, the substance/substances has/have to be administered to prevent unwanted pregnancy.

Contraception, birth control or fertility control all refer likewise to the continuous regular intake of one or more substances at low dosage according to a fixed protocol over a relatively long period of time extending over a plurality of cycles. Intake of the pharmacological contraceptive is independent of the frequency and time of sexual intercourse.

Administration Route

The pharmaceutical compositions according to the invention and their use can be systematic and/or local. To this end, they can be administered in a suitable manner, for example orally, pulmonarily, nasally, dermally or transdermally. Further administration routes are vaginal or intrauterine. Suitable for vaginal administration are tampons, gels, suppositories, pessaries or intravaginal rings. Suitable for intrauterine administration are, inter alia, intrauterine systems or intrauterine pessaries.

Suitable for oral administration are administration forms described in the prior art as being suitable and comprising the EP2 receptor antagonists according to general formula I or Ia according to the invention and COX inhibitors in crystalline and/or amorphized and/or dissolved form, such as tablets (uncoated tablets or coated tablets, for example with enteric coatings or coatings which dissolve in a delayed manner or insoluble coatings controlling the release of the compound according to the invention), tablets which rapidly disintegrate in the oral cavity or films/wafers, films/lyophilizates, capsules (for example hard or soft gelatine capsules), sugar-coated tablets, wafers, granules, pellets, powders, emulsions, suspensions, aerosols or solutions.

Use is also possible in liquid form, such as for example as syrup, to which a sweetener is optionally added. Likewise, for the oral use of such compounds, the clathrates thereof are also suitable, for example the clathrates with alpha, beta or gamma cyclodextrin or else beta-hydroxypropyl cyclodextrin may be mentioned.

Suitable for the other administration routes are, for example, inhalative medicinal forms (inter alia powder inhalers, nebulizers), nasal drops, solutions, sprays; tablets, films/wafers or capsules to be administered lingually, sublingually or buccally, suppositories, aqueous suspensions (lotions, shake mixtures), lipophilic suspensions, ointments, creams, transdermal systems (for example patches), milk, pastes, foams or powders for sprinkling.

The pharmaceutical compositions according to the invention can be converted into the stated administration forms.

This can take place in a manner known per se by mixing with inert non-toxic pharmaceutically suitable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecylsulphate, polyoxysorbitane oleate), binders (for example polyvinylpyrrolidone), synthetic and natural polymers (for example albumin), stabilizers (for example antioxidants such as, for example, ascorbic acid), colorants (for example inorganic pigments such as iron oxides) and taste and/or odour corrigents.

They optionally contain additives, which are for example intended to function as fillers, binders, disintegrants, lubricants, solvents, solution mediators, masking flavours, colorant, or emulsifiers. Types of additive in the sense of the invention are for example saccharides (mono-, di-, tri-, oligo-, and/or polysaccharides), fats, waxes, oils, hydrocarbons, anionic, nonionic, cationic, natural, synthetic or semisynthetic surfactants. In addition, they optionally contain additives such as preservatives, stabilizers, wetting agents or emulsifiers; salts for alteration of the osmotic pressure or buffers.

The present invention furthermore provides medicaments or pharmaceutical compositions comprising at least one EP2 receptor antagonist according to general formula I or Ia according to the invention and at least one COX inhibitor, usually together with one or more inert non-toxic pharmaceutically suitable auxiliaries, and their use for on-demand contraception and fertility control.

The pharmaceutical formulation may comprise at least one EP2 receptor antagonist of the general formula I or Ia and at least one COX inhibitor, either together in one administration form (for example a combination tablet) or in two separate administration forms (for example a tablet), where one administration form comprises at least one EP2 receptor antagonist and the other administration form comprises at least one COX inhibitor.

The person skilled in the art is familiar with how to prepare the pharmaceutical formulation. The preparation of a formulation as combination tablet is described in preparation example 1.

Administration Protocol

The invention furthermore provides an administration protocol for on-demand contraception where a pharmaceutical composition comprising at least one COX inhibitor from the list mentioned above and at least one EP2 receptor antagonist according to general formula I or Ia are administered in a single administration dose over a period of up to 24 hours, preferably 6-12 hours, prior to expected sexual intercourse or of up to 2 hours after sexual intercourse.

In an alternative embodiment, the single dose preparation may also be taken up to at most 24 hours after sexual intercourse.

Also provided is an administration protocol where two separate pharmaceutical compositions each comprising at least one COX inhibitor from the list mentioned above and at least one EP2 receptor antagonist of the general formula I or Ia are administered in succession, at an interval. The compositions of the two pharmaceutical compositions can be identical or different with respect to selection and dosage of the EP2 receptor antagonist of the general formula I or Ia and the COX inhibitor. Administration of the first pharmaceutical composition is within a period of up to 24 hours, preferably 6-12 hours, prior to expected sexual intercourse, and administration of the second pharmaceutical composition is within a period of up to 48 hours after the expected sexual intercourse.

In the cases where the two pharmaceutical compositions are different, the dose of one of the active compounds or of both active compounds of the pharmaceutical composition taken prior to sexual intercourse may be lower than that for the pharmaceutical composition taken after sexual intercourse.

By an appropriate administration protocol, it is possible to achieve sufficiently high active compound plasma levels for a sufficiently long period of time to counteract unwanted pregnancy. Thus, in the female genital tract sperms are viable for about 5 days. If appropriate, administration after sexual intercourse may also take place as a plurality of doses to achieve active plasma concentrations over a period of up to 5 days.

Furthermore, by administering two pharmaceutical compositions it is possible to achieve an even better efficacy of the preparation. Also, in cases where the expected sexual intercourse has not taken place, the active compound load can be reduced by dispensing with the administration which should have taken place after the expected sexual intercourse.

The invention furthermore provides a kit for on-demand contraception, comprising at least two tablets each comprising at least one COX inhibitor and at least one EP2 receptor antagonist of the general formula I or Ia. A first tablet is taken during a period of up to 24 hours, preferably 6-12 hours, prior to the expected sexual intercourse, and at least one further tablet is taken during a period of up to 48 hours after the expected sexual intercourse.

According to the invention, the kit may comprise the two tablets up to 5 times to allow on-demand contraception of 5 expected sexual intercourses at intervals of at least 24 hours.

Process for the Production of the Compounds According to the Invention of the General Formula I and Ia:

The following description of the production process is already contained in patent application PCT/EP2012/073556, unpublished at the priority date of the present specification.

For this, for example a carboxylic acid of the formula VIII is reacted with an amine of the general formula XI by methods known to those skilled in the art to give the compounds according to the invention of the general formula I (Scheme 1).

The reaction takes place in that for example a carboxylic acid of the formula VIII is converted with isobutyl chloroformate in the presence of a tertiary amine, for example triethylamine, into a mixed anhydride, which reacts with an alkali metal salt of the appropriate amine XI in an inert solvent or solvent mixture, for example tetrahydrofuran, N,N-dimethylformamide or dimethoxyethane at temperatures between −30° C. and +60° C. to give the target compounds of the formula I.

It is also possible to activate a carboxylic acid VIII with reagents such as for example dicyclohexylcarbodiimide (DCC), 1-(3-dimethylaminopropyl)-3-ethylcarbodiimide (EDCI), N-hydroxybenzotriazole (HOBT) or N-[(dimethylamino)-(3H-[1,2,3]triazolo[4,5-b]pyridin-3-yloxy)methyliden]-N-methylmethanaminium hexafluorophosphate (HATU). For example the reaction with HATU takes place in an inert solvent, for example N,N-dimethylformamide or dimethyl sulphoxide in the presence of the appropriate amine XI and a tertiary amine, for example triethylamine or diisopropylamine, at temperatures between −30° C. and +60° C.

It is also possible, to convert a carboxylic acid of the formula VIII into the corresponding carboxylic acid chloride with an inorganic acid chloride, for example phosphorus pentachloride, phosphorus trichloride or thionyl chloride and then into the target compounds of the general formula I in pyridine or an inert solvent, such as for example N,N-dimethylformamide, in the presence of the appropriate amine XI and a tertiary amine, for example triethylamine, at temperatures between −30° C. and +60° C.

The compounds according to the invention of the general formula I can also be obtained from bromoindazoles of the general formula VI under palladium(O) catalysis by reaction with an appropriate amine XI and carbon monoxide (CO) or a carbon monoxide source, such as for example molybdenum hexacarbonyl in a suitable solvent or solvent mixture, for example 1,4-dioxan/water or tetrahydrofuran, addition of a base such as for example sodium carbonate or 1,8-diazabicyclo(5.4.0)undec-7-ene (DBU) and a catalyst-ligand mixture, for example palladium(II) acetate or trans bis(acetato)bis[o-(di-o-tolylphosphino)benzyl]-dipalladium (II)/tri-tert-butylphosphinotetrafluoroborate at temperatures between 80° C. and 160° C. (optionally with microwave irradiation between 80-200 watts), and in case of the use of carbon monoxide at a CO pressure of 5-15 bar (Scheme 1).

The compounds according to the invention of the general formula I can also be obtained from amines of the general formula XV by reaction with carboxylic acids (Y=OH), chlorides (Y=Cl) or anhydrides (e.g. Y=O—C(O)—O—$CH_2(CH)_3CH_3$) of the formula IX in the manner described for the production of the compounds I from the compounds VIII and XI (Scheme 2).

Likewise, the compounds of the general formula I can be obtained from compounds of the general formula XVI, wherein LG' for example means Br or I, by reaction with compounds of the formula XVIII (Scheme 2).

Compounds of the formula XVIII are for example (Het) Arylboronic acids ($R^3$-Met=(Het)Ar—$B(OH)_2$) or boronic acid pinacol esters ($R^3$-Met=(Het)Ar—BPin), which are converted to biaryl compounds of the formula I by methods known to those skilled in the art in a suitable solvent, for example N,N-dimethylformamide, tetrahydrofuran, dimethoxyethane and optionally water and addition of a base, for example triethylamine, potassium carbonate, caesium carbonate and a catalyst-ligand mixture, for example of palladium(II) acetate/triphenylphosphine, bis(diphenylphosphino)ferrocenedichloropalladium (II) (/1,1'-bis(diphenylphosphino)ferrocene/Cu(I)Cl) at temperatures between 20° C. and 120° C.

Compounds of the formula XVIII can also be (Het) Arylalcohols ($R^3$-Met=(Het)ArO—H), which are converted into biaryl ethers of the formula I by methods known to those skilled in the art in a suitable solvent, for example N,N-dimethylformamide or dimethyl sulphoxide with addition of a base, for example potassium carbonate, caesium carbonate under copper-(I) catalysis e.g. with copper(I) bromide at temperatures between 60° C. and 120° C.

The carboxylic acids of the general formula VIII can for example be obtained from esters of the formula VII by ester saponification in a suitable solvent or solvent mixture, for example methanol, ethanol or tetrahydrofuran, water with addition of an aqueous solution of an alkali metal hydroxide, for example sodium hydroxide or lithium hydroxide at temperatures between 20° C. and 60° C. (Scheme 1).

In the same manner, the carboxylic acids XIII can be obtained from the esters XII (Scheme 2, PG: e.g. Boc (tert-butyloxycarbonyl) and the carboxylic acids XXI from the esters XX (Scheme 3, LG': e.g. Br or I).

The esters of the general formula VII can be obtained from bromoindazoles of the general formula VI under palladium(O) catalysis by reaction with carbon monoxide or a carbon monoxide source, such as for example molybdenum hexacarbonyl, and methanol in a suitable solvent, for example dimethyl sulphoxide, N,N-dimethylformamide or tetrahydrofuran and addition of a base, for example triethylamine or 1,8-diazabicyclo(5.4.0)undec-7-ene and a catalyst-ligand mixture, for example of palladium(II) acetate/bis-1,3-diphenylphosphinopropane or trans bis(acetato)bis[o-(di-o-tolylphosphino)benzyl]dipalladium(II)/tri-tert-butylphosphinotetrafluoroborate at temperatures between 20° C. and 140° C. (optionally with microwave irradiation between 80-200 watts), and in case of the use of carbon monoxide at a CO pressure of 5-15 bar (Scheme 1).

This method is not restricted to methyl esters, i.e. to the use of methanol, but can also be extended to other esters. Thus for example by use of ethanol instead of methanol in this manner, the corresponding ethyl esters can be synthesized.

In the same manner, the esters XII can be obtained from the bromides IV (Scheme 2, -PG: e.g. -Boc).

The amides of the general formula VII can also be obtained from the amines of the general formula XIX by reaction with compounds of the general formula IX (Scheme 3), analogously to the synthesis of the compounds I from the compounds XV (Scheme 2).

The compounds of the general formula VII can also be obtained from compounds of the formula XX and reaction with compounds of the formula XVIII (Scheme 3), analogously to the described conversion of the compounds XVI to the compounds of the formula I (Scheme 2).

The amides of the general formula VI can be obtained from amines of the general formula V by reaction with carboxylic acids (Y=OH), chlorides (Y=Cl) or anhydrides (e.g. Y=0-C(O)—O—$CH_2(CH)_3CH_3$) of the formula IX (Scheme 1), as described for the conversion of amines XV to amides I (Scheme 2).

The amides of the general formula XVI can be obtained in analogous manner from amines XV and carboxylic acids or carboxylic acid derivatives XVII (Y: e.g. OH, Cl or O—C(O)—O—$CH_2(CH)_3CH_3$; LG': e.g. Br or I) (Scheme 2).

Analogously, amines XX (LG': e.g. Br or I) can be obtained from amines XIX and carboxylic acids or carboxylic acid derivatives XVII (Y: e.g. OH, Cl or O—C(O)—O—$CH_2(CH)_3CH_3$; LG': e.g. Br or I) (Scheme 3).

Likewise, carboxylic acids XIII (PG: e.g. Boc) can be converted with amines XI to amides XIV (Scheme 2) and carboxylic acids XXI (LG': e.g. Br, I) with amines XI to amides XVI (Scheme 3) in this manner.

The secondary amines V can be obtained from the corresponding carbamates IV (PG: e.g. Boc) by methods known to those skilled in the art (Scheme 1).

Thus for example tert-butyl carbamates can be converted into the amines V in an acidic medium with the use of e.g. trifluoroacetic acid or hydrochloric acid in a suitable solvent or solvent mixture such as for example dichloromethane, dioxan or acetone/water. In an anhydrous medium the amines V are formed as the corresponding salts.

Analogously, the amines XV can be obtained from the carbamates XIV (Scheme 2) and the amines XIX from the carbamates XII (Scheme 3).

The 2H-indazoles of the general formulae IV and VI can be produced in various ways.

For example, 2H-indazoles IV can be obtained from 1H-indazoles of the general formula II by alkylation with compounds of the general formula III (PG: e.g. Boc, LG: e.g. Br, I, O-Ts (tosyloxy) or O-Ms (mesyloxy)) in a suitable solvent, for example N,N-dimethylformamide, N,N-dimethylacetamide, dimethyl sulphoxide or else THF, 1,4-dioxan and addition of a base such as for example potassium carbonate or caesium carbonate (optionally with addition of tetrabutylammonium iodide) or else sodium bis(trimethylsilyl)amide, at temperatures between 25° C. and 100° C. or else in case of the use of sodium bis(trimethylsilyl)amide 0° C. and 25° C. (Scheme 1).

Analogously the 2H-indazoles of the general formula VI can be obtained from 1H-indazoles of the general formula II and compounds of the general formula X (LG: e.g. Br, I, O-Ts or O-Ms) (Scheme 1).

The 2H-indazoles of the general formula IV can also be obtained from ortho-nitrobenzaldehydes of the general formula XXVII by reaction with an appropriate amine XXVIII (PG: e.g. Boc) in a suitable solvent, for example 1,4-dioxan and addition of a reducing agent such as for example triethyl phosphite, possibly with addition of potassium carbonate or caesium carbonate or powdered molecular sieve, at temperatures between 100° C. and 160° C. (Scheme 4).

Analogously, the 2H-indazoles of the general formula VI can be obtained from ortho-nitrobenzaldehydes XXVII by reaction with amines XXIX (Scheme 4).

The compounds of the general formula XIV (PG: e.g. Boc) can also be obtained from bromoindazoles of the general formula IV (PG: e.g. Boc) under palladium(0) catalysis by reaction with an appropriate amine XI and carbon monoxide or a carbon monoxide source, such as for example molybdenum hexacarbonyl (Scheme 2), analogously to the described process for the conversion of the bromoindazoles VI to the compounds of the general formula I, (Scheme 1).

The ortho-nitrobenzaldehydes of the general formula XXVII can be produced from the ortho-nitrotoluenes of the general formula XXVI by methods known to those skilled in the art in two reaction steps (Scheme 4).

For this, an ortho-nitrotoluene XXVI is dissolved in a suitable solvent such as N,N-dimethylformamide and converted with N,N-dimethylformamide dimethyl acetal at temperatures of 100-140° C. to the corresponding enamine, which is immediately oxidized at temperatures of 0° C.-20° C. to the corresponding ortho-nitrobenzaldehyde with a suitable oxidizing agent such as for example NaIO$_4$ in a suitable aqueous solvent mixture such as water/N,N-dimethylformamide and optionally with addition of a base such as for example triethylamine, N,N-diisopropylethylamine, sodium hydrogen carbonate or sodium carbonate.

The ortho-nitrotoluenes of the general formula XXVI can be produced from the ortho-methylanilines of the general formula XXV by methods known to those skilled in the art (Scheme 4).

For this, an ortho-methylaniline XXV is dissolved in a suitable solvent such as dichloromethane or chloroform, treated with zirconium(IV) tert-butoxide, ground molecular sieve 3 Å and tert-butyl hydroperoxide and reacted at temperatures of 20-40° C.

The 1H-indazoles of the general formula II can be liberated from the acetamides of the general formula XXIV by methods known to those skilled in the art (Scheme 4).

For this, for example an acetamide XXIV is reacted in a suitable solvent such as methanol or ethanol and addition of 37% hydrochloric acid at temperatures of 40-80° C.

Analogously thereto, the anilines of the formula XXV can be liberated from the acetanilides of the formula XXIII (Scheme 4).

The acetamides of the general formula XXIV can be produced from the ortho-methyl-acetanilides of the general formula XXIII by methods known to those skilled in the art (Scheme 4).

For this, the ortho-methyl-acetanilides XXIII are dissolved in a suitable solvent such as chloroform or toluene, treated with acetic anhydride, isopentyl or tert-butyl nitrite, and optionally potassium acetate and 18-crown-6, and reacted at temperatures of 60-100° C.

The ortho-methyl-acetanilides XXIII can be produced from the acetanilides of the general formula XXII by bromination by methods known to those skilled in the art (Scheme 4).

For this, the acetanilides XXII, which can for example be obtained from the corresponding anilines by reaction with acetic anhydride in a suitable solvent (e.g. toluene) at temperatures of 80-110° C., is reacted with bromine in glacial acetic acid at temperatures of 10-25° C.

The compounds of the general formula III wherein LG means —OTs or —OMs can be produced by methods known to those skilled in the art from the corresponding alcohols.

For this, the alcohols are reacted with p-toluenesulphonyl chloride or methanesulphonyl chloride at temperatures between 0° C. and 40° C. in a suitable solvent, e.g. dichloromethane or tetrahydrofuran or toluene and addition of a suitable base, e.g. pyridine or triethylamine.

The compounds of the general formula X, wherein LG means —OTs or —OMs, can be produced from the corresponding amino alcohols XXX by methods known to those skilled in the art (Scheme 4).

For this, in a first step the amino alcohols XXX are converted to the corresponding amides XXXI in a suitable solvent, e.g. dichloromethane, with arylcarboxylic acid chlorides of the formula Cl—C(O)—Ar—R$^3$ and addition of a suitable base, e.g. triethylamine, at temperatures between 0° C. and 25° C. Optionally, corresponding esters formed as by-products can be separated or else saponified to the corresponding alcohols XXXI under standard conditions, e.g. with use of a base, e.g. potassium hydroxide, in a suitable solvent mixture, e.g. ethanol/water, at temperatures between 20° C. and 40° C.

The N-protected alcohols XXXI thus obtained can be converted into the compounds of the formula X with LG: —OTs or —OMs analogously to the process described for the synthesis of the compounds III. Compounds of the formula X with LG: —Br can be obtained from the corresponding alcohols XXXI by methods known to those skilled in the art by reaction with a brominating agent such as for example CBr$_4$ with addition of PPh$_3$ as an oxophile in a suitable solvent, e.g. chloroform, at temperatures between 20° C. and 40° C.

The compounds of the general formula XXIX, can be produced by methods known to those skilled in the art for example from the amines of the formula XXXII (Scheme 4).

For this, in a first step, the amines XXXII are converted to the corresponding amides XXXIII analogously to the synthesis of the compounds I from the compounds XV.

The tert-butyloxycarbonyl group in compounds of the formula XXXIII is cleaved analogously to the conversion of the compounds IV to the compounds V, hence the compounds of the formula XXIX can be obtained.

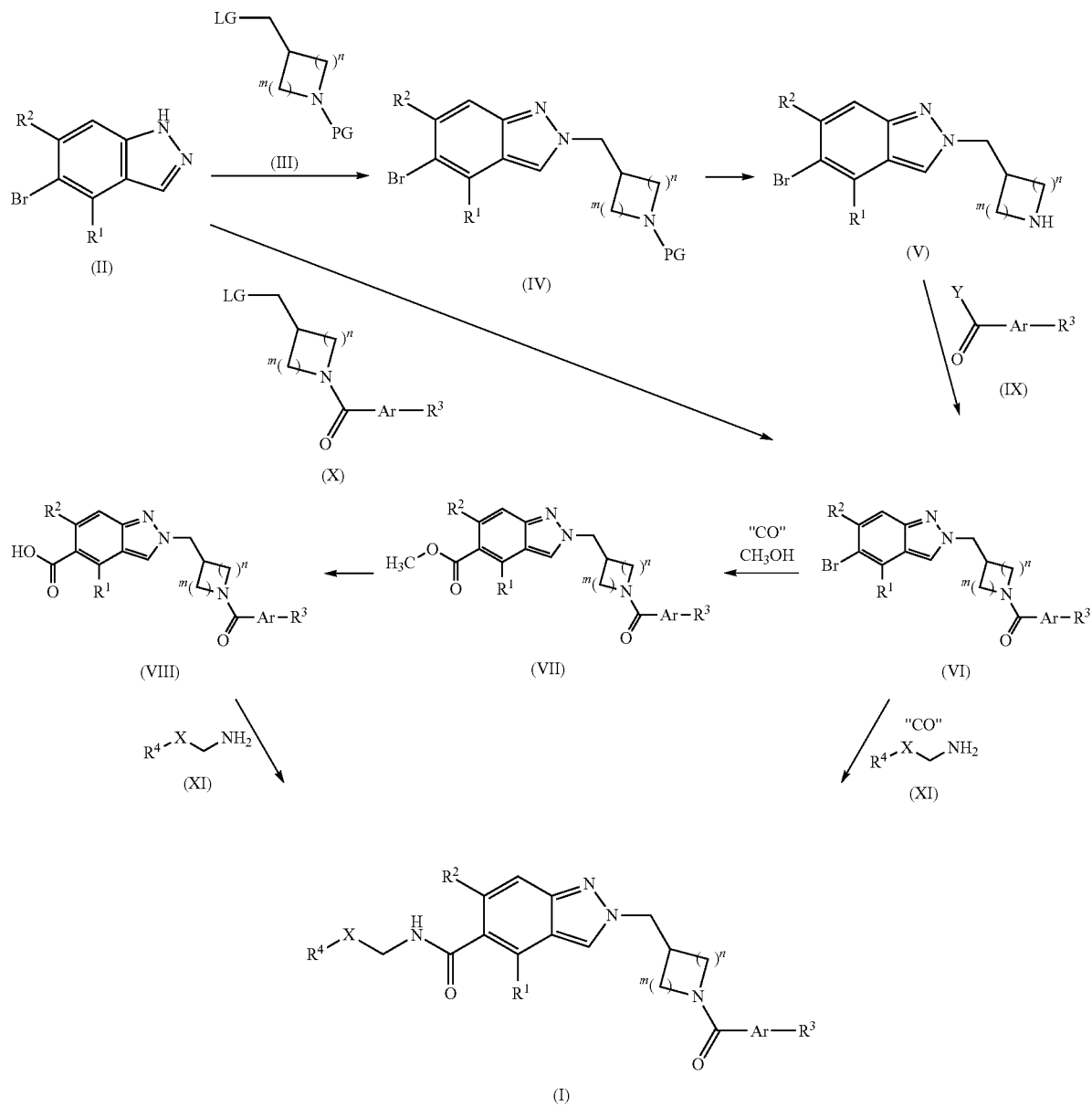
Scheme 1
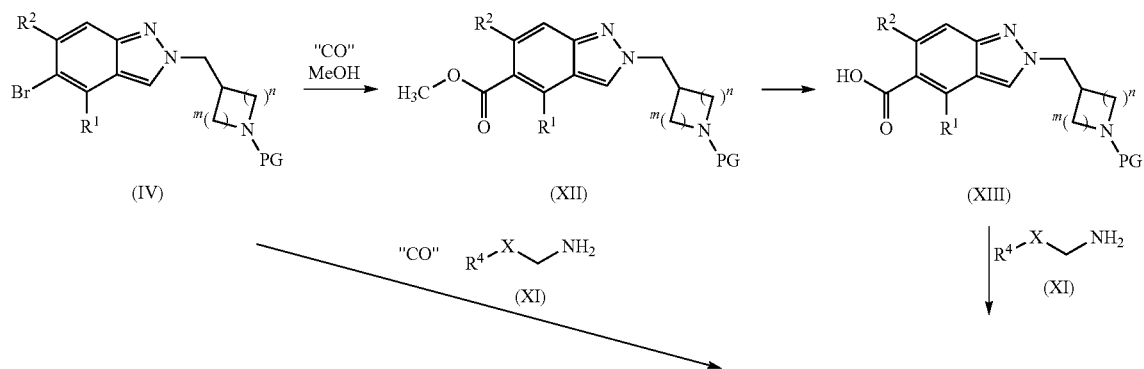
Scheme 2

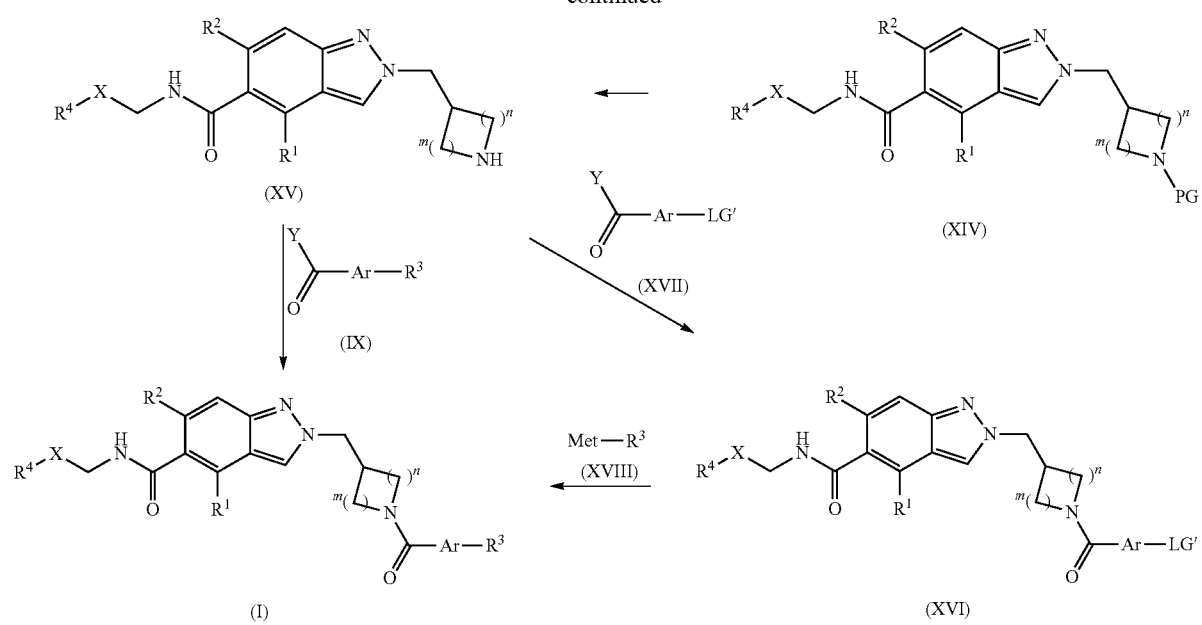
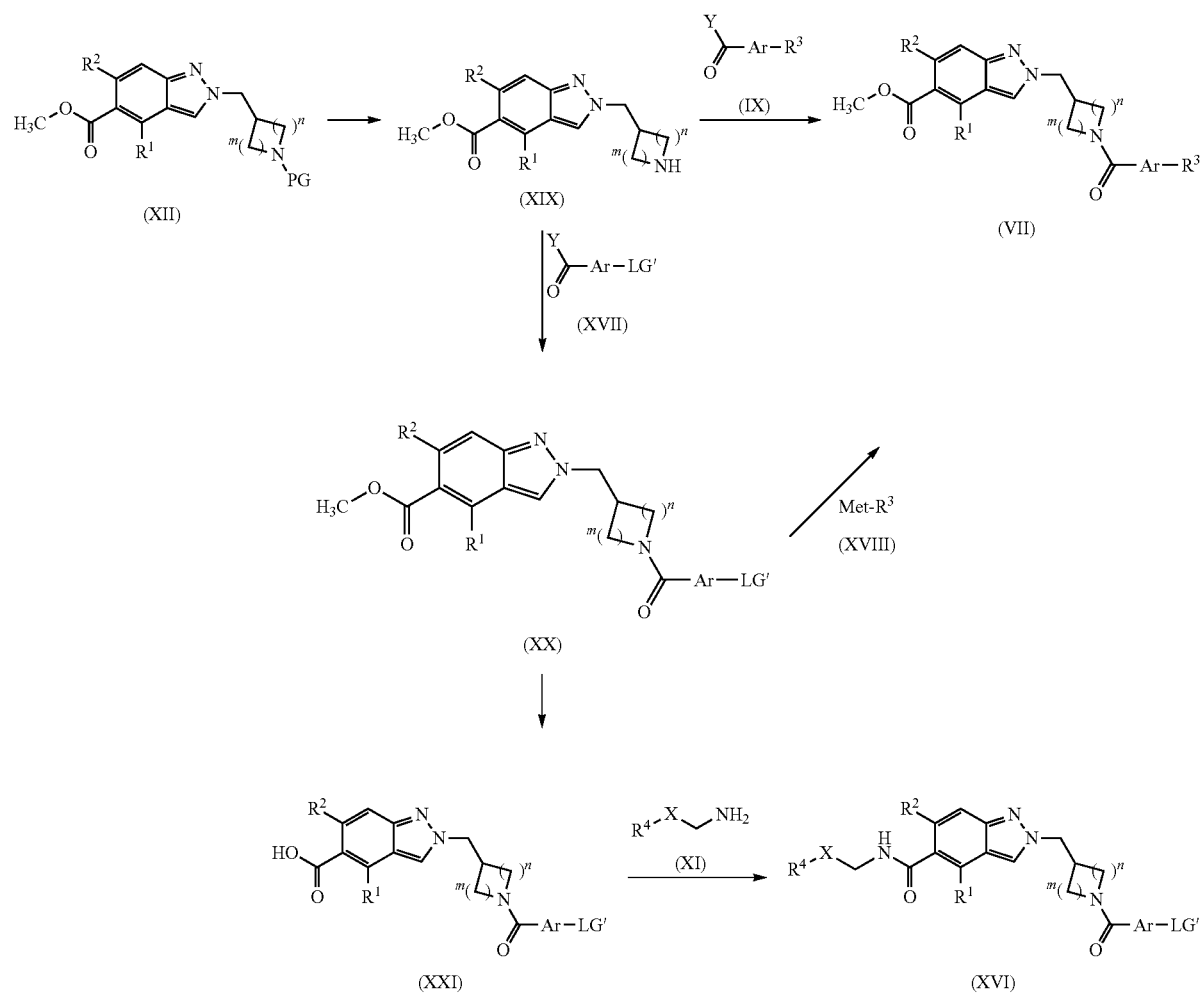
Scheme 3

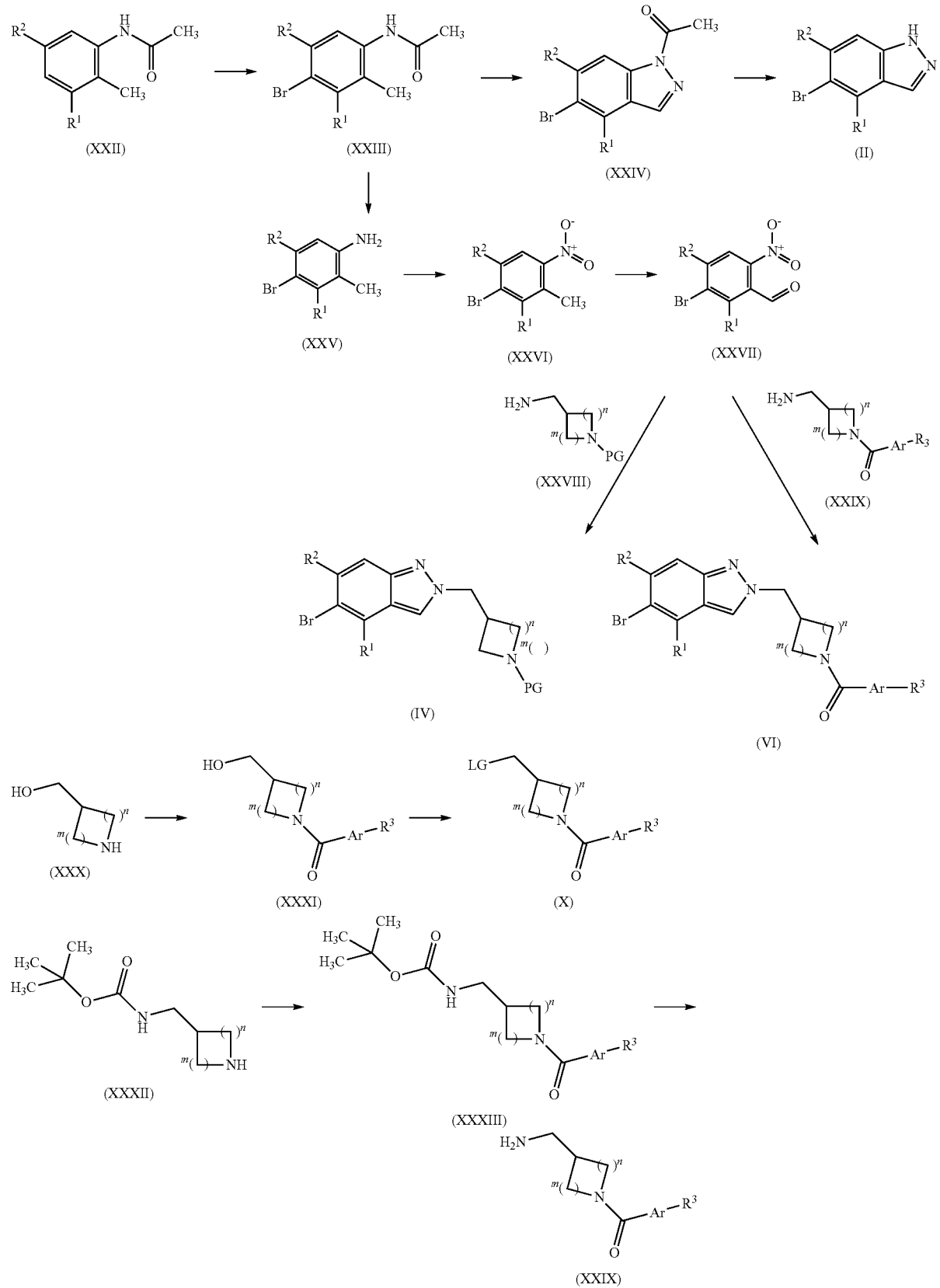
-continued
Scheme 4

Production of the Compounds According to the Invention:

The following description of the production of the compounds according to the invention is already contained in patent application PCT/EP2012/073556, unpublished at the priority date of the present specification.

The following examples illustrate the production of the compounds according to the invention of the general formula (I) and Ia, without limiting the range of the claimed compounds to these examples.

The compounds according to the invention of the general formula (I) can be produced and characterized as described below.

LC-MS: Waters Acquity HPLC/MS 100-800 Daltons; 20 V (Micromass/Waters ZQ 4000); Column: BEHC 18 (Waters), 2.1×50 mm, BEH 1.7 µm; Mobile phase: A: $H_2O$/ 0.05% HCOOH, B: $CH_3CN$/0.05% HCOOH. Gradient: 10-90% B in 1.7 min, 90% B for 0.2 min, 98-2% B in 0.6 min; Flow rate: 1.3 ml/min, Detection: UV=200-400 nm.

Chiral HPLC Separation Method A:

Preparative chiral HPLC: System: Dionex: Pump P 580, Gilson: Liquid Handler 215, Knauer: UV detector K-2501 Column: Chiralpak AD-H 5 µm 250×20 mm; Solvent: hexane/ethanol 50:50; Flow rate: 15 ml/min; injection volume: 0.5 ml; Detection: UV 254 nm.

Analytical chiral HPLC: System: Waters: Alliance 2695, DAD 996, ESA: Corona; Column: Chiralpak AD-H 5 µm 150×4.6 mm Solvent: hexane/ethanol 50:50; Flow rate: 1.0 ml/min; Temperature: 25° C.; injection: 5 µl; Detection: DAD 254 nm.

Chiral HPLC Separation Method B:

Preparative chiral HPLC: System: Dionex: Pump P 580, Gilson: Liquid Handler 215, Knauer: UV detector K-2501 Column: Chiralpak IC 5 µm 250×30 mm; Solvent: ethanol/methanol 50:50; Flow rate: 30 ml/min; injection volume: 0.5 ml; Detection: UV 254 nm.

Analytical chiral HPLC: System: Waters: Alliance 2695, DAD 996, ESA: Corona; Column: Chiralpak IC 5 µm 150×4.6 mm Solvent: ethanol/methanol 50:50; Flow rate: 1.0 ml/min; Temperature: 25° C.; injection: 5 µl; Detection: DAD 254 nm.

Chiral HPLC Separation Method C:

Preparative chiral HPLC: System: Dionex: Pump P 580, Gilson: Liquid Handler 215, Knauer: UV detector K-2501 Column: Chiralpak AD-H 5 µm 250×20 mm; Solvent: hexane/2-propanol 50:50; Flow rate: 15 ml/min; injection volume: 0.25 ml; Detection: UV 254 nm.

Analytical chiral HPLC: System: Waters: Alliance 2695, DAD 996, ESA: Corona; Column: Chiralpak AD-H 5 µm 150×4.6 mm Solvent: hexane/2-propanol 50:50; Flow rate: 1.0 ml/min; Temperature: 25° C.; injection: 5 µl; Detection: DAD 254 nm.

Chiral HPLC Separation Method D:

Preparative chiral HPLC: System: Dionex: Pump P 580, Gilson: Liquid Handler 215, Knauer: UV detector K-2501 Column: Chiralpak IB 5 µm 250×20 mm; Solvent: hexane/ethanol 70:30; Flow rate: 20 ml/min; injection volume: 0.1 ml; Detection: UV 210 nm.

Analytical chiral HPLC: System: Waters: Alliance 2695, DAD 996, ESA: Corona; Column: Chiralpak IB 5 µm 150×4.6 mm Solvent: hexane/ethanol 70:30; Flow rate: 1.0 ml/min; Temperature: 25° C.; injection: 5 µl; Detection: DAD 230 nm.

Chiral HPLC Separation Method E:

Preparative chiral HPLC: System: Dionex: Pump P 580, Gilson: Liquid Handler 215, Knauer: UV detector K-2501 Column: Chiralpak IC 5 µm 250×20 mm; Solvent: ethanol/methanol 50:50; Flow rate: 15 ml/min; injection volume: 0.3 ml; Detection: UV 230 nm.

Analytical chiral HPLC: System: Waters: Alliance 2695, DAD 996, ESA: Corona; Column: Chiralpak IC 5 µm 150×4.6 mm Solvent: ethanol/methanol 50:50; Flow rate: 1.0 ml/min; Temperature: 25° C.; injection: 5 µl; Detection: DAD 230 nm.

Abbreviations

Boc tert-butoxycarbonyl
CO carbon monoxide
DBU 1,8-diazabicyclo[5.4.0]undec-7-ene
DCM dichloromethane
DMF N,N-dimethylformamide
DMSO dimethyl sulphoxide
ESI; ES+ electrospray ionization (in MS); positive charged ion trace
hr(s) hour(s)
HATU   N-[(dimethylamino)-1H-1,2,3-triazolo[4,5-b]pyridin-1-ylmethylen]-N-methylmethanaminium hexafluorophosphate N-oxide
HPLC high pressure, high performance liquid chromatography
conc. concentrated
LC-MS liquid chromatography-coupled mass spectroscopy
M molar
min(s) minute(s)
MS mass spectroscopy
N normal
NMR nuclear resonance spectroscopy
$R_t$ retention time (in HPLC and LC)
RT room temperature
tert tertiary
THF tetrahydrofuran Example 1

2-{[1-(4-cyano-2-fluorobenzoyl)piperidin-4-yl]methyl}-N-(2-methoxyethyl)-4-methyl-2H-indazole-5-carboxamide

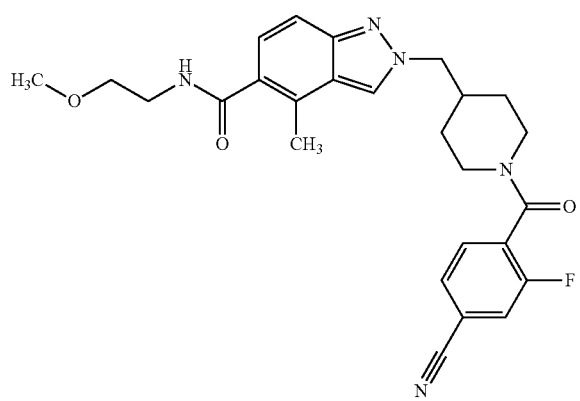 [SMILES: COCCNC(=O)c1ccc2nn(CC3CCN(C(=O)c4ccc(C#N)cc4F)CC3)cc2c1C]

To a solution of 33.7 mg of 4-cyano-2-fluorobenzoic acid in 1.0 ml dimethyl sulphoxide were added 85.5 mg of HATU, 75 mg of the amine prepared in Example 1a and 0.071 ml of N,N-diisopropylethylamine and this was stirred for 1 hour at 25° C. The mixture was concentrated in vacuo and the residue thus obtained purified by HPLC. Yield: 43.3 mg of the title compound.

¹H-NMR (400 MHz, DMSO-d₆): ☐ [ppm], 1.07-1.28 (2H), 1.30-1.44 (1H), 1.47-1.61 (1H), 2.18-2.34 (1H), 2.49 (3H), 2.71-2.83 (1H), 2.92-3.08 (1H), 3.32 (4H), 3.36 (2H), 3.42 (2H), 4.31 (2H), 4.39-4.51 (1H), 7.14 (1H), 7.38 (1H), 7.50-7.63 (1H), 7.71-7.79 (1H), 7.95 (1H), 8.09-8.15 (1H), 8.47 (1H).

The starting material for the above title compound was prepared as follows:

Example 1a

N-(2-methoxyethyl)-4-methyl-2-(4-piperidylmethyl)-2H-indazole-5-carboxamide hydrochloride

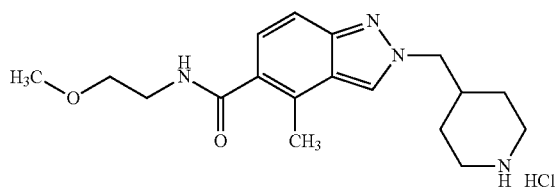 [SMILES: COCCNC(=O)c1ccc2nn(CC3CCNCC3)cc2c1C ; Cl]

To 855.1 mg of 1b were added 4.5 ml of 4M hydrochloric acid in dioxan and 1 ml dioxan. An oily mass was formed, which dissolved on vigorous stirring and gentle warming. The mixture was stirred for 1 hr at ca. 30° C. The reaction mixture was concentrated. Yield: 764.7 mg of the title compound, which was further reacted without further purification.

¹H-NMR (300 MHz, DMSO-d₆): δ [ppm]=1.33-1.50 (2H), 1.52-1.62 (2H), 2.17-2.31 (1H), 2.32-2.38 (1H), 2.49 (3H), 2.67-2.86 (2H), 3.13-3.28 (5H), 3.31-3.46 (4H), 4.33 (2H), 7.16 (1H), 7.38 (1H), 8.13 (1H), 8.53 (1H), 8.71-8.88 (1H), 8.99-9.11 (1H).

Example 1b

Tert-butyl 4-({5-[N-(2-methoxyethyl)carbamoyl]-4-methyl-2H-indazol-2-yl}-methyl)piperidin-1-carboxylate

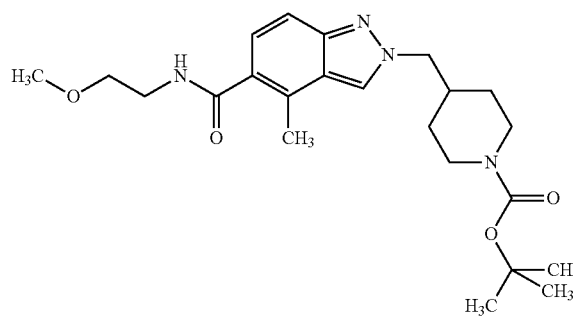 [SMILES: COCCNC(=O)c1ccc2nn(CC3CCN(C(=O)OC(C)(C)C)CC3)cc2c1C]

Version A: 2820 mg of 1c, 1556 mg of 2-methoxyethylamine, 1823 mg of molybdenum hexacarbonyl, 200.4 mg of tri-tert-butylphosphine tetrafluoroborate and 647.5 mg of trans-bis(acetato)-bis[o-(di-o-tolylphosphino)benzyl]dipalladium(II) were placed in portions in three microwave tubes and suspended with 56 ml THF. Then 3.1 ml of DBU were added and the mixtures stirred for 20 mins at 125° C. and 200 watts in the microwave. The reaction mixtures were combined, filtered and diluted with some ethyl acetate and the organic phase washed twice with water and once with saturated sodium chloride solution. This was dried over sodium sulphate, filtered and concentrated. The residue was chromatographed on the Biotage SP4. Gradient: ethyl acetate/methanol 0-10%. Yield: 885.1 mg of the title compound.

Version B: 780 mg of 1 d and 1747 mg of HATU were first dissolved in 10 ml DMSO. Next, 314 mg of 2-methoxyethylamine and 1080 mg of N,N-diisopropylethylamine were added. The mixture was stirred for 1 hr at RT. The reaction mixture was poured into water and extracted three times with ethyl acetate. The combined organic phases were washed with saturated sodium chloride solution, dried over sodium sulphate, filtered and concentrated. The residue was purified chromatographically on the Biotage SP4. Gradient: ethyl acetate/methanol 0-10%. Yield: 740 mg of the title compound.

¹H-NMR (400 MHz, DMSO-d₆): δ [ppm], 1.01-1.13 (2H), 1.34 (9H), 1.36-1.43 (2H), 2.06-2.19 (1H), 2.49 (3H), 2.59-2.70 (2H), 3.29 (3H), 3.33-3.39 (2H), 3.40-3.45 (2H), 3.82-3.93 (2H), 4.28 (2H), 7.14 (1H), 7.38 (1H), 8.09-8.14 (1H), 8.46 (1H).

Example 1c

Tert-butyl 4-[(5-bromo-4-methyl-2H-indazol-2-yl)methyl]piperidin-1-carboxylate

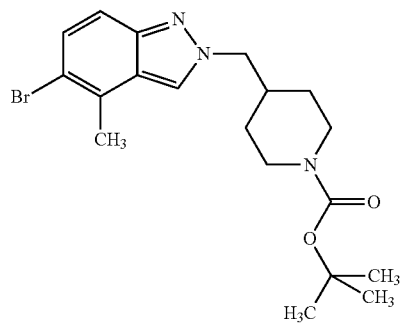 [SMILES: Cc1c(Br)ccc2nn(CC3CCN(C(=O)OC(C)(C)C)CC3)cc12]

5 g of 5-bromo-4-methyl-1H-indazole was dissolved in 110 ml DMF and treated with 11.5 g of caesium carbonate and 7.9 g of N-Boc-4-(bromomethyl)piperidine. The mixture was stirred for 3 hrs at 60° C. and overnight at RT. The reaction mixture was next diluted with ethyl acetate, and the organic phase was washed twice with water, dried over sodium sulphate, filtered and concentrated. The residue was purified chromatographically on the Biotage SP4 via a 65i-Si column. Gradient: hexane/ethyl acetate 0-100%. Yield: 3.53 g of the title compound.

¹H-NMR (300 MHz, DMSO-d₆): δ [ppm], 0.99-1.12 (2H), 1.34 (9H), 1.36-1.44 (2H), 2.04-2.19 (1H), 2.47 (3H), 2.54-2.72 (2H), 3.82-3.93 (2H), 4.27 (2H), 7.29 (1H), 7.34 (1H), 8.46 (1H).

Example 1d

2-{[1-(tert-butoxycarbonyl)piperidin-4-yl]methyl}-4-methyl-2H-indazol-5-carboxylic acid

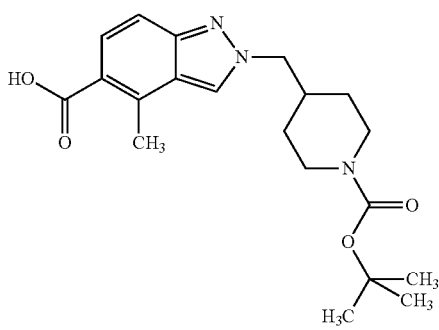 [SMILES: Cc1c(C(=O)O)ccc2nn(CC3CCN(C(=O)OC(C)(C)C)CC3)cc12]

1080 mg of 1e were dissolved in 8 ml methanol and treated with 1235 mg of lithium hydroxide in 10 ml water. A further 2 ml THF were added as solubilizer. The mixture was stirred for 24 hrs at RT. Next the methanol and THF were distilled off. The aqueous residue was diluted with water and washed once with ethyl acetate. The aqueous phase was acidified with 10% sulphuric acid and extracted twice with ethyl acetate. The combined organic phases were dried over sodium sulphate, filtered and concentrated. Yield: 880 mg of the title compound.

$^1$H-NMR (300 MHz, DMSO-d$_6$): δ [ppm]=0.99-1.18 (2H), 1.37-1.48 (2H), 1.34 (9H), 2.05-2.21 (1H), 2.53-2.70 (2H), 2.73 (3H), 3.81-3.94 (2H), 4.29 (2H), 7.39 (1H), 7.62 (1H), 8.62 (1H), 11.92-12.31 (1H).

Example 1e

Methyl 2-{[1-(tert-butoxycarbonyl)piperidin-4-yl]methyl)}-4-methyl-2H-indazol-5-carboxylate

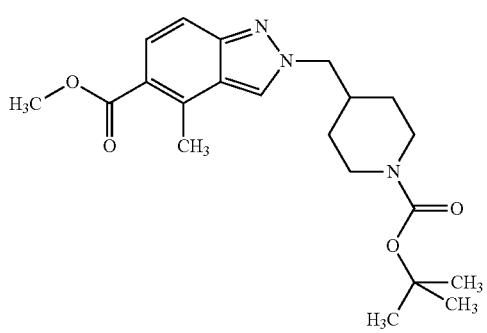 [SMILES: COC(=O)c1ccc2nn(CC3CCN(C(=O)OC(C)(C)C)CC3)cc2c1C]

666 mg of 1c, 156.8 mg of methanol, 645.8 mg of molybdenum hexacarbonyl, 47.3 mg of tri-tert-butylphosphine tetrafluoroborate and 123.5 mg of trans-bis(acetato)-bis[o-(di-o-tolyl-phosphino)benzyl]dipalladium(II) were placed in a microwave tube and suspended in 15 ml THF. Then 0.7 ml of DBU were added and the mixture was stirred for 20 mins at 125° C. and 150 watts in the microwave. Next, it was concentrated, taken up in ethyl acetate and the organic phase washed twice with water and once with saturated sodium chloride solution. It was dried over sodium sulphate, filtered and concentrated. The residue was chromatographed on the Biotage SP4. Gradient: hexane/ethyl acetate 0-100%. Yield: 363 mg of the title compound.

$^1$H-NMR (400 MHz, DMSO-d$_6$): δ [ppm], 1.01-1.12 (2H), 1.34 (9H), 1.37-1.45 (2H), 2.08-2.19 (1H), 2.53-2.69 (2H), 2.73 (3H), 3.79 (3H), 3.83-3.93 (2H), 4.30 (2H), 7.42 (1H), 7.62 (1H), 8.67 (1H).

Example 2

2-({1-[4-tert-(butoxy)benzoyl]piperidin-4-yl}methyl)-N-(2-methoxyethyl)-4-methyl-2H-indazole-5-carboxamide

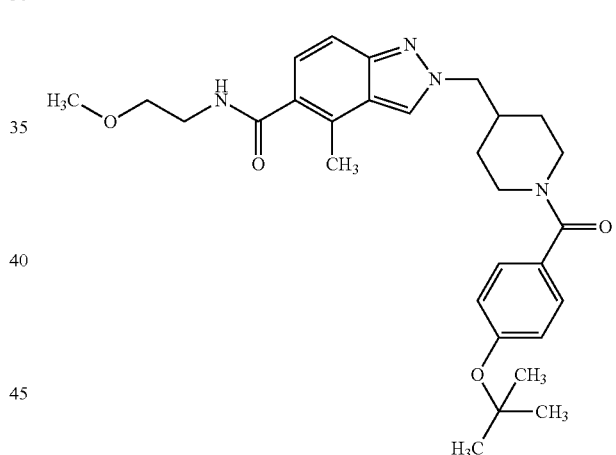

Analogously to Example 1, 35.9 mg of the title compound was obtained from 75 mg of the amine prepared in Example 1a and 39.7 mg of 4-(tert-butoxy)benzoic acid.

$^1$H-NMR (300 MHz, DMSO-d$_6$): δ [ppm], 1.09-1.26 (2H), 1.29 (9H), 1.35-1.58 (2H), 2.15-2.35 (1H), 2.49 (3H), 2.69-2.97 (2H), 3.24 (3H), 3.32-3.47 (4H), 4.23-4.40 (2H), 6.98 (2H), 7.14 (1H), 7.23 (2H), 7.38 (1H), 8.10 (1H), 8.47 (1H).

Example 3

2-({1-[4-(4-fluorophenoxy)benzoyl]piperidin-4-yl}methyl)-N-(2-methoxyethyl)-4-methyl-2H-indazole-5-carboxamide

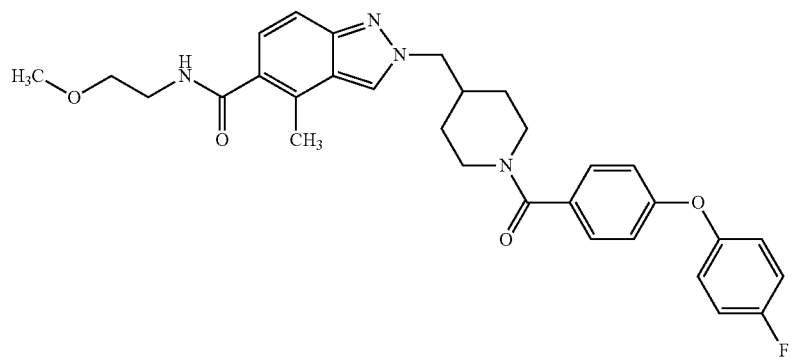 [SMILES: COCCNC(=O)c1ccc2nn(CC3CCN(C(=O)c4ccc(Oc5ccc(F)cc5)cc4)CC3)cc2c1C]

Analogously to Example 1, 51.6 mg of the title compound was obtained from 75 mg of the amine prepared in Example 1a and 47.5 mg of 4-(4-fluorophenoxy)benzoic acid.

$^1$H-NMR (300 MHz, DMSO-d$_6$): δ [ppm], 1.10-1.30 (2H), 1.32-1.58 (2H), 2.19-2.35 (1H), 2.49 (3H), 2.71-3.02 (2H), 3.25 (3H), 3.32-3.39 (2H), 3.40-3.47 (2H), 4.32 (2H), 6.95 (2H), 7.06-7.14 (3H), 7.15-7.27 (3H), 7.31-7.42 (3H), 8.07-8.15 (1H), 8.47 (1H).

Example 4

N-(2-methoxyethyl)-4-methyl-2-{[1-(4-morpholinobenzoyl)piperidin-4-yl]methyl}-2H-indazole-5-carboxamide

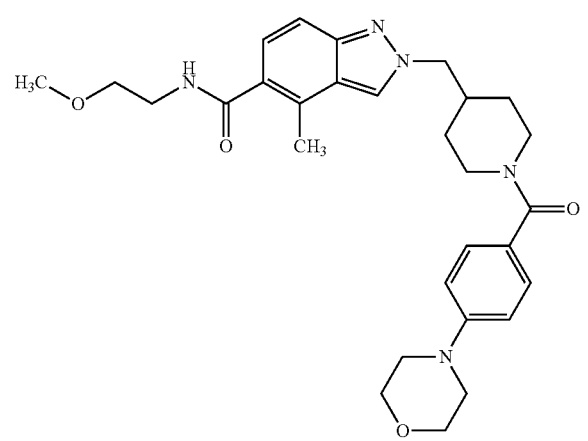 [SMILES: COCCNC(=O)c1ccc2nn(CC3CCN(C(=O)c4ccc(N5CCOCC5)cc4)CC3)cc2c1C]

Analogously to Example 1, 48.1 mg of the title compound was obtained from 75 mg of the amine prepared in Example 1a and 42.3 mg of 4-morpholinobenzoic acid.

$^1$H-NMR (300 MHz, DMSO-d$_6$): δ [ppm], 1.09-1.29 (2H), 1.36-1.53 (2H), 2.16-2.34 (1H), 2.49 (3H), 2.72-2.94 (2H), 3.13 (4H), 3.24 (3H), 3.42 (4H), 3.64-3.75 (4H), 3.92-4.15 (1H), 4.32 (2H), 6.92 (2H), 7.14 (1H), 7.20 (2H), 7.38 (1H), 8.07-8.15 (1H), 8.47 (1H).

Example 5

2-({1-[(4'-fluorobiphenyl-4-yl)carbonyl]piperidin-4-yl}methyl)-N-(2-methoxy-ethyl)-4-methyl-2H-indazole-5-carboxamide

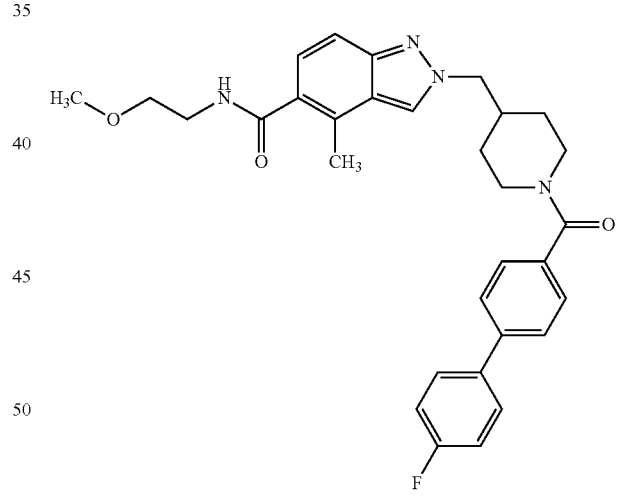

Analogously to Example 1, 50.1 mg of the title compound was obtained from 75 mg of the amine prepared in Example 1a and 44.2 mg of 4-(4-fluorophenyl)benzoic acid.

$^1$H-NMR (300 MHz, DMSO-d$_6$): δ [ppm], 1.11-1.32 (2H), 1.32-1.64 (2H), 2.20-2.36 (1H), 2.49 (3H), 2.63-3.08 (2H), 3.24 (3H), 3.42 (4H), 3.50-3.73 (1H), 4.24-4.55 (3H), 7.10-7.20 (1H), 7.27 2H), 7.41 (3H), 7.67 (4H), 8.03-8.16 (1H), 8.48 (1H).

Example 6

2-{[1-(2-fluoro-4-mesylbenzoyl)piperidin-4-yl]methyl}-N-(2-methoxyethyl)-4-methyl-2H-indazole-5-carboxamide

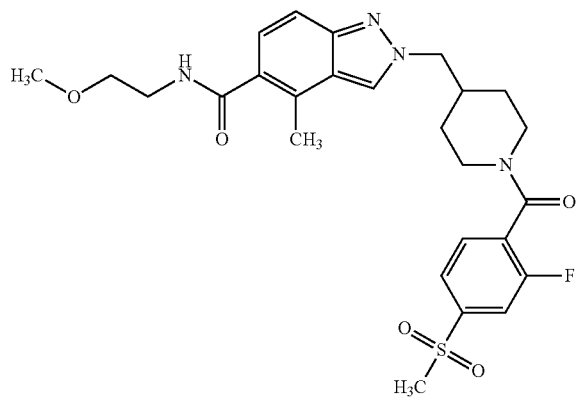 [SMILES: COCCNC(=O)c1ccc2nn(CC3CCN(C(=O)c4ccc(S(C)(=O)=O)cc4F)CC3)cc2c1C]

Analogously to Example 1, 40.1 mg of the title compound was obtained from 75 mg of the amine prepared in Example 1a and 44.6 mg of 2-fluoro-4-mesylbenzoic acid.

$^1$H-NMR (300 MHz, DMSO-$d_6$): δ [ppm], 1.06-1.30 (2H), 1.31-1.45 (1H), 1.51-1.64 (1H), 2.20-2.37 (1H), 2.49 (3H), 2.71-2.85 (1H), 2.91-3.10 (1H), 3.24 (3H), 3.26 (3H), 3.33-3.39 (2H), 3.42 (2H), 4.24-4.39 (2H), 4.40-4.51 (1H), 7.14 (1H), 7.38 (1H), 7.59-7.69 (1H), 7.76-7.89 (2H), 8.07-8.14 (1H), 8.47 (1H).

Example 7

2-{[1-(2-fluoro-4-methoxybenzoyl)piperidin-4-yl]methyl}-N-(2-methoxyethyl)-4-methyl-2H-indazole-5-carboxamide

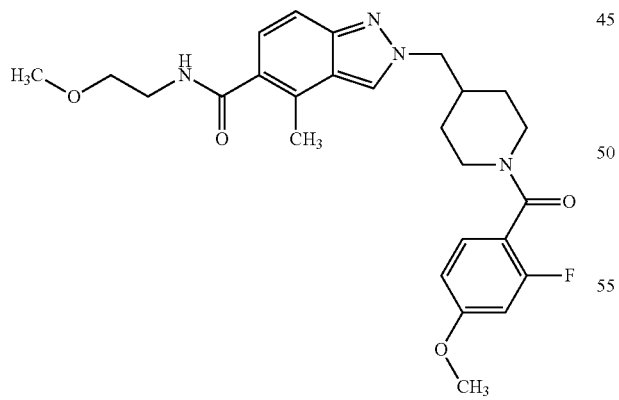

Analogously to Example 1, 43.1 mg of the title compound was obtained from 75 mg of the amine prepared in Example 1a and 34.8 mg of 2-fluoro-4-methoxybenzoic acid.

$^1$H-NMR (300 MHz, DMSO-$d_6$): δ [ppm], 1.05-1.25 (2H), 1.32-1.44 (1H), 1.48-1.61 (1H), 2.18-2.33 (1H), 2.49 (3H), 2.63-2.79 (1H), 2.88-3.05 (1H), 3.24 (3H), 3.42 (d, 5H), 3.75 (3H), 4.27-4.35 (2H), 4.37-4.49 (1H), 6.77-6.89 (2H), 7.14 (1H), 7.24 (1H), 7.38 (1H), 8.07-8.15 (1H), 8.47 (1H).

Example 8

2-{[1-(4-bromo-2-fluorobenzoyl)piperidin-4-yl]methyl}-N-(2-methoxyethyl)-4-methyl-2H-indazole-5-carboxamide

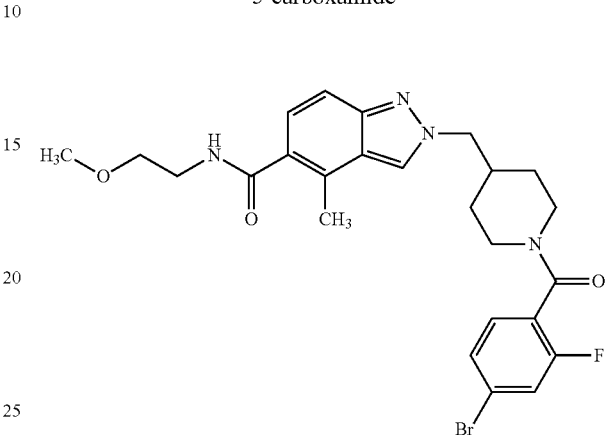

Analogously to Example 1, 51.8 mg of the title compound was obtained from 75 mg of the amine prepared in Example 1a and 44.7 mg of 4-bromo-2-fluorobenzoic acid.

$^1$H-NMR (300 MHz, DMSO-$d_6$): δ [ppm], 1.04-1.27 (2H), 1.32-1.43 (1H), 1.49-1.61 (1H), 2.20-2.33 (1H), 2.48 (3H), 2.67-2.80 (1H), 2.91-3.05 (1H), 3.24 (3H), 3.33-3.46 (5H), 4.24-4.36 (2H), 4.38-4.49 (1H), 7.15 (1H), 7.27-7.34 (1H), 7.35-7.41 (1H), 7.44-7.50 (1H), 7.60-7.66 (1H), 8.07-8.15 (1H), 8.47 (1H).

Example 9

2-{[1-(2-fluoro-4-methylbenzoyl)piperidin-4-yl]methyl}-N-(2-methoxyethyl)-4-methyl-2H-indazole-5-carboxamide

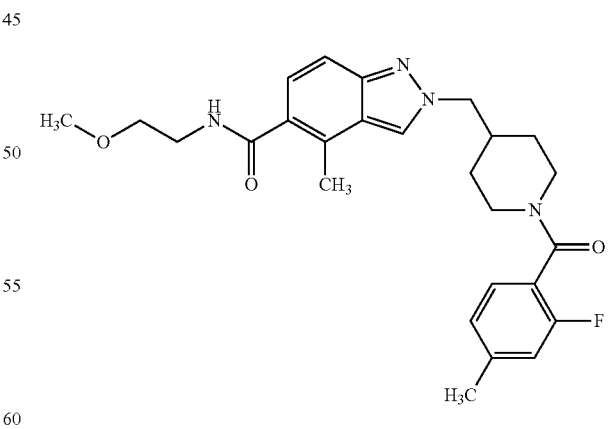

Analogously to Example 1, 38.3 mg of the title compound was obtained from 75 mg of the amine prepared in Example 1a and 31.5 mg of 2-fluoro-4-methylbenzoic acid.

$^1$H-NMR (300 MHz, DMSO-$d_6$): δ [ppm], 1.04-1.26 (2H), 1.31-1.43 (1H), 1.48-1.60 (1H), 2.18-2.35 (4H), 2.48 (3H), 2.64-2.79 (1H), 2.89-3.04 (1H), 3.24 (3H), 3.33-3.39

(3H), 3.39-3.45 (2H), 4.23-4.36 (2H), 4.39-4.49 (1H), 7.01-7.10 (2H), 7.13 (1H), 7.16-7.24 (1H), 7.38 (1H), 8.07-8.14 (1H), 8.47 (1H).

Example 10

2-({1-[2-fluoro-4-(trifluoromethyl)benzoyl]piperidin-4-yl}methyl)-N-(2-methoxy-ethyl)-4-methyl-2H-indazole-5-carboxamide

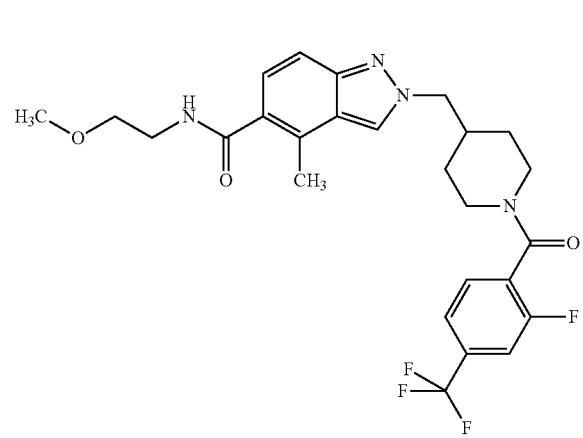 [SMILES: COCCNC(=O)c1ccc2nn(CC3CCN(C(=O)c4ccc(C(F)(F)F)cc4F)CC3)cc2c1C]

Analogously to Example 1, 57.8 mg of the title compound was obtained from 75 mg of the amine prepared in Example 1a and 42.5 mg of 2-fluoro-4-(trifluoromethyl)benzoic acid.

$^1$H-NMR (300 MHz, DMSO-d$_6$): δ [ppm], 1.07-1.29 (2H), 1.32-1.44 (1H), 1.52-1.62 (1H), 2.20-2.36 (1H), 2.49 (3H), 2.67-2.84 (1H), 2.93-3.07 (1H), 3.24 (3H), 3.32-3.39 (3H), 3.39-3.46 (2H), 4.24-4.39 (2H), 4.40-4.51 (1H), 7.14 (1H), 7.38 (1H), 7.56-7.68 (2H), 7.76 (1H), 8.07-8.14 (1H), 8.47 (1H).

Example 11

N-(2-methoxyethyl)-4-methyl-2-({1-[4-(pentafluoro-λ$^6$-sulphanyl)benzoyl]piperidin-4-yl}methyl)-2H-indazole-5-carboxamide Analogously to Example 1, 135.1 mg of the title compound was obtained from 150 mg of the amine prepared in Example 1a and 101.5 mg of 4-(pentafluoro-λ$^6$-sulphanyl)benzoic acid.

$^1$H-NMR (300 MHz, DMSO-d$_6$): δ [ppm], 1.10-1.30 (2H), 1.31-1.42 (1H), 1.50-1.62 (1H), 2.20-2.33 (1H), 2.49 (3H), 2.67-2.83 (1H), 2.91-3.06 (1H), 3.24 (3H), 3.32-3.39 (2H), 3.41 (3H), 4.32 (2H), 4.37-4.48 (1H), 7.14 (1H), 7.38 (1H), 7.55 (2H), 7.94 (2H), 8.12 (1H), 8.47 (1H).

The following compounds were prepared analogously:

| Ex. | Structure | IUPAC name | Analysis |
|---|---|---|---|
| 12 | 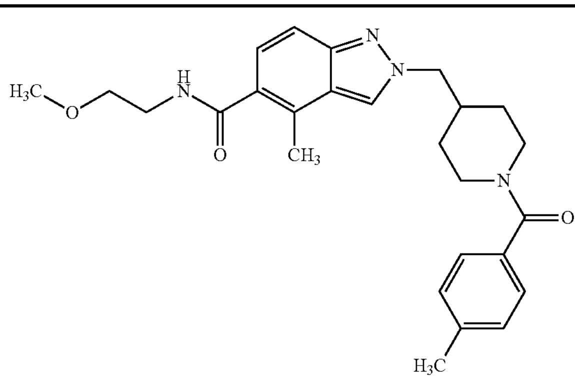 | N-(2-methoxyethyl)-4-methyl-2-{[1-(4-methylbenzoyl)-piperidin-4-yl]-methyl}-2H-indazole-5-carboxamide | $^1$H-NMR (400 MHz, DMSO-d$_6$): δ [ppm] = 1.20 (2H), 1.42 (2H), 2.29 (4H), 2.49 (3H), 2.73 (1H), 2.93 (1H), 3.25 (3H), 3.37 (2H), 3.43 (2H), 3.57 (1H), 4.31 (2H), 4.40 (1H), 7.14 (1H), 7.21 (4H), 7.38 (1H), 8.09 (1H), 8.46 (1H). |

| Ex. | Structure | IUPAC name | Analysis |
|---|---|---|---|
| 13 | 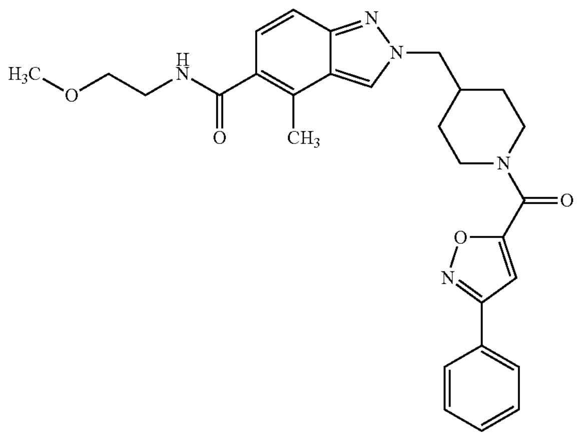 [SMILES: COCCNC(=O)c1ccc2nn(CC3CCN(C(=O)c4cc(-c5ccccc5)no4)CC3)cc2c1C] | N-(2-methoxyethyl)-4-methyl-2-({1-[(3-phenylisoxazol-5-yl)carbonyl]piperidin-4-yl}methyl)-2H-indazole-5-carboxamide | $^1$H-NMR (300 MHz, DMSO-d$_6$): δ [ppm] = 1.25 (2H), 1.55 (2H), 2.34 (1H), 2.49 (3H), 2.83 (1H), 3.15 (1H), 3.24 (3H), 3.40 (4H), 3.87 (1H), 4.35 (3H), 7.15 (1H), 7.40 (1H), 7.46 (1H), 7.50 (3H), 7.90 (2H), 8.13 (1H), 8.49 (1H). |
| 14 | 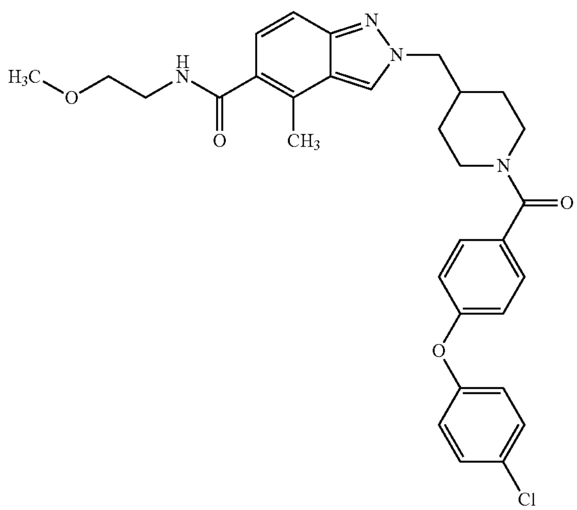 [SMILES: COCCNC(=O)c1ccc2nn(CC3CCN(C(=O)c4ccc(Oc5ccc(Cl)cc5)cc4)CC3)cc2c1C] | 2-({1-[4-(4-chlorophenoxy)benzoyl]-piperidin-4-yl}-methyl)-N-(2-methoxyethyl)-4-methyl-2H-indazole-5-carboxamide | $^1$H-NMR (300 MHz, DMSO-d$_6$): δ [ppm] = 1.21 (2H), 1.45 (2H), 2.26 (1H), 2.49 (3H), 2.76 (1H), 2.94 (1H), 3.24 (3H), 3.40 (4H), 3.62 (1H), 4.33 (3H), 7.04 (4H), 7.15 (1H), 7.40 (5H), 8.12 (1H), 8.47 (1H). |
| 15 | 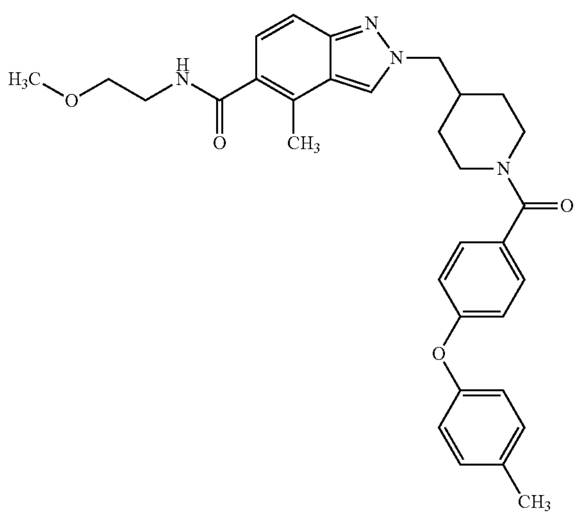 [SMILES: COCCNC(=O)c1ccc2nn(CC3CCN(C(=O)c4ccc(Oc5ccc(C)cc5)cc4)CC3)cc2c1C] | N-(2-methoxyethyl)-4-methyl-2-({1-[4-(4-methylphenoxy)-benzoyl]piperidin-4-yl}methyl)-2H-indazole-5-carboxamide | $^1$H-NMR (300 MHz, DMSO-d$_6$): δ [ppm], 1.20 (2H), 1.43 (2H), 2.26 (4H), 2.48 (3H), 2.76 (1H), 2.90 (1H), 3.24 (3H), 3.38 (4H), 3.62 (1H), 4.32 (3H), 6.92 (4H), 7.71 (3H), 7.34 (3H), 8.12 (1H), 8.47 (1H). |

-continued

| Ex. | Structure | IUPAC name | Analysis |
|---|---|---|---|
| 16 | 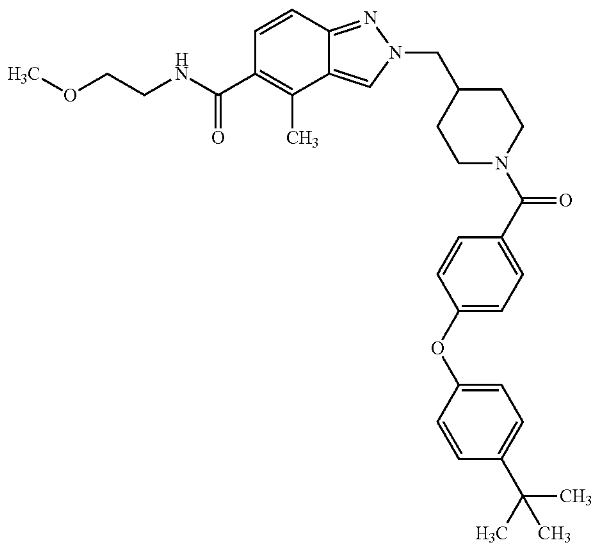 [SMILES: COCCNC(=O)c1ccc2nn(CC3CCN(C(=O)c4ccc(Oc5ccc(C(C)(C)C)cc5)cc4)CC3)cc2c1C] | 2-({1-[4-(4-tert-butylphenoxy)-benzoyl]piperidin-4-yl}methyl)-N-(2-methoxyethyl)-4-methyl-2H-indazole-5-carboxamide | $^1$H-NMR (300 MHz, DMSO-d$_6$): δ [ppm], 1.21 (2H), 1.25 (9H), 1.44 (2H), 2.26 (1H), 2.48 (3H), 2.77 (1H), 2.291 (1H), 3.24 (3H), 3.39 (4H), 3.64 (1H), 4.32 (3H), 6.95 (4H), 7.14 (1H), 7.36 (5H), 8.12 (1H), 8.47 (1H). |
| 17 | 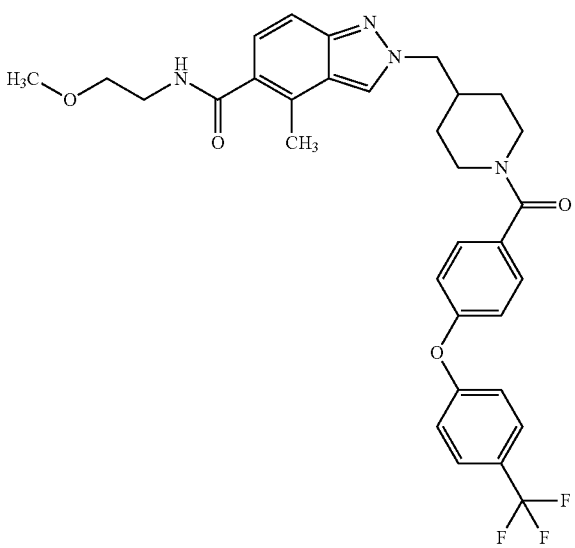 [SMILES: COCCNC(=O)c1ccc2nn(CC3CCN(C(=O)c4ccc(Oc5ccc(C(F)(F)F)cc5)cc4)CC3)cc2c1C] | N-(2-methoxyethyl)-4-methyl-2-[(1-{4-[4-(trifluoromethyl)-phenoxy]benzoyl}-piperidin-4-yl)-methyl]-2H-indazole-5-carboxamide | $^1$H-NMR (300 MHz, DMSO-d$_6$): δ [ppm], 1.22 (2H), 1.45 (2H), 2.27 (1H), 2.49 (3H), 2.77 (1H) 2.97 (1H), 3.24 (3H), 3.39 (4H), 3.61 (1H), 4.33 (3H), 7.15 (5H), 7.39 (3H), 7.73 (2H), 8.12 (1H), 8.48 (1H). |
| 18 | 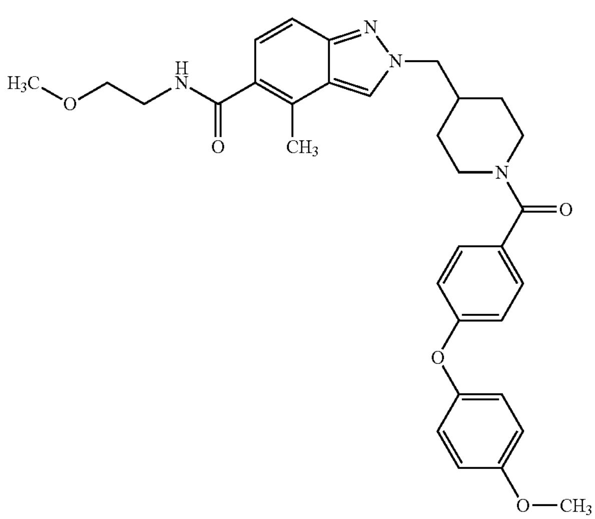 | N-(2-methoxyethyl)-2-({1-[4-(4-methoxy-phenoxy)benzoyl]-piperidin-4-yl}-methyl)-4-methyl-2H-indazole-5-carboxamide | $^1$H-NMR (300 MHz, DMSO-d$_6$): δ [ppm] = 1.19 (2H), 1.44 (2H), 2.25 (1H), 2.48 (3H), 2.86 (2H), 3.24 (3H), 3.40 (4H), 3.64 (1H), 3.72 (3H), 4.32 (3H), 6.88 (2H), 6.95 (2H), 7.02 (2H), 7.14 (1H), 7.31 (2H), 7.38 (1H), 8.12 (1H), 8.47 (1H). |

| Ex. | Structure | IUPAC name | Analysis |
|---|---|---|---|
| 19 | 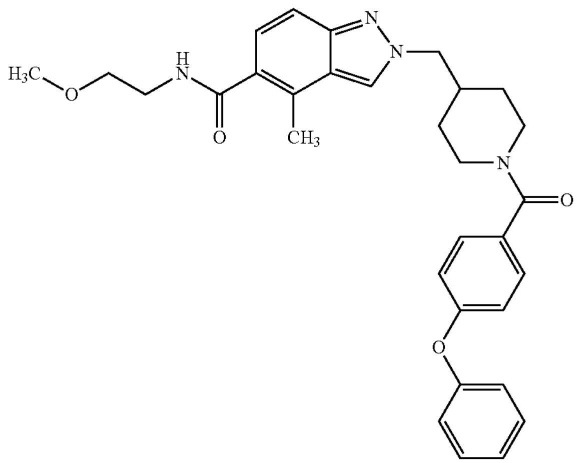 [SMILES: COCCNC(=O)c1ccc2nn(CC3CCN(C(=O)c4ccc(Oc5ccccc5)cc4)CC3)cc2c1C] | N-(2-methoxyethyl)-4-methyl-2-{[1-(4-phenoxybenzoyl)-piperidin-4-yl]-methyl}-2H-indazole-5-carboxamide | $^1$H-NMR (300 MHz, DMSO-d$_6$): δ [ppm] = 1.21 (2H), 1.44 (2H), 2.26 (1H), 2.49 (3H), 2.77 (1H), 2.92 (1H), 3.24 (3H), 3.38 (4H), 3.64 (1H), 4.32 (3H), 6.97 (2H), 7.04 (2H), 7.16 (2H), 7.26 (5H), 8.12 (1H), 8.47 (1H). |
| 20 | 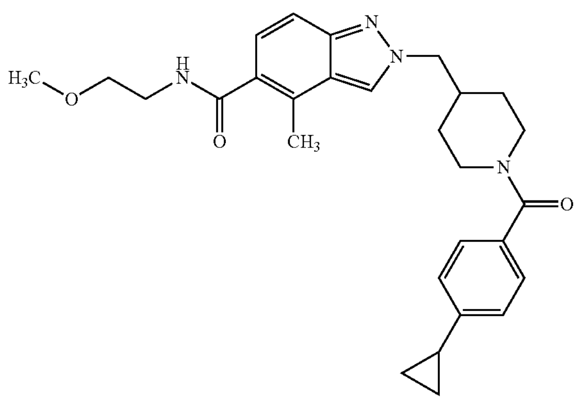 [SMILES: COCCNC(=O)c1ccc2nn(CC3CCN(C(=O)c4ccc(C5CC5)cc4)CC3)cc2c1C] | 2-{[1-(4-cyclopropyl-benzoyl)piperidin-4-yl]methyl}-N-(2-methoxyethyl)-4-methyl-2H-indazole-5-carboxamide | 1H-NMR (300 MHz, DMSO-d$_6$): δ [ppm] = 0.65 (2H), 0.93 (2H), 1.19 (2H), 1.43 (2H), 1.90 (1H), 2.25 (1H), 2.48 (3H), 2.73 (1H), 2.92 (1H), 3.24 (3H), 3.39 (4H), 3.59 (1H), 4.32 (3H), 7.14 (5H), 7.38 (1H), 8.12 (1H), 8.47 (1H). |
| 21 | 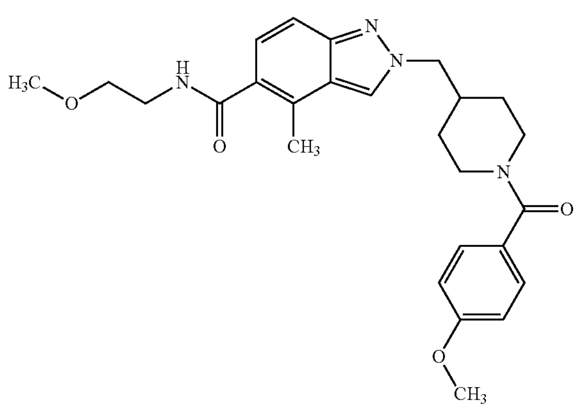 [SMILES: COCCNC(=O)c1ccc2nn(CC3CCN(C(=O)c4ccc(OC)cc4)CC3)cc2c1C] | 2-{[1-(4-methoxy-benzoyl)piperidin-4-yl]methyl}-N-(2-methoxyethyl)-4-methyl-2H-indazole-5-carboxamide | $^1$H-NMR (400 MHz, DMSO-d$_6$): δ [ppm] = 1.19 (2H), 1.44 (2H), 2.26 (1H), 2.49 (3H), 2.82 (2H), 3.24 (3H), 3.36 (2H), 3.42 (2H), 3.50 (1H), 3.74 (3H), 4.31 (3H), 6.93 (2H), 7.14 (1H), 7.29 (2H), 7.38 (1H), 8.12 (1H), 8.47 (1H). |
| 22 | 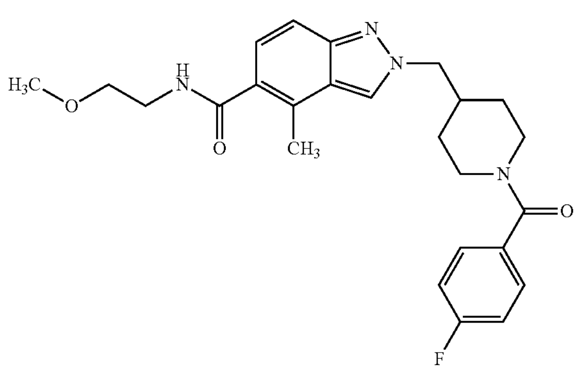 [SMILES: COCCNC(=O)c1ccc2nn(CC3CCN(C(=O)c4ccc(F)cc4)CC3)cc2c1C] | 2-{[1-(4-fluoro-benzoyl)piperidin-4-yl]methyl}-N-(2-methoxyethyl)-4-methyl-2H-indazole-5-carboxamide | $^1$H-NMR (400 MHz, DMSO-d$_6$): δ [ppm] = 1.20 (2H), 1.37 (1H), 1.51 (1H), 2.27 (1H), 2.49 (3H), 2.72 (1H), 2.97 (1H), 3.24 (3H), 3.36 (2H), 3.42 (2H), 3.52 (1H), 4.31 (2H), 4.40 (1H), 7.14 (1H), 7.23 (2H), 7.39 (3H), 8.12 (1H), 8.47 (1H). |

| Ex. | Structure | IUPAC name | Analysis |
|---|---|---|---|
| 23 | 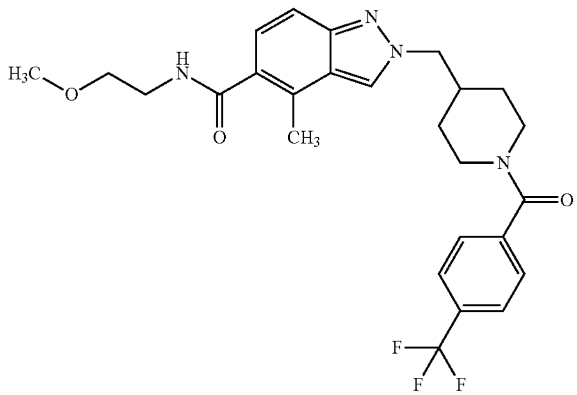 [SMILES: COCCNC(=O)c1ccc2nn(CC3CCN(C(=O)c4ccc(C(F)(F)F)cc4)CC3)cc2c1C] | N-(2-methoxyethyl)-4-methyl-2-({1-[4-(trifluoromethyl)-benzoyl]piperidin-4-yl}methyl)-2H-indazole-5-carboxamide | $^1$H-NMR (400 MHz, DMSO-$d_6$): δ [ppm] = 1.22 (2H), 1.34 (1H), 1.56 (1H), 2.28 (1H), 2.49 (3H), 2.75 (1H), 2.99 (1H), 3.24 (3H), 3.35 (2H), 3.42 (3H), 4.32 (2H), 4.44 (1H), 7.14 (1H), 7.38 (1H), 7.55 (2H), 7.77 (2H), 8.12 (1H), 8.47 (1H). |
| 24 | 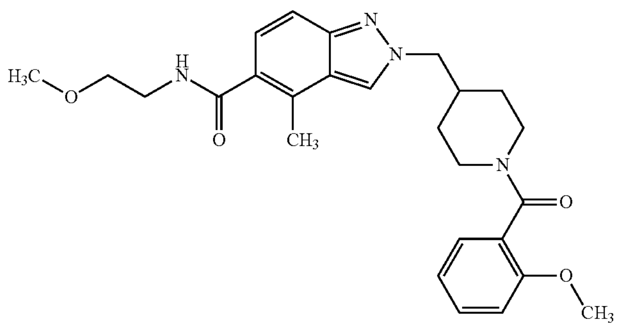 | 2-{[1-(2-methoxy-benzoyl)piperidin-4-yl]methyl}-N-(2-methoxyethyl)-4-methyl-2H-indazole-5-carboxamide | $^1$H-NMR (400 MHz, DMSO-$d_6$): δ [ppm] = 1.11 (2H), 1.35 (1H), 1.52 (1H), 2.23 (1H), 2.49 (3H), 2.66 (1H), 2.87 (1H), 3.22 (1H), 3.24 (3H), 3.35 (2H), 3.42 (2H), 3.71 (3H), 4.29 (1H), 4.33 (1H), 4.45 (1H), 6.94 (1H), 7.07 (3H), 7.33 (1H), 7.39 (1H), 8.12 (1H), 8.48 (1H). |
| 25 | 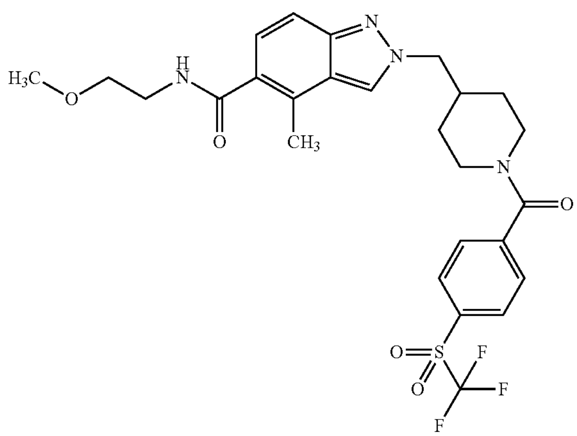 [SMILES: COCCNC(=O)c1ccc2nn(CC3CCN(C(=O)c4ccc(S(=O)(=O)C(F)(F)F)cc4)CC3)cc2c1C] | N-(2-methoxyethyl)-4-methyl-2-[(1-{4-[(trifluoromethyl)-sulphonyl]benzoyl}-piperidin-4-yl)-methyl]-2H-indazole-5-carboxamide | $^1$H-NMR (400 MHz, DMSO-$d_6$): δ [ppm] = 1.23 (2H), 1.36 (1H), 1.57 (1H), 2.29 (1H), 2.49 (3H), 2.77 (1H), 3.01 (1H), 3.24 (3H), 3.35 (3H), 3.42 (2H), 4.32 (2H), 4.44 (1H), 7.14 (1H), 7.38 (1H), 7.77 (2H), 8.15 (3H), 8.47 (1H). |
| 26 | 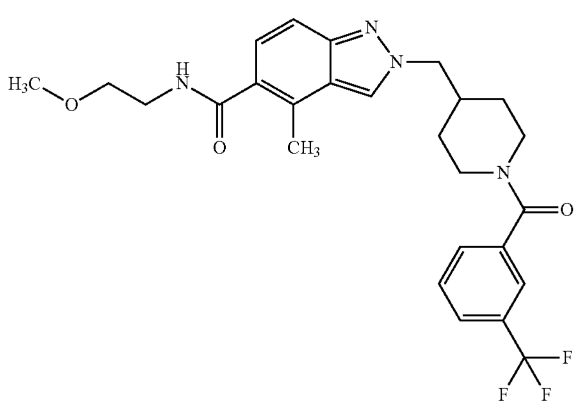 [SMILES: COCCNC(=O)c1ccc2nn(CC3CCN(C(=O)c4cccc(C(F)(F)F)c4)CC3)cc2c1C] | N-(2-methoxyethyl)-4-methyl-2-({1-[3-(trifluoromethyl)-benzoyl]piperidin-4-yl}methyl)-2H-indazole-5-carboxamide | $^1$H-NMR (400 MHz, DMSO-$d_6$): δ [ppm] = 1.24 (2H), 1.37 (1H), 1.55 (1H), 2.28 (1H), 2.49 (3H), 2.75 (1H), 3.01 (1H), 3.24 (3H), 3.36 (3H), 3.42 (3H), 4.32 (2H), 4.43 (1H), 7.14 (1H), 7.38 (1H), 7.65 (3H), 7.78 (1H), 8.12 (1H), 8.47 (1H). |

-continued

| Ex. | Structure | IUPAC name | Analysis |
|---|---|---|---|
| 27 | 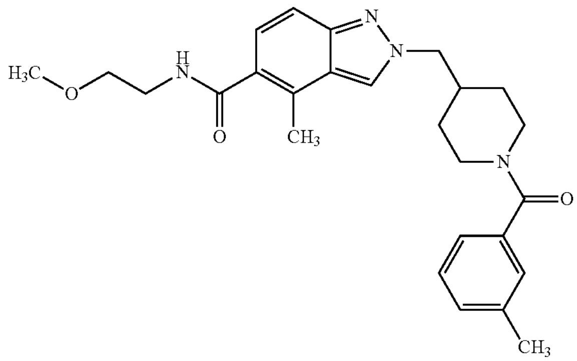 [SMILES: COCCNC(=O)c1ccc2nn(CC3CCN(C(=O)c4cccc(C)c4)CC3)cc2c1C] | N-(2-methoxyethyl)-4-methyl-2-{[1-(3-methylbenzoyl)-piperidin-4-yl]-methyl}-2H-indazole-5-carboxamide | 1H-NMR (400 MHz, DMSO-d$_6$): δ [ppm] = 1.20 (2H), 1.36 (1H), 1.52 (1H), 2.29 (4H), 2.49 (3H), 2.69 (1H), 2.95 (1H), 3.24 (3H), 3.36 (2H), 3.42 (2H), 3.53 (1H), 4.31 (2H), 4.41 (1H), 7.12 (3H), 7.21 (1H), 7.27 (1H), 7.38 (1H), 8.12 (1H), 8.47 (1H). |
| 28 | 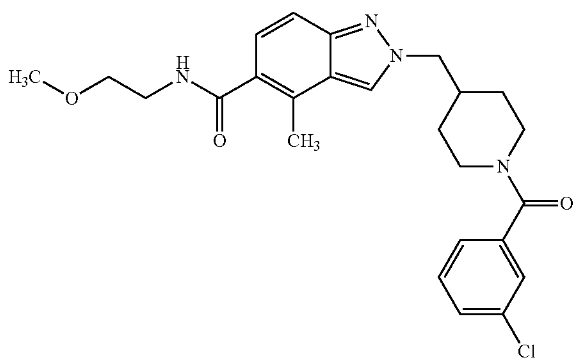 [SMILES: COCCNC(=O)c1ccc2nn(CC3CCN(C(=O)c4cccc(Cl)c4)CC3)cc2c1C] | 2-{[1-(3-chloro-benzoyl)piperidin-4-yl]methyl}-N-(2-methoxyethyl)-4-methyl-2H-indazole-5-carboxamide | $^1$H-NMR (400 MHz, DMSO-d$_6$): δ [ppm] = 1.21 (2H), 1.36 (1H), 1.53 (1H), 2.27 (1H), 2.49 (3H), 2.72 (1H), 2.98 (1H), 3.24 (3H), 3.35 (2H), 3.42 (3H), 4.31 (2H), 4.40 (1H), 7.14 (1H), 7.28 (1H), 7.43 (4H), 8.12 (1H), 8.47 (1H). |
| 29 | 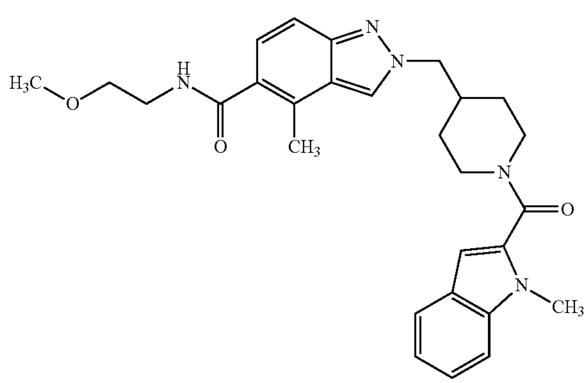 [SMILES: COCCNC(=O)c1ccc2nn(CC3CCN(C(=O)c4cc5ccccc5n4C)CC3)cc2c1C] | N-(2-methoxyethyl)-4-methyl-2-({1-[(1-methyl-1H-indol-2-yl)carbonyl]-piperidin-4-yl}methyl)-2H-indazole-5-carboxamide | $^1$H-NMR (400 MHz, DMSO-d$_6$): δ [ppm] = 1.25 (2H), 1.50 (2H), 2.31 (1H), 2.49 (3H), 2.82 (1H), 3.05 (1H), 3.24 (3H), 3.36 (2H), 3.42 (2H), 3.69 (3H), 3.98 (1H), 4.34 (2H), 4.44 (1H), 6.57 (1H), 7.05 (1H), 7.15 (1H), 7.20 (1H), 7.39 (1H), 7.46 (1H), 7.56 (1H), 8.12 (1H), 8.49 (1H). |

-continued

| Ex. | Structure | IUPAC name | Analysis |
|---|---|---|---|
| 30 | 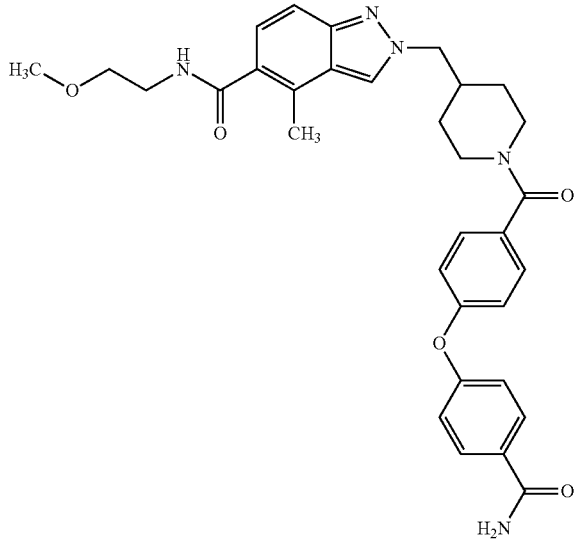 [SMILES: COCCNC(=O)c1ccc2nn(CC3CCN(C(=O)c4ccc(Oc5ccc(C(N)=O)cc5)cc4)CC3)cc2c1C] | 2-({1-[4-(4-carbamoylphenoxy)-benzoyl]piperidin-4-yl}methyl)-N-(2-methoxyethyl)-4-methyl-2H-indazole-5-carboxamide | $^1$H-NMR (400 MHz, DMSO-d$_6$): δ [ppm] = 1.22 (2H), 1.49 (2H), 2.31 (1H), 2.52 (3H), 2.82 (1H), 2.98 (1H), 3.27 (3H), 3.39 (2H), 3.45 (2H), 3.65 (1H), 4.35 (2H), 4.43 (1H), 7.08 (4H), 7.17 (1H), 7.29 (1H), 7.41 (3H), 7.91 (3H), 8.12 (1H), 8.50 (1H). |
| 31 | 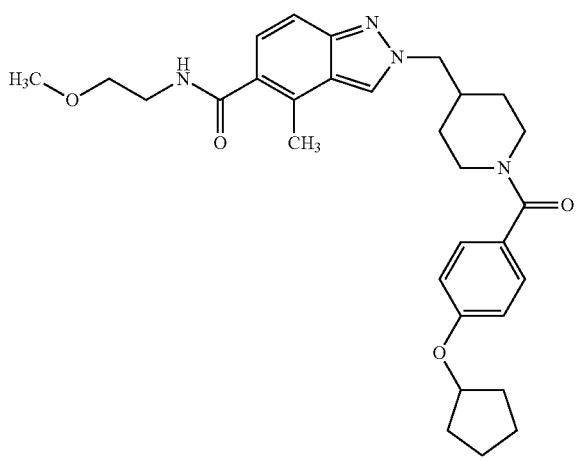 [SMILES: COCCNC(=O)c1ccc2nn(CC3CCN(C(=O)c4ccc(OC5CCCC5)cc4)CC3)cc2c1C] | 2-({1-[4-(cyclo-pentyloxy)benzoyl]-piperidin-4-yl}-methyl)-N-(2-methoxyethyl)-4-methyl-2H-indazole-5-carboxamide | $^1$H-NMR (400 MHz, DMSO-d$_6$): δ [ppm] = 1.23 (2H), 1.47 (2H), 1.57 (2H), 1.68 (4H), 1.90 (2H), 2.28 (1H), 2.52 (3H), 2.86 (2H), 3.27 (3H), 3.39 (2H), 3.45 (2H), 3.85 (2H), 4.34 (2H), 4.83 (1H), 6.91 (2H), 7.17 (1H), 7.28 (2H), 7.41 (1H), 8.12 (1H), 8.49 (1H). |
| 32 | 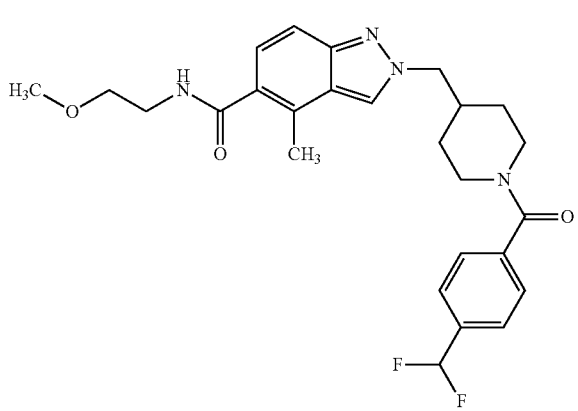 [SMILES: COCCNC(=O)c1ccc2nn(CC3CCN(C(=O)c4ccc(C(F)F)cc4)CC3)cc2c1C] | 2-({1-[4-(difluoro-methyl)benzoyl]-piperidin-4-yl}-methyl)-N-(2-methoxyethyl)-4-methyl-2H-indazole-5-carboxamide | $^1$H-NMR (400 MHz, DMSO-d$_6$): δ [ppm] = 1.24 (2H), 1.39 (1H), 1.57 (1H), 2.30 (1H), 2.52 (3H), 2.76 (1H), 3.01 (1H), 3.27 (3H), 3.39 (2H), 3.45 (3H), 4.35 (2H), 4.45 (1H), 7.18 (2H), 7.41 (1H), 7.49 (2H), 7.62 (2H), 8.12 (1H), 8.49 (1H). |

| Ex. | Structure | IUPAC name | Analysis |
|---|---|---|---|
| 33 | 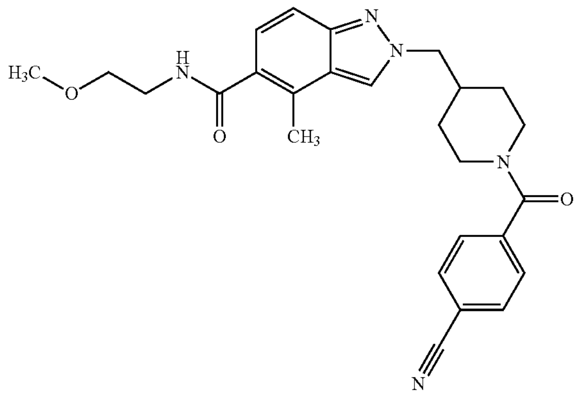 [SMILES: COCCNC(=O)c1ccc2nn(CC3CCN(C(=O)c4ccc(C#N)cc4)CC3)cc2c1C] | 2-{[1-(4-cyano-benzoyl)piperidin-4-yl]methyl}-N-(2-methoxyethyl)-4-methyl-2H-indazole-5-carboxamide | $^1$H-NMR (400 MHz, DMSO-d$_6$): δ [ppm] = 1.24 (2H), 1.39 (1H), 1.58 (1H), 2.30 (1H), 2.52 (3H), 2.77 (1H), 3.01 (1H), 3.27 (3H), 3.39 (3H), 3.45 (2H), 4.34 (2H), 4.44 (1H), 7.17 (1H), 7.41 (1H), 7.54 (2H), 7.90 (2H), 8.12 (1H), 8.49 (1H). |
| 34 | 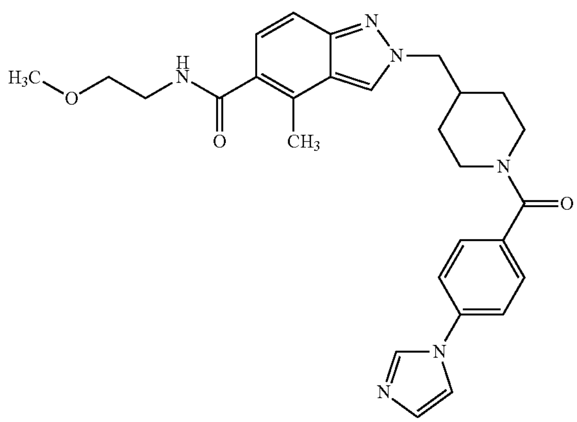 [SMILES: COCCNC(=O)c1ccc2nn(CC3CCN(C(=O)c4ccc(-n5ccnc5)cc4)CC3)cc2c1C] | 2-({1-[4-(1H-imidazol-1-yl)-benzoyl]piperidin-4-yl}methyl)-N-(2-methoxyethyl)-4-methyl-2H-indazole-5-carboxamide | $^1$H-NMR (300 MHz, DMSO-d$_6$): δ [ppm] = 1.24 (2H), 1.39 (1H), 156 (1H), 2.29 (1H), 2.49 (3H), 2.76 (1H), 3.04 (1H), 3.24 (3H), 3.37 (3H), 3.42 (3H), 4.33 (2H), 4.44 (1H), 7.15 (1H), 7.39 (1H), 7.61 (2H), 7.84 (3H), 8.11 (1H), 8.26 (1H), 8.48 (1H). |
| 35 | 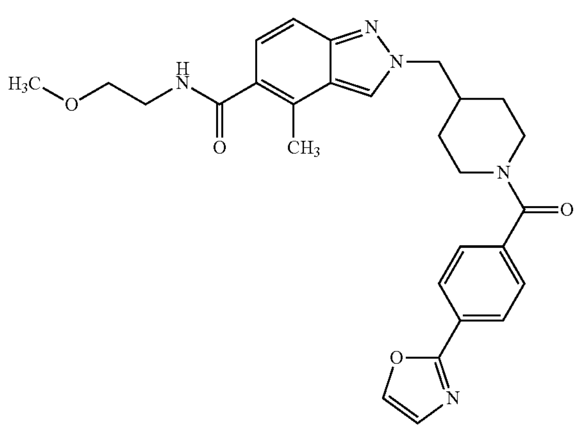 [SMILES: COCCNC(=O)c1ccc2nn(CC3CCN(C(=O)c4ccc(-c5ncco5)cc4)CC3)cc2c1C] | N-(2-methoxyethyl)-4-methyl-2-({1-[4-(oxazol-2-yl)-benzoyl]piperidin-4-yl}methyl)-2H-indazole-5-carboxamide | $^1$H-NMR (300 MHz, DMSO-d$_6$): δ [ppm] = 1.24 (2H), 1.37 (1H), 1.54 (1H), 2.27 (1H), 2.49 (3H), 2.75 (1H), 3.00 (1H), 3.24 (3H), 3.36 (3H), 3.42 (2H), 3.53 (1H), 4.32 (2H), 4.43 (1H), 7.14 (1H), 7.38 (2H), 7.48 (2H), 8.00 (2H), 8.12 (1H), 8.23 (1H), 8.48 (1H). |

| Ex. | Structure | IUPAC name | Analysis |
|---|---|---|---|
| 36 | 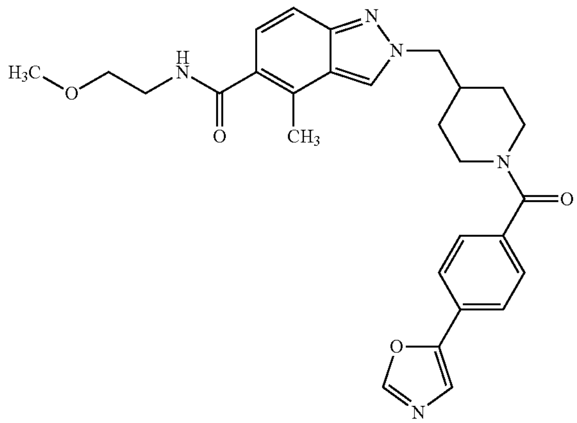 [SMILES: COCCNC(=O)c1ccc2nn(CC3CCN(C(=O)c4ccc(-c5cnco5)cc4)CC3)cc2c1C] | N-(2-methoxyethyl)-4-methyl-2-({1-[4-(oxazol-5-yl)-benzoyl]piperidin-4-yl}methyl)-2H-indazole-5-carboxamide | ¹H-NMR (300 MHz, DMSO-d₆): δ [ppm] = 1.22 (2H), 1.38 (1H), 1.53 (1H), 2.28 (1H), 2.49 (3H), 2.74 (1H), 2.98 (1H), 3.24 (3H), 3.36 (2H), 3.41 (2H), 3.55 (1H), 4.32 (2H), 4.41 (1H), 7.15 (1H), 7.42 (3H), 7.74 (3H), 8.12 (1H), 8.47 (2H). |
| 37 | 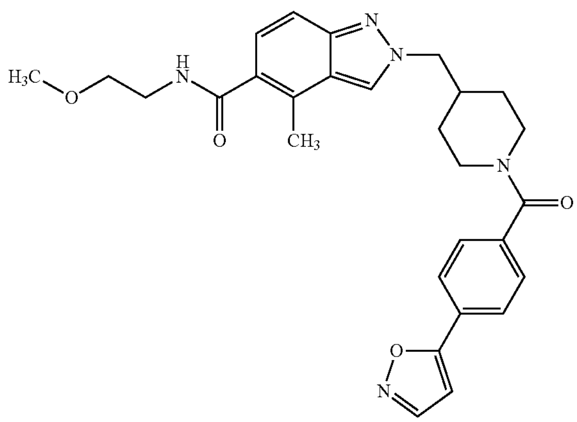 [SMILES: COCCNC(=O)c1ccc2nn(CC3CCN(C(=O)c4ccc(-c5ccno5)cc4)CC3)cc2c1C] | N-(2-methoxyethyl)-4-methyl-2-({1-[4-(isoxazol-5-yl)-benzoyl]piperidin-4-yl}methyl)-2H-indazole-5-carboxamide | ¹H-NMR (300 MHz, DMSO-d₆): δ [ppm] = 1.22 (2H), 1.36 (1H), 1.55 (1H), 2.28 (1H), 2.49 (3H), 2.74 (1H), 2.99 (1H), 3.24 (3H), 3.39 (5H), 4.31 (2H), 4.43 (1H), 4.74 (2H), 7.14 (1H), 7.38 (1H), 7.50 (2H), 7.95 (2H), 8.12 (1H), 8.47 (1H). |
| 38 | 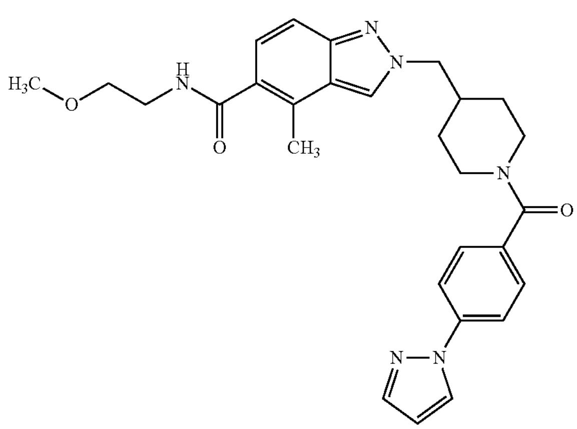 [SMILES: COCCNC(=O)c1ccc2nn(CC3CCN(C(=O)c4ccc(-n5cccn5)cc4)CC3)cc2c1C] | N-(2-methoxyethyl)-4-methyl-2-({1-[4-(1H-pyrazol-1-yl)-benzoyl]piperidin-4-yl}methyl)-2H-indazole-5-carboxamide | ¹H-NMR (300 MHz, DMSO-d₆): δ [ppm] = 1.22 (2H), 1.46 (2H), 2.28 (1H), 2.49 (3H), 2.76 (1H), 2.99 (1H), 3.24 (3H), 3.39 (4H), 3.61 (1H), 4.32 (2H), 4.41 (1H), 6.54 (1H), 7.15 (1H), 7.39 (1H), 7.46 (2H), 7.74 (1H), 7.87 (2H), 8.12 (1H), 8.50 (2H). |

-continued

| Ex. | Structure | IUPAC name | Analysis |
|---|---|---|---|
| 39 | 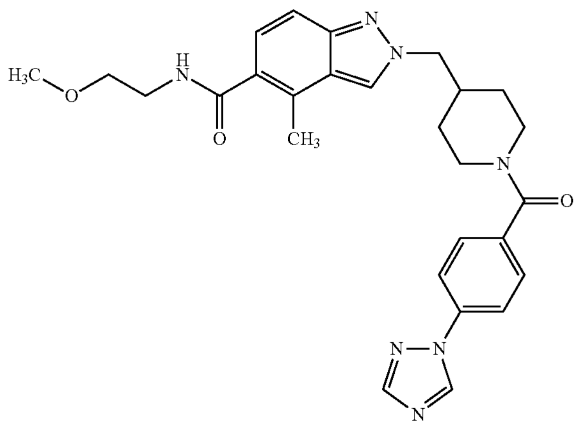 [SMILES: COCCNC(=O)c1ccc2nn(CC3CCN(C(=O)c4ccc(-n5cncn5)cc4)CC3)cc2c1C] | N-(2-methoxyethyl)-4-methyl-2-({1-[4-(1H-1,2,4-triazol-1-yl)benzoyl]piperidin-4-yl}methyl)-2H-indazole-5-carboxamide | $^1$H-NMR (300 MHz, DMSO-d$_6$): δ [ppm] = 1.22 (2H), 1.39 (1H), 1.53 (1H), 2.27 (1H), 2.49 (3H), 2.76 (1H), 3.00 (1H), 3.24 (3H), 3.39 (4H), 3.54 (1H), 4.32 (2H), 4.43 (1H), 7.15 (1H), 7.39 (1H), 7.53 (2H), 7.90 (2H), 8.12 (1H), 8.24 (1H), 8.48 (1H), 9.32 (1H). |
| 40 | 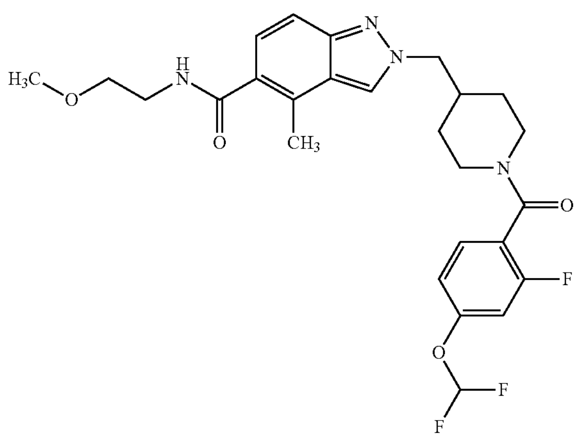 [SMILES: COCCNC(=O)c1ccc2nn(CC3CCN(C(=O)c4ccc(OC(F)F)cc4F)CC3)cc2c1C] | 2-({1-[4-(difluoromethoxy)-2-fluorobenzoyl]piperidin-4-yl}methyl)-N-(2-methoxyethyl)-4-methyl-2H-indazole-5-carboxamide | $^1$H-NMR (300 MHz, DMSO-d$_6$): δ [ppm] = 1.16 (2H), 1.38 (1H), 1.55 (1H), 2.26 (1H), 2.48 (3H), 2.73 (1H), 2.98 (1H), 3.24 (3H), 3.38 (5H), 4.31 (2H), 4.44 (1H), 7.12 (3H), 7.31 (1H), 7.40 (2H), 8.12 (1H), 8.47 (1H). |
| 41 | 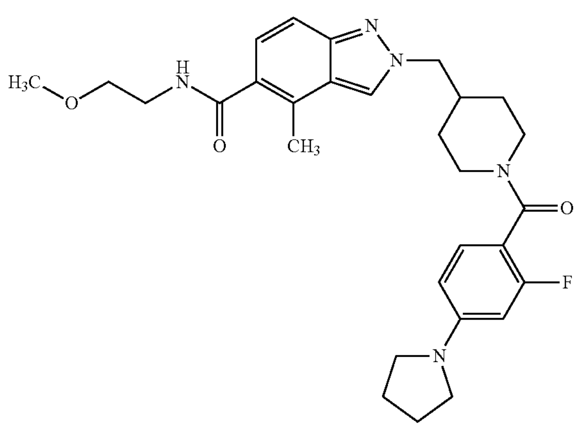 [SMILES: COCCNC(=O)c1ccc2nn(CC3CCN(C(=O)c4ccc(N5CCCC5)cc4F)CC3)cc2c1C] | 2-({1-[2-fluoro-4-(pyrrolidin-1-yl)benzoyl]piperidin-4-yl}methyl)-N-(2-methoxyethyl)-4-methyl-2H-indazole-5-carboxamide | $^1$H-NMR (300 MHz, DMSO-d$_6$): δ [ppm] = 1.14 (2H), 1.43 (2H), 1.90 (4H), 2.23 (1H), 2.48 (3H), 2.68 (1H), 2.94 (1H), 3.19 (4H), 3.24 (3H), 3.36 (2H), 3.42 (3H), 4.31 (2H), 4.39 (1H), 6.29 (2H), 7.10 (2H), 7.38 (1H), 8.12 (1H), 8.47 (1H). |

-continued

| Ex. | Structure | IUPAC name | Analysis |
|---|---|---|---|
| 42 | 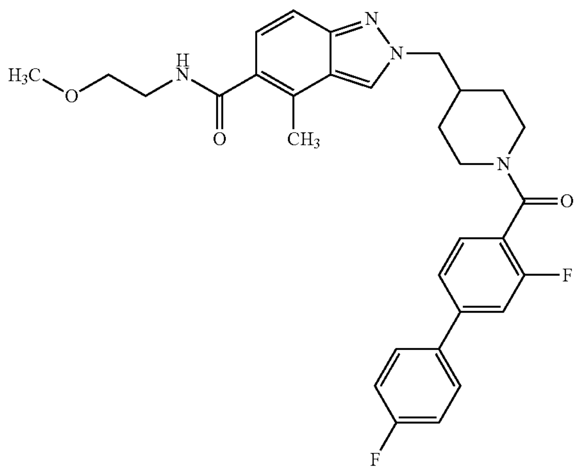 [SMILES: COCCNC(=O)c1ccc2nn(CC3CCN(C(=O)c4ccc(-c5ccc(F)cc5)cc4F)CC3)cc2c1C] | 2-({1-[(3,4'-difluoro-biphenyl-4-yl)-carbonyl]piperidin-4-yl}methyl)-N-(2-methoxyethyl)-4-methyl-2H-indazole-5-carboxamide | $^1$H-NMR (300 MHz, DMSO-d$_6$): δ [ppm] = 1.19 (2H), 1.39 (1H), 1.57 (1H), 2.28 (1H), 2.49 (3H), 2.76 (1H), 3.01 (1H), 3.24 (3H), 3.38 (5H), 4.32 (2H), 4.47 (1H), 7.15 (1H), 7.28 (2H), 7.40 (2H), 7.56 (2H), 7.76 (2H), 8.12 (1H), 8.48 (1H). |
| 43 | 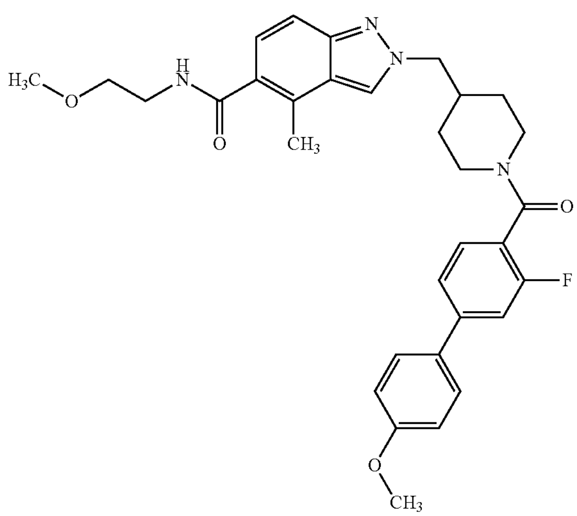 [SMILES: COCCNC(=O)c1ccc2nn(CC3CCN(C(=O)c4ccc(-c5ccc(OC)cc5)cc4F)CC3)cc2c1C] | 2-({1-[(3-fluoro-4'-methoxybiphenyl-4-yl)carbonyl]piperidin-4-yl}methyl)-N-(2-methoxyethyl)-4-methyl-2H-indazole-5-carboxamide | $^1$H-NMR (300 MHz, DMSO-d$_6$): δ [ppm] = 1.19 (2H), 1.39 (1H), 1.57 (1H), 2.28 (1H), 2.49 (3H), 2.76 (1H), 3.01 (1H), 3.24 (3H), 3.38 (5H), 4.32 (2H), 4.47 (1H), 7.15 (1H), 7.28 (2H), 7.40 (2H), 7.56 (2H), 7.76 (2H), 8.12 (1H), 8.48 (1H). |
| 44 | 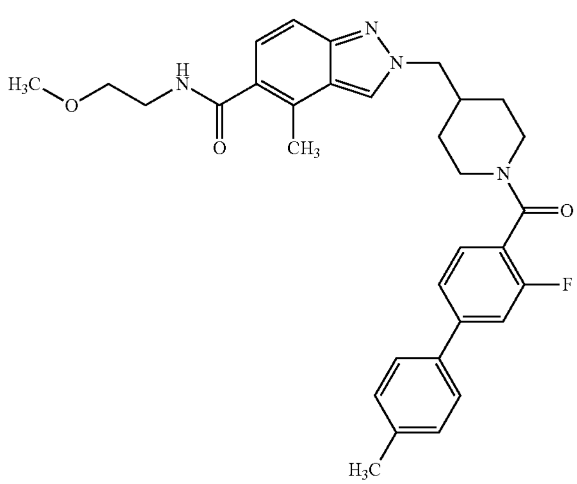 [SMILES: COCCNC(=O)c1ccc2nn(CC3CCN(C(=O)c4ccc(-c5ccc(C)cc5)cc4F)CC3)cc2c1C] | 2-({1-[(3-fluoro-4'-methylbiphenyl-4-yl)carbonyl]piperidin-4-yl}methyl)-N-(2-methoxyethyl)-4-methyl-2H-indazole-5-carboxamide | $^1$H-NMR (400 MHz, DMSO-d$_6$): δ [ppm] = 1.19 (2H), 1.39 (1H), 1.57 (1H), 2.31 (4H), 2.49 (3H), 2.75 (1H), 3.01 (1H), 3.24 (3H), 3.36 (2H), 3.42 (3H), 4.32 (2H), 4.48 (1H), 7.14 (1H), 7.26 (2H), 7.39 (2H), 7.56 (4H), 8.12 (1H), 8.48 (1H). |

| Ex. | Structure | IUPAC name | Analysis |
|---|---|---|---|
| 45 | 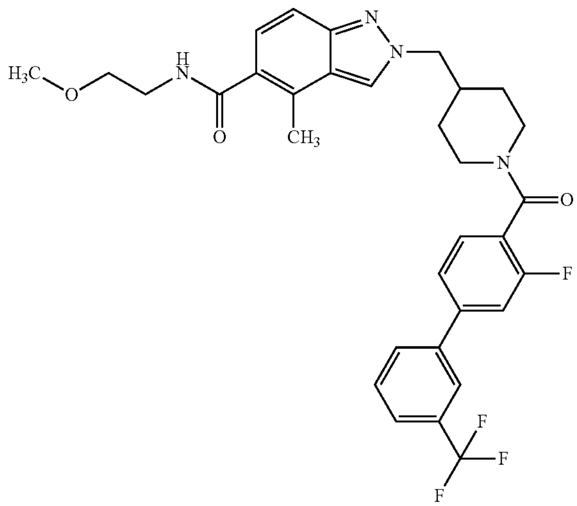 [SMILES: COCCNC(=O)c1ccc2nn(CC3CCN(C(=O)c4ccc(-c5cccc(C(F)(F)F)c5)cc4F)CC3)cc2c1C] | 2-[(1-{[3-fluoro-3'-(trifluoromethyl)-biphenyl-4-yl]-carbonyl}-piperidin-4-yl)-methyl]-N-(2-methoxyethyl)-4-methyl-2H-indazole-5-carboxamide | $^1$H-NMR (400 MHz, DMSO-$d_6$): δ [ppm] = 1.20 (2H), 1.40 (1H), 1.57 (1H), 2.29 (1H), 2.49 (3H), 2.76 (1H), 3.03 (1H), 3.24 (3H), 3.36 (2H), 3.41 (3H), 4.33 (2H), 4.48 (1H), 7.15 (1H), 7.39 (1H), 7.45 (1H), 7.69 (4H), 8.03 (2H), 8.12 (1H), 8.49 (1H). |
| 46 | 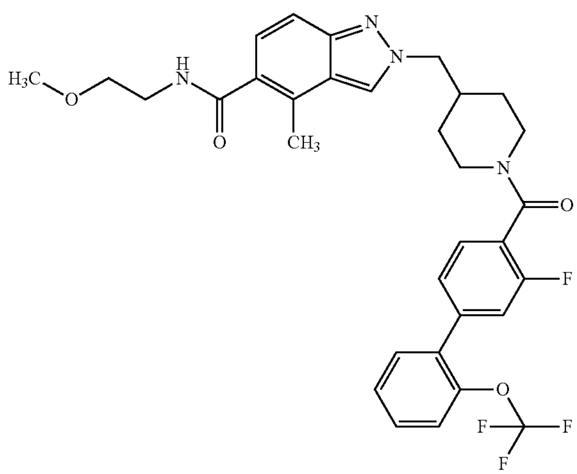 [SMILES: COCCNC(=O)c1ccc2nn(CC3CCN(C(=O)c4ccc(-c5ccccc5OC(F)(F)F)cc4F)CC3)cc2c1C] | 2-[(1-{[3-fluoro-2'-(trifluoromethoxy)-biphenyl-4-yl]-carbonyl}piperidin-4-yl)methyl]-N-(2-methoxyethyl)-4-methyl-2H-indazole-5-carboxamide | $^1$H-NMR (300 MHz, DMSO-$d_6$): δ [ppm] = 1.20 (2H), 1.42 (1H), 1.57 (1H), 2.29 (1H), 2.49 (3H), 2.76 (1H), 3.04 (1H), 3.24 (3H), 3.36 (5H), 4.32 (2H), 4.48 (1H), 7.15 (1H), 7.44 (8H), 8.12 (1H), 8.49 (1H). |
| 47 | 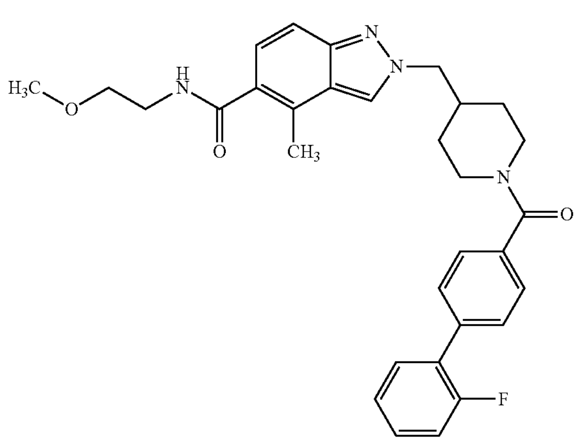 [SMILES: COCCNC(=O)c1ccc2nn(CC3CCN(C(=O)c4ccc(-c5ccccc5F)cc4)CC3)cc2c1C] | 2-({1-[(2'-fluoro-biphenyl-4-yl)-carbonyl]piperidin-4-yl}methyl)-N-(2-methoxyethyl)-4-methyl-2H-indazole-5-carboxamide | $^1$H-NMR (300 MHz, DMSO-$d_6$): δ [ppm] = 1.23 (2H), 1.41 (1H), 1.53 (1H), 2.29 (1H), 2.49 (3H), 2.74 (1H), 3.01 (1H), 3.24 (3H), 3.36 (4H), 3.60 (1H), 4.33 (2H), 4.44 (1H), 7.15 (1H), 7.29 (2H), 7.40 (4H), 7.55 (3H), 8.12 (1H), 8.48 (1H). |

-continued

| Ex. | Structure | IUPAC name | Analysis |
|---|---|---|---|
| 48 | 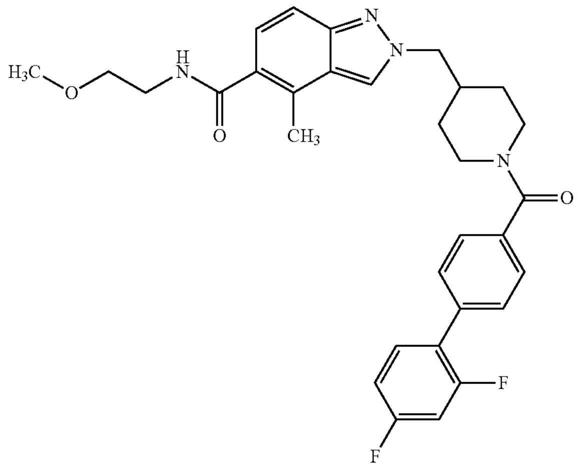 [SMILES: COCCNC(=O)c1ccc2nn(CC3CCN(C(=O)c4ccc(-c5ccc(F)cc5F)cc4)CC3)cc2c1C] | 2-({1-[(2',4'-difluoro-biphenyl-4-yl)-carbonyl]piperidin-4-yl}methyl)-N-(2-methoxyethyl)-4-methyl-2H-indazole-5-carboxamide | $^{1}$H-NMR (300 MHz, DMSO-d$_6$): δ [ppm] = 1.23 (2H), 1.39 (1H), 1.53 (1H), 2.28 (1H), 2.49 (3H), 2.75 (1H), 3.01 (1H), 3.24 (3H), 3.39 (4H), 3.60 (1H), 4.33 (2H), 4.43 (1H), 7.16 (2H), 7.40 (4H), 7.56 (3H), 8.12 (1H), 8.48 (1H). |
| 49 | 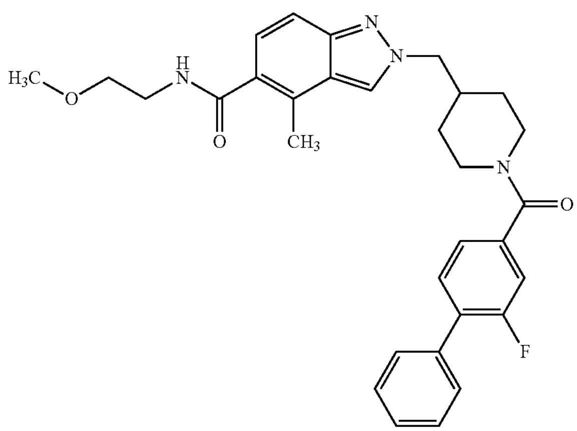 [SMILES: COCCNC(=O)c1ccc2nn(CC3CCN(C(=O)c4ccc(-c5ccccc5)c(F)c4)CC3)cc2c1C] | 2-({1-[(2-fluoro-biphenyl-4-yl)-carbonyl]piperidin-4-yl}methyl)-N-(2-methoxyethyl)-4-methyl-2H-indazole-5-carboxamide | $^{1}$H-NMR (400 MHz, DMSO-d$_6$): δ [ppm] = 1.24 (2H), 1.39 (1H), 1.56 (1H), 2.29 (1H), 2.49 (3H), 2.74 (1H), 3.02 (1H), 3.25 (3H), 3.37 (2H), 3.42 (2H), 3.59 (1H), 4.33 (2H), 4.43 (1H), 7.15 (1H), 7.28 (2H), 7.40 (2H), 7.46 (2H), 7.54 (3H), 8.12 (1H), 8.48 (1H). |
| 50 | 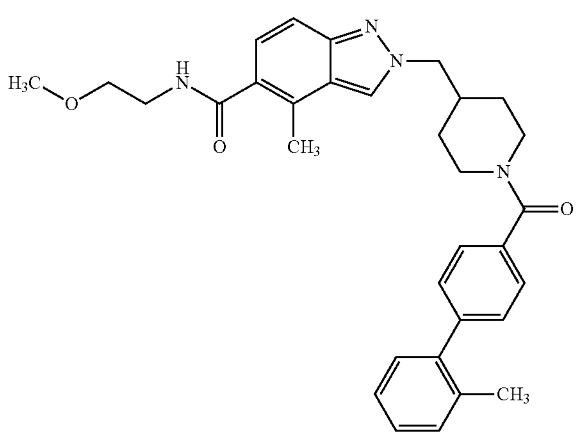 [SMILES: COCCNC(=O)c1ccc2nn(CC3CCN(C(=O)c4ccc(-c5ccccc5C)cc4)CC3)cc2c1C] | N-(2-methoxyethyl)-4-methyl-2-({1-[(2'-methylbiphenyl-4-yl)carbonyl]piperidin-4-yl}methyl)-2H-indazole-5-carboxamide | $^{1}$H-NMR (400 MHz, DMSO-d$_6$): δ [ppm] = 1.24 (2H), 1.42 (1H), 1.55 (1H), 2.20 (3H), 2.29 (1H), 2.49 (3H), 2.75 (1H), 3.02 (1H), 3.25 (3H), 3.37 (2H), 3.42 (2H), 3.64 (1H), 4.33 (2H), 4.42 (1H), 7.21 (5H), 7.38 (5H), 8.12 (1H), 8.49 (1H). |

| Ex. | Structure | IUPAC name | Analysis |
|---|---|---|---|
| 51 | 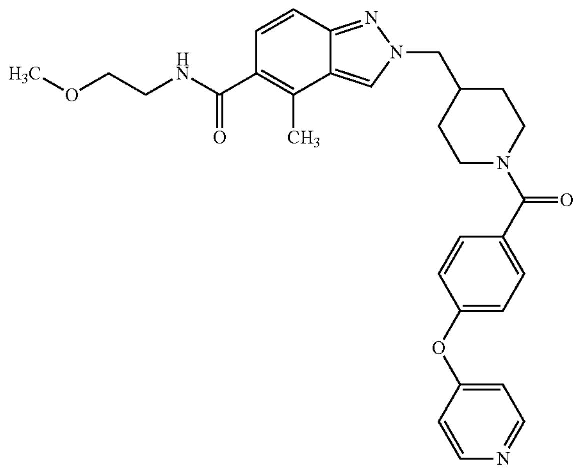 [SMILES: COCCNC(=O)c1ccc2nn(CC3CCN(C(=O)c4ccc(Oc5ccncc5)cc4)CC3)cc2c1C] | N-(2-methoxyethyl)-4-methyl-2-({1-[4-(pyridyloxy)benzoyl]-piperidin-4-yl}methyl)-2H-indazole-5-carboxamide | ¹H-NMR (400 MHz, DMSO-d₆): δ [ppm] = 1.24 (2H), 1.42 (1H), 1.55 (1H), 2.29 (1H), 2.49 (3H), 2.76 (1H), 3.02 (1H), 3.25 (3H), 3.37 (2H), 3.43 (2H), 3.60 (1H), 4.33 (2H), 4.44 (1H), 7.15 (1H), 7.37 (3H), 7.48 (2H), 7.53 (2H), 8.12 (1H), 8.48 (1H), 8.75 (2H). |
| 52 | 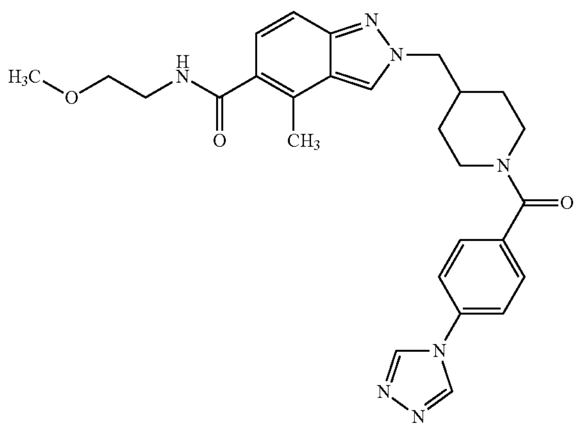 [SMILES: COCCNC(=O)c1ccc2nn(CC3CCN(C(=O)c4ccc(-n5cnnc5)cc4)CC3)cc2c1C] | N-(2-methoxyethyl)-4-methyl-2-({1-[4-(4H-1,2,4-triazol-4-yl)benzoyl]piperidin-4-yl}methyl)-2H-indazole-5-carboxamide | ¹H-NMR (400 MHz, DMSO-d₆): δ [ppm] = 1.23 (2H), 1.38 (1H), 1.54 (1H), 2.28 (1H), 2.49 (3H), 2.74 (1H), 3.02 (1H), 3.24 (3H), 3.36 (2H), 3.42 (2H), 3.53 (1H), 4.32 (2H), 4.42 (1H), 7.14 (1H), 7.38 (1H), 7.55 (2H), 7.75 (2H), 8.14 (1H), 8.48 (1H), 9.15 (2H). |
| 53 | 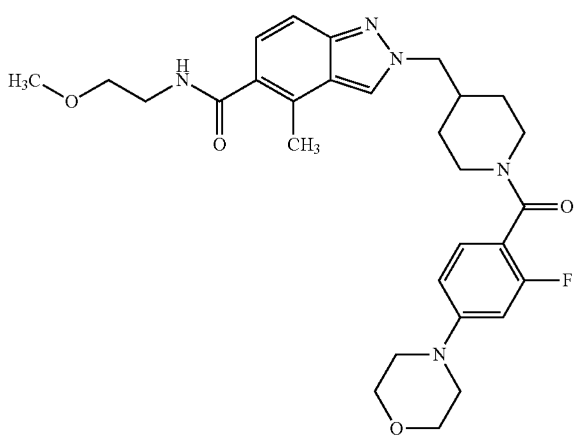 [SMILES: COCCNC(=O)c1ccc2nn(CC3CCN(C(=O)c4ccc(N5CCOCC5)cc4F)CC3)cc2c1C] | 2-({1-[2-fluoro-4-(morpholin-4-yl)benzoyl]-piperidin-4-yl}methyl)-N-(2-methoxyethyl)-4-methyl-2H-indazole-5-carboxamide | ¹H-NMR (600 MHz, DMSO-d₆): δ [ppm] = 1.01 (1H), 1.21 (1H), 1.36 (1H), 1.48 (1H), 1.57 (1H), 2.08 (1H), 2.53 (3H), 2.96 (7H), 3.29 (3H), 3.41 (2H), 3.47 (2H), 3.67 (4H), 4.34 (2H), 4.50 (1H), 6.86 (2H), 7.14 (2H), 7.41 (1H), 8.11 (1H), 8.47 (1H), 8.56 (1H). |

| Ex. | Structure | IUPAC name | Analysis |
|---|---|---|---|
| 54 | 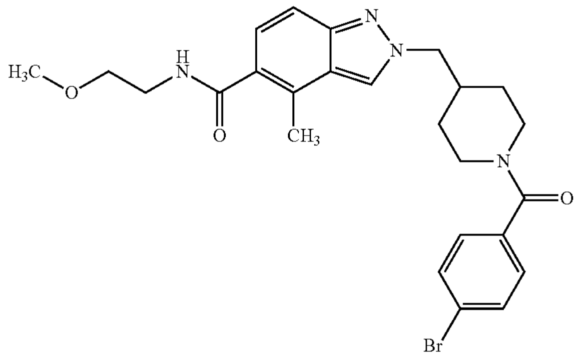 | 2-{[1-(4-bromo-benzoyl)piperidin-4-yl]methyl}-N-(2-methoxyethyl)-4-methyl-2H-indazole-5-carboxamide | $^1$H-NMR (300 MHz, DMSO-$d_6$): δ [ppm] = 1.22 (2H), 1.36 (1H), 1.52 (1H), 2.26 (1H), 2.49 (3H), 2.72 (1H), 2.97 (1H), 3.24 (3H), 3.36 (2H), 3.42 (2H), 3.49 (1H), 4.31 (2H), 4.40 (1H), 7.14 (1H), 7.29 (2H), 7.38 (1H), 7.60 (2H), 8.12 (1H), 8.47 (1H). |

Example 55

N-(2-methoxyethyl)-4-methyl-2-({1-[4-(trifluoromethoxy)benzoyl]piperidin-4-yl}methyl)-2H-indazole-5-carboxamide

Example 56

2-{[1-(4-chlorobenzoyl)piperidin-4-yl]methyl}-N-(2-methoxyethyl)-4-methyl-2H-indazole-5-carboxamide

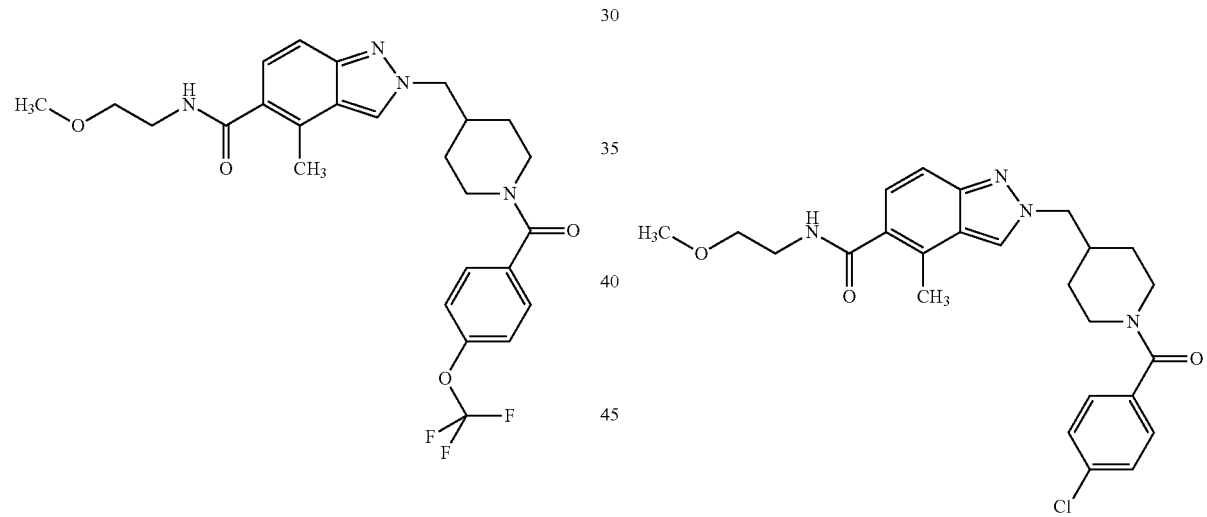

150 mg of the amine prepared in Example 1a were first dissolved in 1.5 ml pyridine. 101 mg of 4-(trifluoromethoxy)benzoyl chloride were then added and the mixture stirred for 30 min at RT. The reaction mixture was then treated with some toluene and concentrated. The residue was taken up in ethyl acetate and washed twice with water, twice with saturated sodium hydrogen carbonate solution (pH 9) and once with saturated sodium chloride solution. The organic phase was dried over sodium sulphate, filtered and concentrated. The residue was purified chromatographically on the Biotage SP4. Gradient: ethyl acetate/methanol 0-10%. Yield: 118.2 mg of the title compound.

$^1$H-NMR (300 MHz, DMSO-$d_6$): ☐ [ppm], 1.17-1.30 (2H), 1.30-1.45 (1H), 1.45-1.62 (1H), 2.19-2.35 (1H), 2.49 (3H), 2.64-2.86 (1H), 2.86-3.07 (1H), 3.24 (3H), 3.31-3.56 (5H), 4.31 (2H), 4.36-4.49 (1H), 7.14 (1H), 7.35-7.42 (3H), 7.43-7.50 (2H), 8.11 (1H), 8.47 (1H).

Analogously to Example 55, 183 mg of the title compound was obtained from 300 mg of the amine prepared in Example 1a and 157.4 mg of 4-chlorobenzoyl chloride.

$^1$H-NMR (400 MHz, DMSO-$d_6$): δ [ppm], 1.10-1.29 (2H), 1.29-1.43 (1H), 1.44-1.61 (1H), 2.20-2.34 (1H), 2.49 (3H), 2.66-2.83 (1H), 2.84-3.06 (1H), 3.25 (3H), 3.32-3.39 (2H), 3.40-3.45 (2H), 3.45-3.55 (1H), 4.26-4.35 (2H), 4.35-4.46 (1H), 7.14 (1H), 7.32-7.41 (3H), 7.47 (2H), 8.09-8.15 (1H), 8.47 (1H).

Example 57

N-(2-methoxyethyl)-4-methyl-2-[(1-{4-[(trifluoromethyl)sulphanyl]benzoyl}piperidin-4-yl)methyl]-2H-indazole-5-carboxamide

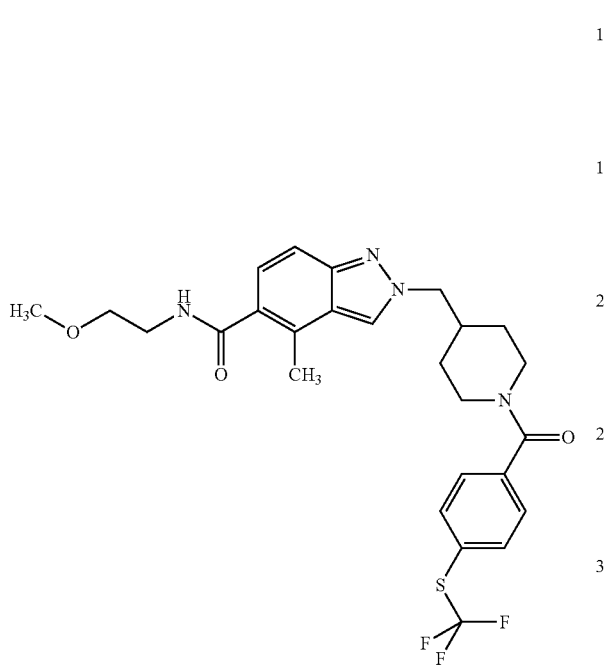

60 mg of the amine prepared in Example 1a were first dissolved in 2 ml DCM at 0° C. 0.034 ml of triethylamine and 43.2 mg of 4-[(trifluoromethyl)sulphanyl]benzoyl chloride were then added and the mixture stirred for 2 hrs at 0° C. The reaction mixture was then diluted with DCM and washed with 1-molar hydrochloric acid, saturated sodium hydrogen carbonate solution (pH 9) and saturated sodium chloride solution. The organic phase was dried over sodium sulphate, filtered and concentrated. The residue was purified chromatographically on the Biotage SP4. Gradient: DCM/Methanol 0-10%. The product fraction was taken up in ethyl acetate and extracted twice with saturated sodium hydrogen carbonate solution. The organic phase was concentrated and the residue again purified by HPLC. Yield: 26.5 mg of the title compound.

$^1$H-NMR (400 MHz, DMSO-d$_6$): δ [ppm], 1.14-1.30 (2H), 1.31-1.42 (1H), 1.49-1.61 (1H), 2.21-2.32 (1H), 2.49 (3H), 2.67-2.80 (1H), 2.93-3.05 (1H), 3.25 (3H), 3.36 (2H), 3.42 (3H), 4.27-4.36 (2H), 4.38-4.48 (1H), 7.14 (1H), 7.38 (1H), 7.48 (2H), 7.75 (2H), 8.09-8.14 (1H), 8.47 (1H).

Example 58

2-({1-[2-fluoro-4-(trifluoromethyl)benzoyl]piperidin-4-yl}methyl)-4-methyl-N-(2-morpholinoethyl)-2H-indazole-5-carboxamide

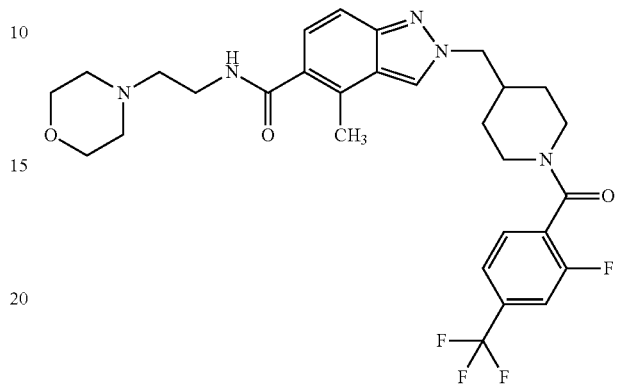

Analogously to Example 1, 34.6 mg of the title compound was obtained from 75 mg of the amine prepared in Example 58a and 37.0 mg of 2-fluoro-4-(trifluoromethyl)benzoic acid.

$^1$H-NMR (400 MHz, methanol-d$_4$): δ [ppm], 1.24-1.43 (2H), 1.50-1.59 (1H), 1.65-1.73 (1H), 2.33-2.45 (1H), 2.65 (3H), 2.80-2.91 (1H), 3.05-3.18 (1H), 3.19-3.26 (2H), 3.39-3.44 (2H), 3.45-3.52 (1H), 3.63-3.70 (2H), 3.71-3.82 (4H), 4.06-4.14 (2H), 4.39 (2H), 4.62-4.70 (1H), 7.39 (1H), 7.47 (1H), 7.54-7.62 (3H), 8.45 (1H).

The starting material was prepared as follows:

Example 58a 4-methyl-N-(2-morpholinoethyl)-2-(4-piperidylmethyl)-2H-indazol-5-carboxamide hydrochloride To 624.4 mg of 58b were added 2.9 ml of 4M hydrochloric acid in dioxan and 0.5 ml dioxan. An oily mass was formed, which dissolved on vigorous stirring and gentle warming. The mixture was stirred for 1 hr at ca. 30° C. The reaction mixture was concentrated. Yield: 980 mg of the title compound, which was further reacted without further purification.

$^1$H-NMR (300 MHz, DMSO-d$_6$): δ [ppm], 1.33-1.51 (2H), 1.58-1.64 (1H), 2.17-2.31 (1H), 2.55 (3H), 2.70-2.86 (2H), 3.02-3.31 (7H), 3.43-3.51 (2H), 3.61-3.71 (2H), 3.72-3.88 (3H), 3.89-3.99 (2H), 4.30-4.36 (2H), 7.29 (1H), 7.40 (1H), 8.46-8.52 (1H), 8.54-8.58 (1H), 8.69-8.85 (1H), 8.96-9.10 (1H).

Example 58b

Tert-butyl 4-({4-methyl-5-[N-(2-morpholinoethyl)carbamoyl]-1H-indazol-2-yl}-methyl)piperidin-1-carboxylate

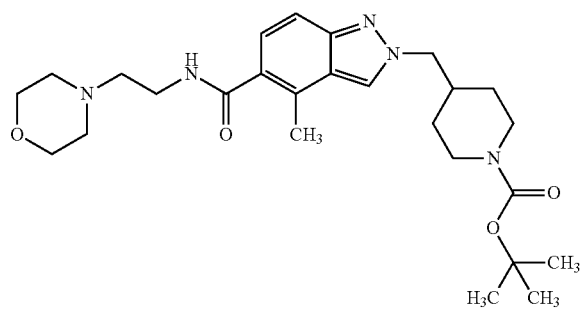 [SMILES: Cc1c(C(=O)NCCN2CCOCC2)ccc2nn(CC3CCN(C(=O)OC(C)(C)C)CC3)cc12]

896 mg of 1c, 857 mg of 2-morpholinoethylamine, 579.3 mg of molybdenum hexacarbonyl, 63.6 mg of tri-tert-butylphosphine tetrafluoroborate and 205.8 mg of trans-bis(acetato)-bis[o-(di-o-tolylphosphino)benzyl]dipalladium(II) were placed in a microwave tube and suspended in 18 ml THF. 1.0 ml of DBU was then added and the mixture was stirred for 20 mins at 125° C. and 200 watts in the microwave. The reaction mixture was diluted with some ethyl acetate and firstly filtered through Celite. The filtrate was diluted with ethyl acetate and the organic phase washed twice with water and once with saturated sodium chloride solution. It was then dried over sodium sulphate, filtered and concentrated. The residue was chromatographed on the Biotage SP4. Gradient: ethyl acetate/methanol 0-10%. Yield: 624.4 mg of the title compound.

$^1$H-NMR (300 MHz, DMSO-$d_6$): δ [ppm], 0.98-1.13 (2H), 1.34 (11H), 2.05-2.27 (2H), 2.33-2.41 (5H), 2.51 (3H), 2.56-2.73 (2H), 3.25-3.37 (2H), 3.51-3.57 (4H), 3.81-3.93 (2H), 4.28 (2H), 7.14 (1H), 7.36-7.41 (1H), 7.95-8.02 (1H), 8.46 (1H).

Example 59

4-methyl-N-(2-morpholinoethyl)-2-({1-[4-(trifluoromethoxy)benzoyl]piperidin-4-yl}methyl)-2H-indazole-5-carboxamide

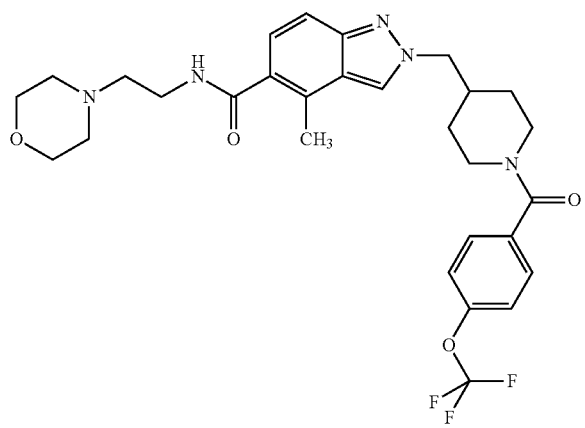 [SMILES: Cc1c(C(=O)NCCN2CCOCC2)ccc2nn(CC3CCN(C(=O)c4ccc(OC(F)(F)F)cc4)CC3)cc12]

Analogously to Example 55, 10.1 mg of the title compound was obtained from 75 mg of the amine prepared in Example 58a and 43.9 mg of 4-(trifluoromethoxy)benzoyl chloride.

$^1$H-NMR (400 MHz, methanol-$d_4$): δ [ppm], 1.24-1.44 (2H), 1.44-1.58 (1H), 1.59-1.74 (1H), 2.32-2.44 (1H), 2.51-2.58 (4H), 2.59-2.65 (5H), 2.77-2.90 (1H), 3.02-3.17 (1H), 3.53 (2H), 3.62-3.72 (5H), 4.35-4.41 (2H), 4.55-4.67 (1H), 7.29 (1H), 7.34 (2H), 7.43 (1H), 7.49 (2H), 8.39 (1H).

Example 60

4-methyl-N-(2-morpholinoethyl)-2-({1-[4-(pentafluoro-$\lambda^6$-sulphanyl)benzoyl]-piperidin-4-yl}methyl)-2H-indazole-5-carboxamide

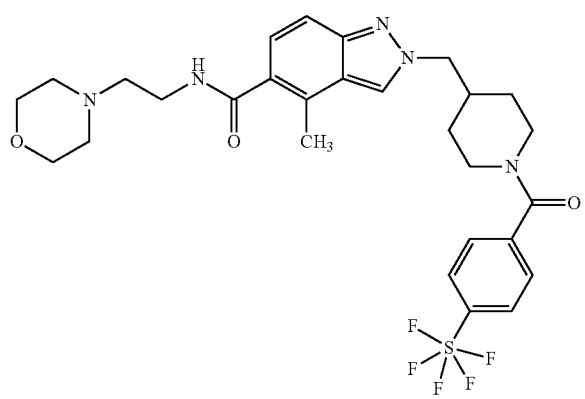 [SMILES: Cc1c(C(=O)NCCN2CCOCC2)ccc2nn(CC3CCN(C(=O)c4ccc(S(F)(F)(F)(F)F)cc4)CC3)cc12]

Analogously to Example 1, 14.0 mg of the title compound was obtained from 75 mg of the amine prepared in Example 58a and 44.1 mg of 4-(pentafluoro-$\lambda^6$-sulphanyl)benzoic acid.

$^1$H-NMR (400 MHz, chloroform-d): δ [ppm], 1.16-1.32 (1H), 1.33-1.48 (1H), 1.50-1.63 (1H), 1.71-1.83 (1H), 1.84-2.08 (2H), 2.44 (1H), 2.55 (4H), 2.60-2.71 (5H), 2.72-2.85 (1H), 2.96-3.10 (1H), 3.60 (2H), 3.67-3.78 (4H), 4.33 (2H), 4.71-4.81 (1H), 6.45 (1H), 7.34 (1H), 7.47 (2H), 7.54 (1H), 7.79 (2H), 7.96 (1H).

Example 61

4-methyl-N-(2-morpholinoethyl)-2-({1-[3-(trifluoromethoxy)benzoyl]piperidin-4-yl}methyl)-2H-indazole-5-carboxamide

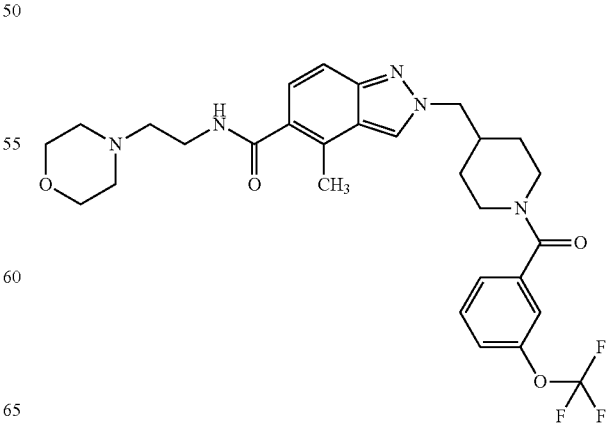

Analogously to Example 55, 18.1 mg of the title compound was obtained from 75 mg of the amine prepared in Example 58a and 43.9 mg of 3-(trifluoromethoxy)benzoyl chloride.

$^1$H-NMR (400 MHz, chloroform-d): δ [ppm], 1.18-1.46 (2H), 1.49-1.63 (1H), 1.66-1.82 (1H), 2.37-2.49 (1H), 2.62 (3H), 2.67 (3H), 2.70-2.78 (4H), 2.79-2.86 (2H), 2.93-3.09 (1H), 3.66-3.74 (2H), 3.83 (4H), 4.32 (2H), 4.66-4.82 (1H), 6.83-6.96 (1H), 7.23-7.29 (2H), 7.29-7.34 (1H), 7.39 (1H), 7.43 (1H), 7.54 (1H), 7.96 (1H).

Example 62

2-{[1-(4-chlorobenzoyl)piperidin-4-yl]methyl}-4-methyl-N-(2-morpholinoethyl)-2H-indazole-5-carboxamide

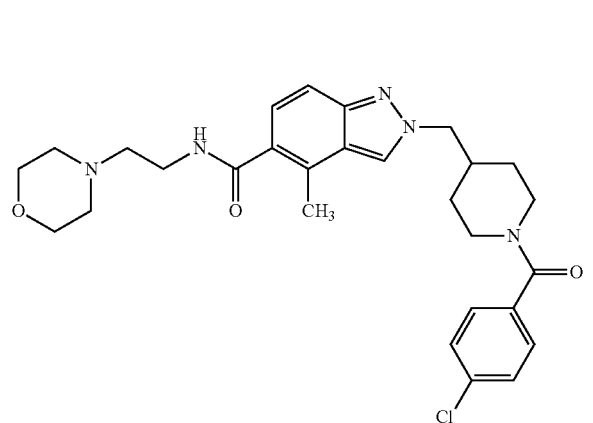 [SMILES: Cc1c(C(=O)NCCN2CCOCC2)ccc2nn(CC3CCN(C(=O)c4ccc(Cl)cc4)CC3)cc12]

Analogously to Example 55, 14.9 mg of the title compound was obtained from 75 mg of the amine prepared in Example 58a and 34.2 mg of 4-chlorobenzoyl chloride.

$^1$H-NMR (400 MHz, methanol-d$_4$): δ [ppm], 1.24-1.42 (2H), 1.46-1.58 (1H), 1.58-1.71 (1H), 2.31-2.43 (1H), 2.63 (5H), 2.65 (3H), 2.73-2.91 (1H), 3.00-3.15 (1H), 3.25-3.33 (2H), 3.63-3.77 (3H), 3.79-4.03 (3H), 4.38 (2H), 4.54-4.67 (1H), 7.38 (3H), 7.42-7.49 (3H), 8.44 (1H).

Example 63

4-methyl-N-(2-morpholinoethyl)-2-({1-[4-(trifluoromethyl)benzoyl]piperidin-4-yl}methyl)-2H-indazole-5-carboxamide

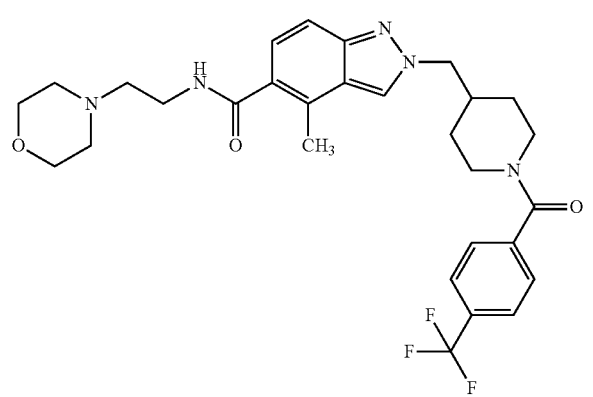 [SMILES: Cc1c(C(=O)NCCN2CCOCC2)ccc2nn(CC3CCN(C(=O)c4ccc(C(F)(F)F)cc4)CC3)cc12]

Analogously to Example 1, 31.7 mg of the title compound was obtained from 75 mg of the amine prepared in Example 58a and 33.8 mg of 4-(trifluoromethyl)benzoic acid.

$^1$H-NMR (400 MHz, methanol-d4): δ [ppm], 1.24-1.43 (2H), 1.45-1.57 (1H), 1.63-1.73 (1H), 2.33-2.45 (1H), 2.66 (3H), 2.79-2.90 (1H), 3.04-3.17 (1H), 3.18-3.27 (2H), 3.39-3.45 (2H), 3.56-3.70 (3H), 3.76 (4H), 4.06-4.14 (2H), 4.36-4.42 (2H), 4.59-4.68 (1H), 7.39 (1H), 7.47 (1H), 7.57 (2H), 7.73 (2H), 8.45 (1H).

Example 64

4-methyl-N-(2-morpholinoethyl)-2-({1-[4-(pentafluoro-λ$^6$-sulphanyl)benzoyl]-piperidin-4-yl}methyl)-2H-indazole-5-carboxamide

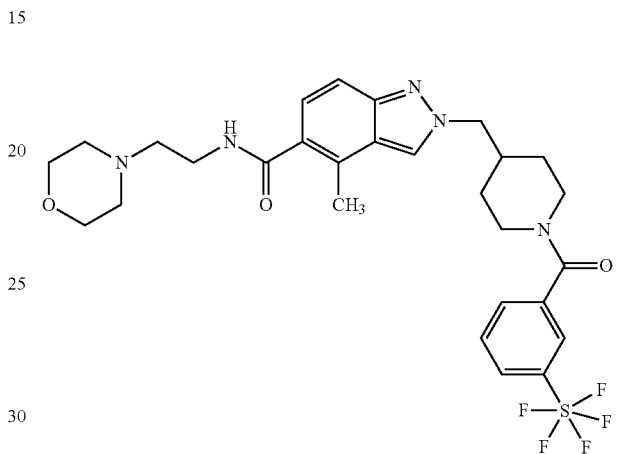

Analogously to Example 1, 24.7 mg of the title compound was obtained from 75 mg of the amine prepared in Example 58a and 44.1 mg of 3-(pentafluoro-λ$^6$-sulphanyl)benzoic acid.

$^1$H-NMR (400 MHz, methanol-d$_4$): δ [ppm], 1.27-1.47 (2H), 1.48-1.60 (1H), 1.60-1.74 (1H), 2.31-2.46 (1H), 2.66 (3H), 2.78-2.93 (1H), 3.04-3.18 (1H), 3.18-3.26 (2H), 3.39-3.43 (2H), 3.57-3.70 (3H), 3.72-3.82 (4H), 4.06-4.14 (2H), 4.39 (2H), 4.55-4.67 (1H), 7.38 (1H), 7.47 (1H), 7.60-7.67 (2H), 7.82-7.86 (1H), 7.89-7.94 (1H), 8.45 (1H).

Example 65

4-methyl-N-(2-morpholinoethyl)-2-({1-[3-(trifluoromethyl)benzoyl]piperidin-4-yl}methyl)-2H-indazole-5-carboxamide

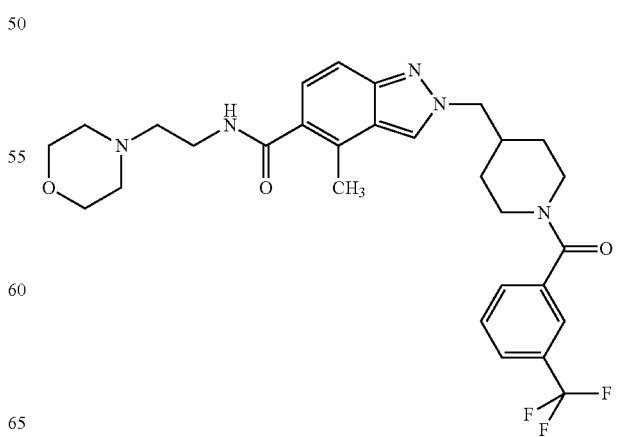

Analogously to Example 1, 14.0 mg of the title compound was obtained from 75 mg of the amine prepared in Example 58a and 33.8 mg of 3-(trifluoromethyl)benzoic acid.

¹H-NMR (400 MHz, methanol-d₄): δ [ppm], 1.28-1.45 (2H), 1.47-1.59 (1H), 1.59-1.73 (1H), 2.32-2.45 (1H), 2.66 (3H), 2.79-2.93 (1H), 3.05-3.18 (1H), 3.19-3.27 (2H), 3.39-3.45 (2H), 3.58-3.70 (3H), 3.72-3.82 (4H), 4.06-4.14 (2H), 4.39 (2H), 4.57-4.68 (1H), 7.39 (1H), 7.47 (1H), 7.64 (2H), 7.67-7.70 (1H), 7.73-7.78 (1H), 8.45 (1H).

The following compounds were prepared analogously:

| Ex. | Structure | IUPAC name | Analysis |
|-----|-----------|------------|----------|
| 66 | 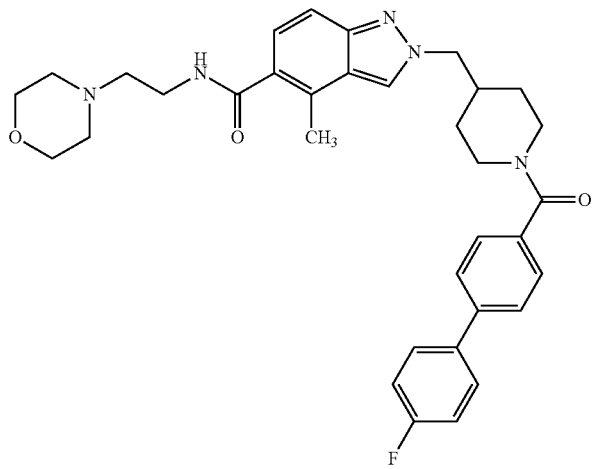 [SMILES: Cc1c(C(=O)NCCN2CCOCC2)ccc2nn(CC3CCN(C(=O)c4ccc(-c5ccc(F)cc5)cc4)CC3)cc12] | 2-({1-[(4'-fluoro-biphenyl-4-yl)-carbonyl]piperidin-4-yl}methyl)-4-methyl-N-(2-morpholino-ethyl)-2H-indazole-5-carboxamide | 1H-NMR (400 MHz, methanol-d₄): δ [ppm] = 1.35 (2H), 1.53 (1H), 1.66 (1H), 2.40 (1H), 2.66 (3H), 2.85 (1H), 3.11 (1H), 3.24 (2H), 3.42 (2H), 3.65 (2H), 3.76 (5H), 4.08 (2H), 4.40 (2H), 4.63 (1H), 7.17 (2H), 7.38 (1H), 7.47 (3H), 7.65 (4H), 8.45 (1H). |
| 67 | 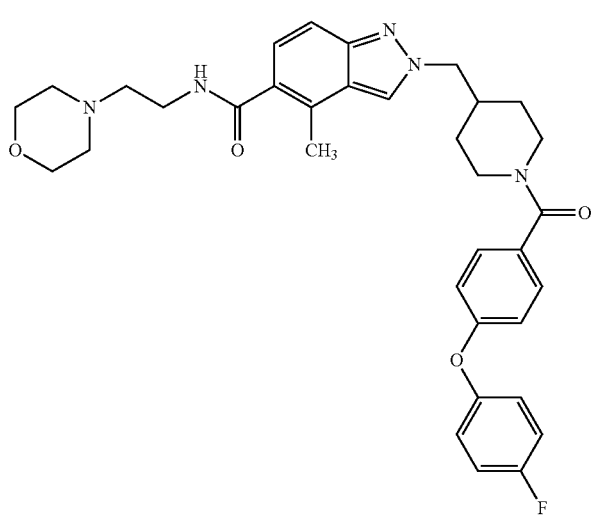 [SMILES: Cc1c(C(=O)NCCN2CCOCC2)ccc2nn(CC3CCN(C(=O)c4ccc(Oc5ccc(F)cc5)cc4)CC3)cc12] | 2-({1-[4-(4-fluoro-phenoxy)benzoyl]-piperidinyl-4-yl}-methyl)-4-methyl-N-(2-morpholinoethyl)-2H-indazole-5-carboxamide | 1H-NMR (400 MHz, methanol-d₄): δ [ppm] = 1.33 (2H), 1.68 (2H), 2.38 (1H), 2.66 (3H), 2.84 (1H), 3.11 (1H), 3.25 (2H), 3.42 (2H), 3.65 (2H), 3.76 (5H), 4.11 (2H), 4.38 (2H), 4.59 (1H), 6.98 (2H), 7.04 (2H), 7.11 (2H), 7.38 (3H), 7.47 (1H), 8.44 (1H). |

Example 68

N-[2-(3,3-difluoropyrrolidin-1-yl)ethyl]-4-methyl-2-({1-[4-(pentafluoro-λ⁶-sulphanyl)benzoyl]piperidin-4-yl}methyl)-2H-indazole-5-carboxamide

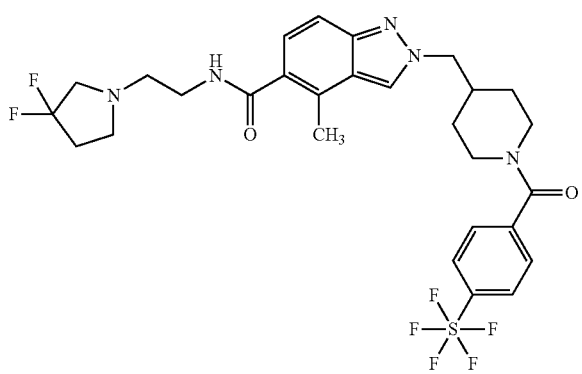 [SMILES: Cc1c(C(=O)NCCN2CCC(F)(F)C2)ccc2nn(CC3CCN(C(=O)c4ccc(S(F)(F)(F)(F)F)cc4)CC3)cc12]

Analogously to Example 57, 61.7 mg of the title compound was obtained from 266.5 mg of the amine prepared in Example 68a and 150.3 mg of 4-(pentafluoro-λ⁶-sulphanyl)benzoyl chloride.

¹H-NMR (300 MHz, chloroform-d): δ [ppm], 1.13-1.46 (2H), 1.48-1.65 (1H), 1.66-1.87 (1H), 2.26-2.50 (3H), 2.66 (3H), 2.71-3.23 (8H), 3.57-3.72 (3H), 4.25-4.42 (2H), 4.67-4.84 (1H), 6.40-6.61 (1H), 7.38 (1H), 7.47 (2H), 7.53 (1H), 7.79 (2H), 7.96 (1H).

The starting material was prepared as follows:

Example 68a

N-[2-(3,3-difluoropyrrolidin-1-yl)ethyl]-4-methyl-2-(4-piperidylmethyl)-2H-indazole-5-carboxamide hydrochloride

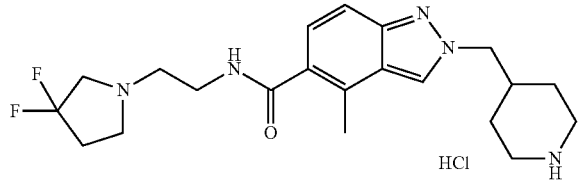 [SMILES: Cc1c(C(=O)NCCN2CCC(F)(F)C2)ccc2nn(CC3CCNCC3)cc12 ; Cl]

To 416.6 mg of 68b were added 1.85 ml of 4M hydrochloric acid in dioxan and 0.5 ml dioxan. An oily mass was formed, which dissolved on vigorous stirring and gentle warming. The mixture was stirred for 1 hr at ca. 30° C. The reaction mixture was concentrated. Yield: 439.2 mg of the title compound, which was further reacted without further purification.

¹H-NMR (400 MHz, DMSO-d₆): δ [ppm], 1.36-1.48 (2H), 1.54-1.63 (2H), 2.18-2.28 (1H), 2.40-2.45 (2H), 2.55 (3H), 2.72-2.83 (2H), 3.14-3.22 (2H), 3.38-3.44 (2H), 3.56-3.63 (2H), 3.65-3.95 (2H), 4.11-4.21 (2H), 7.32 (1H), 7.40 (1H), 8.43-8.48 (1H), 8.57 (1H), 8.68-8.82 (1H), 8.96-9.07 (1H).

Example 68b

Tert-butyl 4-[(5-{N-[2-(3,3-difluoropyrrolidin-1-yl)ethyl]carbamoyl}-4-methyl-2H-indazol-2-yl)methyl]-piperidin-1-carboxylate 220 mg of 1c, 242.7 mg of 2-(3,3-difluoro-pyrrolidin-1-yl)ethylamine, 142.2 mg of molybdenum hexacarbonyl, 15.6 mg of tri-tert-butylphosphine tetrafluoroborate and 50.5 mg of trans-bis(acetato)-bis[o-(di-o-tolylphosphino)benzyl] dipalladium(II) were placed in a microwave tube and suspended in 4.4 ml THF. 0.24 ml of DBU were then added and the mixture stirred for 20 mins at 125° C. and 200 watts in the microwave. The reaction mixture was diluted with some ethyl acetate and firstly filtered through Celite. The filtrate was diluted with ethyl acetate and the organic phase washed twice with water and once with saturated sodium chloride solution. It was dried over sodium sulphate, filtered and concentrated. The residue (209.3 mg) was chromatographed on the Biotage SP4. Gradient: DCM/methanol 0-10%. Yield: 53.4 mg of the title compound.

¹H-NMR (400 MHz, DMSO-d₆): δ [ppm], 1.00-1.12 (2H), 1.32-1.42 (2H), 1.34 (9H), 2.07-2.25 (3H), 2.50 (3H), 2.57 (2H), 2.60-2.68 (2H), 2.72 (2H), 2.91 (2H), 3.30-3.35 (2H), 3.83-3.92 (2H), 4.28 (2H), 7.15 (1H), 7.39 (1H), 8.04-8.09 (1H), 8.47 (1H).

Example 69

2-{[1-(4-chlorobenzoyl)piperidin-4-yl]methyl}-N-[2-(3,3-difluoropyrrolidin-1-yl)ethyl]-4-methyl-2H-indazole-5-carboxamide Analogously to Example 57, 79.9 mg of the title compound was obtained from 125.0 mg of the amine prepared in Example 68a and 54.5 mg of 4-chlorobenzoyl chloride.

¹H-NMR (300 MHz, chloroform-d): δ [ppm], 1.13-1.35 (2H), 1.46-1.84 (2H), 2.27-2.50 (3H), 2.66 (3H), 2.80-3.26 (8H), 3.59-3.83 (3H), 4.25-4.39 (2H), 4.62-4.85 (1H), 6.41-6.69 (1H), 7.30-7.40 (6H), 7.55 (1H), 7.96 (1H).

Example 70

N-[2-(3,3-difluoropyrrolidin-1-yl)ethyl]-4-methyl-2-[(1-{4-[(trifluoromethyl)sulphanyl]benzoyl}piperidin-4-yl)methyl]-2H-indazole-5-carboxamide

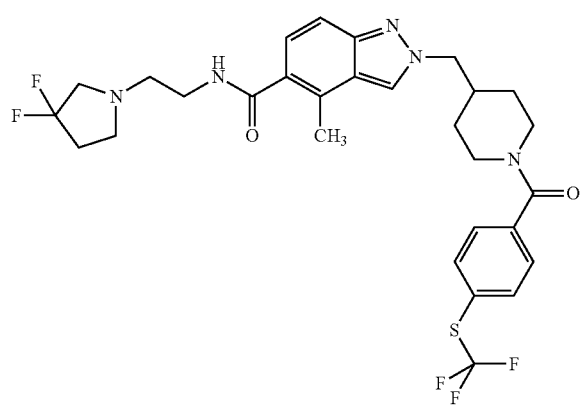 [SMILES: Cc1c(C(=O)NCCN2CCC(F)(F)C2)ccc2nn(CC3CCN(C(=O)c4ccc(SC(F)(F)F)cc4)CC3)cc12]

Analogously to Example 55, 15.2 mg of the title compound was obtained from 23.4 mg of the amine prepared in Example 68a and 14.0 mg of 4-[(trifluoromethyl)sulphanyl]benzoyl chloride.

¹H-NMR (400 MHz, chloroform-d): δ [ppm], 1.23-1.26 (1H), 1.33-1.46 (1H), 1.48-1.61 (1H), 1.77 (1H), 2.20-2.35 (2H), 2.36-2.49 (1H), 2.64 (3H), 2.73-2.85 (5H), 2.90-3.10 (3H), 3.56 (2H), 3.63-3.76 (1H), 4.26-4.39 (2H), 4.70-4.82 (1H), 6.28 (1H), 7.33 (1H), 7.42 (2H), 7.53 (1H), 7.68 (2H), 7.96 (1H).

Example 71

4-methyl-2-({1-[4-(pentafluoro-λ⁶-sulphanyl)benzoyl]piperidin-4-yl}methyl)-N-(2,2,2-trifluoroethyl)-2H-indazole-5-carboxamide

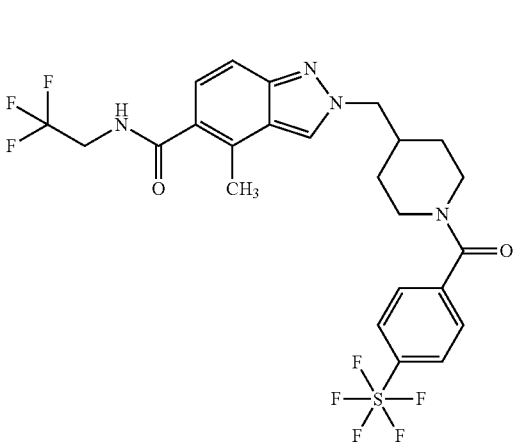 [SMILES: Cc1c(C(=O)NCC(F)(F)F)ccc2nn(CC3CCN(C(=O)c4ccc(S(F)(F)(F)(F)F)cc4)CC3)cc12]

Analogously to Example 1, 124.8 mg of the title compound was obtained from 146.9 mg of the amine prepared in Example 71a and 93.3 mg of 4-(pentafluoro-λ⁶-sulphanyl)benzoic acid.

¹H-NMR (300 MHz, DMSO-d₆): δ [ppm], 1.12-1.31 (2H), 1.31-1.45 (1H), 1.47-1.63 (1H), 2.20-2.36 (1H), 2.50 (3H), 2.67-2.83 (1H), 2.91-3.07 (1H), 3.36-3.47 (1H), 3.96-4.10 (2H), 4.29-4.37 (2H), 4.37-4.48 (1H), 7.17 (1H), 7.43 (1H), 7.56 (2H), 7.94 (2H), 8.50-8.54 (1H), 8.75-8.83 (1H).

The starting material was prepared as follows:

Example 71a 4-methyl-2-(4-piperidylmethyl)-N-(2,2,2-trifluoroethyl)-2H-indazol-5-carboxamide hydrochloride

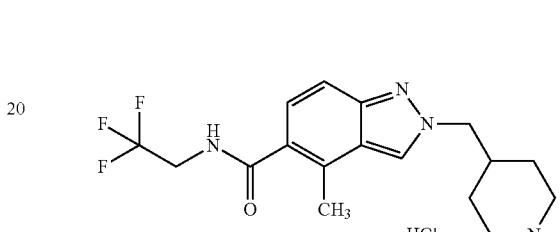

To 425.2 mg of 71b were added 2.35 ml of 4M hydrochloric acid in dioxan and 0.5 ml dioxan. An oily mass was formed, which dissolved on vigorous stirring and gentle warming. The mixture was stirred for 1 hr at ca. 30° C. The reaction mixture was concentrated. Yield: 440.6 mg of the title compound, which was further reacted without further purification.

¹H-NMR (400 MHz, DMSO-d₆): δ [ppm], 1.35-1.49 (2H), 1.53-1.62 (2H), 2.20-2.32 (1H), 2.51 (3H), 2.72-2.85 (2H), 3.14-3.23 (2H), 3.97-4.09 (2H), 4.34 (2H), 7.18 (1H), 7.43 (1H), 8.58 (1H), 8.64-8.77 (1H), 8.78-8.85 (1H), 8.93-9.08 (1H).

Example 71b

Tert-butyl 4-({4-methyl-5-[N-(2,2,2-trifluoroethyl)carbamoyl]-2H-indazol-2-yl}-methyl)piperidin-1-carboxylate

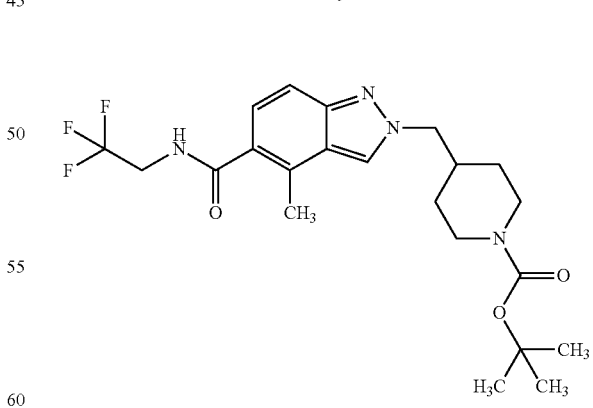

2820 mg of 1c, 2052 mg of 2,2,2-trifluoroethylamine, 1823.2 mg of molybdenum hexacarbonyl, 200.4 mg of tri-tert-butylphosphine tetrafluoroborate and 647.5 mg of trans-bis(acetato)-bis[o-(di-o-tolylphosphino)-benzyl]dipalladium(II) were placed in a microwave tube and suspended in 56 ml THF. 3.1 ml of DBU were then added and the mixture was stirred for 20 mins at 125° C. and 200 watts in the microwave. The reaction mixture was diluted with some ethyl acetate, washed twice with water and once with saturated sodium chloride solution. It was dried over sodium sulphate, filtered and concentrated. The residue was chromatographed on the Biotage SP4. Gradient: hexane/ethyl acetate 0-100%. Yield: 475.2 mg of the title compound.

$^1$H-NMR (300 MHz, DMSO-$d_6$): δ [ppm], 0.99-1.17 (2H), 1.30-1.44 (11H), 2.05-2.21 (1H), 2.50 (3H), 2.54-2.73 (2H), 3.81-3.94 (2H), 3.95-4.10 (2H), 4.29 (2H), 7.18 (1H), 7.43 (1H), 8.51 (1H), 8.74-8.83 (1H).

Example 72

2-{[1-(4-chlorobenzoyl)piperidin-4-yl]methyl}-4-methyl-N-(2,2,2-trifluoroethyl)-2H-indazole-5-carboxamide

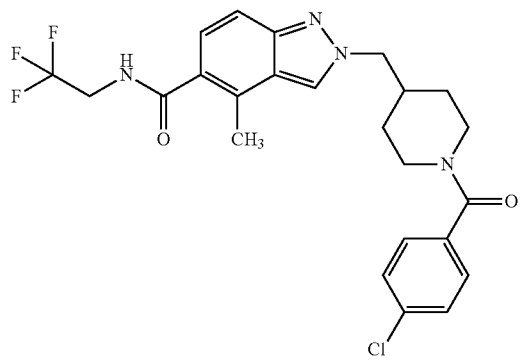 [SMILES: Cc1c(C(=O)NCC(F)(F)F)ccc2nn(CC3CCN(C(=O)c4ccc(Cl)cc4)CC3)cc12]

Analogously to Example 1, 97.8 mg of the title compound was obtained from 146.9 mg of the amine prepared in Example 71a and 58.8 mg of 4-chlorobenzoic acid.

$^1$H-NMR (300 MHz, DMSO-$d_6$): δ [ppm], 1.11-1.29 (2H), 1.31-1.45 (1H), 1.45-1.61 (1H), 2.20-2.35 (1H), 2.50 (3H), 2.63-2.84 (1H), 2.85-3.08 (1H), 3.42-3.59 (1H), 3.96-4.10 (2H), 4.29-4.47 (3H), 7.17 (1H), 7.36 (2H), 7.40-7.50 (3H), 8.52 (1H), 8.75-8.82 (1H).

Example 73

4-methyl-N-(2,2,2-trifluoroethyl)-2-({1-[4-(trifluoromethoxy)benzoyl]piperidin-4-yl}methyl)-2H-indazole-5-carboxamide

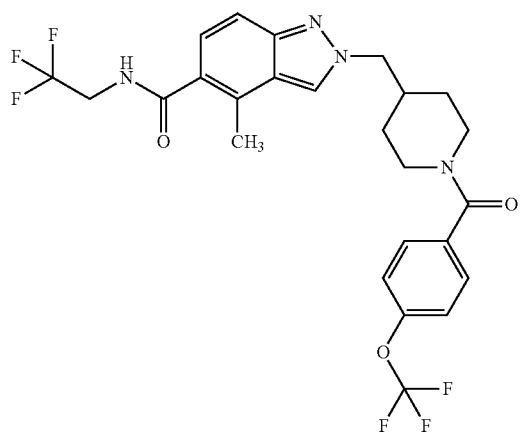 [SMILES: Cc1c(C(=O)NCC(F)(F)F)ccc2nn(CC3CCN(C(=O)c4ccc(OC(F)(F)F)cc4)CC3)cc12]

Analogously to Example 1, 105.4 mg of the title compound was obtained from 146.9 mg of the amine prepared in Example 71a and 77.5 mg of 4-(trifluoromethoxy)benzoic acid.

$^1$H-NMR (300 MHz, DMSO-$d_6$): δ [ppm], 1.12-1.30 (2H), 1.31-1.46 (1H), 1.47-1.64 (1H), 2.20-2.36 (1H), 2.50 (3H), 2.66-2.85 (1H), 2.86-3.09 (1H), 3.40-3.55 (1H), 3.96-4.10 (2H), 4.29-4.48 (3H), 7.17 (1H), 7.36-7.50 (5H), 8.52 (1H), 8.75-8.82 (1H).

Example 74

2-{[1-(4-chlorobenzoyl)piperidin-4-yl]methyl}-6-methyl-N-(2-morpholinoethyl)-2H-indazole-5-carboxamide

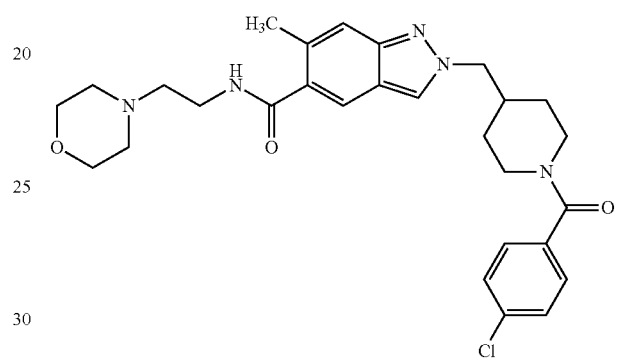

Analogously to Example 55, 30 mg of the title compound was obtained from 79 mg of the amine prepared in Example 74a and 26 mg of 4-chlorobenzoyl chloride.

$^1$NMR (400 MHz, methanol-$d_4$): δ [ppm], 1.31 (2H), 1.50 (1H), 1.65 (1H), 2.35 (1H), 2.47 (3H), 2.63 (6H), 2.81 (1H), 3.07 (1H), 3.53 (2H), 3.71 (5H), 4.34 (2H), 4.59 (1H), 7.36 (2H), 7.43 (3H), 7.75 (1H), 8.24 (1H).

The starting material was prepared as follows:

Example 74a 6-methyl-N-(2-morpholinoethyl)-2-(4-piperidylmethyl)-2H-indazol-5-carboxamide

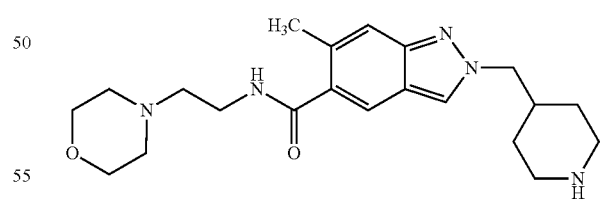

768 mg of (1.58 mmol) of tert-butyl carbamate 74b were dissolved in 4.0 ml 4M hydrochloric acid in dioxan and stirred under nitrogen at room temperature. A further 0.8 ml 4M hydrochloric acid in dioxan were added and the mixture stirred at room temperature. The reaction solution was concentrated and yielded 760 mg of the title compound, which was used in the next reaction without further purification.

$^1$H-NMR (400 MHz, DMSO-$d_6$): δ [ppm], 1.34-1.50 (2H), 1.53-1.67 (2H), 2.21-2.30 (1H), 2.41 (3H), 2.74-2.89

(2H), 3.07-3.33 (8H), 3.62-3.71 (2H), 3.77-3.90 (2H), 3.90-4.03 (2H), 4.35 (2H), 7.39 (1H), 7.88 (1H), 8.44 (1H), 8.57 (1H), 8.62-8.79 (1H), 8.87-9.02 (1H), 11.17 (1H).

Example 74b

Tert-butyl 4-({6-methyl-5-[N-(2-morpholinoethyl)carbamoyl]-2H-indazol-2-yl}-methyl)piperidin-1-carboxylate

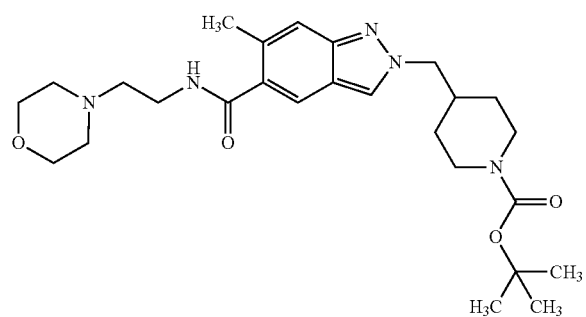 [SMILES: Cc1cc2nn(CC3CCN(C(=O)OC(C)(C)C)CC3)cc2cc1C(=O)NCCN1CCOCC1]

3.00 g (7.35 mmol) of 5-bromoindazole 74c and 2.87 g (22.04 mmol) of 2-morpholinoethylamine were dissolved in 134 ml dioxan and 1.94 g (7.35 mmol) of molybdenum hexacarbonyl, 167 mg (1.47 mmol) of palladium acetate, 213 mg (0.74 mmol) of tributylphosphonium tetrafluoroborate, 2.34 g (22.0 mmol) of sodium carbonate and 2 drops of water were added. The reaction mixture was heated to 125° C. under nitrogen and stirred at this temperature for 2.5 hrs. For the work-up, the suspension was filtered over Celite, rewashed with dioxan, concentrated in vacuo and dried. The crude product was separated by column chromatography. Yield: 518 mg of the title compound.

$^1$H-NMR (300 MHz, DMSO-$d_6$): δ [ppm], 0.93-1.16 (2H), 1.26-1.37 (2H), 1.34 (9H), 1.99-2.17 (1H), 2.32-2.43 (10H), 2.54-2.72 (2H), 3.34 (1H), 3.48-3.59 (4H), 3.86 (2H), 4.26 (2H), 7.35 (1H), 7.63 (1H), 8.09 (1H), 8.32 (1H).

Example 74c

Tert-butyl 4-[(5-bromo-6-methyl-2H-indazol-2-yl)methyl]piperidin-1-carboxylate

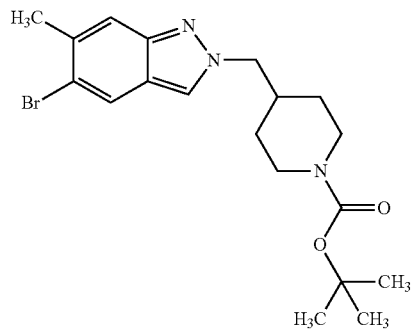 [SMILES: Cc1cc2nn(CC3CCN(C(=O)OC(C)(C)C)CC3)cc2cc1Br]

10.0 g (47.4 mmol) of 5-bromo-4-methyl-1H-indazole and 21.0 g (56.9 mmol) of tert-butyl 4-[(tosyloxy)methyl]piperidin-1-carboxylate were dissolved in 726 ml DMF. To this were added 21.0 g (56.9 mmol) of tetrabutylammonium iodide and 18.5 g (56.9 mmol) of caesium carbonate and the reaction mixture was heated under nitrogen at 80° C. for 1.5 hrs. For the work-up, it was treated with water and ethyl acetate, the organic phase separated and the aqueous phase extracted several times with ethyl acetate. The organic phases were washed with saturated sodium chloride solution, dried over sodium sulphate and concentrated in vacuo. After purification by column chromatography, this yielded the title compound in 5 g yield.

$^1$H-NMR (600 MHz, chloroform-d): δ [ppm], 1.16-1.30 (2H), 1.45 (9H), 1.54 (2H), 2.22-2.33 (1H), 2.51 (3H), 2.67 (2H), 4.03-4.17 (2H), 4.27-4.32 (2H), 7.60 (1H), 7.81 (1H), 7.90 (1H).

The following compounds were prepared analogously:

| Ex. | Structure | IUPAC name | Analysis |
|---|---|---|---|
| 75 | 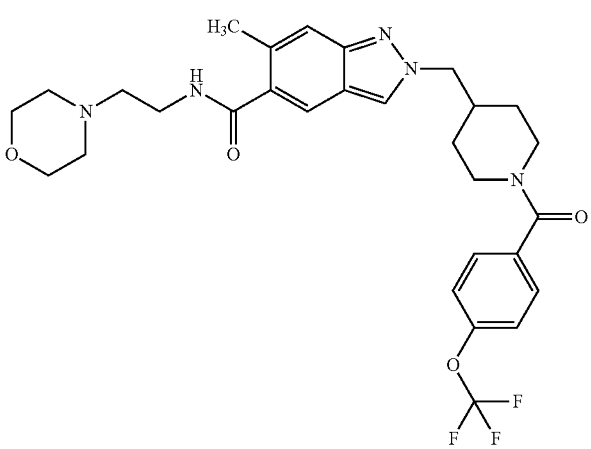 [SMILES: Cc1cc2nn(CC3CCN(C(=O)c4ccc(OC(F)(F)F)cc4)CC3)cc2cc1C(=O)NCCN1CCOCC1] | 6-methyl-N-(2-morpholinoethyl)-2-({1-[4-(trifluoromethoxy)benzoyl]piperidin-4-yl}methyl)-2H-indazole-5-carboxamide | $^1$H-NMR (400 MHz, methanol-$d_4$): δ [ppm] = 1.32 (2H), 1.51 (1H), 1.65 (1H), 2.36 (1H), 2.47 (3H), 2.60 (6H), 2.83 (1H), 3.10 (1H), 3.52 (2H), 3.70 (5H), 4.35 (2H), 4.61 (1H), 7.37 (3H), 7.49 (2H), 7.74 (1H), 8.24 (1H). |

| Ex. | Structure | IUPAC name | Analysis |
|---|---|---|---|
| 76 | 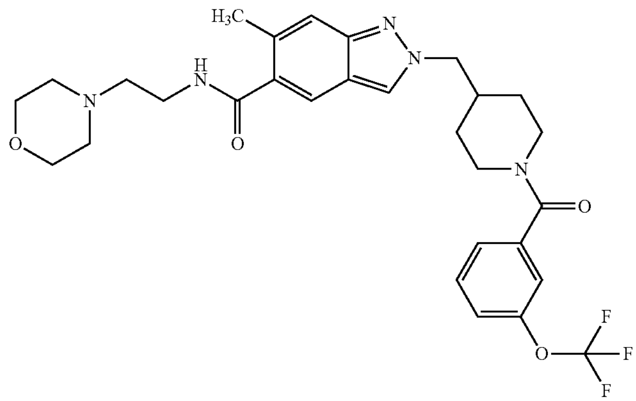 [SMILES: Cc1cc2nn(CC3CCN(C(=O)c4cccc(OC(F)(F)F)c4)CC3)cc2cc1C(=O)NCCN1CCOCC1] | 6-methyl-N-(2-morpholinoethyl)-2-({1-[3-(trifluoromethoxy)benzoyl]piperidin-4-yl}methyl)-2H-indazole-5-carboxamide | $^1$H-NMR (400 MHz, methanol-d$_4$): δ [ppm] = 1.32 (2H), 1.49 (1H), 1.65 (1H), 2.36 (1H), 2.46 (3H), 2.59 (6H), 2.83 (1H), 3.10 (1H), 3.51 (2H), 3.69 (5H), 4.35 (2H), 4.60 (1H), 7.33 (2H), 7.40 (2H), 7.54 (1H), 7.74 (1H), 8.24 (1H). |

Example 77

6-methyl-N-(2-morpholinoethyl)-2-({1-[4-(pentafluoro-λ$^6$-sulphanyl)benzoyl]piperidin-4-yl}methyl)-2H-indazole-5-carboxamide Analogously to Example 1, 23 mg of the title compound was obtained from 79 mg of the amine prepared in Example 74a and 47 mg of the acid.

$^1$H-NMR (400 MHz, methanol-d4): δ [ppm], 1.34 (2H), 1.52 (1H), 1.66 (1H), 2.37 (1H), 2.49 (3H), 2.84 (1H), 3.10 (1H), 3.25 (2H), 3.42 (2H), 3.63 (3H), 3.75 (4H), 4.10 (2H), 4.36 (2H), 4.62 (1H), 7.43 (1H), 7.56 (2H), 7.89 (3H), 8.28 (1H).

The following compounds were prepared analogously:

| Ex. | Structure | IUPAC name | Analysis |
|---|---|---|---|
| 78 | 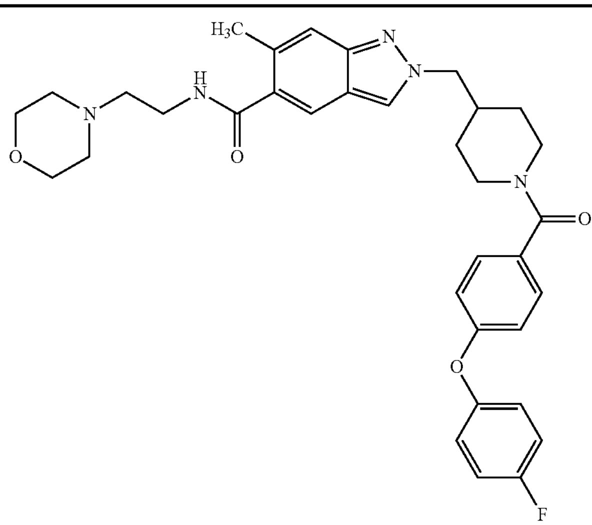 | 2-({1-[4-(4-fluorophenoxy)benzoyl]piperidin-4-yl}methyl)-6-methyl-N-(2-morpholinoethyl)-2H-indazole-5-carboxamide | $^1$H-NMR (400 MHz, methanol-d$_4$): δ [ppm] = 1.31 (2H), 1.58 (2H), 2.35 (1H), 2.49 (3H), 2.40-4.20 (15H), 4.35 (2H), 4.58 (1H), 6.97 (2H), 7.04 (2H), 7.11 (2H), 7.37 (2H), 7.43 (1H), 7.87 (1H), 8.27 (1H). |

| Ex. | Structure | IUPAC name | Analysis |
|---|---|---|---|
| 79 | 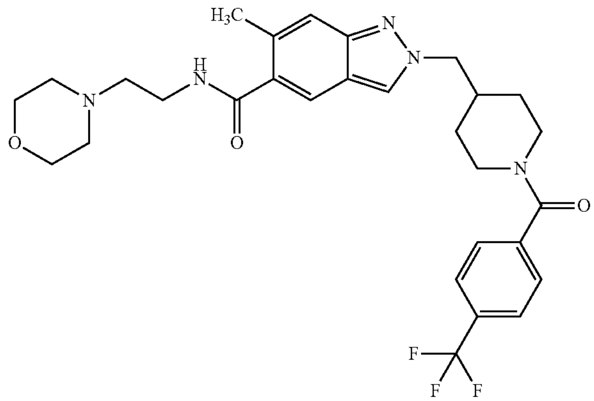 [SMILES: Cc1cc2nn(CC3CCN(C(=O)c4ccc(C(F)(F)F)cc4)CC3)cc2cc1C(=O)NCCN1CCOCC1] | 6-methyl-N-(2-morpholinoethyl)-2-({1-[4-(trifluoromethyl)benzoyl]-piperidin-4-yl}-methyl)-2H-indazole-5-carboxamide | $^1$H-NMR (300 MHz, methanol-$d_4$): δ [ppm] = 1.34 (2H), 1.51 (1H), 1.67 (1H), 2.38 (1H), 2.50 (3H), 2.85 (1H), 3.10 (1H), 3.25 (2H), 3.43 (2H), 3.64 (3H), 3.76 (4H), 4.10 (2H), 4.38 (2H), 4.64 (1H), 7.44 (1H), 7.57 (2H), 7.76 (2H), 7.89 (1H), 8.31 (1H). |
| 80 | 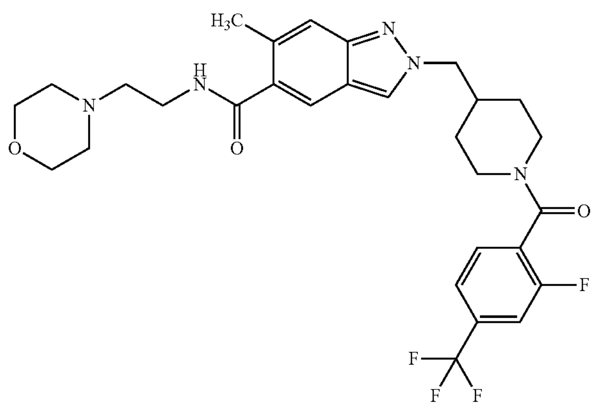 [SMILES: Cc1cc2nn(CC3CCN(C(=O)c4ccc(C(F)(F)F)cc4F)CC3)cc2cc1C(=O)NCCN1CCOCC1] | 2-({1-[2-fluoro-4-(trifluoromethyl)benzoyl]piperidin-4-yl}-methyl)-6-methyl-N-(2-morpholinoethyl)-2H-indazole-5-carboxamide | $^1$H-NMR (300 MHz, methanol-$d_4$): δ [ppm] = 1.34 (2H), 1.54 (1H), 1.68 (1H), 2.38 (1H), 2.50 (3H), 2.86 (1H), 3.12 (1H), 3.26 (2H), 3.43 (3H), 3.66 (2H), 3.76 (4H), 4.11 (2H), 4.37 (2H), 4.67 (1H), 7.44 (1H), 7.59 (3H), 7.89 (1H), 8.31 (1H). |
| 81 | 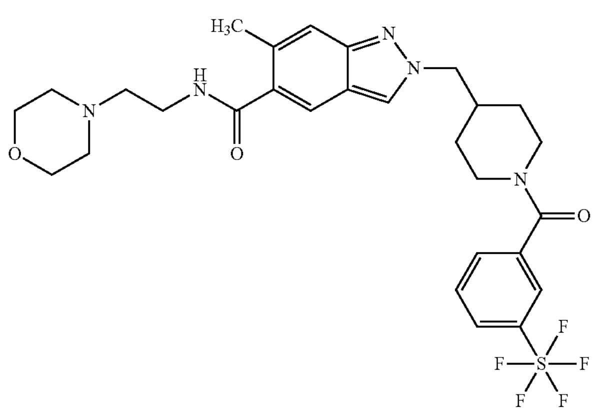 [SMILES: Cc1cc2nn(CC3CCN(C(=O)c4cccc(S(F)(F)(F)(F)F)c4)CC3)cc2cc1C(=O)NCCN1CCOCC1] | 6-methyl-N-(2-morpholinoethyl)-2-({1-[3-(pentafluoro-λ$^6$-sulphanyl)benzoyl]-piperidin-4-yl}-methyl)-2H-indazole-5-carboxamide | $^1$H-NMR (300 MHz, methanol-$d_4$): δ [ppm] = 1.35 (2H), 1.53 (1H), 1.65 (1H), 2.38 (1H), 2.50 (3H), 2.86 (1H), 3.14 (1H), 3.26 (2H), 3.43 (2H), 3.66 (3H), 3.76 (4H), 4.11 (2H), 4.37 (2H), 4.62 (1H), 7.44 (1H), 7.63 (2H), 7.89 (3H), 8.30 (1H). |

| Ex. | Structure | IUPAC name | Analysis |
|---|---|---|---|
| 82 | 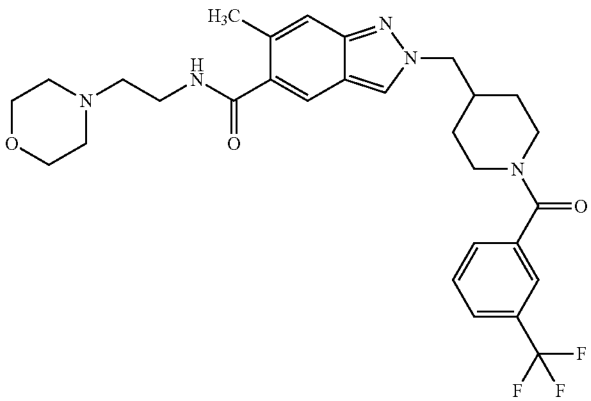 [SMILES: Cc1cc2nn(CC3CCN(C(=O)c4cccc(C(F)(F)F)c4)CC3)cc2cc1C(=O)NCCN1CCOCC1] | 6-methyl-N-(2-morph-olinoethyl)-2-({1-[3-(trifluoromethyl)-benzoyl]piperidin-4-yl}methyl)-2H-indazole-5-carboxamide | $^{1}$H-NMR (300 MHz, methanol-d$_{4}$): δ [ppm] = 1.35 (2H), 1.53 (1H), 1.65 (1H), 2.38 (1H), 2.50 (3H), 2.85 (1H), 3.12 (1H), 3.26 (2H), 3.43 (2H), 3.66 (3H), 3.76 (4H), 4.11 (2H), 4.38 (2H), 4.63 (1H), 7.45 (1H), 7.66 (3H), 7.77 (1H), 7.90 (1H), 8.33 (1H). |
| 83 | 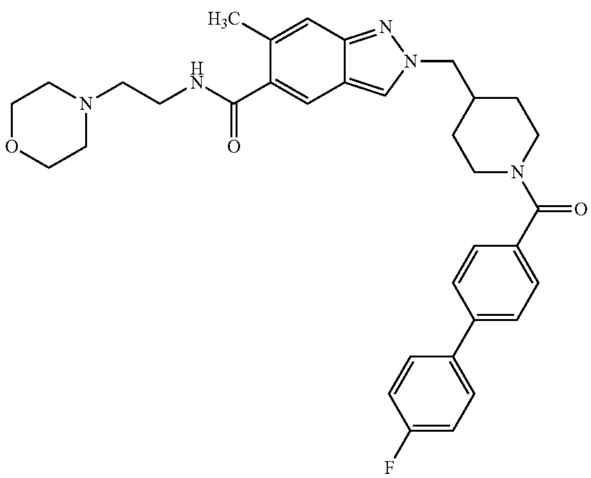 [SMILES: Cc1cc2nn(CC3CCN(C(=O)c4ccc(-c5ccc(F)cc5)cc4)CC3)cc2cc1C(=O)NCCN1CCOCC1] | 2-({1-[(4'-fluoro-biphenyl-4-yl)-carbonyl]piperidin-4-yl}methyl)-6-methyl-N-(2-morpholino-ethyl)-2H-indazole-5-carboxamide | $^{1}$H-NMR (300 MHz, methanol-d$_{4}$): δ [ppm] = 1.35 (2H), 1.53 (1H), 1.65 (1H), 2.39 (1H), 2.50 (1H), 2.85 (1H), 3.12 (1H), 3.26 (2H), 3.42 (2H), 3.63 (3H), 3.74 (4H), 4.08 (2H), 4.37 (2H), 4.64 (1H), 7.18 (2H), 7.46 (3H), 7.66 (4H), 7.88 (1H), 8.30 (1H). |

Example 84

2-{[1-(4-chlorobenzoyl)piperidin-4-yl]methyl}-N-[2-(cyclopropylmethoxy)ethyl]-4-methyl-2H-indazole-5-carboxamide

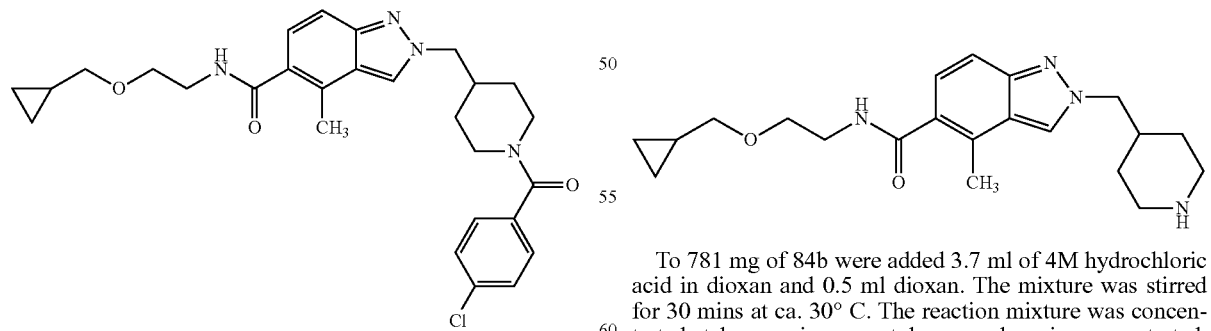

Analogously to Example 1, 38 mg of the title compound was obtained from 75 mg of the amine prepared in Example 84a and 29 mg of 4-chlorobenzoic acid.

$^{1}$H-NMR (400 MHz, DMSO-d$_{6}$): δ [ppm], 0.14 (2H), 0.42 (2H), 0.97 (1H), 1.21 (2H), 1.36 (1H), 1.52 (2H), 2.27 (1H), 2.50 (3H), 2.72 (1H), 2.97 (1H), 3.23 (2H), 3.36 (2H), 3.48 (3H), 4.31 (2H), 4.40 (1H), 7.14 (1H), 7.36 (3H), 7.46 (2H), 8.12 (1H), 8.47 (1H).

The starting material was prepared as follows:

Example 84a

N-[2-(cyclopropylmethoxy)ethyl]-4-methyl-2-(4-piperidylmethyl)-2H-indazole-5-carboxamide To 781 mg of 84b were added 3.7 ml of 4M hydrochloric acid in dioxan and 0.5 ml dioxan. The mixture was stirred for 30 mins at ca. 30° C. The reaction mixture was concentrated, taken up in some toluene and again concentrated. Yield: 751 mg of the title compound, which was further reacted without further purification.

$^{1}$H-NMR (400 MHz, DMSO-d$_{6}$): δ [ppm], 0.14 (2H), 0.42 (2H), 0.97 (1H), 1.43 (2H), 1.58 (2H), 2.26 (1H), 2.50 (3H), 2.65 (1H), 2.78 (2H), 3.18 (2H), 3.22 (2H), 3.36 (2H), 3.49 (2H), 4.33 (2H), 7.16 (2H), 7.38 (1H), 8.11 (1H), 8.53 (1H), 8.80 (1H), 9.06 (1H).

Example 84b

Tert-butyl 4-[(5-{N-[2-(cyclopropylmethoxy)ethyl]carbamoyl}-4-methyl-2H-indazol-2-yl)methyl]piperidin-1-carboxylate

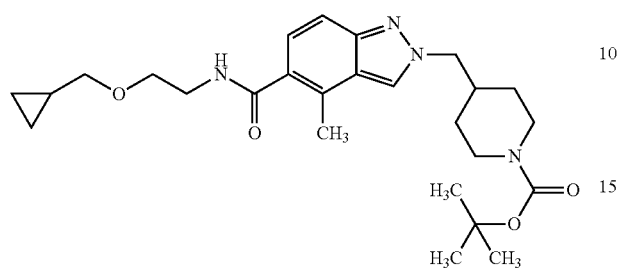

500 mg of 1d was reacted with 203 mg of amine analogously to 1b version B. Yield: 781 mg of the title compound.

$^1$H-NMR (300 MHz, DMSO-d$_6$): δ [ppm], 0.98-1.13 (2H), 1.34 (11H), 2.05-2.27 (2H), 2.33-2.41 (5H), 2.51 (3H), 2.56-2.73 (2H), 3.25-3.37 (2H), 3.51-3.57 (4H), 3.81-3.93 (2H), 4.28 (2H), 7.14 (1H), 7.36-7.41 (1H), 7.95-8.02 (1H), 8.46 (1H).

The following compounds were prepared analogously:

| Ex. | Structure | IUPAC name | Analysis |
|---|---|---|---|
| 85 | 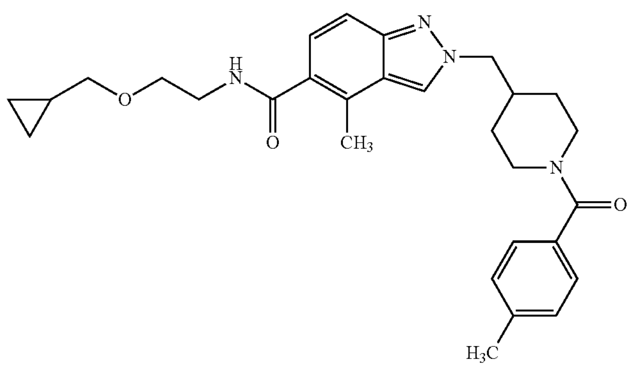 [SMILES: Cc1ccc(C(=O)N2CCC(Cn3cc4c(C)c(C(=O)NCCOCC5CC5)ccc4n3)CC2)cc1] | N-[2-(cyclopropylmethoxy)ethyl]-4-methyl-2-{1-(4-methylbenzoyl)-piperidin-4-yl]-methyl}-2H-indazole-5-carboxamide | $^1$H-NMR (400 MHz, DMSO-d$_6$): δ [ppm] = 0.14 (2H), 0.42 (2H), 0.97 (1H), 1.19 (2H), 1.37 (1H), 1.50 (1H), 2.26 (1H), 2.29 (3H), 2.50 (3H), 2.72 (1H), 2.94 (1H), 3.23 (2H), 3.36 (2H), 3.48 (2H), 3.57 (1H), 4.30 (2H), 4.39 (1H), 7.14 (1H), 7.21 (4H), 7.38 (1H), 8.12 (1H), 8.47 (1H). |
| 86 | 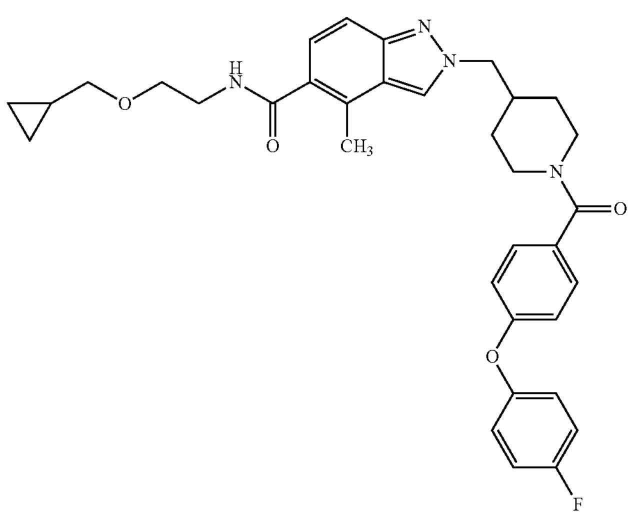 [SMILES: Cc1c(C(=O)NCCOCC2CC2)ccc2nn(CC3CCN(C(=O)c4ccc(Oc5ccc(F)cc5)cc4)CC3)cc12] | N-[2-(cyclopropylmethoxy)ethyl]-2-({1-[4-(4-fluorophenoxy)-benzoyl]piperidin-4-yl}methyl)-4-methyl-2H-indazole-5-carboxamide | $^1$H-NMR (400 MHz, DMSO-d6): δ [ppm] = 0.14 (2H), 0.42 (2H), 0.97 (1H), 1.19 (2H), 1.45 (2H), 2.26 (1H), 2.50 (3H), 2.75 (1H), 2.96 (1H), 3.23 (2H), 3.36 (2H), 3.48 (2H), 3.62 (1H), 4.31 (2H), 4.39 (1H), 6.95 (2H), 7.12 (3H), 7.23 (2H), 7.36 (3H), 8.12 (1H), 8.47 (1H). |

| Ex. | Structure | IUPAC name | Analysis |
|---|---|---|---|
| 87 | 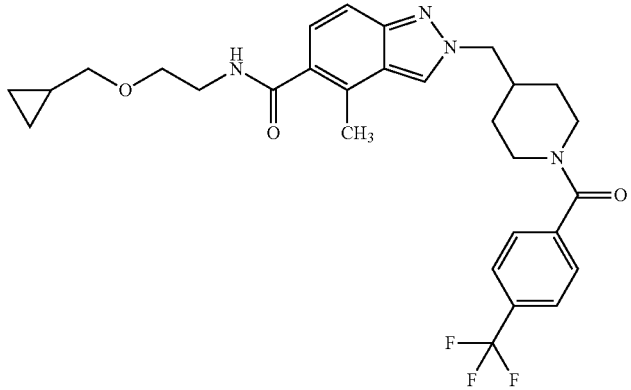 [SMILES: Cc1c(C(=O)NCCOCC2CC2)ccc2nn(CC3CCN(C(=O)c4ccc(C(F)(F)F)cc4)CC3)cc12] | N-[2-(cyclopropyl-methoxy)ethyl]-4-methyl-2-({1-[4-(tri-fluoromethyl)benzoyl]piperidin-4-yl}-methyl)-2H-indazole-5-carboxamide | $^1$H-NMR (400 MHz, DMSO-d$_6$): δ [ppm] = 0.14 (2H), 0.42 (2H), 0.96 (1H), 1.22 (2H), 1.36 (1H), 1.56 (1H), 2.28 (1H), 2.50 (3H), 2.74 (1H), 2.99 (1H), 3.23 (2H), 3.36 (2H), 2.43 (1H), 3.48 (2H), 4.31 (2H), 4.43 (1H), 7.15 (1H), 7.38 (1H), 7.55 (2H), 7.77 (2H), 8.12 (1H), 8.47 (1H). |
| 88 | 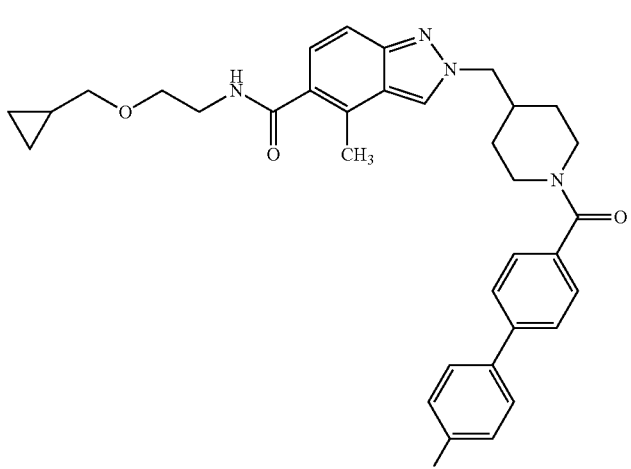 | N-[2-(cyclopropyl-methoxy)ethyl]-2-({1-[(4'-fluorobiphenyl-4-yl)carbonyl]piperidin-4-yl}methyl)-5-methyl-2H-indazole-5-carboxamide | $^1$H-NMR (400 MHz, DMSO-d6): δ [ppm] = 0.14 (2H), 0.42 (2H), 0.96 (1H), 1.23 (2H), 1.39 (1H), 1.55 (1H), 2.28 (1H), 2.50 (3H), 2.74 (1H), 3.01 (1H), 3.23 (2H), 3.36 (2H), 3.48 (2H), 3.61 (1H), 4.33 (2H), 4.44 (1H), 7.15 (1H), 7.28 (2H), 7.40 (3H), 7.69 (4H), 8.12 (1H), 8.48 (1H). |
| 89 | 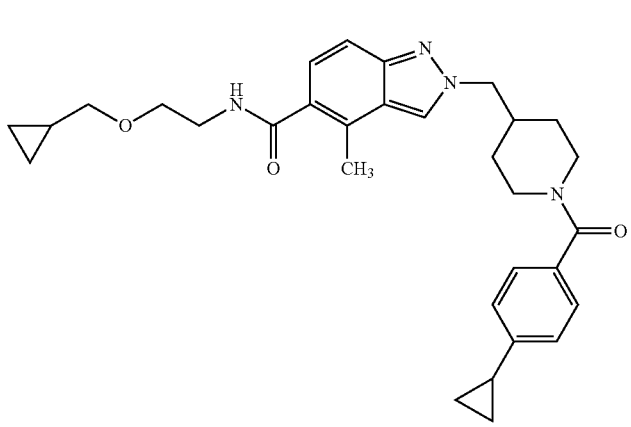 [SMILES: Cc1c(C(=O)NCCOCC2CC2)ccc2nn(CC3CCN(C(=O)c4ccc(C5CC5)cc4)CC3)cc12] | 2-{[1-(4-cyclopropyl-benzoyl)piperidin-4-yl]methyl}-N-[2-(cyclopropylmethoxy)ethyl]-4-methyl-2H-indazole-5-carboxamide | $^1$H-NMR (400 MHz, DMSO-d$_6$): δ [ppm] = 0.17 (2H), 0.45 (2H), 0.69 (2H), 0.97 (3H), 1.21 (2H), 1.47 (2H), 1.93 (1H), 2.27 (1H), 2.52 (3H), 2.78 (1H), 2.93 (1H), 3.26 (2H), 3.37 (2H), 3.51 (2H), 3.62 (1H), 4.34 (2H), 4.41 (1H), 7.10 (2H), 7.17 (1H), 7.22 (2H), 7.41 (1H), 8.11 (1H), 8.49 (1H). |

Example 90

2-{[1-(4-chlorobenzoyl)piperidin-4-yl]methyl}-4-methyl-N-[2-(2,2,2-trifluoro-ethoxy)ethyl]-2H-indazole-5-carboxamide

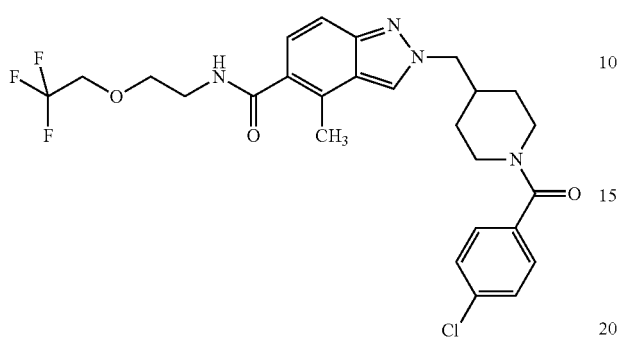

Analogously to Example 1, 40 mg of the title compound was obtained from 75 mg of the amine prepared in Example 90a and 27 mg of 4-chlorobenzoic acid.

$^1$H-NMR (400 MHz, DMSO-$d_6$): □ [ppm], 1.20 (2H), 1.36 (1H), 1.53 (1H), 2.27 (1H), 2.49 (3H), 2.72 (1H), 2.97 (1H), 3.40 (2H), 3.49 (1H), 3.69 (2H), 4.07 (2H), 4.31 (2H), 4.40 (1H), 7.15 (1H), 7.37 (3H), 7.46 (2H), 8.19 (1H), 8.48 (1H).

The starting material was prepared as follows:

Example 90a 4-methyl-2-(4-piperidylmethyl)-N-[2-(2,2,2-trifluoroethoxy)ethyl]-2H-indazole-5-carboxamide 500 mg of 1d was reacted with 240 mg of amine analogously to 1b version B. Yield: 670 mg of the title compound.

$^1$H-NMR (400 MHz, DMSO-$d_6$): δ [ppm], 1.07 (2H), 1.34 (9H), 1.37 (2H), 2.14 (1H), 2.49 (3H), 2.63 (2H), 3.40 (2H), 3.70 (2H), 3.88 (2H), 4.06 (2H), 4.29 (2H), 7.15 (1H), 7.39 (1H), 8.16 (1H), 8.47 (1H).

To 610 mg of 90b were added 3.0 ml of 4M hydrochloric acid in dioxan and 0.5 ml dioxan. The mixture was stirred for 30 mins at ca. 30° C. The reaction mixture was concentrated, taken up in some toluene and again concentrated. Yield: 619 mg of the title compound, which was further reacted without further purification.

$^1$H-NMR (400 MHz, DMSO-$d_6$): δ [ppm], 1.42 (2H), 1.59 (2H), 2.26 (1H), 2.50 (3H), 2.64 (1H), 2.79 (2H), 3.20 (2H), 3.40 (2H), 3.70 (2H), 4.07 (2H), 4.33 (2H), 5.67 (1H), 7.16 (1H), 7.39 (1H), 8.18 (1H), 8.53 (1H), 8.69 (1H), 8.94 (1H).

Example 90b

Tert-butyl 4-[(4-methyl-5-{N-[2-(2,2,2-trifluoroethoxy)ethyl]carbamoyl}-2H-indazol-2-yl)methyl]piperidin-1-carboxylate

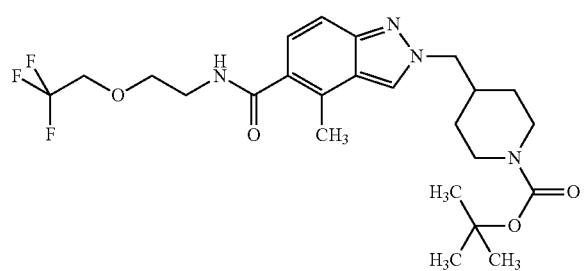 [SMILES: Cc1c(C(=O)NCCOCC(F)(F)F)ccc2nn(CC3CCN(C(=O)OC(C)(C)C)CC3)cc12]

The following compounds were prepared analogously:

| Ex. | Structure | IUPAC name | Analysis |
|---|---|---|---|
| 91 | 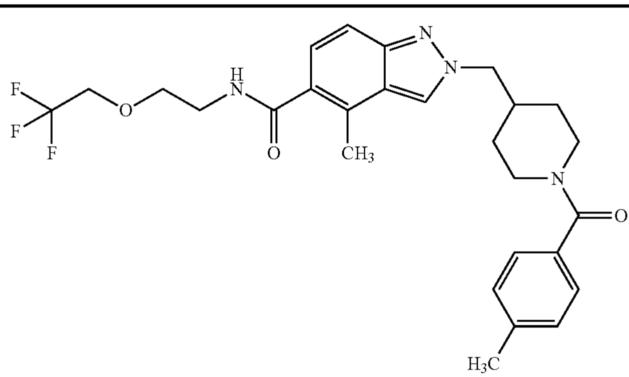 | 4-methyl-2-{[1-(4-methylbenzoyl)-piperidin-4-yl]-methyl}-N-[2-(2,2,2-trifluoro-ethoxy)ethyl]-2H-indazole-5-carboxamide | $^1$H-NMR (400 MHz, DMSO-$d_6$): δ [ppm] = 1.19 (2H), 1.36 (1H), 1.49 (1H), 2.25 (1H), 2.29 (3H), 2.49 (3H), 2.71 (1H), 2.93 (1H), 3.40 (2H), 3.56 (1H), 3.69 (2H), 4.07 (2H), 4.31 (2H), 4.40 (1H), 7.15 (1H), 7.21 (4H), 7.39 (1H), 8.19 (1H), 8.48 (1H). |

-continued

| Ex. | Structure | IUPAC name | Analysis |
|---|---|---|---|
| 92 | 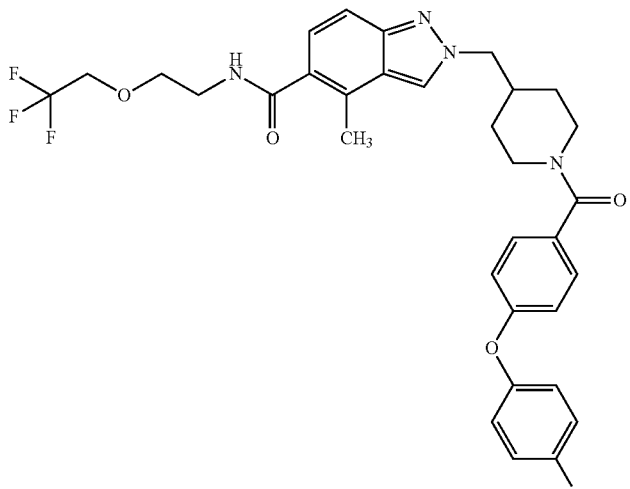 | 2-({1-[4-(4-fluoro-phenoxy)benzoyl]-piperidin-4-yl}-methyl)-4-methyl-N-[2-(2,2,2-tri-fluoroethoxy)ethyl]-2H-indazole-5-carboxamide | $^1$H-NMR (400 MHz, DMSO-d$_6$): δ [ppm] = 1.19 (2H), 1.44 (2H), 2.26 (1H), 2.49 (3H), 2.73 (1H), 2.95 (1H), 3.40 (2H), 3.60 (1H), 3.69 (2H), 4.07 (2H), 4.31 (2H), 4.38 (1H), 6.95 (2H), 7.12 (3H), 7.22 (2H), 7.37 (3H), 8.19 (1H), 8.48 (1H). |
| 93 | 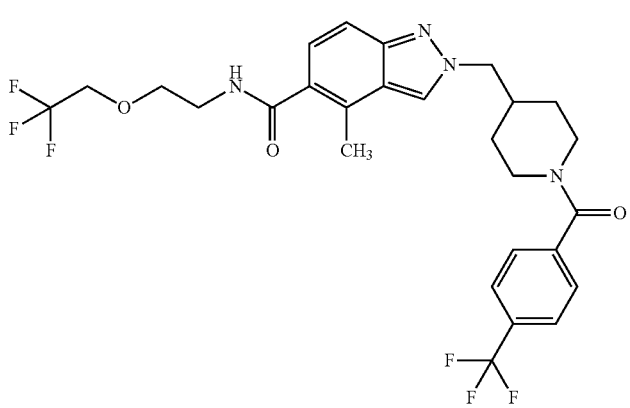 [SMILES: Cc1c(C(=O)NCCOCC(F)(F)F)ccc2nn(CC3CCN(C(=O)c4ccc(C(F)(F)F)cc4)CC3)cc12] | 4-methyl-N-[2-(2,2,2-trifluoro-ethoxy)ethyl]-2-({1-[4-(trifluoro-methyl)benzoyl]-piperidin-4-yl}-methyl)-2H-indazole-5-carboxamide | $^1$H-NMR (400 MHz, DMSO-d$_6$): δ [ppm] = 1.22 (2H), 1.36 (1H), 1.56 (1H), 2.28 (1H), 2.49 (3H), 2.74 (1H), 2.99 (1H), 3.40 (3H), 3.69 (2H), 4.07 (2H), 4.32 (2H), 4.43 (1H), 7.15 (1H), 7.39 (1H), 7.55 (2H), 7.77 (2H), 8.19 (1H), 8.48 (1H). |
| 94 | 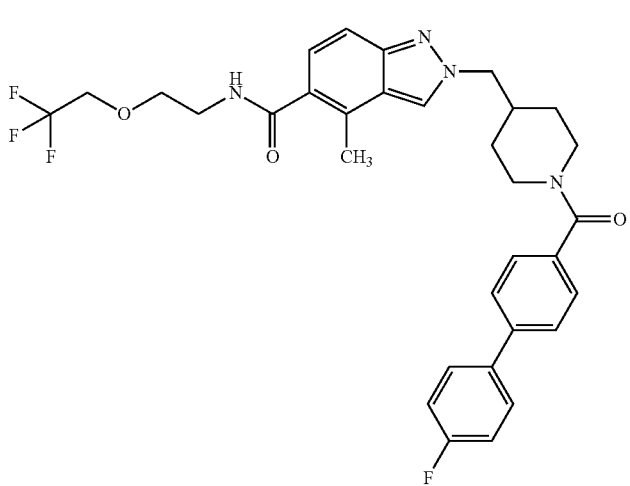 [SMILES: Cc1c(C(=O)NCCOCC(F)(F)F)ccc2nn(CC3CCN(C(=O)c4ccc(-c5ccc(F)cc5)cc4)CC3)cc12] | 2-({1-[(4'-fluoro-biphenyl-4-yl)-carbonyl]piperidin-4-yl}methyl)-4-methyl-N-[2-(2,2,2-trifluoroethoxy)-ethyl]-2H-indazole-5-carboxamide | $^1$H-NMR (300 MHz, DMSO-d$_6$): δ [ppm] = 1.23 (2H), 1.39 (1H), 1.52 (1H), 2.28 (1H), 2.49 (3H), 2.75 (1H), 3.00 (1H), 3.39 (2H), 3.60 (1H), 3.69 (2H), 4.07 (2H), 4.33 (2H), 4.43 (1H), 7.15 (1H), 7.27 (2H), 7.40 (3H), 7.68 (4H), 8.19 (1H), 8.49 (1H). |

| Ex. | Structure | IUPAC name | Analysis |
|---|---|---|---|
| 95 | 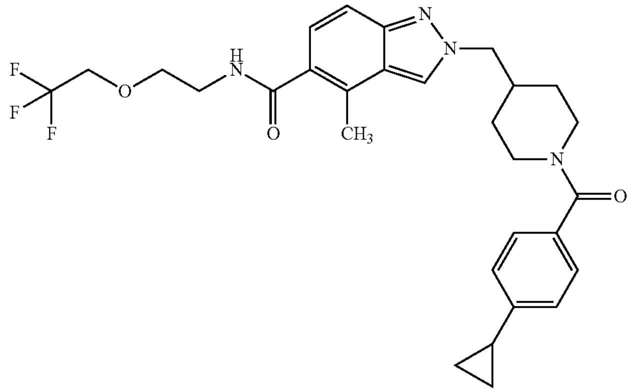 [SMILES: Cc1c(C(=O)NCCOCC(F)(F)F)ccc2nn(CC3CCN(C(=O)c4ccc(C5CC5)cc4)CC3)cc12] | 2-{[1-(4-cyclo-propylbenzoyl)-piperidin-4-yl]-methyl}-4-methyl-N-[2-(2,2,2-tri-fluoroethoxy)ethyl]-2H-indazole-5-carboxamide | $^1$H-NMR (400 MHz, DMSO-d$_6$): δ [ppm] = 0.69 (2H), 0.96 (2H), 1.21 (2H), 1.47 (2H), 1.93 (1H), 2.28 (1H), 2.52 (3H), 2.77 (1H), 2.94 (1H), 3.43 (2H), 3.61 (1H), 3.72 (2H), 4.09 (2H), 4.34 (2H), 4.42 (1H), 7.10 (2H), 7.17 (1H), 7.22 (2H), 7.41 (1H), 8.18 (1H). |

Example 96

2-{[1-(4-chlorobenzoyl)piperidin-4-yl]methyl}-N-(2-isopropoxyethyl)-4-methyl-2H-indazole-5-carboxamide

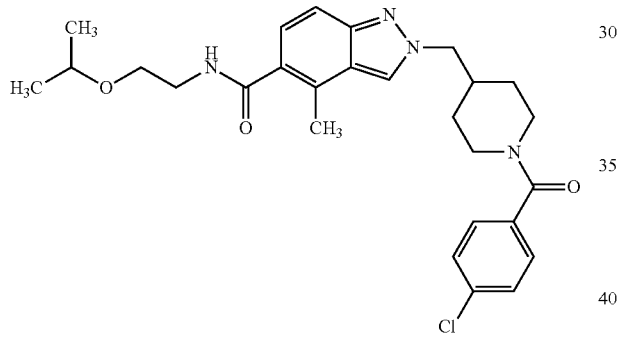

Analogously to Example 1, 36 mg of the title compound was obtained from 75 mg of the amine prepared in Example 96a and 30 mg of 4-chlorobenzoic acid.

$^1$H-NMR (300 MHz, DMSO-d$_6$): δ [ppm], 1.07 (6H), 1.22 (2H), 1.39 (1H), 1.51 (1H), 2.26 (1H), 2.50 (3H), 2.75 (1H), 2.97 (1H), 3.33 (2H), 3.45 (3H), 3.55 (1H), 4.31 (2H), 4.39 (1H), 7.14 (1H), 7.36 (3H), 7.47 (2H), 8.05 (1H), 8.46 (1H).

The starting material was prepared as follows:

Example 96a

N-(2-isopropoxyethyl)-4-methyl-2-(4-piperidylmethyl)-2H-indazol-5-carboxamide

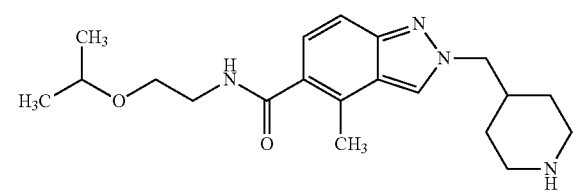 [SMILES: Cc1c(C(=O)NCCOC(C)C)ccc2nn(CC3CCNCC3)cc12]

To 650 mg of 96b were added 3.2 ml of 4M hydrochloric acid in dioxan and 0.5 ml dioxan. The mixture was stirred for 30 mins at ca. 30° C. The reaction mixture was concentrated, taken up in some toluene and again concentrated. Yield: 529 mg of the title compound, which was further reacted without further purification.

$^1$H-NMR (400 MHz, DMSO-d$_6$): δ [ppm], 1.06 (3H), 1.07 (3H), 1.42 (2H), 1.57 (2H), 2.25 (1H), 2.50 (3H), 2.65 (1H), 2.78 (2H), 3.19 (2H), 3.32 (2H), 3.45 (2H), 3.55 (1H), 4.32 (1H), 6.61 (1H), 7.15 (1H), 7.38 (1H), 8.11 (1H), 8.53 (1H), 8.78 (1H), 9.04 (1H).

Example 96b

Tert-butyl 4-({5-[N-(2-isopropoxyethyl)carbamoyl]-4-methyl-2H-indazol-2-yl}-methyl)piperidin-1-carboxylate

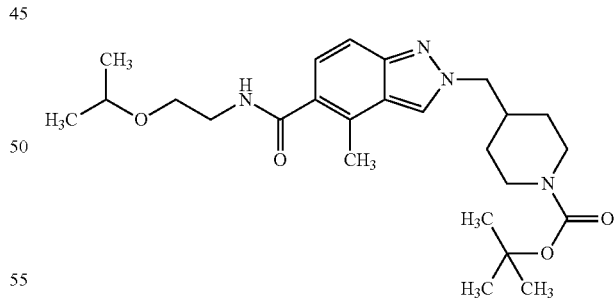

500 mg of 1d was reacted with 138 mg of amine analogously to 1b version B. Yield: 650 mg of the title compound.

$^1$H-NMR (400 MHz, DMSO-d$_6$): δ [ppm]=1.07 (8H), 1.34 (9H), 1.38 (2H), 2.13 (1H), 2.50 (3H), 2.63 (2H), 3.33 (2H), 3.46 (2H), 3.55 (1H), 3.87 (2H), 4.28 (2H), 7.14 (1H), 7.38 (1H), 8.05 (1H), 8.46 (1H).

The following compounds were prepared analogously:

| Ex. | Structure | IUPAC name | Analysis |
|---|---|---|---|
| 97 | 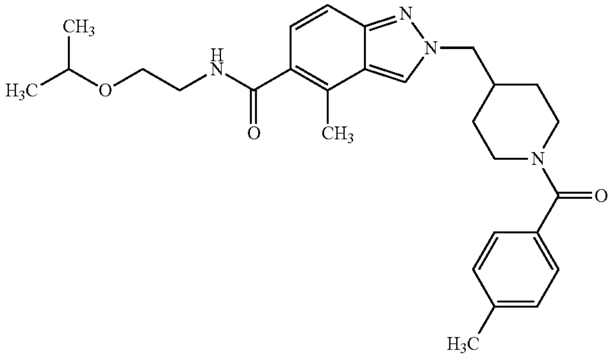 [SMILES: Cc1ccc(C(=O)N2CCC(Cn3cc4c(C)c(C(=O)NCCOC(C)C)ccc4n3)CC2)cc1] | N-(2-isopropoxy-ethyl)-4-methyl-2-{[1-(4-methyl-benzoyl)piperidin-4-yl]methyl}-2H-indazole-5-carboxamide | $^1$H-NMR (300 MHz, DMSO-d$_6$): δ [ppm] = 1.07 (6H), 1.19 (2H), 1.45 (2H), 2.29 (4H), 2.50 (3H), 2.75 (1H), 2.92 (1H), 3.33 (2H), 3.45 (2H), 3.55 (2H), 4.31 (2H), 4.40 (1H), 7.14 (1H), 7.20 (4H), 7.38 (1H), 8.05 (1H), 8.46 (1H). |
| 98 | 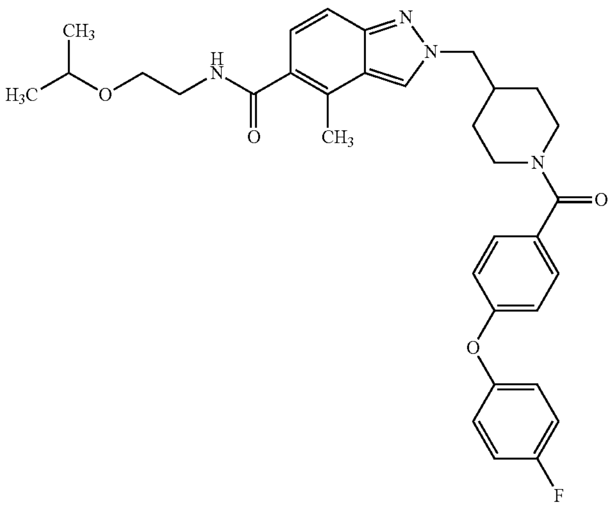 [SMILES: Cc1c(C(=O)NCCOC(C)C)ccc2nn(CC3CCN(C(=O)c4ccc(Oc5ccc(F)cc5)cc4)CC3)cc12] | 2-({1-[4-(4-fluoro-phenoxy)benzoyl]-piperidin-4-yl}-methyl)-N-(2-isopropoxyethyl)-4-methyl-2H-indazole-5-carboxamide | $^1$H-NMR (300 MHz, DMSO-d$_6$): δ [ppm] = 1.07 (6H), 1.21 (2H), 1.45 (2H), 2.25 (1H), 2.49 (3H), 2.85 (2H), 3.31 (2H), 3.45 (2H), 3.55 (2H), 4.31 (2H), 4.40 (1H), 6.95 (2H), 7.10 (3H), 7.22 (2H), 7.36 (3H), 8.05 (1H), 8.46 (1H). |
| 99 | 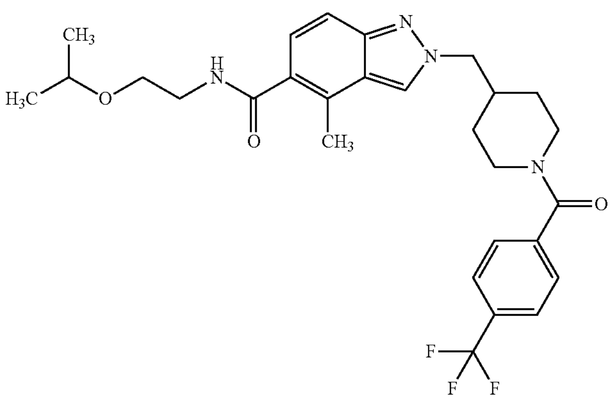 [SMILES: Cc1c(C(=O)NCCOC(C)C)ccc2nn(CC3CCN(C(=O)c4ccc(C(F)(F)F)cc4)CC3)cc12] | N-(2-isopropoxy-ethyl)-4-methyl-2-({1-[4-(trifluoro-methyl)benzoyl]-piperidin-4-yl}-methyl)-2H-indazole-5-carboxamide | $^1$H-NMR (300 MHz, DMSO-d$_6$): δ [ppm] = 1.06 (6H), 1.22 (2H), 1.37 (1H), 1.56 (1H), 2.28 (1H), 2.50 (3H), 2.75 (1H), 2.99 (1H), 3.33 (2H), 3.45 (3H), 3.55 (1H), 4.32 (2H), 4.43 (1H), 7.15 (1H), 7.38 (1H), 7.55 (2H), 7.77 (2H), 8.05 (1H), 8.46 (1H). |

| Ex. | Structure | IUPAC name | Analysis |
|---|---|---|---|
| 100 | 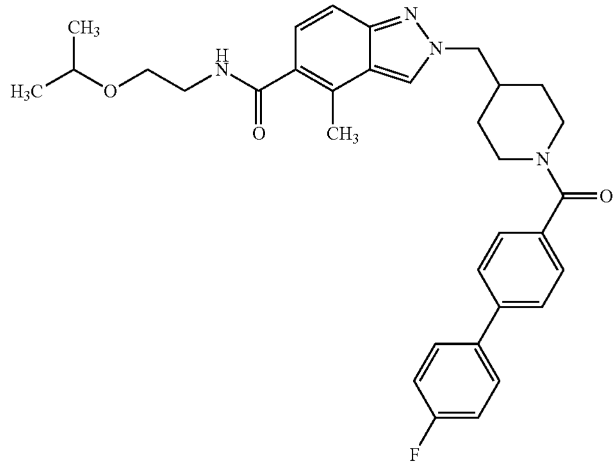 [SMILES: Cc1c(C(=O)NCCOC(C)C)ccc2nn(CC3CCN(C(=O)c4ccc(-c5ccc(F)cc5)cc4)CC3)cc12] | 2-({1-[(4'-fluoro-biphenyl-4-yl)-carbonyl]piperidin-4-yl}methyl)-N-(2-isopropoxyethyl)-4-methyl-2H-indazole-5-carboxamide | $^1$H-NMR (300 MHz, DMSO-$d_6$): δ [ppm] = 1.06 (6H), 1.23 (2H), 1.47 (2H), 2.28 (1H), 2.50 (3H), 2.76 (1H), 2.98 (1H), 3.33 (2H), 3.45 (2H), 3.55 (2H), 4.33 (2H), 4.43 (1H), 7.15 (1H), 7.27 (2H), 7.39 (3H), 7.68 (4H), 8.05 (1H), 8.47 (1H). |
| 101 | 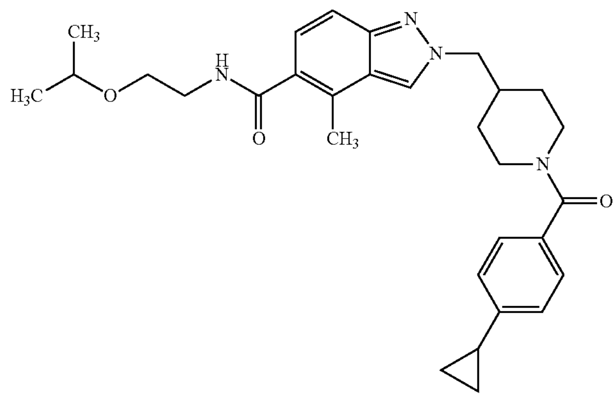 [SMILES: Cc1c(C(=O)NCCOC(C)C)ccc2nn(CC3CCN(C(=O)c4ccc(C5CC5)cc4)CC3)cc12] | 2-{[1-(4-cyclopropyl-benzoyl)piperidin-4-yl]methyl}-N-(2-isopropoxyethyl)-4-methyl-2H-indazole-5-carboxamide | $^1$H-NMR (300 MHz, DMSO-$d_6$): δ [ppm] = 0.66 (2H), 0.94 (2H), 1.06 (6H), 1.20 (2H), 1.44 (2H), 1.90 (1H), 2.24 (1H), 2.49 (3H), 2.82 (2H), 3.32 (2H), 3.45 (2H), 3.55 (2H), 4.31 (2H), 4.39 (1H), 7.12 (5H), 7.38 (1H), 8.05 (1H), 8.46 (1H). |

Example 102

(+/−)-2-{[1-(4-chlorobenzoyl)piperidin-4-yl]methyl}-N-[2-(cyclopropylmethoxy)propyl]-4-methyl-2H-indazole-5-carboxamide

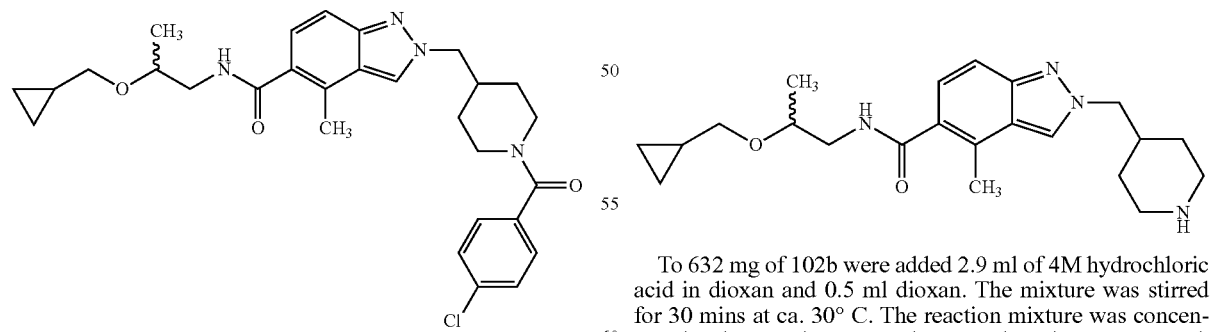

Analogously to Example 1, 41 mg of the title compound was obtained from 100 mg of the amine prepared in Example 102a and 37 mg of 4-chlorobenzoic acid.

$^1$H-NMR (400 MHz, DMSO-$d_6$): δ [ppm], 0.16 (2H), 0.43 (2H), 0.97 (1H), 1.10 (3H), 1.23 (2H), 1.40 (1H), 1.55 (1H), 2.29 (1H), 2.53 (3H), 2.75 (1H), 2.99 (1H), 3.23 (2H), 3.20 (2H), 3.51 (1H), 3.59 (1H), 4.34 (2H), 4.43 (1H), 7.17 (1H), 7.39 (3H), 7.49 (2H), 8.09 (1H), 8.49 (1H).

The starting material was prepared as follows:

Example 102a (+/−)-N-[2-(cyclopropylmethoxy)propyl]-4-methyl-2-(4-piperidylmethyl)-2H-indazole-5-carboxamide To 632 mg of 102b were added 2.9 ml of 4M hydrochloric acid in dioxan and 0.5 ml dioxan. The mixture was stirred for 30 mins at ca. 30° C. The reaction mixture was concentrated, taken up in some toluene and again concentrated. Yield: 561 mg of the title compound, which was further reacted without further purification.

$^1$H-NMR (300 MHz, DMSO-$d_6$): δ [ppm], 0.13 (2H), 0.40 (2H), 0.94 (1H), 1.07 (3H), 1.44 (2H), 1.57 (2H), 2.26 (1H), 2.50 (3H), 2.77 (2H), 3.20 (6H), 3.57 (1H), 4.33 (2H), 6.33 (1H), 7.16 (1H), 7.39 (1H), 8.11 (1H), 8.53 (1H), 8.79 (1H), 9.06 (1H).

Example 102b (+/−)-tert-butyl 4-[(5-{N-[2-(cyclopropylmethoxy)propyl]carbamoyl}-4-methyl-2H-indazol-2-yl)methyl]piperidin-1-carboxylate

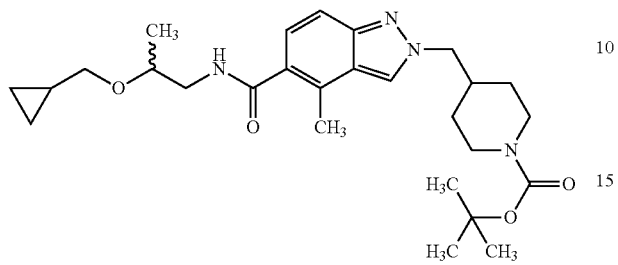

500 mg of 1d was reacted with 222 mg of amine analogously to 1b version B. Yield: 631 mg of the title compound.

$^1$H-NMR (300 MHz, DMSO-$d_6$): δ [ppm], 0.13 (2H), 0.40 (2H), 0-94 (1H), 1.07 (3H), 1.14 (2H), 1.34 (9H), 1.38 (2H), 2.13 (1H), 2.50 (3H), 3.24 (6H), 3.57 (1H), 3.87 (2H), 4.28 (2H), 7.15 (1H), 7.39 (1H), 8.09 (1H), 8.46 (1H).

The following compounds were prepared analogously:

| Ex. | Structure | IUPAC name | Analysis |
|---|---|---|---|
| 103 | 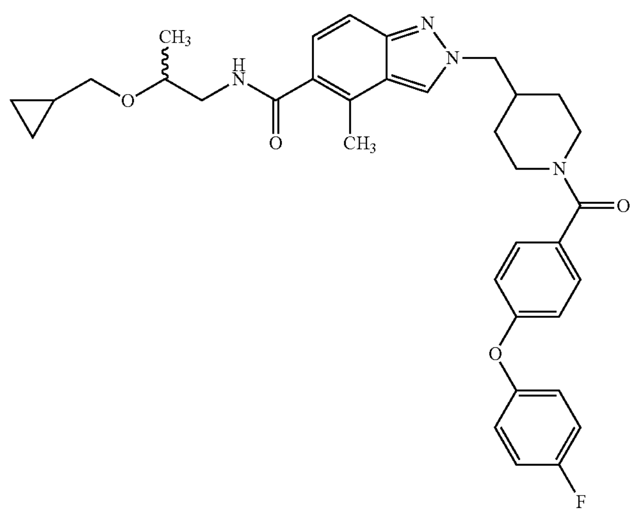 [SMILES: Cc1c(C(=O)NCC(C)OCC2CC2)ccc2nn(CC3CCN(C(=O)c4ccc(Oc5ccc(F)cc5)cc4)CC3)cc12] | (+/−)-N-[2-(cyclopropylmethoxy)propyl]-2-({1-[4-(4-fluorophenoxy)benzoyl]piperidin-4-yl}methyl)-4-methyl-2H-indazole-5-carboxamide | $^1$H-NMR (400 MHz, DMSO-$d_6$): δ [ppm] = 0.16 (2H), 0.43 (2H), 0.97 (1H), 1.10 (3H), 1.22 (2H), 1.48 (2H), 2.29 (1H), 2.53 (3H), 2.81 (1H), 2.92 (1H), 3.23 (2H), 3.28 (2H), 3.60 (1H), 3.70 (1H), 4.34 (2H), 4.42 (1H), 6.98 (2H), 7.14 (3H), 7.25 (2H), 7.39 (3H), 8.09 (1H), 8.49 (1H). |
| 104 | 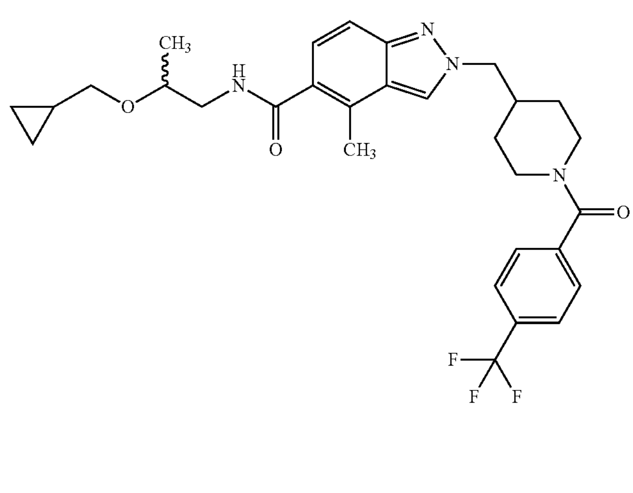 [SMILES: Cc1c(C(=O)NCC(C)OCC2CC2)ccc2nn(CC3CCN(C(=O)c4ccc(C(F)(F)F)cc4)CC3)cc12] | (+/−)-N-[2-(cyclopropylmethoxy)propyl]-4-methyl-2-({1-[4-(trifluoromethyl)benzoyl]piperidin-4-yl}methyl)-2H-indazole-5-carboxamide | $^1$H-NMR (400 MHz, DMSO-$d_6$): δ [ppm] = 0.16 (2H), 0.43 (2H), 0.97 (1H), 1.10 (3H), 1.24 (2H), 1.38 (1H), 1.59 (1H), 2.30 (1H), 2.53 (3H), 2.78 (1H), 3.02 (1H), 3.23 (2H), 3.28 (2H), 3.45 (1H), 3.60 (1H), 4.34 (2H), 4.46 (1H), 7.17 (1H), 7.41 (1H), 7.57 (2H), 7.80 (2H), 8.09 (1H), 8.49 (1H). |

| Ex. | Structure | IUPAC name | Analysis |
|---|---|---|---|
| 105 | 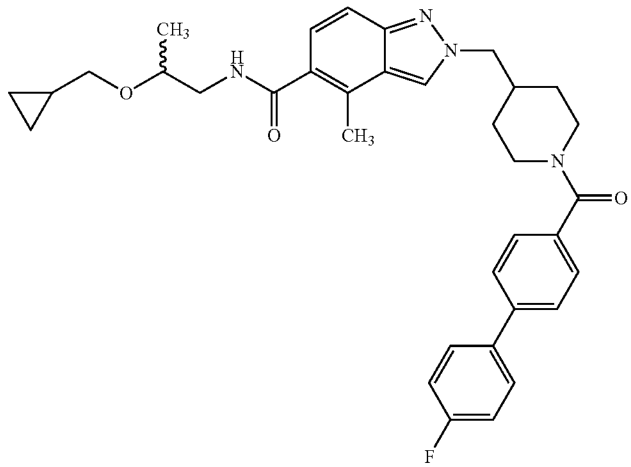 [SMILES: Cc1c(C(=O)NCC(C)OCC2CC2)ccc2nn(CC3CCN(C(=O)c4ccc(-c5ccc(F)cc5)cc4)CC3)cc12] | (+/−)-N-[2-(cyclo-propylmethoxy)-propyl]-2-({1-[(4'-fluorobiphenyl-4-yl)carbonyl]-piperidin-4-yl}-methyl)-4-methyl-2H-indazole-5-carboxamide | ¹H-NMR (400 MHz, DMSO-d₆): δ [ppm] = 0.16 (2H), 0.42 (2H), 0.97 (1H), 1.10 (3H), 1.26 (2H), 1.45 (1H), 1.55 (1H), 2.32 (1H), 2.53 (3H), 2.79 (1H), 3.03 (1H), 3.23 (2H), 3.27 (2H), 3.60 (2H), 4.36 (2H), 4.46 (1H), 7.17 (1H), 7.30 (2H), 7.42 (3H), 7.71 (4H), 8.09 (1H), 8.50 (1H). |
| 106 | 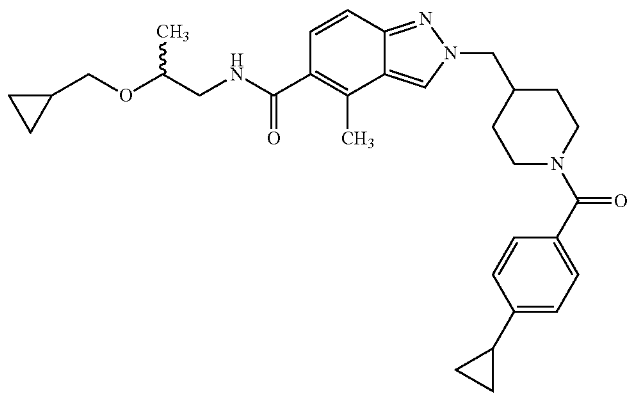 [SMILES: Cc1c(C(=O)NCC(C)OCC2CC2)ccc2nn(CC3CCN(C(=O)c4ccc(C5CC5)cc4)CC3)cc12] | (+/−)-2-{[1-(4-cyclopropylbenzoyl)piperidin-4-yl]-methyl}-N-[2-(cyclopropyl-methoxy)propyl]-4-methyl-2H-indazole-5-carboxamide | ¹H-NMR (400 MHz, DMSO-d₆): δ [ppm] = 0.16 (2H), 0.43 (2H), 0.69 (2H), 0.96 (3H), 1.10 (3H), 1.20 (2H), 1.47 (2H), 1.93 (1H), 2.28 (1H), 2.53 (3H), 2.77 (1H), 2.93 (1H), 3.23 (2H), 3.28 (2H), 3.59 (2H), 4.34 (2H), 4.40 (1H), 7.10 (2H), 7.17 (1H), 7.22 (2H), 7.41 (1H), 8.09 (1H), 8.49 (1H). |

Example 107

2-{[1-(4-chlorobenzoyl)piperidin-4-yl]methyl}-4-methyl-N-[2-(trifluoromethoxy)ethyl]-2H-indazole-5-carboxamide

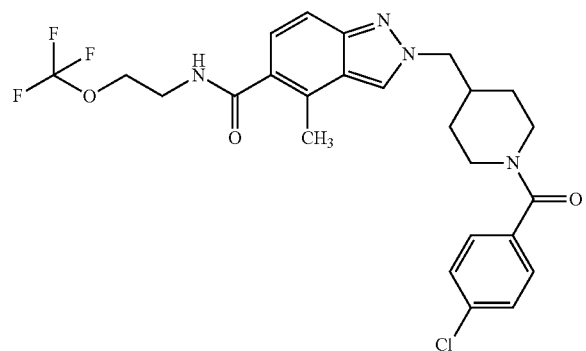 [SMILES: Cc1c(C(=O)NCCOC(F)(F)F)ccc2nn(CC3CCN(C(=O)c4ccc(Cl)cc4)CC3)cc12]

Analogously to Example 1, 26 mg of the title compound was obtained from 75 mg of the amine prepared in Example 107a and 28 mg of 4-chlorobenzoic acid.

¹H-NMR (300 MHz, DMSO-d₆): δ [ppm], 1.20 (2H), 1.36 (1H), 1.52 (1H), 2.27 (1H), 2.49 (3H), 2.72 (1H), 2.97 (1H), 3.51 (3H), 4.17 (2H), 4.33 (3H), 7.15 (1H), 7.41 (5H), 8.37 (1H), 8.49 (1H).

The starting material was prepared as follows:

Example 107a 4-methyl-2-(4-piperidylmethyl)-N-[2-(trifluoromethoxy)ethyl]-2H-indazole-5-carboxamide

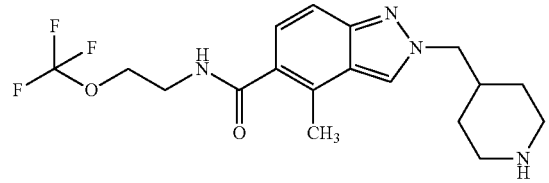 [SMILES: Cc1c(C(=O)NCCOC(F)(F)F)ccc2nn(CC3CCNCC3)cc12]

To 648 mg of 107b were added 3.0 ml of 4M hydrochloric acid in dioxan and 0.5 ml dioxan. The mixture was stirred for 30 mins at ca. 30° C. The reaction mixture was concentrated, taken up in some toluene and again concentrated. Yield: 766 mg of the title compound, which was further reacted without further purification.

$^1$H-NMR (300 MHz, DMSO-$d_6$): δ [ppm], 1.43 (2H), 1.57 (2H), 2.24 (1H), 2.50 (3H), 2.78 (2H), 3.19 (2H), 3.50 (1H), 4.17 (2H), 4.33 (2H), 6.49 (1H), 7.17 (2H), 7.40 (1H), 8.39 (1H), 8.55 (1H), 8.70 (1H), 8.98 (1H).

Example 107b

Tert-butyl 4-[(4-methyl-5-{N-[2-(trifluoromethoxy)ethyl]carbamoyl}-2H-indazol-2-yl)methyl]piperidin-1-carboxylate

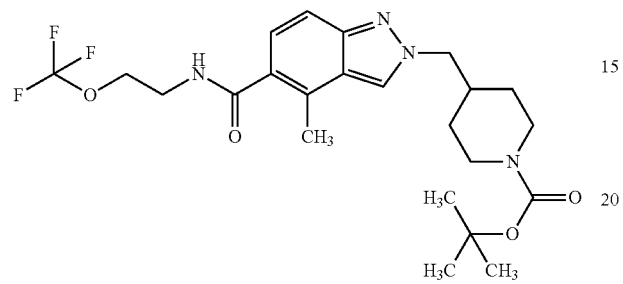

500 mg of 1d was reacted with 293 mg of amine analogously to 1b version B. Yield: 748 mg of the title compound.

$^1$H-NMR (400 MHz, DMSO-$d_6$): δ [ppm], 1.07 (2H), 1.34 (9H), 1.37 (2H), 2.12 (1H), 2.50 (3H), 2.63 (1H), 3.52 (2H), 3.87 (2H), 4.17 (2H), 4.29 (2H), 7.16 (2H), 7.41 (1H), 8.37 (1H), 8.48 (1H).

The following compounds were prepared analogously:

| Ex. | Structure | IUPAC name | Analysis |
|---|---|---|---|
| 108 | 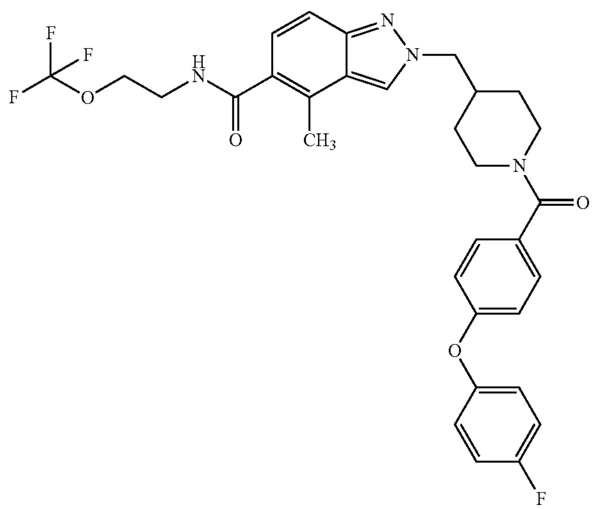 [SMILES: Cc1c(C(=O)NCCOC(F)(F)F)ccc2nn(CC3CCN(C(=O)c4ccc(Oc5ccc(F)cc5)cc4)CC3)cc12] | 2-({1-[4-(4-fluorophenoxy)benzoyl]-piperidin-4-yl}methyl)-4-methyl-N-[2-(trifluoromethoxy)ethyl]-2H-indazole-5-carboxamide | $^1$H-NMR (300 MHz, DMSO-$d_6$): δ [ppm] = 1.19 (2H), 1.46 (2H), 2.26 (1H), 2.49 (3H), 2.87 (2H), 3.51 (3H), 4.17 (2H), 4.33 (3H), 6.95 (2H), 7.16 (5H), 7.38 (3H), 8.36 (1H), 8.49 (1H). |
| 109 | 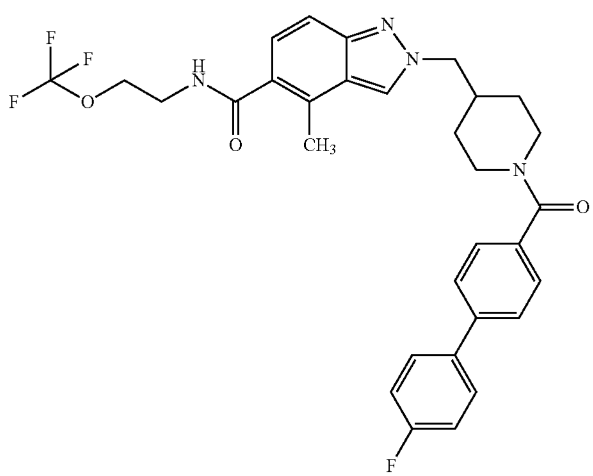 [SMILES: Cc1c(C(=O)NCCOC(F)(F)F)ccc2nn(CC3CCN(C(=O)c4ccc(-c5ccc(F)cc5)cc4)CC3)cc12] | 2-({1-[(4'-fluorobiphenyl-4-yl)-carbonyl]piperidin-4-yl}methyl)-4-methyl-N-[2-(trifluoromethoxy)ethyl]-2H-indazole-5-carboxamide | $^1$H-NMR (300 MHz, DMSO-$d_6$): δ [ppm] = 1.23 (2H), 1.47 (2H), 2.28 (1H), 2.50 (3H), 2.74 (1H), 2.99 (1H), 3.51 (2H), 3.61 (1H), 4.17 (2H), 4.34 (3H), 7.16 (1H), 7.27 (2H), 7.40 (3H), 7.68 (4H), 8.37 (1H), 8.50 (1H). |

| Ex. | Structure | IUPAC name | Analysis |
|---|---|---|---|
| 110 | 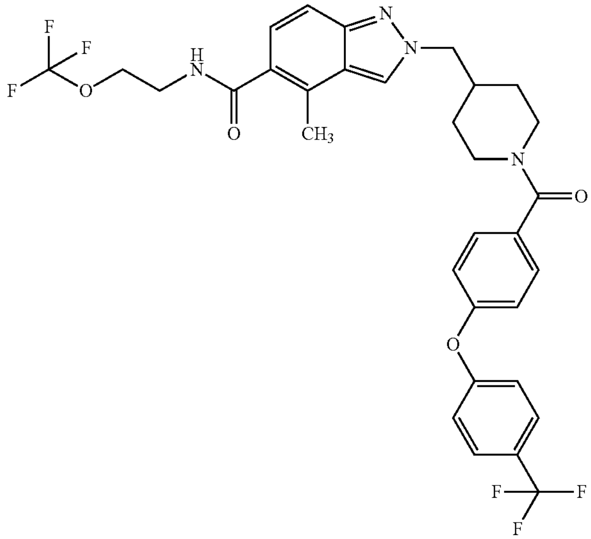 [SMILES: Cc1c(C(=O)NCCOC(F)(F)F)ccc2nn(CC3CCN(C(=O)c4ccc(Oc5ccc(C(F)(F)F)cc5)cc4)CC3)cc12] | 4-methyl-N-[2-(trifluoromethoxy)ethyl]-2-[(1-{4-[4-(trifluoromethyl)phenoxy]benzoyl}piperidin-4-yl)methyl]-2H-indazole-5-carboxamide | ¹H-NMR (300 MHz, DMSO-d₆): δ [ppm] = 1.21 (2H), 1.46 (2H), 2.27 (1H), 2.50 (3H), 2.76 (1H), 2.98 (1H), 3.51 (2H), 3.61 (1H), 4.17 (2H), 4.33 (2H), 4.43 (1H), 7.14 (5H), 7.41 (3H), 7.73 (2H), 8.37 (1H), 8.49 (1H). |

Example 111

N-(2-tert-butoxyethyl)-2-{[1-(4-chlorobenzoyl)piperidin-4-yl]methyl}-4-methyl-2H-indazole-5-carboxamide

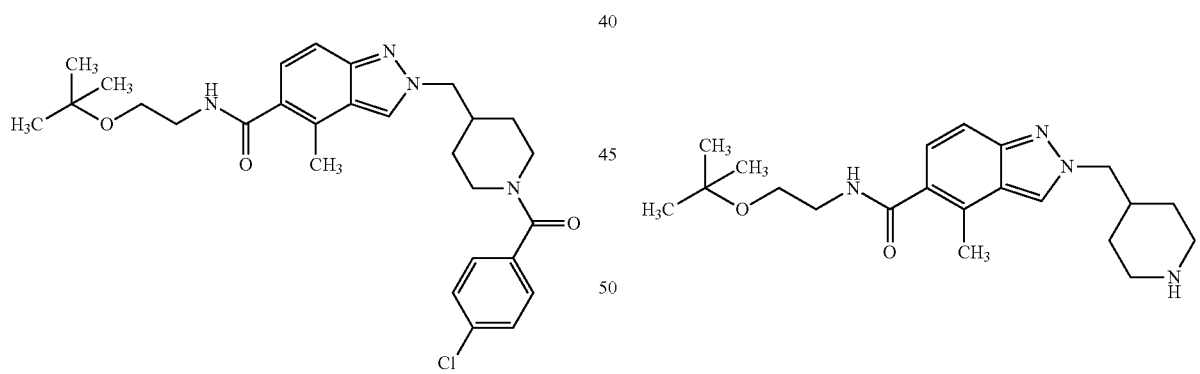

Analogously to Example 1, 8 mg of the title compound was obtained from 75 mg of the amine prepared in Example 111a and 28 mg of 4-chlorobenzoic acid.

¹H-NMR (400 MHz, DMSO-d₆): δ [ppm], 1.12 (9H), 1.21 (2H), 1.36 (1H), 1.53 (1H), 2.27 (1H), 2.50 (3H), 2.72 (1H), 2.97 (1H), 3.29 (2H), 3.43 (3H), 4.31 (2H), 4.40 (1H), 7.14 (1H), 7.36 (3H), 7.46 (2H), 8.04 (1H), 8.46 (1H).

The starting material was prepared as follows:

Example 111a

N-(2-tert-butoxyethyl)-4-methyl-2-(4-piperidylmethyl)-2H-indazol-5-carboxamide

To 743 mg of 111b were added 3.5 ml of 4M hydrochloric acid in dioxan and 0.5 ml dioxan. The mixture was stirred for 30 mins at ca. 30° C. The reaction mixture was concentrated, taken up in some toluene and again concentrated. Yield: 677 mg of the title compound in a mixture with N-(2-hydroxyethyl)-4-methyl-2-(4-piperidylmethyl)-2H-indazole-5-carboxamide, which was further reacted without further purification.

Example 111b

Tert-butyl 4-({5-[N-(2-tert-butoxyethyl)carbamoyl]-4-methyl-2H-indazol-2-yl}methyl)piperidin-1-carboxylate

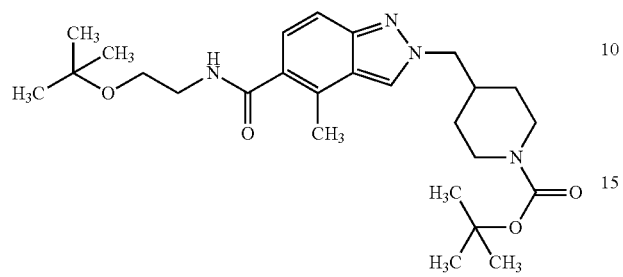

500 mg of 1d was reacted with 206 mg of amine analogously to 1b version B. Yield: 743 mg of the title compound.

$^1$H-NMR (300 MHz, DMSO-d$_6$): δ [ppm], 1.06 (2H), 1.11 (9H), 1.34 (9H), 1.39 (2H), 2.13 (1H), 2.50 (3H), 2.65 (2H), 3.27 (2H), 3.40 (2H), 3.87 (2H), 4.28 (2H), 7.14 (1H), 7.38 (1H), 8.05 (1H), 8.46 (1H).

The following compounds were prepared analogously:

| Ex. | Structure | IUPAC name | Analysis |
| --- | --- | --- | --- |
| 112 | 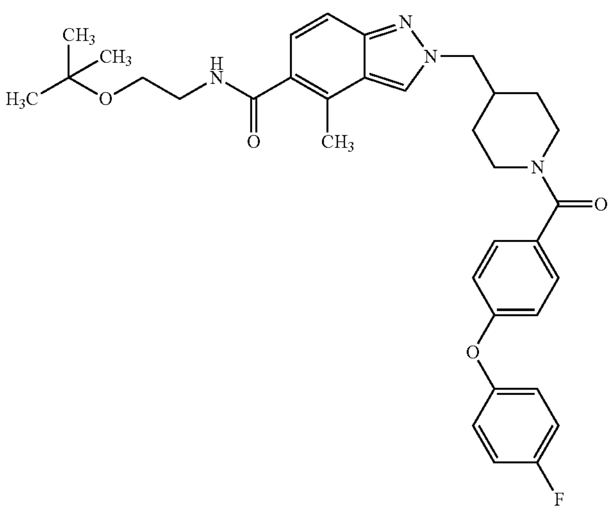 [SMILES: Cc1c(C(=O)NCCOC(C)(C)C)ccc2nn(CC3CCN(C(=O)c4ccc(Oc5ccc(F)cc5)cc4)CC3)cc12] | N-(2-tert-butoxyethyl)-2-({1-[4-(4-fluorophenoxy)benzoyl]-piperidin-4-yl}methyl)-4-methyl-2H-indazole-5-carboxamide | $^1$H-NMR (400 MHz, DMSO-d$_6$): δ [ppm] = 1.12 (9H), 1.20 (2H), 1.44 (2H), 2.26 (1H), 2.50 (3H), 2.76 (1H), 2.93 (1H), 3.30 (2H), 3.40 (2H), 3.57 (1H), 4.31 (2H), 4.39 (1H), 6.95 (2H), 7.12 (3H), 7.23 (2H), 7.36 (3H), 8.04 (1H), 8.46 (1H). |
| 113 | 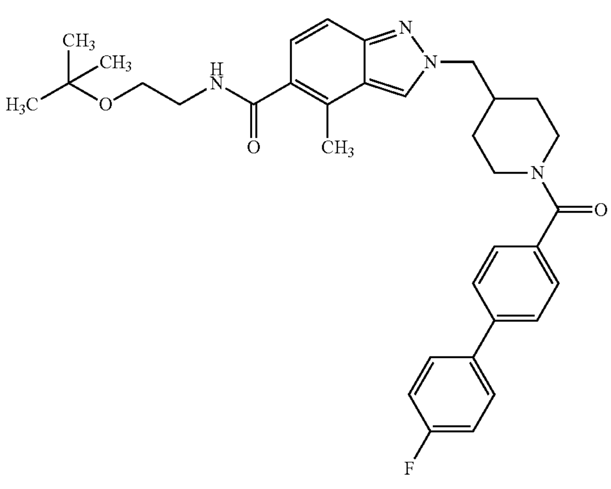 [SMILES: Cc1c(C(=O)NCCOC(C)(C)C)ccc2nn(CC3CCN(C(=O)c4ccc(-c5ccc(F)cc5)cc4)CC3)cc12] | N-(2-tert-butoxyphenyl)-2-({1-[(4'-fluorobiphenyl-4-yl)-carbonyl]piperidin-4-yl}methyl)-4-methyl-2H-indazole-5-carboxamide | $^1$H-NMR (400 MHz, DMSO-d$_6$): δ [ppm] = 1.11 (9H), 1.23 (2H), 1.40 (1H), 1.54 (1H), 2.29 (1H), 2.50 (3H), 2.75 (1H), 3.00 (1H), 3.29 (2H), 3.40 (2H), 3.65 (1H), 4.32 (2H), 4.43 (1H), 7.15 (1H), 7.28 (2H), 7.40 (3H), 7.69 (4H), 8.05 (1H), 8.47 (1H). |

| Ex. | Structure | IUPAC name | Analysis |
|---|---|---|---|
| 114 | 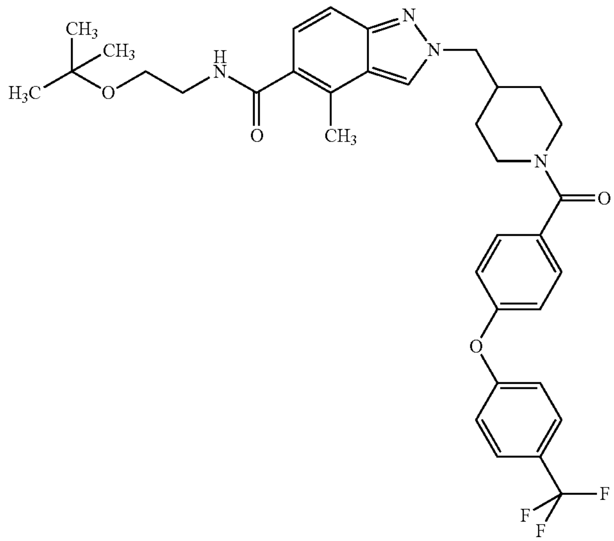 [SMILES: Cc1c(C(=O)NCCOC(C)(C)C)ccc2nn(CC3CCN(C(=O)c4ccc(Oc5ccc(C(F)(F)F)cc5)cc4)CC3)cc12] | N-(tert-butoxyethyl)-4-methyl-2-[(1-{4-[4-(trifluoromethyl)-phenoxy]benzoyl}-piperidin-4-yl)methyl]-2H-indazole-5-carboxamide | $^1$H-NMR (400 MHz, DMSO-d$_6$): δ [ppm] = 1.12 (9H), 1.21 (2H), 1.40 (1H), 1.52 (1H), 2.27 (1H), 2.50 (3H), 2.75 (1H), 2.99 (1H), 3.28 (2H), 3.40 (2H), 3.60 (1H), 4.32 (2H), 4.40 (1H), 7.15 (5H), 7.40 (3H), 7.73 (2H), 8.04 (1H), 8.47 (1H). |

Example 115

2-{[1-(4-chlorobenzoyl)piperidin-4-yl]methyl}-N-(2-[$^2$H$_3$]methoxy [$^2$H$_4$]ethyl)-4-methyl-2H-indazole-5-carboxamide

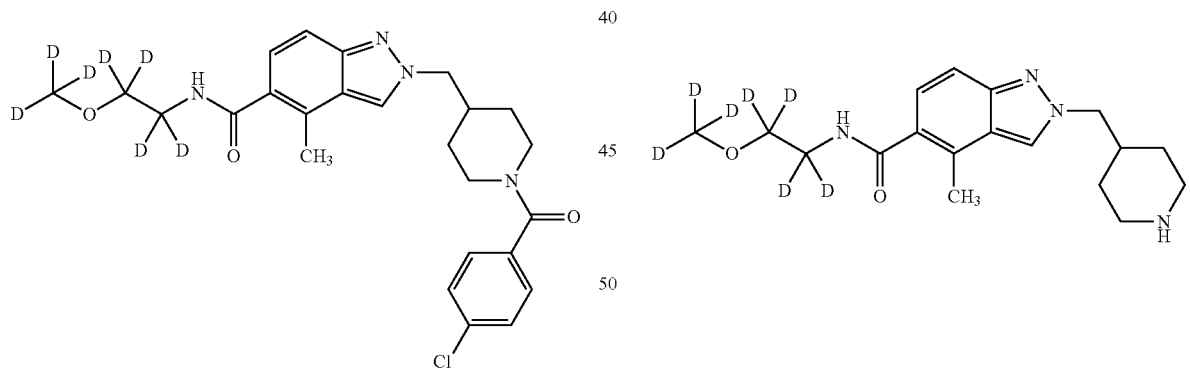

Analogously to Example 1, 1 mg of the title compound was obtained from 54 mg of the amine prepared in Example 115a and 22 mg of 4-chlorobenzoic acid.

$^1$H-NMR (300 MHz, DMSO-d$_6$): δ [ppm], 1.20 (2H), 1.40 (1H), 1.51 (1H), 2.27 (1H), 2.49 (3H), 2.75 (1H), 2.96 (1H), 3.50 (1H), 4.31 (2H), 4.40 (1H), 7.15 (1H), 7.36 (3H), 7.47 (2H), 8.07 (1H), 8.46 (1H).

The starting material was prepared as follows:

Example 115a 4-methyl-N-(2-[$^2$H$_3$]methyloxy[$^2$H$_4$]ethyl)-2-(4-piperidylmethyl)-2H-indazole-5-carboxamide To 131 mg of 115b were added 0.7 ml of 4M hydrochloric acid in dioxan and 0.5 ml dioxan. The mixture was stirred for 30 mins at ca. 30° C. The reaction mixture was concentrated, taken up in some toluene and again concentrated. Yield: 108 mg of the title compound, which was further reacted without further purification.

$^1$H-NMR (400 MHz, DMSO-d$_6$): δ [ppm], 1.42 (2H), 1.58 (2H), 2.26 (1H), 2.49 (3H), 2.78 (2H), 3.19 (2H), 4.33 (2H), 5.55 (1H), 7.16 (1H), 7.38 (1H), 8.12 (1H), 8.53 (1H), 8.70 (1H), 8.97 (1H).

Example 115b

Tert-butyl 4-({4-methyl-5-[N-(2-[²H₃]methyloxy [²H]ethyl)carbamoyl]-2H-indazol-2-yl}methyl)piperidin-1-carboxylate

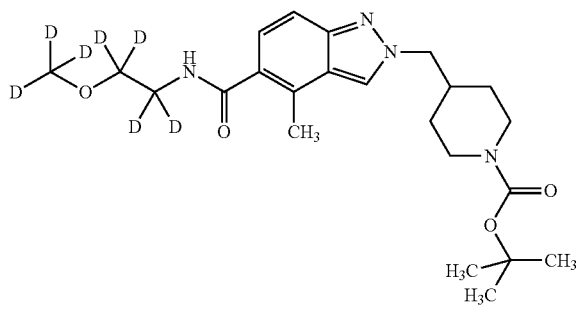 [SMILES: [2H]C([2H])([2H])OC([2H])([2H])C([2H])([2H])NC(=O)c1ccc2nn(CC3CCN(C(=O)OC(C)(C)C)CC3)cc2c1C]

500 mg of 1d was reacted analogously to 1b version B with 110 mg of amine prepared in 115c. Yield: 131 mg of the title compound.

¹H-NMR (300 MHz, DMSO-d₆): δ [ppm], 1.07 (2H), 1.34 (9H), 1.37 (2H), 2.13 (1H), 2.49 (3H), 2.62 (2H), 3.88 (2H), 4.28 (2H), 7.15 (1H), 7.38 (1H), 8.07 (1H), 8.46 (1H).

Example 115c

2-[²H₃]methyloxy[²H₄]ethan-1-amine

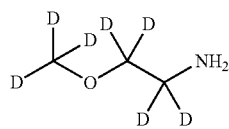

110 mg of (0.51 mmol) of 115d was first placed in 2.2 ml toluene. After addition of 11 mg of palladium/charcoal (10%) and hydrogen under normal pressure, the mixture was stirred for 50 mins at room temperature. The reaction mixture was filtered through Celite and rewashed with toluene. The colourless filtrate was used as solution in the subsequent reaction.

Example 115d

Benzyl N-(2-[²H₃]methyloxy [²H₄]ethyl)carbamate

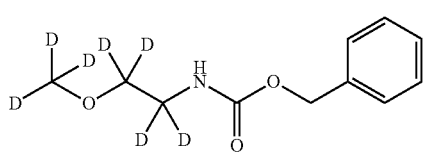 [SMILES: [2H]C([2H])([2H])OC([2H])([2H])C([2H])([2H])NC(=O)OCc1ccccc1]

1.32 g (6.6 mmol) of 115e was dissolved in 23 ml acetonitrile. 2.3 g (9.9 mmol) of silver oxide and 1.64 ml (3.8 g, 26 mmol) of deuterated iodomethane were then added. The reaction mixture was stirred for 1.5 hrs at 40° C., 7.5 hrs at 72° C. and then overnight at room temperature. A further 2.3 g (9.9 mmol) of silver oxide was added and the mixture stirred for 1.5 hrs at 72° C. For the work-up, the black solid was filtered off at the pump and the clear filtrate concentrated. The residue was purified by column chromatography (hexane/ethyl acetate 0-10%). Yield: 1.13 g of the title compound.

¹H-NMR (300 MHz, DMSO-d₆): δ [ppm], 4.97 (2H), 7.31 (5H).

Example 115e

Benzyl N-(2-hydroxy[²H₄]ethyl)carbamate

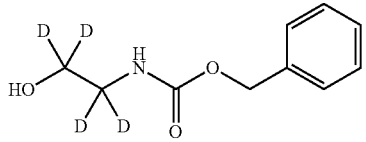 [SMILES: [2H]C([2H])(O)C([2H])([2H])NC(=O)OCc1ccccc1]

1.0 g (15 mmol) of deuterated aminoethanol was first dissolved in 29 ml dichloromethane. Then 2.5 ml (1.8 g, 18 mmol) of triethylamine was added and the reaction mixture cooled to 0° C. At this temperature 2.75 ml (3.34 g, 19.6 mmol) of benzyl chloroformate was now cautiously added dropwise. After completion of the addition, the mixture was stirred for 1 hr more with no ice-bath and in the process warmed up to RT. The reaction mixture was diluted once with some dichloromethane and washed once with saturated sodium chloride solution. The organic phase was dried over sodium sulphate, filtered and concentrated. The crude product was purified twice by column chromatography (dichloromethane/methanol 0-10% and ethyl acetate). Yield: 1.32 g of the title compound.

¹H-NMR (300 MHz, DMSO-d₆): δ [ppm], 4.54 (1H), 4.97 (2H), 7.12 (1H), 7.81 (5H).

The following compound was prepared analogously:

| Ex. | Structure | IUPAC name | Analysis |
|---|---|---|---|
| 116 | 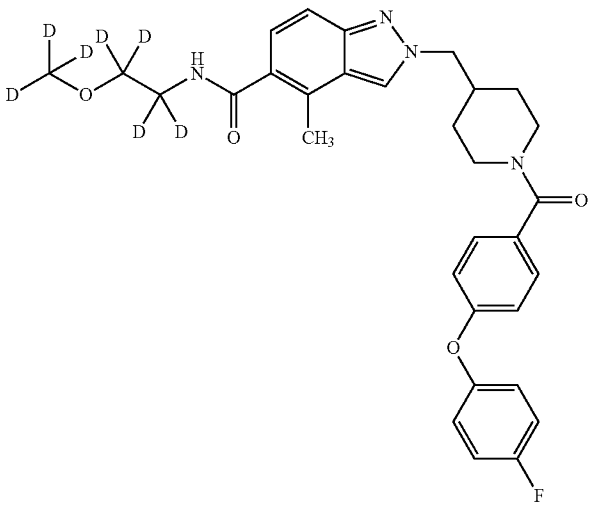 [SMILES: [2H]C([2H])([2H])OC([2H])([2H])C([2H])([2H])NC(=O)c1ccc2nn(CC3CCN(C(=O)c4ccc(Oc5ccc(F)cc5)cc4)CC3)cc2c1C] | 2-({1-[4-(4-fluoro-phenoxy)benzoyl]-piperidin-4-yl}methyl)-4-methyl-N-(2-[²H₃]-methyloxy[²H₄]ethyl)-2H-indazole-5-carboxamide | ¹H-NMR (300 MHz, DMSO-d₆): δ [ppm] = 1.19 (2H), 1.46 (2H), 2.25 (1H), 2.49 (3H), 2.85 (2H), 3.66 (1H), 4.31 (2H), 4.38 (1H), 6.95 (2H), 7.16 (5H), 7.36 (3H), 8.07 (1H), 8.46 (1H). |

Example 117

2-{[1-(4-chlorobenzoyl)azetidin-3-yl]methyl}-N-(2-methoxyethyl)-4-methyl-2H-indazole-5-carboxamide

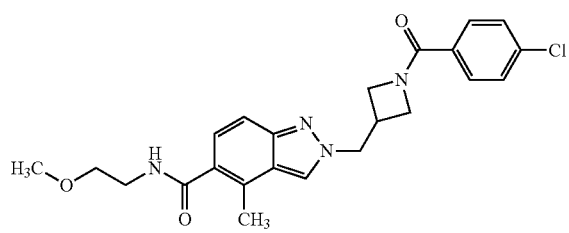 [SMILES: COCCNC(=O)c1ccc2nn(CC3CN(C(=O)c4ccc(Cl)cc4)C3)cc2c1C]

Analogously to Example 55, 471 mg of the title compound was obtained from 500 mg of the compound prepared in Example 117e) and 287 mg of 4-chlorobenzoyl chloride.

¹H-NMR (300 MHz, DMSO-d₆): δ=2.49 (3H), 3.22 (1H), 3.25 (3H), 3.32-3.46 (4H), 3.89 (1H), 4.09 (1H), 4.19 (1H), 4.37 (1H), 4.67 (2H), 7.15 (1H), 7.38 (1H), 7.48 (2H), 7.59 (2H), 8.12 (1H), 8.54 (1H).

The starting material was prepared as follows:

Example 117a

Tert-butyl 3-[(5-bromo-4-methyl-2H-indazol-2-yl)methyl]-azetidin-1-carboxylate

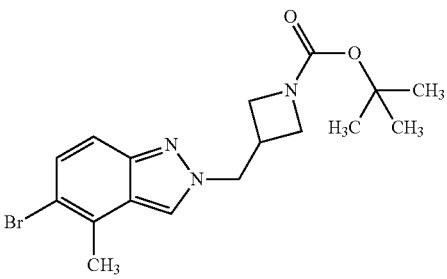 [SMILES: Cc1c(Br)ccc2nn(CC3CN(C(=O)OC(C)(C)C)C3)cc12]

To a solution of 21.1 g of 5-bromo-4-methyl-1H-indazole and 37.6 g of tert-butyl-3-[(tosyloxy)-methyl]azetidin-1-carboxylate in 100 ml dioxan were added 150 ml of a 1M solution of sodium bis(trimethylsilyl)amide in tetrahydrofuran at 25° C. and this was stirred for 6 hrs at 90° C. After cooling, the reaction mixture was treated with ethyl acetate and water, the organic phases separated and the aqueous phase extracted twice with 100 ml portions of ethyl acetate. The combined organic phases were washed with saturated sodium chloride solution, dried over sodium sulphate, and concentrated in vacuo after filtration. The residue thus obtained was purified by chromatography on the Flashmaster (hexane/ethyl acetate 1:0-0:1). 15.0 g of the title compound was obtained.

¹H-NMR (300 MHz, DMSO-d₆): δ=1.32 (9H), 2.48 (3H), 3.07 (1H), 3.69 (2H), 3.87 (2H), 4.59 (2H), 7.28 (1H), 7.35 (1H), 8.53 (1H).

Example 117b

Methyl 2-{[1-(tert-butoxycarbonyl)azetidin-3-yl]methyl}-4-methyl-2H-indazol-5-carboxylate

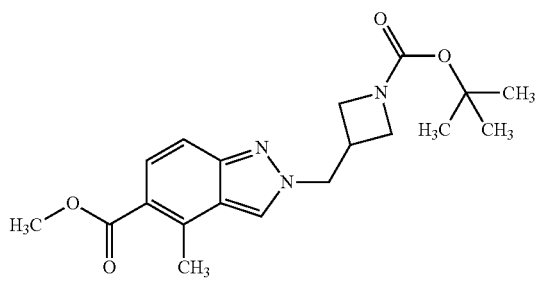 [SMILES: COC(=O)c1ccc2nn(CC3CN(C(=O)OC(C)(C)C)C3)cc2c1C]

To a solution of 8.16 g of the bromide prepared in Example 117a in 65.4 ml methanol, 6.5 g of 1,1 bis(diphenylphosphino)ferrocen-palladium(II) dichloride and 15 g of potassium acetate were added at 25° C. and the mixture was stirred under CO at 10.15 bar and 120° C. for 24 hours in an autoclave. The reaction mixture was then cooled, filtered through Celite at the pump and the filtrate concentrated in vacuo. The residue thus obtained was purified by chromatography on the Flashmaster (hexane/ethyl acetate 1:0-0:1). 6.97 g of the title compound was obtained.

$^1$H-NMR (300 MHz, DMSO-d6): δ=1.32 (9H), 2.73 (3H), 3.09 (1H), 3.71 (2H), 3.79 (3H), 3.87 (2H), 4.62 (2H), 7.42 (1H), 7.63 (1H), 8.74 (1H).

Example 117c

2-{[1-(tert-butoxycarbonyl)azetidin-3-yl]methyl}-4-methyl-2H-indazol-5-carboxylic acid

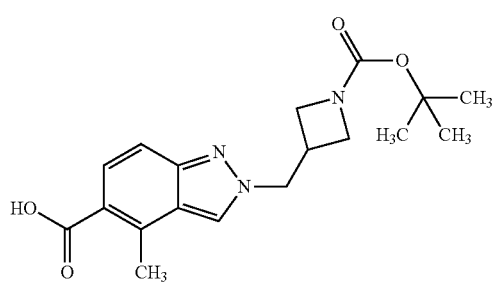 [SMILES: Cc1c(C(=O)O)ccc2nn(CC3CN(C(=O)OC(C)(C)C)C3)cc12]

Analogously to Example 1d, 5.2 g of the title compound was obtained from 15.1 g of the ester prepared in Example 117b.

$^1$H-NMR (300 MHz, DMSO-d6): δ=1.32 (9H), 2.73 (3H), 3.09 (1H), 3.71 (2H), 3.87 (2H), 4.61 (2H), 7.39 (1H), 7.64 (1H), 8.70 (1H), 12.57 (1H).

Example 117d

Tert-butyl 3-({5-[N-(2-methoxyethyl)carbamoyl]-4-methyl-2H-indazol-2-yl}-methyl)azetidin-1-carboxylate

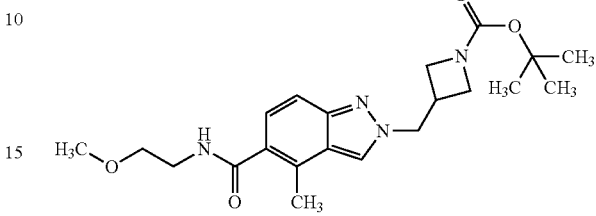

Analogously to Example 1, from 2.5 g of the acid prepared in Example 117c and 0.54 g of 2-methoxyethylamine, a crude product was obtained which through purification with a Biotage unit (ethyl acetate: 0 to 30% methanol) yielded 2.69 g of the title compound.

$^1$H-NMR (300 MHz, DMSO-d6): δ=1.32 (9H), 2.49 (3H), 3.08 (1H), 3.25 (3H), 3.32-3.46 (4H), 3.70 (2H), 3.86 (2H), 4.60 (2H), 7.15 (1H), 7.38 (1H), 8.11 (1H), 8.54 (1H).

Example 117e 2-(azetidin-3-ylmethyl)-N-(2-methoxyethyl)-4-methyl-2H-indazol-5-carboxamide hydrochloride

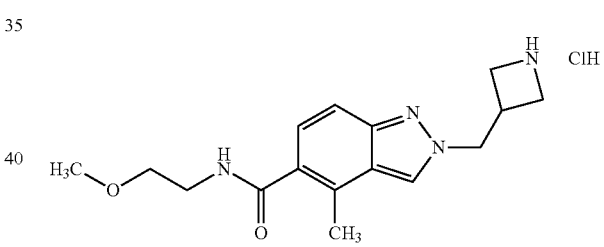

Analogously to Example 1a, from 2.69 g of the amide prepared in Example 117d, 2.59 g of the title compound was obtained, which was reacted without further purification.

Example 118

N-(2-methoxyethyl)-4-methyl-2-[(1-{4-[(trifluoromethyl)sulphanyl]benzoyl}azetidin-3-yl)methyl]-2H-indazole-5-carboxamide

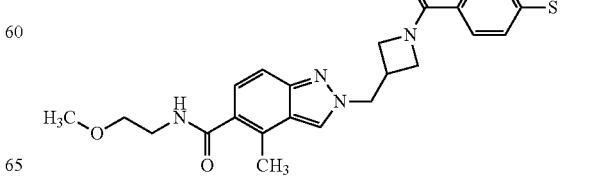

Analogously to Example 55, 29 mg of the title compound was obtained from 55 mg of the compound prepared in Example 117e and 43 mg of 4-[(trifluoromethyl)sulphanyl]benzoyl chloride.

$^1$H-NMR (300 MHz, DMSO-d6): δ=2.49 (3H), 3.22 (1H), 3.25 (3H), 3.36 (2H), 3.42 (2H), 3.92 (1H), 4.11 (1H), 4.20 (1H), 4.39 (1H), 4.67 (2H), 7.15 (1H), 7.38 (1H), 7.69 (2H), 7.76 (2H), 8.12 (1H), 8.54 (1H).

Example 119

N-(2-methoxyethyl)-4-methyl-2-({1-[4-(trifluoromethoxy)benzoyl]azetidin-3-yl}methyl)-2H-indazole-5-carboxamide

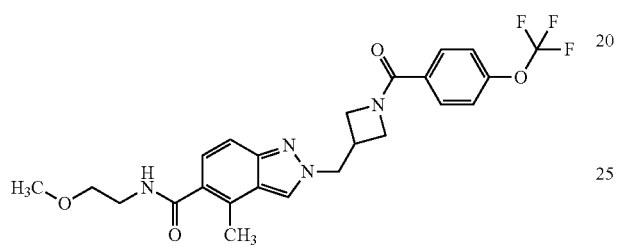

Analogously to Example 55, 27 mg of the title compound was obtained from 55 mg of the compound prepared in Example 117e and 40 mg of 4-(trifluoromethoxy)benzoyl chloride.

$^1$H-NMR (300 MHz, DMSO-d6): δ=2.49 (3H), 3.20 (1H), 3.24 (3H), 3.32-3.46 (4H), 3.91 (1H), 4.10 (1H), 4.20 (1H), 4.39 (1H), 4.67 (2H), 7.15 (1H), 7.35-7.44 (3H), 7.70 (2H), 8.12 (1H), 8.54 (1H).

Example 120

2-({1-[2-fluoro-4-(trifluoromethyl)benzoyl]azetidin-3-yl}methyl)-N-(2-methoxy-ethyl)-4-methyl-2H-indazole-5-carboxamide

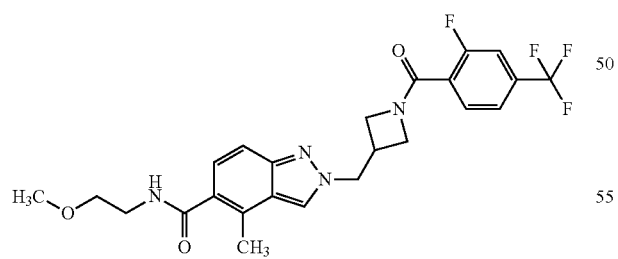

Analogously to Example 55, 17 mg of the title compound was obtained from 55 mg of the compound prepared in Example 117e and 41 mg of 2-fluoro-4-(trifluoromethyl)benzoyl chloride.

$^1$H-NMR (300 MHz, DMSO-d6): δ=2.48 (3H), 3.23 (1H), 3.25 (3H), 3.36 (2H), 3.42 (2H), 3.94 (2H), 4.11 (2H), 4.66 (2H), 7.15 (1H), 7.38 (1H), 7.64 (2H), 7.79 (1H), 8.12 (1H), 8.54 (1H).

Example 121

2-{[1-(4-chloro-2-fluorobenzoyl)azetidin-3-yl]methyl}-N-(2-methoxyethyl)-4-methyl-2H-indazole-5-carboxamide

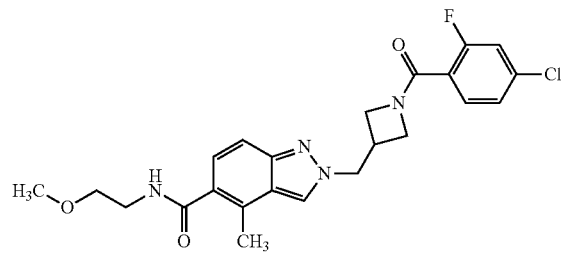 [SMILES: COCCNC(=O)c1ccc2nn(CC3CN(C(=O)c4ccc(Cl)cc4F)C3)cc2c1C]

Analogously to Example 55, 19 mg of the title compound was obtained from 42 mg of the compound prepared in Example 117e and 26 mg of 4-chloro-2-fluorobenzoyl chloride.

$^1$H-NMR (300 MHz, DMSO-d6): δ=2.48 (3H), 3.21 (1H), 3.24 (3H), 3.33-3.46 (4H), 3.86-3.97 (2H), 4.08 (2H), 4.65 (2H), 7.15 (1H), 7.34 (1H), 7.37 (1H), 7.44 (1H), 7.52 (1H), 8.12 (1H), 8.53 (1H).

Example 122

2-({1-[3-fluoro-4-(trifluoromethyl)benzoyl]azetidin-3-yl}methyl)-N-(2-methoxy-ethyl)-4-methyl-2H-indazole-5-carboxamide

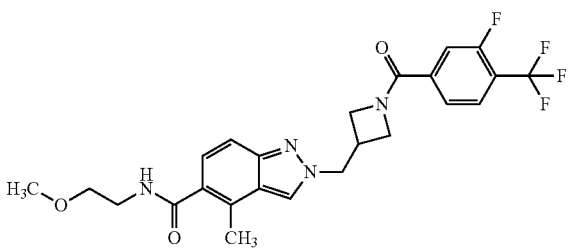 [SMILES: COCCNC(=O)c1ccc2nn(CC3CN(C(=O)c4ccc(C(F)(F)F)c(F)c4)C3)cc2c1C]

Analogously to Example 55, 15 mg of the title compound was obtained from 42 mg of the compound prepared in Example 117e and 31 mg of 3-fluoro-4-(trifluoromethyl)benzoyl chloride.

$^1$H-NMR (300 MHz, DMSO-d6): δ=2.49 (3H), 3.21 (1H), 3.25 (3H), 3.36 (2H), 3.42 (2H), 3.93 (1H), 4.12 (1H), 4.22 (1H), 4.40 (1H), 4.67 (2H), 7.15 (1H), 7.37 (1H), 7.57 (1H), 7.64 (1H), 7.85 (1H), 8.12 (1H), 8.54 (1H).

Example 123

2-({1-[4-chloro-3-(trifluoromethyl)benzoyl]azetidin-3-yl}methyl)-N-(2-methoxy-ethyl)-4-methyl-2H-indazole-5-carboxamide

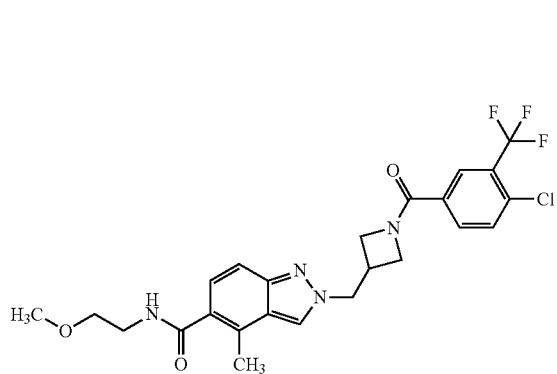 [SMILES: COCCNC(=O)c1ccc2nn(CC3CN(C(=O)c4ccc(Cl)c(C(F)(F)F)c4)C3)cc2c1C]

Analogously to Example 55, 6 mg of the title compound was obtained from 42 mg of the compound prepared in Example 117e and 33 mg of 4-chloro-3-(trifluoromethyl)benzoyl chloride.

$^1$H-NMR (300 MHz, DMSO-d6): δ=2.49 (3H), 3.21 (1H), 3.25 (3H), 3.31-3.46 (4H), 3.92 (1H), 4.11 (1H), 4.22 (1H), 4.41 (1H), 4.67 (2H), 7.15 (1H), 7.37 (1H), 7.79 (1H), 7.86 (1H), 7.94 (1H), 8.12 (1H), 8.53 (1H).

Example 124

2-{[1-(4-cyclopropylbenzoyl)azetidin-3-yl]methyl}-N-(2-methoxyethyl)-4-methyl-2H-indazole-5-carboxamide

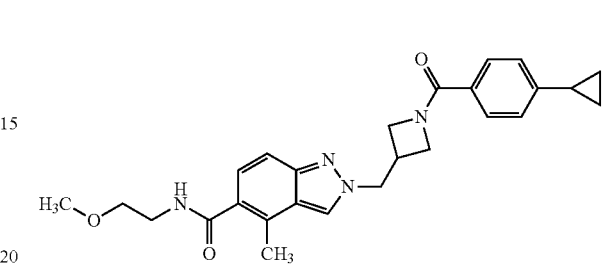

Analogously to Example 1, 76 mg of the title compound was obtained from 163 mg of the compound prepared in Example 117e and 78 mg of 4-cyclopropylbenzoic acid.

$^1$H-NMR (300 MHz, DMSO-d6): δ=0.71 (2H), 0.99 (2H), 1.95 (1H), 2.52 (3H), 3.24 (1H), 3.34-3.41 (5H), 3.45 (2H), 3.90 (1H), 4.09 (1H), 4.20 (1H), 4.38 (1H), 4.68 (2H), 7.12 (2H), 7.18 (1H), 7.41 (1H), 7.48 (2H), 8.12 (1H), 8.57 (1H).

Example 125

N-(2-methoxyethyl)-4-methyl-2-[(1-{4-[4-(trifluoromethyl)phenoxy]benzoyl}azetidin-3-yl)methyl]-2H-indazole-5-carboxamide

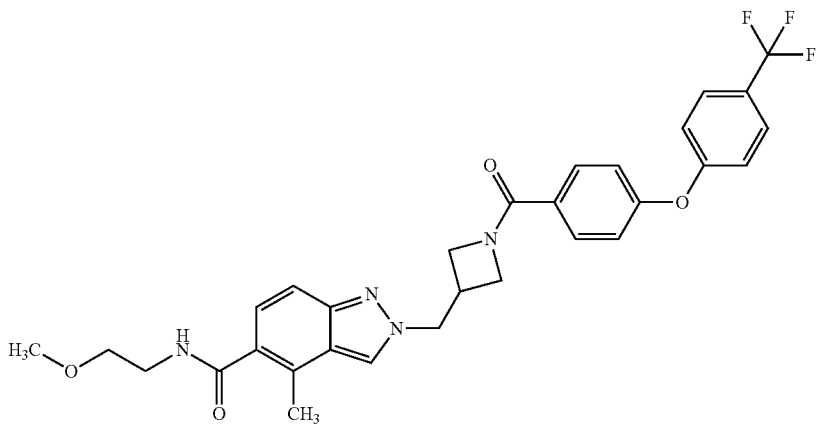

Analogously to Example 1, 478 mg of the title compound was obtained from 1.20 g of the compound prepared in Example 117e and 850 mg of 4-[4-(trifluoromethyl)phenoxy]benzoic acid.

¹H-NMR (300 MHz, DMSO-d6): δ=2.52 (3H), 3.25 (1H), 3.27 (3H), 3.39 (2H), 3.45 (2H), 3.94 (1H), 4.12 (1H), 4.24 (1H), 4.42 (1H), 4.70 (2H), 7.14 (2H), 7.18 (1H), 7.22 (2H), 7.41 (1H), 7.69 (2H), 7.77 (2H), 8.12 (1H), 8.57 (1H).

Example 126

2-{[1-(4-chlorobenzoyl)azetidin-3-yl]methyl}-N-[2-(3,3-difluoropyrrolidin-1-yl)ethyl]-4-methyl-2H-indazole-5-carboxamide

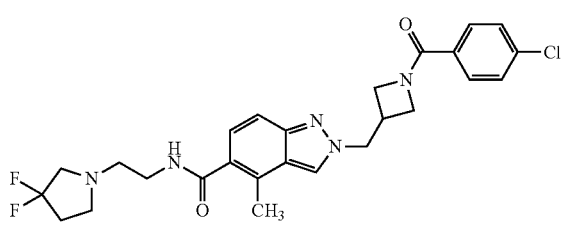 [SMILES: Cc1c(C(=O)NCCN2CCC(F)(F)C2)ccc2nn(CC3CN(C(=O)c4ccc(Cl)cc4)C3)cc12]

Analogously to Example 55, 38 mg of the title compound was obtained from 43 mg of the compound prepared in Example 126a and 20 mg of 4-chlorobenzoyl chloride.

¹H-NMR (300 MHz, DMSO-d6): δ=2.10-2.27 (3H), 2.49 (3H), 2.57 (2H), 2.72 (2H), 2.91 (2H), 3.17-3.36 (2H), 3.89 (1H), 4.08 (1H), 4.19 (1H), 4.36 (1H), 4.67 (2H), 7.14 (1H), 7.38 (1H), 7.48 (2H), 7.59 (2H), 8.05 (1H), 8.54 (1H).

Example 126a 2-(azetidin-3-ylmethyl)-N-[2-(3,3-difluoropyrrolidin-1-yl)ethyl]-4-methyl-2H-indazole-5-carboxamide hydrochloride

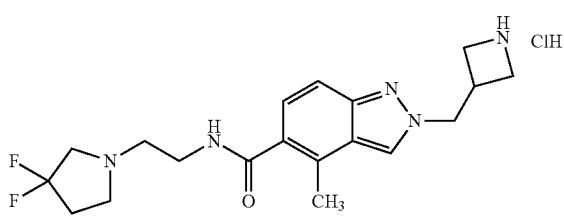 [SMILES: Cc1c(C(=O)NCCN2CCC(F)(F)C2)ccc2nn(CC3CNC3)cc12 ; Cl]

Analogously to Example 1a, from 50 mg of the compound prepared in Example 126b, 43 mg of the title compound was obtained, which was reacted without further purification.

Example 126b

Tert-butyl 3-[(5-{N-[2-(3,3-difluoropyrrolidin-1-yl)ethyl]carbamoyl}-4-methyl-2H-indazol-2-yl)methyl]azetidin-1-carboxylate

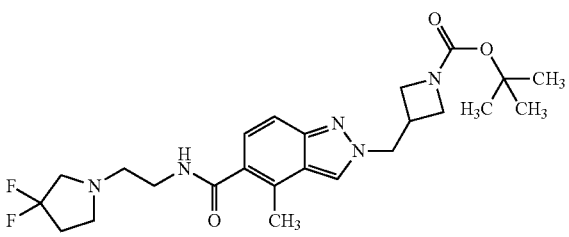 [SMILES: Cc1c(C(=O)NCCN2CCC(F)(F)C2)ccc2nn(CC3CN(C(=O)OC(C)(C)C)C3)cc12]

Analogously to Example 1b, 71 mg of the title compound was obtained from 70 mg of the compound prepared in Example 117a and 83 mg of 2-(3,3-difluoropyrrolidin-1-yl)ethylamine.

¹H-NMR (300 MHz, DMSO-d6): δ=1.32 (9H), 2.10-2.28 (2H), 2.50 (3H), 2.57 (2H), 2.66-2.77 (2H), 2.84-2.98 (2H), 3.08 (1H), 3.23-3.36 (2H), 3.69 (2H), 3.86 (2H), 4.60 (2H), 7.14 (1H), 7.39 (1H), 8.05 (1H), 8.55 (1H).

Example 127

2-{[1-(4-chlorobenzoyl)azetidin-3-yl]methyl}-4-methyl-N-{2-[(trifluoromethyl) sulphanyl]ethyl}-2H-indazole-5-carboxamide

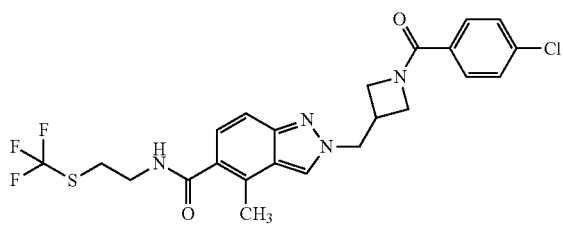

Analogously to Example 55, 143 mg of the title compound was obtained from 130 mg of the compound prepared in Example 127b and 61 mg of 4-chlorobenzoyl chloride.

¹H-NMR (300 MHz, DMSO-d6): δ=2.51 (3H), 3.13-3.29 (3H), 3.50 (2H), 3.90 (1H), 4.09 (1H), 4.19 (1H), 4.37 (1H), 4.67 (2H), 7.19 (1H), 7.40 (1H), 7.48 (2H), 7.59 (2H), 8.38 (1H), 8.57 (1H).

The starting material was prepared as follows:

Example 127a

Tert-butyl 3-{[4-methyl-5-(N-{2-[(trifluoromethyl)sulphanyl]ethyl}carbamoyl)-indazol-2-yl]methyl}azetidin-1-carboxylate

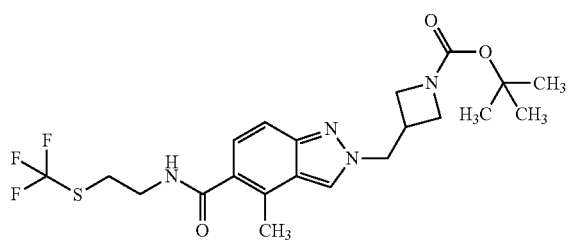

Analogously to Example 1, 674 mg of the title compound was obtained from 500 mg of the compound prepared in Example 117c.

$^1$H-NMR (300 MHz, DMSO-d6): δ=1.32 (9H), 2.52 (3H), 3.08 (1H), 3.17 (2H), 3.50 (2H), 3.69 (2H), 3.86 (2H), 4.61 (2H), 7.19 (1H), 7.41 (1H), 8.38 (1H), 8.57 (1H).

Example 127b 2-(azetidin-3-ylmethyl)-4-methyl-N-{2-[(trifluoromethyl)sulphanyl]ethyl}-2H-indazole-5-carboxamide hydrochloride

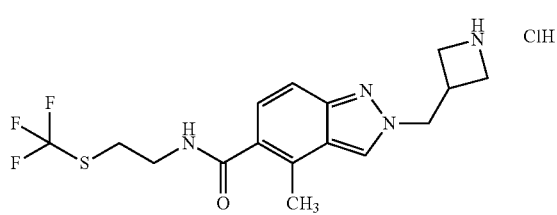 [SMILES: Cl ; Cc1c(C(=O)NCCSC(F)(F)F)ccc2nn(CC3CNC3)cc12]

Analogously to Example 1a, from 150 mg of the compound prepared in Example 127a, 130 mg of the title compound was obtained, which was further reacted without purification.

Example 128

2-{[1-(4-chlorobenzoyl)azetidin-3-yl]methyl}-4-methyl-N-(2-morpholinoethyl)-2H-indazole-5-carboxamide

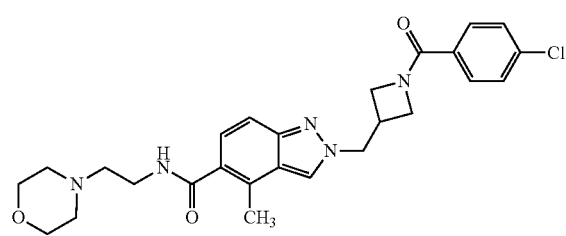 [SMILES: Cc1c(C(=O)NCCN2CCOCC2)ccc2nn(CC3CN(C(=O)c4ccc(Cl)cc4)C3)cc12]

Analogously to Example 55, 30 mg of the title compound was obtained from 50 mg of the compound prepared in Example 128b and 24 mg of 4-chlorobenzoyl chloride.

$^1$H-NMR (300 MHz, DMSO-d6): δ=2.34-2.45 (6H), 2.51 (3H), 3.22 (1H), 3.33 (2H), 3.54 (4H), 3.89 (1H), 4.08 (1H), 4.19 (1H), 4.36 (1H), 4.67 (2H), 7.15 (1H), 7.38 (1H), 7.48 (2H), 7.59 (2H), 7.99 (1H), 8.54 (1H).

The starting material was prepared as follows:

Example 128a

Tert-butyl 3-({4-methyl-5-[N-(2-morpholinoethyl)carbamoyl]-2H-indazol-2-yl}methyl)azetidin-1-carboxylate

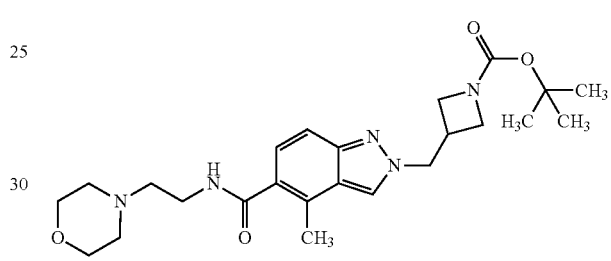

Analogously to Example 1b, 59 mg of the title compound was obtained from 200 mg of the compound prepared in Example 117a and 205 mg of 2-morpholinoethylamine.

$^1$H-NMR (300 MHz, DMSO-d6): δ=1.32 (9H), 2.34-2.44 (6H), 2.52 (3H), 3.08 (1H), 3.33 (2H), 3.54 (4H), 3.69 (2H), 3.86 (2H), 4.61 (2H), 7.15 (1H), 7.39 (1H), 7.98 (1H), 8.55 (1H).

Example 128b 2-(azetidin-3-ylmethyl)-4-methyl-N-(2-morpholinoethyl)-2H-indazole-5-carboxamide hydrochloride

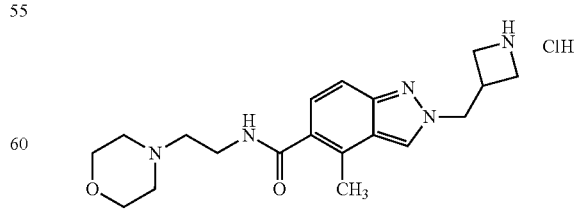

Analogously to Example 1a, from 59 mg of the compound prepared in Example 128a, 63 mg of the title compound was obtained, which was further reacted without purification.

Example 129

2-{[1-(4-chlorobenzoyl)azetidin-3-yl]methyl}-4-methyl-N-(2,2,2-trifluoroethyl)-2H-indazole-5-carboxamide

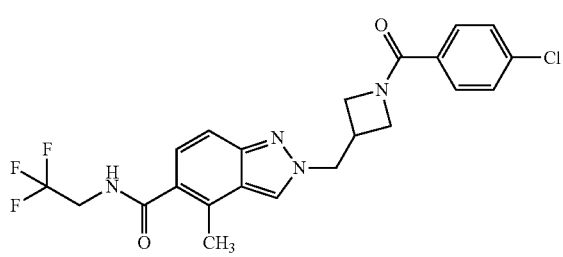 [SMILES: Cc1c(C(=O)NCC(F)(F)F)ccc2nn(CC3CN(C(=O)c4ccc(Cl)cc4)C3)cc12]

Analogously to Example 55, 127 mg of the title compound was obtained from 128 mg of the compound prepared in Example 129b and 68 mg of 4-chlorobenzoyl chloride.

$^1$H-NMR (300 MHz, DMSO-d6): δ=2.50 (3H), 3.22 (1H), 3.90 (1H), 3.96-4.13 (3H), 4.19 (1H), 4.37 (1H), 4.68 (2H), 7.18 (1H), 7.42 (1H), 7.48 (2H), 7.59 (2H), 8.59 (1H), 8.79 (1H).

The starting material was prepared as follows:

Example 129a

Tert-butyl 3-({4-methyl-5-[N-(2,2,2-trifluoroethyl)carbamoyl]-2H-indazol-2-yl}methyl)azetidin-1-carboxylate

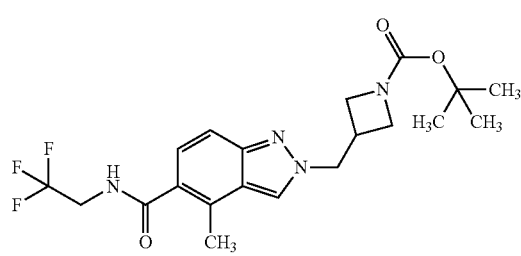 [SMILES: Cc1c(C(=O)NCC(F)(F)F)ccc2nn(CC3CN(C(=O)OC(C)(C)C)C3)cc12]

Analogously to Example 1, 1.02 g of the title compound was obtained from 1.0 g of the compound prepared in Example 117c and 287 mg of 2,2,2-trifluoroethylamine.

$^1$H-NMR (300 MHz, DMSO-d6): δ=1.32 (9H), 2.51 (3H), 3.09 (1H), 3.70 (2H), 3.86 (2H), 4.03 (2H), 4.62 (2H), 7.17 (1H), 7.43 (1H), 8.60 (1H), 8.79 (1H).

Example 129b 2-(azetidin-3-ylmethyl)-4-methyl-N-(2,2,2-trifluoroethyl)-2H-indazole-5-carboxamide hydrochloride

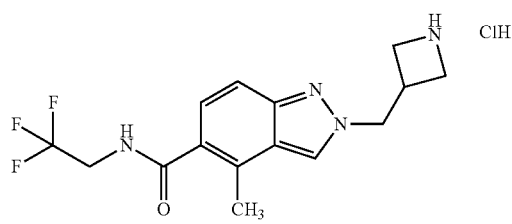 [SMILES: Cl ; Cc1c(C(=O)NCC(F)(F)F)ccc2nn(CC3CNC3)cc12]

Analogously to Example 1a, from 1.0 g of the compound prepared in Example 129a, 852 mg of the title compound was obtained, which was further reacted without purification.

Example 130

4-methyl-N-(2,2,2-trifluoroethyl)-2-({1-[4-(trifluoromethoxy)benzoyl]azetidin-3-yl}methyl)-2H-indazole-5-carboxamide

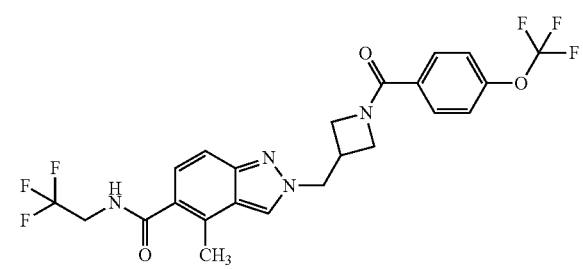 [SMILES: Cc1c(C(=O)NCC(F)(F)F)ccc2nn(CC3CN(C(=O)c4ccc(OC(F)(F)F)cc4)C3)cc12]

Analogously to Example 55, 113 mg of the title compound was obtained from 128 mg of the compound prepared in Example 129b and 87 mg of 4-(trifluoromethoxy)benzoyl chloride.

$^1$H-NMR (300 MHz, DMSO-d6): δ=2.50 (3H), 3.23 (1H), 3.92 (1H), 3.96-4.14 (3H), 4.20 (1H), 4.39 (1H), 4.68 (2H), 7.18 (1H), 7.36-7.46 (3H), 7.70 (2H), 8.59 (1H), 8.79 (1H).

Example 131

2-({1-[2-fluoro-4-(trifluoromethyl)benzoyl]azetidin-3-yl}methyl)-4-methyl-N-(2,2,2-trifluoroethyl)-2H-indazole-5-carboxamide

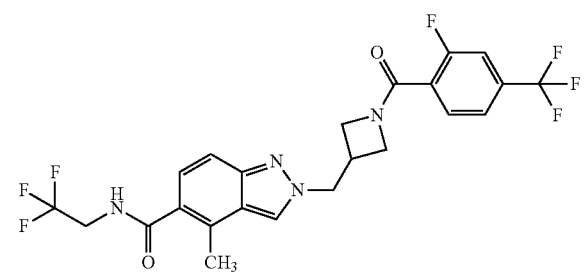 [SMILES: Cc1c(C(=O)NCC(F)(F)F)ccc2nn(CC3CN(C(=O)c4ccc(C(F)(F)F)cc4F)C3)cc12]

Analogously to Example 55, 128 mg of the title compound was obtained from 128 mg of the compound prepared in Example 129b and 88 mg of 2-fluoro-4-(trifluoromethyl)benzoyl chloride.

$^1$H-NMR (300 MHz, DMSO-d6): δ=2.49 (3H), 3.23 (1H), 3.89-4.16 (6H), 4.67 (2H), 7.17 (1H), 7.42 (1H), 7.60-7.67 (2H), 7.79 (1H), 8.58 (1H), 8.80 (1H).

Example 132

4-methyl-2-({1-[4-(pentafluoro-λ$^6$-sulphanyl)benzoyl]azetidin-3-yl}methyl)-N-(2,2,2-trifluoroethyl)-2H-indazole-5-carboxamide

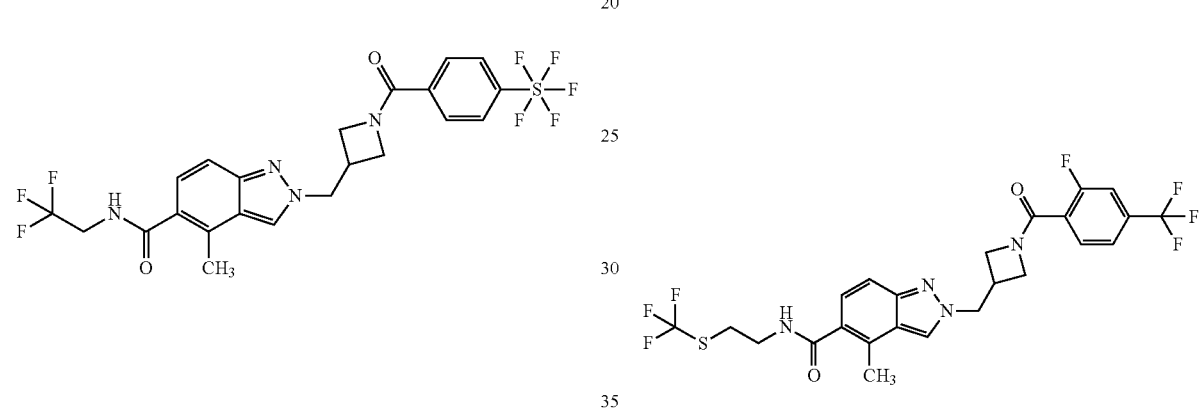

Analogously to Example 1, 121 mg of the title compound was obtained from 128 mg of the compound prepared in Example 129b and 96 mg of 4-(pentafluoro-λ$^6$-sufanyl)benzoic acid.

$^1$H-NMR (300 MHz, DMSO-d6): δ=2.50 (3H), 3.24 (1H), 3.94 (1H), 3.98-4.08 (2H), 4.12 (1H), 4.20 (1H), 4.39 (1H), 4.69 (2H), 7.18 (1H), 7.42 (1H), 7.76 (2H), 7.95 (2H), 8.59 (1H), 8.80 (1H).

Example 133

4-methyl-2-({1-[4-(trifluoromethoxy)benzoyl]azetidin-3-yl}methyl)-N-{2-[(trifluoromethyl)sulphanyl]ethyl}-2H-indazole-5-carboxamide

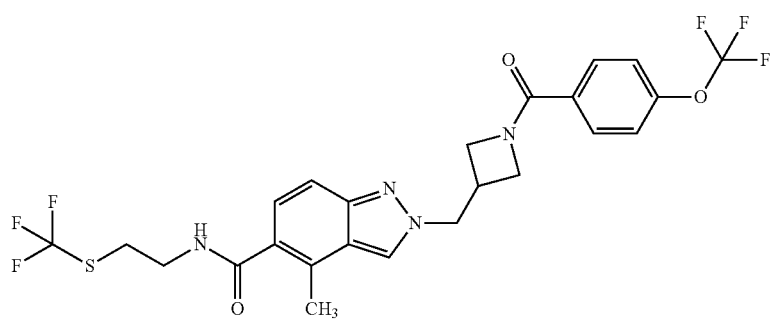 [SMILES: Cc1c(C(=O)NCCSC(F)(F)F)ccc2nn(CC3CN(C(=O)c4ccc(OC(F)(F)F)cc4)C3)cc12]

Analogously to Example 55, 178 mg of the title compound was obtained from 130 mg of the compound prepared in Example 127b and 78 mg of 4-(trifluoromethoxy)benzoyl chloride.

$^1$H-NMR (300 MHz, DMSO-d6): δ=2.51 (3H), 3.13-3.28 (3H), 3.51 (2H), 3.91 (1H), 4.10 (1H), 4.20 (1H), 4.39 (1H), 4.67 (2H), 7.19 (1H), 7.40 (3H), 7.70 (2H), 8.38 (1H), 8.57 (1H).

Example 134

2-({1-[2-fluoro-4-(trifluoromethyl)benzoyl]azetidin-3-yl}methyl)-4-methyl-N-{2-[(trifluoromethyl)sulphanyl]ethyl}-2H-indazole-5-carboxamide

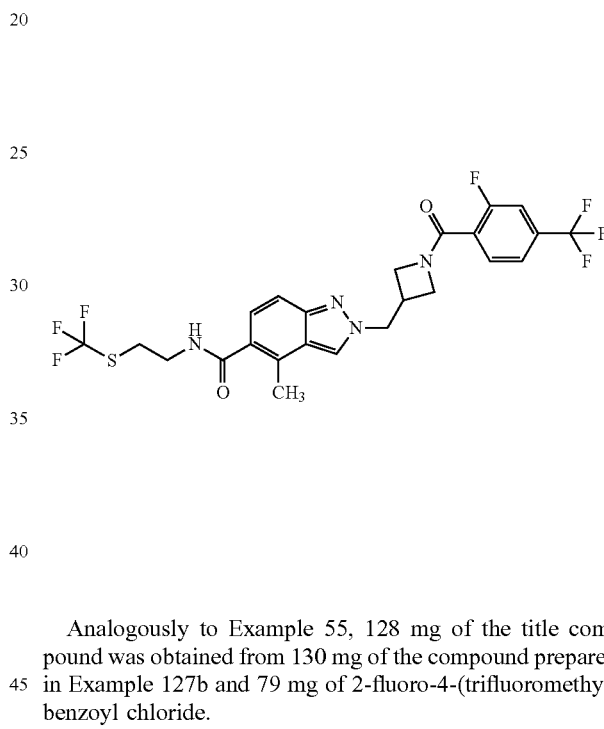

Analogously to Example 55, 128 mg of the title compound was obtained from 130 mg of the compound prepared in Example 127b and 79 mg of 2-fluoro-4-(trifluoromethyl)benzoyl chloride.

$^1$H-NMR (300 MHz, DMSO-d6): δ=2.51 (3H), 3.12-3.25 (3H), 3.50 (2H), 3.89-3.98 (2H), 4.06-4.16 (2H), 4.67 (2H), 7.19 (1H), 7.40 (1H), 7.64 (2H), 7.79 (1H), 8.39 (1H), 8.56 (1H).

Example 135

4-methyl-2-({1-[4-(pentafluoro-λ⁶-sulphanyl)benzoyl]azetidin-3-yl}methyl)-N-{2-[(trifluoromethyl)sulphanyl]ethyl}-2H-indazole-5-carboxamide

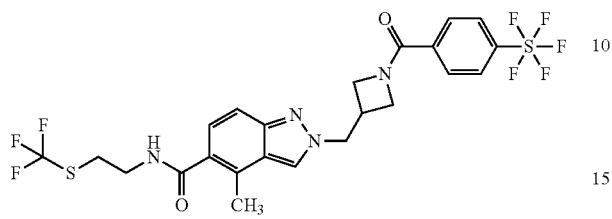

Analogously to Example 1, 84 mg of the title compound was obtained from 130 mg of the compound prepared in Example 127b and 87 mg of 4-(pentafluoro-λ⁶-sulphanyl)benzoic acid.

¹H-NMR (300 MHz, DMSO-d6): δ=2.51 (3H), 3.18 (2H), 3.23 (1H), 3.51 (2H), 3.94 (1H), 4.12 (1H), 4.20 (1H), 4.39 (1H), 4.68 (2H), 7.19 (1H), 7.41 (1H), 7.76 (2H), 7.95 (2H), 8.39 (1H), 8.56 (1H).

Example 136

N-[2-(cyclopropyloxy)ethyl]-4-methyl-2-({1-[4-(trifluoromethoxy)benzoyl]azetidin-3-yl}methyl)-2H-indazole-5-carboxamide

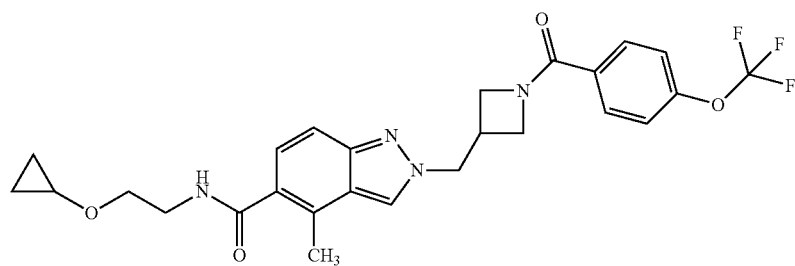 [SMILES: Cc1c(C(=O)NCCOC2CC2)ccc2nn(CC3CN(C(=O)c4ccc(OC(F)(F)F)cc4)C3)cc12]

Analogously to Example 55, 172 mg of the title compound was obtained from 161 mg of the compound prepared in Example 136b and 109 mg of 4-(trifluoromethoxy)benzoyl chloride.

¹H-NMR (300 MHz, DMSO-d6): δ=0.36-0.48 (4H), 2.48 (3H), 3.22 (1H), 3.27 (1H), 3.35 (2H), 3.53 (2H), 3.91 (1H), 4.10 (1H), 4.20 (1H), 4.39 (1H), 4.67 (2H), 7.14 (1H), 7.35-7.44 (3H), 7.71 (2H), 8.11 (1H), 8.54 (1H).

The starting material was prepared as follows:

Example 136a

Tert-butyl 3-[(5-{N-[2-(cyclopropyloxy)ethyl]carbamoyl}-4-methyl-2H-indazol-2-yl)methyl]azetidin-1-carboxylate

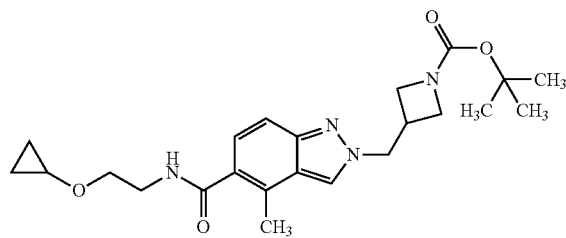 [SMILES: Cc1c(C(=O)NCCOC2CC2)ccc2nn(CC3CN(C(=O)OC(C)(C)C)C3)cc12]

Analogously to Example 1, 189 mg of the title compound was obtained from 150 mg of the compound prepared in Example 118c and 140 mg of 2-cyclopropoxy-ethylammonium trifluoroacetate (preparable according to Example 154a) and 154b) starting from cyclopropanol and bromoacetamide followed by Boc cleavage with trifluoroacetic acid analogously to Example 1a)).

¹H-NMR (300 MHz, DMSO-d6): δ=0.36-0.48 (4H), 1.33 (9H), 2.49 (3H), 3.08 (1H), 3.25-3.39 (3H), 3.53 (2H), 3.70 (2H), 3.87 (2H), 4.61 (2H), 7.14 (1H), 7.38 (1H), 8.10 (1H), 8.54 (1H).

Example 136b 2-(azetidin-3-ylmethyl)-N-[(2-cyclopropyloxy)ethyl]-4-methyl-2H-indazole-5-carboxamide hydrochloride

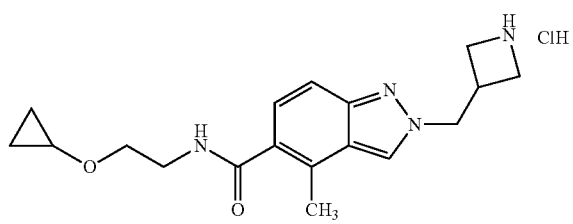 [SMILES: Cc1c(C(=O)NCCOC2CC2)ccc2nn(CC3CNC3)cc12 ; Cl]

Analogously to Example 1a, from 189 mg of the compound prepared in Example 136a, 161 mg of the title compound was obtained, which was further reacted without purification.

Example 137

N-[2-(cyclobutyloxy)ethyl]-4-methyl-2-({1-[4-(trifluoromethoxy)benzoyl]azetidin-3-yl}methyl)-2H-indazole-5-carboxamide

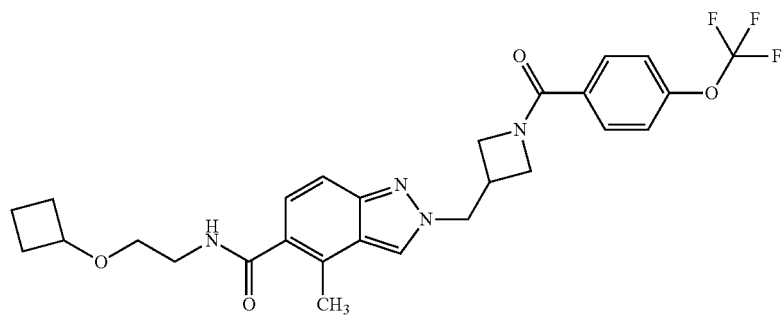 [SMILES: Cc1c(C(=O)NCCOC2CCC2)ccc2nn(CC3CN(C(=O)c4ccc(OC(F)(F)F)cc4)C3)cc12]

Analogously to Example 55, 207 mg of the title compound was obtained from 254 mg of the compound prepared in Example 137b and 166 mg of 4-(trifluoromethoxy)benzoyl chloride.

$^1$H-NMR (300 MHz, DMSO-d6): δ=1.42 (1H), 1.59 (1H), 1.80 (2H), 2.11 (2H), 2.50 (3H), 3.17-3.28 (1H), 3.31-3.41 (4H), 3.85-3.95 (2H), 4.10 (1H), 4.20 (1H), 4.39 (1H), 4.67 (2H), 7.15 (1H), 7.35-7.44 (3H), 7.71 (2H), 8.11 (1H), 8.54 (1H).

The starting material was prepared as follows:

Example 137a

Tert-butyl 3-[(5-{N-[2-(cyclobutyloxy)ethyl]carbamoyl}-4-methyl-2H-indazol-2-yl)methyl]azetidin-1-carboxylate

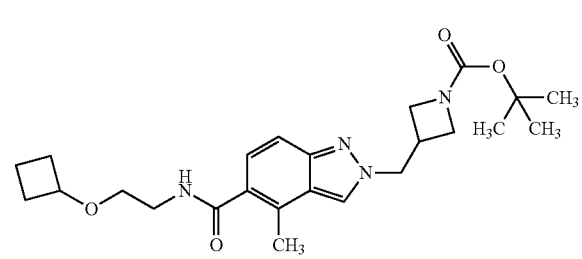

Analogously to Example 1, 297 mg of the title compound was obtained from 220 mg of the compound prepared in Example 117c and 143 mg of 2-(cyclobutyloxy)ethylammonium trifluoroacetate (preparable according to Example 154a) and 154b) starting from cyclobutanol and bromoacetamide followed by Boc cleavage with trifluoroacetic acid analogously to Example 1a)).

$^1$H-NMR (300 MHz, DMSO-d6): δ=1.33 (9H), 1.35-1.49 (1H), 1.59 (1H), 1.80 (2H), 2.11 (2H), 2.50 (3H), 3.08 (1H), 3.30-3.41 (4H), 3.69 (2H), 3.82-3.95 (3H), 4.61 (2H), 7.15 (1H), 7.38 (1H), 8.10 (1H), 8.54 (1H).

Example 137b 2-(azetidin-3-ylmethyl)-N-[(2-(cyclobutyloxy)ethyl]-4-methyl-2H-indazole-5-carboxamide hydrochloride

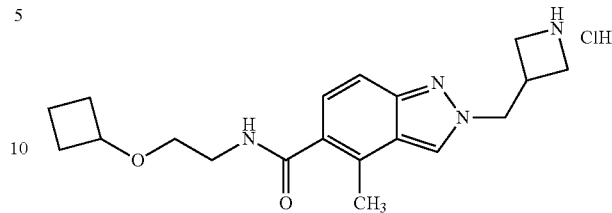

Analogously to Example 1a, from 297 mg of the compound prepared in Example 137a, 254 mg of the title compound was obtained, which was further reacted without purification.

Example 138

(+/−)-2-{[1-(4-chlorobenzoyl)azetidin-3-yl]methyl}-N-(2-methoxypropyl)-4-methyl-2H-indazole-5-carboxamide

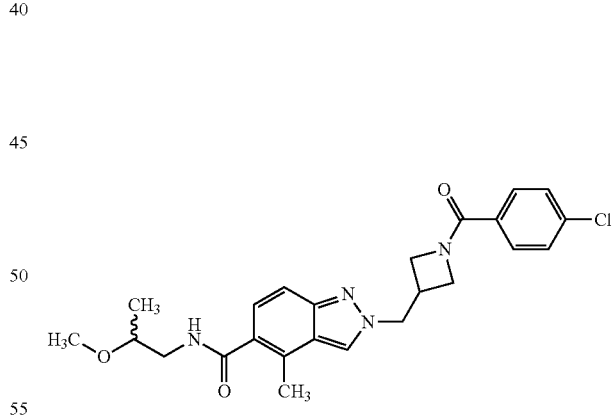

Analogously to Example 55, 166 mg of the title compound was obtained from 237 mg of the compound prepared in Example 138b and 129 mg of 4-chlorobenzoyl chloride.

$^1$H-NMR (300 MHz, DMSO-d6): δ=1.07 (3H), 2.49 (3H), 3.14-3.28 (3H), 3.43 (1H), 3.89 (1H), 4.08 (1H), 4.19 (1H), 4.36 (1H), 4.67 (2H), 7.15 (1H), 7.38 (1H), 7.48 (2H), 7.59 (2H), 8.11 (1H), 8.54 (1H).

The starting material was prepared as follows:

Example 138a (+/−)-tert-butyl 3-({5-[N-(2-methoxypropyl)carbamoyl]-4-methyl-2H-indazol-2-yl}methyl)azetidin-1-carboxylate

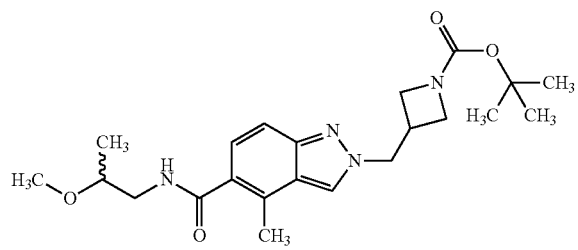 [SMILES: COC(C)CNC(=O)c1ccc2nn(CC3CN(C(=O)OC(C)(C)C)C3)cc2c1C]

Analogously to Example 1, 331 mg of the title compound was obtained from 323 mg of the compound prepared in Example 117c and 117 mg of 2-methoxypropylamine.

$^1$H-NMR (300 MHz, DMSO-d6): δ=1.08 (3H), 1.33 (9H), 2.50 (3H), 3.09 (1H), 3.16-3.31 (2H), 3.44 (1H), 3.69 (2H), 3.85 (2H), 4.61 (2H), 7.15 (1H), 7.39 (1H), 8.08 (1H), 8.54 (1H).

Example 138b (+/−)-2-(azetidin-3-ylmethyl)-N-(2-methoxypropyl)-4-methyl-2H-indazole-5-carboxamide hydrochloride

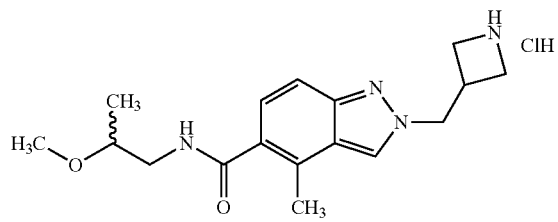 [SMILES: COC(C)CNC(=O)c1ccc2nn(CC3CNC3)cc2c1C ; Cl]

Analogously to Example 1a, from 280 mg of the compound prepared in Example 138a, 247 mg of the title compound was obtained, which was further reacted without purification.

Example 139

(R or S)-2-{[1-(4-chlorobenzoyl)azetidin-3-yl]methyl}-N-(2-methoxypropyl)-4-methyl-2H-indazole-5-carboxamide

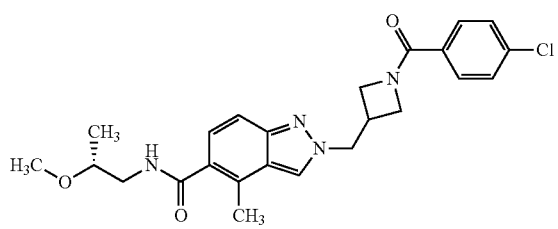

or

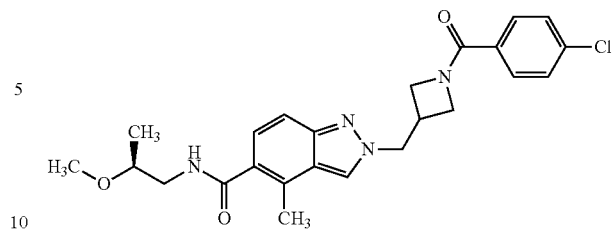

From 158 mg of the racemate prepared in Example 138, 52 mg of the title compound together with 48 mg of the slower-eluting enantiomer (Example 140) were obtained by racemate separation by means of preparative chiral HPLC (Method A).

Analytical chiral HPLC: 14.5 min.

Example 140

(S or R)-2-{[1-(4-chlorobenzoyl)azetidin-3-yl]methyl}-N-(2-methoxypropyl)-4-methyl-2H-indazole-5-carboxamide

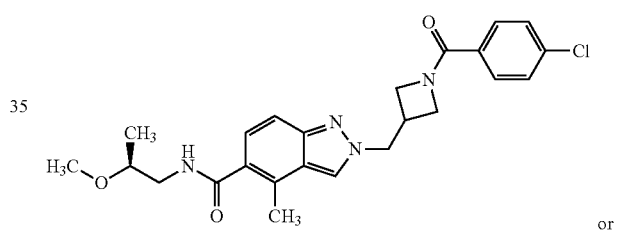

or

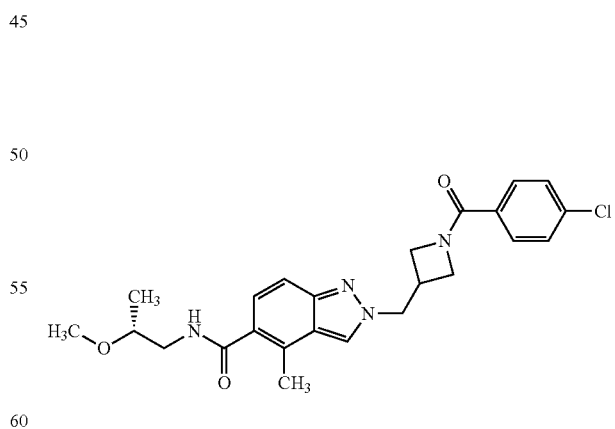

From 158 mg of the racemate prepared in Example 138, 48 mg of the title compound together with 52 mg of the faster-eluting enantiomer (Example 139) were obtained by racemate separation by means of preparative chiral HPLC (Method A).

Analytical chiral HPLC: 17.1 min.

Example 141

(+/−)-2-{[1-(4-chlorobenzoyl)azetidin-3-yl]methyl}-N-(1,4-dioxan-2-ylmethyl)-4-methyl-2H-indazole-5-carboxamide

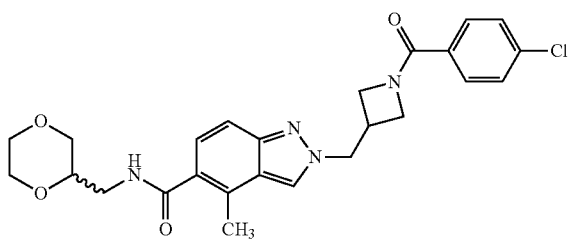 [SMILES: Cc1c(C(=O)NCC2COCCO2)ccc2nn(CC3CN(C(=O)c4ccc(Cl)cc4)C3)cc12]

Analogously to Example 55, 177 mg of the title compound was obtained from 269 mg of the compound prepared in Example 141b and 136 mg of 4-chlorobenzoyl chloride.

$^1$H-NMR (300 MHz, DMSO-d6): δ=2.49 (3H), 3.13-3.28 (4H), 3.38-3.66 (4H), 3.67-3.77 (2H), 3.89 (1H), 4.08 (1H), 4.19 (1H), 4.37 (1H), 4.67 (2H), 7.15 (1H), 7.38 (1H), 7.48 (2H), 7.59 (2H), 8.17 (1H), 8.55 (1H).

The starting material was prepared as follows:

Example 141a (+/−)-tert-butyl 3-({5-[N-(1,4-dioxan-2-ylmethyl)carbamoyl]-4-methyl-2H-indazol-2-yl}methyl)azetidin-1-carboxylate

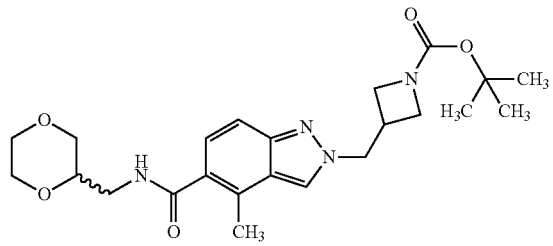 [SMILES: Cc1c(C(=O)NCC2COCCO2)ccc2nn(CC3CN(C(=O)OC(C)(C)C)C3)cc12]

Analogously to Example 1, 364 mg of the title compound was obtained from 323 mg of the compound prepared in Example 117c and 110 mg of 1,4-dioxan-2-ylmethylamine.

$^1$H-NMR (300 MHz, DMSO-d6): δ=1.33 (9H), 2.50 (3H), 3.09 (1H), 3.16-3.29 (3H), 3.40-3.77 (8H), 3.86 (2H), 4.61 (2H), 7.16 (1H), 7.39 (1H), 8.14 (1H), 8.55 (1H).

Example 141b (+/−)-2-(azetidin-3-ylmethyl)-N-(1,4-dioxan-2-ylmethyl)-4-methyl-2H-indazole-5-carboxamide hydrochloride

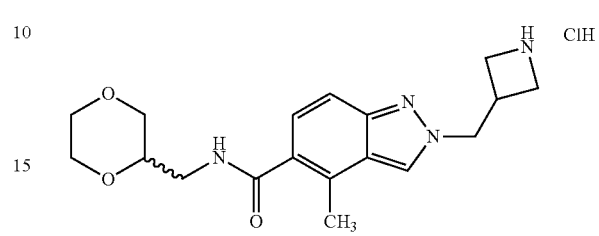

Analogously to Example 1a, from 314 mg of the compound prepared in Example 141a, 274 mg of the title compound was obtained, which was further reacted without purification.

Example 142

(R or S)-2-{[1-(4-chlorobenzoyl)azetidin-3-yl]methyl}-N-(1,4-dioxan-2-yl-methyl)-4-methyl-2H-indazole-5-carboxamide

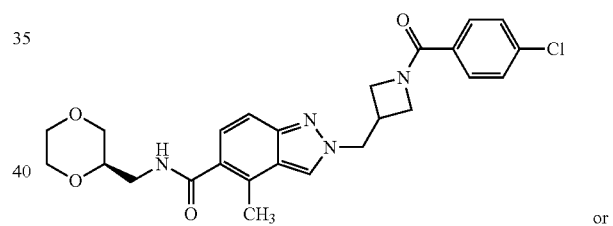

or

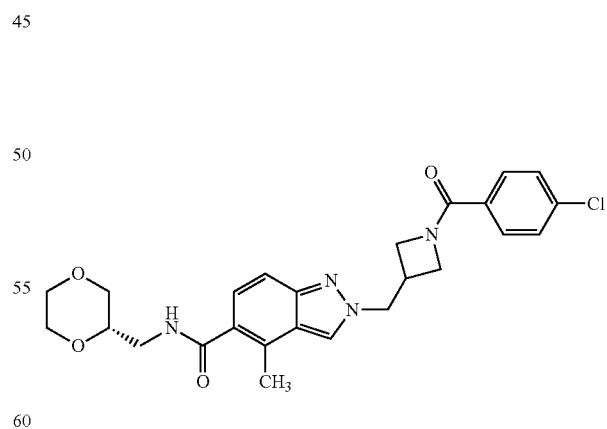

From 172 mg of the racemate prepared in Example 141, 60 mg of the title compound together with 60 mg of the slower-eluting enantiomer (Example 143) were obtained by racemate separation by means of preparative chiral HPLC (Method B).

Analytical chiral HPLC: 5.84 min.

Example 143

(S or R)-2-{[1-(4-chlorobenzoyl)azetidin-3-yl]methyl}-N-(1,4-dioxan-2-yl-methyl)-4-methyl-2H-indazole-5-carboxamide

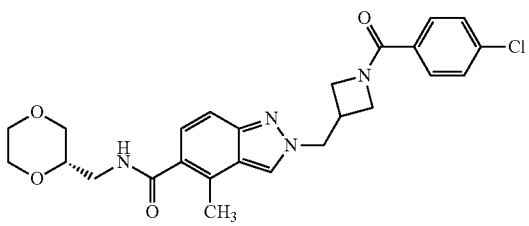

or

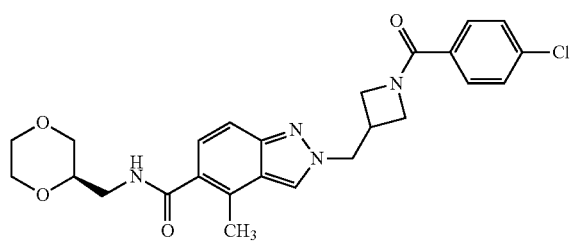

From 172 mg of the racemate prepared in Example 141, 60 mg of the title compound together with 60 mg of the faster-eluting enantiomer (Example 142) were obtained by racemate separation by means of preparative chiral HPLC (Method B).

Analytical chiral HPLC: 6.28 min.

Example 144

(+/−)-2-{[1-(4-chlorobenzoyl)azetidin-3-yl]methyl}-4-methyl-N-(3,4,5,6-tetrahydro-2H-pyran-2-ylmethyl)-2H-indazole-5-carboxamide

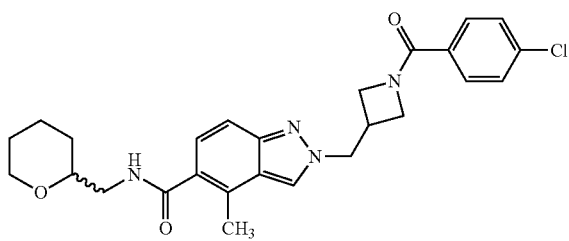

Analogously to Example 55, 144 mg of the title compound was obtained from 255 mg of the compound prepared in Example 144b and 130 mg of 4-chlorobenzoyl chloride.

$^1$H-NMR (300 MHz, DMSO-d6): δ=1.10-1.23 (1H), 1.35-1.47 (3H), 1.61 (1H), 1.71-1.81 (1H), 2.48 (3H), 3.15-3.27 (4H), 3.37 (1H), 3.80-3.93 (2H), 4.08 (1H), 4.19 (1H), 4.36 (1H), 4.66 (2H), 7.14 (1H), 7.37 (1H), 7.48 (2H), 7.59 (2H), 8.09 (1H), 8.54 (1H).

The starting material was prepared as follows:

Example 144a (+/−)-tert-butyl 3-({4-methyl-5-[N-(3,4,5,6-tetrahydro-2H-pyran-2-ylmethyl)-carbamoyl]-2H-indazol-2-yl}methyl)azetidin-1-carboxylate

Analogously to Example 1, 342 mg of the title compound was obtained from 323 mg of the compound prepared in Example 117c and 141 mg of 3,4,5,6-tetrahydro-2H-pyran-2-ylmethylamine hydrochloride.

$^1$H-NMR (300 MHz, DMSO-d6): δ=1.14-1.21 (1H), 1.33 (9H), 1.37-1.49 (3H), 1.61 (1H), 1.71-1.80 (1H), 2.49 (3H), 3.09 (1H), 3.21 (2H), 3.27-3.43 (2H), 3.69 (2H), 3.81-3.91 (3H), 4.61 (2H), 7.15 (1H), 7.38 (1H), 8.06 (1H), 8.53 (1H).

Example 144b (+/−)-2-(azetidin-3-ylmethyl)-4-methyl-N-(3,4,5,6-tetrahydro-2H-pyran-2-yl-methyl)-2H-indazole-5-carboxamide hydrochloride

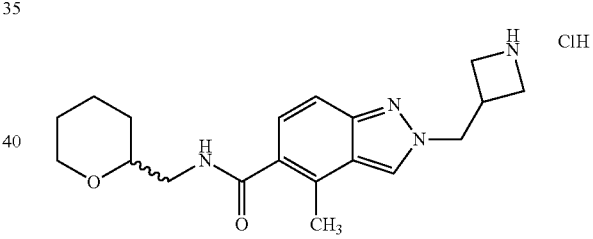

Analogously to Example 1a, from 298 mg of the compound prepared in Example 144a, 261 mg of the title compound was obtained, which was further reacted without purification.

Example 145

(R or S)-2-{[1-(4-chlorobenzoyl)azetidin-3-yl]methyl}-4-methyl-N-(3,4,5,6-tetrahydro-2H-pyran-2-ylmethyl)-2H-indazole-5-carboxamide

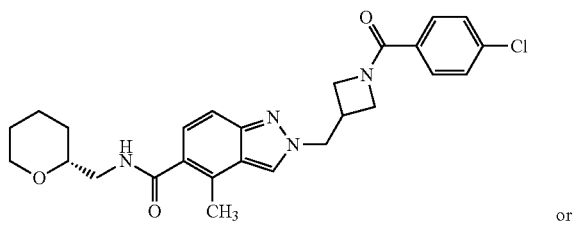

or

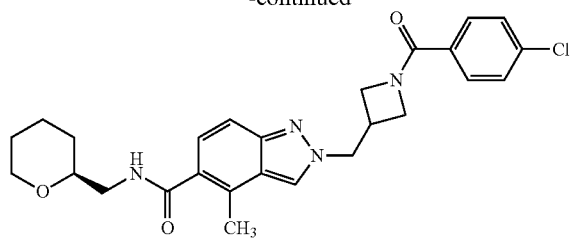

From 140 mg of the racemate prepared in Example 144, 43 mg of the title compound together with 35 mg of the slower-eluting enantiomer (Example 146) were obtained by racemate separation by means of preparative chiral HPLC (Method C).

Analytical chiral HPLC: 4.38 min.

Example 146

(S or R)-2-{[1-(4-chlorobenzoyl)azetidin-3-yl]methyl}-4-methyl-N-(3,4,5,6-tetrahydro-2H-pyran-2-ylmethyl)-2H-indazole-5-carboxamide

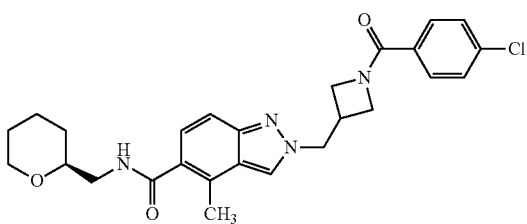 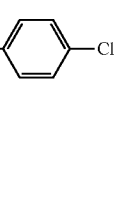

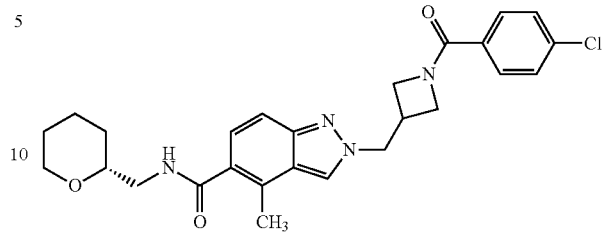

From 140 mg of the racemate prepared in Example 144, 35 mg of the title compound together with 43 mg of the faster-eluting enantiomer (Example 145) were obtained by racemate separation by means of preparative chiral HPLC (Method C).

Analytical chiral HPLC: 4.88 min.

Example 147

(+/−)-2-({1-[4-(4-fluorophenoxy)benzoyl]azetidin-3-yl}methyl)-N-(2-methoxypropyl)-4-methyl-2H-indazole-5-carboxamide

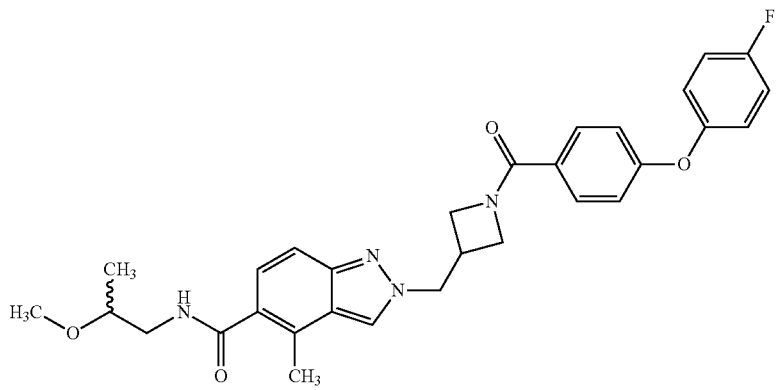 [SMILES: COC(C)CNC(=O)c1ccc2nn(CC3CN(C(=O)c4ccc(Oc5ccc(F)cc5)cc4)C3)cc2c1C]

Analogously to Example 1, from 42 mg of the compound prepared in Example 138b and 28 mg of 4-(4-fluorophenoxy)benzoic acid, a material still contaminated after HPLC purification was obtained, which was further purified by an additional preparative thick layer chromatography with ethyl acetate/methanol in the ratio 9:1 as mobile phase. Yield in this manner: 15 mg of the title compound.

$^1$H-NMR (300 MHz, CDCl3): δ=1.22 (3H), 2.64 (3H), 3.28 (1H), 3.36 (3H), 3.40 (1H), 3.57 (1H), 3.76 (1H), 3.97-4.46 (4H), 4.66 (2H), 6.14 (1H), 6.93 (2H), 6.97-7.11 (4H), 7.32 (1H), 7.51 (1H), 7.60 (2H), 8.00 (1H).

Example 148

(+/−)-N-(1,4-dioxan-2-ylmethyl)-2-({1-[4-(4-fluoro-phenoxy)benzoyl]azetidin-3-yl}methyl)-4-methyl-2H-indazole-5-carboxamide

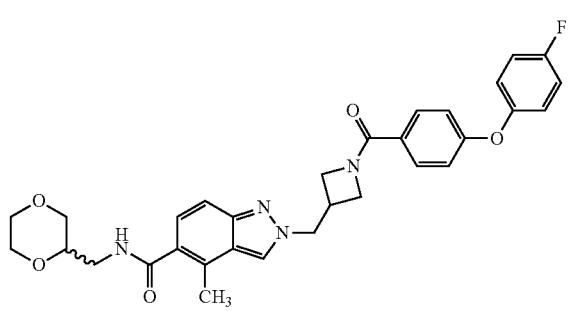 [SMILES: Cc1c(C(=O)NCC2COCCO2)ccc2nn(CC3CN(C(=O)c4ccc(Oc5ccc(F)cc5)cc4)C3)cc12]

Analogously to Example 1, 18 mg of the title compound was obtained from 43 mg of the compound prepared in Example 141b and 26 mg of 4-(4-fluorophenoxy)benzoic acid.

$^1$H-NMR (300 MHz, DMSO-d6): δ=2.49 (3H), 3.13-3.28 (4H), 3.38-3.66 (4H), 3.67-3.77 (2H), 3.89 (1H), 4.07 (1H), 4.19 (1H), 4.37 (1H), 4.66 (2H), 6.94 (2H), 7.08-7.18 (3H), 7.24 (2H), 7.38 (1H), 7.60 (2H), 8.17 (1H), 8.55 (1H).

Example 149

2-{[1-(4-chlorobenzoyl)azetidin-3-yl]methyl}-N-[2-(cyclopropylmethoxy)ethyl]-4-methyl-2H-indazole-5-carboxamide

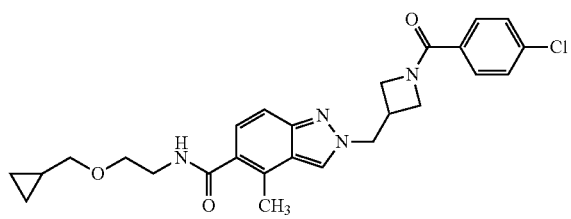 [SMILES: Cc1c(C(=O)NCCOCC2CC2)ccc2nn(CC3CN(C(=O)c4ccc(Cl)cc4)C3)cc12]

Analogously to Example 55, 72 mg of the title compound was obtained from 127 mg of the compound prepared in Example 149b and 65 mg of 4-chlorobenzoyl chloride.

$^1$H-NMR (300 MHz, DMSO-d6): δ=0.17 (2H), 0.45 (2H), 0.99 (1H), 2.51-2.54 (3H), 3.20-3.28 (3H), 3.38 (2H), 3.51 (2H), 3.92 (1H), 4.11 (1H), 4.21 (1H), 4.39 (1H), 4.69 (2H), 7.18 (1H), 7.40 (1H), 7.50 (2H), 7.62 (2H), 8.12 (1H), 8.56 (1H).

The starting material was prepared as follows:

Example 149a

Tert-butyl 3-[(5-{N-[2-(cyclopropylmethoxy)ethyl]carbamoyl}-4-methyl-2H-indazol-2-yl)methyl]azetidin-1-carboxylate

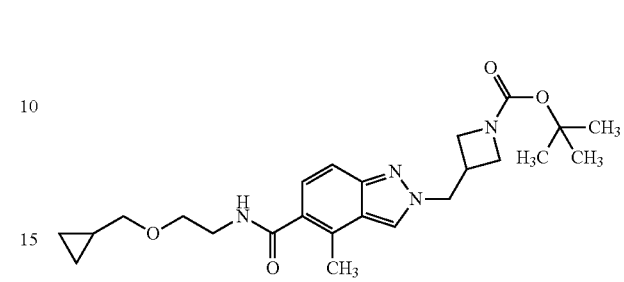

Analogously to Example 1, 448 mg of the title compound was obtained from 400 mg of the compound prepared in Example 117c and 133 mg of 2-(cyclopropylmethoxy)ethylamine hydrochloride.

$^1$H-NMR (300 MHz, DMSO-d6): δ=0.14 (2H), 0.42 (2H), 0.97 (1H), 1.33 (9H), 2.50 (3H), 3.09 (1H), 3.24 (2H), 3.36 (2H), 3.49 (2H), 3.69 (2H), 3.86 (2H), 4.61 (2H), 7.15 (1H), 7.38 (1H), 8.08 (1H), 8.54 (1H).

Example 149b 2-(azetidin-3-ylmethyl)-N-[2-(cyclopropylmethoxy)ethyl]-4-methyl-2H-indazole-5-carboxamide hydrochloride

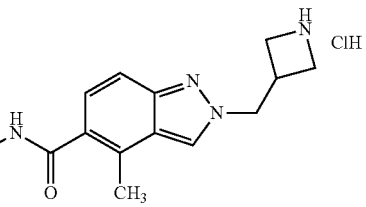

Analogously to Example 1a, from 448 mg of the compound prepared in Example 149a, 390 mg of the title compound was obtained, which was further reacted without purification.

Example 150

N-[2-(cyclopropylmethoxy)ethyl]-2-({1-[4-(4-fluorophenoxy)benzoyl]azetidin-3-yl}methyl)-4-methyl-2H-indazole-5-carboxamide

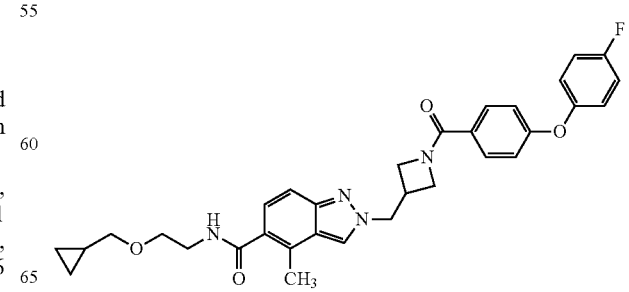

Analogously to Example 1, 48 mg of the title compound was obtained from 102 mg of the compound prepared in Example 149b and 63 mg of 4-(4-fluorophenoxy)benzoic acid.

$^1$H-NMR (300 MHz, CDCl3): δ=0.20 (2H), 0.54 (2H), 1.05 (1H), 2.65 (3H), 3.32 (2H), 3.35-3.45 (1H), 3.63-3.75 (4H), 3.99-4.50 (4H), 4.66 (2H), 6.22 (1H), 6.93 (2H), 6.97-7.11 (4H), 7.34 (1H), 7.51 (1H), 7.61 (2H), 8.00 (1H).

Example 151

N-[2-(cyclopropylmethoxy)ethyl]-4-methyl-2-{[1-(4-methylbenzoyl)azetidin-3-yl]methyl}-2H-indazole-5-carboxamide

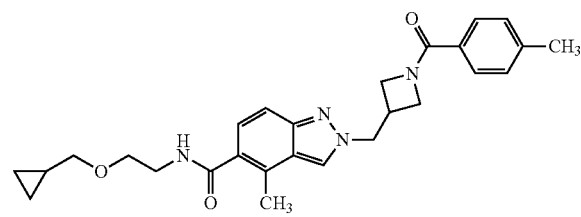 [SMILES: Cc1ccc(C(=O)N2CC(Cn3cc4c(C)c(C(=O)NCCOCC5CC5)ccc4n3)C2)cc1]

Analogously to Example 1, 55 mg of the title compound was obtained from 127 mg of the compound prepared in Example 149b and 46 mg of 4-methylbenzoic acid.

$^1$H-NMR (300 MHz, DMSO-d6): δ=0.17 (2H), 0.45 (2H), 0.99 (1H), 2.33 (3H), 2.53 (3H), 3.19-3.28 (3H), 3.38 (2H), 3.51 (2H), 3.90 (1H), 4.09 (1H), 4.20 (1H), 4.38 (1H), 4.69 (2H), 7.18 (1H), 7.24 (2H), 7.41 (1H), 7.50 (2H), 8.11 (1H), 8.57 (1H).

Example 152

2-{[1-(4-chlorobenzoyl)azetidin-3-yl]methyl}-4-methyl-N-[2-(trifluoromethoxy) ethyl]-2H-indazole-5-carboxamide

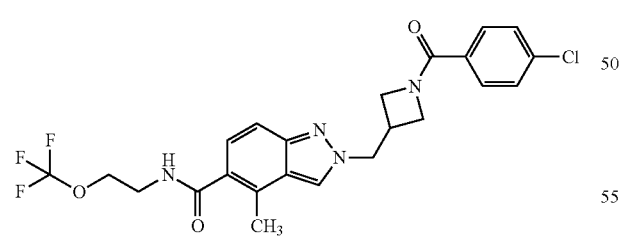

Analogously to Example 55, 122 mg of the title compound was obtained from 234 mg of the compound prepared in Example 152b and 115 mg of 4-chlorobenzoyl chloride.

$^1$H-NMR (300 MHz, DMSO-d6): δ=2.52 (3H), 3.25 (1H), 3.54 (2H), 3.93 (1H), 4.11 (1H), 4.17-4.25 (3H), 4.40 (1H), 4.70 (2H), 7.19 (1H), 7.43 (1H), 7.50 (2H), 7.61 (2H), 8.38 (1H), 8.58 (1H).

The starting material was prepared as follows:

Example 152a

Tert-butyl 3-[(4-methyl-5-{N-[2-(trifluoromethoxy)ethyl]carbamoyl}-2H-indazol-2-yl)methyl]azetidin-1-carboxylate

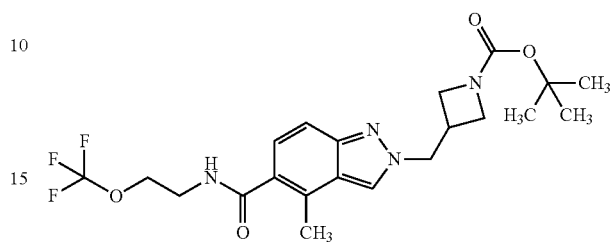

Analogously to Example 1, 272 mg of the title compound was obtained from 250 mg of the compound prepared in Example 117c and 120 mg of 2-(trifluoromethoxy)ethylamine hydrochloride.

$^1$H-NMR (300 MHz, DMSO-d6): δ =1.32 (9H), 2.50 (3H), 3.08 (1H), 3.51 (2H), 3.70 (2H), 3.86 (2H), 4.17 (2H), 4.61 (2H), 7.16 (1H), 7.41 (1H), 8.36 (1H), 8.56 (1H).

Example 152b 2-(azetidin-3-ylmethyl)-4-methyl-N-[2-(trifluoromethoxy)ethyl]-2H-indazole-5-carboxamide hydrochloride

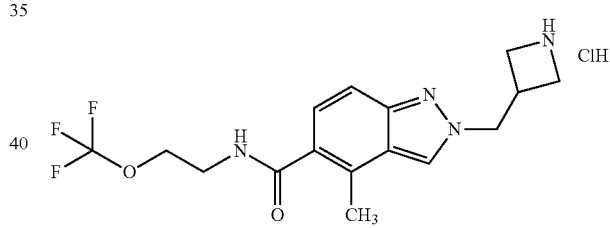

Analogously to Example 1a, from 272 mg of the compound prepared in Example 152a, 240 mg of the title compound was obtained, which was further reacted without purification.

Example 153

N-(2-tert-butoxyethyl)-2-{[1-(4-chlorobenzoyl)azetidin-3-yl]methyl}-4-methyl-2H-indazole-5-carboxamide

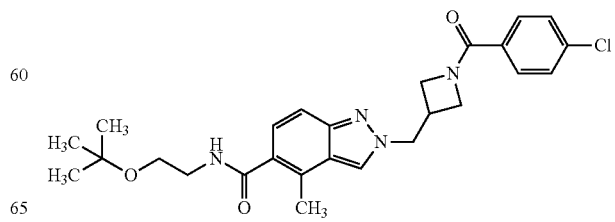

Analogously to Example 55) 12 mg of the title compound was obtained from 160 mg of the compound prepared in Example 153b) and 81 mg of 4-chlorobenzoyl chloride.

¹H-NMR (300 MHz, DMSO-d6): δ=1.14 (9H), 2.53 (3H), 3.19-3.34 (3H), 3.43 (2H), 3.92 (1H), 4.11 (1H), 4.21 (1H), 4.39 (1H), 4.69 (2H), 7.18 (1H), 7.40 (1H), 7.50 (2H), 7.62 (2H), 8.05 (1H), 8.56 (1H).

The starting material was prepared as follows:

Example 153a

Tert-butyl 3-({5-[N-(2-tert-butoxyethyl)carbamoyl]-4-methyl-2H-indazol-2-yl}-methyl)azetidin-1-carboxylate

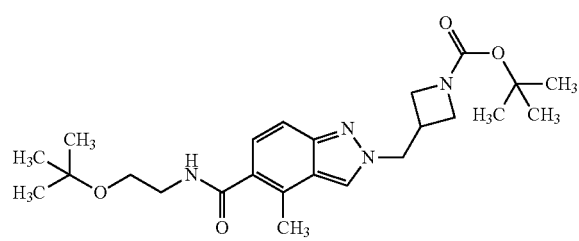 [SMILES: Cc1c(C(=O)NCCOC(C)(C)C)ccc2nn(CC3CN(C(=O)OC(C)(C)C)C3)cc12]

Analogously to Example 1, 284 mg of the title compound was obtained from 250 mg of the compound prepared in Example 117c and 111 mg of 2-tert-butoxyethylamine hydrochloride.

¹H-NMR (300 MHz, DMSO-d6): δ=1.11 (9H), 1.32 (9H), 2.50 (3H), 3.08 (1H), 3.27 (2H), 3.40 (2H), 3.69 (2H), 3.86 (2H), 4.60 (2H), 7.15 (1H), 7.38 (1H), 8.04 (1H), 8.54 (1H).

Example 153b 2-(azetidin-3-ylmethyl)-N-(2-tert-butoxyethyl)-4-methyl-2H-indazol-5-carboxamide hydrochloride

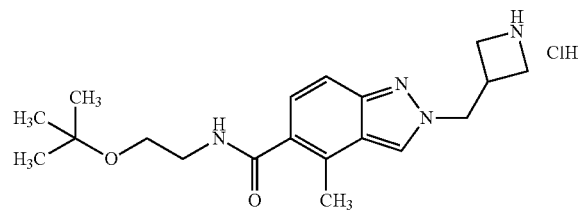 [SMILES: Cc1c(C(=O)NCCOC(C)(C)C)ccc2nn(CC3CNC3)cc12 ; Cl]

Analogously to Example 1a, from 284 mg of the compound prepared in Example 153a, 240 mg of the title compound was obtained, which was further reacted without purification.

Example 154

(+/−)-2-{[1-(4-chlorobenzoyl)azetidin-3-yl]methyl}-N-[2-(cyclobutyloxy)propyl]-4-methyl-2H-indazole-5-carboxamide

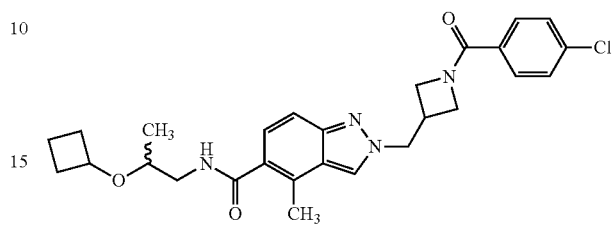

Analogously to Example 55, 135 mg of the title compound was obtained from 222 mg of the compound prepared in Example 154d and 109 mg of 4-chlorobenzoyl chloride.

¹H-NMR (300 MHz, DMSO-d6): δ=1.05 (3H), 1.39 (1H), 1.55 (1H), 1.80 (2H), 2.11 (2H), 2.50 (3H), 3.08-3.23 (3H), 3.55 (1H), 3.89 (1H), 4.03-4.13 (1H), 4.19 (1H), 4.37 (1H), 4.67 (2H), 7.15 (1H), 7.38 (1H), 7.48 (2H), 7.59 (2H), 8.07 (1H), 8.53 (1H).

The starting material was prepared as follows:

Example 154a (+/−)-2-(cyclobutyloxy)-propanamide

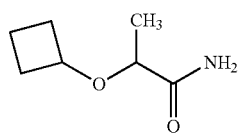

To a suspension of 732 mg of sodium hydride in 15 ml THF, 2.0 g of cyclobutanol in 0.5 ml THF were added dropwise and stirred for 30 minutes at 25° C. The reaction mixture was then cooled to 0° C. and 2.11 g of (+/−) 2-bromopropanamide in 0.5 ml tetrahydrofuran were added dropwise and then stirred for 18 hours at 25° C. The reaction mixture was poured onto ice-water and extracted once with 75 ml dichloromethane. The organic phase was washed with saturated sodium chloride solution, dried over sodium sulphate and concentrated in vacuo after filtration. The crude product thus obtained was purified by column chromatography on silica gel with hexane/0-50% ethyl acetate. Yield: 0.79 g of the title compound.

¹H-NMR (300 MHz, DMSO-d6): δ=1.14 (3H), 1.38 (1H), 1.56 (1H), 1.83 (2H), 2.08 (2H), 3.62 (1H), 3.90 (1H), 7.07 (2H).

Example 154b (+/−)-tert-butyl N-[2-(cyclobutyloxy)propyl]carbamate

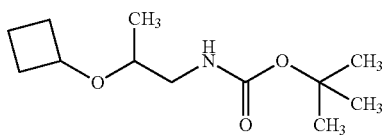 [SMILES: CC(CNC(=O)OC(C)(C)C)OC1CCC1]

To a suspension of 6.9 g of lithium aluminium hydride in 250 ml THF, 6.5 g of the amide prepared in Example 154a in 81 ml THF were cautiously added dropwise at 0° C. The mixture was then first stirred for 30 minutes at 0° C. and then heated for 5 hours under reflux. After cooling, the mixture was cautiously treated with 20 g of sodium sulphate decahydrate and 20 g of potassium fluoride and solid matter removed by filtration shortly afterwards. The filtrate was concentrated in vacuo. The residue thus obtained (5.8 g) was dissolved without further purification in 174 ml dichloromethane and treated with 11.9 g of di-tert-butyl dicarbonate. After 16 hours' stirring at 25° C., this was concentrated in vacuo and the residue thus obtained purified by two-fold column chromatography on silica gel with hexane/0-40% ethyl acetate.

Yield: 8.54 g of the title compound.

$^1$H-NMR (300 MHz, DMSO-d6): δ=0.94 (3H), 1.28-1.42 (10H), 1.53 (1H), 1.76 (2H), 2.07 (2H), 2.76 (1H), 2.90 (1H), 3.34 (1H), 3.92 (1H), 6.72 (1H).

Example 154c (+/−)-tert-butyl 3-[(5-{N-[2-(cyclobutyloxy)propyl]carbamoyl}-4-methyl-2H-indazol-2-yl)methyl]azetidin-1-carboxylate

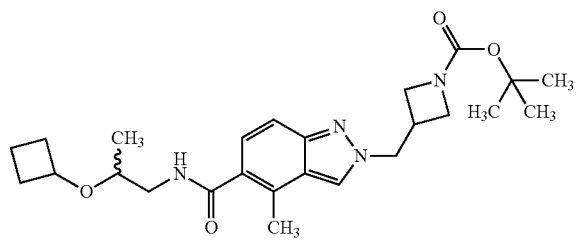 [SMILES: Cc1c(C(=O)NCC(C)OC2CCC2)ccc2nn(CC3CN(C(=O)OC(C)(C)C)C3)cc12]

Analogously to Example 1a, from 200 mg of the compound prepared in Example 154b), 2-(cyclobutyloxy)propylamine was obtained as the hydrochloride, which without further purification together with 250 mg of the compound prepared in Example 117c analogously to Example 1, yielded 259 mg of the title compound.

$^1$H-NMR (300 MHz, DMSO-d6): δ=1.05 (3H), 1.32 (9H), 1.39 (1H), 1.55 (1H), 1.80 (2H), 2.11 (2H), 2.50 (3H), 3.02-3.17 (2H), 3.22 (1H), 3.54 (1H), 3.69 (2H), 3.86 (2H), 3.99 (1H), 4.61 (2H), 7.15 (1H), 7.39 (1H), 8.09 (1H), 8.55 (1H).

Example 154d (+/−)-2-(azetidin-3-ylmethyl)-N-[2-(cyclobutyloxy)propyl]-4-methyl-2H-indazole-5-carboxamide hydrochloride

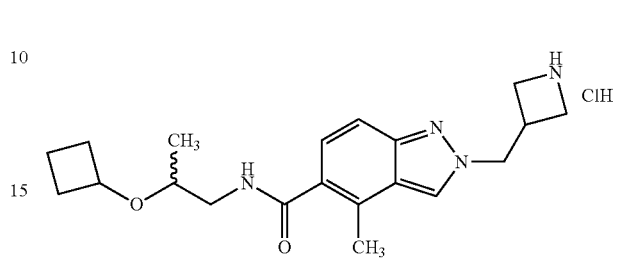

Analogously to Example 1a, from 259 mg of the compound prepared in Example 154c, 225 mg of the title compound was obtained, which was further reacted without purification.

Example 155

(S or R)-2-{[1-(4-chlorobenzoyl)azetidin-3-yl]methyl}-N-[2-(cyclobutyloxy)-propyl]-4-methyl-2H-indazole-5-carboxamide

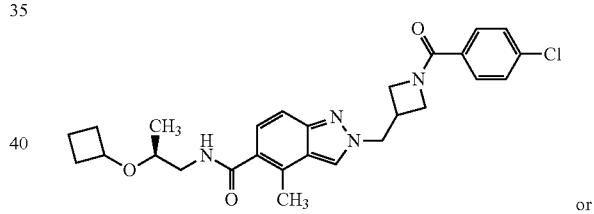

or

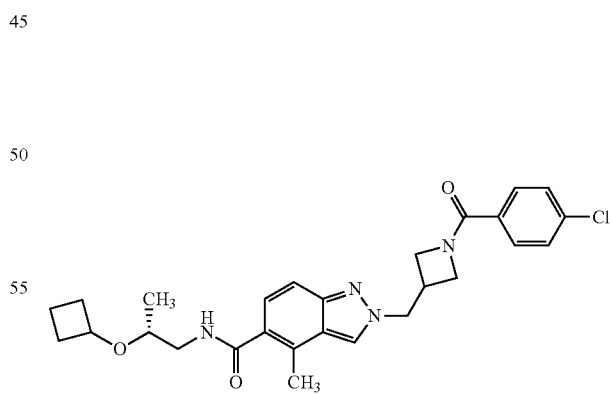

From 135 mg of the racemate prepared in Example 154, 41 mg of the title compound together with 21 mg of the slower-eluting enantiomer (Example 156) were obtained by racemate separation by means of preparative chiral HPLC (Method A).

Analytical chiral HPLC: 10.05 min

Example 156

(R or S)-2-{[1-(4-chlorobenzoyl)azetidin-3-yl]methyl}-N-[2-(cyclobutyloxy)-propyl]-4-methyl-2H-indazole-5-carboxamide

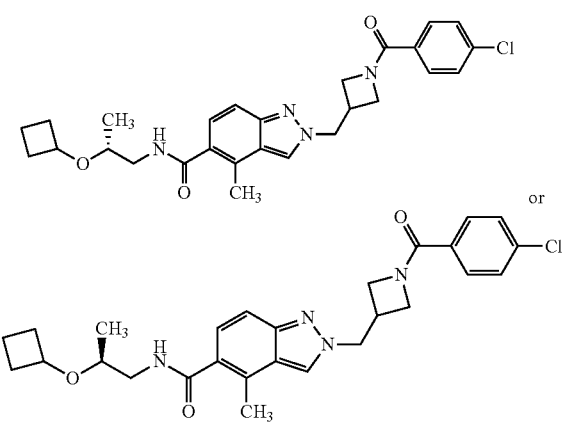

From 135 mg of the racemate prepared in Example 154, 21 mg of the title compound together with 41 mg of the faster-eluting enantiomer (Example 155) were obtained by racemate separation by means of preparative chiral HPLC (Method A).

Analytical chiral HPLC: 13.14 min

Example 157

N-[2-(cyclopropylmethoxy)ethyl]-2-({1-[(4'-fluoro-biphenyl-4-yl)carbonyl]azetidin-3-yl}methyl)-4-methyl-2H-indazole-5-carboxamide

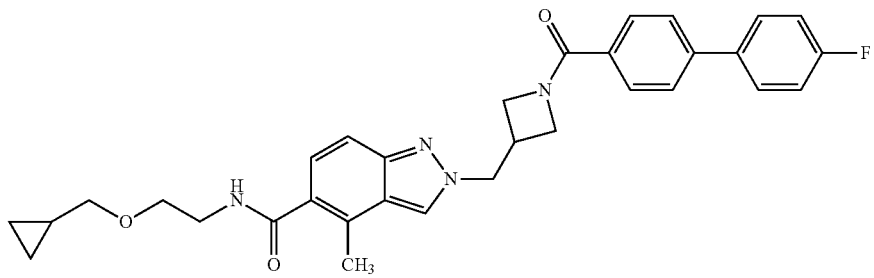 [SMILES: Cc1c(C(=O)NCCOCC2CC2)ccc2nn(CC3CN(C(=O)c4ccc(-c5ccc(F)cc5)cc4)C3)cc12]

Analogously to Example 1, 54 mg of the title compound was obtained from 102 mg of the compound prepared in Example 149b and 58 mg of 4'-fluorobiphenyl-4-carboxylic acid.

$^1$H-NMR (300 MHz, CDCl3): δ=0.20 (2H), 0.54 (2H), 1.05 (1H), 2.66 (3H), 3.32 (2H), 3.42 (1H), 3.61-3.73 (4H), 4.09 (1H), 4.28 (1H), 4.38 (1H), 4.49 (1H), 4.69 (2H), 6.22 (1H), 7.10-7.18 (2H), 7.26 (2H), 7.35 (1H), 7.50-7.59 (3H), 7.70 (2H), 8.01 (1H).

Example 158

2-({1-[(4'-fluorobiphenyl-4-yl)carbonyl]azetidin-3-yl}methyl)-N-(2-methoxy-ethyl)-4-methyl-2H-indazole-5-carboxamide

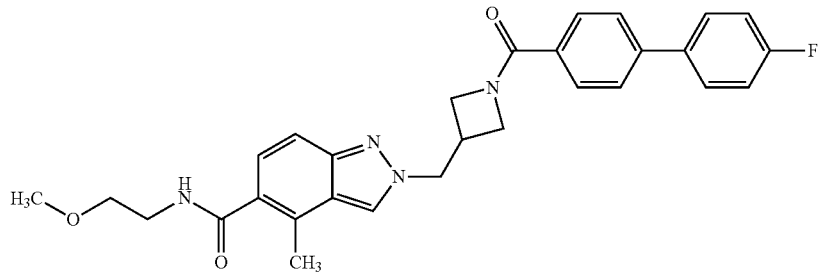 [SMILES: COCCNC(=O)c1ccc2nn(CC3CN(C(=O)c4ccc(-c5ccc(F)cc5)cc4)C3)cc2c1C]

Analogously to Example 1, 54 mg of the title compound was obtained from 108 mg of the compound prepared in Example 117e and 69 mg of 4'-fluorobiphenyl-4-carboxylic acid.

$^1$H-NMR (300 MHz, DMSO-d6): δ=2.49 (3H), 3.17-3.29 (4H), 3.36 (2H), 3.43 (2H), 3.92 (1H), 4.11 (1H), 4.24 (1H), 4.42 (1H), 4.68 (2H), 7.15 (1H), 7.29 (2H), 7.39 (1H), 7.63-7.78 (6H), 8.12 (1H), 8.56 (1H).

Example 159

2-({1-[4-(4-fluorophenoxy)benzoyl]azetidin-3-yl}methyl)-N-(2-methoxyethyl)-4-methyl-2H-indazole-5-carboxamide

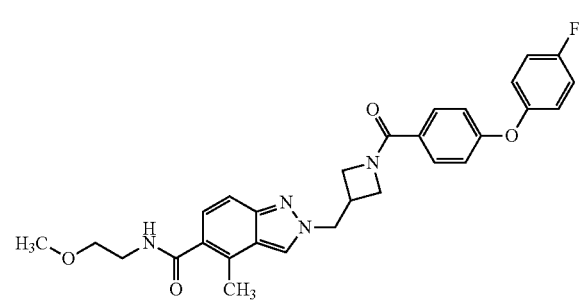 [SMILES: COCCNC(=O)c1ccc2nn(CC3CN(C(=O)c4ccc(Oc5ccc(F)cc5)cc4)C3)cc2c1C]

Analogously to Example 1, 28 mg of the title compound was obtained from 108 mg of the compound prepared in Example 117e and 74 mg of 4-(4-fluorophenoxy)benzoic acid.

$^1$H-NMR (300 MHz, CDCl3): δ=2.65 (3H), 3.31-3.46 (4H), 3.58 (2H), 3.67 (2H), 4.06 (1H), 4.24 (1H), 4.40 (2H), 4.66 (2H), 6.15 (1H), 6.89-7.13 (6H), 7.33 (1H), 7.51 (1H), 7.61 (2H), 8.00 (1H).

Example 160

2-({1-[4-(4-fluorophenoxy)benzoyl]azetidin-3-yl}methyl)-4-methyl-N-(2,2,2-trifluoroethyl)-2H-indazole-5-carboxamide

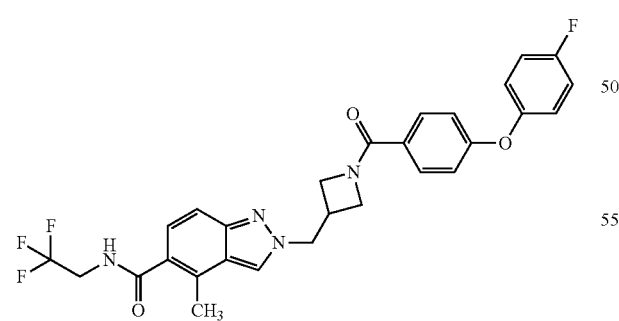

Analogously to Example 1, 47 mg of the title compound was obtained from 115 mg of the compound prepared in Example 129b and 74 mg of 4-(4-fluorophenoxy)benzoic acid.

$^1$H-NMR (300 MHz, CDCl3): δ=2.65 (3H), 3.39 (1H), 3.97-4.52 (6H), 4.67 (2H), 6.04 (1H), 6.89-7.12 (6H), 7.31 (1H), 7.53 (1H), 7.60 (2H), 8.03 (1H).

Example 161

2-({1-[(4'-fluorobiphenyl-4-yl)carbonyl]azetidin-3-yl}methyl)-4-methyl-N-(2,2,2-trifluoroethyl)-2H-indazole-5-carboxamide

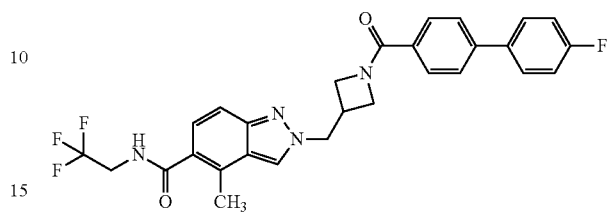

Analogously to Example 1, 28 mg of the title compound was obtained from 115 mg of the compound prepared in Example 129b and 69 mg of 4'-fluorobiphenyl-4-carboxylic acid.

$^1$H-NMR (300 MHz, DMSO-d6): δ=2.65 (3H), 3.42 (1H), 4.01-4.54 (6H), 4.69 (2H), 6.02 (1H), 7.15 (2H), 7.32 (1H), 7.51-7.62 (5H), 7.69 (2H), 8.04 (1H).

Example 162

2-{[1-(4-chlorobenzoyl)azetidin-3-yl]methyl}-4-methyl-N-[2-(2,2,2-trifluoro-ethoxy)ethyl]-2H-indazole-5-carboxamide

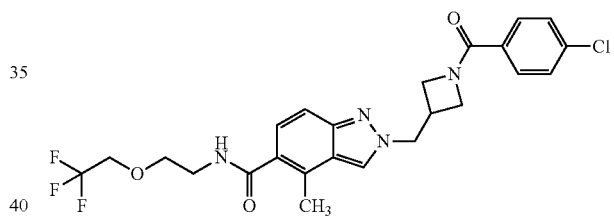

Analogously to Example 55, 197 mg of the title compound was obtained from 252 mg of the compound prepared in Example 162a and 108 mg of 4-chlorobenzoyl chloride.

$^1$H-NMR (300 MHz, DMSO-d6): δ=2.49 (3H), 3.22 (1H), 3.40 (2H), 3.69 (2H), 3.90 (1H), 4.03-4.13 (3H), 4.19 (1H), 4.37 (1H), 4.67 (2H), 7.15 (1H), 7.38 (1H), 7.48 (2H), 7.59 (2H), 8.19 (1H), 8.55 (1H).

The starting material was prepared as follows:

Example 162a 2-(azetidin-3-ylmethyl)-4-methyl-N-[2-(2,2,2-trifluoroethoxy)ethyl]-2H-indazole-5-carboxamide hydrochloride

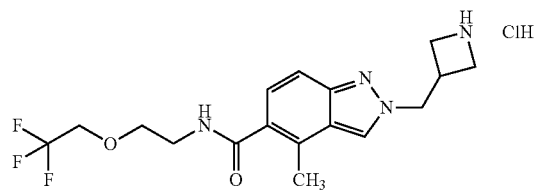 [SMILES: Cc1c(C(=O)NCCOCC(F)(F)F)ccc2nn(CC3CNC3)cc12 ; Cl]

Analogously to Example 1a, from 583 mg of the compound prepared in Example 162b, 505 mg of the title compound was obtained, which was further reacted without purification.

Example 162b

Tert-butyl 3-[(4-methyl-5-{N-[2-(2,2,2-trifluoroethoxy)ethyl]carbamoyl}-2H-indazol-2-yl)methyl]azetidin-1-carboxylate Analogously to Example 1, 580 mg of the title compound was obtained from 500 mg of the compound prepared in Example 117c and 260 mg of 2-(2,2,2-trifluoroethoxy)ethylamine hydrochloride.

$^1$H-NMR (300 MHz, DMSO-d6): δ=1.32 (9H), 2.50 (3H), 3.08 (1H), 3.40 (2H), 3.61-3.76 (4H), 3.86 (2H), 4.07 (2H), 4.61 (2H), 7.15 (1H), 7.39 (1H), 8.18 (1H), 8.55 (1H).

Example 163

4-methyl-N-[2-(2,2,2-trifluoroethoxy)ethyl]-2-[(1-{4-[4-(trifluoromethyl) phenoxy]benzoyl}azetidin-3-yl)methyl]-2H-indazole-5-carboxamide Analogously to Example 1, 89 mg of the title compound was obtained from 252 mg of the compound prepared in Example 162a and 175 mg of 4-[4-(trifluoromethyl)phenoxy]benzoic acid.

$^1$H-NMR (300 MHz, DMSO-d6): δ=2.49 (3H), 3.23 (1H), 3.40 (2H), 3.69 (2H), 3.90 (1H), 4.01-4.14 (3H), 4.21 (1H), 4.40 (1H), 4.68 (2H), 7.11 (2H), 7.15 (1H), 7.20 (2H), 7.39 (1H), 7.66 (2H), 7.75 (2H), 8.19 (1H), 8.56 (1H).

Example 164

4-methyl-N-(2,2,2-trifluoroethyl)-2-[(1-{4-[4-(trifluoromethyl)phenoxy]benzoyl}azetidin-3-yl)methyl]-2H-indazole-5-carboxamide

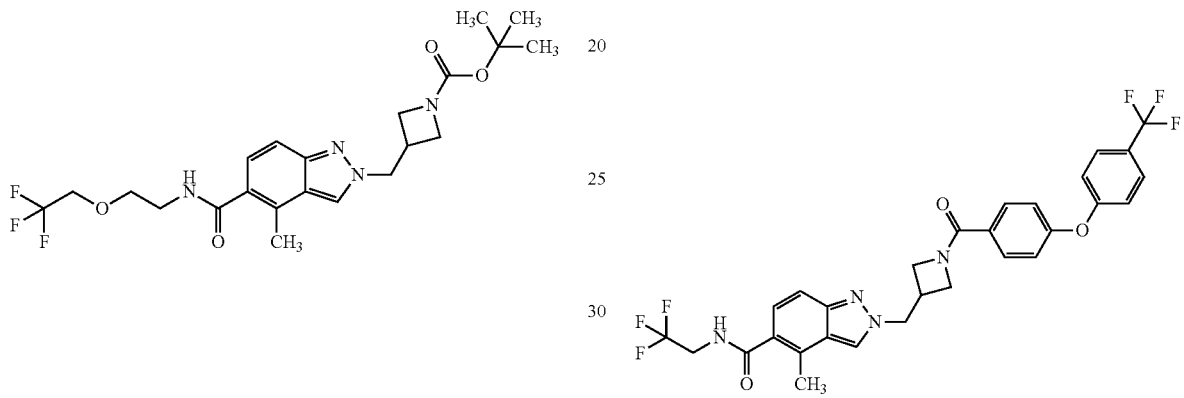

Analogously to Example 1, 64 mg of the title compound was obtained from 225 mg of the compound prepared in Example 129b and 149 mg of 4-[4-(trifluoromethyl)phenoxy]benzoic acid.

$^1$H-NMR (300 MHz, DMSO-d6): δ=2.50 (3H), 3.24 (1H), 3.91 (1H), 3.95-4.15 (3H), 4.22 (1H), 4.40 (1H), 4.69 (2H), 7.11 (2H), 7.15-7.23 (3H), 7.43 (1H), 7.66 (2H), 7.75 (2H), 8.60 (1H), 8.79 (1H).

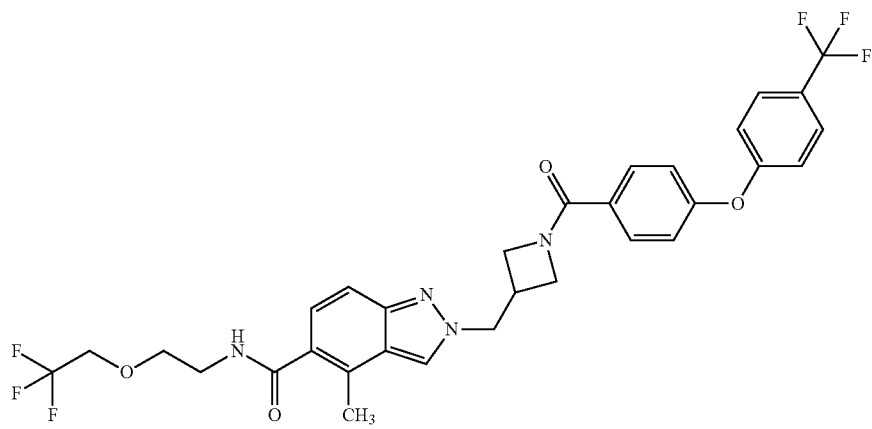 [SMILES: Cc1c(C(=O)NCCOCC(F)(F)F)ccc2nn(CC3CN(C(=O)c4ccc(Oc5ccc(C(F)(F)F)cc5)cc4)C3)cc12]

Example 165

2-({1-[4-(4-chlorophenoxy)benzoyl]azetidin-3-yl}methyl)-4-methyl-N-(2,2,2-trifluoroethyl)-2H-indazole-5-carboxamide Analogously to Example 1, 97 mg of the title compound was obtained from 225 mg of the compound prepared in Example 129b and 131 mg of 4-(4-chlorophenoxy)benzoic acid.

$^1$H-NMR (300 MHz, DMSO-d6): δ=2.50 (3H), 3.23 (1H), 3.90 (1H), 3.96-4.12 (3H), 4.20 (1H), 4.38 (1H), 4.68 (2H), 7.00 (2H), 7.09 (2H), 7.18 (1H), 7.40-7.48 (3H), 7.62 (2H), 8.60 (1H), 8.79 (1H)

Example 166

2-({1-[4-(4-chlorophenoxy)benzoyl]azetidin-3-yl}methyl)-N-(2-methoxyethyl)-4-methyl-2H-indazole-5-carboxamide Analogously to Example 1, 99 mg of the title compound was obtained from 225 mg of the compound prepared in Example 117e and 140 mg of 4-(4-chlorophenoxy)benzoic acid.

$^1$H-NMR (300 MHz, DMSO-d6): δ=2.49 (3H), 3.16-3.27 (4H), 3.36 (2H), 3.42 (2H), 3.89 (1H), 4.08 (1H), 4.19 (1H), 4.38 (1H), 4.67 (2H), 7.00 (2H), 7.09 (2H), 7.15 (1H), 7.38 (1H), 7.45 (2H), 7.62 (2H), 8.12 (1H), 8.55 (1H).

Example 167

2-({1-[(5-fluoro-1-methyl-1H-indol-2-yl)carbonyl]azetidin-3-yl}methyl)-4-methyl-N-(2,2,2-trifluoroethyl)-2H-indazole-5-carboxamide

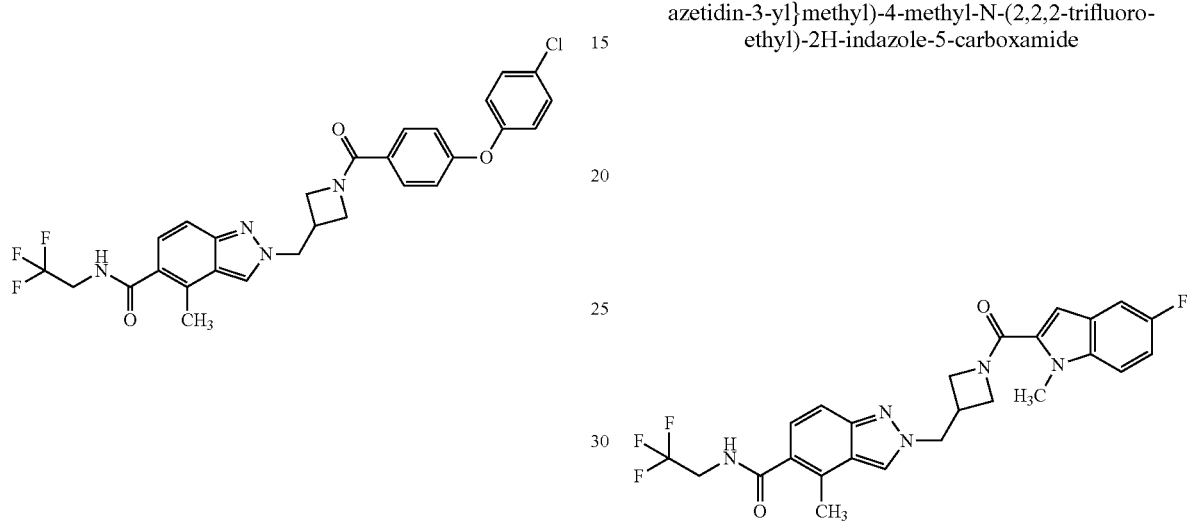

Analogously to Example 1, 48 mg of the title compound was obtained from 180 mg of the compound prepared in Example 129b and 82 mg of 5-fluoro-1-methyl-1H-indol-2-carboxylic acid.

$^1$H-NMR (300 MHz, CDCl3): δ=2.66 (3H), 2.80 (3H), 3.36-3.51 (1H), 4.01 (3H), 4.04-4.63 (6H), 4.70 (2H), 6.03 (1H), 6.68 (1H), 7.08 (1H), 7.22-7.36 (3H), 7.55 (1H), 8.05 (1H).

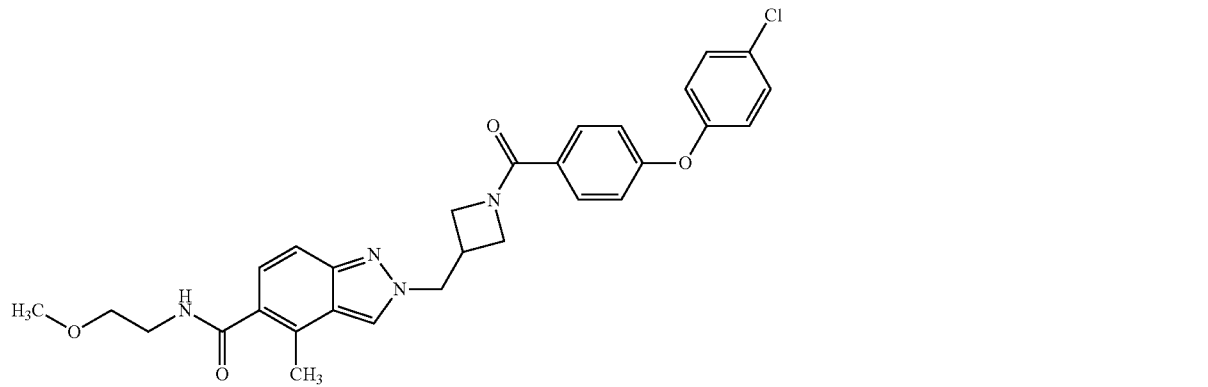 [SMILES: COCCNC(=O)c1ccc2nn(CC3CN(C(=O)c4ccc(Oc5ccc(Cl)cc5)cc4)C3)cc2c1C]

Example 168

2-({1-[(5-methoxy-1-methyl-1H-indol-2-yl)carbonyl]azetidin-3-yl}methyl)-4-methyl-N-(2,2,2-trifluoroethyl)-2H-indazole-5-carboxamide

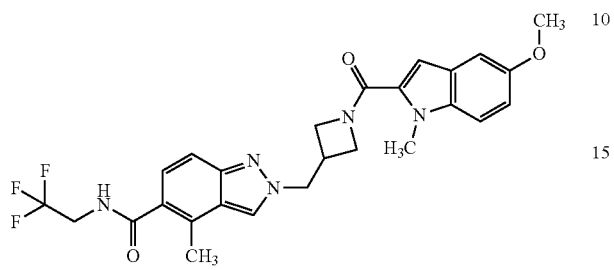

Analogously to Example 1, 15 mg of the title compound was obtained from 180 mg of the compound prepared in Example 129b and 87 mg of 5-methoxy-1-methyl-1H-indol-2-carboxylic acid.

$^1$H-NMR (300 MHz, CDCl3): δ=2.66 (3H), 3.43 (1H), 3.84 (3H), 4.00 (3H), 4.03-4.59 (6H), 4.70 (2H), 6.02 (1H), 6.66 (1H), 7.02 (1H), 7.27-7.35 (3H), 7.56 (1H), 8.06 (1H).

Example 169

2-({1-[(6-methoxy-1-methyl-1H-indol-2-yl)carbonyl]azetidin-3-yl}methyl)-4-methyl-N-(2,2,2-trifluoroethyl)-2H-indazole-5-carboxamide

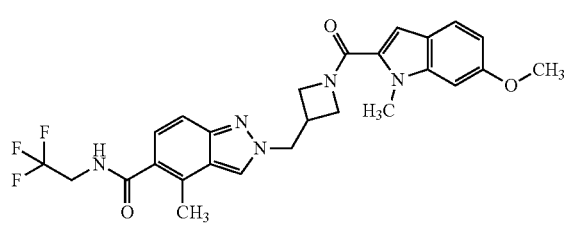 [SMILES: COc1ccc2cc(C(=O)N3CC(Cn4cc5c(C)c(C(=O)NCC(F)(F)F)ccc5n4)C3)n(C)c2c1]

Analogously to Example 1, 57 mg of the title compound was obtained from 180 mg of the compound prepared in Example 129b and 87 mg of 6-methoxy-1-methyl-1H-indol-2-carboxylic acid.

$^1$H-NMR (300 MHz, CDCl3): δ=2.66 (3H), 3.43 (1H), 3.89 (3H), 3.99 (3H), 4.05-4.60 (6H), 4.70 (2H), 6.01 (1H), 6.69 (1H), 6.77 (1H), 6.81 (1H), 7.32 (1H), 7.48 (1H), 7.56 (1H), 8.05 (1H).

Example 170

2-({1-[(5-fluoro-1-methyl-1H-indol-2-yl)carbonyl]azetidin-3-yl}methyl)-N-(2-methoxyethyl)-4-methyl-2H-indazole-5-carboxamide

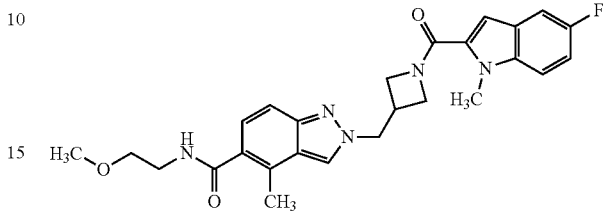

Analogously to Example 1, 95 mg of the title compound was obtained from 180 mg of the compound prepared in Example 117e and 87 mg of 5-fluoro-1-methyl-1H-indol-2-carboxylic acid.

$^1$H-NMR (300 MHz, CDCl3): δ=2.65 (3H), 3.35-3.51 (4H), 3.58 (2H), 3.67 (2H), 4.01 (3H), 4.02-4.62 (4H), 4.69 (2H), 6.15 (1H), 6.68 (1H), 7.08 (1H), 7.21-7.38 (3H), 7.53 (1H), 8.02 (1H).

Example 171

2-({1-[(5-chloro-1-methyl-1H-indol-2-yl)carbonyl]azetidin-3-yl}methyl)-N-(2-methoxyethyl)-4-methyl-2H-indazole-5-carboxamide

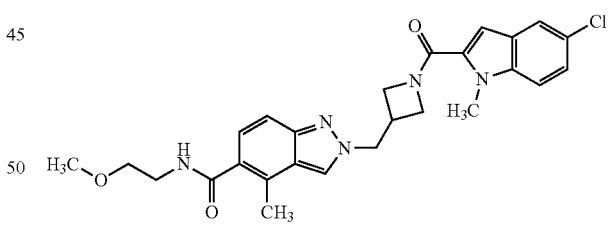

Analogously to Example 1, 90 mg of the title compound was obtained from 180 mg of the compound prepared in Example 117e and 95 mg of 5-chloro-1-methyl-1H-indol-2-carboxylic acid.

$^1$H-NMR (300 MHz, CDCl3): δ=2.66 (3H), 3.37-3.49 (4H), 3.58 (2H), 3.67 (2H), 4.00 (3H), 4.08 (1H), 4.37 (2H), 4.56 (1H), 4.70 (2H), 6.15 (1H), 6.66 (1H), 7.27-7.38 (3H), 7.53 (1H), 7.58 (1H), 8.02 (1H).

Example 172

N-(2-methoxyethyl)-2-({1-[(5-methoxy-1-methyl-1H-indol-2-yl)carbonyl]azetidin-3-yl}methyl)-4-methyl-2H-indazole-5-carboxamide

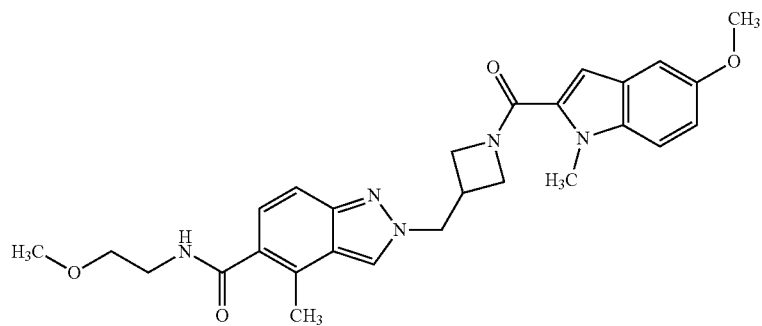

Analogously to Example 1, 86 mg of the title compound was obtained from 180 mg of the compound prepared in Example 117e and 93 mg of 5-methoxy-1-methyl-1H-indol-2-carboxylic acid.

$^1$H-NMR (300 MHz, CDCl3): δ=2.65 (3H), 3.36-3.50 (4H), 3.58 (2H), 3.67 (2H), 3.84 (3H), 4.00 (3H), 4.07 (1H), 4.35 (2H), 4.55 (1H), 4.69 (2H), 6.15 (1H), 6.66 (1H), 6.97-7.06 (2H), 7.28 (1H), 7.34 (1H), 7.53 (1H), 8.02 (1H).

Example 173

N-(2-methoxyethyl)-2-({1-[(6-methoxy-1-methyl-1H-indol-2-yl)carbonyl]azetidin-3-yl}methyl)-4-methyl-2H-indazole-5-carboxamide

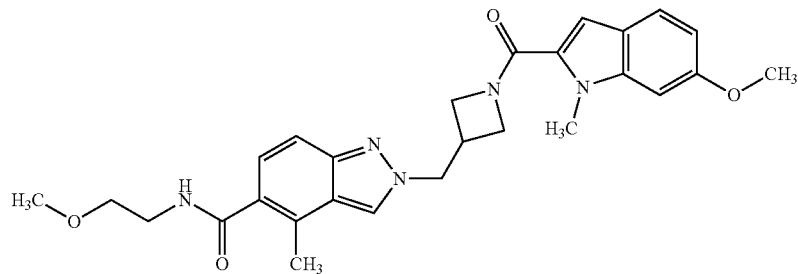

Analogously to Example 1, 97 mg of the title compound was obtained from 180 mg of the compound prepared in Example 117e and 93 mg of 6-methoxy-1-methyl-1H-indol-2-carboxylic acid.

$^1$H-NMR (300 MHz, CDCl3): δ=2.66 (3H), 3.37-3.47 (4H), 3.58 (2H), 3.67 (2H), 3.89 (3H), 3.99 (3H), 4.02-4.60 (4H), 4.69 (2H), 6.15 (1H), 6.69 (1H), 6.77 (1H), 6.81 (1H), 7.34 (1H), 7.48 (1H), 7.53 (1H), 8.02 (1H).

Example 174

N-(2-methoxyethyl)-4-methyl-2-{[1-(4-{[5-(trifluoromethyl)pyridin-2-yl]oxy}benzoyl)azetidin-3-yl]methyl}-2H-indazole-5-carboxamide

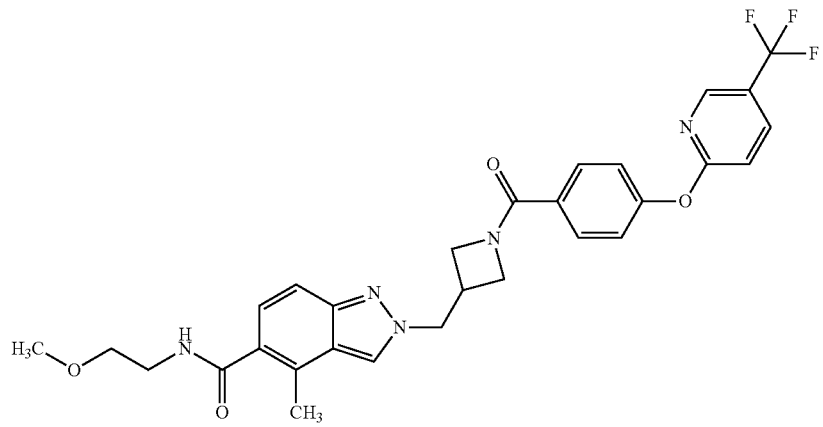 [SMILES: COCCNC(=O)c1ccc2nn(CC3CN(C(=O)c4ccc(Oc5ccc(C(F)(F)F)cn5)cc4)C3)cc2c1C]

Analogously to Example 1, 66 mg of the title compound was obtained from 135 mg of the compound prepared in Example 117e and 96 mg of 4-{[5-(trifluoromethyl)pyridin-2-yl]oxy}-benzoic acid.

$^1$H-NMR (300 MHz, DMSO-d6): δ=2.50 (3H), 3.18-3.27 (4H), 3.36 (2H), 3.42 (2H), 3.91 (1H), 4.10 (1H), 4.24 (1H), 4.42 (1H), 4.68 (2H), 7.15 (1H), 7.24 (2H), 7.28 (1H), 7.39 (1H), 7.67 (2H), 8.12 (1H), 8.24 (1H), 8.56 (2H).

Example 175

N-(2-methoxyethyl)-2-{[1-(7-methoxy-2-naphthoyl)azetidin-3-yl]methyl}-4-methyl-2H-indazole-5-carboxamide

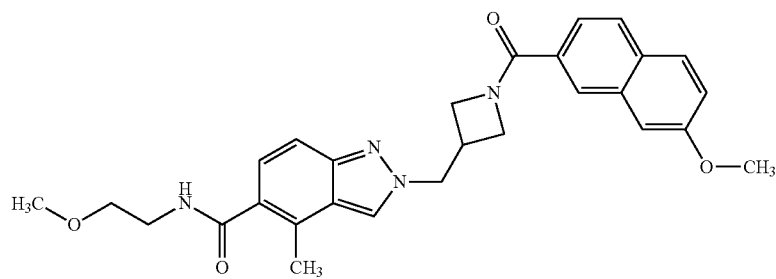

Analogously to Example 1, 72 mg of the title compound was obtained from 135 mg of the compound prepared in Example 117e and 69 mg of 7-methoxy-naphthalen-2-carboxylic acid.

$^1$H-NMR (300 MHz, DMSO-d6): δ=2.50 (3H), 3.21-3.28 (4H), 3.36 (2H), 3.42 (2H), 3.85 (3H), 3.93-3.99 (1H), 4.14 (1H), 4.26 (1H), 4.47 (1H), 4.69 (2H), 7.15 (1H), 7.22 (1H), 7.38 (1H), 7.43 (1H), 7.50 (1H), 7.81-7.88 (2H), 8.05 (1H), 8.12 (1H), 8.56 (1H).

Example 176

N-(2-methoxyethyl)-2-{[1-(6-methoxy-2-naphthoyl)azetidin-3-yl]methyl}-4-methyl-2H-indazole-5-carboxamide

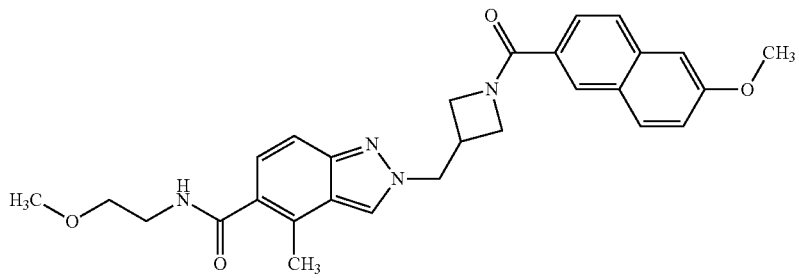

Analogously to Example 1, 72 mg of the title compound was obtained from 135 mg of the compound prepared in Example 117e and 69 mg of 6-methoxynaphthalen-2-carboxylic acid.

$^1$H-NMR (300 MHz, DMSO-d6): δ=2.49 (3H), 3.21-3.28 (4H), 3.33-3.39 (2H), 3.42 (2H), 3.86 (3H), 3.91-3.98 (1H), 4.13 (1H), 4.27 (1H), 4.48 (1H), 4.69 (2H), 7.15 (1H), 7.19 (1H), 7.34 (1H), 7.38 (1H), 7.63 (1H), 7.82 (1H), 7.92 (1H), 8.08-8.14 (2H), 8.56 (1H).

Example 177

4-methyl-N-(2,2,2-trifluoroethyl)-2-{[1-(4-{[5-(trifluoromethyl)pyridin-2-yl]oxy}benzoyl)azetidin-3-yl]methyl}-2H-indazole-5-carboxamide

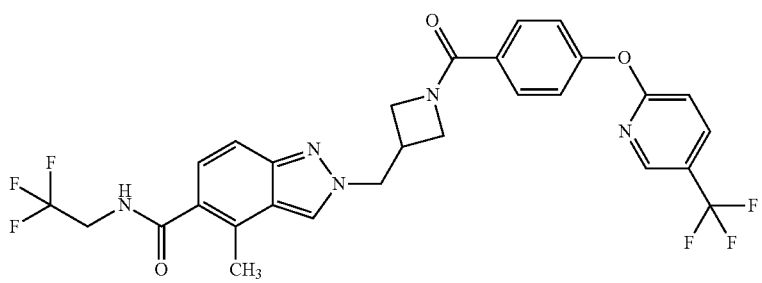 [SMILES: Cc1c(C(=O)NCC(F)(F)F)ccc2nn(CC3CN(C(=O)c4ccc(Oc5ccc(C(F)(F)F)cn5)cc4)C3)cc12]

Analogously to Example 1, 68 mg of the title compound was obtained from 170 mg of the compound prepared in Example 129b and 113 mg of 4-{[5-(trifluoromethyl)pyridin-2-yl]oxy}benzoic acid.

$^1$H-NMR (300 MHz, DMSO-d6): δ=2.35 (3H), 3.21 (1H), 3.89 (1H), 3.96-4.13 (3H), 4.21 (1H), 4.40 (1H), 4.68 (2H), 7.24 (2H), 7.28 (1H), 7.40 (1H), 7.66 (2H), 7.72 (1H), 8.24 (1H), 8.48 (1H), 8.56 (1H), 8.89 (1H).

Example 178

2-{[1-(4-chlorobenzoyl)azetidin-3-yl]methyl}-N-(2-methoxyethyl)-6-methyl-2H-indazole-5-carboxamide

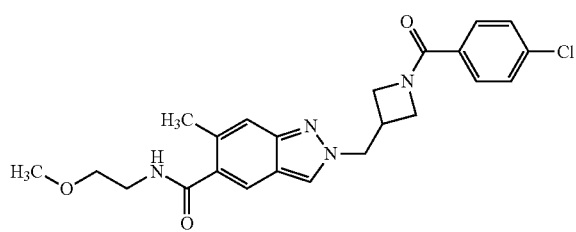 [SMILES: COCCNC(=O)c1cc2cn(CC3CN(C(=O)c4ccc(Cl)cc4)C3)nc2cc1C]

Analogously to Example 55, 154 mg of the title compound was obtained from 210 mg of the compound prepared in Example 178e and 119 mg of 4-chlorobenzoyl chloride.

$^1$H-NMR (300 MHz, DMSO-d6): δ=2.34 (3H), 3.19 (1H), 3.24 (3H), 3.34 (2H), 3.42 (2H), 3.87 (1H), 4.07 (1H), 4.16 (1H), 4.34 (1H), 4.65 (2H), 7.35 (1H), 7.48 (2H), 7.59 (2H), 7.63 (1H), 8.21 (1H), 8.41 (1H).

The starting material was prepared as follows:

Example 178a

Tert-butyl 3-[(5-bromo-6-methyl-2H-indazol-2-yl)methyl]azetidin-1-carboxylate

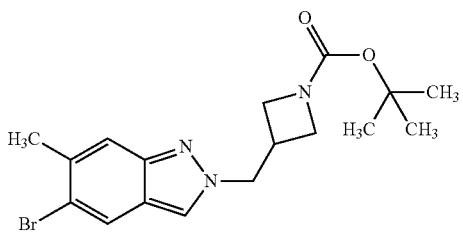 [SMILES: Cc1cc2nn(CC3CN(C(=O)OC(C)(C)C)C3)cc2cc1Br]

To a solution of 6.18 g of 5-bromo-6-methyl-1H-indazole and 15 g of tert-butyl-3-[(tosyl-oxy)methyl]azetidin-1-carboxylate in 200 ml DMF were added 9.54 g of caesium carbonate and 10.8 g of tetrabutylammonium iodide at 25° C., and this was then heated under reflux for 1.5 hrs. After cooling, the reaction mixture was treated with 1:1 hexane/ether and water, the phases separated and the aqueous phase extracted twice with 250 ml portions of 1:1 hexane/ether. The combined organic phases were washed with saturated sodium chloride solution, dried over sodium sulphate, and concentrated in vacuo after filtration.

The residue thus obtained was purified by twofold column chromatography on silica gel with hexane/0-20% ethyl acetate. 2.88 g of the title compound was obtained.

$^1$H-NMR (300 MHz, DMSO-d6): δ=1.32 (9H), 2.37 (3H), 3.05 (1H), 3.67 (2H), 3.85 (2H), 4.59 (2H), 7.56 (1H), 7.97 (1H), 8.33 (1H).

Example 178b

Methyl 2-{[1-(tert-butoxycarbonyl)azetidin-3-yl]methyl}-6-methyl-2H-indazol-5-carboxylate

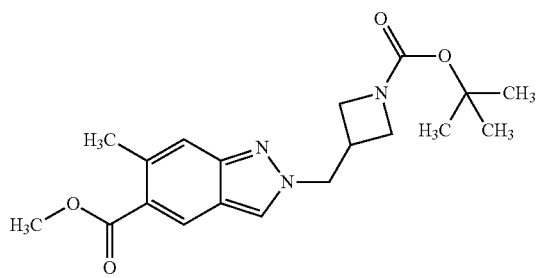 [SMILES: COC(=O)c1cc2cn(CC3CN(C(=O)OC(C)(C)C)C3)nc2cc1C]

To a solution of 730 mg of the bromide prepared in Example 178a in 17.5 ml tetrahydrofuran were added 0.23 ml of methanol, 145 mg of trans-bis(acetato)-bis[o-(di-o-tolylphosphino)-benzyl]dipalladium(II), 877 mg of DBU and 760 mg of molybdenum hexacarbonyl This reaction mixture was then heated in the microwave (120 watts) for 20 minutes at 125° C. Seven further preparations were performed in the same manner and all worked up together. For this, they were concentrated in vacuo and the residue taken up in water and ethyl acetate. After phase separation, the aqueous phase was extracted three times with 75 ml portions of ethyl acetate and the combined organic phases washed with saturated sodium chloride solution, dried over sodium sulphate and concentrated in vacuo after filtration. The residue thus obtained was purified by twofold column chromatography on silica gel with hexane/0-30% ethyl acetate. Yield: 4.0 g of the title compound.

$^1$H-NMR (300 MHz, DMSO-d6): δ=1.32 (9H), 2.52 (3H), 3.07 (1H), 3.69 (2H), 3.86 (2H), 3.78 (3H), 4.62 (2H), 7.43 (1H), 8.33 (1H), 8.53 (1H).

Example 178c

2-{[1-(tert-butoxycarbonyl)azetidin-3-yl]methyl}-6-methyl-2H-indazol-5-carboxylic acid

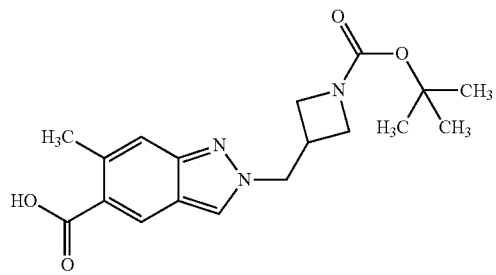 [SMILES: Cc1cc2nn(CC3CN(C(=O)OC(C)(C)C)C3)cc2cc1C(=O)O]

Analogously to Example 1d, 3.2 g of the title compound was obtained from 4.0 g of the ester prepared in Example 178b.

$^1$H-NMR (300 MHz, DMSO-d6): δ=1.32 (9H), 2.53 (3H), 3.07 (1H), 3.69 (2H), 3.86 (2H), 4.61 (2H), 7.39 (1H), 8.31 (1H), 8.50 (1H), 12.48 (1H).

Example 178d

Tert-butyl 3-({5-[1\1-(2-methoxyethyl)carbamoyl]-6-methyl-2H-indazol-2-yl}-methyl)azetidin-1-carboxylate

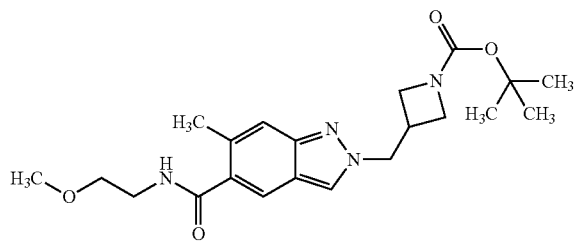 [SMILES: COCCNC(=O)c1cc2cn(CC3CN(C(=O)OC(C)(C)C)C3)nc2cc1C]

Analogously to Example 1, 603 mg of the title compound was obtained from 500 mg of the acid prepared in Example 178c and 109 mg of 2-methoxyethylamine.

$^1$H-NMR (300 MHz, DMSO-d6): δ=1.32 (9H), 2.34 (3H), 3.06 (1H), 3.25 (3H), 3.32-3.45 (4H), 3.67 (2H), 3.84 (2H), 4.59 (2H), 7.35 (1H), 7.64 (1H), 8.21 (1H), 8.41 (1H).

Example 178e 2-(azetidin-3-ylmethyl)-N-(2-methoxyethyl)-6-methyl-2H-indazol-5-carboxamide hydrochloride

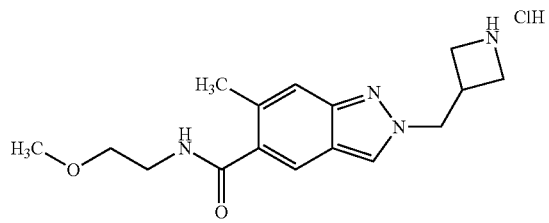 [SMILES: Cl ; COCCNC(=O)c1cc2cn(CC3CNC3)nc2cc1C]

Analogously to Example 1a, from 250 mg of the amide prepared in Example 178d, 275 mg of the title compound was obtained, which was reacted without further purification.

Example 179

2-{[1-(3,5-Difluorobenzoyl)azetidin-3-yl]methyl}-N-(2-methoxyethyl)-6-methyl-2H-indazole-5-carboxamide

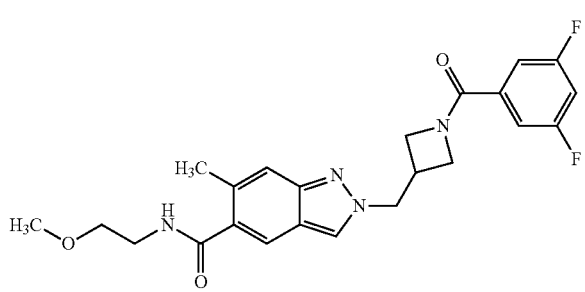 [SMILES: COCCNC(=O)c1cc2cn(CC3CN(C(=O)c4cc(F)cc(F)c4)C3)nc2cc1C]

Analogously to Example 55, 51 mg of the title compound was obtained from 77 mg of the compound prepared in Example 178e and 44 mg of 3,5-difluorobenzoyl chloride.

$^1$H-NMR (300 MHz, DMSO-d6): δ=2.33 (3H), 3.18 (1H), 3.24 (3H), 3.34 (2H), 3.42 (2H), 3.87 (1H), 4.03-4.11 (1H), 4.20 (1H), 4.38 (1H), 4.65 (2H), 7.20-7.28 (2H), 7.34 (1H), 7.36-7.45 (2H), 7.64 (1H), 8.22 (1H), 8.42 (1H).

Example 180

N-(2-methoxyethyl)-6-methyl-2-[(1-{4-[(trifluoromethyl)sulphanyl]benzoyl}azetidin-3-yl)methyl]-2H-indazole-5-carboxamide

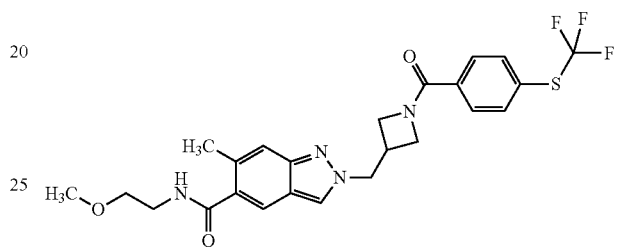

Analogously to Example 55, 30 mg of the title compound was obtained from 43 mg of the compound prepared in Example 178e and 34 mg of 4-[(trifluoromethyl)sulphanyl]benzoyl chloride.

$^1$H-NMR (300 MHz, DMSO-d6): δ=2.34 (3H), 3.20 (1H), 3.24 (3H), 3.34 (2H), 3.42 (2H), 3.89 (1H), 4.09 (1H), 4.17 (1H), 4.36 (1H), 4.65 (2H), 7.34 (1H), 7.63 (1H), 7.69 (2H), 7.76 (2H), 8.21 (1H), 8.41 (1H).

Example 181

N-(2-methoxyethyl)-6-methyl-2-({1-[4-(trifluoromethoxy)benzoyl]azetidin-3-yl}methyl)-2H-indazole-5-carboxamide

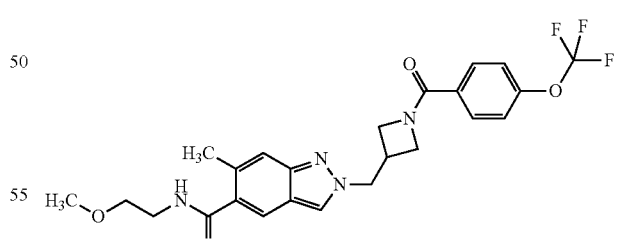

Analogously to Example 55, 221 mg of the title compound was obtained from 294 mg of the compound prepared in Example 178e and 214 mg of 4-(trifluoromethoxy)benzoyl chloride.

$^1$H-NMR (300 MHz, DMSO-d6): δ=2.34 (3H), 3.20 (1H), 3.25 (3H), 3.34 (2H), 3.42 (2H), 3.89 (1H), 4.08 (1H), 4.18 (1H), 4.36 (1H), 4.65 (2H), 7.35 (1H), 7.40 (2H), 7.64 (1H), 7.70 (2H), 8.21 (1H), 8.42 (1H).

Example 182

2-({1-[2-fluoro-4-(trifluoromethyl)benzoyl]azetidin-3-yl}methyl)-N-(2-methoxy-ethyl)-6-methyl-2H-indazole-5-carboxamide

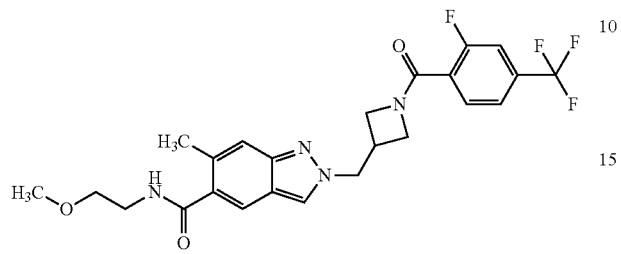

Analogously to Example 55, 11 mg of the title compound was obtained from 43 mg of the compound prepared in Example 178e and 32 mg of 2-fluoro-4-(trifluoromethyl)benzoyl chloride.

$^1$H-NMR (300 MHz, DMSO-d6): δ=2.33 (3H), 3.20 (1H), 3.24 (3H), 3.35 (2H), 3.42 (2H), 3.86-3.95 (2H), 4.02-4.16 (2H), 4.65 (2H), 7.34 (1H), 7.61-7.69 (3H), 7.79 (1H), 8.21 (1H), 8.41 (1H).

Example 183

2-{[1-(4-chloro-2-fluorobenzoyl)azetidin-3-yl]methyl}-N-(2-methoxyethyl)-6-methyl-2H-indazole-5-carboxamide

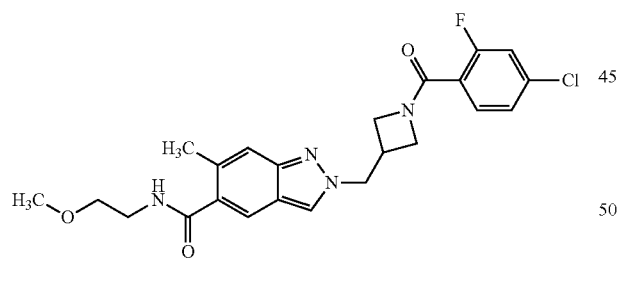

Analogously to Example 55, from 70 mg of the compound prepared in Example 178e and 44 mg of 4-chloro-2-fluorobenzoyl chloride, a material still contaminated after HPLC purification was obtained, which was further purified by additional preparative thick layer chromatography with ethyl acetate/methanol in the ratio 9:1 as mobile phase. This yielded 12 mg of the title compound.

$^1$H-NMR (300 MHz, DMSO-d6): δ=2.34 (3H), 3.19 (1H), 3.25 (3H), 3.34 (2H), 3.42 (2H), 3.84-3.93 (2H), 4.02-4.10 (2H), 4.64 (2H), 7.32-7.36 (2H), 7.46 (1H), 7.53 (1H), 7.63 (1H), 8.22 (1H), 8.41 (1H).

Example 184

2-({1-[3-fluoro-4-(trifluoromethyl)benzoyl]azetidin-3-yl}methyl)-N-(2-methoxy-ethyl)-6-methyl-2H-indazole-5-carboxamide

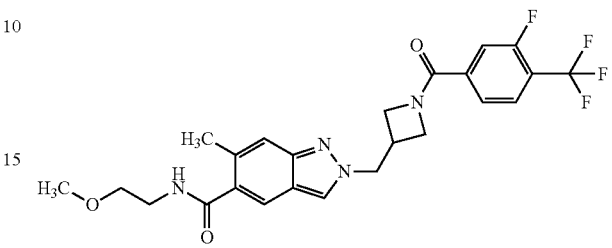

Analogously to Example 55, 32 mg of the title compound was obtained from 70 mg of the compound prepared in Example 178e and 52 mg of 3-fluoro-4-(trifluoromethyl)benzoyl chloride.

$^1$H-NMR (300 MHz, DMSO-d6): δ=2.34 (3H), 3.20 (1H), 3.24 (3H), 3.30-3.38 (2H), 3.42 (2H), 3.90 (1H), 4.10 (1H), 4.19 (1H), 4.38 (1H), 4.66 (2H), 7.34 (1H), 7.57 (1H), 7.60-7.67 (2H), 7.85 (1H), 8.21 (1H), 8.41 (1H).

Example 185

2-({1-[4-chloro-3-(trifluoromethyl)benzoyl]azetidin-3-yl}methyl)-N-(2-methoxy-ethyl)-6-methyl-2H-indazole-5-carboxamide

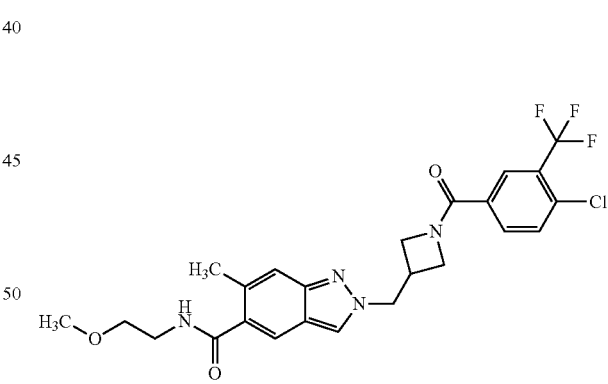

Analogously to Example 55, 30 mg of the title compound was obtained from 70 mg of the compound prepared in Example 178e and 55 mg of 4-chloro-3-(trifluoromethyl)benzoyl chloride.

$^1$H-NMR (300 MHz, DMSO-d6): δ=2.34 (3H), 3.19 (1H), 3.24 (3H), 3.34 (2H), 3.42 (2H), 3.89 (1H), 4.10 (1H), 4.20 (1H), 4.35-4.43 (1H), 4.65 (2H), 7.33 (1H), 7.64 (1H), 7.78 (1H), 7.85 (1H), 7.93 (1H), 8.21 (1H), 8.40 (1H).

Example 186

N-(2-methoxyethyl)-6-methyl-2-({1-[4-(trifluoromethyl)benzoyl]azetidin-3-yl}methyl)-2H-indazole-5-carboxamide

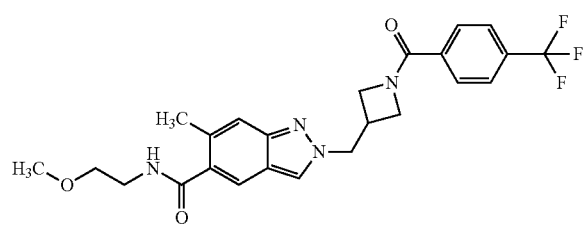 [SMILES: COCCNC(=O)c1cc2cn(CC3CN(C(=O)c4ccc(C(F)(F)F)cc4)C3)nc2cc1C]

Analogously to Example 55, 31 mg of the title compound was obtained from 70 mg of the compound prepared in Example 178e and 47 mg of 4-(trifluoromethyl)benzoyl chloride.

$^1$H-NMR (300 MHz, DMSO-d6): δ=2.34 (3H), 3.20 (1H), 3.24 (3H), 3.35 (2H), 3.42 (2H), 3.90 (1H), 4.06-4.21 (2H), 4.35 (1H), 4.66 (2H), 7.34 (1H), 7.63 (1H), 7.73-7.82 (4H), 8.21 (1H), 8.41 (1H).

Example 187

6-methyl-2-({1-[4-(pentafluoro-λ$^6$-sulphanyl)benzoyl]azetidin-3-yl}methyl)-N-{2-[(trifluoromethyl)sulphanyl]ethyl}-2H-indazole-5-carboxamide

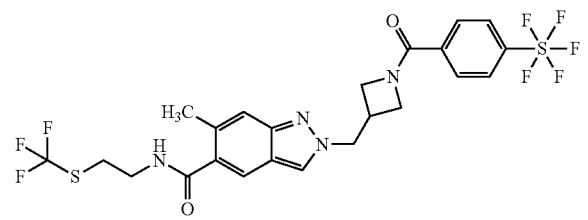 [SMILES: Cc1cc2nn(CC3CN(C(=O)c4ccc(S(F)(F)(F)(F)F)cc4)C3)cc2cc1C(=O)NCCSC(F)(F)F]

Analogously to Example 1, 35 mg of the title compound was obtained from 170 mg of the compound prepared in Example 187b and 103 mg of 4-(pentafluoro-29-sulphanyl)benzoic acid.

$^1$H-NMR (300 MHz, DMSO-d6): δ=2.36 (3H), 3.12-3.23 (3H), 3.49 (2H), 3.91 (1H), 4.06-4.21 (2H), 4.36 (1H), 4.66 (2H), 7.36 (1H), 7.69 (1H), 7.76 (2H), 7.95 (2H), 8.44 (1H), 8.46 (1H).

The starting material was prepared as follows:

Example 187a

Tert-butyl 3-{[6-methyl-5-(N-{2-[(trifluoromethyl)sulphanyl]ethyl}carbamoyl)-2H-indazol-2-yl]methyl}azetidin-1-carboxylate

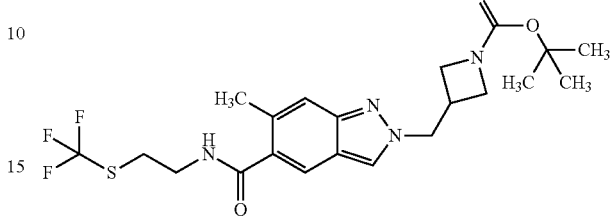

Analogously to Example 1, 998 mg of the title compound was obtained from 800 mg of the acid prepared in Example 178c and 336 mg of 2-[(trifluoromethyl)sulphanyl]ethylamine.

$^1$H-NMR (300 MHz, DMSO-d6): δ=1.32 (9H), 2.36 (3H), 3.06 (1H), 3.13-3.21 (2H), 3.49 (2H), 3.67 (2H), 3.84 (2H), 4.59 (2H), 7.37 (1H), 7.70 (1H), 8.44 (1H), 8.47 (1H).

Example 187b 2-(azetidin-3-ylmethyl)-6-methyl-N-{2-[(trifluoromethyl)sulphanyl]ethyl}-2H-indazole-5-carboxamide hydrochloride

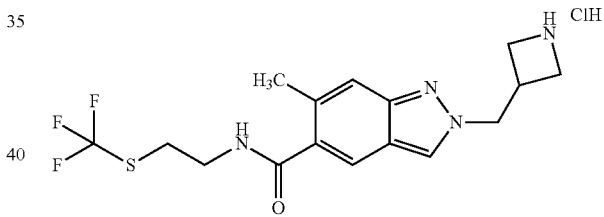

Analogously to Example 1a), from 395 mg of the amide prepared in Example 187a), 402 mg of the title compound was obtained, which was reacted without further purification.

Example 188

6-methyl-2-({-[4-(pentafluoro-λ$^6$-sulphanyl)benzoyl]azetidin-3-yl}methyl)-N-(2,2,2-trifluoroethyl)-2H-indazole-5-carboxamide

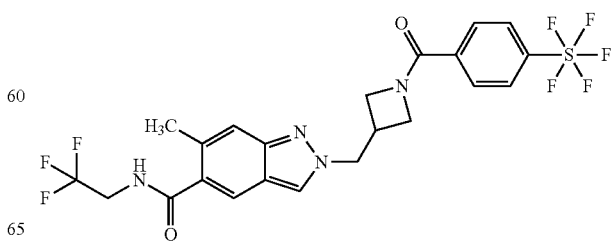

Analogously to Example 1, 25 mg of the title compound was obtained from 136 mg of the compound prepared in Example 188b and 93 mg of 4-(pentafluoro-λ⁶-sulphanyl)benzoic acid.

¹H-NMR (300 MHz, DMSO-d6): δ=2.34 (3H), 3.20 (1H), 3.91 (1H), 3.95-4.21 (4H), 4.36 (1H), 4.67 (2H), 7.38 (1H), 7.71 (1H), 7.76 (2H), 7.95 (2H), 8.45 (1H), 8.86 (1H).

The starting material was prepared as follows:

Example 188a

Tert-butyl 3-({6-methyl-5-[N-(2,2,2-trifluoroethyl)carbamoyl]-2H-indazol-2-yl}methyl)azetidin-1-carboxylate

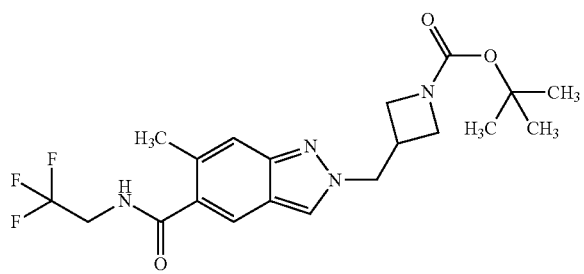 [SMILES: Cc1cc2nn(CC3CN(C(=O)OC(C)(C)C)C3)cc2cc1C(=O)NCC(F)(F)F]

Analogously to Example 1, 550 mg of the title compound was obtained from 560 mg of the acid prepared in Example 178c and 160 mg of 2,2,2-trifluoroethylamine.

¹H-NMR (300 MHz, DMSO-d6): δ=1.32 (9H), 2.34 (3H), 3.06 (1H), 3.67 (2H), 3.84 (2H), 3.93-4.10 (2H), 4.60 (2H), 7.40 (1H), 7.71 (1H), 8.46 (1H), 8.88 (1H).

Example 188b 2-(azetidin-3-ylmethyl)-6-methyl-N-(2,2,2-trifluoroethyl)-2H-indazole-5-carboxamide hydrochloride

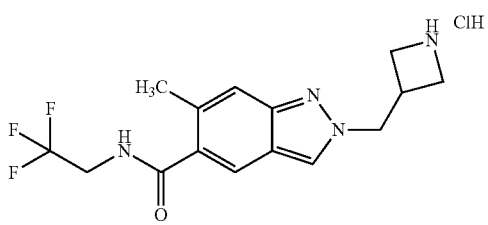 [SMILES: Cl ; Cc1cc2nn(CC3CNC3)cc2cc1C(=O)NCC(F)(F)F]

Analogously to Example 1a, from 550 mg of the amide prepared in Example 188a, 530 mg of the title compound was obtained, which was reacted without further purification.

Example 189

2-{[1-(4-chlorobenzoyl)azetidin-3-yl]methyl}-6-methyl-N-{2-[(trifluoromethyl)sulphanyl]ethyl}-2H-indazole-5-carboxamide

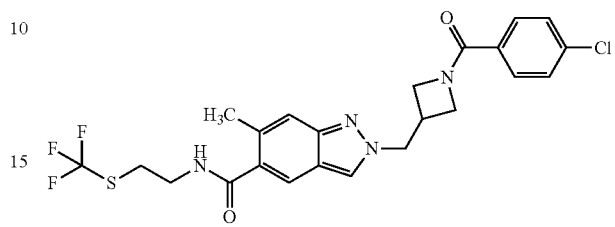

Analogously to Example 55, 45 mg of the title compound was obtained from 170 mg of the compound prepared in Example 187b and 80 mg of 4-chlorobenzoyl chloride.

¹H-NMR (300 MHz, DMSO-d6): δ=2.39 (3H), 3.17-3.27 (3H), 3.52 (2H), 3.90 (1H), 4.10 (1H), 4.19 (1H), 4.37 (1H), 4.68 (2H), 7.39 (1H), 7.50 (2H), 7.61 (2H), 7.72 (1H), 8.47 (1H), 8.49 (1H).

Example 190

2-{[1-(4-chlorobenzoyl)azetidin-3-yl]methyl}-6-methyl-N-(2,2,2-trifluoroethyl)-2H-indazole-5-carboxamide

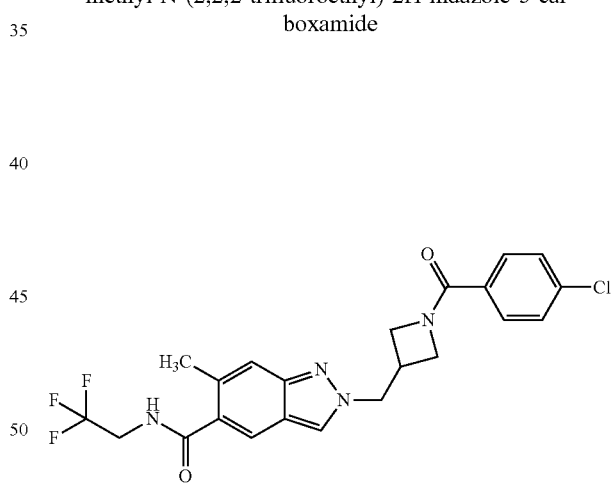

Analogously to Example 55, 60 mg of the title compound was obtained from 136 mg of the compound prepared in Example 188b and 72 mg of 4-chlorobenzoyl chloride.

¹H-NMR (300 MHz, DMSO-d6): δ=2.34 (3H), 3.20 (1H), 3.87 (1H), 3.94-4.11 (3H), 4.16 (1H), 4.35 (1H), 4.66 (2H), 7.39 (1H), 7.48 (2H), 7.59 (2H), 7.71 (1H), 8.46 (1H), 8.89 (1H).

Example 191

(+/−)-2-{[1-(4-chlorobenzoyl)azetidin-3-yl]methyl}-6-methyl-N-(3,4,5,6-tetrahydro-2H-pyran-2-ylmethyl)-2H-indazole-5-carboxamide

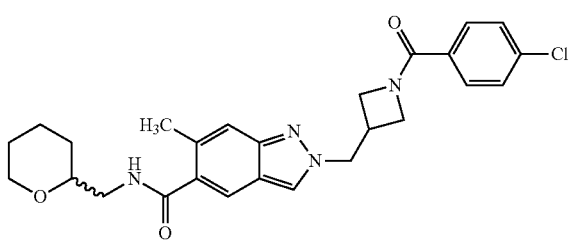 [SMILES: Cc1cc2nn(CC3CN(C(=O)c4ccc(Cl)cc4)C3)cc2cc1C(=O)NCC1CCCCO1]

Analogously to Example 55, 49 mg of the title compound was obtained from 120 mg of the compound prepared in Example 191b and 61 mg of 4-chlorobenzoyl chloride.

$^1$H-NMR (300 MHz, DMSO-d6): δ=1.08-1.23 (1H), 1.36-1.49 (3H), 1.62 (1H), 1.72-1.80 (1H), 2.34 (3H), 3.10-3.43 (5H), 3.80-3.92 (2H), 4.07 (1H), 4.16 (1H), 4.34 (1H), 4.65 (2H), 7.34 (1H), 7.47 (2H), 7.59 (2H), 7.63 (1H), 8.16 (1H), 8.40 (1H).

The starting material was prepared as follows:

Example 191a (+/−)-tert-butyl 3-({6-methyl-5-[N-(3,4,5,6-tetrahydro-2H-pyran-2-ylmethyl)-carbamoyl]-2H-indazol-2-yl}methyl)azetidin-1-carboxylate

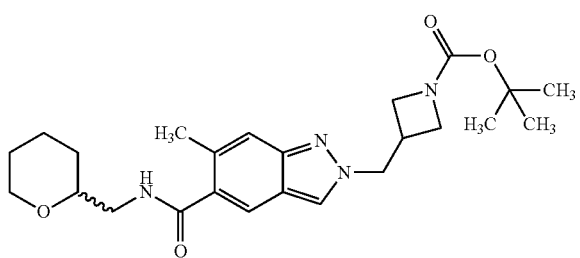 [SMILES: Cc1cc2nn(CC3CN(C(=O)OC(C)(C)C)C3)cc2cc1C(=O)NCC1CCCCO1]

Analogously to Example 1, 140 mg of the title compound was obtained from 300 mg of the acid prepared in Example 178c and 105 mg of 3,4,5,6-tetrahydro-2H-pyran-2-ylmethylamine.

$^1$H-NMR (300 MHz, DMSO-d6): δ=1.07-1.24 (1H), 1.27-1.49 (12H), 1.62 (1H), 1.76 (1H), 2.33 (3H), 3.06 (1H), 3.20 (2H), 3.29-3.45 (2H), 3.67 (2H), 3.78-3.90 (3H), 4.59 (2H), 7.35 (1H), 7.63 (1H), 8.16 (1H), 8.40 (1H).

Example 191b (+/−)-2-(azetidin-3-ylmethyl)-6-methyl-N-(3,4,5,6-tetrahydro-2H-pyran-2-ylmethyl)-2H-indazole-5-carboxamide hydrochloride

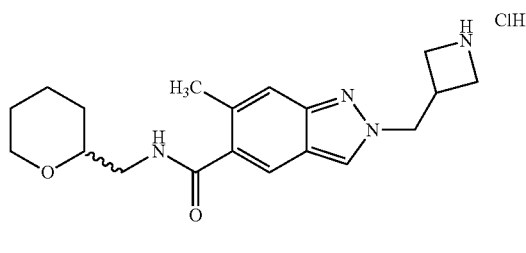 [SMILES: Cl ; Cc1cc2nn(CC3CNC3)cc2cc1C(=O)NCC1CCCCO1]

Analogously to Example 1a, from 140 mg of the amide prepared in Example 191a, 132 mg of the title compound was obtained, which was reacted without further purification.

Example 192

(+/−)-2-{[1-(4-chlorobenzoyl)azetidin-3-yl]methyl}-N-(2-methoxypropyl)-6-methyl-2H-indazole-5-carboxamide

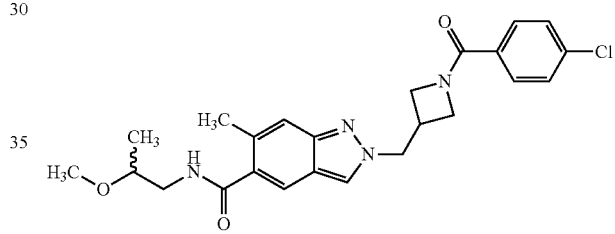

Analogously to Example 55, 89 mg of the title compound was obtained from 151 mg of the compound prepared in Example 192b and 82 mg of 4-chlorobenzoyl chloride.

$^1$H-NMR (300 MHz, DMSO-d6): δ=1.08 (3H), 2.34 (3H), 3.13-3.32 (6H), 3.43 (1H), 3.87 (1H), 4.07 (1H), 4.16 (1H), 4.34 (1H), 4.65 (2H), 7.35 (1H), 7.48 (2H), 7.59 (2H), 7.63 (1H), 8.18 (1H), 8.41 (1H).

The starting material was prepared as follows:

Example 192a (+/−)-tert-butyl 3-({5-[N-(2-methoxypropyl)carbamoyl]-6-methyl-2H-indazol-2-yl}methyl)azetidin-1-carboxylate

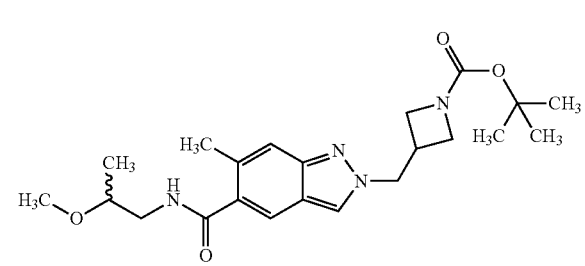 [SMILES: COC(C)CNC(=O)c1cc2cn(CC3CN(C(=O)OC(C)(C)C)C3)nc2cc1C]

Analogously to Example 1, 358 mg of the title compound was obtained from 300 mg of the acid prepared in Example 178c and 77 mg of 2-methoxypropan-1-amine.

¹H-NMR (300 MHz, DMSO-d6): δ=1.08 (3H), 1.32 (9H), 2.34 (3H), 3.06 (1H), 3.13-3.31 (5H), 3.43 (1H), 3.67 (2H), 3.84 (2H), 4.59 (2H), 7.35 (1H), 7.64 (1H), 8.18 (1H), 8.40 (1H).

Example 192b (+/−)-2-(azetidin-3-ylmethyl)-N-(2-methoxypropyl)-6-methyl-2H-indazole-5-carboxamide hydrochloride

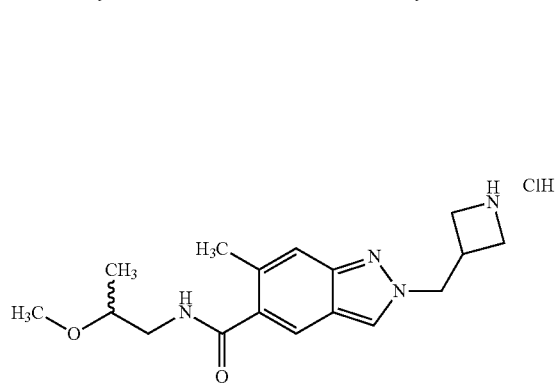

Analogously to Example 1a), from 358 mg of the amide prepared in Example 192a), 319 mg of the title compound was obtained, which was reacted without further purification.

Example 193

(+/−)-N-(2-methoxypropyl)-6-methyl-2-({1-[4-(trifluoromethoxy)benzoyl]-azetidin-3-yl}methyl)-2H-indazole-5-carboxamide

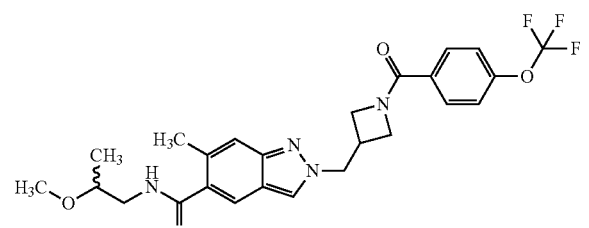

Analogously to Example 55, 87 mg of the title compound was obtained from 151 mg of the compound prepared in Example 192b and 106 mg of 4-(trifluoromethoxy)benzoyl chloride.

¹H-NMR (300 MHz, DMSO-d6): δ=1.08 (3H), 2.34 (3H), 3.13-3.31 (6H), 3.43 (1H), 3.88 (1H), 4.08 (1H), 4.17 (1H), 4.36 (1H), 4.65 (2H), 7.35 (1H), 7.40 (2H), 7.64 (1H), 7.70 (2H), 8.18 (1H), 8.41 (1H).

Example 194

6-methyl-2-({1-[4-(trifluoromethoxy)benzoyl]azetidin-3-yl}methyl)-N-{2-[(trifluoromethyl)sulphanyl]ethyl}-2H-indazole-5-carboxamide

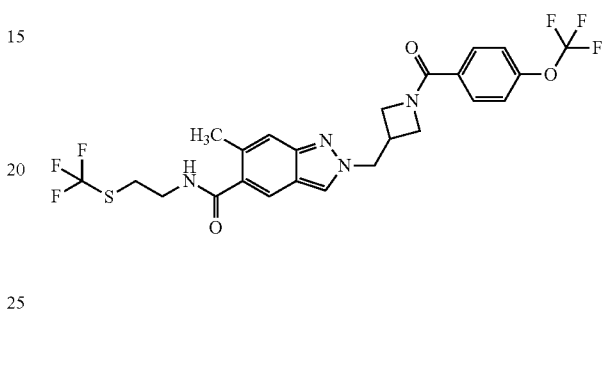

Analogously to Example 55, 87 mg of the title compound was obtained from 173 mg of the compound prepared in Example 187b and 105 mg of 4-(trifluoromethoxy)benzoyl chloride.

¹H-NMR (300 MHz, DMSO-d6): δ=2.36 (3H), 3.11-3.24 (3H), 3.49 (2H), 3.89 (1H), 4.09 (1H), 4.17 (1H), 4.36 (1H), 4.66 (2H), 7.36 (1H), 7.40 (2H), 7.66-7.74 (3H), 8.44 (1H), 8.46 (1H).

Example 195

6-methyl-N-(2,2,2-trifluoroethyl)-2-({1-[4-(trifluoromethoxy)benzoyl]azetidin-3-yl}methyl)-2H-indazole-5-carboxamide

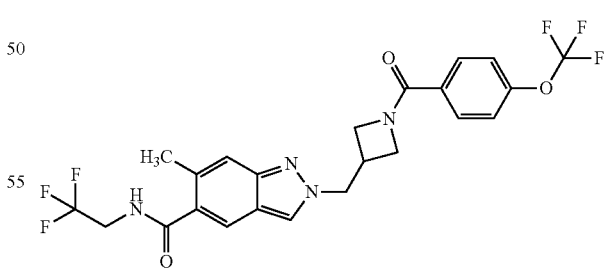

Analogously to Example 55, 70 mg of the title compound was obtained from 170 mg of the compound prepared in Example 188b and 116 mg of 4-(trifluoromethoxy)benzoyl chloride.

¹H-NMR (300 MHz, DMSO-d6): δ=2.35 (3H), 3.21 (1H), 3.89 (1H), 3.95-4.13 (3H), 4.18 (1H), 4.36 (1H), 4.67 (2H), 7.40 (3H), 7.66-7.75 (3H), 8.45 (1H), 8.86 (1H).

Example 196

6-methyl-2-({1-[4-(trifluoromethoxy)benzoyl]azetidin-3-yl}methyl)-N-[2-(trifluoromethoxy)ethyl]-2H-indazole-5-carboxamide

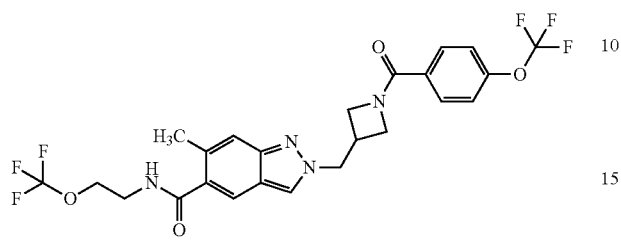

Analogously to Example 55, 22 mg of the title compound was obtained from 179 mg of the compound prepared in Example 196b and 113 mg of 4-(trifluoromethoxy)benzoyl chloride.

$^1$H-NMR (300 MHz, DMSO-d6): δ=2.34 (3H), 3.20 (1H), 3.50 (2H), 3.89 (1H), 4.08 (1H), 4.14-4.21 (3H), 4.36 (1H), 4.66 (2H), 7.36 (1H), 7.40 (2H), 7.66 (1H), 7.70 (2H), 8.44 (1H), 8.46 (1H).

The starting material was prepared as follows:

Example 196a

Tert-butyl 3-[(6-methyl-5-{N-[2-(trifluoromethoxy)ethyl]carbamoyl}-2H-indazol-2-yl)methyl]azetidin-1-carboxylate

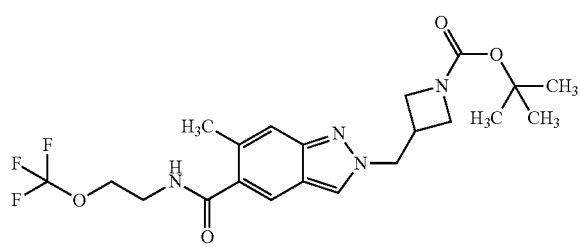 [SMILES: Cc1cc2nn(CC3CN(C(=O)OC(C)(C)C)C3)cc2cc1C(=O)NCCOC(F)(F)F]

Analogously to Example 1, 417 mg of the title compound was obtained from 300 mg of the acid prepared in Example 178c and 144 mg of 2-(trifluoromethoxy)ethylamine hydrochloride.

$^1$H-NMR (300 MHz, DMSO-d6): δ=1.32 (9H), 2.34 (3H), 3.06 (1H), 3.50 (2H), 3.68 (2H), 3.84 (2H), 4.16 (2H), 4.59 (2H), 7.37 (1H), 7.66 (1H), 8.44 (1H), 8.46 (1H).

Example 196b 2-(azetidin-3-ylmethyl)-6-methyl-N-[2-(trifluoromethoxy)ethyl]-2H-indazole-5-carboxamide hydrochloride

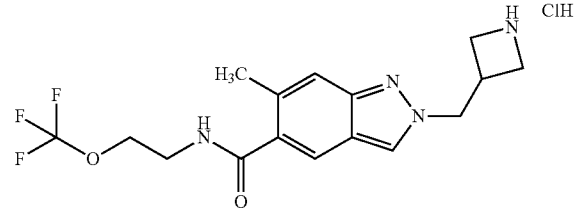 [SMILES: Cl ; Cc1cc2nn(CC3CNC3)cc2cc1C(=O)NCCOC(F)(F)F]

Analogously to Example 1a, from 417 mg of the amide prepared in Example 196a, 369 mg of the title compound was obtained, which was reacted without further purification.

Example 197

2-{[1-(4-chlorobenzoyl)azetidin-3-yl]methyl}-6-methyl-N-[2-(trifluoromethoxy)ethyl]-2H-indazole-5-carboxamide

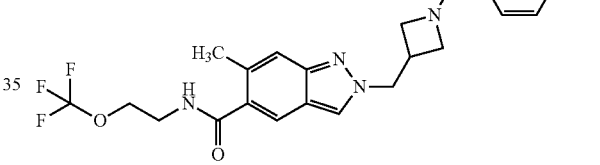

Analogously to Example 55, 41 mg of the title compound was obtained from 179 mg of the compound prepared in Example 196b and 88 mg of 4-chlorobenzoyl chloride.

$^1$H-NMR (300 MHz, DMSO-d6): δ=2.34 (3H), 3.19 (1H), 3.50 (2H), 3.87 (1H), 4.07 (1H), 4.13-4.21 (3H), 4.34 (1H), 4.65 (2H), 7.36 (1H), 7.48 (2H), 7.59 (2H), 7.66 (1H), 8.44 (1H), 8.46 (1H).

Example 198

2-{[1-(4-chlorobenzoyl)azetidin-3-yl]methyl}-N-[2-(cyclopropylmethoxy)ethyl]-6-methyl-2H-indazole-5-carboxamide

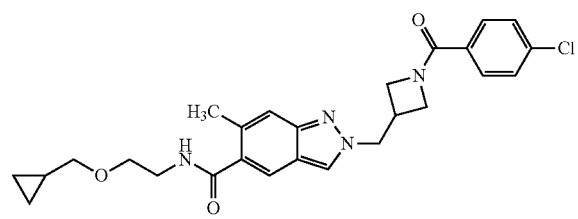 [SMILES: Cc1cc2nn(CC3CN(C(=O)c4ccc(Cl)cc4)C3)cc2cc1C(=O)NCCOCC1CC1]

Analogously to Example 55, 107 mg of the title compound was obtained from 214 mg of the compound prepared in Example 198b and 109 mg of 4-chlorobenzoyl chloride.

¹H-NMR (300 MHz, DMSO-d6): δ=0.14 (2H), 0.42 (2H), 0.97 (1H), 2.34 (3H), 3.12-3.26 (3H), 3.34 (2H), 3.47 (2H), 3.87 (1H), 4.07 (1H), 4.16 (1H), 4.34 (1H), 4.65 (2H), 7.35 (1H), 7.48 (2H), 7.59 (2H), 7.63 (1H), 8.21 (1H), 8.42 (1H).

The starting material was prepared as follows:

Example 198a

Tert-butyl 3-[(5-{N-[2-(cyclopropylmethoxy)ethyl] carbamoyl}-6-methyl-2H-indazol-2-yl)methyl]azetidin-1-carboxylate

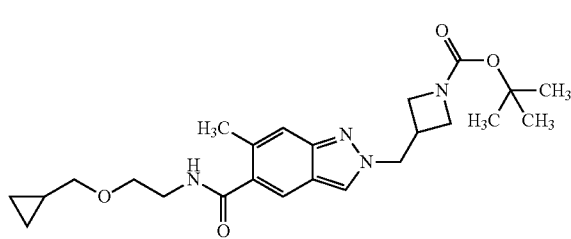 [SMILES: Cc1cc2nn(CC3CN(C(=O)OC(C)(C)C)C3)cc2cc1C(=O)NCCOCC1CC1]

Analogously to Example 1, 247 mg of the title compound was obtained from 245 mg of the acid prepared in Example 178c and 82 mg of 2-(cyclopropylmethoxy)ethylamine hydrochloride.

¹H-NMR (300 MHz, DMSO-d6): δ=0.14 (2H), 0.43 (2H), 0.97 (1H), 1.32 (9H), 2.35 (3H), 3.06 (1H), 3.23 (2H), 3.34 (2H), 3.48 (2H), 3.67 (2H), 3.85 (2H), 4.59 (2H), 7.35 (1H), 7.64 (1H), 8.18 (1H), 8.41 (1H).

Example 198b 2-(azetidin-3-ylmethyl)-N-[2-(cyclopropylmethoxy)ethyl]-6-methyl-2H-indazole-5-carboxamide hydrochloride Analogously to Example 1a, from 247 mg of the amide prepared in Example 198a, 214 mg of the title compound was obtained, which was reacted without further purification.

Example 199

2-({1-[4-(4-fluorophenoxy)benzoyl]azetidin-3-yl}methyl)-6-methyl-N-{2-[(trifluoromethyl)sulphanyl]ethyl}-2H-indazole-5-carboxamide

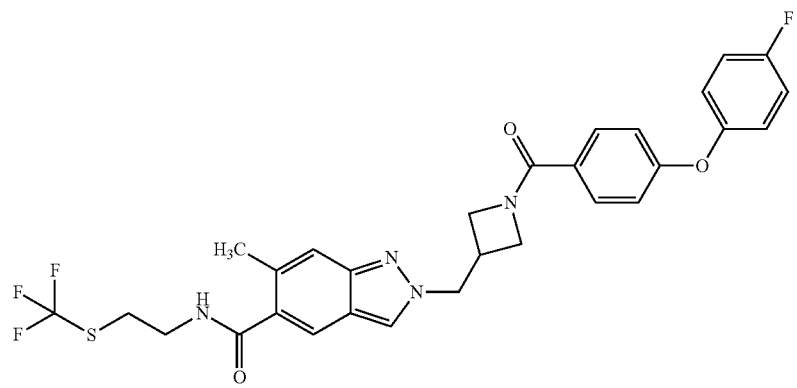 [SMILES: Cc1cc2nn(CC3CN(C(=O)c4ccc(Oc5ccc(F)cc5)cc4)C3)cc2cc1C(=O)NCCSC(F)(F)F]

Analogously to Example 1, 56 mg of the title compound was obtained from 173 mg of the compound prepared in Example 187b and 98 mg of 4-(4-fluorophenoxy)benzoic acid.

¹H-NMR (300 MHz, DMSO-d6): δ=2.38 (3H), 3.16-3.27 (3H), 3.52 (2H), 3.90 (1H), 4.08 (1H), 4.19 (1H), 4.38 (1H), 4.68 (2H), 6.97 (2H), 7.14 (2H), 7.27 (2H), 7.39 (1H), 7.62 (2H), 7.72 (1H), 8.47 (1H), 8.49 (1H).

Example 200

2-{[1-(4-cyclopropylbenzoyl)azetidin-3-yl]methyl}-N-(2-methoxyethyl)-6-methyl-2H-indazole-5-carboxamide

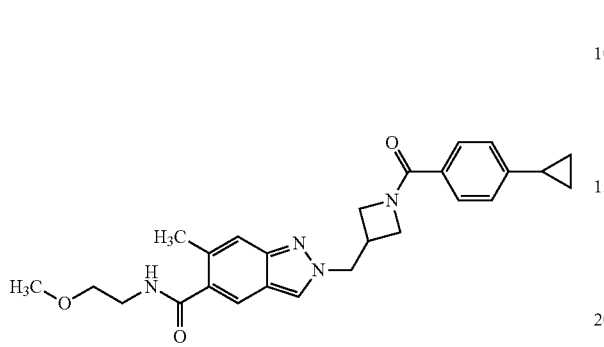

Analogously to Example 1, 86 mg of the title compound was obtained from 168 mg of the compound prepared in Example 178e and 80 mg of 4-cyclopropylbenzoic acid.

$^1$H-NMR (300 MHz, DMSO-d6): δ=0.71 (2H), 0.99 (2H), 1.95 (1H), 2.37 (3H), 3.21 (1H), 3.27 (3H), 3.37 (2H), 3.45 (2H), 3.88 (1H), 4.07 (1H), 4.17 (1H), 4.35 (1H), 4.67 (2H), 7.12 (2H), 7.38 (1H), 7.47 (2H), 7.66 (1H), 8.22 (1H), 8.44 (1H).

Example 201

6-methyl-N-(2,2,2-trifluoroethyl)-2-[(1-{4-[4-(trifluoromethyl)phenoxy]benzoyl}azetidin-3-yl)methyl]-2H-indazole-5-carboxamide

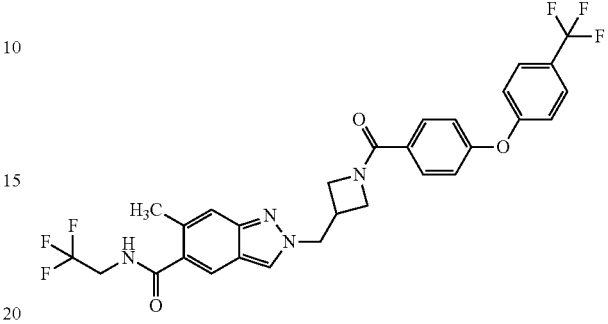

Analogously to Example 1, 71 mg of the title compound was obtained from 180 mg of the compound prepared in Example 188b and 95 mg of 4-[4-(trifluoromethyl)phenoxy]benzoic acid.

$^1$H-NMR (300 MHz, DMSO-d6): δ=2.34 (3H), 3.21 (1H), 3.88 (1H), 3.95-4.13 (3H), 4.19 (1H), 4.37 (1H), 4.67 (2H), 7.11 (2H), 7.19 (2H), 7.39 (1H), 7.65 (2H), 7.69-7.79 (3H), 8.47 (1H), 8.88 (1H).

Example 202

N-(2-methoxyethyl)-6-methyl-2-[(1-{4-[4-(trifluoromethyl)phenoxy]benzoyl}-azetidin-3-yl)methyl]-2H-indazole-5-carboxamide

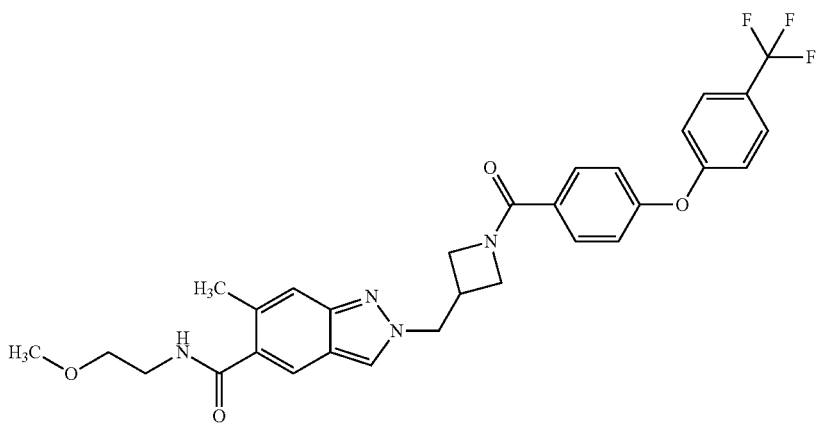 [SMILES: COCCNC(=O)c1cc2cn(CC3CN(C(=O)c4ccc(Oc5ccc(C(F)(F)F)cc5)cc4)C3)nc2cc1C]

Analogously to Example 1, 108 mg of the title compound was obtained from 180 mg of the compound prepared in Example 178e and 102 mg of 4-[4-(trifluoromethyl)phenoxy]benzoic acid.

$^1$H-NMR (300 MHz, DMSO-d6): δ=2.34 (3H), 3.14-3.26 (4H), 3.34 (2H), 3.42 (2H), 3.88 (1H), 4.07 (1H), 4.19 (1H), 4.37 (1H), 4.66 (2H), 7.11 (2H), 7.19 (2H), 7.35 (1H), 7.61-7.68 (3H), 7.75 (2H), 8.21 (1H), 8.42 (1H).

Example 203

2-({1-[(4'-fluorobiphenyl-4-yl)carbonyl]azetidin-3-yl}methyl)-6-methyl-N-(2,2,2-trifluoroethyl)-2H-indazole-5-carboxamide

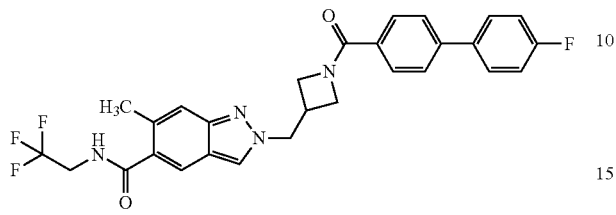

Analogously to Example 1, 104 mg of the title compound was obtained from 180 mg of the compound prepared in Example 188b and 73 mg of 4'-fluorobiphenyl-4-carboxylic acid.

$^1$H-NMR (300 MHz, DMSO-d6): δ=2.34 (3H), 3.22 (1H), 3.90 (1H), 3.95-4.14 (3H), 4.21 (1H), 4.40 (1H), 4.68 (2H), 7.28 (2H), 7.40 (1H), 7.60-7.77 (7H), 8.48 (1H), 8.89 (1H).

Example 204

2-({1-[(4'-fluorobiphenyl-4-yl)carbonyl]azetidin-3-yl}methyl)-N-(2-methoxy-ethyl)-6-methyl-2H-indazole-5-carboxamide

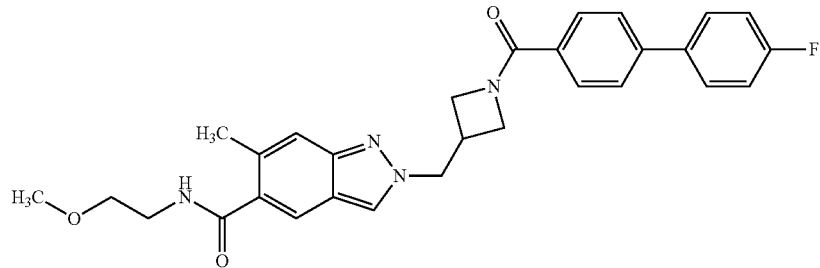 [SMILES: COCCNC(=O)c1cc2cn(CC3CN(C(=O)c4ccc(-c5ccc(F)cc5)cc4)C3)nc2cc1C]

Analogously to Example 1, 73 mg of the title compound was obtained from 180 mg of the compound prepared in Example 178e and 78 mg of 4'-fluorobiphenyl-4-carboxylic acid.

$^1$H-NMR (300 MHz, DMSO-d6): δ=2.34 (3H), 3.14-3.26 (4H), 3.34 (2H), 3.41 (2H), 3.89 (1H), 4.09 (1H), 4.21 (1H), 4.39 (1H), 4.66 (2H), 7.28 (2H), 7.35 (1H), 7.61-7.77 (7H), 8.21 (1H), 8.43 (1H).

Example 205

2-{[1-(4-chlorobenzoyl)piperidin-4-yl]methyl}-N-(2-methoxyethyl)-6-methyl-2H-indazole-5-carboxamide

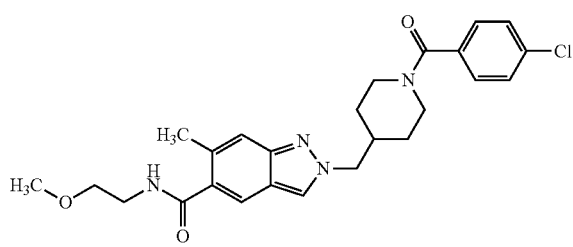 [SMILES: COCCNC(=O)c1cc2cn(CC3CCN(C(=O)c4ccc(Cl)cc4)CC3)nc2cc1C]

Analogously to Example 55, from 85 mg of the compound prepared in Example 205c and 45 mg of 4-chlorobenzoyl chloride, a material still contaminated after column chromatography was obtained which was further purified by additional preparative thick layer chromatography with dichloromethane/methanol in the ratio 95:5 as mobile phase. Yield: 48 mg of the title compound.

$^1$H-NMR (300 MHz, DMSO-d6): δ=1.09-1.53 (4H), 2.24 (1H), 2.34 (3H), 2.71 (1H), 2.97 (1H), 3.24 (3H), 3.34 (2H), 3.38-3.54 (3H), 7.31-7.37 (3H), 7.46 (2H), 7.63 (1H), 8.21 (1H), 8.33 (H).

The starting material was prepared as follows:

Example 205a

Tert-butyl 4-[(5-bromo-6-methyl-2H-indazol-2-yl)methyl]piperidin-1-carboxylate

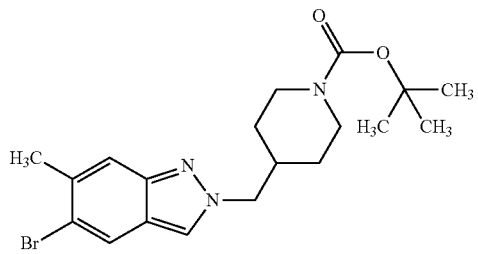 [SMILES: Cc1cc2nn(CC3CCN(C(=O)OC(C)(C)C)CC3)cc2cc1Br]

Analogously to Example 1c, 2.99 g of the title compound was obtained from 5.7 g of 5-bromo-6-methyl-1H-indazole and 15.0 g of tert-butyl-4-[(tosyloxy)methyl]piperidin-1-carboxylate.

$^{1}$H-NMR (300 MHz, CDCl3): δ=1.14-1.30 (2H), 1.44 (9H), 1.53 (2H), 2.24 (1H), 2.50 (3H), 2.66 (2H), 4.11 (2H), 4.23 (2H), 7.55 (1H), 7.77 (1H), 7.87 (1H).

Example 205b

Tert-butyl 4-({5-[N-(2-methoxyethyl)carbamoyl]-6-methyl-2H-indazol-2-yl}-methyl)piperidin-1-carboxylate

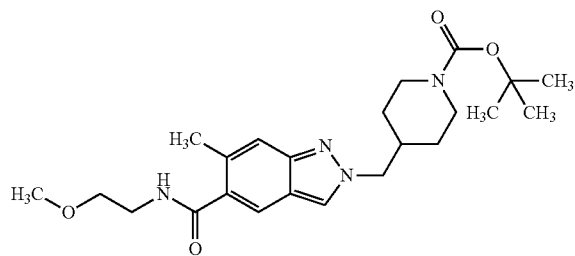 [SMILES: COCCNC(=O)c1cc2cn(CC3CCN(C(=O)OC(C)(C)C)CC3)nc2cc1C]

Analogously to Example 1b, 3.56 g of the title compound was obtained from 600 mg of the bromide prepared in Example 205a and 331 mg of 2-methoxyethylamine after four runs and twofold purification by chromatography.

$^{1}$H-NMR (300 MHz, DMSO-d6): δ=0.96-1.15 (2H), 1.29-1.42 (10H), 2.03-2.18 (1H), 2.34 (3H), 2.51-2.73 (3H), 3.25 (3H), 3.31-3.45 (4H), 3.86 (2H), 4.26 (2H), 7.35 (1H), 7.63 (1H), 8.21 (1H), 8.32 (1H).

Example 205c

N-(2-methoxyethyl)-6-methyl-2-(4-piperidylmethyl)-2H-indazole-5-carboxamide hydrochloride

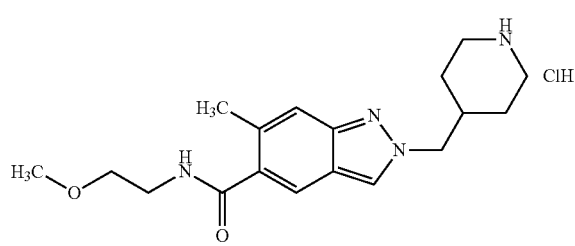 [SMILES: COCCNC(=O)c1cc2cn(CC3CCNCC3)nc2cc1C ; Cl]

Analogously to Example 1a, from 100 mg of the amide prepared in Example 205b, 85 mg of the title compound was obtained, which was reacted without further purification.

Example 206

2-({1-[2-fluoro-4-(trifluoromethyl)benzoyl]piperidin-4-yl}methyl)-N-(2-methoxy-ethyl)-6-methyl-2H-indazole-5-carboxamide

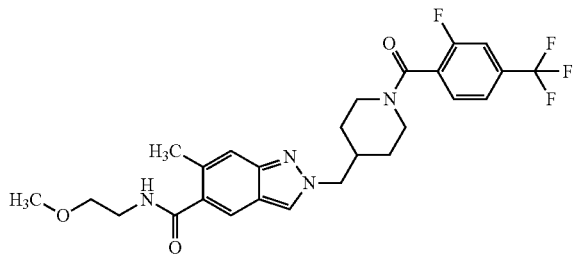 [SMILES: COCCNC(=O)c1cc2cn(CC3CCN(C(=O)c4ccc(C(F)(F)F)cc4F)CC3)nc2cc1C]

Analogously to Example 55, from 85 mg of the compound prepared in Example 205c and 58 mg of 2-fluoro-4-(trifluoromethyl)benzoyl chloride, a material still contaminated after column chromatography was obtained which was further purified by additional preparative thick layer chromatography with dichloromethane/methanol in the ratio 95:5 as mobile phase. Yield: 40 mg of the title compound.

$^{1}$H-NMR (300 MHz, DMSO-d6): δ=1.03-1.28 (2H), 1.37 (1H), 1.53 (1H), 2.23 (1H), 2.34 (3H), 2.77 (1H), 3.00 (1H), 3.26-3.49 (11H), 4.30 (2H), 4.44 (1H), 7.35 (1H), 7.54-7.67 (3H), 7.78 (1H), 8.21 (1H), 8.34 (1H).

Example 207

2-{[1-(4-chloro-2-fluorobenzoyl)piperidin-4-yl]methyl}-N-(2-methoxyethyl)-6-methyl-2H-indazole-5-carboxamide

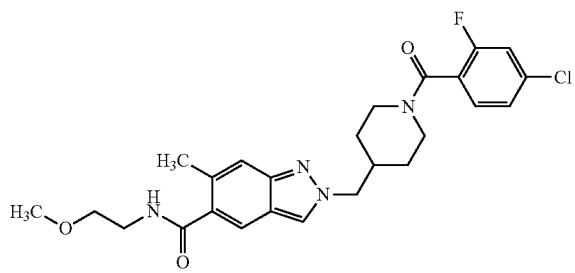 [SMILES: COCCNC(=O)c1cc2cn(CC3CCN(C(=O)c4ccc(Cl)cc4F)CC3)nc2cc1C]

Analogously to Example 55, 68 mg of the title compound was obtained from 85 mg of the compound prepared in Example 205c and 49 mg of 4-chloro-2-fluorobenzoyl chloride.

$^{1}$H-NMR (300 MHz, DMSO-d6): δ=1.04-1.25 (2H), 1.37 (1H), 1.51 (1H), 2.23 (1H), 2.34 (3H), 2.73 (1H), 2.98 (1H), 3.21-3.48 (3H), 3.30-3.38 (3H), 3.42 (2H), 4.29 (2H), 4.42 (1H), 7.29-7.42 (3H), 7.51 (1H), 7.63 (1H), 8.21 (1H), 8.33 (1H).

Example 208

2-({1-[3-fluoro-4-(trifluoromethyl)benzoyl]piperidin-4-yl}methyl)-N-(2-methoxyethyl)-6-methyl-2H-indazole-5-carboxamide

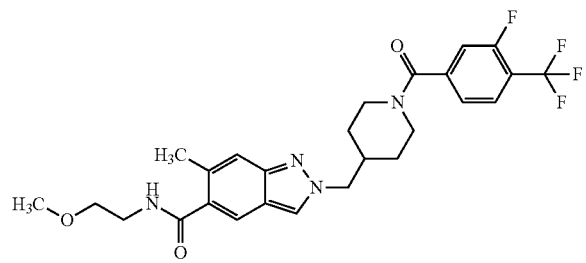 [SMILES: COCCNC(=O)c1cc2cn(CC3CCN(C(=O)c4ccc(C(F)(F)F)c(F)c4)CC3)nc2cc1C]

Analogously to Example 55, 70 mg of the title compound was obtained from 85 mg of the compound prepared in Example 205c and 58 mg of 3-fluoro-4-(trifluoromethyl)benzoyl chloride.

$^{1}$H-NMR (300 MHz, DMSO-d6): δ=1.13-1.27 (2H), 1.35 (1H), 1.51 (1H), 2.23 (1H), 2.34 (3H), 2.74 (1H), 2.98 (1H), 3.22-3.45 (8H), 4.29 (2H), 4.40 (1H), 7.32-7.38 (2H), 7.52 (1H), 7.63 (1H), 7.82 (1H), 8.21 (1H), 8.33 (1H).

Example 209

2-({1-[4-chloro-3-(trifluoromethyl)benzoyl]piperidin-4-yl}methyl)-N-(2-methoxyethyl)-6-methyl-2H-indazole-5-carboxamide

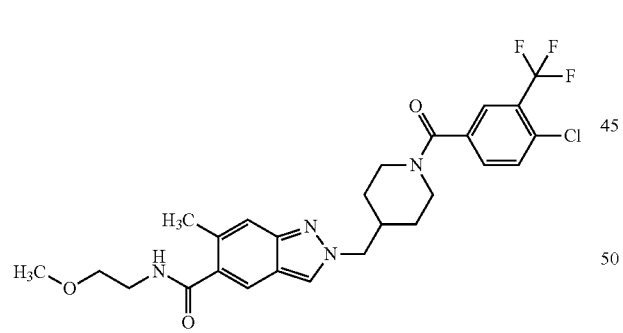

Analogously to Example 55, 92 mg of the title compound was obtained from 85 mg of the compound prepared in Example 205c and 62 mg of 4-chloro-3-(trifluoromethyl)benzoyl chloride.

$^{1}$H-NMR (300 MHz, DMSO-d6): δ=1.14-1.28 (2H), 1.35 (1H), 1.44-1.53 (1H), 2.25 (1H), 2.34 (3H), 2.74 (1H), 3.01 (1H), 3.24 (3H), 3.34 (2H), 3.39-3.50 (3H), 4.29 (2H), 4.39 (1H), 7.35 (1H), 7.61-7.68 (2H), 7.74-7.80 (2H), 8.21 (1H), 8.33 (1H).

Example 210

N-(2-methoxyethyl)-6-methyl-2-({1-[4-(pentafluoro-λ$^{6}$-sulphanyl)benzoyl]-piperidin-4-yl}methyl)-2H-indazole-5-carboxamide

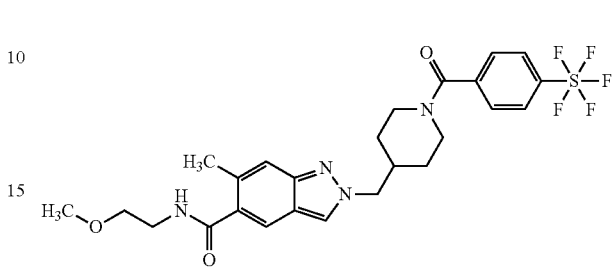

Analogously to Example 1, 126 mg of the title compound was obtained from 85 mg of the compound prepared in Example 205c and 58 mg of 4-(pentafluoro-λ$^{6}$-sulphanyl)benzoic acid.

$^{1}$H-NMR (300 MHz, DMSO-d6): δ=1.12-1.27 (2H), 1.35 (1H), 1.51 (1H), 2.24 (1H), 2.34 (3H), 2.74 (1H), 2.99 (1H), 3.24 (3H), 3.34-3.46 (5H), 4.30 (2H), 4.41 (1H), 7.35 (1H), 7.55 (2H), 7.63 (1H), 7.94 (2H), 8.21 (1H), 8.33 (1H).

Example 211

N-(2-methoxyethyl)-6-methyl-2-({1-[4-(trifluoromethyl)benzoyl]piperidin-4-yl}-methyl)-2H-indazole-5-carboxamide

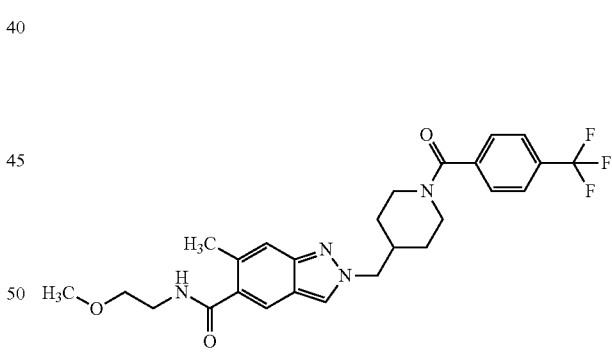

Analogously to Example 55, 69 mg of the title compound was obtained from 85 mg of the compound prepared in Example 205c and 53 mg of 4-(trifluoromethyl)benzoyl chloride.

$^{1}$H-NMR (300 MHz, DMSO-d6): δ=1.10-1.26 (2H), 1.35 (1H), 1.51 (1H), 2.19-2.30 (1H), 2.34 (3H), 2.74 (1H), 2.98 (1H), 3.21-3.47 (8H), 4.30 (2H), 4.42 (1H), 7.35 (1H), 7.54 (2H), 7.63 (1H), 7.77 (2H), 8.21 (1H), 8.33 (1H).

Example 212

2-{[1-(4-chlorobenzoyl)piperidin-4-yl]methyl}-4-ethyl-N-(2-methoxyethyl)-2H-indazole-5-carboxamide

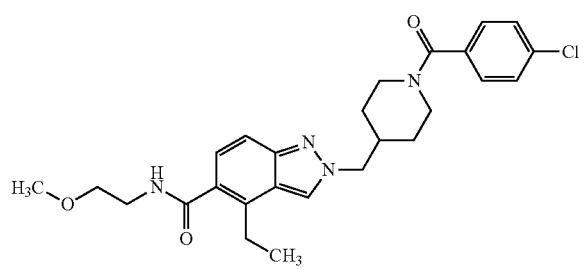 [SMILES: CCc1c(C(=O)NCCOC)ccc2nn(CC3CCN(C(=O)c4ccc(Cl)cc4)CC3)cc12]

Analogously to Example 55, 61 mg of the title compound was obtained from 91 mg of the compound prepared in Example 212i and 46 mg of 4-chlorobenzoyl chloride.

$^1$H-NMR (300 MHz, DMSO-d6): δ=1.14-1.28 (5H), 1.31-1.60 (2H), 2.27 (1H), 2.63-3.04 (4H), 3.24 (3H), 3.31-3.56 (5H), 4.31 (2H), 4.39 (1H), 7.10 (1H), 7.32-7.41 (3H), 7.46 (2H), 8.11 (1H), 8.50 (1H).

The starting material was prepared as follows:

Example 212a 4-bromo-3-ethyl-2-methylaniline

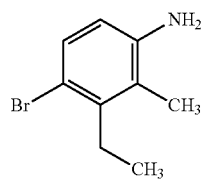

A suspension of 3 g of 3-ethyl-2-methylaniline hydrochloride in 200 ml ethyl acetate was washed twice with 30 ml portions of saturated sodium carbonate solution and twice with 20 ml portions of saturated sodium chloride solution, dried over sodium sulphate and concentrated in vacuo after filtration. This yielded 2.69 g of ethyl-2-methylaniline, which was further reacted without purification.

To a solution of 2.36 g of the amine prepared above in 29 ml DMF, a solution of 3.1 g of N-bromosuccinimide in 14.5 ml DMF was added dropwise at 0° C. and stirred for 30 minutes at 0° C. Then the reaction mixture was diluted with 400 ml ethyl acetate and washed once with 30 ml of a 10% aqueous sodium carbonate solution and once with 30 ml water. After drying over sodium sulphate and filtration, this was concentrated in vacuo. The crude product thus obtained (3.86 g) was used in the next step without purification.

Example 212b

N-(4-bromo-3-ethyl-2-methylphenyl)acetamide

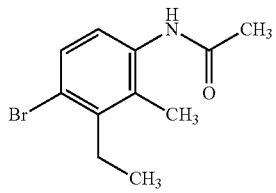

To a solution of 3.86 g of the bromide prepared in Example 212a in 48 ml pyridine, 2.04 ml of acetic anhydride was added dropwise at 0° C. and stirred for 20 hours at 25° C. The reaction mixture was concentrated in vacuo and the crude product thus obtained was purified by column chromatography on silica gel with hexane/0-100% ethyl acetate. In this manner, 3.73 g of the title compound was obtained.

$^1$H-NMR (300 MHz, CDCl3): δ=1.13 (3H), 2.20 (3H), 2.25 (3H), 2.86 (2H), 6.91 (1H), 7.33 (1H), 7.40 (1H).

Example 212c 1-(5-bromo-4-ethyl-1H-indazol-1-yl)ethan-1-one

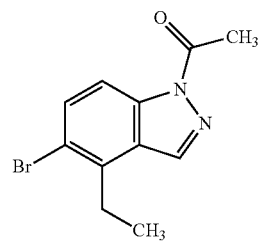

To a solution of 3.72 g of the acetamide prepared in Example 212b in 31.5 ml chloroform were added 4.1 ml of acetic anhydride and 2.85 g of potassium acetate, and 192 mg of 18-crown-6 and 3.4 g of isopentyl nitrite were then added dropwise. The reaction mixture was heated for 20 hours under reflux and after cooling diluted with 200 ml ethyl acetate. The organic phase was washed with 20 ml sodium carbonate solution and once with saturated sodium chloride solution. After drying over sodium sulphate and filtration, this was concentrated in vacuo and the crude product thus obtained purified by column chromatography on silica gel with hexane/0-50% ethyl acetate. Yield: 3.78 g of the title compound.

$^1$H-NMR (300 MHz, DMSO-d6): δ=1.18 (3H), 2.68 (3H), 3.04 (2H), 7.73 (1H), 8.03 (1H), 8.64 (1H).

Example 212d 5-bromo-4-ethyl-1H-indazole

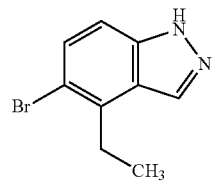

A mixture of 3.78 g of the compound prepared in Example 212c in 7.3 ml methanol and 26.3 ml of 37% hydrochloric acid was heated under reflux for 2 hours. This was then diluted with 400 ml ethyl acetate. The organic phase was washed three times with 50 ml portions of sodium hydrogen carbonate solution and once with 50 ml saturated sodium chloride solution, dried over sodium sulphate and concentrated in vacuo. The crude product thus obtained was purified by column chromatography on silica gel with hexane/0-50% ethyl acetate. Yield: 2.97 g of the title compound.

$^1$H-NMR (300 MHz, DMSO-d6): δ=1.17 (3H), 2.98 (2H), 7.30 (1H), 7.41 (1H), 8.16 (1H), 13.17 (1H).

Example 212e

Tert-butyl 4-[(5-bromo-4-ethyl-2H-indazol-2-yl)methyl]piperidin-1-carboxylate

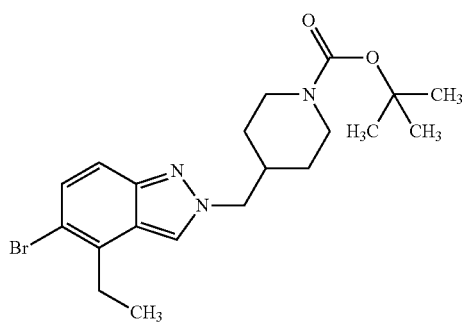 [SMILES: CCc1c(Br)ccc2nn(CC3CCN(C(=O)OC(C)(C)C)CC3)cc12]

Analogously to Example 1c, 961 mg of the title compound was obtained from 2.97 g of the indazole prepared in Example 212d and 7.3 g of tert-butyl-4-[(tosyloxy)methyl]piperidin-1-carboxylate.

$^1$H-NMR (300 MHz, DMSO-d6): δ=1.01-1.13 (2H), 1.16 (3H), 1.34 (9H), 1.41 (2H), 2.12 (1H), 2.63 (2H), 2.90 (2H), 3.87 (2H), 4.27 (2H), 7.27 (1H), 7.35 (1H), 8.49 (1H).

Example 212f

Methyl 2-{[1-(tert-butoxycarbonyl)piperidin-4-yl]methyl}-4-ethyl-2H-indazol-5-carboxylate

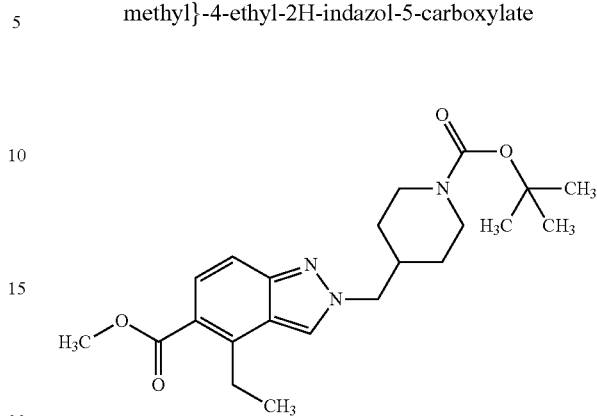

Analogously to Example 1e, after two runs 571 mg of the title compound was obtained from 347 mg of the bromide prepared in Example 212e and 0.1 ml of methanol.

$^1$H-NMR (300 MHz, DMSO-d6): δ=1.02-1.15 (2H), 1.17-1.24 (3H), 1.34 (9H), 1.42 (2H), 2.14 (1H), 2.63 (2H), 3.17 (2H), 3.79 (3H), 3.88 (2H), 4.30 (2H), 7.43 (1H), 7.60 (1H), 8.68 (1H).

Example 212g

2-{[1-(tert-butoxycarbonyl)piperidin-4-yl]methyl}-4-ethyl-2H-indazol-5-carboxylic acid

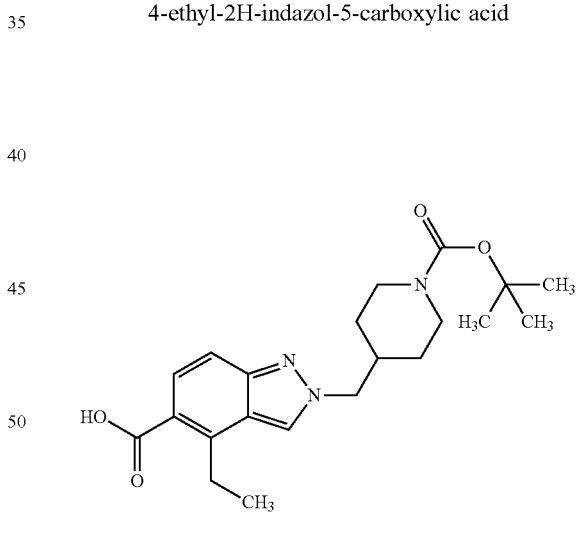

Analogously to Example 1d, 427 mg of the title compound was obtained from 371 mg of the ester in Example 212f.

$^1$H-NMR (300 MHz, DMSO-d6): δ=1.00-1.15 (2H), 1.20 (3H), 1.34 (9H), 1.42 (2H), 2.14 (1H), 2.64 (2H), 3.19 (2H), 3.88 (2H), 4.29 (2H), 7.39 (1H), 7.61 (1H), 8.63 (1H), 12.33 (1H).

Example 212h

Tert-butyl 4-({4-ethyl-5-[N-(2-methoxyethyl)carbamoyl]-2H-indazol-2-yl}-methyl)piperidin-1-carboxylate

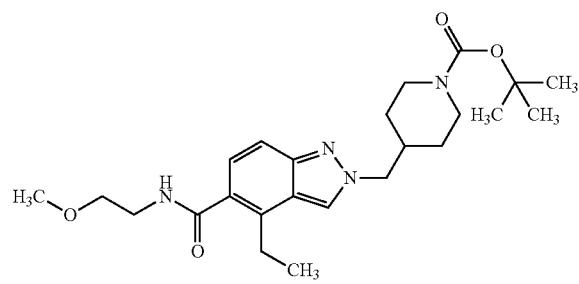 [SMILES: CCc1c(C(=O)NCCOC)ccc2nn(CC3CCN(C(=O)OC(C)(C)C)CC3)cc12]

Analogously to Example 1, 215 mg of the title compound was obtained from 427 mg of the acid prepared in Example 212g and 83 mg of 2-methoxy-ethylamine.

$^1$H-NMR (300 MHz, DMSO-d6): δ=0.98-1.14 (2H), 1.19 (3H), 1.30-1.47 (11H), 2.13 (1H), 2.65 (2H), 2.90 (2H), 3.24 (3H), 3.32-3.45 (4H), 3.87 (2H), 4.28 (2H), 7.10 (1H), 7.38 (1H), 8.12 (1H), 8.50 (1H).

Example 212i 4-ethyl-N-(2-methoxyethyl)-2-(4-piperidylmethyl)-2H-indazole-5-carboxamide hydrochloride

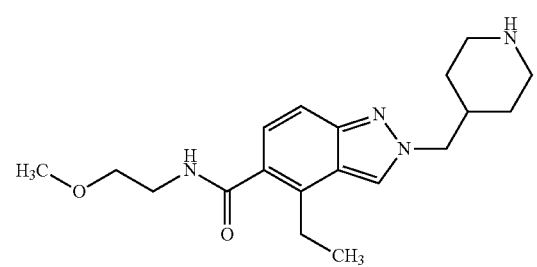

Analogously to Example 1a, from 215 mg of the amide prepared in Example 212h, 258 mg of the title compound was obtained, which was reacted without further purification.

Example 213

4-Ethyl-N-(2-methoxyethyl)-2-({1-[4-(trifluoromethoxy)benzoyl]piperidin-4-yl}methyl)-2H-indazole-5-carboxamide

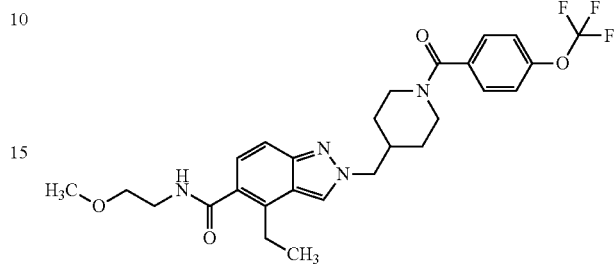

Analogously to Example 55, 32 mg of the title compound was obtained from 91 mg of the compound prepared in Example 212i and 59 mg of 4-(trifluoromethoxy)benzoyl chloride.

$^1$H-NMR (300 MHz, DMSO-d6): δ=1.14-1.29 (5H), 1.31-1.61 (2H), 2.20-2.35 (1H), 2.66-3.06 (4H), 3.24 (3H), 3.30-3.56 (5H), 4.31 (2H), 4.41 (1H), 7.10 (1H), 7.34-7.43 (3H), 7.47 (2H), 8.11 (1H), 8.50 (1H).

Example 214

2-{[1-(4-chlorobenzoyl)azetidin-3-yl]methyl}-4-methoxy-N-(2-methoxyethyl)-2H-indazole-5-carboxamide

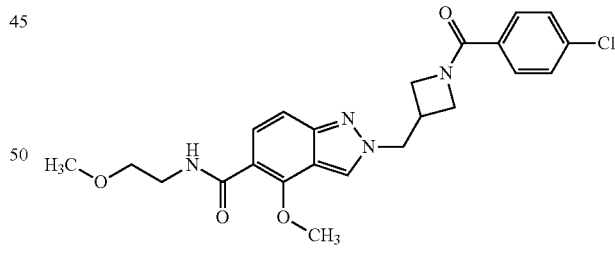

Analogously to Example 55, 691 mg of the title compound was obtained from 68 mg of the compound prepared in Example 214c and 37 mg of 4-chlorobenzoyl chloride.

$^1$H-NMR (300 MHz, DMSO-d6): δ=3.22 (1H), 3.27 (3H), 3.40-3.47 (4H), 3.92 (1H), 4.10 (1H), 4.16 (3H), 4.19 (1H), 4.38 (1H), 4.66 (2H), 7.21 (1H), 7.48 (2H), 7.55-7.67 (3H), 8.18 (1H), 8.87 (1H).

The starting material was prepared as follows:

Example 214a

Tert-butyl 3-[(5-bromo-4-methoxy-2H-indazol-2-yl)methyl]azetidin-1-carboxylate

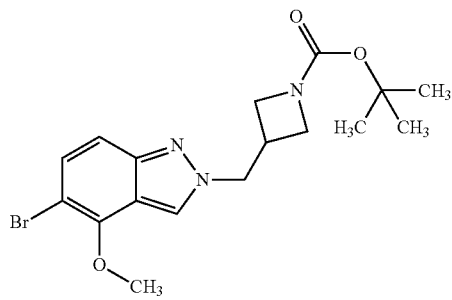 [SMILES: COc1c(Br)ccc2nn(CC3CN(C(=O)OC(C)(C)C)C3)cc12]

To a solution of 1.94 g of tert-butyl 3-[(tosyloxy)methyl]azetidin-1-carboxylate in 15.5 ml acetone were added 837 mg of lithium iodide and the reaction mixture was stirred for 16 hours at 35° C. After cooling, it was diluted with 200 ml ethyl acetate and the organic phase washed twice with 30 ml portions of water and once with 20 ml saturated sodium chloride solution. After drying over sodium sulphate and filtration, this was concentrated in vacuo. In this manner, 1.6 g of tert-butyl-3-(iodomethyl)azetidin-1-carboxylate were obtained, which was further reacted without purification.

To a solution of 620 mg of 5-bromo-7-methoxy-1H-indazole in 24 ml DMF were added 1.11 g of potassium carbonate and the mixture stirred at 25° C. for 30 minutes. Then 1.25 g of the iodide prepared above was added and the reaction mixture stirred for 3 hours at 60° C. After cooling, it was diluted with 200 ml 1:1 tert-butyl methyl ether/hexane, washed once each with 20 ml portions of water and saturated sodium chloride solution, dried over sodium sulphate and concentrated in vacuo and the crude product thus obtained purified by column chromatography on silica gel with a hexane/ethyl acetate gradient. Yield: 263 mg of the title compound.

$^1$H-NMR (300 MHz, CDCl3): δ=1.43 (9H), 3.23 (1H), 3.78 (2H), 4.07 (2H), 4.10 (3H), 4.59 (2H), 7.28 (1H), 7.36 (1H), 8.03 (1H).

Example 214b

Tert-butyl 3-({4-methoxy-5-[N-(2-methoxyethyl)carbamoyl]-2H-indazol-2-yl}methyl)azetidin-1-carboxylate

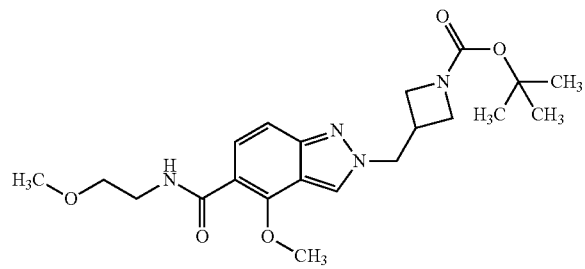 [SMILES: COCCNC(=O)c1ccc2nn(CC3CN(C(=O)OC(C)(C)C)C3)cc2c1OC]

Analogously to Example 1b, a total of 193 mg of the title compound was obtained from 110 and 252 mg respectively of the compound prepared in Example 214a and 63 and 143 mg respectively of 2-methoxyethylamine.

$^1$H-NMR (300 MHz, DMSO-d6): δ=1.32 (9H), 3.10 (1H), 3.27 (3H), 3.38-3.48 (4H), 3.72 (2H), 3.82-3.94 (2H), 4.17 (3H), 4.60 (2H), 7.21 (1H), 7.63 (1H), 8.18 (1H), 8.87 (1H).

Example 214c 2-(azetidin-3-ylmethyl)-4-methoxy-N-(2-methoxyethyl)-2H-indazole-5-carboxamide hydrochloride

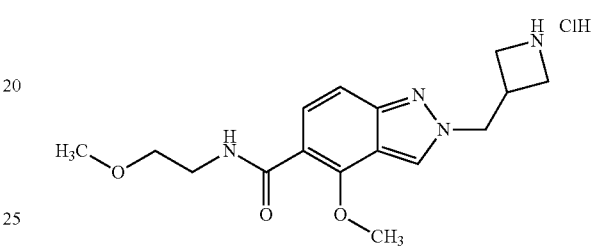

Analogously to Example 1a, from 50 mg of the compound prepared in Example 214b, 42 mg of the title compound was obtained, which was further reacted without purification.

Example 215

4-methoxy-N-(2-methoxyethyl)-2-[(1-{4-[(trifluoromethyl)sulphanyl]benzoyl}azetidin-3-yl)methyl]-2H-indazole-5-carboxamide

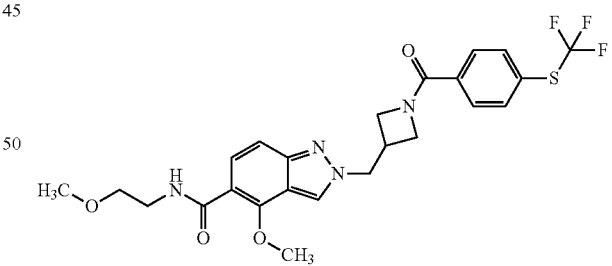

Analogously to Example 55, 56 mg of the title compound was obtained from 42 mg of the compound prepared in Example 214c and 32 mg of 4-[(trifluoromethyl)sulphany]benzoyl chloride.

$^1$H-NMR (300 MHz, DMSO-d6): δ=3.21 (1H), 3.27 (3H), 3.38-3.49 (4H), 3.95 (1H), 4.12 (1H), 4.16 (3H), 4.21 (1H), 4.40 (1H), 4.67 (2H), 7.20 (1H), 7.63 (1H), 7.69 (2H), 7.76 (2H), 8.18 (1H), 8.87 (1H).

Example 216

2-{[1-(4-bromobenzoyl)azetidin-3-yl]methyl}-4-methoxy-N-(2-methoxyethyl)-2H-indazole-5-carboxamide

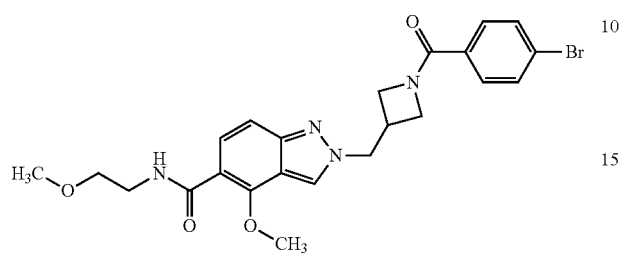

Analogously to Example 55, 48 mg of the title compound was obtained from 42 mg of the compound prepared in Example 214c and 29 mg of 4-bromobenzoyl chloride.

$^1$H-NMR (300 MHz, DMSO-d6): δ=3.23 (1H), 3.26 (3H), 3.38-3.48 (4H), 3.92 (1H), 4.09 (1H), 4.16 (3H), 4.19 (1H), 4.38 (1H), 4.66 (2H), 7.20 (1H), 7.51 (2H), 7.58-7.68 (3H), 8.18 (1H), 8.86 (1H).

Example 217

2-{[(R)-1-(4-chlorobenzoyl)pyrrolidin-3-yl]methyl}-N-(2-methoxyethyl)-4-methyl-2H-indazole-5-carboxamide

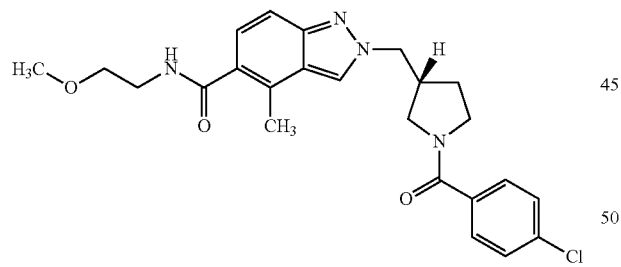

Analogously to Example 55, 50 mg of the title compound was obtained from 106 mg of the compound prepared in Example 217e and 58 mg of 4-chlorobenzoyl chloride.

$^1$H-NMR (300 MHz, DMSO-d6): δ=1.57-1.73 (1H), 1.81-1.97 (1H), 2.47/2.51 (3H), 2.78-2.93 (1H), 3.25 (3H), 3.19-3.61 (8H), 4.39/4.51 (2H), 7.11-7.18 (1H), 7.33-7.43 (1H), 7.45 (2H), 7.50 (2H), 8.09-8.16 (1H), 8.47/8.55 (1H).

The starting material was prepared as follows:

Example 217a (R)-tert-butyl-3-[(5-bromo-4-methyl-2H-indazol-2-yl)methyl]pyrrolidine-1-carboxylate

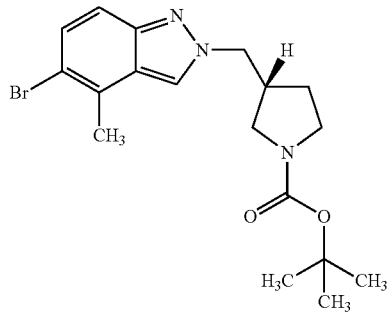 [SMILES: Cc1c(Br)ccc2nn(C[C@@H]3CCN(C(=O)OC(C)(C)C)C3)cc12]

To a solution of 9.0 g of (R)-tert-butyl 3-(hydroxymethyl) pyrrolidin-1-carboxylate in 100 ml pyridine was added 12.8 g of p-toluenesulphonyl chloride at 0° C. under nitrogen and stirred for 3 hours at 25° C. The reaction mixture was diluted with ethyl acetate and stirred for 30 minutes with sodium hydrogen carbonate. The phases were then separated and the organic phase washed with saturated sodium chloride solution, dried over sodium sulphate and concentrated in vacuo after filtration. The residue thus obtained was purified by column chromatography on silica gel with hexane/0-100% ethyl acetate. Yield: 11.4 g of (R)-tert-butyl-3-[(tosyloxy) methyl]pyrrolidin-1-carboxylate.

Analogously to Example 1c, 1.97 g of the title compound was obtained from 4.53 g of 5-bromo-4-methyl-1H-indazole and 11.4 g of the (R)-tert-butyl-3-[(tosyloxy)methyl]pyrrolidin-1-carboxylate prepared above with addition of 7.9 g of tetrabutylammonium iodide.

$^1$H-NMR (300 MHz, DMSO-d6): δ=1.34 (9H), 1.50-1.66 (1H), 1.81 (1H), 2.48 (3H), 2.78 (1H), 3.01 (1H), 3.16 (1H), 3.25-3.37 (2H), 4.41 (2H), 7.29 (1H), 7.36 (1H), 8.51 (1H).

Example 217b

Methyl 2-{[(R)-1-(tert-butoxycarbonyl)pyrrolidin-3-yl]methyl}-4-methyl-2H-indazol-5-carboxylate

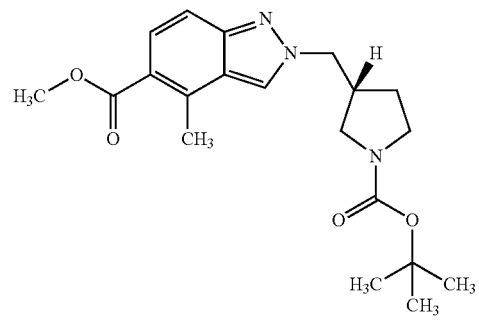 [SMILES: COC(=O)c1ccc2nn(C[C@@H]3CCN(C(=O)OC(C)(C)C)C3)cc2c1C]

Analogously to Example 1e, after two runs 820 mg of the title compound was obtained from 563 mg of the bromide prepared in Example 217a and 0.17 ml of methanol.

¹H-NMR (300 MHz, DMSO-d6): δ=1.34 (9H), 1.58 (1H), 1.83 (1H), 2.73 (3H), 2.80 (1H), 3.03 (1H), 3.17 (1H), 3.25-3.37 (2H), 3.79 (3H), 4.37-4.49 (2H), 7.44 (1H), 7.64 (1H), 8.72 (1H).

Example 217c

2-{[(R)-1-(tert-butoxycarbonyl)pyrrolidin-3-yl]methyl}-4-methyl-2H-indazol-5-carboxylic acid

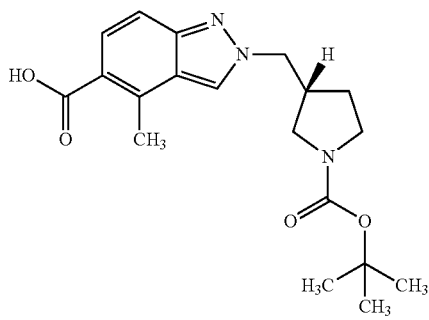 [SMILES: Cc1c(C(=O)O)ccc2nn(C[C@@H]3CCN(C(=O)OC(C)(C)C)C3)cc12]

Analogously to Example 1d, 701 mg of the title compound was obtained from 620 mg of the ester prepared in Example 217b.

¹H-NMR (300 MHz, DMSO-d6): δ=1.34 (9H), 1.50-1.69 (1H), 1.82 (1H), 1.75-1.86 (1H), 2.69-2.88 (4H), 3.03 (1H), 3.17 (1H), 3.24-3.38 (1H), 4.42 (2H), 7.40 (1H), 7.65 (1H), 8.68 (1H), 12.28 (1H).

Example 217d (R)-tert-butyl 3-({5-[N-(2-methoxyethyl)carbamoyl]-4-methyl-2H-indazol-2-yl}methyl)pyrrolidin-1-carboxylate

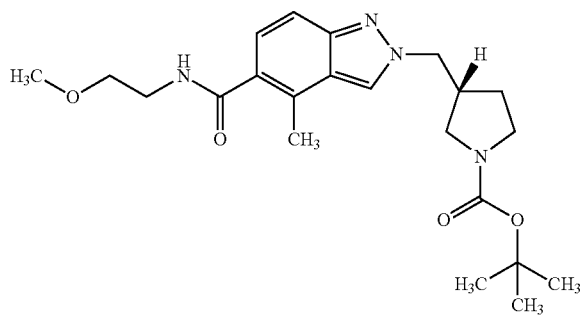 [SMILES: COCCNC(=O)c1ccc2nn(C[C@@H]3CCN(C(=O)OC(C)(C)C)C3)cc2c1C]

Analogously to Example 1, 376 mg of the title compound was obtained from 350 mg of the acid prepared in Example 217c and 73 mg of 2-methoxyethylamine.

¹H-NMR (300 MHz, DMSO-d6): δ=1.35 (9H), 1.57 (1H), 1.80 (1H), 2.50 (3H), 2.73-2.86 (1H), 3.01 (1H), 3.11-3.22 (1H), 3.25 (3H), 3.26-3.39 (3H), 3.39-3.46 (2H), 4.42 (2H), 7.15 (1H), 7.39 (1H), 8.13 (1H), 8.52 (1H).

Example 217e

N-(2-methoxyethyl)-4-methyl-2-[(R)-pyrrolidin-3-ylmethyl]-2H-indazole-5-carboxamide hydrochloride

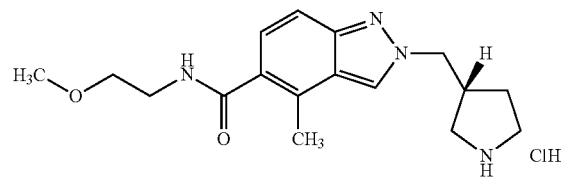 [SMILES: COCCNC(=O)c1ccc2nn(C[C@@H]3CCNC3)cc2c1C ; Cl]

Analogously to Example 1a, from 376 mg of the amide prepared in Example 217d, 465 mg of the title compound was obtained, which was reacted without further purification.

Example 218

N-(2-methoxyethyl)-4-methyl-2-({(R)-1-[4-(trifluoromethoxy)benzoyl]-pyrrolidin-3-yl}methyl)-2H-indazole-5-carboxamide

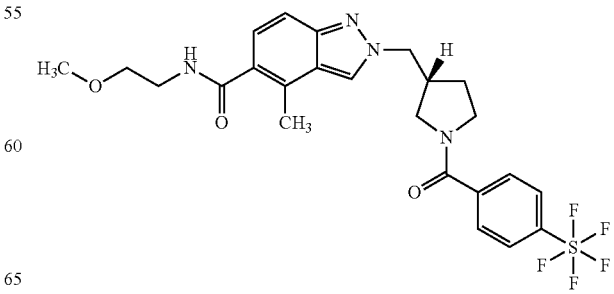

Analogously to Example 55, 61 mg of the title compound was obtained from 106 mg of the compound prepared in Example 217e and 74 mg of 4-(trifluoromethoxy)benzoyl chloride.

¹H-NMR (300 MHz, DMSO-d6): δ=1.57-1.74 (1H), 1.81-1.97 (1H), 2.47/2.51 (3H), 2.77-2.94 (1H), 3.25-3.62 (11H), 4.40/4.51 (2H), 7.09-7.19 (1H), 7.31-7.44 (3H), 7.61 (2H), 8.08-8.16 (1H), 8.47/8.55 (1H).

Example 219

N-(2-methoxyethyl)-4-methyl-2-({(3R)-1-[4-(pentafluoro-$\lambda^6$-sulphanyl)benzoyl]-pyrrolidin-3-yl}methyl)-2H-indazole-5-carboxamide Analogously to Example 1, 29 mg of the title compound was obtained from 106 mg of the compound prepared in Example 217e and 75 mg of 4-(pentafluoro-λ⁶-sulphanyl)benzoic acid.

¹H-NMR (300 MHz, DMSO-d6): δ=1.57-1.76 (1H), 1.81-1.99 (1H), 2.50 (3H), 2.77-2.94 (1H), 3.16-3.62 (11H), 4.39/4.52 (2H), 7.09-7.19 (1H), 7.32-7.44 (1H), 7.68 (2H), 7.90-7.97 (2H), 8.10-8.17 (1H), 8.46/8.55 (1H).

Example 220

2-{[(R)-1-(4-chlorobenzoyl)pyrrolidin-3-yl]methyl}-4-methyl-N-{2-[(trifluoro-methyl)sulphanyl]ethyl}-2H-indazole-5-carboxamide

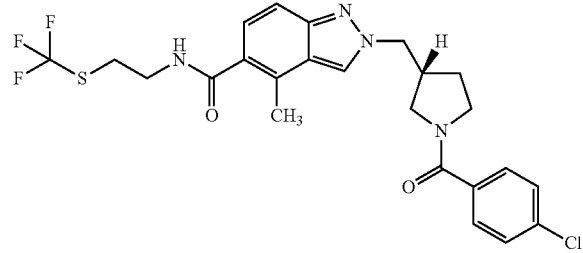 [SMILES: Cc1c(C(=O)NCCSC(F)(F)F)ccc2nn(C[C@@H]3CCN(C(=O)c4ccc(Cl)cc4)C3)cc12]

Analogously to Example 55, 29 mg of the title compound was obtained from 106 mg of the compound prepared in Example 220b and 48 mg of 4-chlorobenzoyl chloride.

¹H-NMR (300 MHz, DMSO-d6): δ=1.57-1.73 (1H), 1.81-1.96 (1H), 2.48/2.53 (3H), 2.79-2.93 (1H), 3.13-3.60 (8H), 4.40/4.51 (2H), 7.14-7.23 (1H), 7.33-7.53 (5H), 8.35-8.42 (1H), 8.49/8.58 (1H).

The starting material was prepared as follows:

Example 220a (R)-tert-butyl 3-{[4-methyl-5-(N-{2-[(trifluoromethyl)sulphanyl]ethyl}-carbamoyl)-2H-indazol-2-yl]methyl}pyrrolidin-1-carboxylate

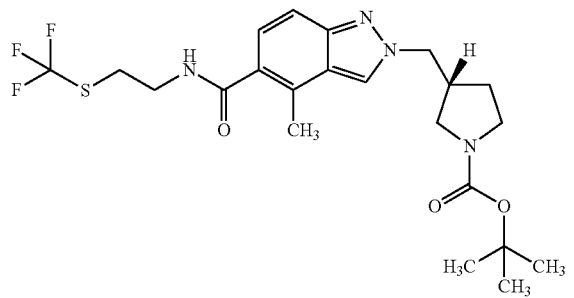 [SMILES: Cc1c(C(=O)NCCSC(F)(F)F)ccc2nn(C[C@@H]3CCN(C(=O)OC(C)(C)C)C3)cc12]

Analogously to Example 1, 245 mg of the title compound was obtained from 350 mg of the acid prepared in Example 217c and 141 mg of 2-[(trifluoromethyl)sulphanyl]ethylamine.

¹H-NMR (300 MHz, DMSO-d6): δ=1.35 (9H), 1.52-1.64 (1H), 1.81 (1H), 2.52 (3H), 2.71-2.96 (2H), 2.97-3.05 (12H), 3.18 (2H), 3.23-3.28 (1H), 3.51 (2H), 4.42 (2H), 7.19 (1H), 7.42 (1H), 8.39 (1H), 8.54 (1H).

Example 220b 4-methyl-2-[(R)-pyrrolidin-3-ylmethyl]-N-{2-[(trifluoromethyl)sulphanyl]-ethyl}-2H-indazole-5-carboxamide hydrochloride

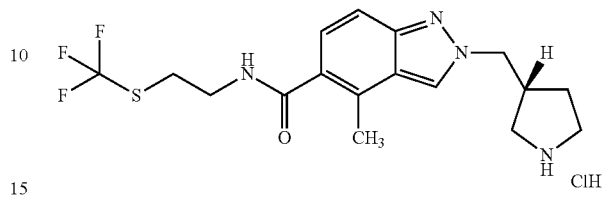

Analogously to Example 1a, from 245 mg of the amide prepared in Example 220a, 410 mg of the title compound was obtained, which was reacted without further purification.

Example 221

4-methyl-2-({(R)-1-[4-(trifluoromethoxy)benzoyl]pyrrolidin-3-yl}methyl)-N-{2-[(trifluoromethyl)sulphanyl]ethyl}-2H-indazole-5-carboxamide

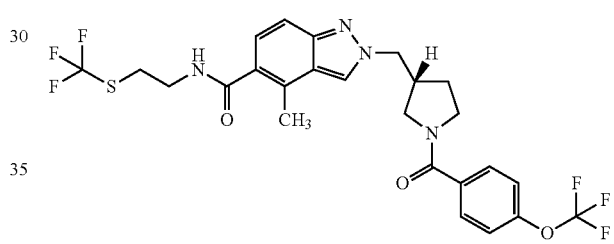

Analogously to Example 55, 49 mg of the title compound was obtained from 106 mg of the compound prepared in Example 220b and 62 mg of 4-(trifluoromethoxy)benzoyl chloride.

¹H-NMR (300 MHz, DMSO-d6): δ=1.58-1.74 (1H), 1.81-1.98 (1H), 2.48/2.53 (3H), 2.78-2.94 (1H), 3.12-3.62 (8H), 4.40/4.52 (2H), 7.14-7.23 (1H), 7.32-7.49 (3H), 7.61 (2H), 8.35-8.43 (1H), 8.49/8.58 (1H).

Example 222

2-{[(S)-1-(4-chlorobenzoyl)pyrrolidin-3-yl]methyl}-N-(2-methoxyethyl)-4-methyl-2H-indazole-5-carboxamide

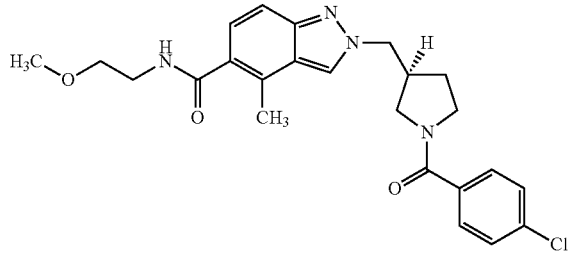 [SMILES: COCCNC(=O)c1ccc2nn(C[C@H]3CCN(C(=O)c4ccc(Cl)cc4)C3)cc2c1C]

Analogously to Example 55, 67 mg of the title compound was obtained from 134 mg of the compound prepared in Example 222a and 73 mg of 4-chlorobenzoyl chloride.

¹H-NMR (300 MHz, CDCl3): δ=1.72-1.86 (1H), 1.99-2.20 (1H), 2.64 (3H), 2.93-3.13 (1H), 3.29-3.36 (1H), 3.39 (3H), 3.45-3.71 (6H), 3.76-3.86 (1H), 4.31-4.57 (2H), 6.12-6.20 (1H), 7.30-7.42 (3H), 7.43-7.56 (3H), 7.90/8.02 (1H).

The starting material was prepared as follows:

Example 222a (S)-tert-butyl 3-({5-[N-(2-methoxyethyl)carbamoyl]-4-methyl-2H-indazol-2-yl}methyl)pyrrolidin-1-carboxylate

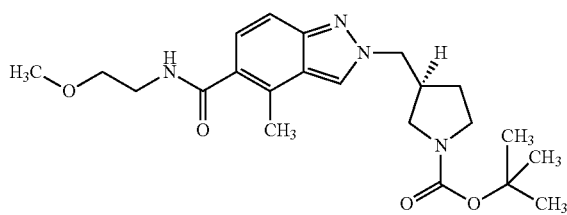 [SMILES: COCCNC(=O)c1ccc2nn(C[C@H]3CCN(C(=O)OC(C)(C)C)C3)cc2c1C]

Analogously to Example 217a to 217d, this title compound was prepared in a quantity of 760 mg starting from (S)-tert-butyl-3-(hydroxymethyl)pyrrolidin-1-carboxylate.

¹H-NMR (300 MHz, DMSO-d6): δ=1.35 (9H), 1.52-1.64 (1H), 1.77-1.87 (1H), 1.76-1.82 (1H), 2.50 (3H), 2.74-2.86 (1H), 3.02 (1H), 3.12-3.20 (1H), 3.25 (3H), 3.31 (1H), 3.36 (2H), 3.43 (2H), 4.42 (2H), 7.16 (1H), 7.39 (1H), 8.10 (1H), 8.51 (1H).

Example 222b

N-(2-methoxyethyl)-4-methyl-2-[(S)-pyrrolidin-3-ylmethyl]-2H-indazole-5-carboxamide hydrochloride

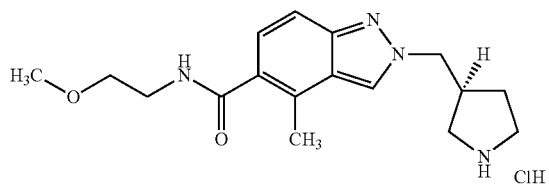 [SMILES: COCCNC(=O)c1ccc2nn(C[C@H]3CCNC3)cc2c1C ; Cl]

Analogously to Example 1a, from 159 mg of the amide prepared in Example 222a, 134 mg of the title compound was obtained, which was reacted without further purification.

Example 223

2-({(S)-1-[(4'-fluorobiphenyl-4-yl)carbonyl]pyrrolidin-3-yl}methyl)-N-(2-methoxyethyl)-4-methyl-2H-indazole-5-carboxamide

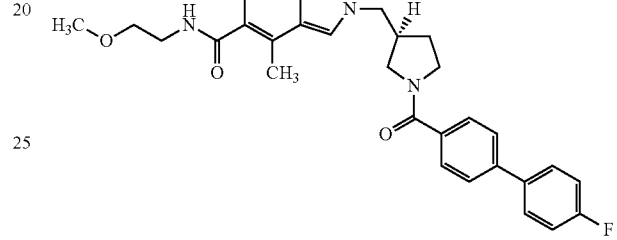

Analogously to Example 1, 128 mg of the title compound was obtained from 230 mg of the compound prepared in Example 222b and 141 mg of 4'-fluorobiphenyl-4-carboxylic acid.

¹H-NMR (300 MHz, CDCl3): δ=1.73-1.89 (1H), 1.98-2.24 (1H), 2.60/2.67 (3H), 2.94-3.18 (1H), 3.37/3.39 (3H), 3.49-3.76 (6H), 3.79-3.91 (2H), 4.32-4.61 (2H), 6.08-6.21 (1H), 7.09-7.20 (2H), 7.28-7.38 (1H), 7.46-7.62 (7H), 7.91/8.04 (1H).

Example 224

N-(2-methoxyethyl)-4-methyl-2-{[(S)-1-{4-[4-(trifluoromethyl)phenoxy]benzoyl}pyrrolidin-3-yl]methyl}-2H-indazole-5-carboxamide

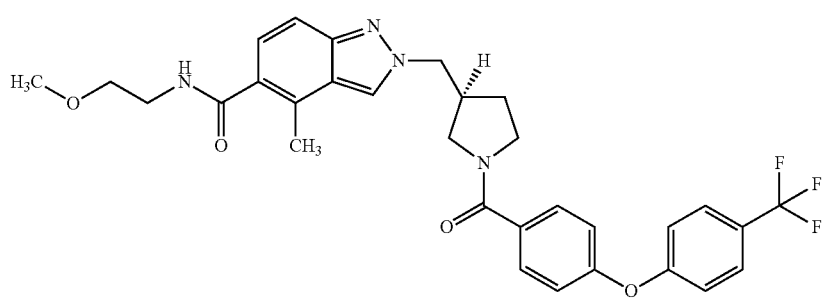 [SMILES: COCCNC(=O)c1ccc2nn(C[C@H]3CCN(C(=O)c4ccc(Oc5ccc(C(F)(F)F)cc5)cc4)C3)cc2c1C]

Analogously to Example 1, 102 mg of the title compound was obtained from 230 mg of the compound prepared in Example 222b and 184 mg of 4-[4-(trifluoromethyl)phenoxy]benzoic acid.

$^1$H-NMR (300 MHz, CDCl3): δ=1.70-2.25 (2H), 2.63/2.66 (3H), 2.94-3.17 (1H), 3.39 (3H), 3.47-3.92 (8H), 4.33-4.59 (2H), 6.15 (1H), 7.00-7.11 (4H), 7.30-7.40 (1H), 7.47-7.65 (5H), 7.91/8.03 (1H).

Example 225

2-{[1-(4-chlorobenzoyl)piperidin-4-yl]methyl}-4-(difluoromethoxy)-N-(2-methoxyethyl)-2H-indazole-5-carboxamide

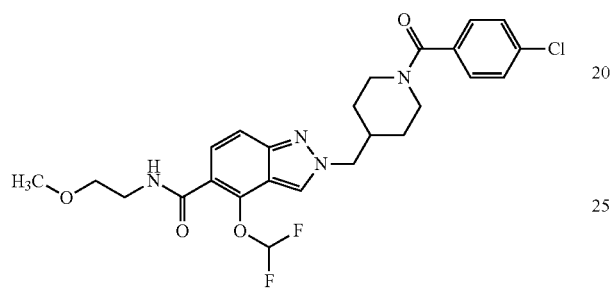

Analogously to Example 55, 90 mg of the title compound was obtained from 106 mg of the compound prepared in Example 225h and 49 mg of 4-chlorobenzoyl chloride.

$^1$H-NMR (300 MHz, DMSO-d6): δ=1.14-1.58 (4H), 2.19-2.34 (1H), 2.67-2.81 (1H), 2.97 (1H), 3.22-3.53 (9H), 4.37 (2H), 7.13 (1H), 7.31-7.39 (3H), 7.47 (2H), 7.54 (1H), 8.21 (1H), 8.50 (1H).

The starting material was prepared as follows:

Example 225a

N-[4-bromo-3-(difluoromethoxy)-2-methylphenyl]acetamide

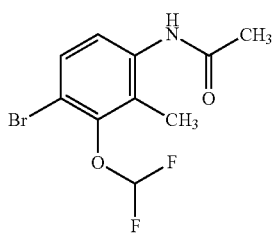 [SMILES: CC(=O)Nc1ccc(Br)c(OC(F)F)c1C]

To a solution of 5.0 g of 3-difluoromethoxy-2-methylaniline in 48 ml DMF, a solution of 5.1 g of N-bromosuccinimide in 24 ml DMF was added dropwise at 0° C. and stirred for 1 hour at 0° C. Then the reaction mixture was diluted with 400 ml hexane/ethyl acetate, and washed once with 50 ml of a 10% aqueous sodium carbonate solution and three times with 50 ml portions of water. After drying over sodium sulphate and filtration, this was concentrated in vacuo. The crude product thus obtained (6.68 g) was used in the next step without purification.

To a solution of 6.39 g of the bromide prepared above in 70 ml pyridine, 3.0 ml of acetic anhydride were added dropwise at 0° C. and stirred for 20 hours at 25° C. The reaction mixture was concentrated in vacuo and the crude product thus obtained purified by column chromatography on silica gel with hexane/0-100% ethyl acetate. The substance was then recrystallized from hexane. In this manner, 6.39 g of the title compound was obtained.

$^1$H-NMR (300 MHz, CDCl3): δ=2.22 (3H), 2.27 (3H), 6.51 (1H), 6.95 (1H), 7.46 (1H), 7.71 (1H).

Example 225b

1-[5-bromo-4-(difluoromethoxy)-1H-indazol-1-yl]ethan-1-one

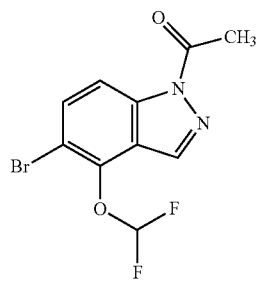 [SMILES: CC(=O)n1ncc2c(OC(F)F)c(Br)ccc21]

Analogously to Example 212c, 5.32 g of the title compound was obtained from 6.38 g of the amide prepared in Example 225a.

$^1$H-NMR (300 MHz, DMSO-d6): δ=2.70 (3H), 7.34 (1H), 7.90 (1H), 8.16 (1H), 8.46 (1H).

Example 225c 5-bromo-4-(difluoromethoxy)-1H-indazole

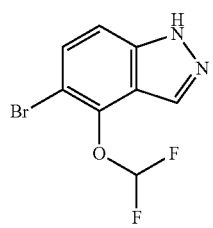 [SMILES: FC(F)Oc1c(Br)ccc2[nH]ncc12]

Analogously to Example 212d, 4.12 g of the title compound was obtained from 5.32 g of the indazole prepared in Example 225b.

$^1$H-NMR (300 MHz, DMSO-d6): δ=7.30 (1H), 7.44 (1H), 7.56 (1H), 8.06 (1H), 13.54 (1H).

Example 225d

Tert-butyl 4-{[5-bromo-4-(difluoromethoxy)-2H-indazol-2-yl]methyl}-piperidin-1-carboxylate

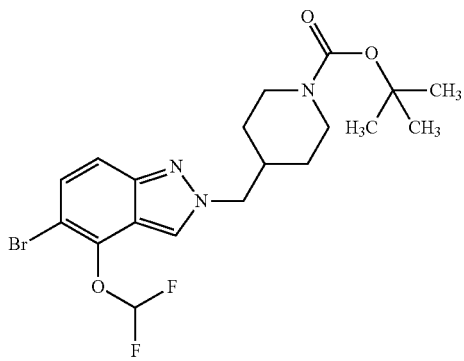 [SMILES: CC(C)(C)OC(=O)N1CCC(Cn2cc3c(OC(F)F)c(Br)ccc3n2)CC1]

Analogously to Example 212e, 2.06 g of the title compound was obtained from 4.1 g of the indazole prepared in Example 225c and 8.7 g of tert-butyl 4-[(tosyloxy)methyl]piperidin-1-carboxylate.

$^1$H-NMR (300 MHz, CDCl3): δ=1.19-1.28 (2H), 1.45 (9H), 1.51-1.59 (2H), 2.25 (1H), 2.68 (2H), 4.12 (2H), 4.27 (2H), 6.61 (1H), 7.41 (1H), 7.50 (1H), 7.95 (1H).

Example 225e

Methyl 2-{[1-(tert-butoxycarbonyl)piperidin-4-yl]methyl}-4-(difluoromethoxy)-2H-indazol-5-carboxylate

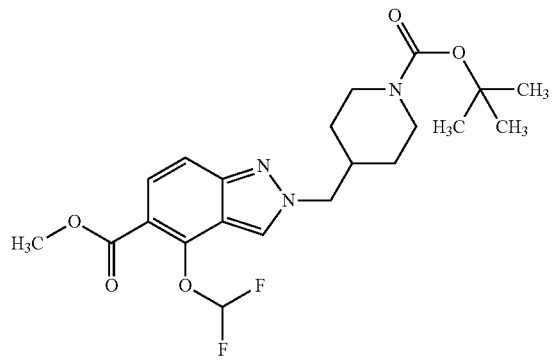 [SMILES: COC(=O)c1ccc2nn(CC3CCN(C(=O)OC(C)(C)C)CC3)cc2c1OC(F)F]

Analogously to Example 1e, after three runs 1.28 g of the title compound was obtained from 683 mg of the bromide prepared in Example 225d and 0.18 ml of methanol.

$^1$H-NMR (300 MHz, DMSO-d6): δ=0.96-1.22 (2H), 1.28-1.47 (11H), 2.14 (1H), 2.54-2.74 (2H), 3.81 (3H), 3.87 (2H), 4.36 (2H), 7.17 (1H), 7.58 (1H), 7.65 (1H), 8.62 (1H).

Example 225f

2-{[1-(tert-butoxycarbonyl)piperidin-4-yl]methyl}-4-(difluoromethoxy)-2H-indazol-5-carboxylic acid

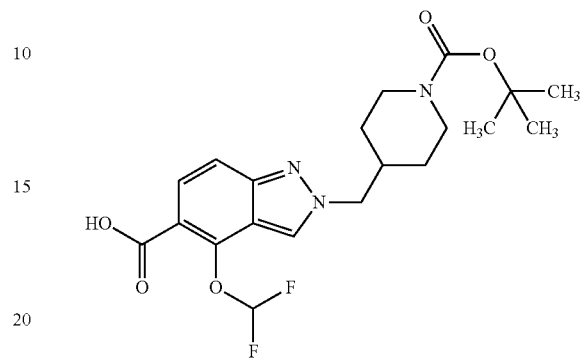

Analogously to Example 1d, 1.05 g of the title compound was obtained from 1.28 g of the ester prepared in Example 225e.

$^1$H-NMR (300 MHz, DMSO-d6): δ=0.97-1.16 (2H), 1.28-1.47 (11H), 2.13 (1H), 2.63 (2H), 3.87 (2H), 4.35 (2H), 7.14 (1H), 7.54 (1H), 7.65 (1H), 8.58 (1H), 13.05 (1H).

Example 225g

Tert-butyl 4-({4-(difluoromethoxy)-5-[N-(2-methoxyethyl)carbamoyl]-2H-indazol-2-yl}methyl)piperidin-1-carboxylate

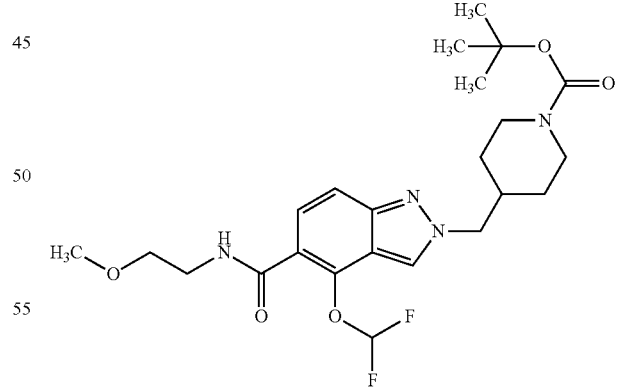

Analogously to Example 1, 503 mg of the title compound was obtained from 520 mg of the compound prepared in Example 225f and 92 mg of 2-methoxyethylamine.

$^1$H-NMR (300 MHz, DMSO-d6): δ=1.01-1.13 (2H), 1.34 (9H), 1.38 (2H), 2.13 (1H), 2.59-2.71 (6H), 3.24 (3H), 3.34-3.44 (2H), 3.87 (2H), 4.34 (2H), 7.14 (1H), 7.33 (1H), 7.54 (1H), 8.21 (1H), 8.50 (1H).

Example 225h 4-(difluoromethoxy)-N-(2-methoxyethyl)-2-(4-piperidylmethyl)-2H-indazole-5-carboxamide hydrochloride

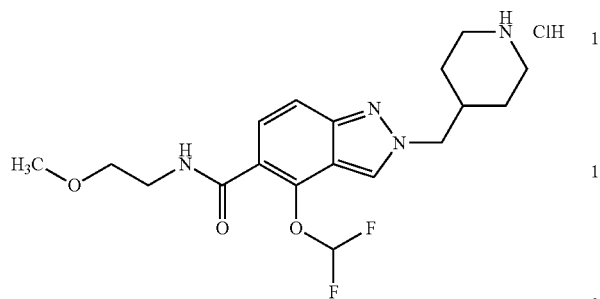

Analogously to Example 1a, from 122 mg of the amide prepared in Example 225g, 106 mg of the title compound was obtained, which was reacted without further purification.

Example 226

4-(difluoromethoxy)-2-({1-[4-(4-fluorophenoxy)benzoyl]piperidin-4-yl}methyl)-N-(2-methoxyethyl)-2H-indazole-5-carboxamide

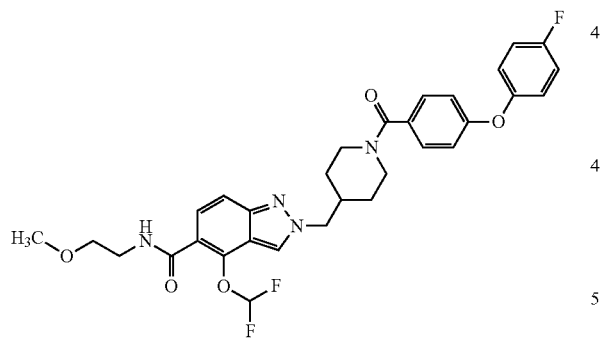

Analogously to Example 1, 11 mg of the title compound was obtained from 106 mg of the compound prepared in Example 225h and 59 mg of 4-(4-fluorophenoxy)benzoic acid.

$^1$H-NMR (300 MHz, DMSO-d6): δ=1.10-1.59 (4H), 2.23-2.33 (1H), 2.75-3.01 (2H), 3.24 (3H), 3.33-3.51 (5H), 3.51-3.72 (1H), 4.37 (2H), 6.95 (2H), 7.07-7.12 (2H), 7.13 (1H), 7.17-7.26 (2H), 7.28-7.39 (3H), 7.54 (1H), 8.21 (1H), 8.50 (1H).

Example 227

4-(difluoromethoxy)-2-({1-[(4'-fluorobiphenyl-4-yl)carbonyl]piperidin-4-yl}methyl)-N-(2-methoxyethyl)-2H-indazole-5-carboxamide

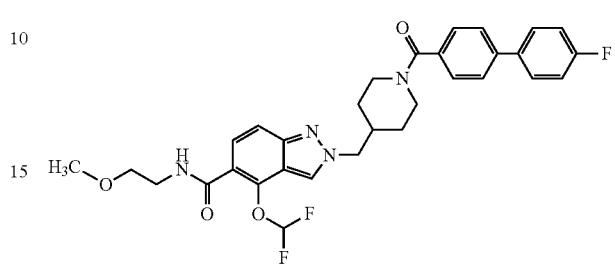

Analogously to Example 1, 38 mg of the title compound was obtained from 106 mg of the compound prepared in Example 225h and 55 mg of 4'-fluorobiphenyl-4-carboxylic acid.

$^1$H-NMR (300 MHz, DMSO-d6): δ=1.14-1.62 (4H), 2.23-2.35 (1H), 2.68-2.85 (1H), 2.91-3.09 (1H), 3.24 (3H), 3.32-3.48 (5H), 3.50-3.70 (1H), 4.38 (2H), 7.14 (1H), 7.28 (2H), 7.33 (1H), 7.40 (2H), 7.55 (1H), 7.64-7.75 (4H), 8.21 (1H), 8.51 (1H).

Example 228

2-{[1-(4-cyclopropylbenzoyl)piperidin-4-yl]methyl}-4-(difluoromethoxy)-N-(2-methoxyethyl)-2H-indazole-5-carboxamide

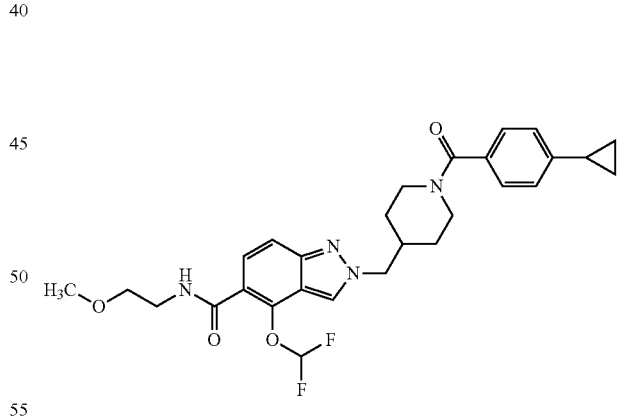

Analogously to Example 1, 75 mg of the title compound was obtained from 106 mg of the compound prepared in Example 225h and 41 mg of 4-cyclopropylbenzoic acid.

$^1$H-NMR (300 MHz, DMSO-d6): δ=0.66 (2H), 0.94 (2H), 1.10-1.54 (4H), 1.90 (1H), 2.14-2.31 (1H), 2.72-3.02 (2H), 3.03-3.18 (1H), 3.24 (3H), 3.33-3.47 (4H), 3.49-3.68 (1H), 4.37 (2H), 7.07 (2H), 7.13 (1H), 7.19 (2H), 7.33 (1H), 7.54 (1H), 8.21 (1H), 8.50 (1H).

Example 229

2-{[1-(4-chlorobenzoyl)piperidin-4-yl]methyl}-N-[2-(cyclopropylmethoxy)-ethyl]-4-(difluoromethoxy)-2H-indazole-5-carboxamide

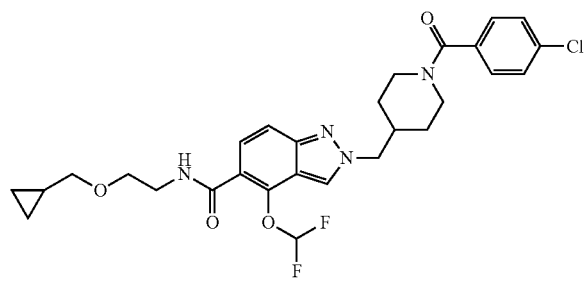 [SMILES: O=C(NCCOCC1CC1)c1ccc2nn(CC3CCN(C(=O)c4ccc(Cl)cc4)CC3)cc2c1OC(F)F]

Analogously to Example 55, 170 mg of the title compound was obtained from 127 mg of the compound prepared in Example 229b and 53 mg of 4-chlorobenzoyl chloride.

$^1$H-NMR (300 MHz, DMSO-d6): δ=0.14 (2H), 0.42 (2H), 0.96 (1H), 1.10-1.27 (2H), 1.37 (1H), 1.51 (1H), 2.26 (1H), 2.71 (1H), 2.97 (1H), 3.20-3.55 (8H), 4.37 (2H), 7.14 (1H), 7.31-7.38 (3H), 7.47 (2H), 7.55 (1H), 8.21 (1H), 8.51 (1H).

The starting material was prepared as follows:

Example 229a

Tert-butyl 4-{[5-{N-[2-(cyclopropylmethoxy)ethyl]carbamoyl}-4-(difluoromethoxy)-2H-indazol-2-yl]methyl}piperidin-1-carboxylate

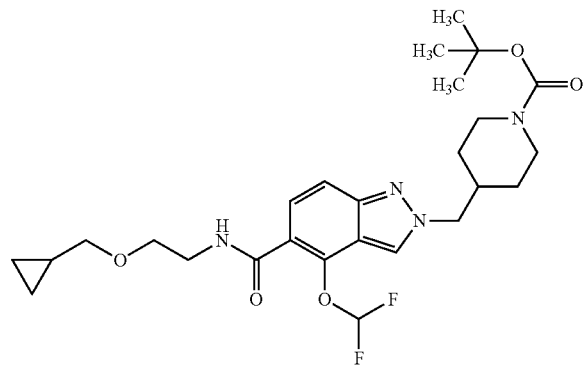 [SMILES: CC(C)(C)OC(=O)N1CCC(Cn2cc3c(OC(F)F)c(C(=O)NCCOCC4CC4)ccc3n2)CC1]

Analogously to Example 1, 453 mg of the title compound was obtained from 520 mg of the compound prepared in Example 225f and 185 mg of 2-(cyclopropylmethoxy)ethylamine.

$^1$H-NMR (300 MHz, DMSO-d6): δ=0.14 (2H), 0.42 (2H), 0.97 (1H), 1.07 (2H), 1.34 (9H), 1.39 (2H), 2.13 (1H), 2.56-2.72 (2H), 3.23 (2H), 3.37 (2H), 3.48 (2H), 3.87 (2H), 4.34 (2H), 7.15 (1H), 7.34 (1H), 7.55 (1H), 8.21 (1H), 8.50 (1H).

Example 229b

N-[(2-cyclopropylmethoxy)ethyl]-4-(difluoromethoxy)-2-(4-piperidylmethyl)-2H-indazole-5-carboxamide hydrochloride

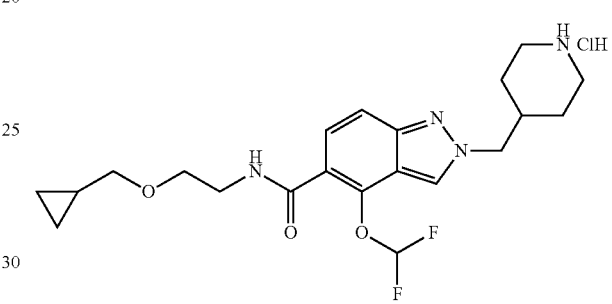

Analogously to Example 1a, from 145 mg of the amide prepared in Example 229a, 127 mg of the title compound was obtained, which was reacted without further purification.

Example 230

N-[2-(cyclopropylmethoxy)ethyl]-4-(difluoromethoxy)-2-({1-[4-(4-fluoro-phenoxy)benzoyl]piperidin-4-yl}methyl)-2H-indazole-5-carboxamide

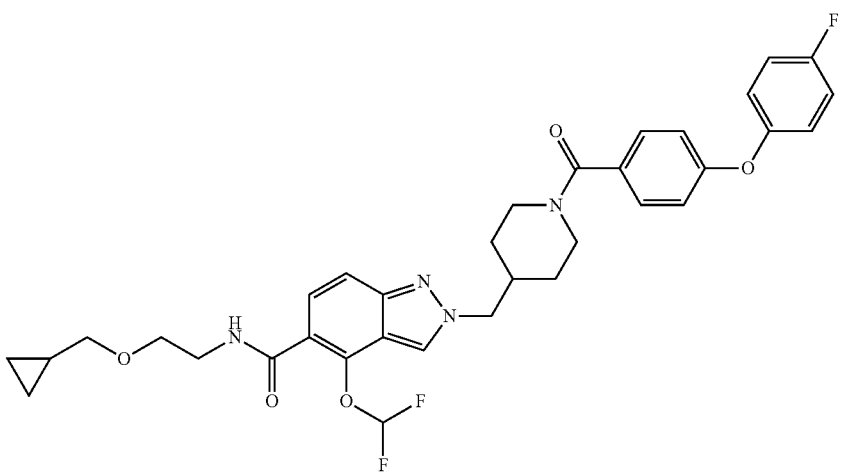 [SMILES: O=C(NCCOCC1CC1)c1ccc2nn(CC3CCN(C(=O)c4ccc(Oc5ccc(F)cc5)cc4)CC3)cc2c1OC(F)F]

Analogously to Example 1, 156 mg of the title compound was obtained from 127 mg of the compound prepared in Example 229b and 64 mg of 4-(4-fluorophenoxy)benzoic acid.

$^1$H-NMR (300 MHz, DMSO-d6): δ=0.14 (2H), 0.42 (2H), 0.96 (1H), 1.10-1.54 (4H), 2.18-2.33 (1H), 2.71-3.02 (2H), 3.03-3.16 (1H), 3.22 (2H), 3.37 (2H), 3.47 (2H), 3.55-3.68 (1H), 4.37 (2H), 6.95 (2H), 7.10 (2H), 7.14 (1H), 7.22 (2H), 7.34 (3H), 7.55 (1H), 8.21 (1H), 8.51 (1H).

Example 231

N-[2-(cyclopropylmethoxy)ethyl]-4-(difluoromethoxy)-2-({1-[(4'-fluorobiphenyl-4-yl)carbonyl]piperidin-4-yl}methyl)-2H-indazole-5-carboxamide

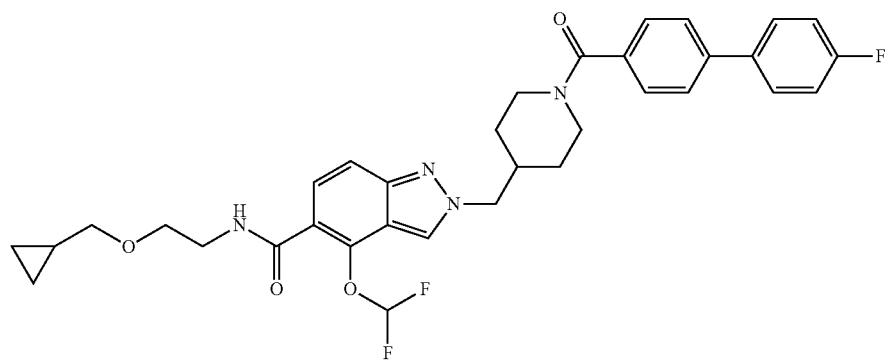 [SMILES: O=C(NCCOCC1CC1)c1ccc2nn(CC3CCN(C(=O)c4ccc(-c5ccc(F)cc5)cc4)CC3)cc2c1OC(F)F]

Analogously to Example 1, 164 mg of the title compound was obtained from 127 mg of the compound prepared in Example 229b and 60 mg of 4'-fluorobiphenyl-4-carboxylic acid.

$^1$H-NMR (300 MHz, DMSO-d6): δ=0.14 (2H), 0.42 (2H), 0.96 (1H), 1.14-1.60 (4H), 2.27 (1H), 2.70-3.04 (1H), 2.87 (1H), 3.03-3.15 (1H), 3.22 (2H), 3.37 (2H), 3.47 (2H), 3.60 (1H), 4.38 (2H), 7.14 (1H), 7.28 (2H), 7.34 (1H), 7.41 (2H), 7.55 (1H), 7.64-7.75 (4H), 8.21 (1H), 8.52 (1H).

Example 232

2-{[1-(4-chlorobenzoyl)piperidin-4-yl]methyl}-N-(2-methoxyethyl)-4-(2,2,2-trifluoroethoxy)-2H-indazole-5-carboxamide

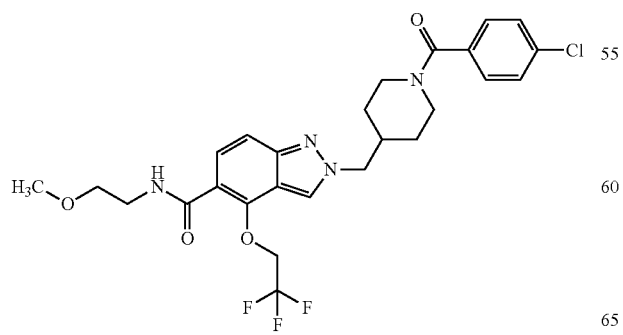

Analogously to Example 55, 113 mg of the title compound was obtained from 109 mg of the compound prepared in Example 232h and 46 mg of 4-chlorobenzoyl chloride.

$^1$H-NMR (300 MHz, DMSO-d6): δ=1.12-1.61 (3H), 2.19-2.34 (1H), 2.67-3.07 (2H), 3.23 (3H), 3.33-3.56 (4H), 4.28-4.47 (3H), 4.95 (2H), 7.31-7.39 (3H), 7.40-7.50 (3H), 7.99 (1H), 8.65 (1H).

The starting material was prepared as follows:

Example 232a

N-[4-bromo-2-methyl-3-(2,2,2-trifluoroethoxy)phenyl]acetamide

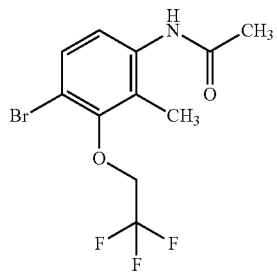 [SMILES: CC(=O)Nc1ccc(Br)c(OCC(F)(F)F)c1C]

Analogously to Example 225a, 6.13 g of the title compound was obtained from 5.0 g of 2-methyl-3-(2,2,2-trifluoroethoxy)aniline $^1$H-NMR (300 MHz, DMSO-d6): δ=2.07 (3H), 2.18 (3H), 4.55 (2H), 7.29 (1H), 7.45 (1H), 9.42 (1H).

Example 232b

1-[5-bromo-4-(2,2,2-trifluoroethoxy)-1H-indazol-1-yl]ethan-1-one

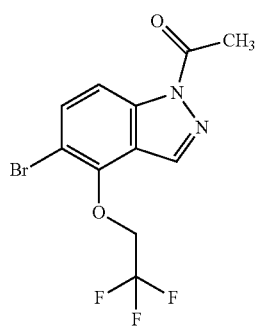 [SMILES: CC(=O)n1ncc2c(OCC(F)(F)F)c(Br)ccc21]

Analogously to Example 212c, 5.08 g of the title compound was obtained from 6.13 g of the amide prepared in Example 232a.

$^1$H-NMR (300 MHz, DMSO-d6): δ=2.69 (3H), 5.14 (2H), 7.80 (1H), 7.99 (1H), 8.64 (1H).

Example 232c 5-bromo-4-(2,2,2-trifluoroethoxy)-1H-indazole

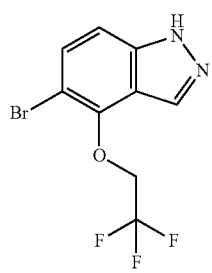 [SMILES: FC(F)(F)COc1c(Br)ccc2[nH]ncc12]

Analogously to Example 212d, 3.57 g of the title compound was obtained from 5.08 g of the indazole prepared in Example 232b.

$^1$H-NMR (300 MHz, DMSO-d6): δ=5.05 (2H), 7.24 (1H), 7.45 (1H), 8.26 (1H), 13.38 (1H).

Example 232d

Tert-butyl 4-{[5-bromo-4-(2,2,2-trifluoroethoxy)-2H-indazol-2-yl]methyl}-piperidin-1-carboxylate

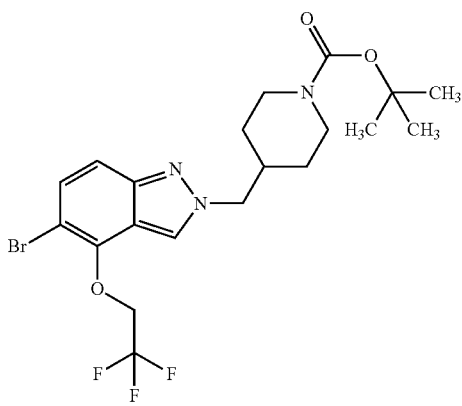 [SMILES: CC(C)(C)OC(=O)N1CCC(Cn2cc3c(OCC(F)(F)F)c(Br)ccc3n2)CC1]

Analogously to Example 212e, 1.77 g of the title compound was obtained from 3.57 g of the indazole prepared in Example 232c and 6.7 g of tert-butyl 4-[(tosyloxy)methyl]piperidin-1-carboxylate.

$^1$H-NMR (300 MHz, CDCl3): δ=1.16-1.31 (2H), 1.45 (9H), 1.54 (2H), 2.25 (1H), 2.68 (2H), 4.05-4.21 (2H), 4.27 (2H), 4.54 (2H), 7.35 (1H), 7.41 (1H), 7.91 (1H).

Example 232e

Methyl 2-{[1-(tert-butoxycarbonyl)piperidin-4-yl]methyl}-4-(2,2,2-trifluoro-ethoxy)-2H-indazole-5-carboxylate

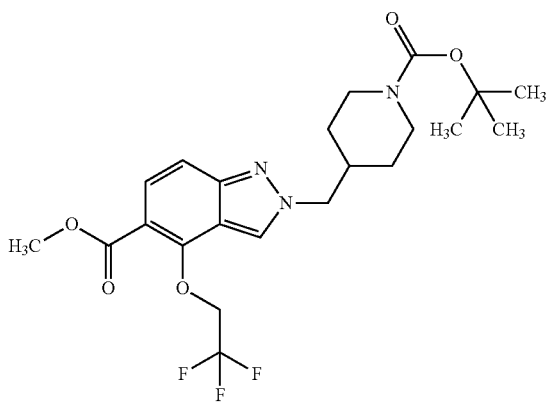 [SMILES: COC(=O)c1ccc2nn(CC3CCN(C(=O)OC(C)(C)C)CC3)cc2c1OCC(F)(F)F]

Analogously to Example 1e, after three runs 857 mg of the title compound was obtained from 590 mg of the bromide prepared in Example 232d and 0.15 ml of methanol.

$^1$H-NMR (300 MHz, DMSO-d6): δ=1.00-1.17 (2H), 1.34 (9H), 1.37-1.47 (2H), 2.13 (1H), 2.55-2.74 (2H), 3.79 (3H), 3.87 (2H), 4.32 (2H), 4.89 (2H), 7.39 (1H), 7.56 (1H), 8.67 (1H).

Example 232f

2-{[1-(tert-butoxycarbonyl)piperidin-4-yl]methyl}-4-(2,2,2-trifluoroethoxy)-2H-indazole-5-carboxylic acid

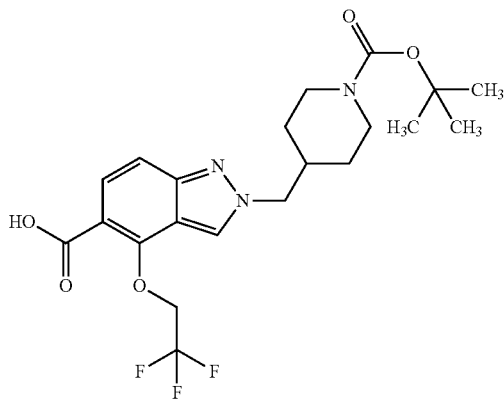 [SMILES: CC(C)(C)OC(=O)N1CCC(Cn2cc3c(OCC(F)(F)F)c(C(=O)O)ccc3n2)CC1]

Analogously to Example 1d, 724 mg of the title compound was obtained from 854 mg of the ester prepared in Example 232e.

¹H-NMR (300 MHz, DMSO-d6): δ=1.01-1.17 (2H), 1.34 (9H), 1.40 (2H), 2.13 (1H), 2.53-2.75 (2H), 3.87 (2H), 4.32 (2H), 4.84 (2H), 7.37 (1H), 7.58 (1H), 8.60 (1H), 12.74 (1H).

Example 232g

Tert-butyl 4-({5-[N-(2-methoxyethyl)carbamoyl]-4-(2,2,2-trifluoroethoxy)-2H-indazol-2-yl}methyl)piperidin-1-carboxylate

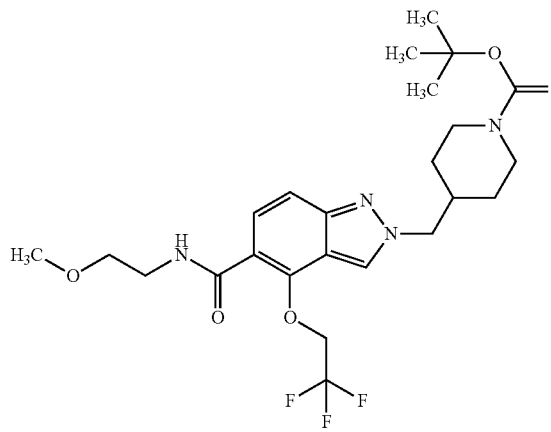

Analogously to Example 1, 386 mg of the title compound was obtained from 360 mg of the compound prepared in Example 232f and 59 mg of 2-methoxyethylamine.

¹H-NMR (300 MHz, DMSO-d6): δ=0.98-1.18 (2H), 1.34 (9H), 1.43 (2H), 2.14 (1H), 2.65 (2H), 3.23 (3H), 3.35-3.47 (4H), 3.88 (2H), 4.30 (2H), 4.96 (2H), 7.35 (1H), 7.43 (1H), 7.99 (1H), 8.65 (1H).

Example 232h

N-(2-methoxyethyl)-2-(4-piperidylmethyl)-4-(2,2,2-trifluoroethoxy)-2H-indazole-5-carboxamide hydrochloride

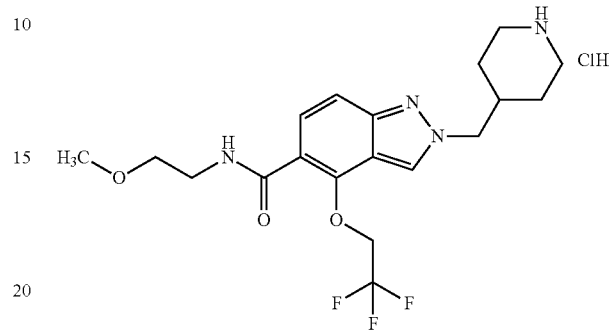

Analogously to Example 1a, from 109 mg of the amide prepared in Example 232g, 113 mg of the title compound was obtained, which was reacted without further purification.

Example 233

2-({1-[4-(4-fluorophenoxy)benzoyl]piperidin-4-yl}methyl)-N-(2-methoxyethyl)-4-(2,2,2-trifluoroethoxy)-2H-indazole-5-carboxamide

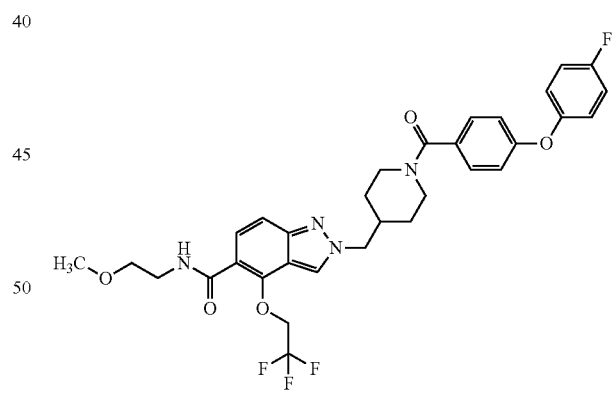

Analogously to Example 1, 51 mg of the title compound was obtained from 109 mg of the compound prepared in Example 232h and 56 mg of 4-(4-fluorophenoxy)benzoic acid.

¹H-NMR (300 MHz, DMSO-d6): δ=1.10-1.31 (1H), 1.48 (2H), 2.18-2.37 (1H), 2.69-3.04 (2H), 3.23 (3H), 3.37-3.48 (4H), 3.56-3.71 (1H), 4.33 (2H), 4.95 (2H), 6.95 (2H), 7.06-7.15 (2H), 7.18-7.27 (2H), 7.31-7.38 (3H), 7.40-7.47 (1H), 7.99 (1H), 8.66 (1H).

Example 234

2-({1-[(4'-fluorobiphenyl-4-yl)carbonyl]piperidin-4-yl}methyl)-N-(2-methoxy-ethyl)-4-(2,2,2-trifluoroethoxy)-2H-indazole-5-carboxamide

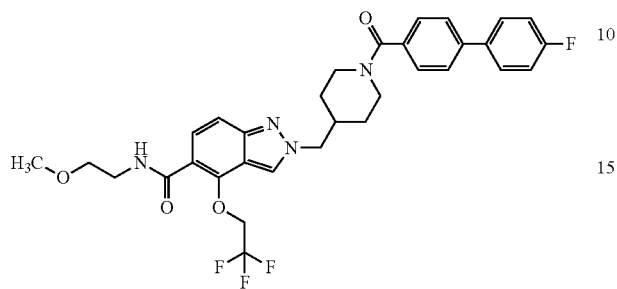

Analogously to Example 1, 61 mg of the title compound was obtained from 109 mg of the compound prepared in Example 232h and 52 mg of 4-(4-fluorophenyl)benzoic acid.

$^1$H-NMR (300 MHz, DMSO-d6): δ=1.14-1.63 (3H), 2.19-2.37 (1H), 2.68-3.09 (2H), 3.23 (3H), 3.34-3.48 (4H), 3.62 (1H), 4.28-4.42 (2H), 4.96 (2H), 7.22-7.47 (6H), 7.64-7.76 (4H), 7.99 (1H), 8.66 (1H).

Example 235

2-{[1-(4-chlorobenzoyl)piperidin-4-yl]methyl}-N-[2-(cyclopropylmethoxy)-ethyl]-4-(2,2,2-trifluoroethoxy)-2H-indazole-5-carboxamide

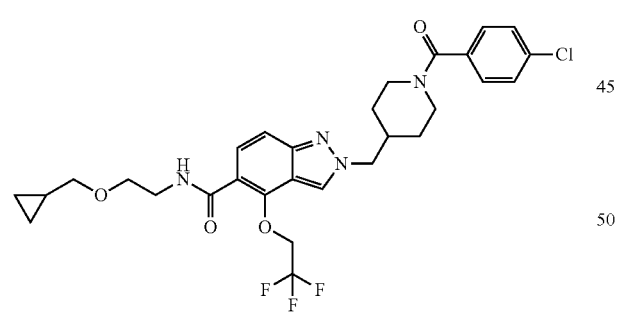

Analogously to Example 55, 122 mg of the title compound was obtained from 122 mg of the compound prepared in Example 235b and 48 mg of 4-chlorobenzoyl chloride.

$^1$H-NMR (300 MHz, DMSO-d6): δ=0.13 (2H), 0.41 (2H), 0.95 (1H), 1.11-1.62 (3H), 2.19-2.34 (1H), 2.73 (1H), 2.98 (1H), 3.21 (2H), 3.33-3.57 (5H), 4.33 (2H), 4.95 (2H), 7.31-7.51 (6H), 8.00 (1H), 8.65 (1H).

The starting material was prepared as follows:

Example 235a

Tert-butyl 4-{[5-{N-[2-(cyclopropylmethoxy)ethyl]carbamoyl}-4-(2,2,2-trifluoroethoxy)-2H-indazol-2-yl]methyl}piperidin-1-carboxylate

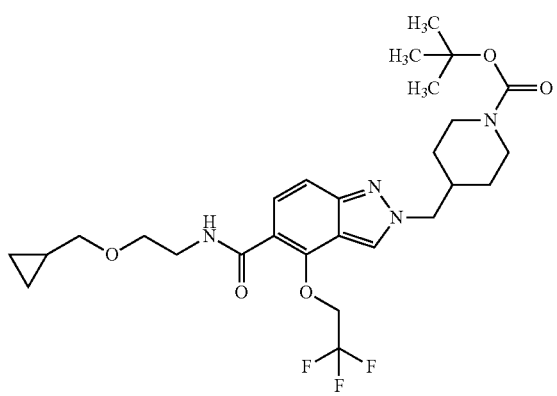 [SMILES: CC(C)(C)OC(=O)N1CCC(Cn2cc3c(OCC(F)(F)F)c(C(=O)NCCOCC4CC4)ccc3n2)CC1]

Analogously to Example 1, 429 mg of the title compound was obtained from 360 mg of the compound prepared in Example 232f and 119 mg of 2-(cyclopropylmethoxy)ethylamine.

$^1$H-NMR (300 MHz, DMSO-d6): δ=0.13 (2H), 0.42 (2H), 0.95 (1H), 1.08 (2H), 1.34 (9H), 1.41 (2H), 2.14 (1H), 3.22 (2H), 3.41 (2H), 3.48 (2H), 3.88 (2H), 4.30 (2H), 4.95 (2H), 7.35 (1H), 7.42 (1H), 8.00 (1H), 8.65 (1H).

Example 235b

N-[2-(cyclopropylmethoxy)ethyl]-2-(4-piperidylmethyl)-4-(2,2,2-trifluoro-ethoxy)-2H-indazole-5-carboxamide hydrochloride

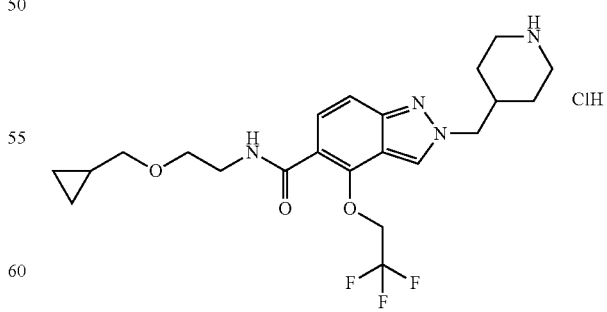

Analogously to Example 1a, from 138 mg of the amide prepared in Example 235a, 122 mg of the title compound was obtained, which was reacted without further purification.

Example 236

N-[2-(cyclopropylmethoxy)ethyl]-2-({1-[4-(4-fluorophenoxy)benzoyl]piperidin-4-yl}methyl)-4-(2,2,2-trifluoroethoxy)-2H-indazole-5-carboxamide

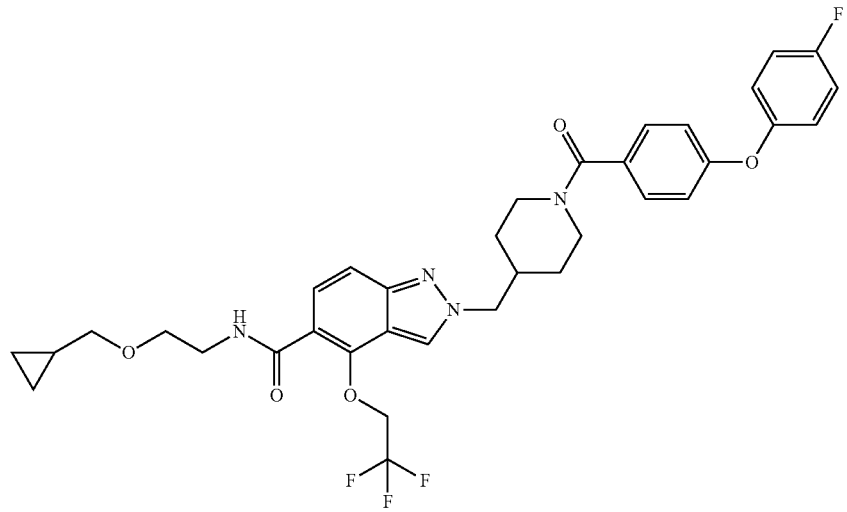 [SMILES: O=C(NCCOCC1CC1)c1ccc2nn(CC3CCN(C(=O)c4ccc(Oc5ccc(F)cc5)cc4)CC3)cc2c1OCC(F)(F)F]

Analogously to Example 1, 95 mg of the title compound was obtained from 122 mg of the compound prepared in Example 235b and 58 mg of 4-(4-fluorophenoxy)benzoic acid.

$^1$H-NMR (300 MHz, DMSO-d6): δ=0.13 (2H), 0.41 (2H), 0.95 (1H), 1.09-1.60 (3H), 2.17-2.36 (1H), 2.68-3.06 (2H), 3.22 (2H), 3.34-3.76 (5H), 4.33 (2H), 4.95 (2H), 6.95 (2H), 7.06-7.14 (2H), 7.17-7.27 (2H), 7.30-7.38 (3H), 7.42 (1H), 7.99 (1H), 8.65 (1H).

Example 237

N-[2-(cyclopropylmethoxy)ethyl]-2-({1-[(4'-fluorobiphenyl-4-yl)carbonyl]piperidin-4-yl}methyl)-4-(2,2,2-trifluoroethoxy)-2H-indazole-5-carboxamide

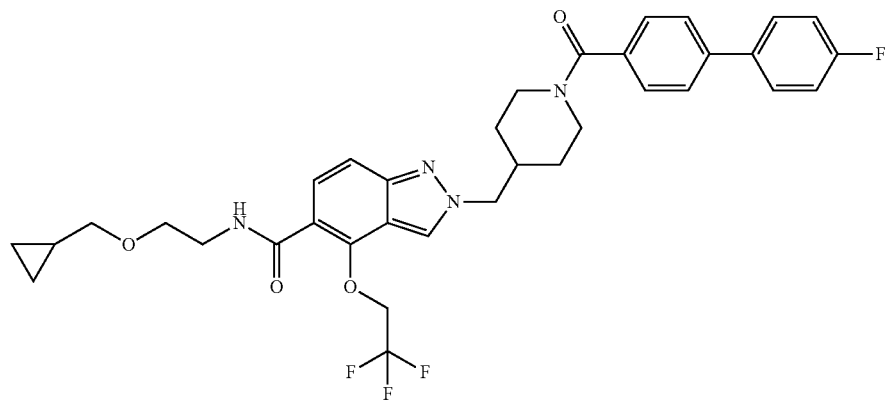 [SMILES: O=C(NCCOCC1CC1)c1ccc2nn(CC3CCN(C(=O)c4ccc(-c5ccc(F)cc5)cc4)CC3)cc2c1OCC(F)(F)F]

Analogously to Example 1, 98 mg of the title compound was obtained from 122 mg of the compound prepared in Example 235b and 54 mg of 4-(4-fluorophenoxy)benzoic acid.

$^1$H-NMR (300 MHz, DMSO-d6): δ=0.12 (2H), 0.41 (2H), 0.95 (1H), 1.15-1.64 (3H), 2.21-2.36 (1H), 2.70-3.10 (2H), 3.21 (2H), 3.35-3.69 (5H), 4.35 (2H), 4.95 (2H), 7.22-7.46 (6H), 7.63-7.77 (4H), 7.99 (1H), 8.66 (1H).

Example 238

2-{[1-(4-chlorobenzoyl)piperidin-4-yl]methyl}-N-[2-(3-methoxyazetidin-1-yl) ethyl]-4-methyl-2H-indazole-5-carboxamide

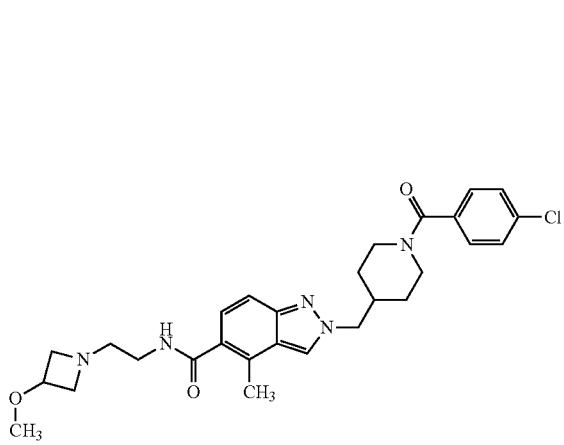 [SMILES: COC1CN(CCNC(=O)c2ccc3nn(CC4CCN(C(=O)c5ccc(Cl)cc5)CC4)cc3c2C)C1]

Analogously to Example 1, 33 mg of the title compound was obtained from 120 mg of the compound prepared in Example 238c and 40 mg of 2-(3-methoxyazetidin-1-yl) ethylamine (prepared analogously to WO2006/104406).

$^1$H-NMR (300 MHz, CDCl3): δ=0.83 (1H), 1.20-2.01 (4H), 2.38 (1H), 2.66 (3H), 2.69-3.09 (2H), 3.31 (3H), 3.43 (2H), 3.56-3.90 (5H), 4.18-4.32 (3H), 4.43 (2H), 6.91 (1H), 7.30-7.41 (5H), 7.52 (1H), 7.95 (1H).

The starting material was prepared as follows:

Example 238a methyl 4-methyl-2-(4-piperidylmethyl)-2H-indazol-5-carboxylate hydrochloride

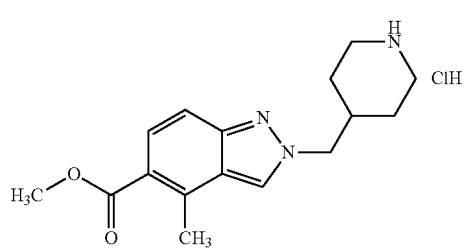

Analogously to Example 1a, from 3.0 g of the ester prepared in Example 1e, 2.51 g of the title compound was obtained, which was reacted without further purification.

Example 238b

Methyl 2-{[1-(4-chlorobenzoyl)piperidin-4-yl]methyl}-4-methyl-2H-indazol-5-carboxylate

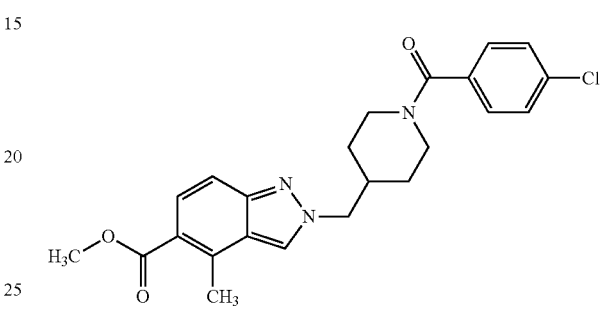

Analogously to Example 55, 3.27 g of the title compound was obtained from 2.5 g of the compound prepared in Example 238a and 1.5 g of 4-chlorobenzoyl chloride.

$^1$H-NMR (300 MHz, DMSO-d6): δ=1.16-1.63 (4H), 2.21-2.33 (1H), 2.73 (4H), 2.90-3.05 (1H), 3.44-3.55 (1H), 3.79 (3H), 4.32 (2H), 4.36-4.47 (1H), 7.36 (2H), 7.42 (1H), 7.46 (2H), 7.63 (1H), 8.67 (1H).

Example 238c

2-{[1-(4-chlorobenzoyl)piperidin-4-yl]methyl}-4-methyl-2H-indazol-5-carboxylic acid

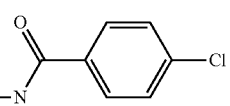

Analogously to Example 1d, 470 mg of the title compound was obtained from 485 mg of the ester prepared in Example 238b.

Example 239

(+/−)-2-{[1-(4-chlorobenzoyl)piperidin-4-yl]methyl}-4-methyl-N-(3,4,5,6-tetrahydro-2H-pyran-2-ylmethyl)-2H-indazole-5-carboxamide

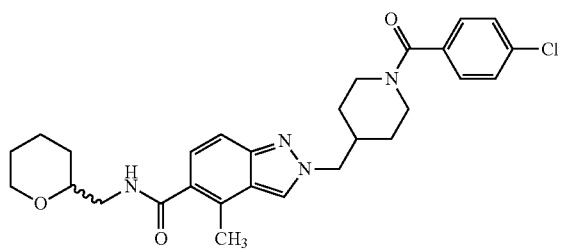 [SMILES: Cc1c(C(=O)NCC2CCCCO2)ccc2nn(CC3CCN(C(=O)c4ccc(Cl)cc4)CC3)cc12]

Analogously to Example 1, 188 mg of the title compound was obtained from 300 mg of the compound prepared in Example 238c and 92 mg of 3,4,5,6-tetrahydro-2H-pyran-2-ylmethylamine hydrochloride.

$^1$H-NMR (300 MHz, DMSO-d6): δ=1.01-1.27 (3H), 1.29-1.64 (7H), 2.19-2.32 (1H), 2.48 (3H), 2.66-2.80 (1H), 2.89-3.00 (1H), 3.00-3.08 (1H), 3.16-3.25 (2H), 3.34-3.42 (1H), 3.43-3.55 (1H), 3.77-3.88 (1H), 4.31 (2H), 4.39 (1H), 7.14 (1H), 7.32-7.40 (2H), 7.46 (2H), 7.83 (1H), 8.09 (1H), 8.46 (1H).

Example 240

(R or S)-2-{[1-(4-chlorobenzoyl)piperidin-4-yl]methyl}-4-methyl-N-(3,4,5,6-tetrahydro-2H-pyran-2-ylmethyl)-2H-indazole-5-carboxamide

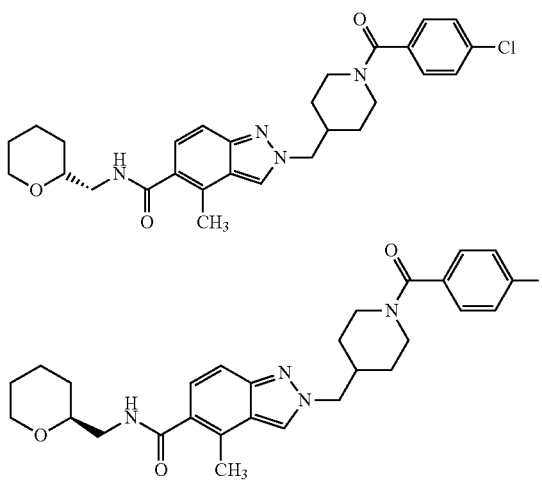

From 185 mg of the racemate prepared in Example 239, 51 mg of the title compound together with 53 mg of the slower-eluting enantiomer (Example 241) were obtained by racemate separation by means of preparative chiral HPLC (Method B).

Analytical chiral HPLC: 7.02 min.

Example 241

(S or R)-2-{[1-(4-chlorobenzoyl)piperidin-4-yl]methyl}-4-methyl-N-(3,4,5,6-tetrahydro-2H-pyran-2-ylmethyl)-2H-indazole-5-carboxamide

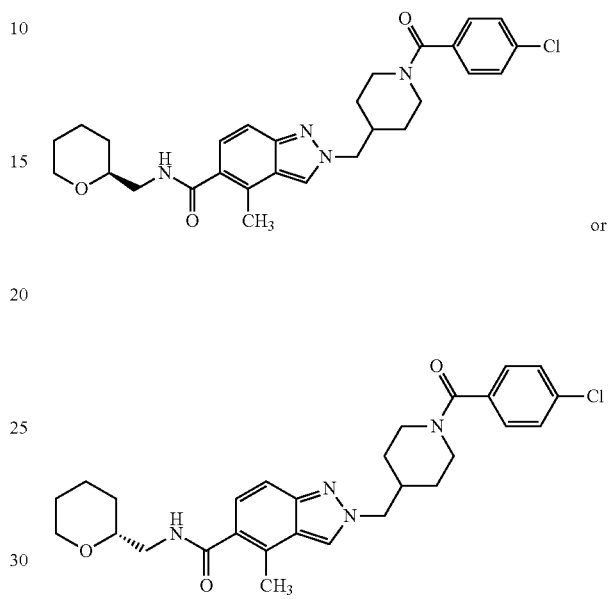

From 185 mg of the racemate prepared in Example 239, 53 mg of the title compound together with 51 mg of the faster-eluting enantiomer (Example 240) were obtained by racemate separation by means of preparative chiral HPLC (Method B).

Analytical chiral HPLC: 8.24 min.

Example 242

2-{[1-(4-chlorobenzoyl)piperidin-4-yl]methyl}-N-ethyl-4-methyl-2H-indazole-5-carboxamide

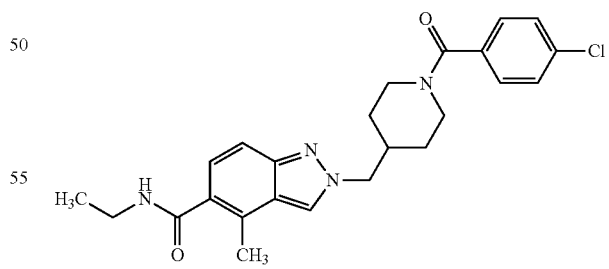

Analogously to Example 1, 85 mg of the title compound was obtained from 300 mg of the compound prepared in Example 238c and 43 mg of ethylamine 2M in THF.

$^1$H-NMR (300 MHz, DMSO-d6): δ=1.08 (3H), 1.16-1.60 (4H), 2.20-2.33 (1H), 2.48 (3H), 2.63-3.07 (2H), 3.22 (2H), 3.48 (1H), 4.24-4.46 (3H), 7.14 (1H), 7.31-7.42 (3H), 7.46 (2H), 8.08 (1H), 8.46 (1H).

Example 243

2-{[1-(4-chlorobenzoyl)piperidin-4-yl]methyl}-N-isobutyl-4-methyl-2H-indazole-5-carboxamide

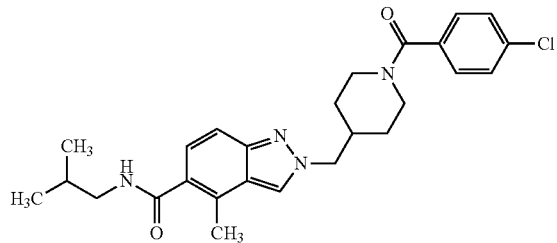 [SMILES: Cc1c(C(=O)NCC(C)C)ccc2nn(CC3CCN(C(=O)c4ccc(Cl)cc4)CC3)cc12]

Analogously to Example 1, 92 mg of the title compound was obtained from 300 mg of the compound prepared in Example 238c and 69 mg of isobutylamine.

$^1$H-NMR (300 MHz, DMSO-d6): δ=0.85-0.90 (6H), 1.13-1.57 (4H), 1.75-1.83 (1H), 2.21-2.34 (1H), 2.49 (3H), 3.03 (4H), 3.48 (1H), 4.27-4.45 (3H), 7.14 (1H), 7.31-7.41 (3H), 7.46 (2H), 8.11 (1H), 8.47 (1H).

Example 244

2-{[1-(4-chlorobenzoyl)piperidin-4-yl]methyl}-N-(2-mesylethyl)-4-methyl-2H-indazole-5-carboxamide

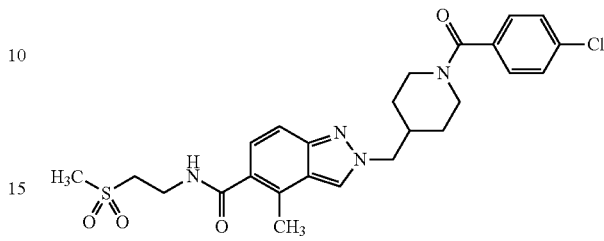

Analogously to Example 1, 132 mg of the title compound was obtained from 300 mg of the compound prepared in Example 238c and 151 mg of 2-mesylethylamine hydrochloride.

$^1$H-NMR (300 MHz, DMSO-d6): δ=1.19-1.62 (4H), 2.24-2.36 (1H), 2.54 (3H), 2.70-3.05 (2H), 3.05 (3H), 3.38 (2H), 3.52 (1H), 3.65 (2H), 4.30-4.49 (3H), 7.22 (1H), 7.38 (2H), 7.42 (1H), 7.49 (2H), 8.33 (1H), 8.52 (1H).

Example 245

N-(2-mesylethyl)-4-methyl-2-[(1-{4-[4-(trifluoromethyl)phenoxy]benzoyl}-piperidin-4-yl)methyl]-2H-indazole-5-carboxamide

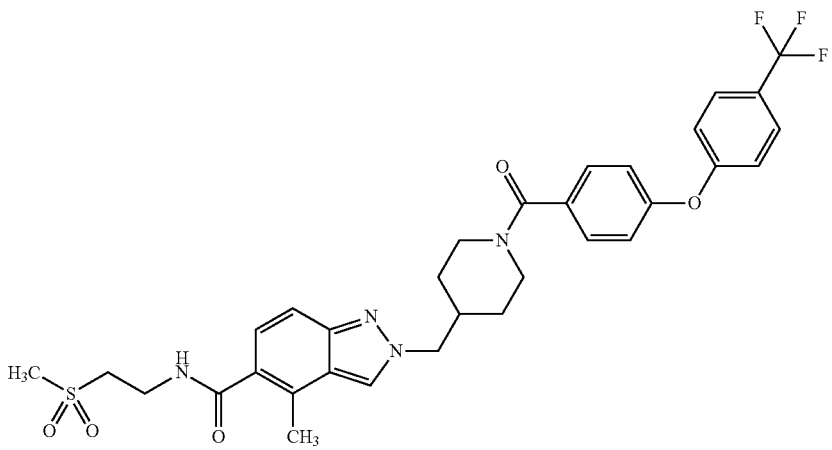 [SMILES: Cc1c(C(=O)NCCS(C)(=O)=O)ccc2nn(CC3CCN(C(=O)c4ccc(Oc5ccc(C(F)(F)F)cc5)cc4)CC3)cc12]

Analogously to Example 1, 67 mg of the title compound was obtained from 137 mg of the compound prepared in Example 245b and 41 mg of 2-mesylethylamine hydrochloride.

$^1$H-NMR (300 MHz, DMSO-d6): δ=1.15-1.62 (4H), 2.22-2.33 (1H), 2.50 (3H), 2.68-3.01 (2H), 3.02 (2H), 3.35 (1H), 3.52-3.69 (3H), 4.28-4.47 (2H), 7.12 (1H), 7.15-7.22 (2H), 7.37-7.44 (2H), 7.73 (1H), 8.32 (1H), 8.50 (1H).

249

The starting material was prepared as follows:

Example 245a

Methyl 4-methyl-2-[(1-{4-[4-(trifluoromethyl)phenoxy]benzoyl}piperidin-4-yl)methyl]-2H-indazol-5-carboxylate

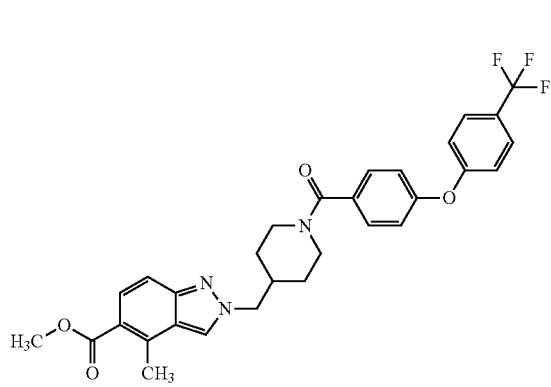 [SMILES: COC(=O)c1ccc2nn(CC3CCN(C(=O)c4ccc(Oc5ccc(C(F)(F)F)cc5)cc4)CC3)cc2c1C]

Analogously to Example 1, 2.73 g of the title compound was obtained from 3.76 g of the compound prepared in Example 238a and 3.28 g of 4-[4-(trifluoromethyl)phenoxy]benzoic acid.
$^{1}$H-NMR (300 MHz, DMSO-d6): δ=1.25 (2H), 1.35-1.70 (2H), 2.20-2.37 (1H), 2.65-2.70 (3H), 2.75-3.10 (2H), 3.52-3.72 (1H), 3.82 (4H), 4.36 (2H), 7.14 (2H), 7.20 (2H), 7.39-7.48 (3H), 7.66 (1H), 7.75 (2H), 8.70 (1H).

250

Example 245b 4-methyl-2-[(1-{4-[4-(trifluoromethyl)phenoxy]benzoyl}piperidin-4-yl)-methyl]-2H-indazol-5-carboxylic acid

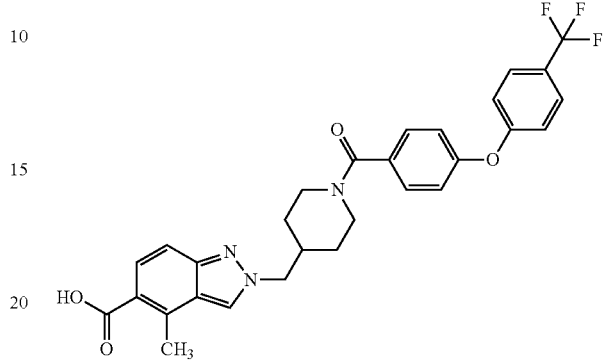

Analogously to Example 1d, 1.1 g of the title compound was obtained from 2.73 g of the ester prepared in Example 245a.

Example 246

N-(2-cyanoethyl)-4-methyl-2-[(1-{4-[4-(trifluoromethyl)phenoxy]benzoyl}piperidin-4-yl)methyl]-2H-indazole-5-carboxamide

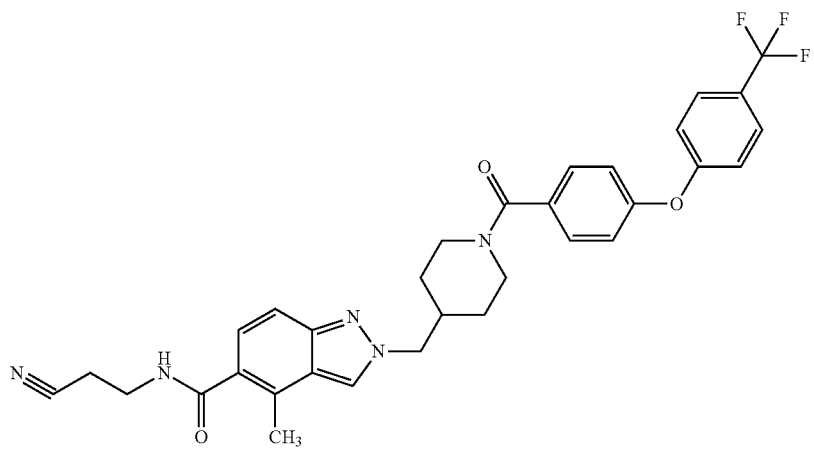 [SMILES: Cc1c(C(=O)NCCC#N)ccc2nn(CC3CCN(C(=O)c4ccc(Oc5ccc(C(F)(F)F)cc5)cc4)CC3)cc12]

Analogously to Example 1, 144 mg of the title compound was obtained from 137 mg of the compound prepared in Example 245b and 18 mg of 3-aminopropanenitrile.
$^{1}$H-NMR (300 MHz, DMSO-d6): δ=1.13-1.58 (4H), 2.21-2.33 (1H), 2.52 (3H), 2.75 (2H), 2.80-3.16 (2H), 3.44 (2H), 3.59 (1H), 4.27-4.50 (3H), 7.12 (2H), 7.15-7.21 (3H), 7.37-7.44 (3H), 7.73 (2H), 8.46 (1H), 8.51 (1H)

Example 247

N-(cyanomethyl)-4-methyl-2-[(1-{4-[4-(trifluoromethyl)phenoxy]benzoyl}piperidin-4-yl)methyl]-2H-indazole-5-carboxamide

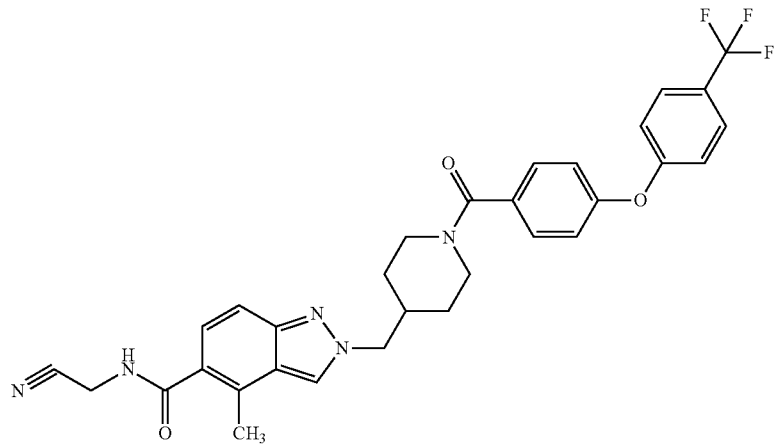 [SMILES: Cc1c(C(=O)NCC#N)ccc2nn(CC3CCN(C(=O)c4ccc(Oc5ccc(C(F)(F)F)cc5)cc4)CC3)cc12]

Analogously to Example 1, 125 mg of the title compound was obtained from 137 mg of the compound prepared in Example 245b and 24 mg of 2-aminoacetonitrile hydrochloride.

$^1$H-NMR (300 MHz, DMSO-d6): δ=1.16-1.60 (4H), 2.23-2.34 (1H), 2.53 (3H), 2.69-3.06 (2H), 3.59 (1H), 4.26 (2H), 4.29-4.50 (3H), 7.08-7.23 (5H), 7.38-7.46 (3H), 7.73 (2H), 8.54 (1H), 8.83 (1H).

Example 248

(+/−)-4-methyl-N-(3,4,5,6-tetrahydro-2H-pyran-2-ylmethyl)-2-[(1-{4-[4-(trifluoromethyl)phenoxy]benzoyl}piperidin-4-yl)methyl]-2H-indazole-5-carboxamide

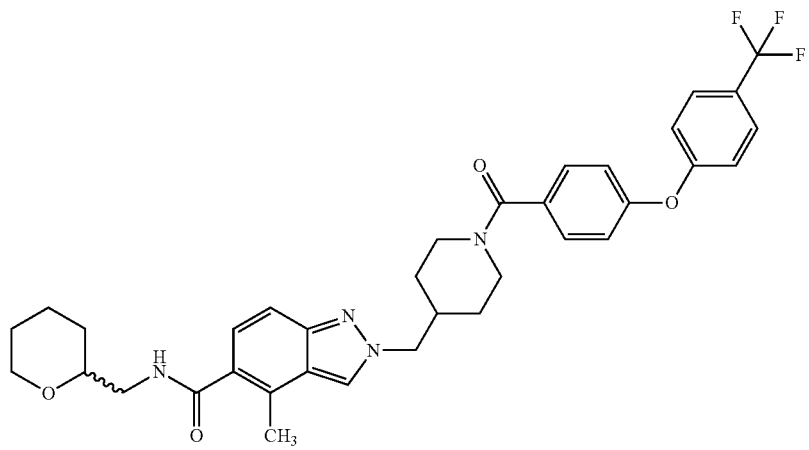 [SMILES: Cc1c(C(=O)NCC2CCCCO2)ccc2nn(CC3CCN(C(=O)c4ccc(Oc5ccc(C(F)(F)F)cc5)cc4)CC3)cc12]

Analogously to Example 1, 231 mg of the title compound was obtained from 254 mg of the compound prepared in Example 245b and 72 mg of 3,4,5,6-tetrahydro-2H-pyran-2-ylmethylamine.

$^1$H-NMR (300 MHz, DMSO-d6): δ=1.01-1.66 (10H), 2.24-2.32 (1H), 2.70-3.15 (4H), 3.21 (3H), 3.34-3.43 (1H), 3.54-3.64 (1H), 3.76-3.89 (2H), 4.32 (3H), 7.09-7.21 (5H), 7.35-7.44 (3H), 7.73 (2H), 8.09 (1H), 8.47 (1H).

Example 249

(+/−)-N-(1,4-dioxan-2-ylmethyl)-4-methyl-2-[(1-{4-[4-(trifluoromethyl)phenoxy]benzoyl}piperidin-4-yl)methyl]-2H-indazole-5-carboxamide

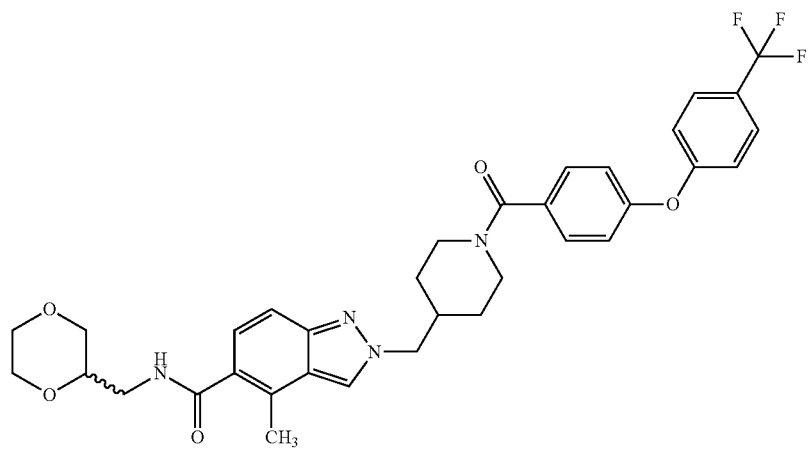

Analogously to Example 1, 280 mg of the title compound was obtained from 254 mg of the compound prepared in Example 245b and 73 mg of 1,4-dioxan-2-ylmethylamine.

$^1$H-NMR (300 MHz, DMSO-d6): δ=1.13-1.61 (4H), 2.23-2.32 (1H), 2.49 (3H), 2.75 (1H), 2.94-3.27 (4H), 3.38-3.77 (8H), 4.32 (2H), 7.09-7.21 (5H), 7.36-7.44 (3H), 7.73 (2H), 8.16 (1H), 8.48 (1H).

Example 250

2-{[1-(4-chlorobenzoyl)piperidin-4-yl]methyl}-N-(cyclobutylmethyl)-4-methyl-2H-indazole-5-carboxamide

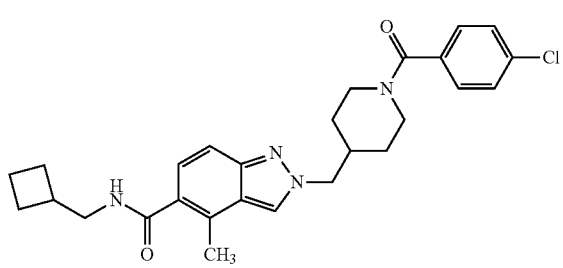 [SMILES: Cc1c(C(=O)NCC2CCC2)ccc2nn(CC3CCN(C(=O)c4ccc(Cl)cc4)CC3)cc12]

Analogously to Example 1, 79 mg of the title compound was obtained from 300 mg of the compound prepared in Example 238c and 115 mg of cyclobutylmethylamine hydrochloride.

$^1$H-NMR (300 MHz, DMSO-d6): δ=1.16-1.58 (4H), 1.64-1.86 (4H), 1.90-2.01 (2H), 2.19-2.32 (1H), 2.48 (3H), 2.50 (1H), 2.66-3.05 (2H), 3.19-3.25 (2H), 3.48 (1H), 4.27-4.47 (3H), 7.12 (1H), 7.31-7.40 (3H), 7.46 (2H), 8.09 (1H), 8.46 (1H).

Example 251

2-{[1-(4-chlorobenzoyl)piperidin-4-yl]methyl}-N-(2,2-dimethylpropyl)-4-methyl-2H-indazole-5-carboxamide

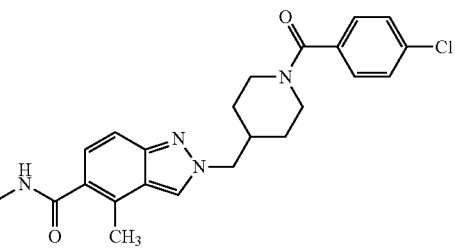

Analogously to Example 1, 108 mg of the title compound was obtained from 300 mg of the compound prepared in Example 238c and 83 mg of 2,2-dimethylpropan-1-amine $^1$H-NMR (300 MHz, DMSO-d6): δ=0.91 (9H), 1.17-1.63 (4H), 2.24-2.36 (1H), 2.52 (3H), 2.70-3.04 (2H), 3.07 (2H), 3.52 (1H), 4.30-4.50 (3H), 7.17 (1H), 7.38 (2H), 7.42 (1H), 7.49 (2H), 8.07 (1H), 8.49 (1H).

Example 252

2-{[1-(4-chlorobenzoyl)piperidin-4-yl]methyl}-N-(2-hydroxyethyl)-4-methyl-2H-indazole-5-carboxamide

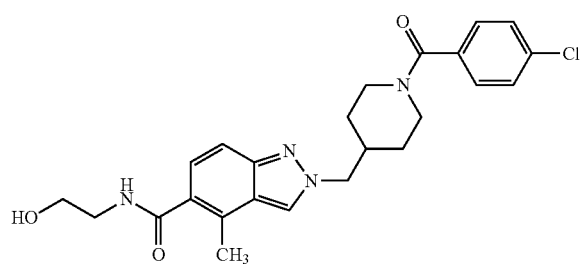 [SMILES: Cc1c(C(=O)NCCO)ccc2nn(CC3CCN(C(=O)c4ccc(Cl)cc4)CC3)cc12]

Analogously to Example 1, 84 mg of the title compound was obtained from 370 mg of the compound prepared in Example 238c and 54 mg of 2-aminoethanol.

$^1$H-NMR (300 MHz, DMSO-d6): δ=1.14-1.64 (4H), 2.24-2.35 (1H), 2.53 (3H), 2.69-3.09 (2H), 3.30 (2H), 3.43-3.58 (3H), 4.27-4.50 (3H), 4.67 (1H), 7.20 (1H), 7.35-7.43 (3H), 7.49 (2H), 8.02 (1H), 8.49 (1H).

Example 253

2-{[1-(4-chlorobenzoyl)piperidin-4-yl]methyl}-N-(3-hydroxypropyl)-4-methyl-2H-indazole-5-carboxamide

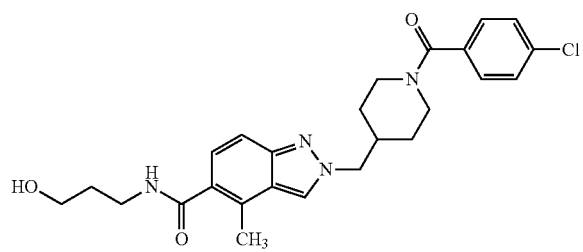 [SMILES: Cc1c(C(=O)NCCCO)ccc2nn(CC3CCN(C(=O)c4ccc(Cl)cc4)CC3)cc12]

Analogously to Example 1, 95 mg of the title compound was obtained from 370 mg of the compound prepared in Example 238c and 66 mg of 3-aminopropan-1-ol.

$^1$H-NMR (300 MHz, DMSO-d6): δ=1.17-1.60 (4H), 1.66 (2H), 2.22-2.35 (1H), 2.53 (3H), 2.70-3.09 (2H), 3.27 (2H), 3.47 (2H), 3.47-3.67 (1H), 4.34 (2H), 4.41 (1H), 4.45 (1H), 7.17 (1H), 7.35-7.43 (3H), 7.49 (2H), 8.07 (1H), 8.49 (1H).

Example 254

4-methoxy-N-(2-methoxyethyl)-2-({1-[4-(trifluoromethoxy)benzoyl]azetidin-3-yl}methyl)-2H-indazole-5-carboxamide

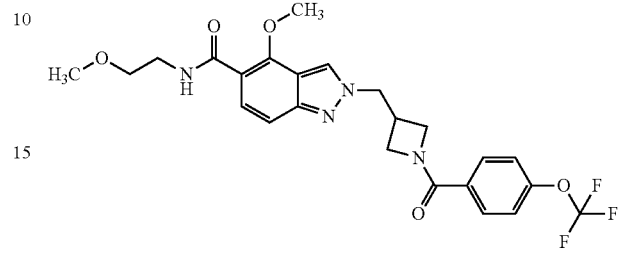

Analogously to Example 1, 90 mg of the title compound was obtained from 100 mg of the compound prepared in Example 214c and 97 mg of 4-(trifluoromethoxy)benzoic acid in DMF.

$^1$H-NMR (400 MHz, DMSO-d$_6$): δ [ppm], 3.24-3.29 (1H), 3.29-3.32 (3H), 3.43-3.51 (4H), 3.91-4.04 (1H), 4.10-4.18 (1H), 4.20 (3H), 4.22-4.29 (1H), 4.44 (1H), 4.70 (2H), 7.24 (1H), 7.37-7.51 (2H), 7.66 (1H), 7.70-7.80 (2H), 8.22 (1H), 8.91 (1H).

Example 255

2-({1-[2-fluoro-4-(trifluoromethyl)benzoyl]azetidin-3-yl}methyl)-4-methoxy-N-(2-methoxyethyl)-2H-indazole-5-carboxamide

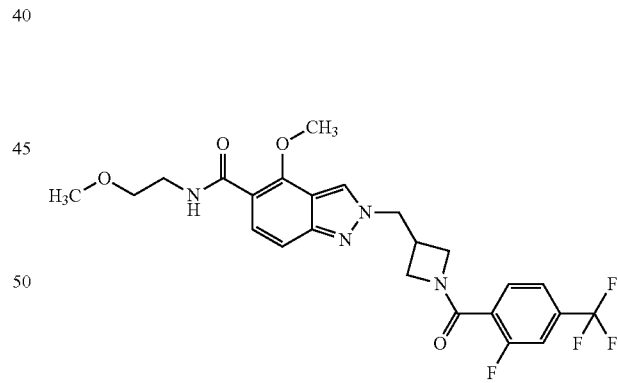

Analogously to Example 1, 40 mg of the title compound was obtained from 100 mg of the compound prepared in Example 214c and 98 mg of 2-fluoro-4-(trifluoromethyl)benzoic acid in DMF.

$^1$H-NMR (400 MHz, DMSO-d$_6$): δ [ppm]=3.30 (4H), 3.44-3.50 (4H), 3.94-4.04 (2H), 4.15 (2H), 4.20 (3H), 4.70 (2H), 7.24 (1H), 7.60-7.75 (3H), 7.78-7.89 (1H), 8.16-8.27 (1H), 8.90 (1H).

Example 256

2-({1-[4-chloro-3-(trifluoromethyl)benzoyl]azetidin-3-yl}methyl)-4-methoxy-N-(2-methoxyethyl)-2H-indazole-5-carboxamide

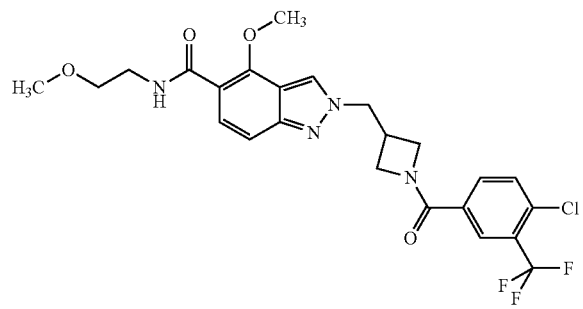 [SMILES: COCCNC(=O)c1ccc2nn(CC3CN(C(=O)c4ccc(Cl)c(C(F)(F)F)c4)C3)cc2c1OC]

Analogously to Example 1, 40 mg of the title compound was obtained from 100 mg of the compound prepared in Example 214c and 106 mg of 4-chloro-3-(trifluoromethyl) benzoic acid in DMF.

$^1$H-NMR (400 MHz, DMSO-d$_6$): δ [ppm], 3.30 (4H), 3.43-3.53 (4H), 3.95-4.05 (1H), 4.20 (4H), 4.23-4.31 (1H), 4.47 (1H), 4.71 (2H), 7.23 (1H), 7.67 (1H), 7.78-7.85 (1H), 7.86-7.93 (1H), 7.96 (1H), 8.22 (1H), 8.90 (1H).

Example 257

2-{[1-(4-chloro-2-fluorobenzoyl)azetidin-3-yl]methyl}-4-methoxy-N-(2-methoxyethyl)-2H-indazole-5-carboxamide

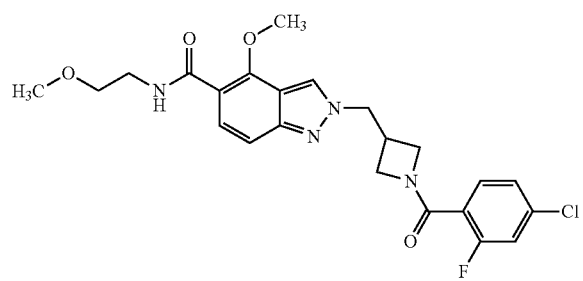 [SMILES: COCCNC(=O)c1ccc2nn(CC3CN(C(=O)c4ccc(Cl)cc4F)C3)cc2c1OC]

Analogously to Example 1, 20 mg of the title compound was obtained from 100 mg of the compound prepared in Example 214c and 82 mg of 4-chloro-2-fluorobenzoic acid in DMF.

$^1$H-NMR (400 MHz, DMSO-d$_6$): δ [ppm], 3.30 (4H), 3.42-3.51 (4H), 3.98 (2H), 4.14 (2H), 4.20 (3H), 4.69 (2H), 7.24 (1H), 7.38 (1H), 7.48 (1H), 7.56 (1H), 7.66 (1H), 8.15-8.30 (1H), 8.90 (1H).

Example 258

2-{[1-(4-chlorobenzoyl)azetidin-3-yl]methyl}-4-methoxy-N-(2-morpholinoethyl)-2H-indazole-5-carboxamide

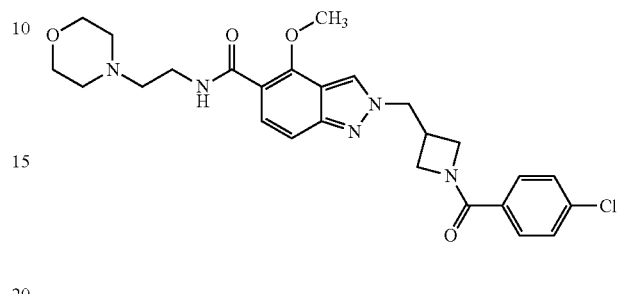

Analogously to Example 1b Version B, 67 mg of the title compound was obtained from 66 mg of the compound prepared in Example 258d and 32 mg of 2-morpholinoethylamine in DMF.

$^1$H-NMR (400 MHz, DMSO-d$_6$): δ [ppm], 2.44 (4H), 3.21-3.36 (3H), 3.42 (2H), 3.61 (4H), 3.88-4.04 (1H), 4.07-4.18 (1H), 4.23 (4H), 4.35-4.50 (1H), 4.70 (2H), 7.25 (1H), 7.41-7.56 (2H), 7.59-7.66 (2H), 7.70 (1H), 8.32 (1H), 8.91 (1H).

The starting material was prepared as follows:

Example 258a

Methyl 2-{[1-(tert-butoxycarbonyl)azetidin-3-yl]methyl}-4-methoxy-2H-indazol-5-carboxylate

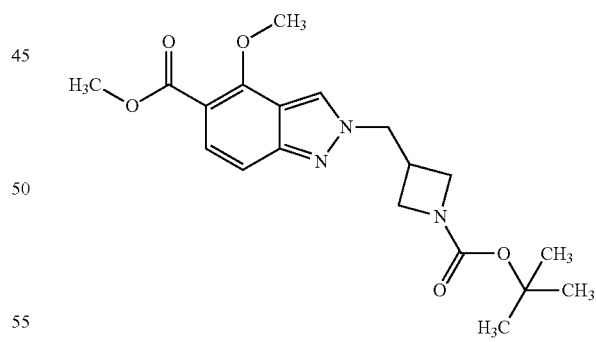

Analogously to Example 1e, 448 mg of the title compound was obtained from 750 mg of the compound prepared in Example 214a and 546 mg of methanol.

$^1$H-NMR (400 MHz, DMSO-d$_6$): δ [ppm], 1.27-1.44 (9H), 3.01-3.22 (1H), 3.78 (5H), 3.85-3.99 (2H), 4.14 (3H), 4.64 (2H), 7.24 (1H), 7.51 (1H), 8.94 (1H).

Example 258b

Methyl 2-(azetidin-3-ylmethyl)-4-methoxy-2H-indazol-5-carboxylate

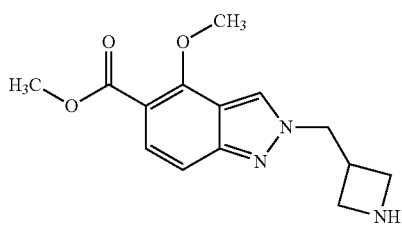 [SMILES: COC(=O)c1ccc2nn(CC3CNC3)cc2c1OC]

800 mg of 258a were first placed in 40 ml acetone, treated with 40 ml of semiconcentrated hydrochloric acid, stirred until complete conversion and concentrated to dryness. Yield: 414 mg of the title compound.

$^1$H-NMR (400 MHz, DMSO-$d_6$): δ [ppm], 3.39 (1H), 3.79 (3H), 3.84-3.95 (2H), 3.96-4.07 (2H), 4.15 (3H), 4.72 (2H), 7.25 (1H), 7.52 (1H), 8.92 (1H).

Example 258c

Methyl 2-{[1-(4-chlorobenzoyl)azetidin-3-yl]methyl}-4-methoxy-2H-indazol-5-carboxylate

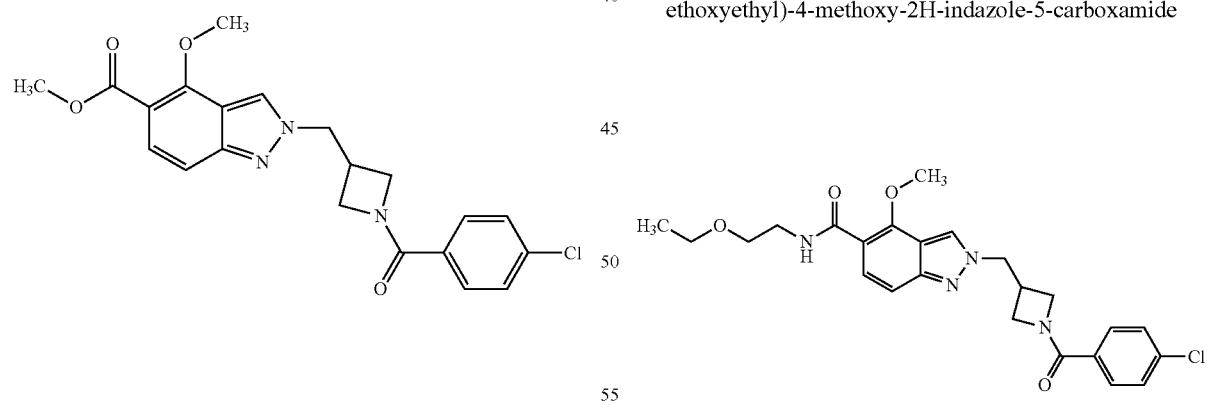

404 mg of 258b were first placed in 30 ml DCM at 0° C., treated with 0.21 ml of 4-chlorobenzoyl chloride and 0.75 ml of N-ethyldiisopropylamine and stirred at room temperature until complete conversion. For the work-up, the reaction solution was treated with saturated sodium hydrogen carbonate solution, extracted with DCM and the combined organic phases dried with sodium sulphate and concentrated to dryness. This yielded 608 mg of the title compound, which was used in the next step without further purification.

Example 258d

2-{[1-(4-chlorobenzoyl)azetidin-3-yl]methyl}-4-methoxy-2H-indazol-5-carboxylic acid

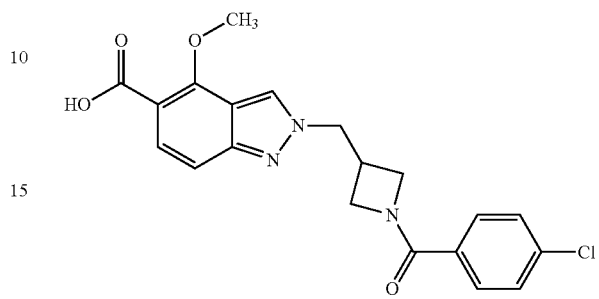

550 mg of 258c were first placed in 20 ml ethanol, treated with 20 ml of 2N sodium hydroxide and stirred until complete conversion. For the work-up, the reaction solution was adjusted to a pH of 3 with 1N hydrochloric acid, extracted with ethyl acetate, and the combined organic phases dried with sodium sulphate and concentrated to dryness. Yield after purification by column chromatography on silica gel with a hexane/ethyl acetate gradient: 213 mg of the title compound.

$^1$H-NMR (400 MHz, DMSO-$d_6$): δ [ppm], 3.27 (1H), 3.97 (1H), 4.07-4.17 (4H), 4.24 (1H), 4.42 (1H), 4.70 (2H), 7.22 (1H), 7.46-7.57 (3H), 7.59-7.68 (2H), 8.88 (1H), 12.61 (m, 1H).

Example 259

2-{[1-(4-chlorobenzoyl)azetidin-3-yl]methyl}-N-(2-ethoxyethyl)-4-methoxy-2H-indazole-5-carboxamide Analogously to Example 1b Version B, 30 mg of the title compound was obtained from 66 mg of the compound prepared in Example 258d and 22 mg of 2-ethoxyethylamine in DMF.

$^1$H-NMR (400 MHz, DMSO-$d_6$): δ [ppm], 1.07-1.21 (3H), 3.30 (1H), 3.40-3.57 (6H), 3.90-4.02 (1H), 4.08-4.17 (1H), 4.21 (4H), 4.34-4.48 (1H), 4.70 (2H), 7.24 (1H), 7.45-7.57 (2H), 7.60-7.74 (3H), 8.24 (1H), 8.91 (1H).

Example 260

2-{[1-(4-chlorobenzoyl)azetidin-3-yl]methyl}-N-[2-(3,3-difluoropyrrolidin-1-yl)ethyl]-4-methoxy-2H-indazole-5-carboxamide

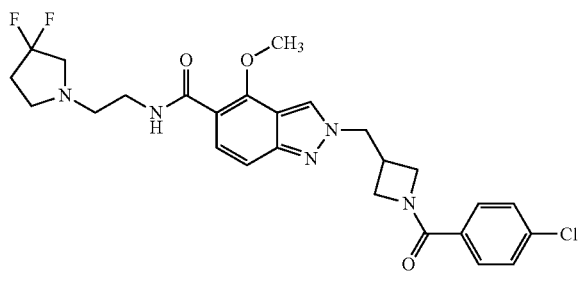 [SMILES: COc1c(C(=O)NCCN2CCC(F)(F)C2)ccc2nn(CC3CN(C(=O)c4ccc(Cl)cc4)C3)cc12]

Analogously to Example 1b Version B, 58 mg of the title compound was obtained from 66 mg of the compound prepared in Example 258d and 37 mg of 2-(3,3-difluoropyrrolidin-1-yl)ethylamine in DMF.

$^1$H-NMR (400 MHz, DMSO-$d_6$): δ [ppm], 2.27 (2H), 2.64 (2H), 2.77 (2H), 2.96 (2H), 3.22-3.30 (1H), 3.41 (2H), 3.92-4.01 (1H), 4.11 (1H), 4.19 (4H), 4.35-4.48 (1H), 4.70 (2H), 7.24 (1H), 7.51 (2H), 7.57-7.75 (3H), 8.32 (1H), 8.90 (1H).

Example 261

2-{[1-(4-chlorobenzoyl)piperidin-4-yl]methyl}-4-methoxy-N-(2-morpholinoethyl)-2H-indazole-5-carboxamide

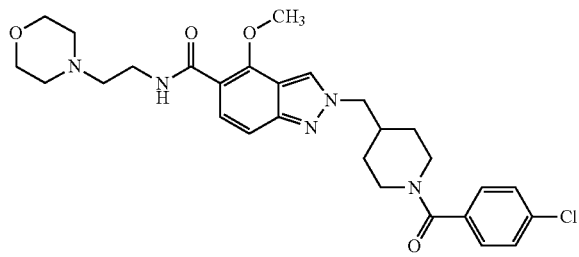 [SMILES: COc1c(C(=O)NCCN2CCOCC2)ccc2nn(CC3CCN(C(=O)c4ccc(Cl)cc4)CC3)cc12]

Analogously to Example 1b, Version B, 77 mg of the title compound was obtained from 100 mg of the compound prepared in Example 261e and 46 mg of 2-morpholinoethylamine in DMF.

$^1$H-NMR (400 MHz, DMSO-$d_6$): δ [ppm], 1.11-1.33 (2H), 1.35-1.75 (2H), 2.18-2.39 (1H), 2.65-2.88 (2H), 2.90-3.23 (3H), 3.41-3.82 (8H), 3.84-4.12 (2H), 4.24 (3H), 4.35 (3H), 7.26 (1H), 7.33-7.44 (2H), 7.46-7.58 (2H), 7.69 (1H), 8.27-8.52 (1H), 8.87 (1H).

The starting material was prepared as follows:

Example 261a

Tert-butyl 4-[(5-bromo-4-methoxy-2H-indazol-2-yl)methyl]piperidin-1-carboxylate

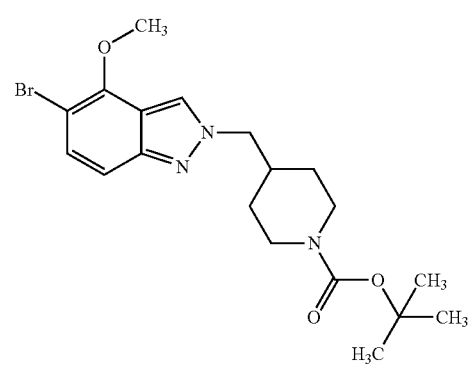 [SMILES: COc1c(Br)ccc2nn(CC3CCN(C(=O)OC(C)(C)C)CC3)cc12]

Analogously to Example 1c, 5.57 g of the title compound was obtained from 9.65 g of 5-bromo-4-methoxy-1H-indazole and 23.55 g of tert-butyl-4-[(tosyloxy)methyl]piperidin-1-carboxylate.

$^1$H-NMR (400 MHz, chloroform-d): δ [ppm], 1.16-1.31 (2H), 1.39-1.49 (9H), 1.52-1.64 (2H), 2.16-2.36 (1H), 2.56-2.80 (2H), 4.11 (5H), 4.26 (2H), 7.28-7.33 (1H), 7.34-7.39 (1H), 7.99 (1H).

Example 261b

Methyl 2-{[1-(tert-butoxycarbonyl)piperidin-4-yl]methyl}-4-methoxy-2H-indazol-5-carboxylate

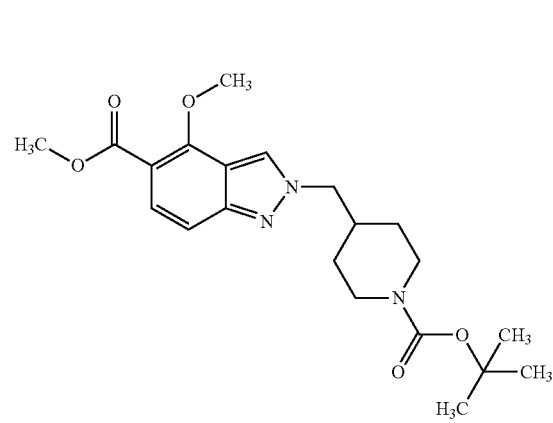 [SMILES: COC(=O)c1ccc2nn(CC3CCN(C(=O)OC(C)(C)C)CC3)cc2c1OC]

Analogously to Example 1e, 1.1 g of the title compound was obtained from 2.4 g of the compound prepared in Example 261a and 1.63 g of methanol.

Example 261c

Methyl 4-methoxy-2-(4-piperidylmethyl)-2H-indazol-5-carboxylate

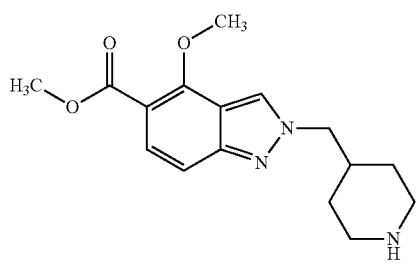 [SMILES: COC(=O)c1ccc2nn(CC3CCNCC3)cc2c1OC]

Analogously to Example 258b, from 1.1 g of the compound prepared in Example 261b 1.1 g of the title compound was obtained, which was reacted in the next step without further purification.

Example 261d

Methyl 2-{[1-(4-chlorobenzoyl)piperidin-4-yl]methyl}-4-methoxy-2H-indazol-5-carboxylate

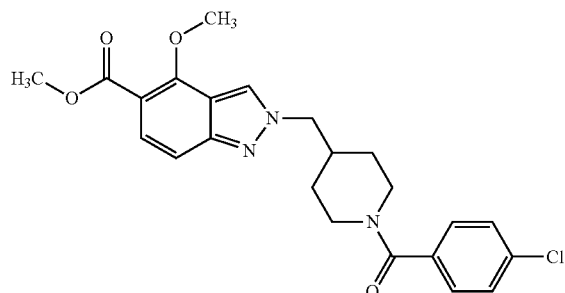

Analogously to Example 258c, from 1.1 g of the compound prepared in Example 261c and 762 mg of 4-chlorobenzoyl chloride, 980 mg of the title compound was obtained after purification by column chromatography on silica gel with a hexane/ethyl acetate gradient.

$^1$H-NMR (300 MHz, DMSO-$d_6$): δ [ppm], 1.24 (2H), 1.36-1.76 (2H), 2.18-2.40 (1H), 2.65-2.88 (1H), 2.91-3.12 (1H), 3.42-3.67 (1H), 3.78 (3H), 4.05-4.21 (3H), 4.35 (3H), 7.24 (1H), 7.34-7.43 (2H), 7.45-7.56 (3H), 8.86 (1H).

Example 261e

2-{[1-(4-chlorobenzoyl)piperidin-4-yl]methyl}-4-methoxy-2H-indazol-5-carboxylic acid

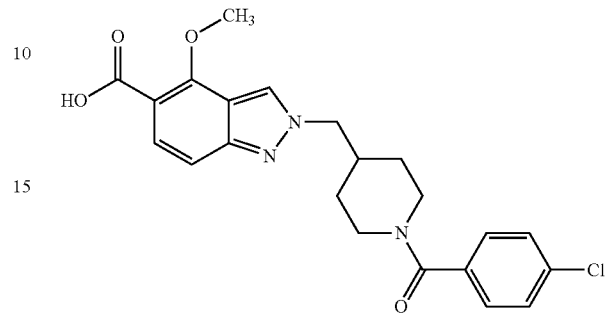 [SMILES: COC(=O)c1ccc2nn(CC3CCN(C(=O)c4ccc(Cl)cc4)CC3)cc2c1OC]

Analogously to Example 258d, 547 mg of the title compound was obtained from 980 mg of the compound prepared in Example 261d.

$^1$H-NMR (400 MHz, DMSO-$d_6$): δ [ppm], 1.12-1.35 (2H), 1.35-1.73 (2H), 2.21-2.40 (1H), 2.63-3.12 (2H), 3.14-3.70 (3H), 4.34 (3H), 5.76 (s, 1H), 7.21 (1H), 7.32-7.45 (2H), 7.46-7.58 (3H), 8.76 (1H).

Example 262

2-{[1-(4-chlorobenzoyl)piperidin-4-yl]methyl}-4-methoxy-N-(2-methoxyethyl)-2H-indazole-5-carboxamide

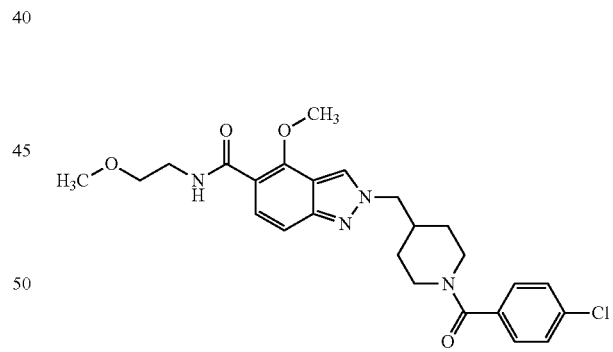

Analogously to Example 1b, Version B, 50 mg of the title compound was obtained from 100 mg of the compound prepared in Example 261e and 26 mg of 2-methoxyethylamine in DMF.

$^1$H-NMR (400 MHz, DMSO-$d_6$): δ [ppm], 1.11-1.35 (2H), 1.35-1.72 (2H), 2.21-2.39 (1H), 2.69-2.88 (1H), 2.92-3.11 (1H), 3.30 (s, 3H), 3.38-3.64 (5H), 4.20 (3H), 4.34 (3H), 7.25 (1H), 7.34-7.43 (2H), 7.45-7.57 (2H), 7.66 (1H), 8.22 (1H), 8.83 (1H).

Example 263

2-{[1-(4-chlorobenzoyl)piperidin-4-yl]methyl}-4-methoxy-N-(2,2,2-trifluoro-ethyl)-2H-indazole-5-carboxamide

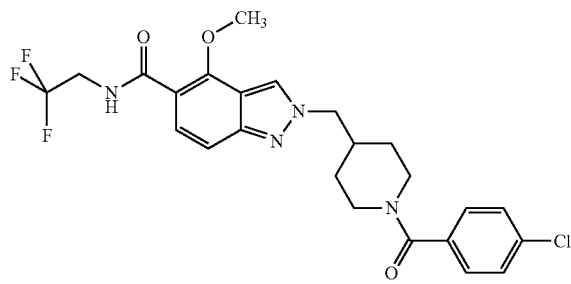 [SMILES: COc1c(C(=O)NCC(F)(F)F)ccc2nn(CC3CCN(C(=O)c4ccc(Cl)cc4)CC3)cc12]

Analogously to Example 1b, Version B, 68 mg of the title compound was obtained from 100 mg of the compound prepared in Example 261e and 35 mg of 2,2,2-trifluoroethylamine in DMF.

$^1$H-NMR (400 MHz, DMSO-$d_6$): δ [ppm], 1.09-1.35 (2H), 1.37-1.75 (2H), 2.21-2.41 (1H), 2.69-2.88 (1H), 2.92-3.19 (1H), 3.42-3.69 (1H), 4.13 (2H), 4.23 (3H), 4.35 (3H), 7.26 (1H), 7.34-7.45 (2H), 7.46-7.55 (2H), 7.61 (1H), 8.59 (1H), 8.88 (1H).

Example 264

2-{[1-(4-chlorobenzoyl)piperidin-4-yl]methyl}-N-(2-ethoxyethyl)-4-methoxy-2H-indazole-5-carboxamide

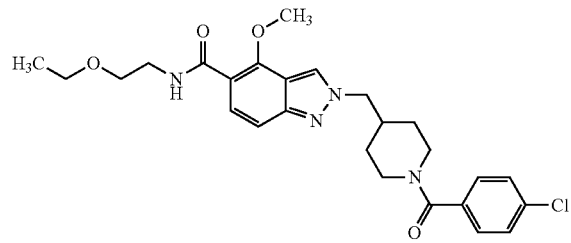 [SMILES: CCOCCNC(=O)c1ccc2nn(CC3CCN(C(=O)c4ccc(Cl)cc4)CC3)cc2c1OC]

Analogously to Example 1b, Version B, 60 mg of the title compound was obtained from 100 mg of the compound prepared in Example 261e and 31 mg of 2-ethoxyethylamine in DMF.

$^1$H-NMR (400 MHz, DMSO-$d_6$): δ [ppm], 1.14 (3H), 1.19-1.35 (2H), 1.37-1.72 (2H), 2.23-2.43 (1H), 2.68-2.88 (1H), 2.91-3.15 (1H), 3.41-3.56 (m, 7H), 4.20 (3H), 4.34 (3H), 7.25 (1H), 7.33-7.45 (2H), 7.46-7.55 (2H), 7.67 (1H), 8.23 (1H), 8.83 (1H).

Example 265

2-{[1-(4-chlorobenzoyl)piperidin-4-yl]methyl}-4-methoxy-N-{2-[(trifluoro-methyl)sulphanyl]ethyl}-2H-indazole-5-carboxamide

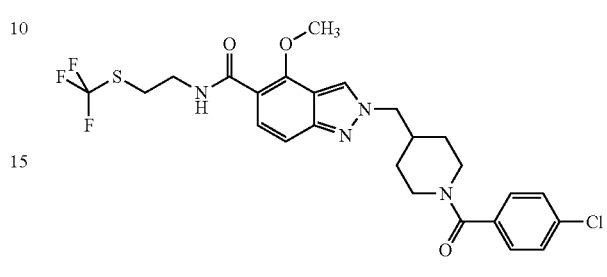

Analogously to Example 1b, Version B, 68 mg of the title compound was obtained from 100 mg of the compound prepared in Example 261e and 51 mg of 2-[(trifluoromethyl)sulphanyl]-ethylamine in DMF.

$^1$H-NMR (400 MHz, DMSO-$d_6$): δ [ppm], 1.14-1.35 (2H), 1.36-1.72 (2H), 2.18-2.40 (1H), 2.66-2.87 (1H), 2.91-3.11 (1H), 3.21 (2H), 3.42-3.70 (3H), 4.22 (3H), 4.34 (3H), 7.24 (1H), 7.32-7.45 (2H), 7.46-7.55 (2H), 7.64 (1H), 8.45 (1H), 8.85 (1H).

Example 266

4-methoxy-N-(2-methoxyethyl)-2-({1-[4-(trifluoromethoxy)benzoyl]piperidin-4-yl}methyl)-2H-indazole-5-carboxamide

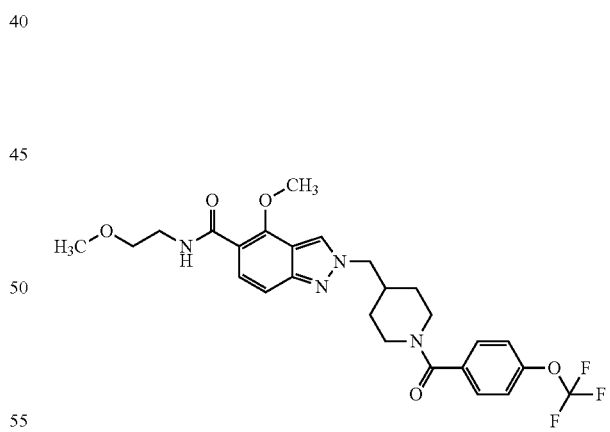

Analogously to Example 1b, Version B, 84 mg of the title compound was obtained from 100 mg of the compound prepared in Example 266b and 89 mg of 4-(trifluoromethoxy)benzoic acid in DMF.

LC-MS: $R_t$=1.16 min, MS (ES+): m/z=435 (M+H)$^+$.

The starting material was prepared as follows:

Example 266a

Tert-butyl 4-({4-methoxy-5-[N-(2-methoxyethyl)carbamoyl]-2H-indazol-2-yl}methyl)piperidin-1-carboxylate

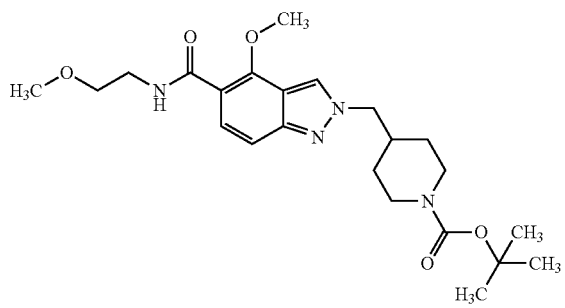 [SMILES: COCCNC(=O)c1ccc2nn(CC3CCN(C(=O)OC(C)(C)C)CC3)cc2c1OC]

3 g of compound 261a, 1.59 g of 2-methoxyethylamine, 1.87 g of molybdenum hexacarbonyl, 204 mg of tri-tert-butylphosphine tetrafluoroborate and 316 mg of palladium (II) acetate were first suspended in 100 ml 1,4-dioxan. Then 2.25 g of sodium carbonate and a few drops of water were added, and the mixture stirred for 25 mins at 140° C. and 150 watts in the microwave. The reaction mixture was concentrated and the residue was purified by column chromatography on silica gel using a hexane/ethyl acetate/methanol gradient. Yield: 1.3 g of the title compound.

$^1$H-NMR (300 MHz, DMSO-$d_6$): δ [ppm], 0.99-1.22 (2H), 1.29-1.55 (11H), 2.03-2.33 (1H), 2.60-2.83 (2H), 3.28-3.31 (3H), 3.43-3.52 (4H), 3.82-4.03 (2H), 4.20 (3H), 4.31 (2H), 7.25 (1H), 7.66 (1H), 8.21 (1H), 8.82 (1H).

Example 266b 4-methoxy-N-(2-methoxyethyl)-2-(4-piperidylmethyl)-2H-indazol-5-carboxamide

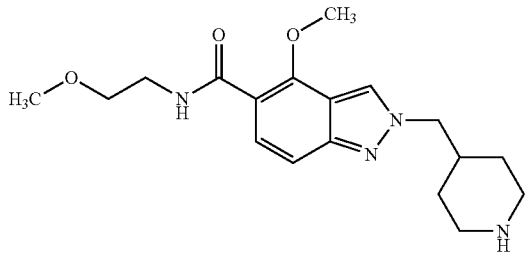 [SMILES: COCCNC(=O)c1ccc2nn(CC3CCNCC3)cc2c1OC]

Analogously to Example 258b, from 1.3 g of the compound prepared in Example 266a, 1.48 g of the title compound was obtained, which was used in the subsequent reactions without further purification.

Example 267

2-({1-[2-fluoro-4-(trifluoromethyl)benzoyl]piperidin-4-yl}methyl)-4-methoxy-N-(2-methoxyethyl)-2H-indazole-5-carboxamide

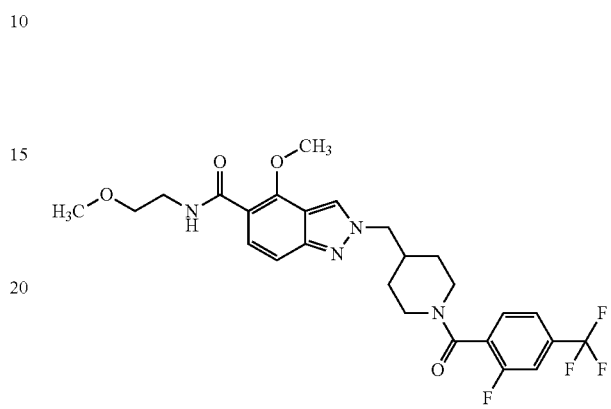

Analogously to Example 1b, Version B, 20 mg of the title compound was obtained from 100 mg of the compound prepared in Example 266b and 90 mg of 2-fluoro-4-(trifluoromethyl)benzoic acid in DMF.

$^1$H-NMR (400 MHz, DMSO-$d_6$): δ [ppm], 1.05-1.36 (2H), 1.39-1.53 (1H), 1.56-1.72 (1H), 2.21-2.40 (1H), 2.75-2.90 (1H), 2.92-3.15 (1H), 3.27-3.35 (4H), 3.44-3.53 (4H), 4.20 (3H), 4.27-4.43 (2H), 4.44-4.58 (1H), 7.25 (1H), 7.54-7.74 (3H), 7.81 (1H), 8.20 (1H), 8.83 (1H).

Example 268

4-methoxy-N-(2-methoxyethyl)-2-({1-[4-(pentafluoro-$\lambda^6$-sulphanyl)benzoyl]-piperidin-4-yl}methyl)-2H-indazole-5-carboxamide

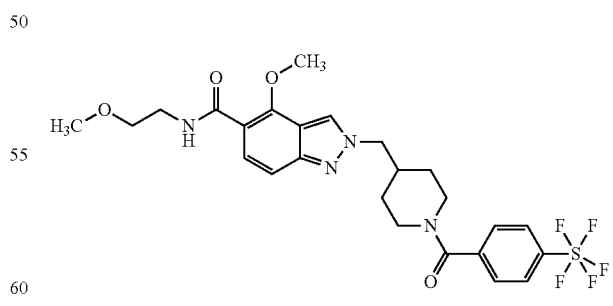

Analogously to Example 1b, Version B, 39 mg of the title compound was obtained from 100 mg of the compound prepared in Example 266b and 107 mg of 4-(pentafluoro-$\lambda^6$-sulphanyl)benzoic acid in DMF.

LC-MS: $R_t$=1.18 min, MS (ES+): m/z=577 (M+H)$^+$.

Example 269

4-methoxy-N-(2-methoxyethyl)-2-[(1-{4-[(trifluoromethyl)sulphanyl]benzoyl}-piperidin-4-yl)methyl]-2H-indazole-5-carboxamide

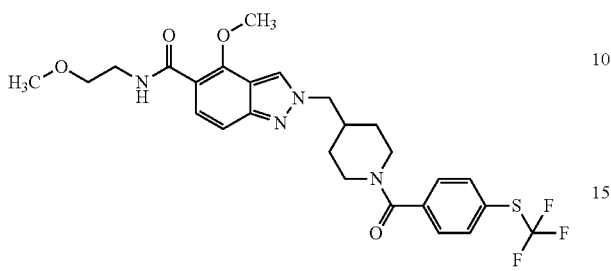

Analogously to Example 1b, Version B, 25 mg of the title compound was obtained from 100 mg of the compound prepared in Example 266b and 96 mg of 4-[(trifluoromethyl)sulphanyl]benzoic acid in DMF.

$^1$H-NMR (400 MHz, DMSO-d6): δ [ppm], 1.09-1.37 (2H), 1.38-1.72 (2H), 2.23-2.39 (1H), 2.70-2.93 (1H), 2.95-3.16 (1H), 3.30 (3H), 3.40-3.55 (5H), 4.20 (3H), 4.35 (d, 3H), 7.25 (1H), 7.46-7.58 (2H), 7.66 (1H), 7.78 (2H), 8.20 (1H), 8.82 (1H).

Example 270

2-({1-[4-chloro-3-(trifluoromethyl)benzoyl]piperidin-4-yl}methyl)-4-methoxy-N-(2-methoxyethyl)-2H-indazole-5-carboxamide

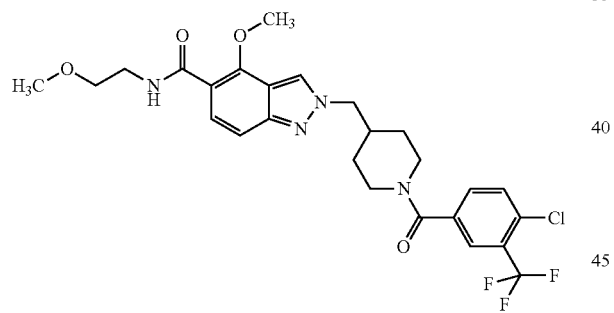

Analogously to Example 1b, Version B, 27 mg of the title compound was obtained from 100 mg of the compound prepared in Example 266b and 97 mg of 4-chloro-3-(trifluoromethyl)benzoic acid in DMF.

$^1$H-NMR (400 MHz, DMSO-d$_6$): δ [ppm], 1.15-1.37 (2H), 1.38-1.73 (2H), 2.14-2.41 (1H), 2.70-2.88 (1H), 2.95-3.18 (1H), 3.30 (3H), 3.39-3.62 (5H), 4.20 (3H), 4.35 (3H), 7.25 (1H), 7.59-7.73 (2H), 7.75-7.86 (2H), 8.20 (1H), 8.82 (1H).

Example 271

2-{[1-(4-chloro-2-fluorobenzoyl)piperidin-4-yl]methyl}-4-methoxy-N-(2-methoxyethyl)-2H-indazole-5-carboxamide

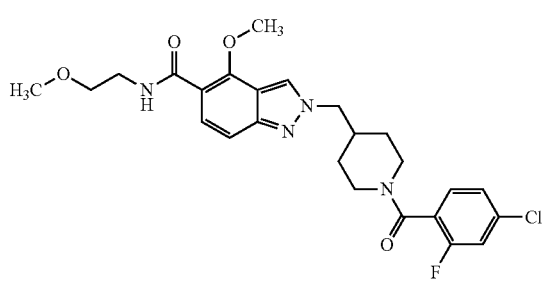 [SMILES: COCCNC(=O)c1ccc2nn(CC3CCN(C(=O)c4ccc(Cl)cc4F)CC3)cc2c1OC]

Analogously to Example 1b, Version B, 17 mg of the title compound was obtained from 100 mg of the compound prepared in Example 266b and 75 mg of 4-chloro-2-fluorobenzoic acid in DMF.

$^1$H-NMR (400 MHz, DMSO-d$_6$): δ [ppm]=1.08-1.33 (2H), 1.37-1.52 (1H), 1.53-1.70 (1H), 2.20-2.42 (1H), 2.72-2.88 (1H), 2.94-3.12 (1H), 3.30 (3H), 3.37 (1H), 3.43-3.51 (4H), 4.20 (3H), 4.34 (2H), 4.42-4.55 (1H), 7.25 (1H), 7.31-7.48 (2H), 7.55 (1H), 7.66 (1H), 8.20 (1H), 8.83 (1H).

Example 272

2-({1-[3-fluoro-4-(trifluoromethoxy)benzoyl]piperidin-4-yl}methyl)-4-methoxy-N-(2-methoxyethyl)-2H-indazole-5-carboxamide

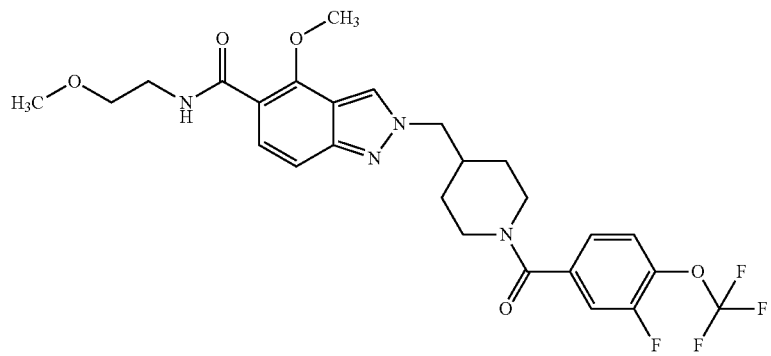 [SMILES: COCCNC(=O)c1ccc2nn(CC3CCN(C(=O)c4ccc(OC(F)(F)F)c(F)c4)CC3)cc2c1OC]

Analogously to Example 1b, Version B, 12 mg of the title compound was obtained from 100 mg of the compound prepared in Example 266b and 97 mg of 3-fluoro-4-(trifluoromethoxy)benzoic acid in DMF.

LC-MS: $R_t$=1.18 min, MS (ES+): m/z=553 (M+H)$^+$.

Example 273

4-methoxy-N-(2-methoxyethyl)-2-({1-[(1-methyl-1H-indol-3-yl)carbonyl]-piperidin-4-yl}methyl)-2H-indazole-5-carboxamide

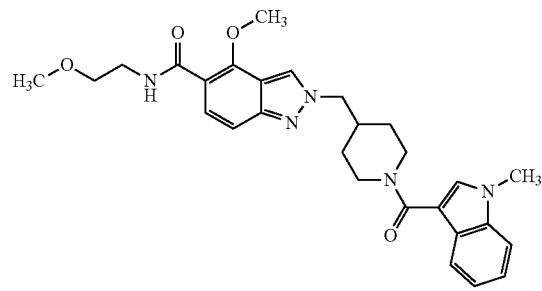

Analogously to Example 1b, Version B, 19 mg of the title compound was obtained from 100 mg of the compound prepared in Example 266b and 76 mg of 1-methyl-1H-indol-3-carboxylic acid in DMF.

$^1$H-NMR (300 MHz, DMSO-d$_6$): δ [ppm], 1.11-1.40 (2H), 1.54 (2H), 2.18-2.42 (1H), 2.93 (2H), 3.30 (3H), 3.40-3.45 (4H), 3.70-3.91 (3H), 4.12-4.48 (7H), 7.00-7.34 (3H), 7.48 (1H), 7.66 (3H), 8.22 (1H), 8.84 (1H).

Example 274

2-{[1-(4-chlorobenzoyl)piperidin-4-yl]methyl}-4-ethoxy-N-(2-methoxyethyl)-2H-indazole-5-carboxamide

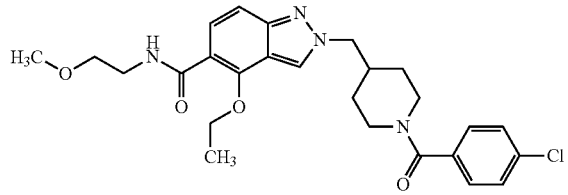 [SMILES: CCOc1c(C(=O)NCCOC)ccc2nn(CC3CCN(C(=O)c4ccc(Cl)cc4)CC3)cc12]

Analogously to Example 1b, Version B, 47 mg of the title compound was obtained from 110 mg of the compound prepared in Example 274c and 72 mg of 4-chlorobenzoic acid in DMF.

$^1$H-NMR (400 MHz, DMSO-d$_6$): δ [ppm], 1.10-1.33 (2H), 1.44 (5H), 2.20-2.39 (1H), 2.68-2.85 (1H), 2.92-3.12 (1H), 3.32 (7H), 3.51-3.62 (1H), 4.20-4.59 (5H), 7.26 (1H), 7.33-7.44 (2H), 7.47-7.55 (2H), 7.70 (1H), 8.30 (1H), 8.79 (1H).

The starting material was prepared as follows:

Example 274a

Tert-butyl 4-[(5-bromo-4-ethoxy-2H-indazol-2-yl)methyl]piperidin-1-carboxylate

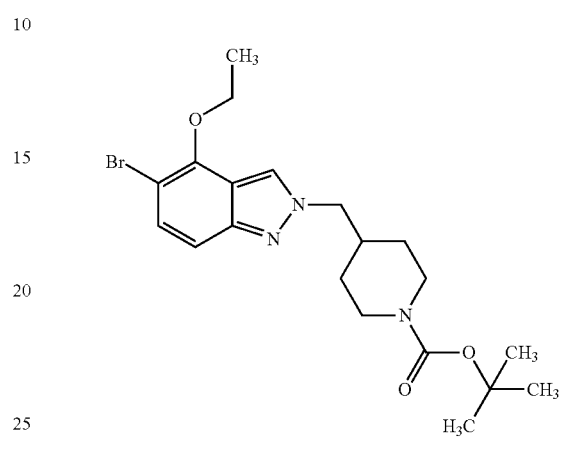

Analogously to Example 74c, 285 mg of the title compound was obtained from 484 mg of 5-bromo-4-ethoxy-1H-indazole and 1.11 g of tert-butyl-4-[(5-bromo-4-ethoxy-2H-indazol-2-yl)-methyl]piperidin-1-carboxylate.

$^1$H-NMR (400 MHz, chloroform-d): δ [ppm], 1.13-1.34 (2H), 1.46 (9H), 1.49 (3H), 1.56-1.63 (2H), 2.16-2.37 (1H), 2.54-2.80 (2H), 4.02-4.21 (2H), 4.26 (2H), 4.33 (2H), 7.28-7.43 (2H), 7.93 (1H).

Example 274b

Tert-butyl 4-({4-ethoxy-5-[N-(2-methoxyethyl)carbamoyl]-2H-indazol-2-yl}-methyl)piperidin-1-carboxylate

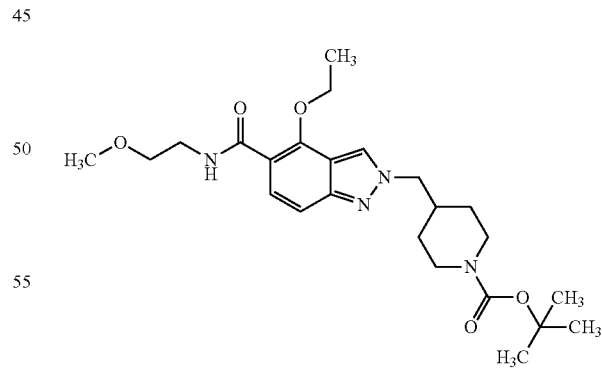

Analogously to Example 266a, 235 mg of the title compound was obtained from 285 mg of the compound prepared in Example 274a and 146 mg of 2-methoxyethylamine.

$^1$H-NMR (300 MHz, DMSO-d$_6$): δ [ppm], 0.97-1.22 (2H), 1.29-1.56 (14H), 2.06-2.31 (1H), 2.59-2.86 (2H), 3.33 (3H), 3.49 (4H), 3.80-4.02 (2H), 4.30 (2H), 4.51 (2H), 7.26 (1H), 7.71 (1H), 8.31 (1H), 8.79 (1H).

Example 274c 4-ethoxy-N-(2-methoxyethyl)-2-(4-piperidylmethyl)-2H-indazole-5-carboxamide

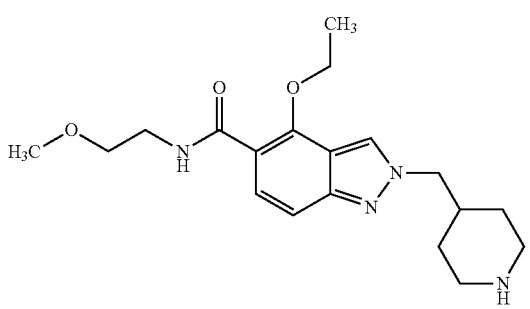 [SMILES: CCOc1c(C(=O)NCCOC)ccc2nn(CC3CCNCC3)cc12]

Analogously to Example 258b, from 235 mg of the compound prepared in Example 274b, 237 mg of the title compound was obtained, which was reacted in the next step without further purification.

Example 275

4-ethoxy-N-(2-methoxyethyl)-2-({1-[4-(pentafluoro-$\lambda^6$-sulphanyl)benzoyl]-piperidin-4-yl}methyl)-2H-indazole-5-carboxamide

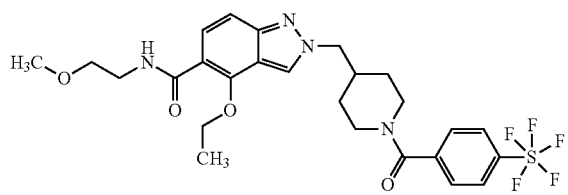 [SMILES: CCOc1c(C(=O)NCCOC)ccc2nn(CC3CCN(C(=O)c4ccc(S(F)(F)(F)(F)F)cc4)CC3)cc12]

Analogously to Example 1b, Version B, 30 mg of the title compound was obtained from 110 mg of the compound prepared in Example 274c and 113 mg of 4-(pentafluoro-$2^6$-sulphanyl)benzoic acid in DMF.

$^1$H-NMR (400 MHz, DMSO-$d_6$): δ [ppm], 1.10-1.36 (2H), 1.44 (4H), 1.54-1.69 (1H), 2.22-2.40 (1H), 2.70-2.87 (1H), 2.93-3.13 (1H), 3.30 (3H), 3.48 (5H), 4.34 (2H), 4.41-4.63 (3H), 7.26 (1H), 7.59 (2H), 7.70 (1H), 7.98 (2H), 8.30 (1H), 8.79 (1H).

Example 276

2-{[1-(4-chlorobenzoyl)azetidin-3-yl]methyl}-4-ethoxy-N-(2-methoxyethyl)-2H-indazole-5-carboxamide

Analogously to Example 1b, Version B, 25 mg of the title compound was obtained from 50 mg of the compound prepared in Example 276c and 35 mg of 4-chlorobenzoic acid in DMF.

$^1$H-NMR (400 MHz, DMSO-$d_6$): δ [ppm], 1.44 (3H), 3.21-3.29 (1H), 3.31 (3H), 3.49 (4H), 3.96 (1H), 4.06-4.30 (2H), 4.34-4.59 (3H), 4.69 (2H), 7.25 (1H), 7.51 (2H), 7.62 (2H), 7.71 (1H), 8.30 (1H), 8.86 (1H).

The starting material was prepared as follows:

Example 276a

Tert-butyl 3-[(5-bromo-4-ethoxy-2H-indazol-2-yl)methyl]azetidin-1-carboxylate

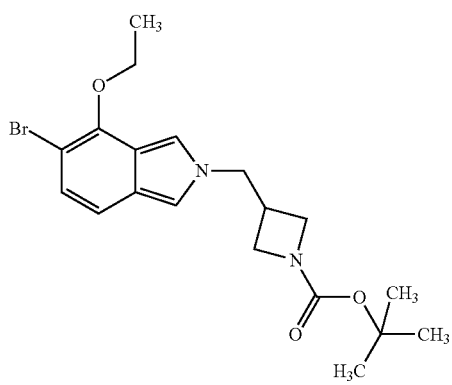 [SMILES: CCOc1c(Br)ccc2cn(CC3CN(C(=O)OC(C)(C)C)C3)cc12]

Analogously to Example 74c, 204 mg of the title compound was obtained from 500 mg of 5-bromo-4-ethoxy-1H-indazole and 1.06 g of tert-butyl-3-[(tosyloxy)methyl]azetidin-1-carboxylate.

$^1$H-NMR (600 MHz, chloroform-d): δ [ppm], 1.44 (9H), 1.49 (3H), 3.14-3.30 (1H), 3.72-3.83 (2H), 4.07 (2H), 4.33 (2H), 4.59 (2H), 7.29 (1H), 7.37 (1H), 7.98 (1H).

Example 276b

Tert-butyl 3-({4-ethoxy-5-[N-(2-methoxyethyl)carbamoyl]-2H-indazol-2-yl}-methyl)azetidin-1-carboxylate

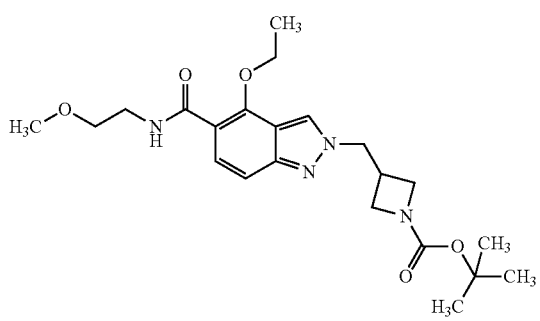 [SMILES: CCOc1c(C(=O)NCCOC)ccc2nn(CC3CN(C(=O)OC(C)(C)C)C3)cc12]

Analogously to Example 266a, from 191 mg of the compound prepared in Example 276a and 105 mg of 2-methoxyethylamine, 121 mg of the title compound was obtained, which was reacted in the next step without further purification.

Example 276c 2-(azetidin-3-ylmethyl)-4-ethoxy-N-(2-methoxy-ethyl)-2H-indazol-5-carboxamide

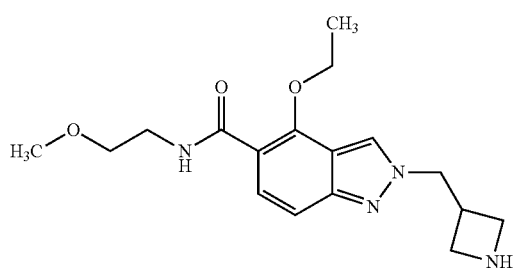 [SMILES: CCOc1c(C(=O)NCCOC)ccc2nn(CC3CNC3)cc12]

Analogously to Example 258b, from 121 mg of the compound prepared in Example 276b, 93 mg of the title compound was obtained, which was reacted in the next step without further purification.

Example 277

4-ethoxy-N-(2-methoxyethyl)-2-({1-[4-(pentafluoro-$\lambda^6$-sulphanyl)benzoyl]-azetidin-3-yl}methyl)-2H-indazole-5-carboxamide

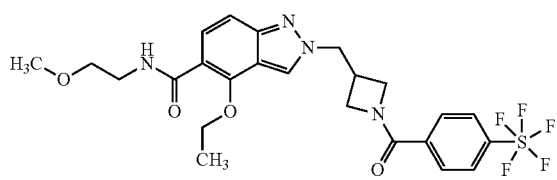 [SMILES: CCOc1c(C(=O)NCCOC)ccc2nn(CC3CN(C(=O)c4ccc(S(F)(F)(F)(F)F)cc4)C3)cc12]

Analogously to Example 1b, Version B, 35 mg of the title compound was obtained from 50 mg of 276c and 56 mg of 4-(pentafluoro-$\lambda 2^6$-sulphanyl)benzoic acid in DMF.

$^1$H-NMR (400 MHz, DMSO-$d_6$): δ [ppm], 1.37-1.50 (3H), 3.26 (1H), 3.31 (3H), 3.43-3.57 (4H), 3.92-4.05 (1H), 4.10-4.31 (2H), 4.38-4.57 (3H), 4.70 (2H), 7.25 (1H), 7.66-7.87 (3H), 7.98 (2H), 8.30 (1H), 8.86 (1H).

Example 278

2-{[1-(4-chlorobenzoyl)azetidin-3-yl]methyl}-6-methyl-N-(2-morpholinoethyl)-2H-indazole-5-carboxamide

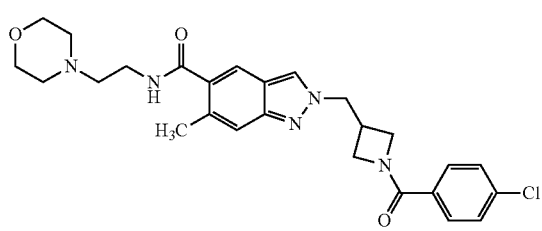 [SMILES: Cc1cc2nn(CC3CN(C(=O)c4ccc(Cl)cc4)C3)cc2cc1C(=O)NCCN1CCOCC1]

Analogously to Example 1b, Version B, 23 mg of the title compound was obtained from 100 mg of 278b and 66 mg of 4-chlorobenzoic acid in DMF.

$^1$H-NMR (400 MHz, DMSO-$d_6$): δ [ppm], 2.42 (s, 3H), 3.09-3.27 (m, 3H), 3.29-3.33 (2H), 3.49-3.73 (m, 6H), 3.84-3.96 (m, 1H), 3.97-4.15 (m, 3H), 4.16-4.27 (m, 1H), 4.31-4.45 (m, 1H), 4.62-4.80 (m, 2H), 7.36-7.47 (1H), 7.48-7.57 (2H), 7.58-7.70 (2H), 7.77-7.89 (1H), 8.41-8.58 (2H).

The starting material was prepared as follows:

Example 278a

Tert-butyl 3-({6-methyl-5-[N-(2-morpholinoethyl)carbamoyl]-2H-indazol-2-yl}methyl)azetidin-1-carboxylate

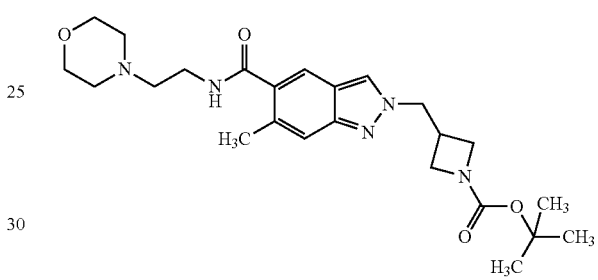

Analogously to Example 1b, Version B, 418 mg of the title compound was obtained from 410 mg of 178c and 232 mg of 2-morpholinoethylamine in DMF.

$^1$H-NMR (400 MHz, DMSO-$d_6$): δ [ppm], 1.36 (9H), 2.39 (3H), 2.44 (4H), 2.95-3.17 (1H), 3.24-3.43 (4H), 3.58 (4H), 3.64-3.79 (2H), 3.88 (2H), 4.62 (2H), 7.39 (1H), 7.68 (1H), 8.04-8.22 (1H), 8.45 (1H).

Example 278b 2-(azetidin-3-ylmethyl)-6-methyl-N-(2-morpholinoethyl)-2H-indazole-5-carboxamide

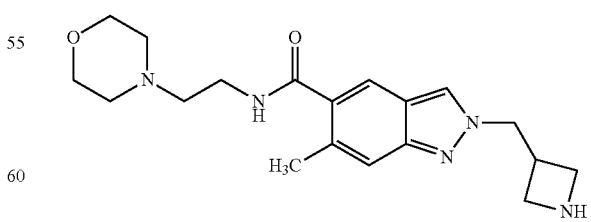

Analogously to Example 258b, from 400 mg of the compound prepared in Example 278a, 372 mg of the title compound was obtained, which was reacted in the next step without further purification.

Example 279

6-methyl-N-(2-morpholinoethyl)-2-({1-[4-(trifluoromethoxy)benzoyl]azetidin-3-yl}methyl)-2H-indazole-5-carboxamide

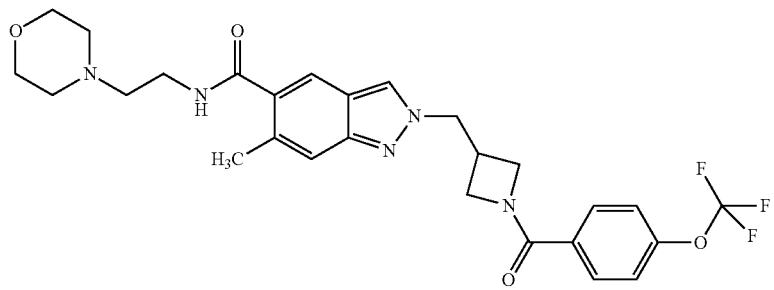 [SMILES: Cc1cc2nn(CC3CN(C(=O)c4ccc(OC(F)(F)F)cc4)C3)cc2cc1C(=O)NCCN1CCOCC1]

Analogously to Example 1b, Version B, 44 mg of the title compound was obtained from 100 mg of 278b and 86 mg of 4-(trifluoromethoxy)benzoic acid in DMF.

$^1$H-NMR (300 MHz, DMSO-d$_6$): δ [ppm], 2.42 (3H), 3.07-3.27 (5H), 3.48-3.74 (6H), 3.85-4.17 (4H), 4.18-4.29 (1H), 4.33-4.48 (1H), 4.61-4.82 (2H), 7.30-7.54 (3H), 7.68-7.78 (2H), 7.79-7.88 (1H), 8.43-8.60 (2H).

Example 280

6-methyl-N-(2-morpholinoethyl)-2-({1-[4-(pentafluoro-λ$^6$-sulphanyl)benzoyl]-azetidin-3-yl}methyl)-2H-indazole-5-carboxamide

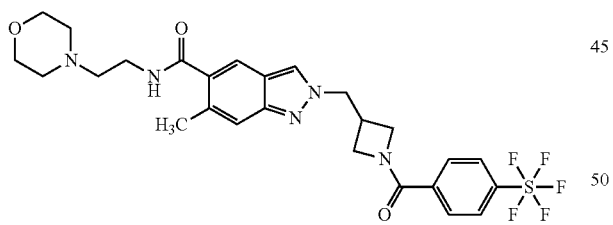

Analogously to Example 1b, Version B, 37 mg of the title compound was obtained from 100 mg of 278b and 104 mg of 4-(pentafluoro-λ$^6$-sulphanyl)benzoic acid in DMF.

$^1$H-NMR (300 MHz, DMSO-d$_6$): δ [ppm], 2.42 (3H), 3.06-3.27 (5H), 3.47-3.75 (6H), 3.87-4.08 (3H), 4.09-4.29 (2H), 4.33-4.49 (1H), 4.61-4.80 (2H), 7.34-7.52 (1H), 7.71-7.88 (3H), 7.92-8.07 (2H), 8.39-8.59 (2H).

Example 281

N-(2-methoxyethyl)-6-methyl-2-({1-[(1-methyl-1H-indol-3-yl)carbonyl]-piperidin-4-yl}methyl)-2H-indazole-5-carboxamide

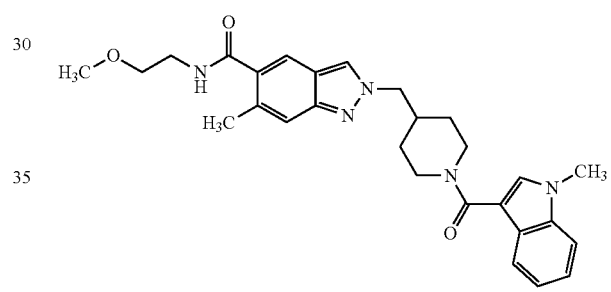

Analogously to Example 1b, Version B, 4.2 mg of the title compound was obtained from 150 mg of 205c and 119 mg of 1-methyl-1H-indol-3-carboxylic acid in DMF.

LC-MS: R$_t$=1.01 min, MS (ES+): m/z=489 (M+H)$^+$.

Example 282

N-(2-methoxyethyl)-4-methyl-2-({1-[(1-methyl-1H-indol-3-yl)carbonyl]azetidin-3-yl}methyl)-2H-indazole-5-carboxamide

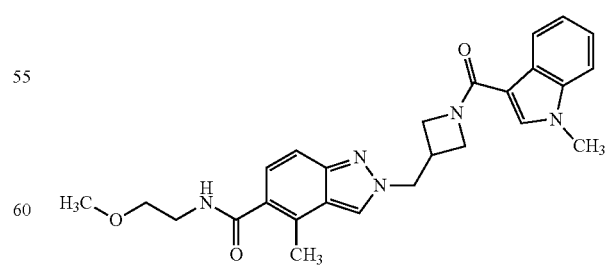

Analogously to Example 1b, Version B, 35 mg of the title compound was obtained from 175 mg of 117e and 122 mg of 1-methyl-1H-indol-3-carboxylic acid in DMF.

LC-MS: R$_t$=0.95 min, MS (ES+): m/z=460 (M+H)$^+$.

Example 283

2-({1-[4-(4-fluorophenoxy)benzoyl]piperidin-4-yl}methyl)-4-methyl-N-(2,2,2-trifluoroethyl)-2H-indazole-5-carboxamide

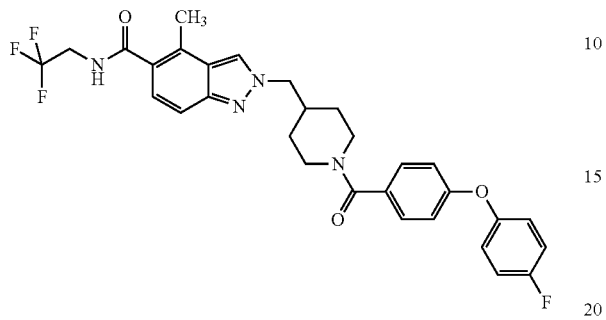

Analogously to Example 1b, Version B, 267 mg of the title compound was obtained from 250 mg of 71a and 246 mg of 4-(4-fluorophenoxy)benzoic acid in DMF.

$^1$H-NMR (400 MHz, DMSO-d$_6$): δ [ppm]=1.16-1.32 (2H), 1.35-1.69 (2H), 2.20-2.39 (1H), 2.54 (3H), 2.70-3.15 (2H), 3.50-3.83 (1H), 4.07 (2H), 4.36 (3H), 6.91-7.05 (2H), 7.08-7.31 (5H), 7.34-7.42 (2H), 7.46 (1H), 8.56 (1H), 8.83 (1H).

Example 284

2-({1-[4-(4-chlorophenoxy)benzoyl]piperidin-4-yl}methyl)-4-methyl-N-(2,2,2-trifluoroethyl)-2H-indazole-5-carboxamide

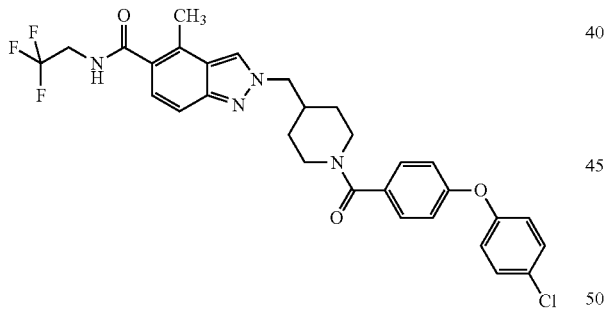

Analogously to Example 1b, Version B, 55 mg of the title compound was obtained from 100 mg of 71a and 105 mg of 4-(4-chlorophenoxy)benzoic acid in DMF.

$^1$H-NMR (400 MHz, DMSO-d$_6$): δ [ppm], 1.23 (2H), 1.34-1.72 (2H), 2.21-2.41 (1H), 2.54 (3H), 2.67-3.20 (2H), 3.51-3.83 (1H), 4.07 (2H), 4.36 (3H), 6.92-7.15 (4H), 7.20 (1H), 7.35-7.53 (5H), 8.56 (1H), 8.84 (1H).

Example 285

4-methyl-2-({1-[4-(4-methylphenoxy)benzoyl]piperidin-4-yl}methyl)-N-(2,2,2-trifluoroethyl)-2H-indazole-5-carboxamide

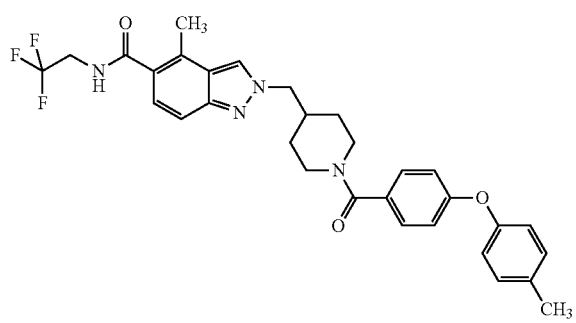 [SMILES: Cc1ccc(Oc2ccc(C(=O)N3CCC(Cn4cc5c(C)c(C(=O)NCC(F)(F)F)ccc5n4)CC3)cc2)cc1]

Analogously to Example 1b, Version B, 60 mg of the title compound was obtained from 100 mg of 71a and 97 mg of 4-(4-methylphenoxy)benzoic acid in DMF.

$^1$H-NMR (400 MHz, DMSO-d$_6$): δ [ppm], 1.23 (2H), 1.36-1.71 (2H), 2.30 (4H), 2.54 (3H), 2.64-3.17 (2H), 3.49-3.82 (1H), 4.07 (2H), 4.36 (3H), 6.85-7.04 (4H), 7.21 (3H), 7.29-7.41 (2H), 7.46 (1H), 8.56 (1H), 8.84 (s1H).

Example 286

2-({1-[(4'-fluorobiphenyl-4-yl)carbonyl]piperidin-4-yl}methyl)-4-methyl-N-(2,2,2-trifluoroethyl)-2H-indazole-5-carboxamide

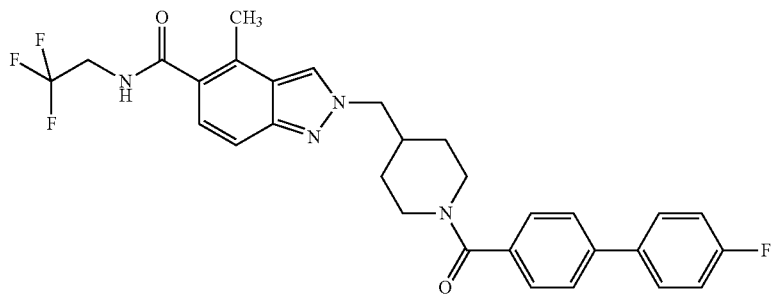 [SMILES: Cc1c(C(=O)NCC(F)(F)F)ccc2nn(CC3CCN(C(=O)c4ccc(-c5ccc(F)cc5)cc4)CC3)cc12]

Analogously to Example 1b, Version B, 39 mg of the title compound was obtained from 100 mg of 71a and 92 mg of 4-(4-fluorophenyl)benzoic acid in DMF.

$^1$H-NMR (400 MHz, DMSO-d$_6$): δ [ppm], 1.14-1.36 (2H), 1.36-1.73 (2H), 2.18-2.41 (1H), 2.54 (3H), 2.70-3.16 (2H), 3.51-3.82 (1H), 4.07 (2H), 4.38 (3H), 7.21 (1H), 7.31 (2H), 7.40-7.53 (3H), 7.64-7.85 (4H), 8.56 (1H), 8.81 (1H).

Example 287

4-methyl-2-{[1-(4-morpholinobenzoyl)piperidin-4-yl]methyl}-N-(2,2,2-trifluoro-ethyl)-2H-indazole-5-carboxamide

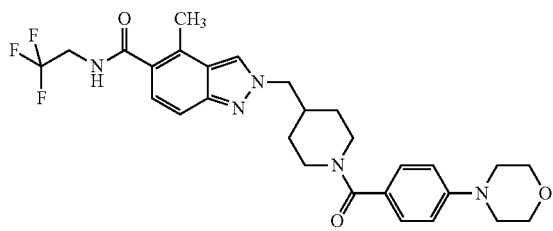 [SMILES: Cc1c(C(=O)NCC(F)(F)F)ccc2nn(CC3CCN(C(=O)c4ccc(N5CCOCC5)cc4)CC3)cc12]

Analogously to Example 1b, Version B, 45 mg of the title compound was obtained from 100 mg of 71a and 88 mg of 4-morpholinobenzoic acid in DMF.

$^1$H-NMR (400 MHz, DMSO-d$_6$): δ [ppm], 1.24 (2H), 1.40-1.60 (2H), 2.20-2.40 (1H), 2.54 (3H), 2.73-3.01 (2H), 3.38 (4H), 3.64-3.81 (5H), 4.07 (3H), 4.36 (2H), 6.94 (2H), 7.16-7.30 (3H), 7.46 (1H), 8.55 (1H), 8.81 (1H).

Example 288

4-methyl-N-(2,2,2-trifluoroethyl)-2-[(1-{4-[(trifluoromethyl)sulphanyl]benzoyl}-piperidin-4-yl)methyl]-2H-indazole-5-carboxamide

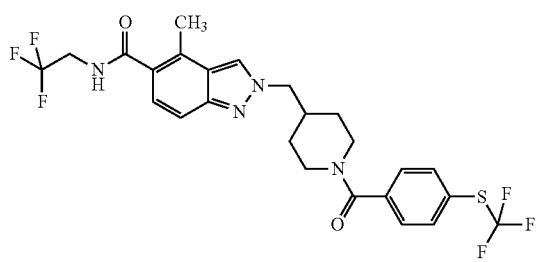 [SMILES: Cc1c(C(=O)NCC(F)(F)F)ccc2nn(CC3CCN(C(=O)c4ccc(SC(F)(F)F)cc4)CC3)cc12]

Analogously to Example 1b, Version B, 67 mg of the title compound was obtained from 100 mg of 71a and 94 mg of 4-[(trifluoromethyl)sulphanyl]benzoic acid in DMF.

$^1$H-NMR (400 MHz, DMSO-d$_6$): δ [ppm], 1.12-1.35 (2H), 1.35-1.70 (2H), 2.21-2.40 (1H), 2.54 (3H), 2.70-2.88 (1H), 2.94-3.12 (1H), 3.38-3.61 (1H), 4.07 (2H), 4.36 (3H), 7.21 (1H), 7.37-7.60 (3H), 7.78 (2H), 8.55 (1H), 8.81 (1H).

Example 289

4-methyl-2-({1-[(1-methyl-1H-indol-3-yl)carbonyl]piperidin-4-yl}methyl)-N-(2,2,2-trifluoroethyl)-2H-indazole-5-carboxamide

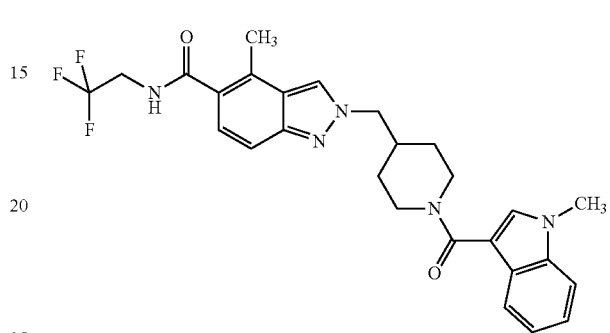

Analogously to Example 1b, Version B, 43 mg of the title compound was obtained from 100 mg of 71a and 74 mg of 1-methyl-1H-indol-3-carboxylic acid in DMF.

$^1$H-NMR (400 MHz, DMSO-d$_6$): δ [ppm], 1.27 (2H), 1.52 (2H), 2.20-2.40 (1H), 2.54 (3H), 2.92 (2H), 3.82 (3H), 4.07 (2H), 4.27 (2H), 4.38 (2H), 6.92-7.33 (3H), 7.47 (2H), 7.61-7.76 (2H), 8.56 (1H), 8.81 (1H).

Example 290

4-methyl-2-({1-[(1-methyl-1H-indol-2-yl)carbonyl]piperidin-4-yl}methyl)-N-(2,2,2-trifluoroethyl)-2H-indazole-5-carboxamide

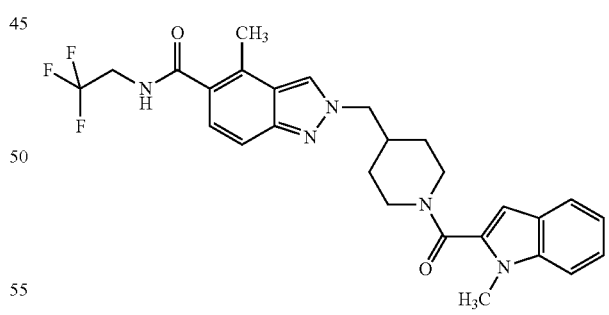

Analogously to Example 1b, Version B, 51 mg of the title compound was obtained from 100 mg of 71a and 74 mg of 1-methyl-1H-indol-2-carboxylic acid in DMF.

$^1$H-NMR (400 MHz, DMSO-d$_6$): δ [ppm], 1.17-1.41 (2H), 1.43-1.73 (2H), 2.19-2.43 (1H), 2.54 (3H), 2.74-3.23 (2H), 3.73 (3H), 4.07 (3H), 4.39 (3H), 6.60 (s, 1H), 7.03-7.14 (1H), 7.16-7.30 (2H), 7.48 (2H), 7.59 (1H), 8.57 (1H), 8.81 (1H).

Example 291

4-methyl-N-(2,2,2-trifluoroethyl)-2-[(1-{4-[4-(trifluoromethyl)phenoxy]-benzoyl}piperidin-4-yl)methyl]-2H-indazole-5-carboxamide

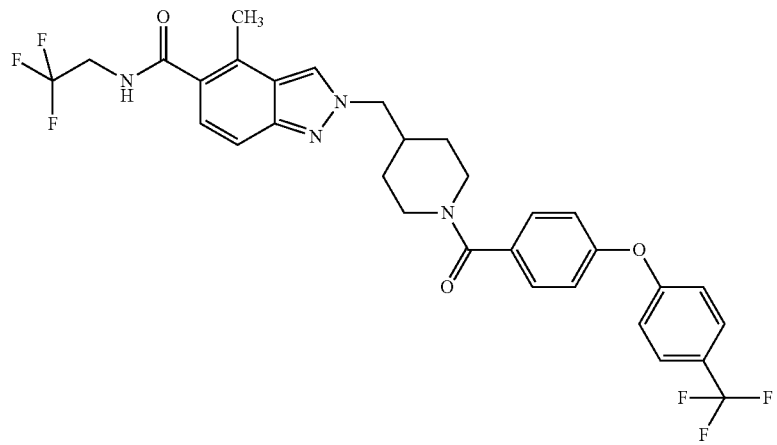

Analogously to Example 1b, Version B, 156 mg of the title compound was obtained from 150 mg of 71a and 179 mg of 4-[4-(trifluoromethyl)phenoxy]benzoic acid in DMF.

$^1$H-NMR (400 MHz, DMSO-d$_6$): δ [ppm], 1.23 (2H), 1.36-1.68 (2H), 2.20-2.43 (1H), 2.54 (3H), 2.68-3.17 (2H), 3.50-3.79 (1H), 4.07 (2H), 4.37 (3H), 7.09-7.28 (5H), 7.35-7.51 (3H), 7.76 (2H), 8.56 (1H), 8.83 (1H).

Example 292

2-({1-[(5-fluoro-1-methyl-1H-indol-2-yl)carbonyl]piperidin-4-yl}methyl)-4-methyl-N-(2,2,2-trifluoroethyl)-2H-indazole-5-carboxamide

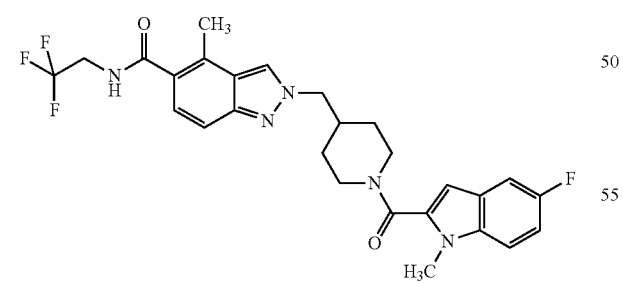

Analogously to Example 1b, Version B, 28 mg of the title compound was obtained from 100 mg of 71a and 82 mg of 5-fluoro-1-methyl-1H-indol-2-carboxylic acid in DMF.

$^1$H-NMR (400 MHz, DMSO-d$_6$): δ [ppm], 1.18-1.38 (2H), 1.39-1.72 (2H), 2.25-2.42 (1H), 2.54 (3H), 2.74-3.25 (2H), 3.73 (3H), 4.07 (3H), 4.38 (3H), 6.58 (1H), 7.09 (1H), 7.21 (1H), 7.36 (1H), 7.47 (2H), 8.57 (1H), 8.83 (1H).

Example 293

2-({1-[(5-methoxy-1-methyl-1H-indol-2-yl)carbonyl]piperidin-4-yl}methyl)-4-methyl-N-(2,2,2-trifluoroethyl)-2H-indazole-5-carboxamide

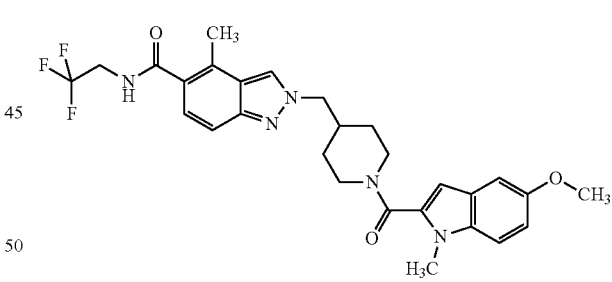

Analogously to Example 1b, Version B, 37 mg of the title compound was obtained from 100 mg of 71a and 87 mg of 5-methoxy-1-methyl-1H-indol-2-carboxylic acid in DMF.

$^1$H-NMR (400 MHz, DMSO-d$_6$): δ [ppm], 1.30 (2H), 1.41-1.71 (2H), 2.26-2.43 (1H), 2.54 (3H), 2.71-3.22 (2H), 3.69 (3H), 3.75 (3H), 4.07 (3H), 4.39 (3H), 6.51 (1H), 6.88 (1H), 7.07 (1H), 7.21 (1H), 7.34-7.54 (2H), 8.57 (1H), 8.83 (1H).

Example 294

2-({1-[(5-chloro-1-methyl-1H-indol-2-yl)carbonyl]piperidin-4-yl}methyl)-4-methyl-N-(2,2,2-trifluoroethyl)-2H-indazole-5-carboxamide

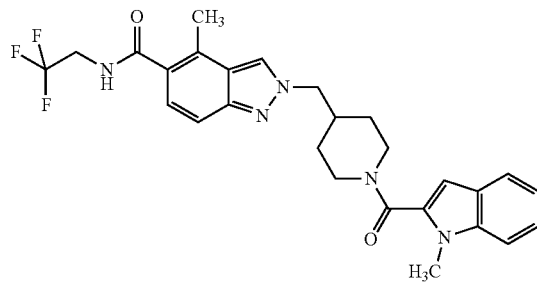 [SMILES: Cc1c(C(=O)NCC(F)(F)F)ccc2nn(CC3CCN(C(=O)c4cc5ccccc5n4C)CC3)cc12]

Analogously to Example 1b, Version B, 43 mg of the title compound was obtained from 100 mg of 71a and 89 mg of 5-chloro-1-methyl-1H-indol-2-carboxylic acid in DMF.

$^1$H-NMR (400 MHz, DMSO-d$_6$): δ [ppm], 1.29 (2H), 1.38-1.72 (2H), 2.26-2.43 (1H), 2.54 (3H), 2.71-3.21 (2H), 3.73 (3H), 3.84-4.18 (3H), 4.38 (3H), 6.59 (1H), 7.15-7.28 (2H), 7.47 (1H), 7.55 (1H), 7.65 (1H), 8.57 (1H), 8.83 (1H).

Example 295

2-({1-[(6-methoxy-1-methyl-1H-indol-2-yl)carbonyl]piperidin-4-yl}methyl)-4-methyl-N-(2,2,2-trifluoroethyl)-2H-indazole-5-carboxamide

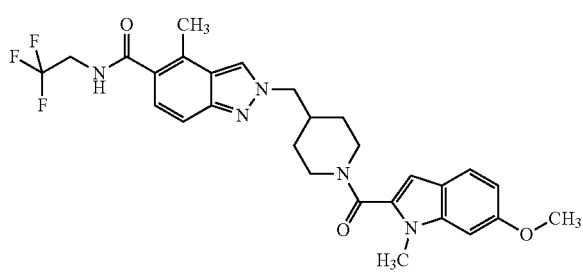 [SMILES: COc1ccc2cc(C(=O)N3CCC(Cn4cc5c(C)c(C(=O)NCC(F)(F)F)ccc5n4)CC3)n(C)c2c1]

Analogously to Example 1b, Version B, 36 mg of the title compound was obtained from 100 mg of 71a and 87 mg of 6-methoxy-1-methyl-1H-indol-2-carboxylic acid in DMF.

$^1$H-NMR (400 MHz, DMSO-d$_6$): δ [ppm], 1.28 (2H), 1.52 (2H), 2.25-2.43 (1H), 2.54 (3H), 2.78-3.16 (2H), 3.70 (3H), 3.82 (3H), 3.97-4.63 (6H), 6.54 (1H), 6.73 (1H), 7.01 (1H), 7.21 (1H), 7.39-7.53 (2H), 8.57 (1H), 8.83 (t1H).

Example 296

2-{[1-(1H-Indol-2-ylcarbonyl)piperidin-4-yl]methyl}-4-methyl-N-(2,2,2-trifluoroethyl)-2H-indazole-5-carboxamide

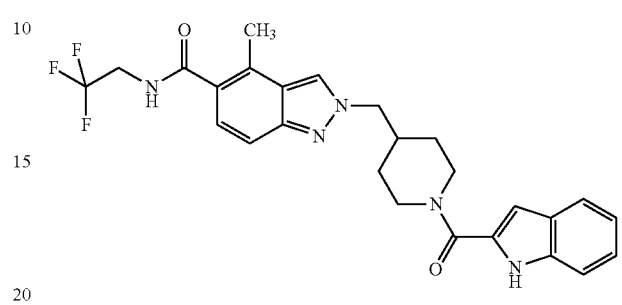

Analogously to Example 1b, Version B, 43 mg of the title compound was obtained from 100 mg of 71a and 68 mg of indol-2-carboxylic acid in DMF.

$^1$H-NMR (400 MHz, DMSO-d$_6$): δ [ppm], 1.16-1.40 (2H), 1.58 (2H), 2.27-2.44 (1H), 2.55 (3H), 2.77-3.24 (2H), 4.07 (2H), 4.30-4.59 (4H), 6.74 (1H), 6.95-7.08 (1H), 7.10-7.26 (2H), 7.40 (1H), 7.48 (1H), 7.59 (1H), 8.58 (1H), 8.84 (1H), 11.54 (1H).

Example 297

4-methyl-2-({1-[(1-methyl-1H-benzimidazol-2-yl)carbonyl]piperidin-4-yl}-methyl)-N-(2,2,2-trifluoroethyl)-2H-indazole-5-carboxamide

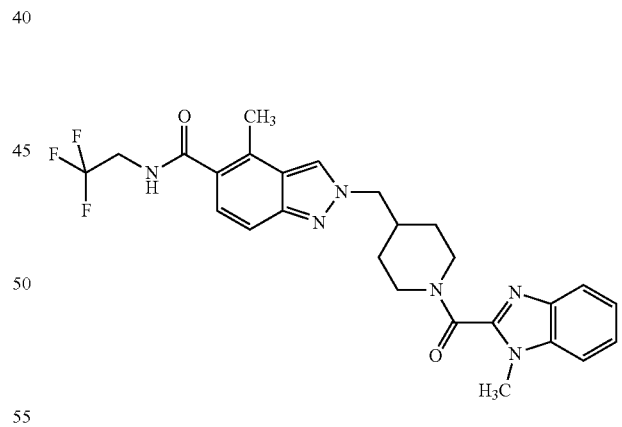

Analogously to Example 1b, Version B, 26 mg of the title compound was obtained from 100 mg of 71a and 75 mg of 1-methyl-1H-benzimidazol-2-carboxylic acid in DMF.

$^1$H-NMR (400 MHz, DMSO-d$_6$): δ [ppm], 1.17-1.42 (2H), 1.46 (1H), 1.57-1.75 (1H), 2.27-2.44 (1H), 2.54 (3H), 2.87 (1H), 3.11 (1H), 3.83 (3H), 4.07 (3H), 4.40 (2H), 4.48-4.62 (1H), 7.13-7.41 (3H), 7.47 (1H), 7.58-7.76 (2H), 8.58 (1H), 8.83 (1H).

Example 298

4-methyl-2-({1-[(2-phenylthiazol-5-yl)carbonyl]piperidin-4-yl}methyl)-N-(2,2,2-trifluoroethyl)-2H-indazole-5-carboxamide

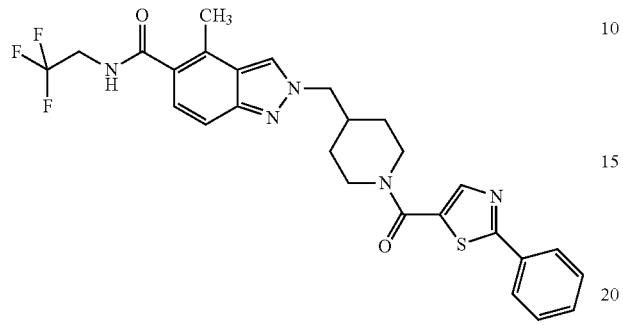

Analogously to Example 1b, Version B, 53 mg of the title compound was obtained from 100 mg of 71a and 87 mg of 2-phenylthiazol-5-carboxylic acid in DMF.

$^1$H-NMR (400 MHz, DMSO-$d_6$): δ [ppm], 1.18-1.41 (2H), 1.56 (2H), 2.27-2.44 (1H), 2.54 (3H), 2.73-3.29 (2H), 3.93-4.53 (6H), 7.21 (1H), 7.42-7.61 (4H), 7.93-8.03 (2H), 8.14 (1H), 8.57 (1H), 8.83 (1H).

Example 299

2-{[1-(benzoxazol-2-ylcarbonyl)piperidin-4-yl]methyl}-4-methyl-N-(2,2,2-trifluoroethyl)-2H-indazole-5-carboxamide

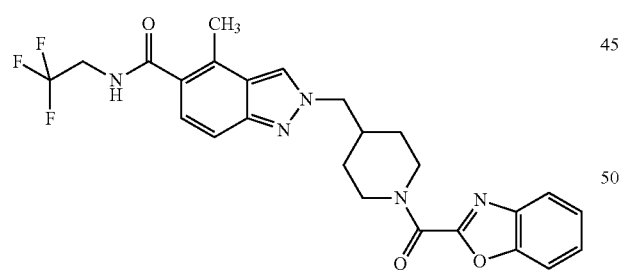

Analogously to Example 1b, Version B, 20 mg of the title compound was obtained from 100 mg of 71a and 69 mg of benzoxazol-2-carboxylic acid in DMF.

$^1$H-NMR (400 MHz, DMSO-$d_6$): δ [ppm], 1.19-1.44 (2H), 1.48-1.72 (2H), 2.29-2.46 (1H), 2.54 (3H), 2.82-3.01 (1H), 3.12-3.31 (1H), 4.07 (2H), 4.40 (4H), 7.21 (1H), 7.42-7.61 (3H), 7.78-7.95 (2H), 8.58 (1H), 8.83 (1H).

Example 300

4-methyl-2-({1-[(2-phenyloxazol-5-yl)carbonyl]piperidin-4-yl}methyl)-N-(2,2,2-trifluoroethyl)-2H-indazole-5-carboxamide

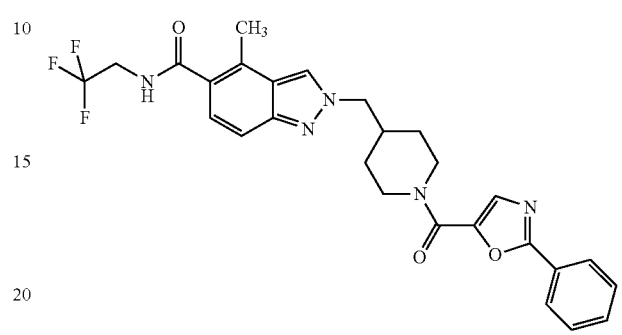

Analogously to Example 1b, Version B, 20 mg of the title compound was obtained from 100 mg of 71a and 80 mg of 2-phenyloxazol-5-carboxylic acid in DMF.

$^1$H-NMR (400 MHz, DMSO-$d_6$): δ [ppm], 1.15-1.43 (2H), 1.59 (2H), 2.31-2.45 (1H), 2.55 (3H), 2.70-3.35 (2H), 4.07 (2H), 4.39 (4H), 7.21 (1H), 7.48 (1H), 7.53-7.67 (3H), 7.80 (1H), 7.94-8.07 (2H), 8.58 (1H), 8.83 (1H).

Example 301

4-methyl-N-(2,2,2-trifluoroethyl)-2-{[1-(4-{[5-(trifluoromethyl)pyridin-2-yl]-oxy}benzoyl)piperidin-4-yl]methyl}-2H-indazole-5-carboxamide

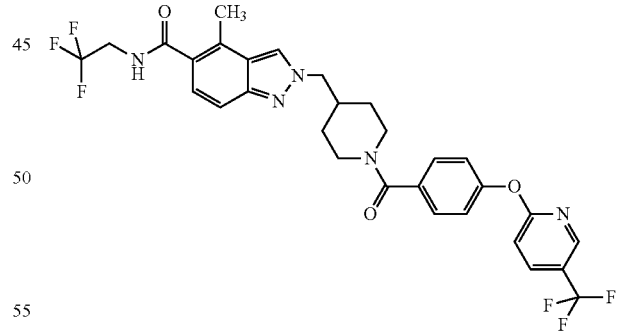

Analogously to Example 1b, Version B, 23 mg of the title compound was obtained from 75 mg of 71a and 90 mg of 4-{[5-(trifluoromethyl)pyridin-2-yl]oxy}benzoic acid in DMF.

$^1$H-NMR (300 MHz, DMSO-$d_6$): δ [ppm], 1.13-1.35 (2H), 1.37-1.72 (2H), 2.19-2.42 (1H), 2.54 (3H), 2.69-3.17 (2H), 3.55-3.82 (1H), 3.91-4.18 (2H), 4.26-4.60 (3H), 7.28 (4H), 7.38-7.56 (3H), 8.16-8.33 (1H), 8.49-8.63 (2H), 8.75-8.91 (1H).

Example 302

2-{[1-(benzothiazol-2-ylcarbonyl)piperidin-4-yl]methyl}-4-methyl-N-(2,2,2-trifluoroethyl)-2H-indazole-5-carboxamide

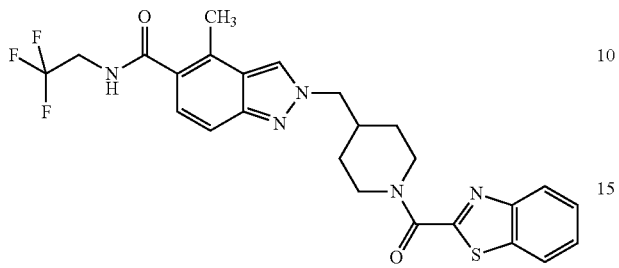

Analogously to Example 1b, Version B, 35 mg of the title compound was obtained from 75 mg of 71a and 57 mg of benzothiazol-2-carboxylic acid in DMF.

$^1$H-NMR (300 MHz, DMSO-d$_6$): δ [ppm], 1.36 (2H), 1.59 (2H), 2.31-2.46 (1H), 2.55 (3H), 2.91 (1H), 3.26 (1H), 4.07 (2H), 4.31-4.61 (3H), 4.95-5.23 (1H), 7.21 (1H), 7.41-7.69 (3H), 8.05-8.28 (2H), 8.58 (1H), 8.83 (1H).

Example 303

4-methyl-N-(2,2,2-trifluoroethyl)-2-{[1-(4-{[6-(trifluoromethyl)pyridin-3-yl]-oxy}benzoyl)piperidin-4-yl]methyl}-2H-indazole-5-carboxamide Analogously to Example 1b, Version B, 42 mg of the title compound was obtained from 75 mg of 71a and 90 mg of the carboxylic acid prepared in Example 303b) in DMF.

$^1$H-NMR (400 MHz, DMSO-d$_6$): δ [ppm], 1.16-1.33 (2H), 1.34-1.67 (2H), 2.21-2.39 (1H), 2.54 (3H), 2.68-3.16 (2H), 3.52-3.76 (1H), 3.95-4.16 (2H), 4.28-4.61 (3H), 7.13-7.31 (3H), 7.46 (3H), 7.59-7.71 (1H), 7.92 (1H), 8.52-8.65 (2H), 8.84 (1H).

The starting material was prepared as follows:

Example 303a

4-{[6-(trifluoromethyl)pyridin-3-yl]oxy}benzonitrile

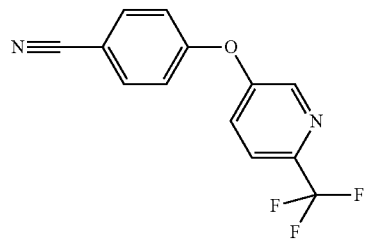 [SMILES: N#Cc1ccc(Oc2ccc(C(F)(F)F)nc2)cc1]

2.5 g of 5-bromo-2-(trifluoromethyl)pyridine, 5.8 g of 4-hydroxybenzonitrile, 10.8 g of caesium carbonate and 1.87 g of molybdenum hexacarbonyl in 100 ml 1,4-dioxan were heated under reflux until complete conversion. The reaction mixture was diluted with water, extracted several times with ethyl acetate, and the combined organic phases washed with saturated sodium chloride solution, dried over sodium sulphate and concentrated. The residue was purified by column chromatography on silica gel using a hexane/ethyl acetate gradient. Yield: 1.35 g of the title compound.

$^1$H-NMR (300 MHz, DMSO-d6): δ [ppm], 7.35 (2H), 7.75-7.84 (1H), 7.89-8.03 (3H), 8.66 (1H).

Example 303b

4-{[6-(trifluoromethyl)pyridin-2-yl]oxy}benzoic acid

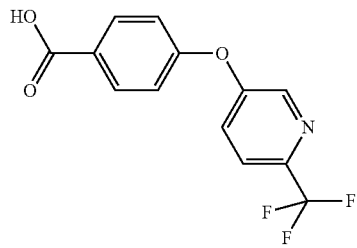 [SMILES: O=C(O)c1ccc(Oc2ccc(C(F)(F)F)nc2)cc1]

1.33 g of the compound prepared in Example 303a in 64 ml ethanol was treated with 32 ml of 40% potassium hydroxide solution and heated under reflux until complete conversion. The reaction mixture was diluted with water and extracted with ethyl acetate. The organic phase was washed with saturated sodium chloride solution, dried over sodium sulphate and concentrated. Yield: 1.32 g of the title compound.

$^1$H-NMR (400 MHz, DMSO-d$_6$): δ [ppm], 7.19-7.33 (2H), 7.68-7.81 (1H), 7.90-8.08 (3H), 8.64 (1H), 12.71-13.28 (1H).

Example 304

4-methyl-N-(2,2,2-trifluoroethyl)-2-{[1-(4-{[6-(trifluoromethyl)pyridin-2-yl]-oxy}benzoyl)piperidin-4-yl]methyl}-2H-indazole-5-carboxamide

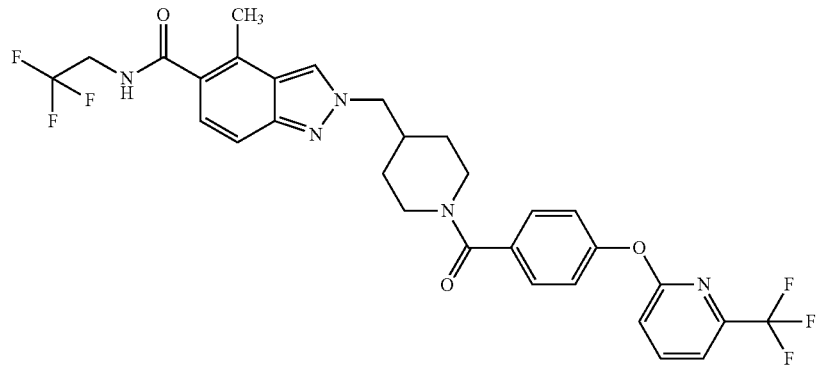 [SMILES: Cc1c(C(=O)NCC(F)(F)F)ccc2nn(CC3CCN(C(=O)c4ccc(Oc5cccc(C(F)(F)F)n5)cc4)CC3)cc12]

Analogously to Example 1b, Version B, 48 mg of the title compound was obtained from 75 mg of 71a and 90 mg of 4-{[6-(trifluoromethyl)pyridin-2-yl]oxy}benzoic acid in DMF.

$^1$H-NMR (400 MHz, DMSO-d$_6$): δ [ppm], 1.15-1.34 (2H), 1.35-1.71 (2H), 2.23-2.41 (1H), 2.54 (3H), 2.67-3.17 (2H), 3.51-3.77 (1H), 3.97-4.18 (2H), 4.22-4.65 (3H), 7.13-7.31 (3H), 7.37 (1H), 7.41-7.53 (3H), 7.67 (1H), 8.07-8.20 (1H), 8.57 (1H), 8.75-8.92 (1H).

Example 305

4-methyl-2-({1-[(3-phenyl-1,2,4-oxadiazol-5-yl)carbonyl]piperidin-4-yl}methyl)-N-(2,2,2-trifluoroethyl)-2H-indazole-5-carboxamide

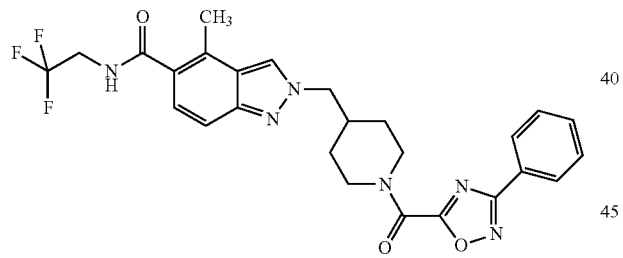

Analogously to Example 1b, Version B, 40 mg of the title compound was obtained from 90 mg of 71a and 73 mg of 3-phenyl-1,2,4-oxadiazol-5-carboxylic acid in DMF.

$^1$H-NMR (400 MHz, DMSO-d$_6$): δ [ppm], 1.18-1.43 (2H), 1.48-1.72 (2H), 2.33-2.47 (1H), 2.54 (3H), 2.95 (1H), 3.24 (1H), 3.94-4.17 (3H), 4.33-4.53 (3H), 7.21 (1H), 7.47 (1H), 7.55-7.70 (3H), 7.96-8.12 (2H), 8.57 (1H), 8.83 (1H).

Example 306

2-({1-[4-(4-cyanophenoxy)benzoyl]piperidin-4-yl}methyl)-4-methyl-N-(2,2,2-trifluoroethyl)-2H-indazole-5-carboxamide

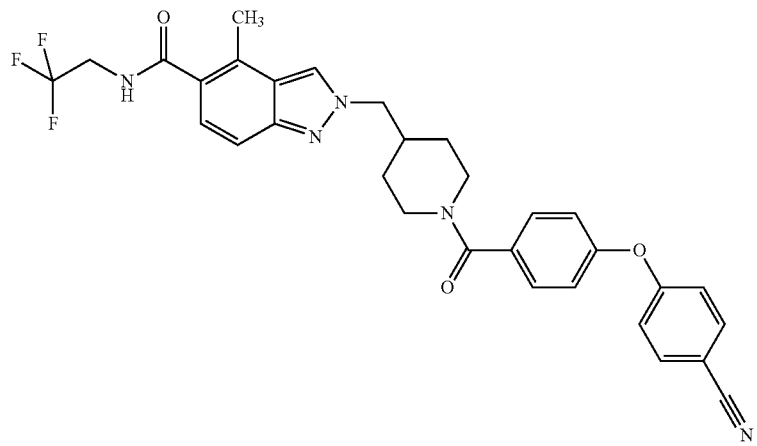 [SMILES: Cc1c(C(=O)NCC(F)(F)F)ccc2nn(CC3CCN(C(=O)c4ccc(Oc5ccc(C#N)cc5)cc4)CC3)cc12]

Analogously to Example 1b, Version B, 59 mg of the title compound was obtained from 110 mg of 71a and 101 mg of 4-(4-cyanophenoxy)benzoic acid in DMF.

$^1$H-NMR (400 MHz, DMSO-d$_6$): δ [ppm], 1.17-1.34 (2H), 1.35-1.70 (2H), 2.18-2.41 (1H), 2.54 (3H), 2.70-3.18 (2H), 3.54-3.79 (1H), 4.07 (2H), 4.37 (3H), 7.10-7.28 (5H), 7.41-7.52 (3H), 7.79-7.94 (2H), 8.56 (s1H), 8.81 (s1H).

Example 307

2-({1-[4-(3-fluorophenoxy)benzoyl]piperidin-4-yl}methyl)-4-methyl-N-(2,2,2-trifluoroethyl)-2H-indazole-5-carboxamide

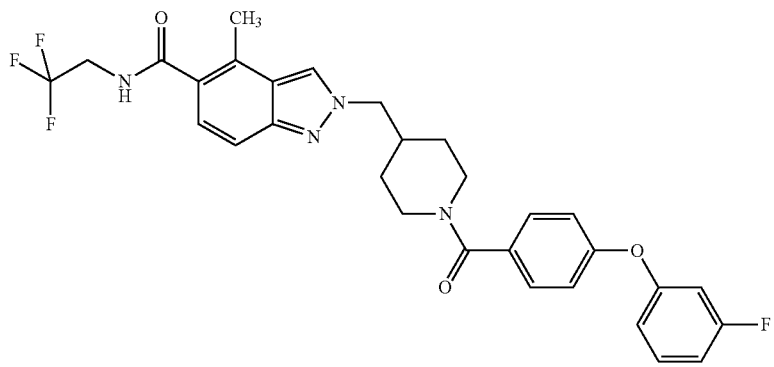 [SMILES: Cc1c(C(=O)NCC(F)(F)F)ccc2nn(CC3CCN(C(=O)c4ccc(Oc5cccc(F)c5)cc4)CC3)cc12]

Analogously to Example 1b, Version B, 40 mg of the title compound was obtained from 100 mg of 71a and 89 mg of 4-(3-fluorophenoxy)benzoic acid in DMF.

$^1$H-NMR (400 MHz, DMSO-d$_6$): δ [ppm], 1.14-1.34 (2H), 1.36-1.70 (2H), 2.22-2.44 (1H), 2.54 (3H), 2.70-3.13 (2H), 3.52-3.86 (1H), 4.07 (2H), 4.37 (3H), 6.79-7.12 (5H), 7.21 (1H), 7.35-7.52 (4H), 8.55 (1H), 8.81 (1H).

Example 308

4-methyl-N-(2,2,2-trifluoroethyl)-2-[(1-{4-[3-(trifluoromethyl)phenoxy]-benzoyl}piperidin-4-yl)methyl]-2H-indazole-5-carboxamide

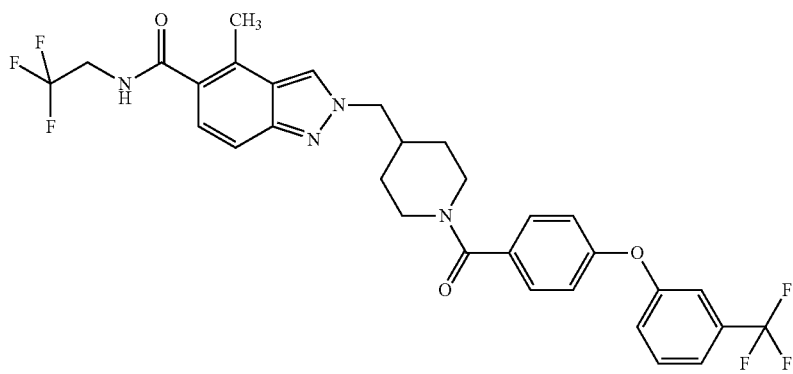 [SMILES: Cc1c(C(=O)NCC(F)(F)F)ccc2nn(CC3CCN(C(=O)c4ccc(Oc5cccc(C(F)(F)F)c5)cc4)CC3)cc12]

Analogously to Example 1b, Version B, 47 mg of the title compound was obtained from 100 mg of 71a and 119 mg of 4-[3-(trifluoromethyl)phenoxy]benzoic acid in DMF.

$^1$H-NMR (400 MHz, DMSO-d$_6$): δ [ppm], 1.16-1.34 (2H), 1.37-1.66 (2H), 2.22-2.38 (1H), 2.54 (3H), 2.69-3.14 (2H), 3.50-3.83 (1H), 4.07 (2H), 4.37 (3H), 7.10 (2H), 7.21 (1H), 7.36 (1H), 7.39-7.50 (4H), 7.54 (1H), 7.61-7.75 (1H), 8.55 (1H), 8.81 (1H).

Example 309

4-methyl-2-({1-[(5-phenyloxazol-2-yl)carbonyl]piperidin-4-yl}methyl)-N-(2,2,2-trifluoroethyl)-2H-indazole-5-carboxamide

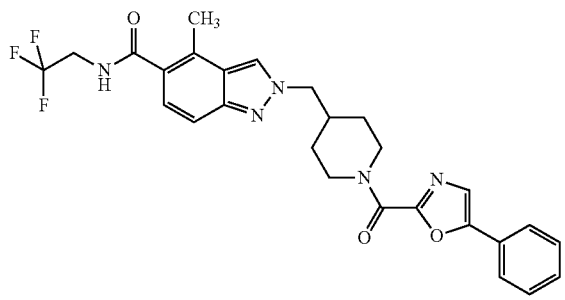 [SMILES: Cc1c(C(=O)NCC(F)(F)F)ccc2nn(CC3CCN(C(=O)c4ncc(-c5ccccc5)o4)CC3)cc12]

Analogously to Example 1b, Version B, 10 mg of the title compound was obtained from 100 mg of 71a and 73 mg of 5-phenyloxazol-2-carboxylic acid in DMF.

$^1$H-NMR (400 MHz, DMSO-d$_6$): δ [ppm], 1.24 (2H), 1.58 (2H), 2.29-2.45 (1H), 2.55 (3H), 2.86 (1H), 3.21 (1H), 4.07 (2H), 4.31-4.52 (3H), 4.62 (1H), 7.21 (1H), 7.39-7.57 (4H), 7.74-7.83 (2H), 7.88 (1H), 8.57 (1H), 8.81 (1H).

Example 310

2-[(1-{4-[(5-cyanopyridin-2-yl)oxy]benzoyl}piperidin-4-yl)methyl]-4-methyl-N-(2,2,2-trifluoroethyl)-2H-indazole-5-carboxamide

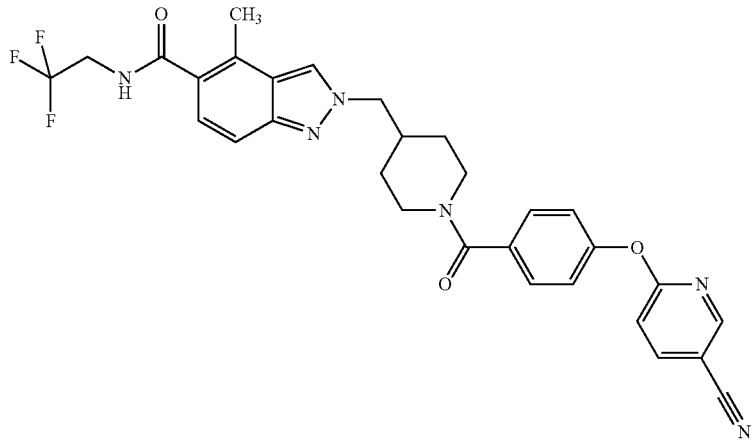 [SMILES: Cc1c(C(=O)NCC(F)(F)F)ccc2nn(CC3CCN(C(=O)c4ccc(Oc5ccc(C#N)cn5)cc4)CC3)cc12]

Analogously to Example 1b, Version B, 47 mg of the title compound was obtained from 100 mg of 71a and 119 mg of 4-[3-(trifluoromethyl)phenoxy]benzoic acid in DMF.

$^1$H-NMR (400 MHz, DMSO-d$_6$): δ [ppm], 1.16-1.34 (2H), 1.37-1.66 (2H), 2.22-2.38 (1H), 2.54 (3H), 2.69-3.14 (2H), 3.50-3.83 (1H), 4.07 (2H), 4.37 (3H), 7.10 (2H), 7.21 (1H), 7.36 (1H), 7.39-7.50 (4H), 7.54 (1H), 7.61-7.75 (1H), 8.55 (1H), 8.81 (1H).

Example 311

2-[(1-{4-[(5-chloropyridin-2-yl)oxy]benzoyl}piperidin-4-yl)methyl]-4-methyl-N-(2,2,2-trifluoroethyl)-2H-indazole-5-carboxamide

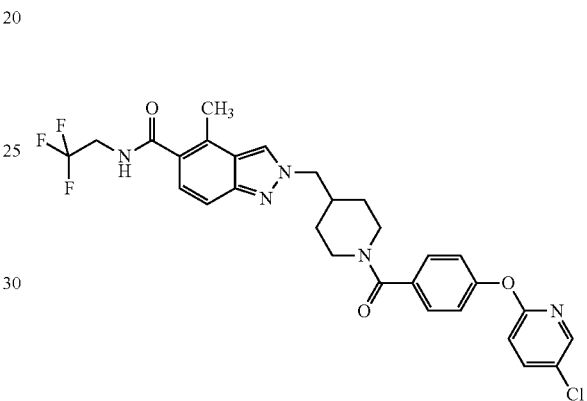

Analogously to Example 1b, Version B, 72 mg of the title compound was obtained from 100 mg of 71a and 96 mg of 4-[(5-chloropyridin-2-yl)oxy]benzoic acid in DMF.

$^1$H-NMR (400 MHz, DMSO-d$_6$): δ [ppm], 1.17-1.34 (2H), 1.36-1.73 (2H), 2.22-2.41 (1H), 2.54 (3H), 2.69-3.18 (2H), 3.47-3.88 (1H), 4.07 (2H), 4.37 (3H), 7.06-7.28 (4H), 7.34-7.52 (3H), 7.99 (1H), 8.22 (1H), 8.56 (1H), 8.81 (1H).

Example 312

4-methyl-N-(2,2,2-trifluoroethyl)-2-[(1-{4-[5-(trifluoromethyl)pyridin-2-yl]-benzoyl}piperidin-4-yl)methyl]-2H-indazole-5-carboxamide

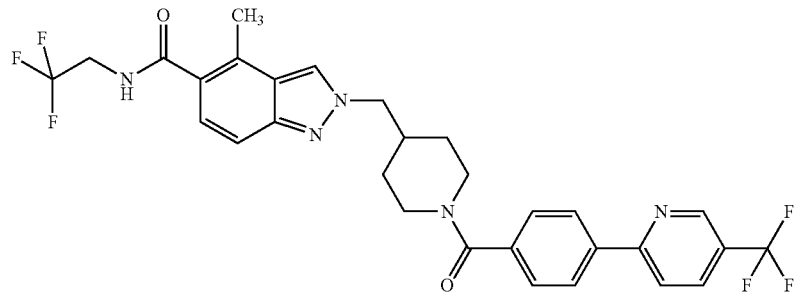 [SMILES: Cc1c(C(=O)NCC(F)(F)F)ccc2nn(CC3CCN(C(=O)c4ccc(-c5ccc(C(F)(F)F)cn5)cc4)CC3)cc12]

Analogously to Example 1b, Version B, 83 mg of the title compound was obtained from 100 mg of 71a and 103 mg of 4-[5-(trifluoromethyl)pyridin-2-yl]benzoic acid in DMF.

$^1$H-NMR (400 MHz, DMSO-$d_6$): δ [ppm], 1.28 (2H), 1.36-1.73 (2H), 2.33 (1H), 2.54 (3H), 2.70-3.18 (2H), 3.47-3.76 (1H), 3.96-4.16 (2H), 4.38 (3H), 7.21 (1H), 7.41-7.60 (3H), 8.17-8.40 (4H), 8.56 (1H), 8.81 (1H), 9.07 (1H).

Example 313

2-({1-[4-(2,4-difluorophenoxy)benzoyl]piperidin-4-yl}methyl)-4-methyl-N-(2,2,2-trifluoroethyl)-2H-indazole-5-carboxamide

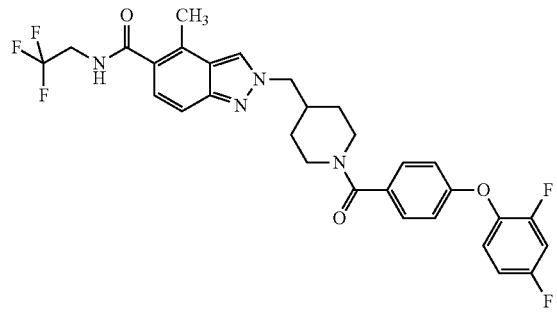 [SMILES: Cc1c(C(=O)NCC(F)(F)F)ccc2nn(CC3CCN(C(=O)c4ccc(Oc5ccc(F)cc5F)cc4)CC3)cc12]

Analogously to Example 1b, Version B, 87 mg of the title compound was obtained from 100 mg of 71a and 96 mg of 4-(2,4-difluorophenoxy)benzoic acid in DMF.

$^1$H-NMR (400 MHz, DMSO-$d_6$): δ [ppm], 1.23 (2H), 1.34-1.72 (2H), 2.18-2.42 (1H), 2.52-2.58 (3H), 2.69-3.20 (2H), 3.43-3.84 (1H), 4.07 (2H), 4.36 (3H), 6.92-7.06 (2H), 7.09-7.25 (2H), 7.28-7.42 (3H), 7.43-7.61 (2H), 8.55 (1H), 8.81 (1H).

Example 314

2-({1-[4-(3,4-difluorophenoxy)benzoyl]piperidin-4-yl}methyl)-4-methyl-N-(2,2,2-trifluoroethyl)-2H-indazole-5-carboxamide

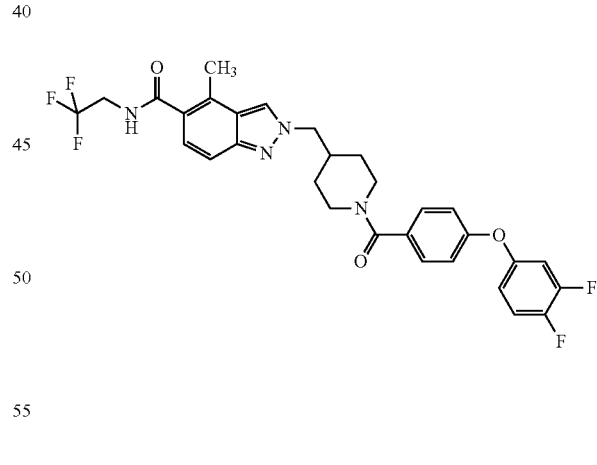

Analogously to Example 1b, Version B, 48 mg of the title compound was obtained from 100 mg of 71a and 96 mg of 4-(3,4-difluorophenoxy)benzoic acid in DMF.

$^1$H-NMR (400 MHz, DMSO-$d_6$): δ [ppm], 1.24 (2H), 1.36-1.72 (2H), 2.19-2.42 (1H), 2.54 (3H), 2.70-3.17 (2H), 3.44-3.86 (1H), 3.99-4.17 (2H), 4.36 (3H), 6.86-6.97 (1H), 7.01-7.11 (2H), 7.21 (1H), 7.29 (1H), 7.35-7.55 (4H), 8.55 (1H), 8.81 (1H).

Example 315

4-methyl-N-(2,2,2-trifluoroethyl)-2-[(1-{[4'-(trifluoromethyl)biphenyl-4-yl]-carbonyl}piperidin-4-yl)methyl]-2H-indazole-5-carboxamide

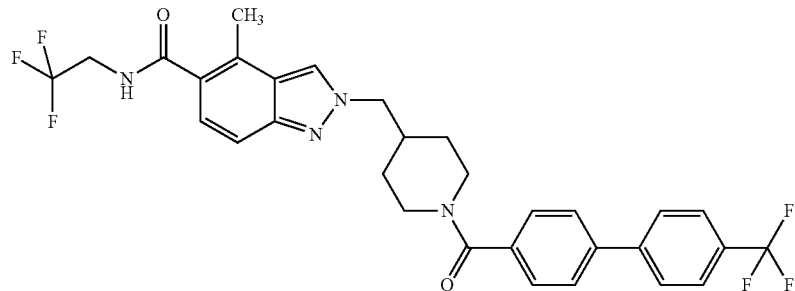 [SMILES: Cc1c(C(=O)NCC(F)(F)F)ccc2nn(CC3CCN(C(=O)c4ccc(-c5ccc(C(F)(F)F)cc5)cc4)CC3)cc12]

Analogously to Example 1b, Version B, 32 mg of the title compound was obtained from 100 mg of 71a and 102 mg of 4'-(trifluoromethyl)biphenyl-4-carboxylic acid in DMF.

$^1$H-NMR (400 MHz, DMSO-d$_6$): δ [ppm], 1.27 (2H), 1.37-1.71 (2H), 2.24-2.39 (1H), 2.53 (3H), 2.70-3.18 (2H), 3.43-3.51 (2H), 3.54-3.86 (1H), 4.37 (3H), 7.18 (1H), 7.38-7.57 (3H), 7.72-7.88 (4H), 7.89-7.98 (2H), 8.13 (1H), 8.51 (1H).

Example 316

2-{[1-(4-bromobenzoyl)piperidin-4-yl]methyl}-4-methyl-N-(2,2,2-trifluoro-ethyl)-2H-indazole-5-carboxamide

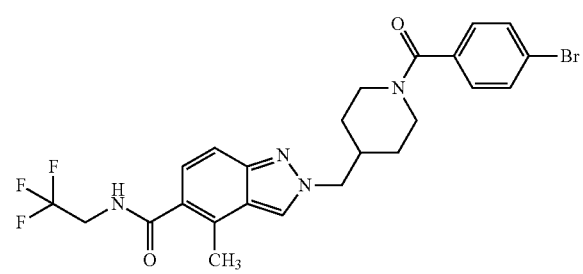 [SMILES: Cc1c(C(=O)NCC(F)(F)F)ccc2nn(CC3CCN(C(=O)c4ccc(Br)cc4)CC3)cc12]

Analogously to Example 1b, Version B, 6.96 g of the title compound was obtained from 5.61 g 71a and 2.89 g of 4-bromobenzoic acid.

$^1$H-NMR (300 MHz, DMSO-d$_6$): δ [ppm], 1.17-1.32 (2H), 1.34-1.74 (2H), 2.19-2.41 (1H), 2.54 (3H), 2.88-3.22 (2H), 3.42-3.74 (1H), 3.94-4.18 (2H), 4.36 (3H), 7.20 (1H), 7.32 (2H), 7.46 (1H), 7.64 (2H), 8.55 (1H), 8.83 (1H).

Example 317

2-({1-[4-(5-chloropyridin-2-yl)benzoyl]piperidin-4-yl}methyl)-4-methyl-N-(2,2,2-trifluoroethyl)-2H-indazole-5-carboxamide

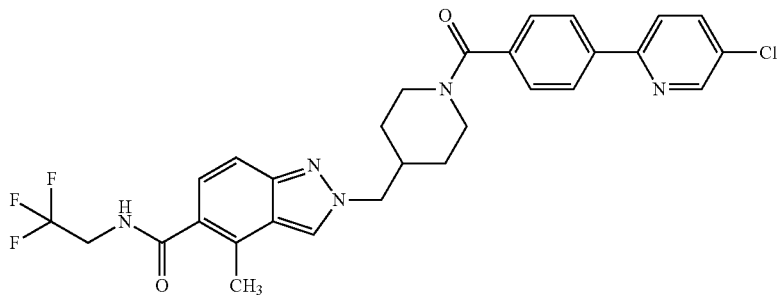 [SMILES: Cc1c(C(=O)NCC(F)(F)F)ccc2nn(CC3CCN(C(=O)c4ccc(-c5ccc(Cl)cn5)cc4)CC3)cc12]

80 mg of the aryl bromide prepared in Example 316 together with 32 mg of (5-chloropyridin-2-yl)boronic acid was first placed in 1 ml tetrahydrofuran, treated with 17.3 mg of 1,1'-bis(diphenylphosphino)ferrocenodichloropalladium(II) and 0.17 ml of 1M potassium carbonate solution and heated in the microwave for 10 minutes at 120° C. (100 watts). After fresh addition of 11 mg of (5-chloropyridin-2-yl)boronic acid and 17.3 mg of the palladium(II) catalyst, the reaction mixture was again heated in the microwave for 10 minutes at 120° C. (100 watts) until complete conversion. The reaction mixture was concentrated. After HPLC purification, this yielded 15 mg of the title compound.

$^1$H-NMR (300 MHz, DMSO-$d_6$): δ [ppm], 1.18-1.36 (2H), 1.37-1.75 (2H), 2.28-2.38 (1H), 2.54 (3H), 2.73-3.18 (2H), 3.49-3.74 (1H), 3.95-4.16 (2H), 4.28-4.62 (3H), 7.22 (1H), 7.33-7.65 (5H), 7.98-8.22 (3H), 8.56 (1H), 8.77-8.91 (1H).

Example 318

2-({1-[(4'-methoxy-2'-methylbiphenyl-4-yl)carbonyl]piperidin-4-yl}methyl)-4-methyl-N-(2,2,2-trifluoroethyl)-2H-indazole-5-carboxamide

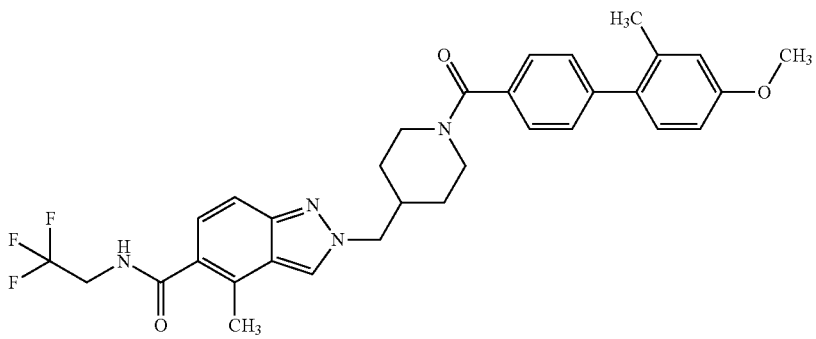 [SMILES: COc1ccc(-c2ccc(C(=O)N3CCC(Cn4cc5c(C)c(C(=O)NCC(F)(F)F)ccc5n4)CC3)cc2)c(C)c1]

Analogously to Example 317, 50 mg of the title compound was obtained from 125 mg of 316 and 53 mg of (4-methoxy-2-methyl-phenyl)boronic acid.

$^1$H-NMR (300 MHz, DMSO-$d_6$): δ [ppm], 1.16-1.36 (2H), 1.37-1.74 (2H), 2.23 (3H), 2.29-2.38 (1H), 2.54 (3H), 2.72-3.12 (2H), 3.77 (4H), 3.97-4.17 (2H), 4.38 (3H), 6.75-6.94 (2H), 7.07-7.26 (2H), 7.29-7.56 (5H), 8.56 (1H), 8.81 (1H).

Example 319

4-methyl-2-({1-[4-(6-methylpyridin-3-yl)benzoyl]piperidin-4-yl}methyl)-N-(2,2,2-trifluoroethyl)-2H-indazole-5-carboxamide

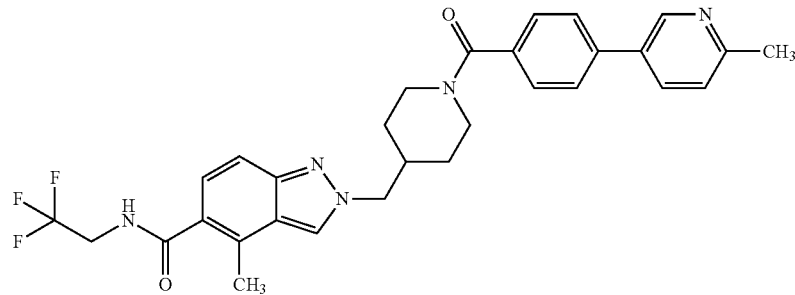 [SMILES: Cc1ccc(-c2ccc(C(=O)N3CCC(Cn4cc5c(C)c(C(=O)NCC(F)(F)F)ccc5n4)CC3)cc2)cn1]

Analogously to Example 317, 37 mg of the title compound was obtained from 125 mg of 316 and 44 mg of (6-methylpyridin-3-yl)boronic acid under reflux.

$^1$H-NMR (300 MHz, DMSO-$d_6$): δ [ppm], 1.15-1.35 (2H), 1.37-1.71 (2H), 2.20-2.40 (1H), 2.52 (3H), 2.54 (3H), 2.74-3.15 (2H), 3.52-3.82 (1H), 4.07 (2H), 4.38 (3H), 7.20 (1H), 7.37 (1H), 7.47 (3H), 7.77 (2H), 8.01 (1H), 8.57 (1H), 8.72-8.92 (2H).

Example 320

2-({1-[(4'-fluoro-2'-methoxybiphenyl-4-yl)carbonyl]piperidin-4-yl}methyl)-4-methyl-N-(2,2,2-trifluoroethyl)-2H-indazole-5-carboxamide

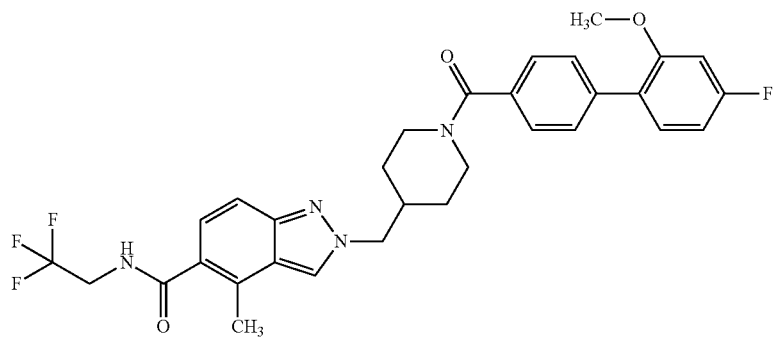 [SMILES: COc1cc(F)ccc1-c1ccc(C(=O)N2CCC(Cn3cc4c(C)c(C(=O)NCC(F)(F)F)ccc4n3)CC2)cc1]

Analogously to Example 317, 60 mg of the title compound was obtained from 125 mg of 316 and 75 g of (4-fluoro-2-methoxyphenyl)boronic acid under reflux.

$^1$H-NMR (300 MHz, DMSO-d$_6$): δ [ppm], 1.16-1.37 (2H), 1.38-1.75 (2H), 2.25-2.37 (1H), 2.54 (3H), 2.72-3.17 (2H), 3.79 (4H), 4.07 (2H), 4.38 (3H), 6.87 (1H), 7.04 (1H), 7.21 (1H), 7.27-7.58 (6H), 8.56 (1H), 8.81 (1H).

Example 321

4-methyl-N-(2,2,2-trifluoroethyl)-2-[(1-{4-[6-(trifluoromethyl)pyridin-3-yl]-benzoyl}piperidin-4-yl)methyl]-2H-indazole-5-carboxamide

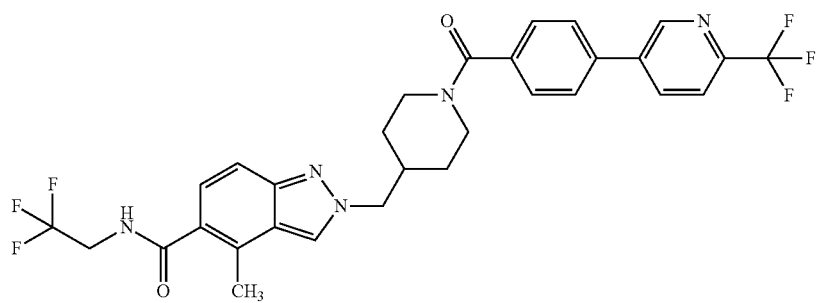 [SMILES: Cc1c(C(=O)NCC(F)(F)F)ccc2nn(CC3CCN(C(=O)c4ccc(-c5ccc(C(F)(F)F)nc5)cc4)CC3)cc12]

Analogously to Example 317, 45 mg of the title compound was obtained from 125 mg of 316 and 84 mg of [6-(trifluoromethyl)pyridin-3-yl]boronic acid under reflux.

$^1$H-NMR (300 MHz, DMSO-d$_6$): δ [ppm], 1.15-1.37 (2H), 1.37-1.71 (2H), 2.22-2.41 (1H), 2.54 (3H), 2.73-3.20 (2H), 3.45-3.74 (1H), 3.93-4.17 (2H), 4.29-4.62 (3H), 7.21 (1H), 7.39-7.62 (4H), 7.89 (2H), 8.01 (1H), 8.57 (1H), 8.73-8.92 (1H), 9.13 (1H).

Example 322

2-({1-[4-(6-methoxypyridin-3-yl)benzoyl]piperidin-4-yl}methyl)-4-methyl-N-(2,2,2-trifluoroethyl)-2H-indazole-5-carboxamide

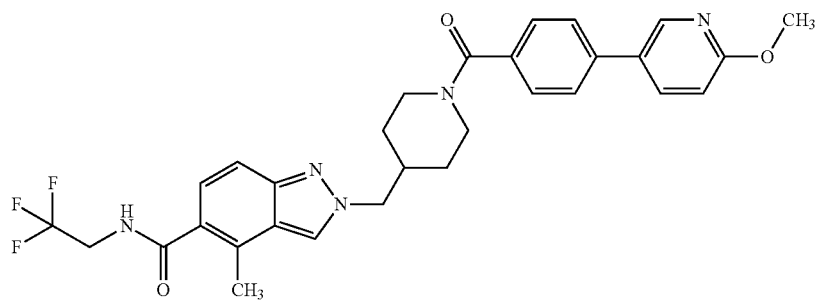 [SMILES: COc1ccc(-c2ccc(C(=O)N3CCC(Cn4cc5c(C)c(C(=O)NCC(F)(F)F)ccc5n4)CC3)cc2)cn1]

Analogously to Example 317, 54 mg of the title compound was obtained from 125 mg of 316 and 68 mg of (6-methoxypyridin-3-yl)boronic acid under reflux.

$^1$H-NMR (300 MHz, DMSO-$d_6$): δ [ppm], 1.13-1.35 (2H), 1.36-1.71 (2H), 2.20-2.40 (1H), 2.54 (3H), 2.73-3.16 (2H), 3.51-3.77 (1H), 3.90 (3H), 3.96-4.19 (2H), 4.37 (3H), 6.93 (1H), 7.20 (1H), 7.39-7.52 (3H), 7.73 (2H), 8.05 (1H), 8.47-8.63 (2H), 8.83 (1H).

Example 323

2-({1-[4-(6-methoxypyridin-2-yl)benzoyl]piperidin-4-yl}methyl)-4-methyl-N-(2,2,2-trifluoroethyl)-2H-indazole-5-carboxamide

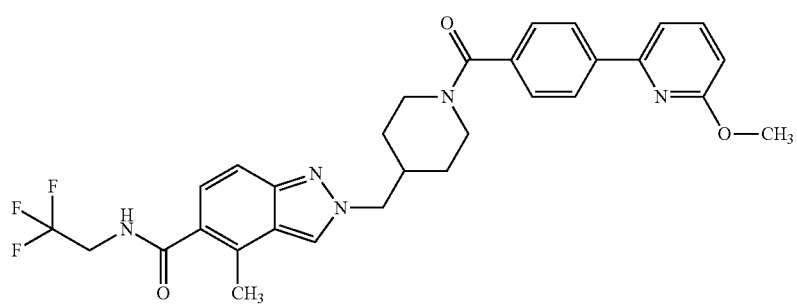 [SMILES: COc1cccc(-c2ccc(C(=O)N3CCC(Cn4cc5c(C)c(C(=O)NCC(F)(F)F)ccc5n4)CC3)cc2)n1]

Analogously to Example 317, 55 mg of the title compound was obtained from 125 mg of 316 and 49 mg of (6-methoxypyridin-2-yl)boronic acid under reflux.

$^1$H-NMR (300 MHz, DMSO-$d_6$): δ [ppm], 1.16-1.36 (2H), 1.37-1.69 (2H), 2.20-2.41 (1H), 2.54 (3H), 2.74-3.16 (2H), 3.47-3.81 (1H), 3.96 (3H), 4.06 (2H), 4.38 (3H), 6.81 (1H), 7.21 (1H), 7.47 (3H), 7.60 (1H), 7.74-7.90 (1H), 8.15 (2H), 8.56 (1H), 8.81 (1H).

Example 324

4-methyl-2-({1-[4-(5-methylpyridin-2-yl)benzoyl]piperidin-4-yl}methyl)-N-(2,2,2-trifluoroethyl)-2H-indazole-5-carboxamide

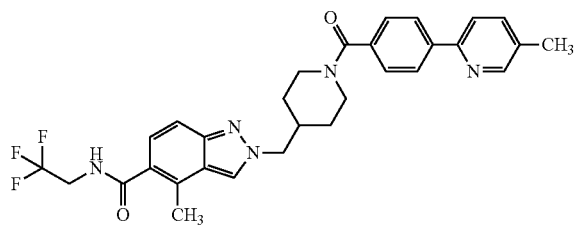 [SMILES: Cc1ccc(-c2ccc(C(=O)N3CCC(Cn4cc5c(C)c(C(=O)NCC(F)(F)F)ccc5n4)CC3)cc2)nc1]

Analogously to Example 317, 9 mg of the title compound was obtained from 125 mg of 316 and 44 mg of (5-methylpyridin-2-yl)boronic acid under reflux.

$^1$H-NMR (300 MHz, DMSO-d$_6$): δ [ppm], 1.16-1.36 (2H), 1.37-1.71 (2H), 2.24-2.30 (1H), 2.34 (3H), 2.54 (3H), 2.74-3.16 (2H), 3.52-3.79 (1H), 3.93-4.17 (2H), 4.38 (3H), 7.20 (1H), 7.37-7.54 (3H), 7.66-7.78 (1H), 7.89 (1H), 8.11 (2H), 8.45-8.61 (2H), 8.74-8.88 (1H).

Example 325

2-({1-[4-(5-fluoropyridin-2-yl)benzoyl]piperidin-4-yl}methyl)-4-methyl-N-(2,2,2-trifluoroethyl)-2H-indazole-5-carboxamide

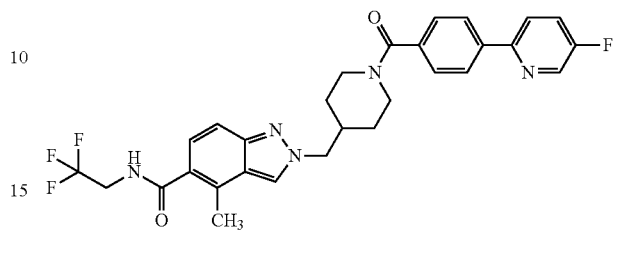

Analogously to Example 317, 35 mg of the title compound was obtained from 125 mg of 316 and 45 mg of (5-fluoropyridin-2-yl)boronic acid under reflux.

$^1$H-NMR (400 MHz, DMSO-d$_6$): δ [ppm], 1.17-1.34 (2H), 1.35-1.69 (2H), 2.22-2.41 (1H), 2.54 (3H), 2.69-3.19 (2H), 3.51-3.78 (1H), 4.07 (2H), 4.38 (3H), 7.20 (1H), 7.40-7.53 (3H), 7.85 (1H), 8.04-8.17 (3H), 8.57 (1H), 8.68 (1H), 8.83 (1H).

Example 326

2-({1-[4-(5-methoxypyridin-2-yl)benzoyl]piperidin-4-yl}methyl)-4-methyl-N-(2,2,2-trifluoroethyl)-2H-indazole-5-carboxamide

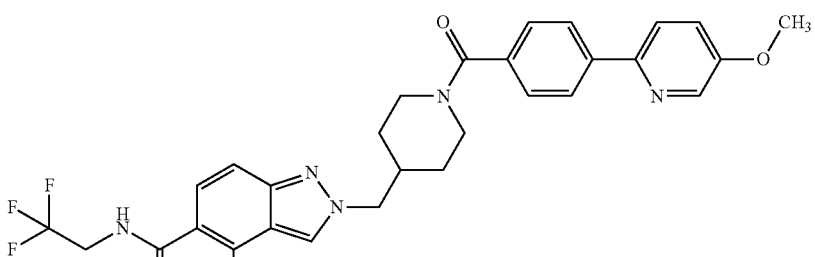

Analogously to Example 317, 94 mg of the title compound was obtained from 125 mg of 316 and 49 mg of (5-methoxypyridin-2-yl)boronic acid under reflux.

$^1$H-NMR (300 MHz, DMSO-d$_6$): δ [ppm], 1.19-1.36 (2H), 1.37-1.69 (2H), 2.28-2.40 (1H), 2.54 (3H), 2.73-3.19 (2H), 3.48-3.79 (1H), 3.88 (3H), 4.07 (2H), 4.38 (3H), 7.20 (1H), 7.38-7.55 (4H), 7.96 (1H), 8.07 (2H), 8.39 (1H), 8.57 (1H), 8.82 (1H).

Example 327

4-methyl-2-({1-[4-(2-methylpyrimidin-5-yl)benzoyl]piperidin-4-yl}methyl)-N-(2,2,2-trifluoroethyl)-2H-indazole-5-carboxamide

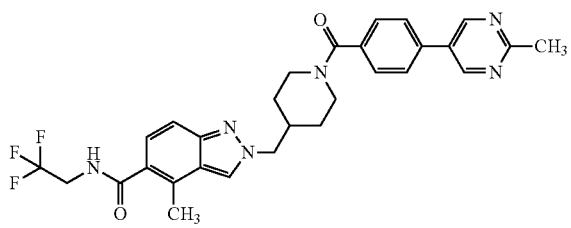 [SMILES: Cc1ncc(-c2ccc(C(=O)N3CCC(Cn4cc5c(C)c(C(=O)NCC(F)(F)F)ccc5n4)CC3)cc2)cn1]

Analogously to Example 317, 46 mg of the title compound was obtained from 125 mg of 316 and 102 mg of (2-methylpyrimidin-5-yl)boronic acid pinacol ester under reflux.

$^1$H-NMR (400 MHz, DMSO-d$_6$): δ [ppm], 1.16-1.35 (2H), 1.35-1.67 (2H), 2.21-2.42 (1H), 2.54 (3H), 2.67 (3H), 2.71-2.89 (1H), 2.93-3.20 (1H), 3.50-3.73 (1H), 4.07 (2H), 4.37 (3H), 7.20 (1H), 7.40-7.57 (3H), 7.85 (2H), 8.57 (1H), 8.84 (1H), 9.05 (2H).

Example 328

4-methyl-N-(2,2,2-trifluoroethyl)-2-[(1-{4-[2-(trifluoromethyl)pyrimidin-5-yl]-benzoyl}piperidin-4-yl)methyl]-2H-indazole-5-carboxamide

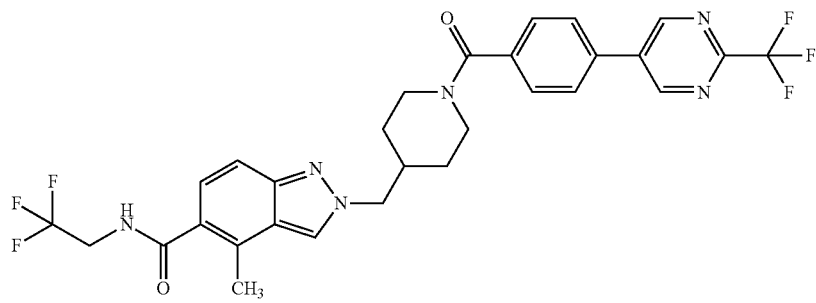 [SMILES: Cc1c(C(=O)NCC(F)(F)F)ccc2nn(CC3CCN(C(=O)c4ccc(-c5cnc(C(F)(F)F)nc5)cc4)CC3)cc12]

Analogously to Example 317, 34 mg of the title compound was obtained from 125 mg of 316 and 89 mg of [2-(trifluoromethyl)pyrimidin-5-yl]boronic acid under reflux.

$^1$H-NMR (400 MHz, DMSO-d$_6$): δ [ppm], 1.21-1.35 (2H), 1.36-1.71 (2H), 2.23-2.41 (1H), 2.54 (3H), 2.71-2.89 (1H), 2.94-3.17 (1H), 3.48-3.72 (1H), 4.05 (2H), 4.28-4.61 (3H), 7.21 (1H), 7.47 (1H), 7.57 (2H), 7.98 (2H), 8.57 (1H), 8.84 (1H), 9.44 (2H).

Example 329

4-methyl-N-(2,2,2-trifluoroethyl)-2-[(1-{4-[6-(trifluoromethyl)pyridin-2-yl]-benzoyl}piperidin-4-yl)methyl]-2H-indazole-5-carboxamide

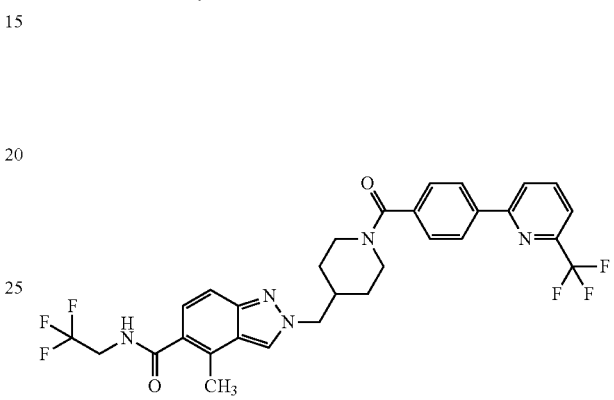

Analogously to Example 317, 70 mg of the title compound was obtained from 125 mg of 316 and 121 mg of [6-(trifluoromethyl)pyridin-2-yl]boronic acid pinacol ester under reflux.

$^1$H-NMR (400 MHz, DMSO-d$_6$): δ [ppm], 1.19-1.36 (2H), 1.37-1.72 (2H), 2.23-2.39 (1H), 2.54 (3H), 2.68-2.90 (1H), 2.92-3.16 (1H), 3.50-3.73 (1H), 4.06 (2H), 4.38 (3H), 7.20 (1H), 7.41-7.60 (3H), 7.89 (1H), 8.11-8.27 (3H), 8.33 (1H), 8.56 (1H), 8.81 (1H).

Example 330

2-({1-[4-(4-cyanophenoxy)benzoyl]piperidin-4-yl}methyl)-N-(2-methoxyethyl)-4-methyl-2H-indazole-5-carboxamide

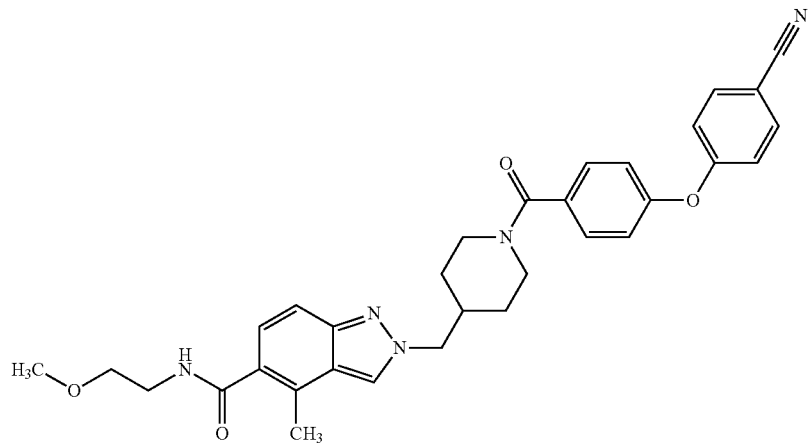 [SMILES: COCCNC(=O)c1ccc2nn(CC3CCN(C(=O)c4ccc(Oc5ccc(C#N)cc5)cc4)CC3)cc2c1C]

Analogously to Example 1b, Version B, 151 mg of the title compound was obtained from 213 mg of 71a and 153 mg of 4-(4-cyanophenoxy)benzoic acid in DMF.

$^1$H-NMR (300 MHz, DMSO-d$_6$): δ [ppm], 1.22 (2H), 1.31-1.66 (2H), 2.15-2.36 (1H), 2.49 (3H), 2.70-3.12 (2H), 3.24 (3H), 3.36 (2H), 3.39-3.46 (2H), 3.50-3.79 (1H), 4.32 (3H), 7.00-7.23 (5H), 7.30-7.49 (3H), 7.75-7.91 (2H), 8.12 (1H), 8.48 (1H).

Example 331

N-(2-methoxyethyl)-4-methyl-2-({1-[(1-methyl-1H-indol-3-yl)carbonyl]-piperidin-4-yl}methyl)-2H-indazole-5-carboxamide

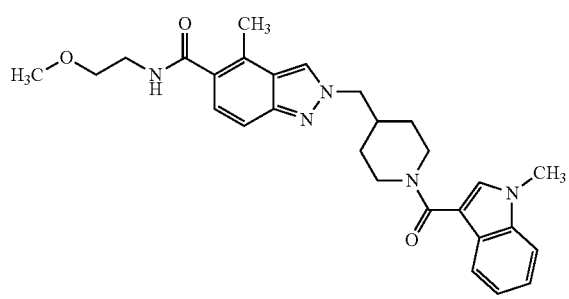

Analogously to Example 1b, Version B, 26 mg of the title compound was obtained from 38 mg of 71a and 36 mg of 1-methyl-1H-indol-3-carboxylic acid in DMF.

$^1$H-NMR (300 MHz, DMSO-d$_6$): δ [ppm], 1.23 (2H), 1.43-1.64 (2H), 2.20-2.39 (1H), 2.53 (3H), 2.80-3.03 (2H), 3.28 (3H), 3.37-3.50 (4H), 3.81 (3H), 4.37 (4H), 7.18 (3H), 7.36-7.53 (2H), 7.67 (2H), 8.04-8.25 (1H), 8.52 (1H).

Example 332

2-{[1-(4-bromo-3-methylbenzoyl)piperidin-4-yl]methyl}-N-(2-methoxyethyl)-4-methyl-2H-indazole-5-carboxamide

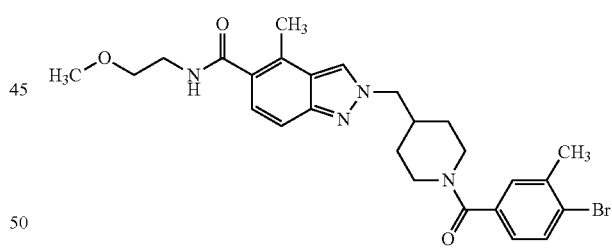

Analogously to Example 1b, Version B, 498 mg of the title compound was obtained from 807 mg of 71a and 788 mg of 4-bromo-3-methylbenzoic acid in DMF.

$^1$H-NMR (300 MHz, DMSO-d$_6$): δ [ppm], 1.20-1.32 (2H), 1.33-1.67 (2H), 2.24-2.33 (1H), 2.36 (3H), 2.52 (3H), 2.73 (1H), 2.91-3.13 (1H), 3.28 (3H), 3.35-3.63 (5H), 4.34 (3H), 7.03-7.23 (2H), 7.30-7.49 (2H), 7.63 (1H), 8.15 (1H), 8.51 (1H).

Example 333

2-{[1-(4-tert-butylbenzoyl)piperidin-4-yl]methyl}-N-(2-methoxyethyl)-4-methyl-2H-indazole-5-carboxamide

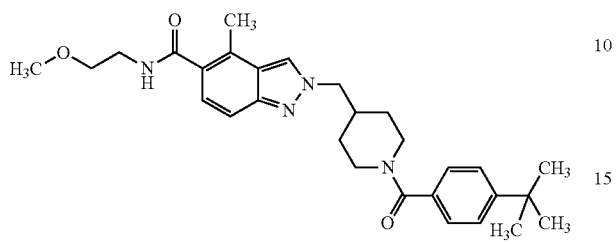

Analogously to Example 1b, Version B, 50 mg of the title compound was obtained from 100 mg of 71a and 81 mg of 4-tert-butylbenzoic acid in DMF.

$^1$H-NMR (400 MHz, DMSO-d$_6$): δ [ppm], 1.20-1.33 (11H), 1.33-1.67 (2H), 2.21-2.37 (1H), 2.52 (3H), 2.68-3.10 (2H), 3.28 (3H), 3.36-3.43 (2H), 3.45 (2H), 3.52-3.74 (1H), 4.35 (3H), 7.18 (1H), 7.25-7.35 (2H), 7.36-7.52 (3H), 8.15 (1H), 8.50 (1H).

Example 334

2-({1-[4-(1-hydroxy-1-methylethyl)benzoyl]piperidin-4-yl}methyl)-N-(2-methoxyethyl)-4-methyl-2H-indazole-5-carboxamide

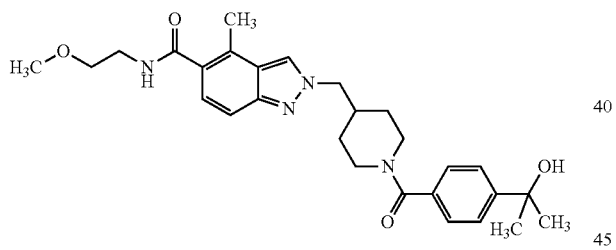

Analogously to Example 1b, Version B, 28 mg of the title compound was obtained from 100 mg of 71a and 82 mg of 4-(1-hydroxy-1-methylethyl)benzoic acid in DMF.

$^1$H-NMR (400 MHz, DMSO-d$_6$): δ [ppm], 1.24 (2H), 1.42 (8H), 2.20-2.40 (1H), 2.52 (3H), 2.64-3.11 (2H), 3.28 (3H), 3.34-3.43 (2H), 3.43-3.51 (2H), 3.53-3.71 (1H), 4.35 (3H), 4.76-5.43 (1H), 7.18 (1H), 7.28 (2H), 7.42 (1H), 7.46-7.56 (2H), 8.15 (1H), 8.51 (1H).

Example 335

2-{[1-(4-cyclohexylbenzoyl)piperidin-4-yl]methyl}-N-(2-methoxyethyl)-4-methyl-2H-indazole-5-carboxamide

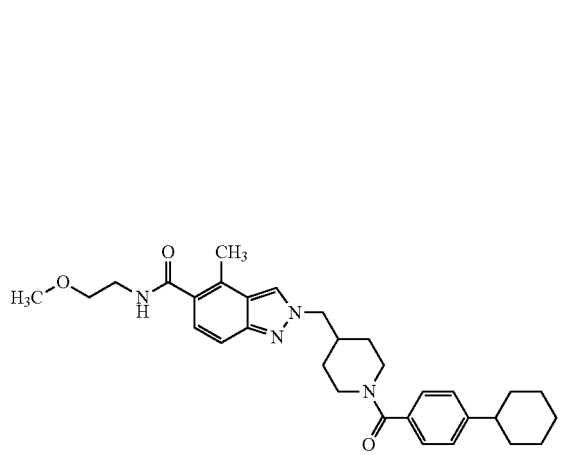 [SMILES: COCCNC(=O)c1ccc2nn(CC3CCN(C(=O)c4ccc(C5CCCCC5)cc4)CC3)cc2c1C]

Analogously to Example 1b, Version B, 75 mg of the title compound was obtained from 100 mg of 71a and 93 mg of 4-cyclohexylbenzoic acid in DMF.

$^1$H-NMR (400 MHz, DMSO-d$_6$): δ [ppm], 1.10-1.63 (9H), 1.64-1.89 (5H), 2.17-2.40 (1H), 2.52 (3H), 2.69-3.08 (2H), 3.28 (3H), 3.38-3.43 (2H), 3.43-3.49 (2H), 3.53-3.73 (1H), 4.35 (3H), 7.18 (1H), 7.27 (4H), 7.42 (1H), 8.15 (1H), 8.50 (1H).

Example 336

N-(2-methoxyethyl)-2-{[1-(6-methoxy-2-naphthoyl)piperidin-4-yl]methyl}-4-methyl-2H-indazole-5-carboxamide

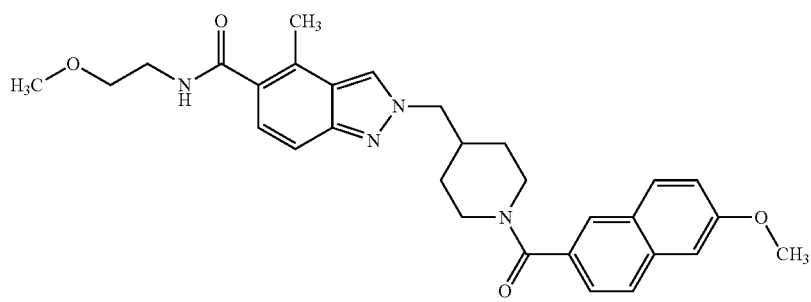

Analogously to Example 1b, Version B, 23 mg of the title compound was obtained from 100 mg of 71a) and 92 mg of 6-methoxy-naphthalen-2-carboxylic acid in DMF.

¹H-NMR (400 MHz, DMSO-d₆): δ [ppm], 1.23 (2H), 1.37-1.72 (2H), 2.23-2.39 (1H), 2.52 (3H), 2.72-3.12 (2H), 3.28 (3H), 3.36-3.42 (2H), 3.43-3.49 (2H), 3.59-3.81 (1H), 3.89 (3H), 4.36 (3H), 7.09-7.27 (2H), 7.33-7.49 (3H), 7.79-7.95 (3H), 8.15 (1H), 8.51 (1H).

Example 337

N-(2-methoxyethyl)-4-methyl-2-({1-[(2-phenylthiazol-5-yl)carbonyl]piperidin-4-yl}methyl)-2H-indazole-5-carboxamide

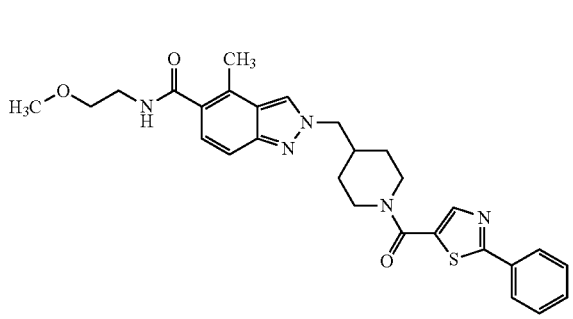 [SMILES: COCCNC(=O)c1ccc2nn(CC3CCN(C(=O)c4cnc(-c5ccccc5)s4)CC3)cc2c1C]

Analogously to Example 1b, Version B, 36 mg of the title compound was obtained from 100 mg of 71a and 93 mg of 2-phenylthiazol-5-carboxylic acid in DMF.

¹H-NMR (400 MHz, DMSO-d₆): δ [ppm], 1.23 (2H), 1.55 (2H), 2.19-2.45 (1H), 2.52-2.56 (3H), 2.70-3.24 (2H), 3.28 (3H), 3.36-3.43 (2H), 3.44-3.49 (2H), 4.37 (4H), 7.19 (1H), 7.43 (1H), 7.49-7.62 (3H), 7.90-8.03 (2H), 8.08-8.25 (2H), 8.52 (1H).

Example 338

N-(2-methoxyethyl)-4-methyl-2-({1-[(1-methyl-1H-benzimidazol-2-yl)carbonyl]-piperidin-4-yl}methyl)-2H-indazole-5-carboxamide

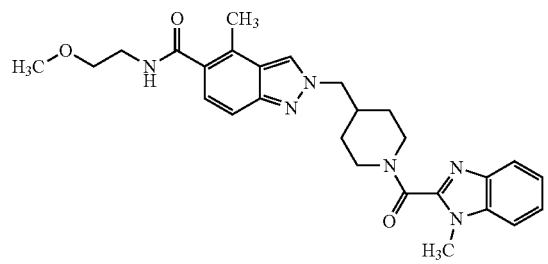 [SMILES: COCCNC(=O)c1ccc2nn(CC3CCN(C(=O)c4nc5ccccc5n4C)CC3)cc2c1C]

Analogously to Example 1b, Version B, 39 mg of the title compound was obtained from 100 mg of 71a and 80 mg of 1-methyl-1H-benzimidazol-2-carboxylic acid in DMF.

¹H-NMR (400 MHz, DMSO-d₆): δ [ppm], 1.22-1.43 (2H), 1.43-1.53 (1H), 1.59-1.70 (1H), 2.27-2.44 (1H), 2.53 (3H), 2.87 (1H), 3.11 (1H), 3.28 (3H), 3.36-3.42 (2H), 3.43-3.48 (2H), 3.83 (3H), 4.00-4.14 (1H), 4.39 (2H), 4.48-4.61 (1H), 7.18 (1H), 7.23-7.46 (3H), 7.58-7.74 (2H), 8.10-8.20 (1H), 8.53 (1H).

Example 339

N-(2-methoxyethyl)-4-methyl-2-({1-[(2-phenyloxazol-5-yl)carbonyl]piperidin-4-yl}methyl)-2H-indazole-5-carboxamide

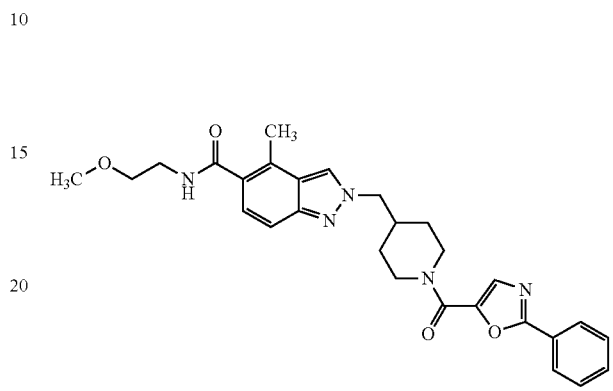

Analogously to Example 1b, Version B, 30 mg of the title compound was obtained from 100 mg of 71a and 86 mg of 2-phenyloxazol-5-carboxylic acid in DMF.

¹H-NMR (400 MHz, DMSO-d₆): δ [ppm], 1.14-1.48 (2H), 1.59 (2H), 2.24-2.46 (1H), 2.52-2.56 (3H), 2.71-3.01 (1H), 3.11-3.26 (1H), 3.28 (3H), 3.36-3.43 (2H), 3.43-3.50 (2H), 4.38 (4H), 7.19 (1H), 7.43 (1H), 7.52-7.67 (3H), 7.80 (1H), 7.97-8.05 (2H), 8.16 (1H), 8.53 (1H).

Example 340

2-{[1-(benzoxazol-2-ylcarbonyl)piperidin-4-yl]methyl}-N-(2-methoxyethyl)-4-methyl-2H-indazole-5-carboxamide

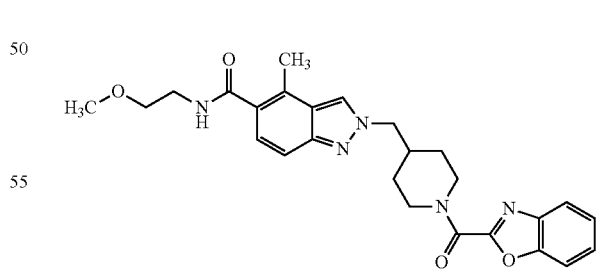

Analogously to Example 1b, Version B, 37 mg of the title compound was obtained from 100 mg of 71a and 84 mg of benzoxazol-2-carboxylic acid in DMF.

¹H-NMR (400 MHz, DMSO-d₆): δ [ppm], 1.19-1.43 (2H), 1.48-1.73 (2H), 2.28-2.45 (1H), 2.53 (3H), 2.91 (1H), 3.22 (1H), 3.33-3.57 (m, 7H), 4.25-4.60 (4H), 7.18 (1H), 7.36-7.62 (3H), 7.78-7.95 (2H), 8.16 (1H), 8.53 (1H).

Example 341

2-({1-[4-(1-cyano-1-methylethyl)benzoyl]piperidin-4-yl}methyl)-N-(2-methoxy-ethyl)-4-methyl-2H-indazole-5-carboxamide

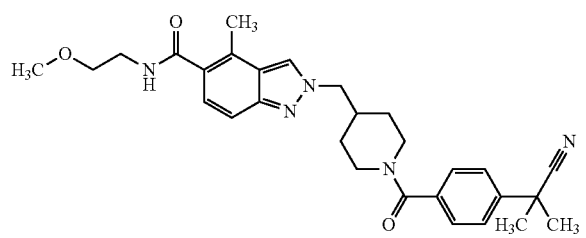 [SMILES: COCCNC(=O)c1ccc2nn(CC3CCN(C(=O)c4ccc(C(C)(C)C#N)cc4)CC3)cc2c1C]

Analogously to Example 1b, Version B, 20 mg of the title compound was obtained from 100 mg of 71a and 86 mg of 4-(1-cyano-1-methylethyl)benzoic acid in DMF.

$^1$H-NMR (300 MHz, DMSO-d$_6$): δ [ppm], 1.17-1.34 (2H), 1.35-1.64 (2H), 1.70 (6H), 2.16-2.40 (1H), 2.52 (3H), 2.64-3.13 (2H), 3.28 (3H), 3.40 (2H), 3.43-3.49 (2H), 3.49-3.67 (1H), 4.35 (3H), 7.18 (1H), 7.42 (3H), 7.58 (2H), 8.15 (1H), 8.50 (1H).

Example 342

N-(2-methoxyethyl)-4-methyl-2-({1-[4-(pyrimidin-2-yloxy)benzoyl]piperidin-4-yl}methyl)-2H-indazole-5-carboxamide

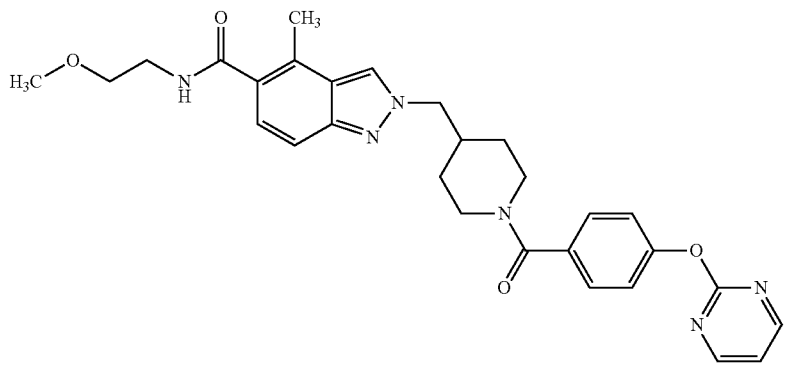 [SMILES: COCCNC(=O)c1ccc2nn(CC3CCN(C(=O)c4ccc(Oc5ncccn5)cc4)CC3)cc2c1C]

Analogously to Example 1b, Version B, 37 mg of the title compound was obtained from 100 mg of 71a and 98 mg of 4-(2-pyrimidinyloxy)benzoic acid in DMF.

$^1$H-NMR (400 MHz, DMSO-d$_6$): δ [ppm], 1.26 (2H), 1.38-1.66 (2H), 2.20-2.40 (1H), 2.52-2.56 (3H), 2.70-3.16 (2H), 3.28 (3H), 3.36-3.43 (2H), 3.43-3.49 (2H), 3.64-3.77 (m, 1H), 4.36 (3H), 7.18 (1H), 7.22-7.33 (3H), 7.39-7.49 (3H), 8.15 (1H), 8.43-8.57 (1H), 8.66 (2H).

Example 343

N-(2-methoxyethyl)-4-methyl-2-({1-[4-(pyridin-3-yloxy)benzoyl]piperidin-4-yl}methyl)-2H-indazole-5-carboxamide

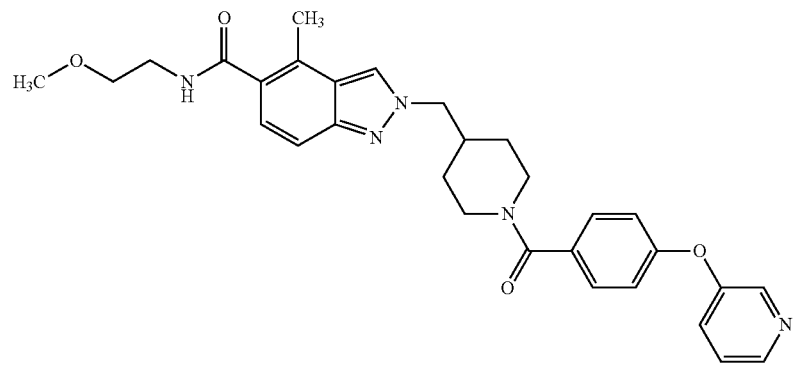 [SMILES: COCCNC(=O)c1ccc2nn(CC3CCN(C(=O)c4ccc(Oc5cccnc5)cc4)CC3)cc2c1C]

Analogously to Example 1b, Version B, 7 mg of the title compound was obtained from 75 mg of 71a and 73 mg of 4-(3-pyridyloxy)benzoic acid in DMF.

$^1$H-NMR (400 MHz, DMSO-d$_6$): δ [ppm], 1.17-1.32 (2H), 1.35-1.69 (2H), 2.19-2.38 (1H), 2.52 (3H), 2.70-3.14 (2H), 3.28 (3H), 3.34-3.43 (2H), 3.43-3.51 (2H), 3.55-3.70 (1H), 4.35 (3H), 7.04-7.13 (2H), 7.18 (1H), 7.37-7.46 (3H), 7.47-7.54 (1H), 7.58 (1H), 8.15 (1H), 8.38-8.55 (3H).

Example 344

N-(2-methoxyethyl)-2-{[1-(7-methoxy-2-naphthoyl)piperidin-4-yl]methyl}-4-methyl-2H-indazole-5-carboxamide

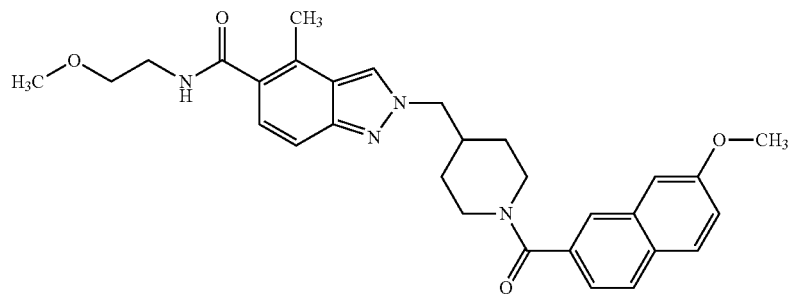

Analogously to Example 1b, Version B, 28 mg of the title compound was obtained from 75 mg of 71a and 69 mg of the carboxylic acid prepared in Example 344c) in DMF.

$^1$H-NMR (400 MHz, DMSO-d$_6$): δ [ppm], 1.21-1.35 (2H), 1.37-1.75 (2H), 2.23-2.39 (1H), 2.52 (3H), 2.73-3.13 (2H), 3.28 (3H), 3.35-3.42 (2H), 3.45 (2H), 3.53-3.74 (1H), 3.88 (3H), 4.37 (3H), 7.13-7.25 (2H), 7.29 (1H), 7.36-7.48 (2H), 7.77-7.93 (3H), 8.15 (1H), 8.52 (1H).

The starting material was prepared as follows:

Example 344a 7-methoxynaphthalen-2-yl-1,1,2,2,3,3,4,4,4-nonafluorobutan-1-sulphonate

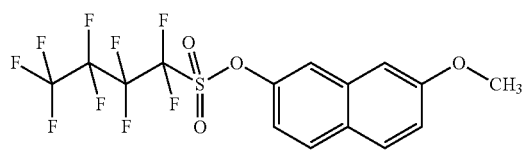 [SMILES: COc1ccc2ccc(OS(=O)(=O)C(F)(F)C(F)(F)C(F)(F)C(F)(F)F)cc2c1]

5.12 g of 7-methoxy-2-naphthol were dissolved in 50 ml toluene and cooled to 0° C. 30.7 ml of N,N-diisopropylethylamine and 17.6 ml of nonafluorobutanesulphonyl fluoride were successively added dropwise to this and the reaction mixture was then stirred at room temperature until complete conversion. The reaction mixture was poured into 600 ml of saturated ammonium chloride solution, the deposited brown oil separated and the aqueous phase extracted several times with ethyl acetate. The combined organic phases were washed with water and saturated sodium chloride solution, dried and concentrated. The residue was purified by column chromatography on silica gel using a hexane/ethyl acetate gradient. Yield: 11.45 g of the title compound.

$^1$H-NMR (400 MHz, DMSO-d$_6$): δ [ppm], 3.89 (3H), 7.28 (1H), 7.41 (1H), 7.52 (1H), 7.90-8.00 (2H), 8.05 (1H).

Example 344b

Methyl 7-methoxynaphthalen-2-carboxylate

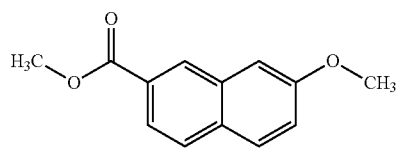

Analogously to Example 1e, 2.34 g of the title compound was obtained from 11.0 g of 344a and 8.8 ml of methanol.

$^1$H-NMR (400 MHz, DMSO-d$_6$): δ [ppm], 3.89 (3H), 3.91 (3H), 7.31 (1H), 7.57 (1H), 7.82 (1H), 7.94 (2H), 8.54 (1H).

Example 344c 7-methoxynaphthalen-2-carboxylic acid

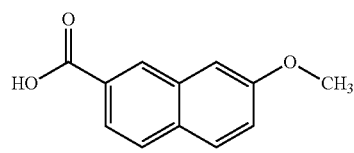

Analogously to Example 258d, 1.27 g of the title compound was obtained from 2.0 g of 344b.

$^1$H-NMR (300 MHz, DMSO-d6): δ [ppm], 3.89 (3H), 7.30 (1H), 7.53 (1H), 7.78-7.86 (1H), 7.87-8.01 (2H), 8.50 (1H), 12.99 (1H).

Example 345

N-(2-methoxyethyl)-4-methyl-2-{[1-(4-{[5-(trifluoromethyl)pyridin-2-yl]oxy}-benzoyl)piperidin-4-yl]methyl}-2H-indazole-5-carboxamide

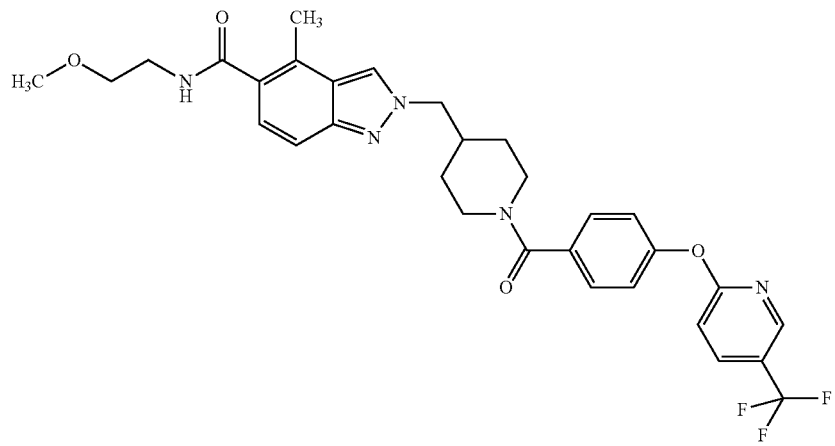 [SMILES: COCCNC(=O)c1ccc2nn(CC3CCN(C(=O)c4ccc(Oc5ccc(C(F)(F)F)cn5)cc4)CC3)cc2c1C]

Analogously to Example 1b, Version B, 221 mg of the title compound was obtained from 200 mg of 71a and 232 mg of 4-{[5-(trifluoromethyl)pyridin-2-yl]oxy}benzoic acid in DMF.

$^1$H-NMR (400 MHz, DMSO-d$_6$): δ [ppm], 1.21-1.34 (2H), 1.36-1.72 (2H), 2.23-2.39 (1H), 2.53 (3H), 2.89 (2H), 3.31 (3H), 3.36-3.43 (2H), 3.43-3.50 (2H), 3.53-3.86 (1H), 4.36 (3H), 7.18 (1H), 7.23-7.33 (3H), 7.37-7.50 (3H), 8.13 (1H), 8.25 (1H), 8.51 (1H), 8.55-8.63 (1H).

Example 346

N-(2-methoxyethyl)-4-methyl-2-({1-[4-(pyridin-2-yloxy)benzoyl]piperidin-4-yl}-methyl)-2H-indazole-5-carboxamide

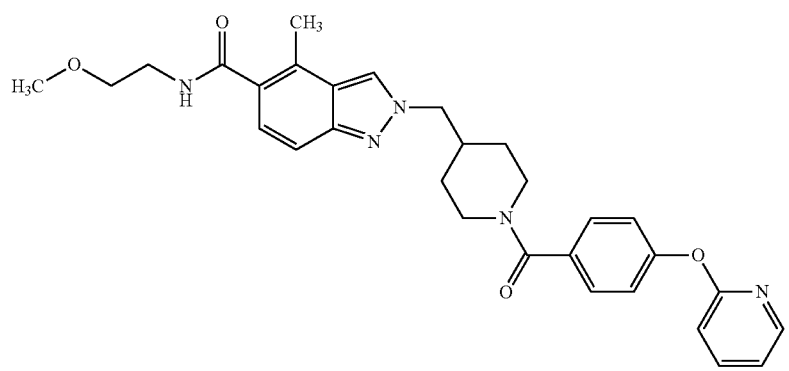 [SMILES: COCCNC(=O)c1ccc2nn(CC3CCN(C(=O)c4ccc(Oc5ccccn5)cc4)CC3)cc2c1C]

Analogously to Example 1b, Version B, 29 mg of the title compound was obtained from 100 mg of 71a and 98 mg of 4-(2-pyridyloxy)benzoic acid in DMF.

$^1$H-NMR (400 MHz, DMSO-d$_6$): δ [ppm], 1.23 (2H), 1.39-1.68 (2H), 2.24-2.39 (1H), 2.52-2.56 (3H), 2.71-3.13 (2H), 3.28 (3H), 3.36-3.43 (2H), 3.45 (2H), 3.53-3.87 (1H), 4.36 (3H), 7.08 (1H), 7.13-7.26 (4H), 7.34-7.52 (3H), 7.88 (1H), 8.07-8.23 (2H), 8.51 (1H).

Example 347

N-(2-methoxyethyl)-4-methyl-2-{[1-(4-{[4-(trifluoromethyl)pyrimidin-2-yl]-oxy}benzoyl)piperidin-4-yl]methyl}-2H-indazole-5-carboxamide

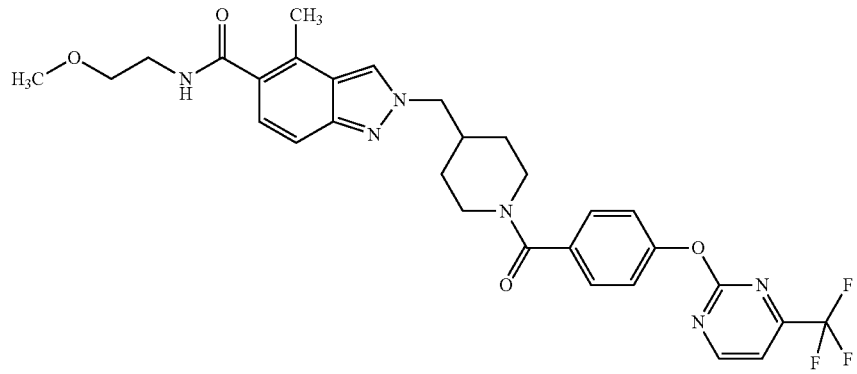 [SMILES: COCCNC(=O)c1ccc2nn(CC3CCN(C(=O)c4ccc(Oc5nccc(C(F)(F)F)n5)cc4)CC3)cc2c1C]

Analogously to Example 1b, Version B, 11 mg of the title compound was obtained from 75 mg of 71a and 97 mg of 4-{[4-(trifluoromethyl)pyrimidin-2-yl]oxy}benzoic acid in DMF.

$^1$H-NMR (400 MHz, DMSO-d$_6$): δ [ppm], 1.23 (2H), 1.37-1.69 (2H), 2.19-2.39 (1H), 2.53 (3H), 2.68-3.18 (2H), 3.28 (3H), 3.36-3.43 (2H), 3.45 (2H), 3.51-3.79 (1H), 4.36 (3H), 7.18 (1H), 7.31-7.39 (2H), 7.39-7.53 (3H), 7.81 (1H), 8.15 (1H), 8.51 (1H), 9.00 (1H).

Example 348

2-{[1-(benzothiazol-2-ylcarbonyl)piperidin-4-yl]methyl}-N-(2-methoxyethyl)-4-methyl-2H-indazole-5-carboxamide

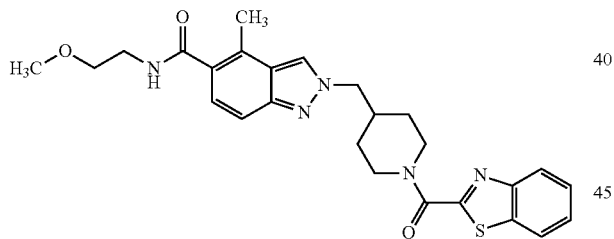

Analogously to Example 1b, Version B, 28 mg of the title compound was obtained from 75 mg of 71a and 61 mg of benzothiazol-2-carboxylic acid in DMF.

$^1$H-NMR (300 MHz, DMSO-d$_6$): δ [ppm], 1.34 (2H), 1.62 (2H), 2.32-2.45 (1H), 2.53 (3H), 2.82-3.00 (1H), 3.26 (1H), 3.28 (3H), 3.40 (2H), 3.43-3.50 (2H), 4.38 (3H), 4.98-5.23 (1H), 7.19 (1H), 7.43 (1H), 7.59 (2H), 8.01-8.30 (3H), 8.53 (1H).

Example 349

N-(2-methoxyethyl)-4-methyl-2-{[1-(4-{[6-(trifluoromethyl)pyridin-3-yl]oxy}-benzoyl)piperidin-4-yl]methyl}-2H-indazole-5-carboxamide

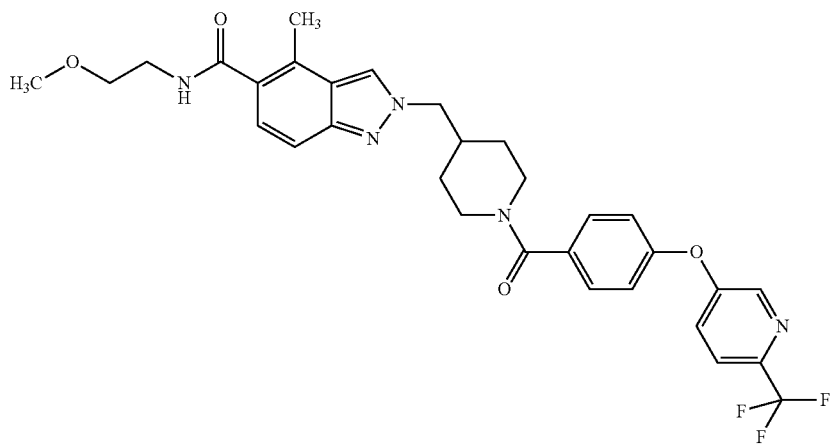 [SMILES: COCCNC(=O)c1ccc2nn(CC3CCN(C(=O)c4ccc(Oc5ccc(C(F)(F)F)nc5)cc4)CC3)cc2c1C]

Analogously to Example 1b, Version B, 34 mg of the title compound was obtained from 75 mg of 71a and 96 mg of 303b in DMF.

¹H-NMR (400 MHz, DMSO-d₆): δ [ppm], 1.24 (2H), 1.37-1.68 (2H), 2.22-2.38 (1H), 2.53 (3H), 2.71-3.14 (2H), 3.28 (3H), 3.36-3.43 (2H), 3.44-3.49 (2H), 3.52-3.84 (1H), 4.36 (3H), 7.09-7.29 (3H), 7.35-7.53 (3H), 7.65 (1H), 7.92 (1H), 8.13 (1H), 8.51 (1H), 8.60 (1H).

Example 350

N-(2-methoxyethyl)-4-methyl-2-{[1-(4-{[6-(trifluoromethyl)pyridin-2-yl]oxy}-benzoyl)piperidin-4-yl]methyl}-2H-indazole-5-carboxamide

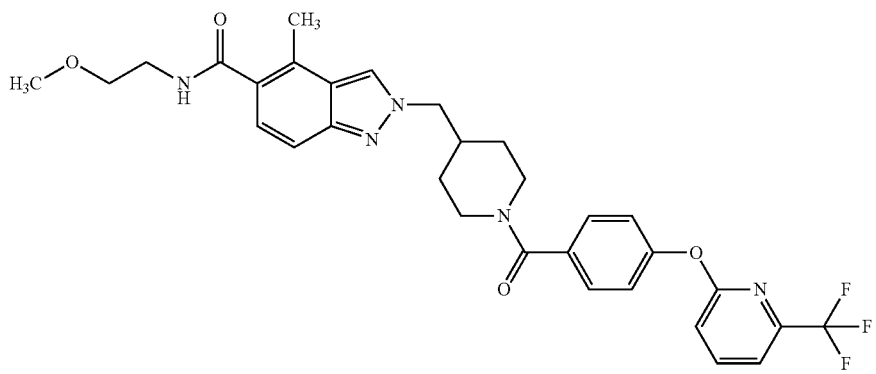 [SMILES: COCCNC(=O)c1ccc2nn(CC3CCN(C(=O)c4ccc(Oc5cccc(C(F)(F)F)n5)cc4)CC3)cc2c1C]

Analogously to Example 1b, Version B, 36 mg of the title compound was obtained from 100 mg of 71a and 129 mg of 4-{[6-(trifluoromethyl)pyridin-2-yl]oxy}benzoic acid in DMF.

¹H-NMR (400 MHz, DMSO-d₆): δ [ppm], 1.20-1.34 (2H), 1.36-1.66 (2H), 2.24-2.39 (1H), 2.53 (3H), 2.70-3.16 (2H), 3.28 (3H), 3.36-3.43 (2H), 3.44-3.49 (2H), 3.53-3.82 (1H), 4.36 (3H), 7.18 (1H), 7.22-7.30 (2H), 7.32-7.50 (4H), 7.67 (1H), 8.06-8.21 (2H), 8.51 (1H).

Example 351

2-({1-[(4'-methoxybiphenyl-4-yl)carbonyl]piperidin-4-yl}methyl)-N-(2-methoxy-ethyl)-4-methyl-2H-indazole-5-carboxamide

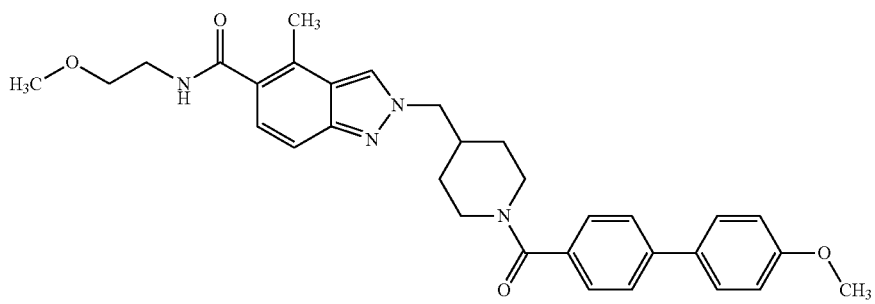

Analogously to Example 1b, Version B, 15 mg of the title compound was obtained from 100 mg of 71a and 104 mg of 4'-methoxy-biphenyl-4-carboxylic acid in DMF.

¹H-NMR (300 MHz, DMSO-d₆): δ [ppm], 1.24 (2H), 1.37-1.64 (2H), 2.19-2.32 (1H), 2.53 (3H), 2.74-3.10 (2H), 3.28 (3H), 3.40 (2H), 3.45 (2H), 3.67-3.91 (4H), 4.21-4.64 (3H), 7.04 (2H), 7.19 (1H), 7.41 (2H), 7.66 (5H), 8.04-8.22 (1H), 8.51 (1H).

Example 352

N-(2-methoxyethyl)-4-methyl-2-({1-[(3-phenyl-1,2,4-oxadiazol-5-yl)carbonyl]-piperidin-4-yl}methyl)-2H-indazole-5-carboxamide

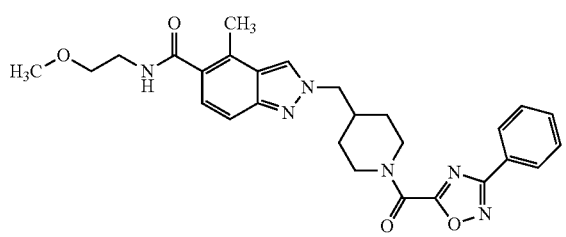 [SMILES: COCCNC(=O)c1ccc2nn(CC3CCN(C(=O)c4nc(-c5ccccc5)no4)CC3)cc2c1C]

Analogously to Example 1b, Version B, 12 mg of the title compound was obtained from 100 mg of 71a and 78 mg of 3-phenyl-1,2,4-oxadiazol-5-carboxylic acid in DMF.

$^1$H-NMR (300 MHz, DMSO-d$_6$): δ [ppm], 1.33 (2H), 1.50-1.72 (2H), 2.31-2.45 (1H), 2.53 (3H), 2.86-3.04 (1H), 3.16-3.26 (1H), 3.28 (3H), 3.41 (2H), 3.43-3.51 (2H), 3.94-4.13 (1H), 4.28-4.55 (3H), 7.19 (1H), 7.43 (1H), 7.52-7.72 (3H), 7.96-8.09 (2H), 8.13 (1H), 8.52 (1H).

Example 353

N-(2-methoxyethyl)-4-methyl-2-({1-[4-(3,4,5,6-tetrahydro-2H-pyran-4-yloxy)-benzoyl]piperidin-4-yl}methyl)-2H-indazole-5-carboxamide

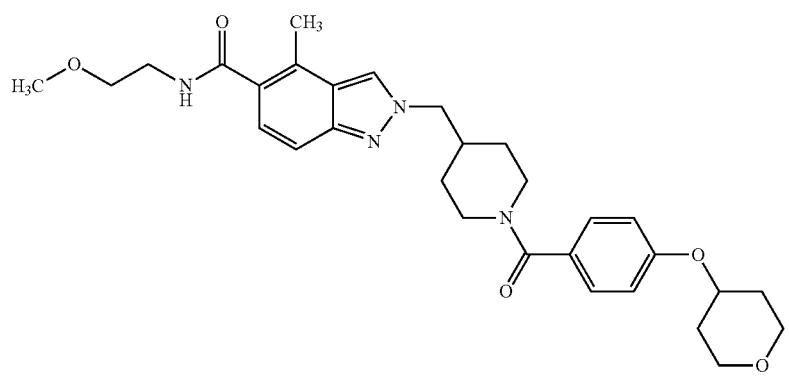 [SMILES: COCCNC(=O)c1ccc2nn(CC3CCN(C(=O)c4ccc(OC5CCOCC5)cc4)CC3)cc2c1C]

Analogously to Example 1b, Version B, 21 mg of the title compound was obtained from 100 mg of 71a and 91 mg of 4-(3,4,5,6-tetrahydro-2H-pyran-4-yloxy)benzoic acid in DMF.

$^1$H-NMR (300 MHz, DMSO-d$_6$): δ [ppm], 1.23 (2H), 1.38-1.70 (4H), 1.97 (2H), 2.18-2.41 (1H), 2.53 (3H), 2.75-3.02 (2H), 3.28 (3H), 3.35-3.54 (8H), 3.84 (2H), 4.35 (2H), 4.52-4.77 (1H), 7.00 (2H), 7.18 (1H), 7.30 (2H), 7.42 (1H), 8.13 (1H), 8.50 (1H).

Example 354

N-(2-methoxyethyl)-4-methyl-2-({1-[(5-phenyloxazol-2-yl)carbonyl]piperidin-4-yl}methyl)-2H-indazole-5-carboxamide

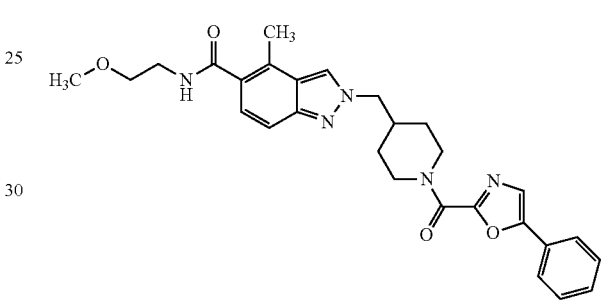

Analogously to Example 1b, Version B, 10 mg of the title compound was obtained from 100 mg of 71a and 77 mg of 5-phenyl-oxazol-2-carboxylic acid in DMF.

$^1$H-NMR (400 MHz, DMSO-d$_6$): δ [ppm], 1.17-1.41 (2H), 1.59 (2H), 2.28-2.45 (1H), 2.52-2.56 (3H), 2.85 (1H), 3.20 (1H), 3.28 (3H), 3.36-3.43 (2H), 3.44-3.50 (2H), 4.38 (3H), 4.57-4.74 (1H), 7.19 (1H), 7.39-7.57 (4H), 7.74-7.82 (2H), 7.88 (1H), 8.13 (1H), 8.52 (1H).

Example 355

N-(2-methoxyethyl)-4-methyl-2-[(1-{4-[3-(trifluoromethyl)phenoxy]benzoyl}-piperidin-4-yl)methyl]-2H-indazole-5-carboxamide

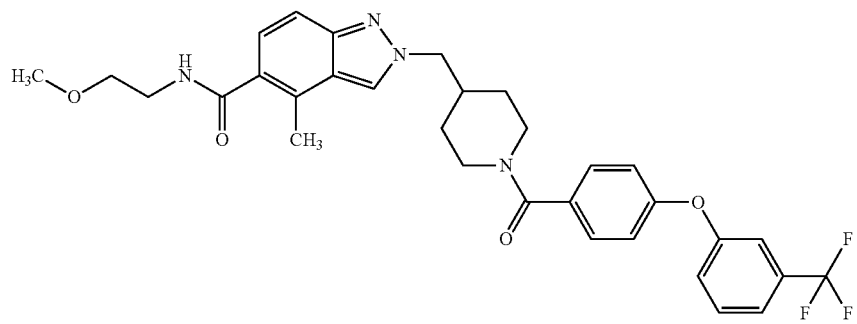 [SMILES: COCCNC(=O)c1ccc2nn(CC3CCN(C(=O)c4ccc(Oc5cccc(C(F)(F)F)c5)cc4)CC3)cc2c1C]

Analogously to Example 1b, Version B, 40 mg of the title compound was obtained from 100 mg of 71a and 115 mg of 4-[(3-(trifluoromethyl)phenoxy]benzoic acid in DMF.

$^1$H-NMR (400 MHz, DMSO-d$_6$): δ [ppm], 1.23 (2H), 1.35-1.65 (2H), 2.19-2.38 (1H), 2.52-2.56 (3H), 2.71-3.12 (2H), 3.28 (3H), 3.36-3.43 (2H), 3.43-3.50 (2H), 3.53-3.87 (1H), 4.35 (3H), 7.07-7.15 (2H), 7.18 (1H), 7.30-7.48 (5H), 7.54 (1H), 7.64 (1H), 8.13 (1H), 8.50 (1H).

Example 356

2-[(1-{4-[(5-cyanopyridin-2-yl)oxy]benzoyl}piperidin-4-yl)methyl]-N-(2-methoxyethyl)-4-methyl-2H-indazole-5-carboxamide

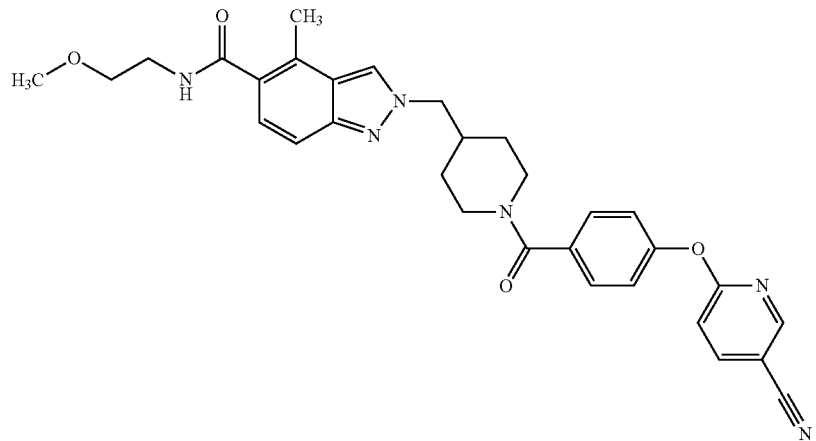 [SMILES: COCCNC(=O)c1ccc2nn(CC3CCN(C(=O)c4ccc(Oc5ccc(C#N)cn5)cc4)CC3)cc2c1C]

Analogously to Example 1b, Version B, 15 mg of the title compound was obtained from 100 mg of 71a and 98 mg of 4-[(5-cyanopyridin-2-yl)oxy]benzoic acid in DMF.

$^1$H-NMR (400 MHz, DMSO-d$_6$): δ [ppm], 1.21-1.35 (2H), 1.36-1.75 (2H), 2.23-2.39 (1H), 2.53 (3H), 2.69-3.19 (2H), 3.28 (3H), 3.36-3.43 (2H), 3.46 (2H), 3.53-3.85 (1H), 4.36 (3H), 7.18 (1H), 7.23-7.33 (3H), 7.36-7.53 (3H), 8.13 (1H), 8.34 (1H), 8.51 (1H), 8.66 (1H).

Example 357

2-[(1-{4-[(5-chloropyridin-2-yl)oxy]
benzoyl}piperidin-4-yl)methyl]-N-(2-methoxy-
ethyl)-4-methyl-2H-indazole-5-carboxamide

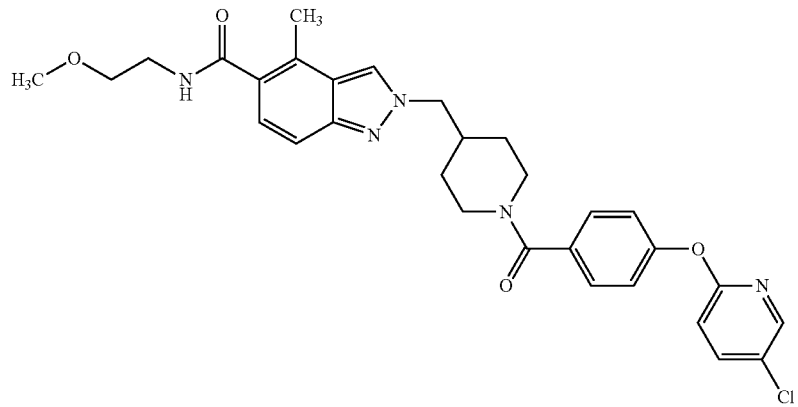 [SMILES: COCCNC(=O)c1ccc2nn(CC3CCN(C(=O)c4ccc(Oc5ccc(Cl)cn5)cc4)CC3)cc2c1C]

Analogously to Example 1b, Version B, 40 mg of the title compound was obtained from 100 mg of 71a and 102 mg of 4-[(5-chloropyridin-2-yl)oxy]benzoic acid in DMF.

$^1$H-NMR (300 MHz, DMSO-$d_6$): δ [ppm], 1.25 (2H), 1.36-1.70 (2H), 2.20-2.39 (1H), 2.53 (3H), 2.66-3.15 (2H), 3.28 (3H), 3.40 (2H), 3.43-3.50 (2H), 3.55-3.90 (1H), 4.36 (3H), 7.08-7.28 (4H), 7.42 (3H), 7.99 (1H), 8.10-8.30 (2H), 8.51 (1H).

Example 358

2-({1-[4-(2,4-difluorophenoxy)benzoyl]piperidin-4-yl}methyl)-N-(2-methoxy-ethyl)-4-methyl-2H-indazole-5-carboxamide

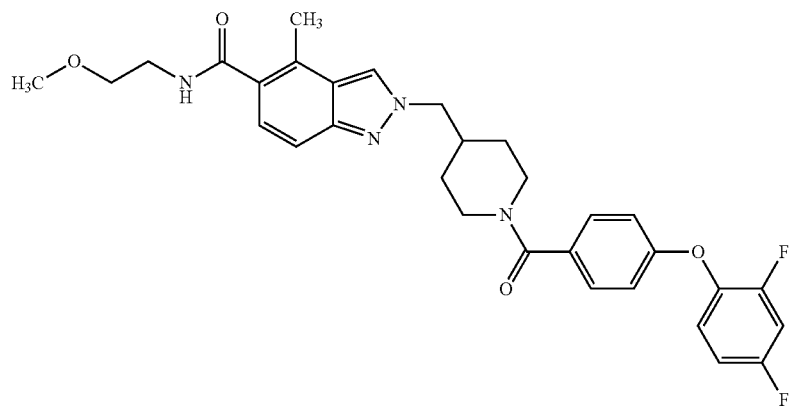 [SMILES: COCCNC(=O)c1ccc2nn(CC3CCN(C(=O)c4ccc(Oc5ccc(F)cc5F)cc4)CC3)cc2c1C]

Analogously to Example 1b, Version B, 22 mg of the title compound was obtained from 100 mg of 71a and 102 mg of 4-(2,4-difluorophenoxy)benzoic acid in DMF.

$^1$H-NMR (400 MHz, DMSO-$d_6$): δ [ppm], 1.21 (2H), 1.33-1.76 (2H), 2.20-2.39 (1H), 2.52 (3H), 2.69-3.13 (2H), 3.28 (3H), 3.36-3.43 (2H), 3.43-3.50 (2H), 3.53-3.90 (1H), 4.35 (3H), 6.91-7.04 (2H), 7.11-7.22 (2H), 7.30-7.46 (4H), 7.51 (1H), 8.13 (1H), 8.50 (1H).

Example 359

2-({1-[4-(3,4-difluorophenoxy)benzoyl]piperidin-4-yl}methyl)-N-(2-methoxy-ethyl)-4-methyl-2H-indazole-5-carboxamide

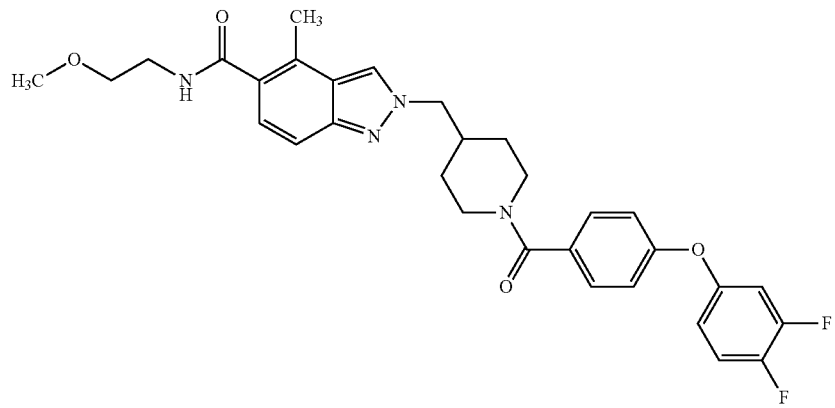 [SMILES: COCCNC(=O)c1ccc2nn(CC3CCN(C(=O)c4ccc(Oc5ccc(F)c(F)c5)cc4)CC3)cc2c1C]

Analogously to Example 1b, Version B, 23 mg of the title compound was obtained from 100 mg of 71a and 102 mg of 4-(3,4-difluorophenoxy)benzoic acid in DMF.

$^1$H-NMR (300 MHz, DMSO-d$_6$): δ [ppm], 1.17-1.30 (2H), 1.35-1.70 (2H), 2.20-2.40 (1H), 2.52 (3H), 2.74-3.14 (2H), 3.28 (3H), 3.40 (2H), 3.43-3.51 (2H), 3.52-3.89 (1H), 4.35 (3H), 6.94 (1H), 7.05 (2H), 7.18 (1H), 7.30 (1H), 7.36-7.59 (4H), 8.15 (1H), 8.51 (1H).

Example 360

N-(2-methoxyethyl)-4-methyl-2-[(1-{[4'-(trifluoromethyl)biphenyl-4-yl]-carbonyl}piperidin-4-yl)methyl]-2H-indazole-5-carboxamide

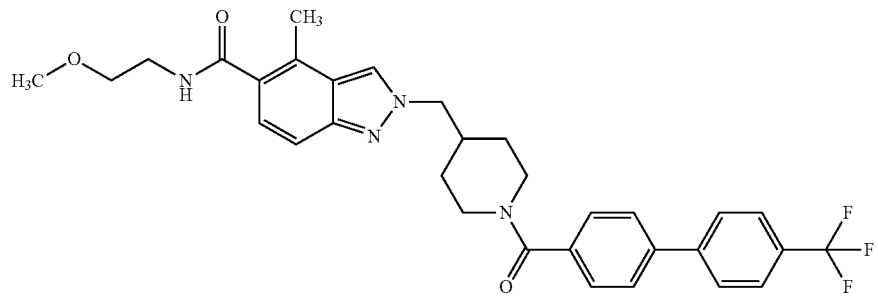 [SMILES: COCCNC(=O)c1ccc2nn(CC3CCN(C(=O)c4ccc(-c5ccc(C(F)(F)F)cc5)cc4)CC3)cc2c1C]

Analogously to Example 1b, Version B, 44 mg of the title compound was obtained from 100 mg of 71a and 109 mg of 4'-(trifluoromethyl)biphenyl-4-carboxylic acid in DMF LC-MS: R$_t$=1.28 min, MS (ES+): m/z=579 (M+H)$^+$.

Example 361

2-({1-[4-(3-fluorophenoxy)benzoyl]piperidin-4-yl}methyl)-N-(2-methoxyethyl)-4-methyl-2H-indazole-5-carboxamide

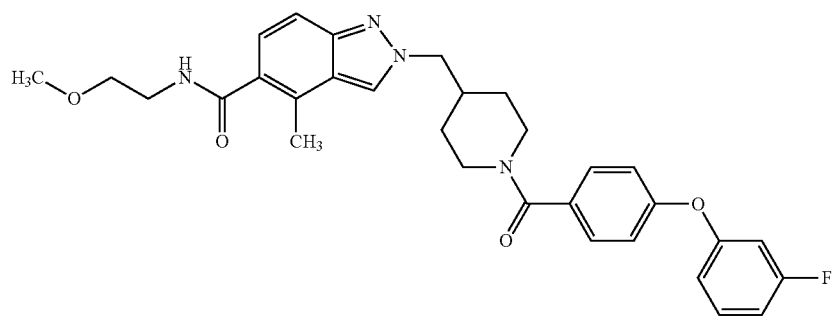 [SMILES: COCCNC(=O)c1ccc2nn(CC3CCN(C(=O)c4ccc(Oc5cccc(F)c5)cc4)CC3)cc2c1C]

Analogously to Example 1b, Version B, 43 mg of the title compound was obtained from 100 mg of 71a and 95 mg of 4-(3-fluorophenoxy)benzoic acid in DMF.

$^1$H-NMR (400 MHz, DMSO-$d_6$): δ [ppm], 1.17-1.31 (2H), 1.33-1.69 (2H), 2.19-2.38 (1H), 2.52 (3H), 2.70-3.11 (2H), 3.28 (3H), 3.36-3.43 (2H), 3.43-3.49 (2H), 3.54-3.85 (1H), 4.35 (3H), 6.85-7.13 (5H), 7.18 (1H), 7.35-7.55 (4H), 8.15 (1H), 8.51 (1H).

Example 362

2-{[1-(2-fluoro-4-isopropoxybenzoyl)piperidin-4-yl]methyl}-N-(2-methoxy-ethyl)-4-methyl-2H-indazole-5-carboxamide

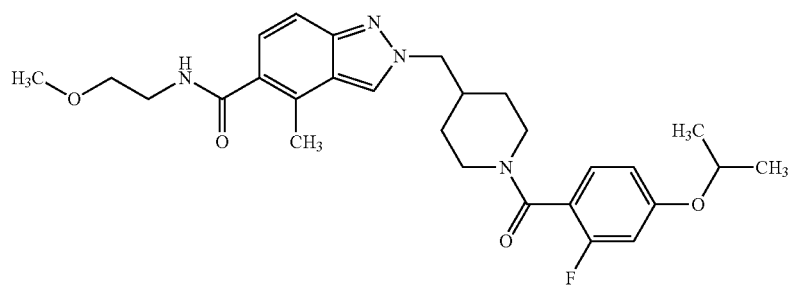 [SMILES: COCCNC(=O)c1ccc2nn(CC3CCN(C(=O)c4ccc(OC(C)C)cc4F)CC3)cc2c1C]

Analogously to Example 1b, Version B, 31 mg of the title compound was obtained from 75 mg of 71a and 41 mg of 2-fluoro-4-isopropoxybenzoic acid.

$^1$H-NMR (300 MHz, chloroform-d): δ [ppm], 1.21-1.42 (8H), 1.51 (1H), 1.69 (1H), 2.38 (1H), 2.56-2.80 (4H), 2.87-3.08 (1H), 3.36 (3H), 3.48-3.73 (4H), 4.28 (2H), 4.51 (1H), 4.74 (1H), 5.28 (1H), 6.19 (1H), 6.54 (1H), 6.67 (1H), 7.13-7.38 (2H), 7.50 (1H), 7.94 (1H).

Example 363

2-({1-[(3-fluoro-3',4'-dimethylbiphenyl-4-yl)carbonyl]piperidin-4-yl}methyl)-N-(2-methoxyethyl)-4-methyl-2H-indazole-5-carboxamide

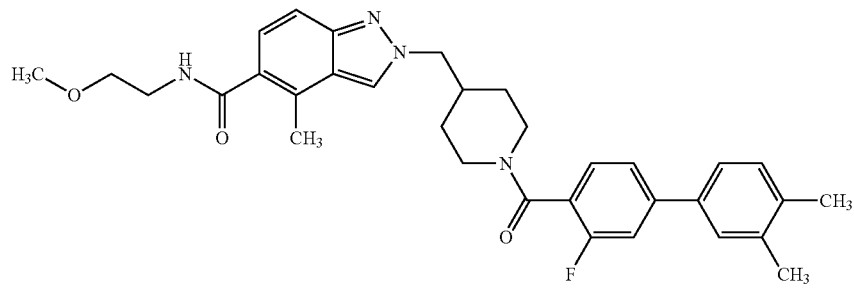

Analogously to Example 1b, Version B, 35 mg of the title compound was obtained from 75 mg of 71a and 50 mg of 3-fluoro-3',4'-dimethylbiphenyl-4-carboxylic acid.

$^1$H-NMR (300 MHz, chloroform-d): δ [ppm], 1.25-1.51 (2H), 1.57 (1H), 1.76 (1H), 2.25-2.37 (6H), 2.45 (1H), 2.61-2.71 (3H), 2.79 (1H), 3.06 (1H), 3.40 (3H), 3.53-3.77 (5H), 4.34 (2H), 4.83 (1H), 6.04-6.30 (1H), 7.15-7.47 (7H), 7.55 (1H), 7.98 (1H).

Example 364

2-({1-[(2',3-difluoro-4'-methoxybiphenyl-4-yl)carbonyl]piperidin-4-yl}methyl)-N-(2-methoxyethyl)-4-methyl-2H-indazole-5-carboxamide

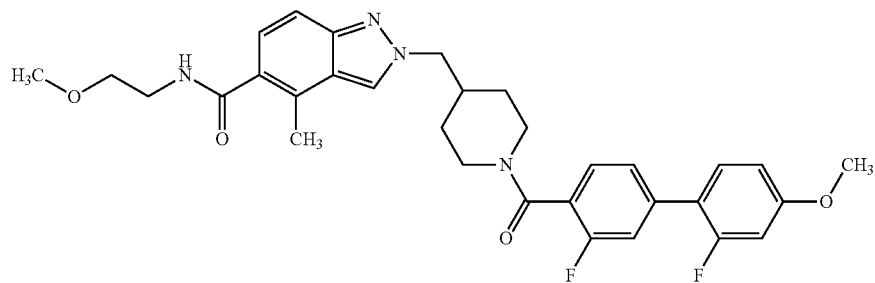

Analogously to Example 1b, Version B, 28 mg of the title compound was obtained from 90 mg of 71a and 65 mg of 3,2'-difluoro-4'-methoxybiphenyl-4-carboxylic acid.

$^1$H-NMR (300 MHz, chloroform-d): δ [ppm], 1.25-1.50 (2H), 1.50-1.84 (2H), 2.44 (1H), 2.66 (3H), 2.78 (1H), 3.03 (1H), 3.39 (3H), 3.53-3.76 (5H), 3.85 (3H), 4.23-4.45 (2H), 4.83 (1H), 6.17 (1H), 6.64-6.92 (2H), 7.18-7.48 (5H), 7.54 (1H), 7.97 (1H).

Example 365

2-({1-[4-(difluoromethoxy)benzoyl]piperidin-4-yl}methyl)-N-(2-methoxyethyl)-4-methyl-2H-indazole-5-carboxamide

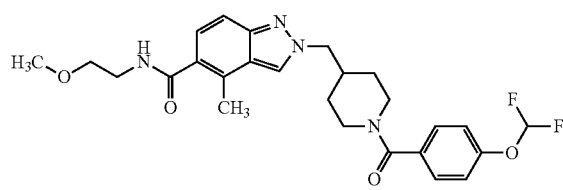 [SMILES: COCCNC(=O)c1ccc2nn(CC3CCN(C(=O)c4ccc(OC(F)F)cc4)CC3)cc2c1C]

Analogously to Example 1b, Version B, 23 mg of the title compound was obtained from 75 mg of 71a and 38 mg of 4-(difluoromethoxy)benzoic acid.

$^1$H-NMR (300 MHz, chloroform-d): δ [ppm], 1.26 (2H), 1.59 (2H), 2.26-2.49 (1H), 2.62 (3H), 2.84 (2H), 3.36 (3H), 3.43 (1H), 3.50-3.96 (4H), 4.29 (2H), 4.46-5.02 (1H), 6.13-6.25 (1H), 6.26-6.82 (1H), 7.11 (2H), 7.22-7.43 (3H), 7.50 (1H), 7.93 (1H).

Example 366

2-({1-[4-(2-fluorophenoxy)benzoyl]piperidin-4-yl}methyl)-N-(2-methoxyethyl)-4-methyl-2H-indazole-5-carboxamide

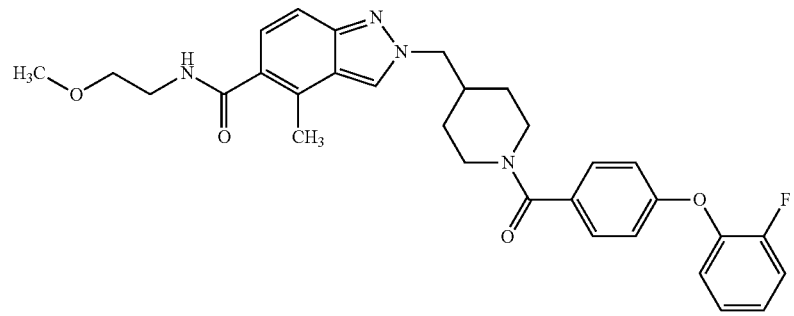 [SMILES: COCCNC(=O)c1ccc2nn(CC3CCN(C(=O)c4ccc(Oc5ccccc5F)cc4)CC3)cc2c1C]

120 mg of compound 54, 26 mg of o-fluorophenol, 152 mg of caesium carbonate, 6.7 mg of copper(I) bromide and 3.2 mg of (2-pyridyl)acetone were suspended in 6 ml dimethyl sulphoxide and stirred for 3 days at 80° C. The reaction mixture was filtered, the filter cake washed with water and ethyl acetate, and the aqueous phase extracted several times with ethyl acetate. The combined organic phases were dried with sodium sulphate and concentrated. The residue was purified by HPLC and 12 mg of the title compound was obtained.

$^1$H-NMR (300 MHz, chloroform-d): δ [ppm], 1.16-1.47 (2H), 1.62 (2H), 2.43 (1H), 2.66 (3H), 2.85 (2H), 3.39 (3H), 3.53-3.74 (4H), 3.79-4.19 (1H), 4.33 (2H), 4.47-5.02 (1H), 6.15 (1H), 6.96 (2H), 7.07-7.23 (3H), 7.30-7.45 (3H), 7.54 (1H), 7.96 (1H).

Example 367

2-({1-[(4'-cyano-2'-methylbiphenyl-4-yl)carbonyl]piperidin-4-yl}methyl)-N-(2-methoxyethyl)-4-methyl-2H-indazole-5-carboxamide

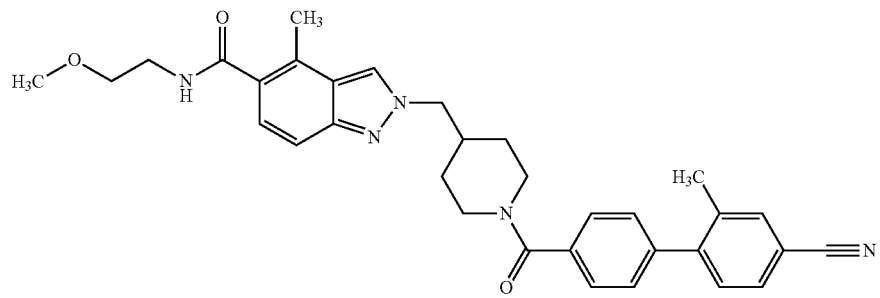 [SMILES: COCCNC(=O)c1ccc2nn(CC3CCN(C(=O)c4ccc(-c5ccc(C#N)cc5C)cc4)CC3)cc2c1C]

Analogously to Example 317, 40 mg of the title compound was obtained from 80 mg of 54 and 38 mg of (2-methyl-4-cyanophenyl)boronic acid under reflux.

$^1$H-NMR (400 MHz, DMSO-$d_6$): δ [ppm], 1.20-1.34 (2H), 1.36-1.69 (2H), 2.28 (4H), 2.53 (3H), 2.69-3.19 (2H), 3.28 (3H), 3.36-3.43 (2H), 3.43-3.50 (2H), 3.54-3.77 (1H), 4.37 (3H), 7.18 (1H), 7.37-7.50 (6H), 7.74 (1H), 7.83 (1H), 8.15 (1H), 8.52 (1H).

Example 368

2-({1-[4-(5-chloropyridin-2-yl)benzoyl]piperidin-4-yl}methyl)-N-(2-methoxy-ethyl)-4-methyl-2H-indazole-5-carboxamide

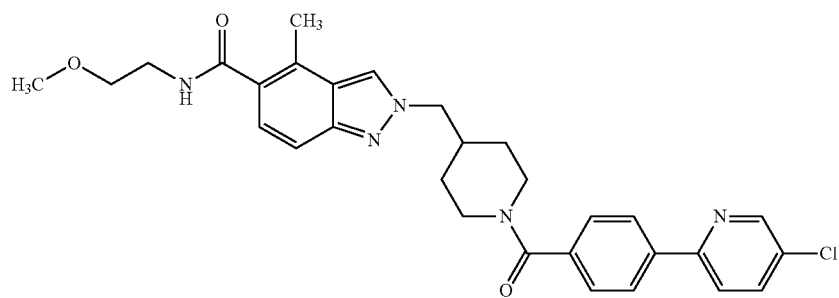 [SMILES: COCCNC(=O)c1ccc2nn(CC3CCN(C(=O)c4ccc(-c5ccc(Cl)cn5)cc4)CC3)cc2c1C]

200 mg of the aryl bromide prepared in Example 54 together with 187 mg of (5-chloropyridin-2-yl)-2-boronic acid pinacol ester were first placed in 3 ml DMF, treated with 48 mg of 1,1'-bis(diphenylphosphino)ferrocenodichloropalladium(II), 39 mg of copper(I)chloride 254 mg of caesium carbonate and 22 mg of 1,1'-bis(diphenylphosphino)ferrocene and heated for ca. 1 day at 70° C., until further progress of the reaction could no longer be observed. The reaction mixture was treated with water and saturated sodium hydrogen carbonate solution, treated several times with ethyl acetate, and the combined organic phases dried with sodium sulphate and concentrated. After HPLC purification, this yielded 92 mg of the title compound.

$^1$H-NMR (400 MHz, DMSO-$d_6$): δ [ppm], 1.19-1.36 (2H), 1.37-1.72 (2H), 2.23-2.41 (1H), 2.52-2.57 (3H), 2.70-3.13 (2H), 3.28 (3H), 3.39 (2H), 3.45 (2H), 3.51-3.80 (1H), 4.36 (3H), 7.18 (1H), 7.36-7.52 (3H), 8.05 (2H), 8.09-8.22 (3H), 8.51 (1H), 8.73 (1H).

Example 369

N-(2-methoxyethyl)-4-methyl-2-[(1-{4-[6-(trifluoromethyl)pyridin-2-yl]-benzoyl}piperidin-4-yl)methyl]-2H-indazole-5-carboxamide

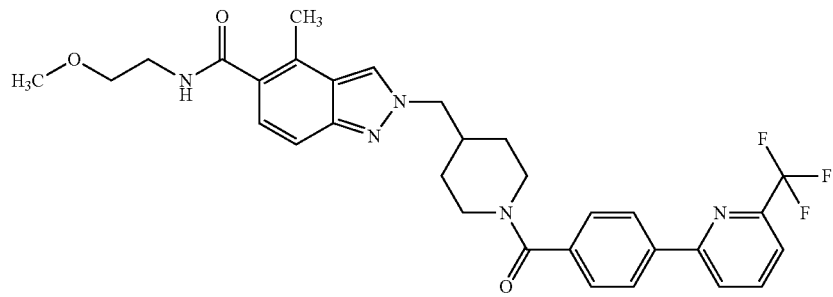 [SMILES: COCCNC(=O)c1ccc2nn(CC3CCN(C(=O)c4ccc(-c5cccc(C(F)(F)F)n5)cc4)CC3)cc2c1C]

Analogously to Example 317, 33 mg of the title compound was obtained from 100 mg of 54 and 80 mg of [6-(trifluoromethyl)pyridin-2-yl]boronic acid pinacol ester under reflux.

$^1$H-NMR (400 MHz, DMSO-$d_6$): δ [ppm], 1.18-1.35 (2H), 1.36-1.67 (2H), 2.25-2.41 (1H), 2.53 (3H), 2.70-3.15 (2H), 3.28 (3H), 3.35-3.43 (2H), 3.43-3.51 (2H), 3.53-3.73 (1H), 4.37 (3H), 7.18 (1H), 7.42 (1H), 7.53 (2H), 7.89 (1H), 8.06-8.26 (4H), 8.33 (1H), 8.51 (1H).

Example 370

N-(2-methoxyethyl)-2-({1-[(4'-methoxy-2'-methylbiphenyl-4-yl)carbonyl]-piperidin-4-yl}methyl)-4-methyl-2H-indazole-5-carboxamide

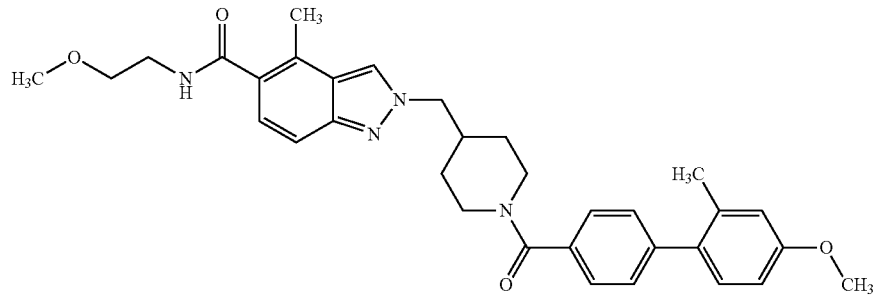

Analogously to Example 317, 52 mg of the title compound was obtained from 100 mg of 54 and 48 mg of (4-methoxy-2-methylphenyl)boronic acid under reflux.

$^1$H-NMR (400 MHz, DMSO-$d_6$): δ [ppm]=1.16-1.35 (2H), 1.37-1.67 (2H), 2.23 (3H), 2.26-2.42 (1H), 2.53 (3H), 2.70-3.12 (2H), 3.28 (3H), 3.36-3.43 (2H), 3.43-3.50 (2H), 3.77 (4H), 4.36 (3H), 6.77-6.92 (2H), 7.10-7.22 (2H), 7.39 (5H), 8.15 (1H), 8.52 (1H).

Example 371

2-({1-[(4'-chloro-2'-methylbiphenyl-4-yl)carbonyl]piperidin-4-yl}methyl)-N-(2-methoxyethyl)-4-methyl-2H-indazole-5-carboxamide

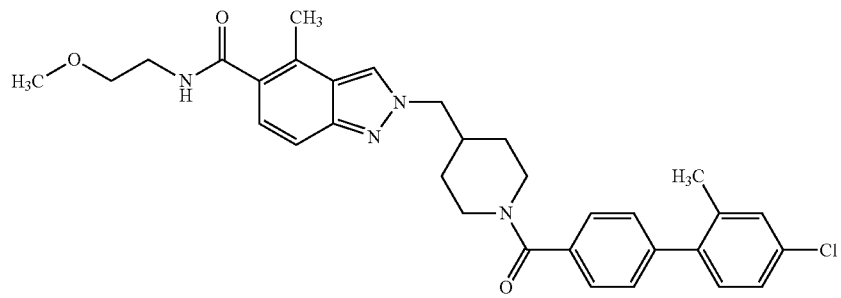 [SMILES: COCCNC(=O)c1ccc2nn(CC3CCN(C(=O)c4ccc(-c5ccc(Cl)cc5C)cc4)CC3)cc2c1C]

Analogously to Example 317, 43 mg of the title compound was obtained from 100 mg of 54 and 50 mg of (4-chloro-2-methylphenyl)boronic acid under reflux.

$^1$H-NMR (400 MHz, DMSO-$d_6$): δ [ppm], 1.27 (2H), 1.38-1.70 (2H), 2.23 (4H), 2.53 (3H), 2.70-3.15 (2H), 3.28 (3H), 3.36-3.43 (2H), 3.43-3.49 (2H), 3.55-3.84 (1H), 4.36 (3H), 7.12-7.27 (2H), 7.28-7.35 (1H), 7.36-7.47 (6H), 8.15 (1H), 8.52 (1H).

Example 372

2-[(1-{[4'-(2-cyanopropan-2-yl)biphenyl-4-yl]carbonyl}piperidin-4-yl)-methyl]-N-(2-methoxyethyl)-4-methyl-2H-indazole-5-carboxamide

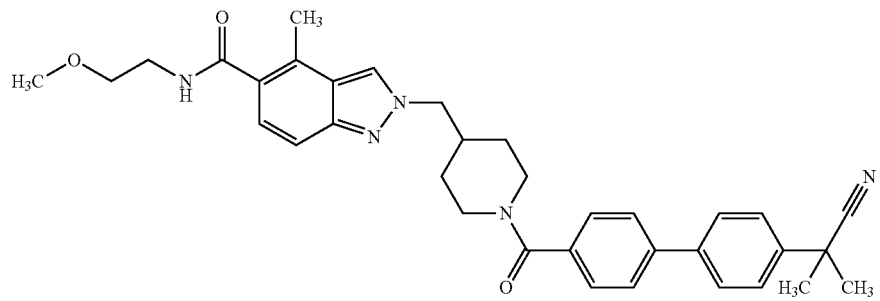 [SMILES: COCCNC(=O)c1ccc2nn(CC3CCN(C(=O)c4ccc(-c5ccc(C(C)(C)C#N)cc5)cc4)CC3)cc2c1C]

Analogously to Example 317, 67 mg of the title compound was obtained from 100 mg of 54 and 55 mg of [4-(1-cyano-1-methylethyl)phenyl]boronic acid under reflux.

$^1$H-NMR (400 MHz, DMSO-$d_6$): δ [ppm], 1.28 (2H), 1.36-1.65 (2H), 1.72 (6H), 2.24-2.40 (1H), 2.53 (3H), 2.70-3.14 (2H), 3.28 (3H), 3.36-3.43 (2H), 3.43-3.49 (2H), 3.54-3.77 (1H), 4.36 (3H), 7.18 (1H), 7.38-7.50 (3H), 7.62 (2H), 7.75 (4H), 8.15 (1H), 8.52 (1H).

Example 373

N-(2-methoxyethyl)-2-({1-[4-(5-methoxypyridin-2-yl)benzoyl]piperidin-4-yl}-methyl)-4-methyl-2H-indazole-5-carboxamide

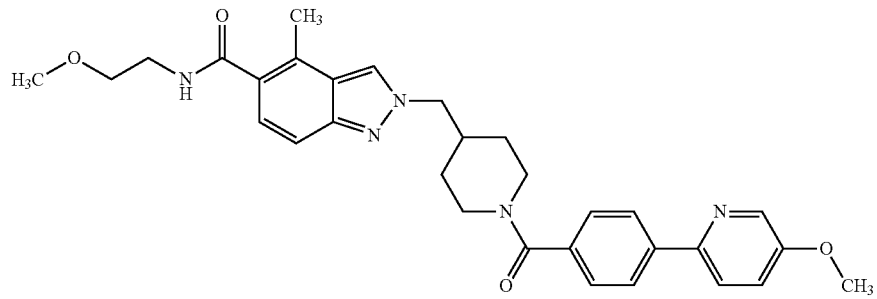

Analogously to Example 368, 12 mg of the title compound was obtained from 200 mg of 54 and 183 mg of (5-methoxypyridin-2-yl)boronic acid pinacol ester under reflux.

$^1$H-NMR (400 MHz, DMSO-d6): δ [ppm], 1.22-1.33 (2H), 1.36-1.66 (2H), 2.23-2.38 (1H), 2.53 (3H), 2.68-3.12 (2H), 3.28 (3H), 3.35-3.42 (2H), 3.43-3.50 (2H), 3.54-3.78 (1H), 3.88 (3H), 4.36 (3H), 7.18 (1H), 7.36-7.55 (4H), 7.96 (1H), 8.07 (2H), 8.13 (1H), 8.39 (1H), 8.51 (1H).

Example 374

N-(2-methoxyethyl)-4-methyl-2-[(1-{4-[6-(trifluoromethyl)pyridin-3-yl]-benzoyl}piperidin-4-yl)methyl]-2H-indazole-5-carboxamide

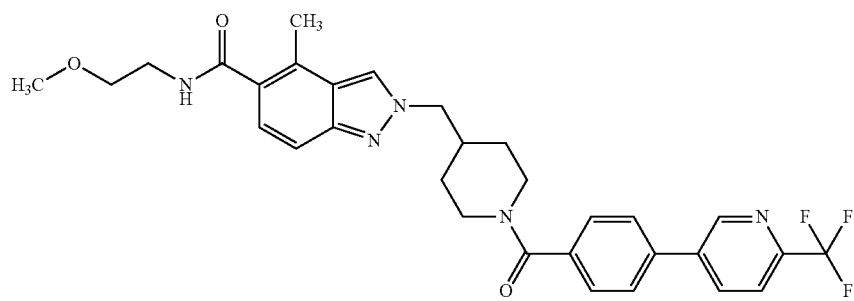 [SMILES: COCCNC(=O)c1ccc2nn(CC3CCN(C(=O)c4ccc(-c5ccc(C(F)(F)F)nc5)cc4)CC3)cc2c1C]

Analogously to Example 317, 37 mg of the title compound was obtained from 100 mg of 54 and 56 mg of [2-(trifluoromethyl)pyridin-5-yl]boronic acid under reflux.

$^1$H-NMR (400 MHz, DMSO-d$_6$): δ [ppm], 1.19-1.36 (2H), 1.36-1.69 (2H), 2.21-2.42 (1H), 2.53 (3H), 2.70-3.14 (2H), 3.28 (3H), 3.36-3.43 (2H), 3.43-3.50 (2H), 3.53-3.72 (1H), 4.36 (3H), 7.18 (1H), 7.42 (1H), 7.53 (2H), 7.89 (2H), 8.01 (1H), 8.15 (1H), 8.41 (1H), 8.52 (1H), 9.13 (1H).

Example 375

N-(2-methoxyethyl)-2-({1-[4-(6-methoxypyridin-3-yl)benzoyl]piperidin-4-yl}-methyl)-4-methyl-2H-indazole-5-carboxamide

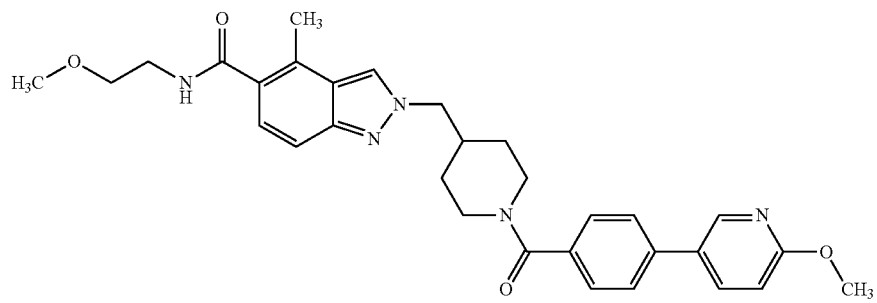

Analogously to Example 317, 50 mg of the title compound was obtained from 100 mg of 54 and 47 mg of (2-methoxypyridin-5-yl)boronic acid under reflux.

$^1$H-NMR (400 MHz, DMSO-$d_6$): δ [ppm], 1.26 (2H), 1.34-1.70 (2H), 2.21-2.40 (1H), 2.53 (3H), 2.69-3.15 (2H), 3.28 (3H), 3.36-3.43 (2H), 3.43-3.49 (2H), 3.51-3.79 (1H), 3.90 (3H), 4.36 (3H), 6.93 (1H), 7.18 (1H), 7.36-7.52 (3H), 7.72 (2H), 8.05 (1H), 8.15 (1H), 8.46-8.57 (2H).

Example 376

2-({1-[(4'-fluoro-2'-methylbiphenyl-4-yl)carbonyl]piperidin-4-yl}methyl)-N-(2-methoxyethyl)-4-methyl-2H-indazole-5-carboxamide

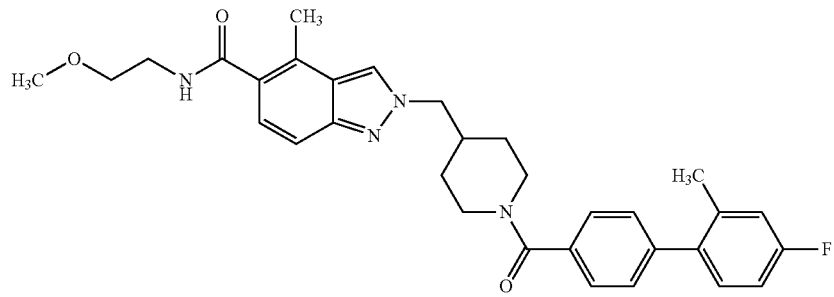 [SMILES: COCCNC(=O)c1ccc2nn(CC3CCN(C(=O)c4ccc(-c5ccc(F)cc5C)cc4)CC3)cc2c1C]

Analogously to Example 317, 261 mg of the title compound was obtained from 300 mg of 54 and 135 mg of (4-fluoro-2-methylphenyl)boronic acid under reflux.

$^1$H-NMR (400 MHz, DMSO-$d_6$): δ [ppm], 1.27 (2H), 1.37-1.70 (2H), 2.24 (4H), 2.53 (3H), 2.71-3.14 (2H), 3.28 (3H), 3.36-3.43 (2H), 3.43-3.50 (2H), 3.55-3.83 (1H), 4.37 (3H), 7.05-7.12 (1H), 7.18 (2H), 7.22-7.30 (1H), 7.40 (5H), 8.14 (1H), 8.52 (1H).

Example 377

N-(2-methoxyethyl)-4-methyl-2-({1-[4-(6-methyl-pyridin-3-yl)benzoyl]piperidin-4-yl}methyl)-2H-indazole-5-carboxamide

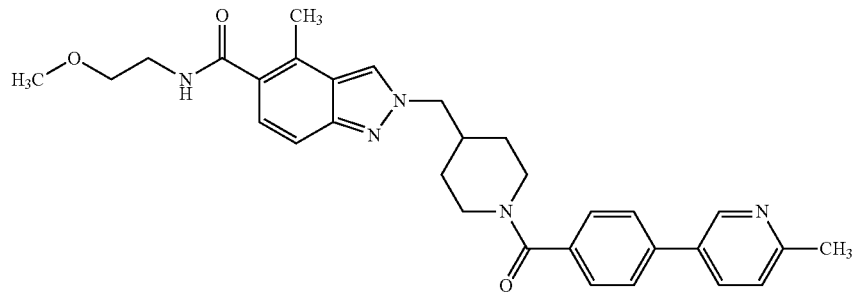

Analogously to Example 317, 45 mg of the title compound was obtained from 80 mg of 54 and 32 mg of (2-methylpyridin-5-yl)boronic acid under reflux.

$^1$H-NMR (300 MHz, DMSO-$d_6$): δ [ppm], 1.26 (2H), 1.37-1.71 (2H), 2.18-2.39 (1H), 2.52-2.58 (3H), 2.73-3.16 (2H), 3.28 (3H), 3.36-3.43 (2H), 3.45 (2H), 3.54-3.79 (1H), 4.36 (3H), 7.18 (1H), 7.30-7.54 (4H), 7.76 (2H), 8.00 (1H), 8.15 (1H), 8.51 (1H), 8.78 (1H).

Example 378

N-(2-methoxyethyl)-2-({1-[4-(6-methoxypyridin-2-yl)benzoyl]piperidin-4-yl}methyl)-4-methyl-2H-indazole-5-carboxamide

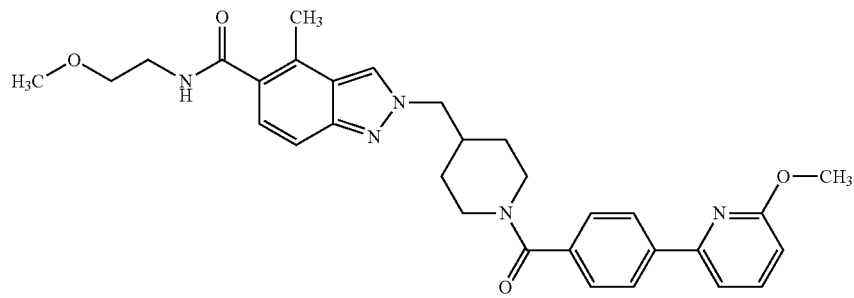

Analogously to Example 317, 30 mg of the title compound was obtained from 100 mg of 54 and 45 mg of (6-methoxypyridin-2-yl)boronic acid under reflux.

$^1$H-NMR (400 MHz, DMSO-$d_6$): δ [ppm], 1.26 (2H), 1.35-1.68 (2H), 2.32 (1H), 2.52 (3H), 2.70-3.13 (2H), 3.28 (3H), 3.36-3.43 (2H), 3.43-3.50 (2H), 3.53-3.74 (1H), 3.96 (3H), 4.36 (3H), 6.81 (1H), 7.18 (1H), 7.37-7.67 (4H), 7.81 (1H), 8.15 (3H), 8.51 (1H).

Example 379

N-(2-methoxyethyl)-4-methyl-2-({1-[4-(2-methylpyrimidin-5-yl)benzoyl]-piperidin-4-yl}methyl)-2H-indazole-5-carboxamide

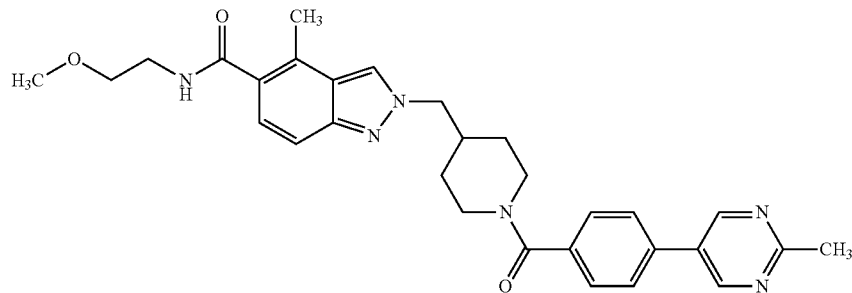

Analogously to Example 317, 36 mg of the title compound was obtained from 100 mg of 54 and 64 mg of (2-methylpyrimidin-5-yl)boronic acid pinacol ester under reflux.

$^1$H-NMR (300 MHz, DMSO-d$_6$): δ [ppm], 1.27 (2H), 1.38-1.70 (2H), 2.21-2.40 (1H), 2.53 (3H), 2.67 (3H), 2.73-3.16 (2H), 3.28 (3H), 3.40 (2H), 3.43-3.50 (2H), 3.53-3.76 (1H), 4.36 (3H), 7.18 (1H), 7.42 (1H), 7.51 (2H), 7.84 (2H), 8.13 (1H), 8.51 (1H), 9.05 (2H).

Example 380

2-({1-[(4'-fluoro-2'-methoxybiphenyl-4-yl)carbonyl]piperidin-4-yl}methyl)-N-(2-methoxyethyl)-4-methyl-2H-indazole-5-carboxamide

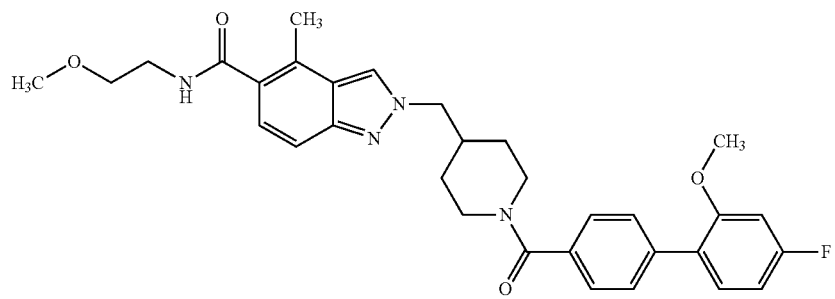 [SMILES: COCCNC(=O)c1ccc2nn(CC3CCN(C(=O)c4ccc(-c5ccc(F)cc5OC)cc4)CC3)cc2c1C]

Analogously to Example 317, 47 mg of the title compound was obtained from 100 mg of 54 and 50 mg of (4-fluoro-2-methoxyphenyl)boronic acid under reflux.

$^1$H-NMR (400 MHz, DMSO-d6): δ [ppm], 1.19-1.34 (2H), 1.37-1.71 (2H), 2.22-2.40 (1H), 2.53 (3H), 2.70-3.15 (2H), 3.28 (3H), 3.36-3.43 (2H), 3.43-3.50 (2H), 3.56-3.75 (1H), 3.79 (3H), 4.36 (3H), 6.87 (1H), 6.99-7.10 (1H), 7.18 (1H), 7.30-7.46 (4H), 7.50 (2H), 8.13 (1H), 8.51 (1H).

Example 381

2-({1-[(4'-chloro-2'-methoxybiphenyl-4-yl)carbonyl]piperidin-4-yl}methyl)-N-(2-methoxyethyl)-4-methyl-2H-indazole-5-carboxamide

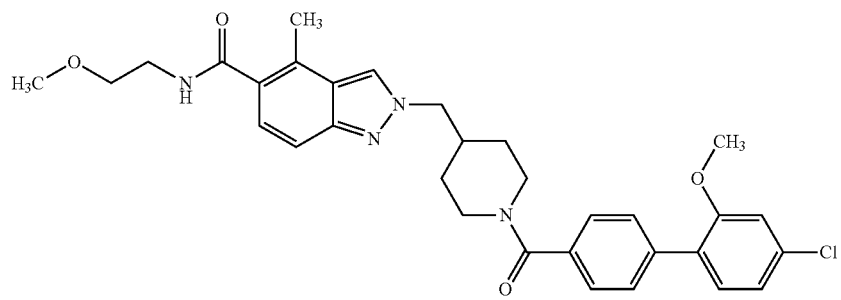 [SMILES: COCCNC(=O)c1ccc2nn(CC3CCN(C(=O)c4ccc(-c5ccc(Cl)cc5OC)cc4)CC3)cc2c1C]

Analogously to Example 317, 87 mg of the title compound was obtained from 100 mg of 54 and 54 mg of (4-fluoro-2-methoxyphenyl)boronic acid under reflux.

$^1$H-NMR (300 MHz, DMSO-d$_6$): δ [ppm]=1.26 (2H), 1.39-1.69 (2H), 2.19-2.39 (1H), 2.53 (3H), 2.75-3.14 (2H), 3.28 (3H), 3.40 (2H), 3.45 (2H), 3.57-3.74 (1H), 3.81 (3H), 4.36 (3H), 7.04-7.25 (3H), 7.28-7.62 (6H), 8.13 (1H), 8.51 (1H).

Example 382

N-(2-methoxyethyl)-4-methyl-2-[(1-{4-[2-(trifluoromethyl)pyrimidin-5-yl]-benzoyl}piperidin-4-yl)methyl]-2H-indazole-5-carboxamide

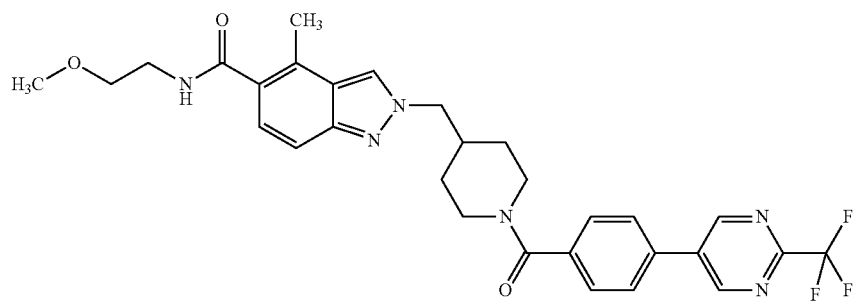 [SMILES: COCCNC(=O)c1ccc2nn(CC3CCN(C(=O)c4ccc(-c5cnc(C(F)(F)F)nc5)cc4)CC3)cc2c1C]

Analogously to Example 317, 14 mg of the title compound was obtained from 100 mg of 54 and 56 mg of [2-(trifluoromethyl)pyrimidin-5-yl]boronic acid under reflux.

$^1$H-NMR (400 MHz, DMSO-d6): δ [ppm], 1.24 (2H), 1.38-1.73 (2H), 2.22-2.41 (1H), 2.53 (3H), 2.70-2.89 (1H), 2.94-3.18 (1H), 3.28 (3H), 3.36-3.43 (2H), 3.44-3.49 (2H), 3.51-3.70 (1H), 4.37 (3H), 7.18 (1H), 7.42 (1H), 7.57 (2H), 7.97 (2H), 8.13 (1H), 8.51 (1H), 9.43 (2H).

Example 383

2-({1-[(4'-chloro-2'-fluorobiphenyl-4-yl)carbonyl]piperidin-4-yl}methyl)-N-(2-methoxyethyl)-4-methyl-2H-indazole-5-carboxamide

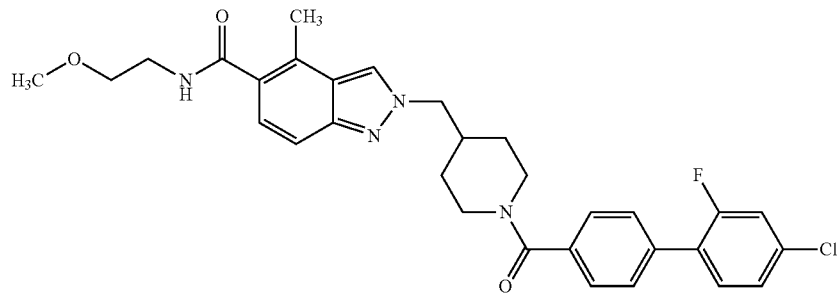 [SMILES: COCCNC(=O)c1ccc2nn(CC3CCN(C(=O)c4ccc(-c5ccc(Cl)cc5F)cc4)CC3)cc2c1C]

Analogously to Example 317, 51 mg of the title compound was obtained from 100 mg of 54 and 51 mg of (4-chloro-2-fluorophenyl)boronic acid under reflux.

$^1$H-NMR (400 MHz, DMSO-d$_6$): δ [ppm], 1.27 (2H), 1.38-1.68 (2H), 2.32 (1H), 2.53 (3H), 2.71-2.91 (1H), 2.93-3.16 (1H), 3.28 (3H), 3.40 (2H), 3.45 (2H), 3.53-3.78 (m, 1H), 4.37 (3H), 7.18 (1H), 7.33-7.52 (4H), 7.53-7.74 (4H), 8.13 (1H), 8.51 (1H).

Example 384

2-({1-[(2'-chloro-4'-fluorobiphenyl-4-yl)carbonyl]piperidin-4-yl}methyl)-N-(2-methoxyethyl)-4-methyl-2H-indazole-5-carboxamide

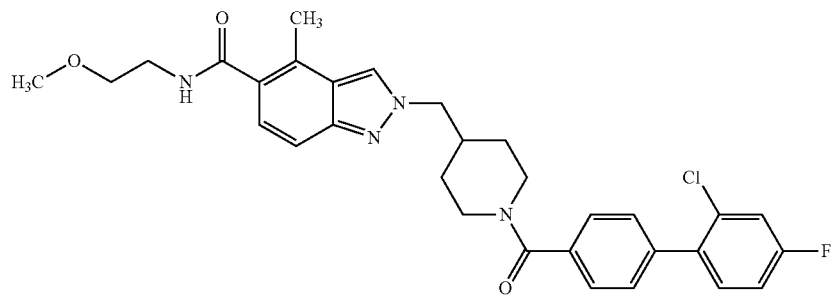

Analogously to Example 317, 26 mg of the title compound was obtained from 100 mg of 54 and 51 mg of (2-chloro-4-fluorophenyl)boronic acid under reflux.

$^1$H-NMR (400 MHz, DMSO-d$_6$): δ [ppm], 1.28 (2H), 1.38-1.67 (2H), 2.23-2.39 (1H), 2.53 (3H), 2.71-2.91 (1H), 2.94-3.15 (1H), 3.28 (3H), 3.36-3.43 (2H), 3.43-3.50 (2H), 3.54-3.74 (1H), 4.37 (3H), 7.18 (1H), 7.33 (1H), 7.39-7.63 (7H), 8.13 (1H), 8.51 (1H).

Example 385

2-({1-[4-(5-chloropyridin-3-yl)benzoyl]piperidin-4-yl}methyl)-N-(2-methoxy-ethyl)-4-methyl-2H-indazole-5-carboxamide

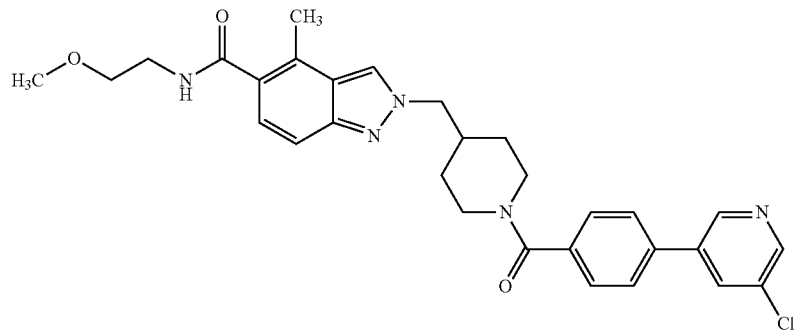 [SMILES: COCCNC(=O)c1ccc2nn(CC3CCN(C(=O)c4ccc(-c5cncc(Cl)c5)cc4)CC3)cc2c1C]

Analogously to Example 317, 22 mg of the title compound was obtained from 100 mg of 54 and 46 mg of (5-chloropyridin-3-yl)boronic acid under reflux.

$^1$H-NMR (300 MHz, DMSO-$d_6$): δ [ppm], 1.21-1.35 (2H), 1.36-1.69 (2H), 2.23-2.40 (1H), 2.53 (3H), 2.69-2.90 (1H), 2.92-3.16 (1H), 3.28 (3H), 3.40 (2H), 3.45 (2H), 3.53-3.73 (1H), 4.36 (3H), 7.18 (1H), 7.35-7.57 (3H), 7.86 (2H), 8.15 (1H), 8.30 (1H), 8.52 (1H), 8.65 (1H), 8.90 (1H).

Example 386

2-({1-[4-(5-fluoropyridin-3-yl)benzoyl]piperidin-4-yl}methyl)-N-(2-methoxy-ethyl)-4-methyl-2H-indazole-5-carboxamide

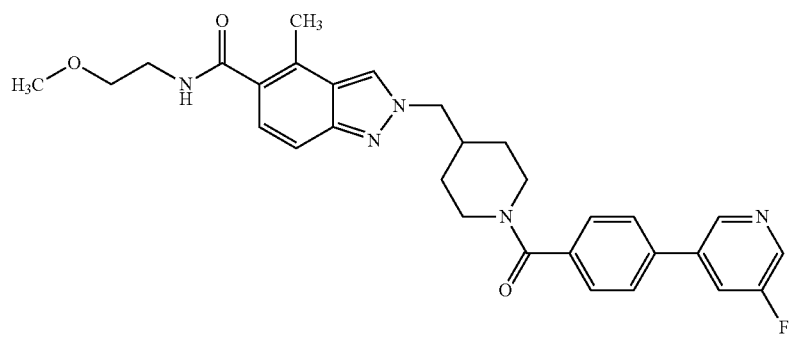 [SMILES: COCCNC(=O)c1ccc2nn(CC3CCN(C(=O)c4ccc(-c5cncc(F)c5)cc4)CC3)cc2c1C]

Analogously to Example 317, 57 mg of the title compound was obtained from 100 mg of 54 and 41 mg of (5-fluoropyridin-3-yl)boronic acid under reflux.

$^1$H-NMR (400 MHz, DMSO-$d_6$): δ [ppm], 1.27 (2H), 1.37-1.70 (2H), 2.24-2.40 (1H), 2.52-2.55 (3H), 2.70-2.89 (1H), 2.93-3.15 (1H), 3.28 (3H), 3.36-3.43 (2H), 3.43-3.50 (2H), 3.53-3.73 (1H), 4.36 (3H), 7.18 (1H), 7.42 (1H), 7.50 (2H), 7.86 (2H), 8.07-8.18 (2H), 8.51 (1H), 8.61 (1H), 8.84 (1H).

Example 387

N-(2-methoxyethyl)-4-methyl-2-[(1-{4-[5-(trifluoromethyl)pyridin-3-yl]-benzoyl}piperidin-4-yl)methyl]-2H-indazole-5-carboxamide

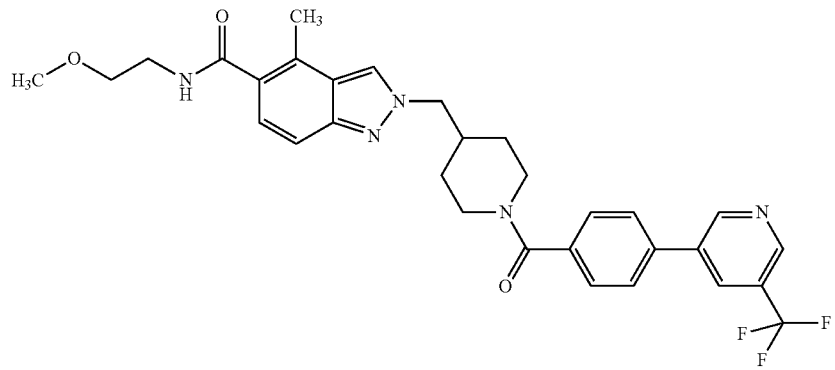 [SMILES: COCCNC(=O)c1ccc2nn(CC3CCN(C(=O)c4ccc(-c5cncc(C(F)(F)F)c5)cc4)CC3)cc2c1C]

Analogously to Example 317, 73 mg of the title compound was obtained from 100 mg of 54 and 56 mg of [5-(trifluoromethyl)pyridin-3-yl]boronic acid under reflux.

$^1$H-NMR (400 MHz, DMSO-$d_6$): δ [ppm], 1.20-1.35 (2H), 1.36-1.67 (2H), 2.23-2.40 (1H), 2.53 (3H), 2.69-2.92 (1H), 2.93-3.17 (1H), 3.28 (3H), 3.35-3.43 (2H), 3.43-3.49 (2H), 3.53-3.75 (1H), 4.37 (3H), 7.18 (1H), 7.42 (1H), 7.52 (2H), 7.93 (2H), 8.07-8.20 (1H), 8.45-8.58 (2H), 9.00 (1H), 9.24 (1H).

Example 388

2-[(1-{[4'-(2-hydroxypropan-2-yl)biphenyl-4-yl]carbonyl}piperidin-4-yl)-methyl]-N-(2-methoxyethyl)-4-methyl-2H-indazole-5-carboxamide

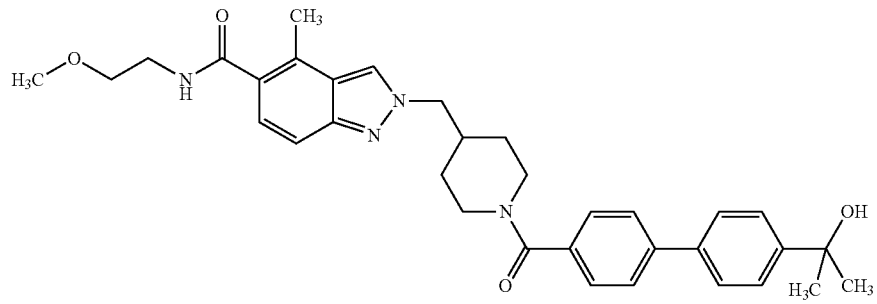 [SMILES: COCCNC(=O)c1ccc2nn(CC3CCN(C(=O)c4ccc(-c5ccc(C(C)(C)O)cc5)cc4)CC3)cc2c1C]

Analogously to Example 317, 46 mg of the title compound was obtained from 100 mg of 54 and 77 mg of (4-hydroxy-tert-butylphenyl)boronic acid pinacol ester under reflux.

$^1$H-NMR (300 MHz, DMSO-$d_6$): δ [ppm], 1.26 (2H), 1.45 (8H), 2.22-2.42 (1H), 2.53 (3H), 2.71-2.90 (1H), 2.91-3.14 (1H), 3.28 (3H), 3.40 (2H), 3.43-3.50 (2H), 3.56-3.80 (1H), 4.36 (3H), 5.06 (1H), 7.18 (d, 1H), 7.37-7.50 (3H), 7.50-7.67 (4H), 7.71 (2H), 8.15 (1H), 8.52 (1H).

Example 389

2-({1-[(3',5'-difluorobiphenyl-4-yl)carbonyl]piperidin-4-yl}methyl)-N-(2-methoxyethyl)-4-methyl-2H-indazole-5-carboxamide

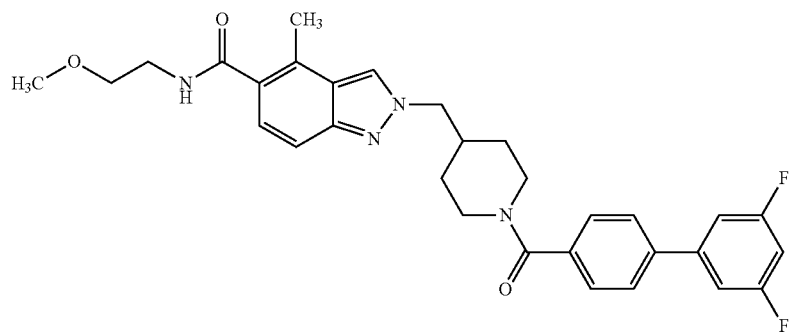 [SMILES: COCCNC(=O)c1ccc2nn(CC3CCN(C(=O)c4ccc(-c5cc(F)cc(F)c5)cc4)CC3)cc2c1C]

Analogously to Example 317, 22 mg of the title compound was obtained from 100 mg of 54 and 46 mg of (3,5-difluorophenyl)boronic acid under reflux.

$^1$H-NMR (400 MHz, DMSO-d$_6$): δ [ppm], 1.18-1.35 (2H), 1.36-1.70 (2H), 2.19-2.39 (1H), 2.52-2.56 (3H), 2.71-2.92 (1H), 2.93-3.17 (1H), 3.28 (3H), 3.36-3.43 (2H), 3.43-3.49 (2H), 3.52-3.71 (1H), 4.36 (3H), 7.11-7.33 (2H), 7.37-7.54 (5H), 7.81 (2H), 8.13 (1H), 8.51 (1H).

Example 390

2-({1-[(4'-fluoro-2-methylbiphenyl-4-yl)carbonyl]piperidin-4-yl}methyl)-N-(2-methoxyethyl)-4-methyl-2H-indazole-5-carboxamide

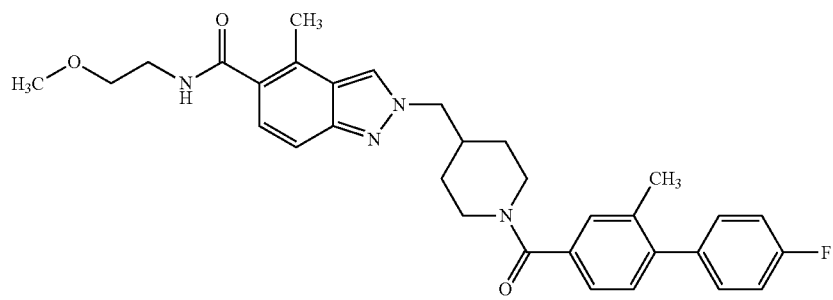 [SMILES: COCCNC(=O)c1ccc2nn(CC3CCN(C(=O)c4ccc(-c5ccc(F)cc5)c(C)c4)CC3)cc2c1C]

Analogously to Example 317, 25 mg of the title compound was obtained from 60 mg of 332 and 19 mg of (4-fluorophenyl)boronic acid under reflux.

$^1$H-NMR (400 MHz, DMSO-d$_6$): δ [ppm], 1.25 (2H), 1.37-1.67 (2H), 2.24 (4H), 2.53 (3H), 2.69-2.87 (1H), 2.92-3.14 (1H), 3.28 (3H), 3.36-3.43 (2H), 3.43-3.50 (2H), 3.56-3.81 (1H), 4.36 (3H), 7.11-7.34 (6H), 7.36-7.46 (3H), 8.15 (1H), 8.52 (1H).

Example 391

2-({1-[(3',5'-difluoro-2-methylbiphenyl-4-yl)carbonyl]piperidin-4-yl}methyl)-N-(2-methoxyethyl)-4-methyl-2H-indazole-5-carboxamide

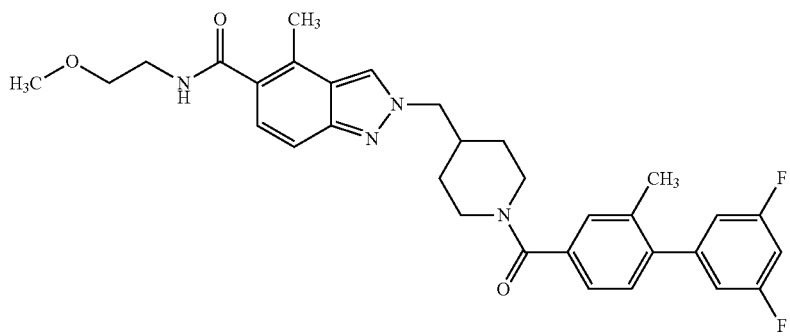 [SMILES: COCCNC(=O)c1ccc2nn(CC3CCN(C(=O)c4ccc(-c5cc(F)cc(F)c5)c(C)c4)CC3)cc2c1C]

Analogously to Example 317, 30 mg of the title compound was obtained from 60 mg of 332 and 27 mg of (3,5-difluorophenyl)boronic acid under reflux.

$^1$H-NMR (400 MHz, DMSO-$d_6$): δ [ppm], 1.23 (2H), 1.36-1.69 (2H), 2.27 (4H), 2.53 (3H), 2.69-2.90 (1H), 2.92-3.15 (1H), 3.28 (3H), 3.36-3.43 (2H), 3.45 (2H), 3.53-3.76 (1H), 4.36 (3H), 7.08-7.21 (3H), 7.22-7.34 (4H), 7.42 (1H), 8.15 (1H), 8.52 (1H).

Example 392

N-(2-methoxyethyl)-4-methyl-2-({1-[3-methyl-4-(3-pyridyl)benzoyl]piperidin-4-yl}methyl)-2H-indazole-5-carboxamide

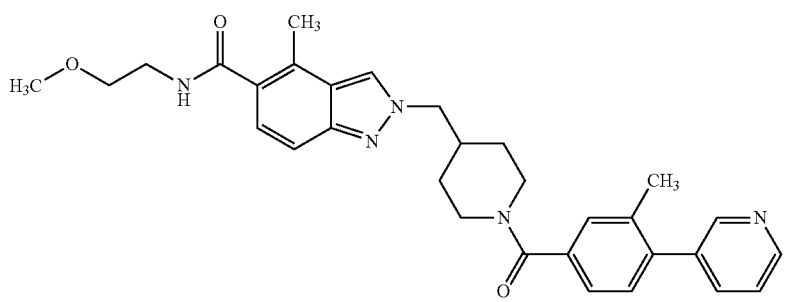

Analogously to Example 317, 19 mg of the title compound was obtained from 60 mg of 332 and 21 mg of pyridine-3-ylboronic acid under reflux.

$^1$H-NMR (400 MHz, DMSO-$d_6$): δ [ppm], 1.20-1.33 (2H), 1.37-1.71 (2H), 2.26 (4H), 2.53 (3H), 2.70-2.88 (1H), 2.94-3.17 (1H), 3.28 (3H), 3.36-3.43 (2H), 3.43-3.49 (2H), 3.56-3.82 (1H), 4.36 (3H), 7.18 (1H), 7.23-7.37 (3H), 7.39-7.56 (2H), 7.83 (1H), 8.15 (1H), 8.52 (1H), 8.56-8.65 (2H).

Example 393

N-(2-methoxyethyl)-4-methyl-2-({1-[3-methyl-4-(4-pyridyl)benzoyl]piperidin-4-yl}methyl)-2H-indazole-5-carboxamide

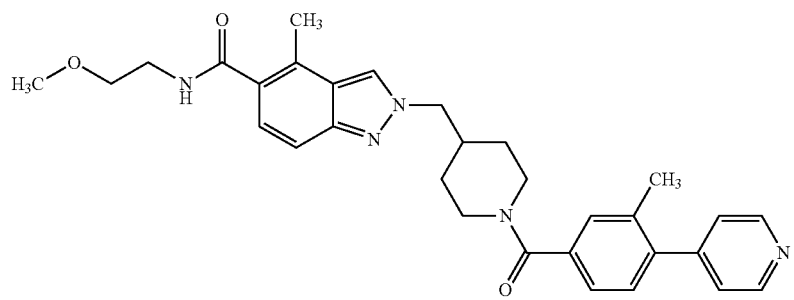 [SMILES: COCCNC(=O)c1ccc2nn(CC3CCN(C(=O)c4ccc(-c5ccncc5)c(C)c4)CC3)cc2c1C]

Analogously to Example 317, 19 mg of the title compound was obtained from 60 mg of 332 and 21 mg of pyridine-4-ylboronic acid under reflux.

$^1$H-NMR (400 MHz, DMSO-d$_6$): δ [ppm], 1.18-1.33 (2H), 1.37-1.67 (2H), 2.27 (4H), 2.52-2.56 (3H), 2.70-2.86 (1H), 2.93-3.13 (1H), 3.28 (3H), 3.36-3.43 (2H), 3.43-3.49 (2H), 3.55-3.75 (1H), 4.36 (3H), 7.18 (1H), 7.23-7.36 (3H), 7.38-7.48 (3H), 8.15 (1H), 8.52 (1H), 8.60-8.69 (2H).

Example 394

N-(2-methoxyethyl)-4-methyl-2-({1-[(2-methylbiphenyl-4-yl)carbonyl]piperidin-4-yl}methyl)-2H-indazole-5-carboxamide

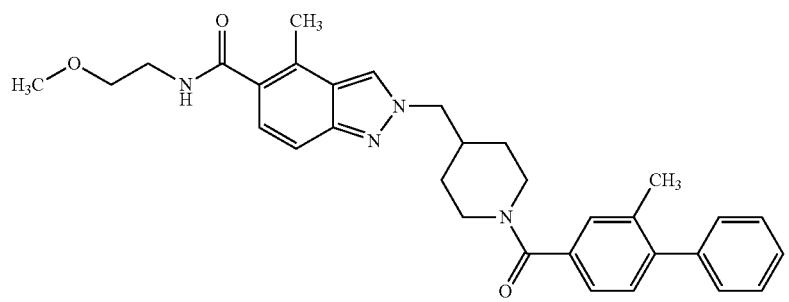 [SMILES: COCCNC(=O)c1ccc2nn(CC3CCN(C(=O)c4ccc(-c5ccccc5)c(C)c4)CC3)cc2c1C]

Analogously to Example 317, 57 mg of the title compound was obtained from 60 mg of 332 and 21 mg of phenylboronic acid under reflux.

$^1$H-NMR (400 MHz, DMSO-d$_6$): δ [ppm], 1.19-1.34 (2H), 1.37-1.67 (2H), 2.25 (4H), 2.53 (3H), 2.68-2.88 (1H), 2.92-3.17 (1H), 3.28 (3H), 3.36-3.43 (2H), 3.45 (2H), 3.59-3.81 (1H), 4.36 (3H), 7.13-7.32 (4H), 7.33-7.50 (6H), 8.15 (1H), 8.52 (1H).

Example 395

2-{[1-(4-bromobenzoyl)piperidin-4-yl]methyl}-N-(2-mesylethyl)-4-methyl-2H-indazole-5-carboxamide

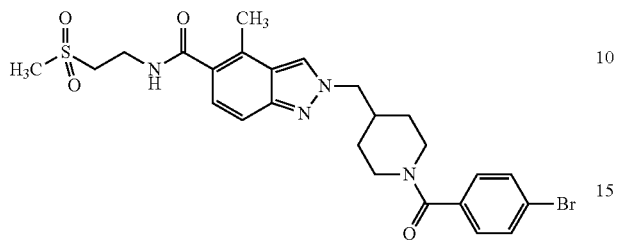

Analogously to Example 1b, Version B, 383 mg of the title compound was obtained from 1 g of 395b and 797 mg of 4-bromobenzoic acid in DMF.

$^1$H-NMR (400 MHz, DMSO-d$_6$): δ [ppm], 1.21-1.32 (2H), 1.34-1.67 (2H), 2.21-2.38 (1H), 2.55 (3H), 2.68-2.87 (1H), 3.05 (4H), 3.39 (2H), 3.45-3.59 (1H), 3.66 (2H), 4.35 (3H), 7.23 (1H), 7.28-7.37 (2H), 7.43 (1H), 7.59-7.70 (2H), 8.34 (1H), 8.52 (1H).

The starting material was prepared as follows:

Example 395a

Tert-butyl 4-({5-[N-(2-mesylethyl)carbamoyl]-4-methyl-2H-indazol-2-yl}-methyl)piperidin-1-carboxylate

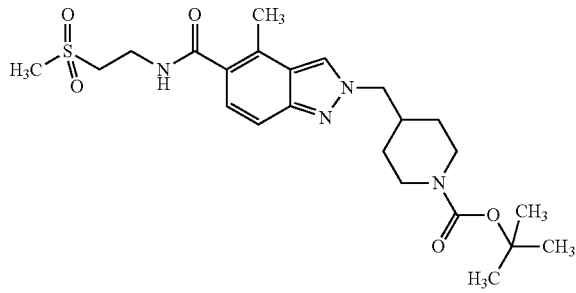 [SMILES: Cc1c(C(=O)NCCS(C)(=O)=O)ccc2nn(CC3CCN(C(=O)OC(C)(C)C)CC3)cc12]

Analogously to Example 266a, 1.26 g of the title compound was obtained from 2.506 g of 1c and 3.022 g of 2-mesylethylamine hydrochloride.

$^1$H-NMR (300 MHz, DMSO-d$_6$): δ [ppm], 1.02-1.17 (2H), 1.34-1.54 (11H), 2.08-2.24 (1H), 2.55 (3H), 2.73 (2H), 3.06 (3H), 3.34-3.47 (2H), 3.57-3.76 (2H), 3.91 (2H), 4.32 (2H), 7.23 (1H), 7.43 (1H), 8.33 (1H), 8.52 (1H).

Example 395b

N-(2-mesylethyl)-4-methyl-2-(4-piperidylmethyl)-2H-indazole-5-carboxamide hydrochloride

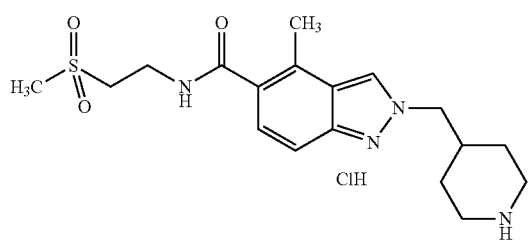 [SMILES: Cc1c(C(=O)NCCS(C)(=O)=O)ccc2nn(CC3CCNCC3)cc12 ; Cl]

Analogously to Example 258b from 1.26 g of compound 395a, 1.29 g of the title compound was obtained, which was reacted without further purification.

Example 396

N-(2-mesylethyl)-4-methyl-2-{[1-(4-{[5-(trifluoromethyl)pyridin-2-yl]oxy}-benzoyl)piperidin-4-yl]methyl}-2H-indazole-5-carboxamide

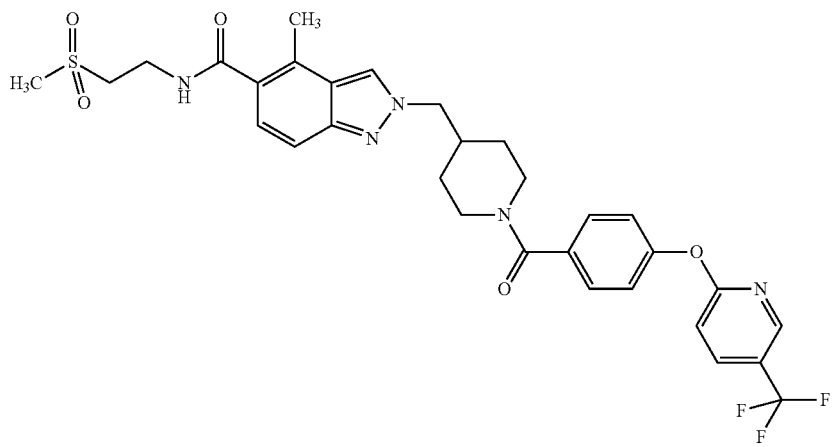 [SMILES: Cc1c(C(=O)NCCS(C)(=O)=O)ccc2nn(CC3CCN(C(=O)c4ccc(Oc5ccc(C(F)(F)F)cn5)cc4)CC3)cc12]

Analogously to Example 1b, Version B, 30 mg of the title compound was obtained from 80 mg of 395b and 90 mg of 4-{[5-(trifluoromethyl)pyridin-2-yl]oxy}benzoic acid in DMF.

$^1$H-NMR (400 MHz, DMSO-d$_6$): δ [ppm], 1.19-1.35 (2H), 1.36-1.72 (2H), 2.22-2.41 (1H), 2.55 (3H), 3.06 (5H), 3.39 (2H), 3.49-3.89 (3H), 4.37 (3H), 7.20-7.32 (4H), 7.40-7.49 (3H), 8.25 (1H), 8.34 (1H), 8.53 (1H), 8.58 (1H).

Example 397

N-(2-mesylethyl)-4-methyl-2-{[1-(4-{[6-(trifluoromethyl)pyridin-3-yl]oxy}-benzoyl)piperidin-4-yl]methyl}-2H-indazole-5-carboxamide

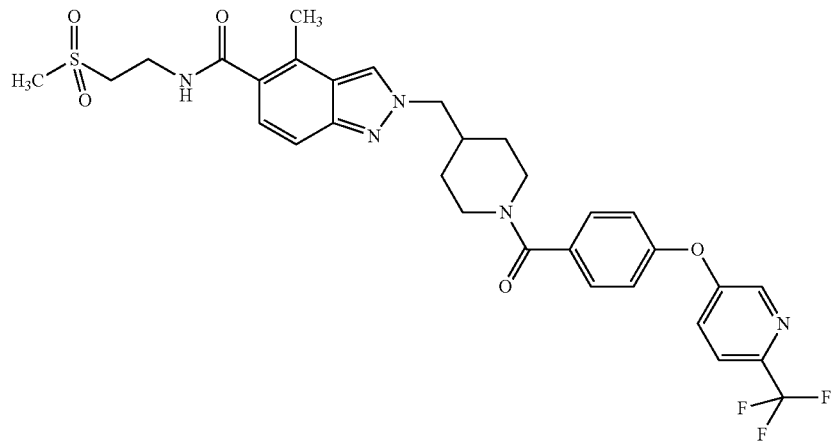

Analogously to Example 1b, Version B, 30 mg of the title compound was obtained from 80 mg of 395b and 90 mg of 303b in DMF.

$^1$H-NMR (400 MHz, DMSO-d$_6$): δ [ppm], 1.24 (2H), 1.35-1.70 (2H), 2.22-2.40 (1H), 2.55 (3H), 3.06 (5H), 3.39 (2H), 3.55-3.75 (3H), 4.36 (3H), 7.20-7.28 (3H), 7.40-7.49 (3H), 7.65 (1H), 7.92 (1H), 8.34 (1H), 8.53 (1H), 8.60 (1H).

Example 398

2-({1-[(2',4'-difluorobiphenyl-4-yl)carbonyl]piperidin-4-yl}methyl)-N-(2-mesylethyl)-4-methyl-2H-indazole-5-carboxamide

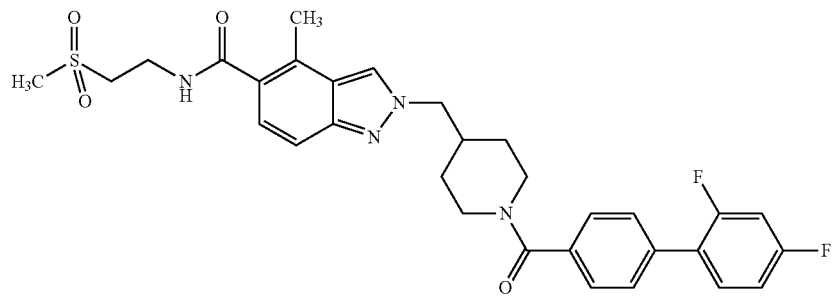 [SMILES: Cc1c(C(=O)NCCS(C)(=O)=O)ccc2nn(CC3CCN(C(=O)c4ccc(-c5ccc(F)cc5F)cc4)CC3)cc12]

Analogously to Example 1b, Version B, 25 mg of the title compound was obtained from 80 mg of 395b and 74 mg of 2',4'-difluoro-biphenyl-4-carboxylic acid in DMF.

$^1$H-NMR (400 MHz, DMSO-d$_6$): δ [ppm], 1.21-1.35 (2H), 1.37-1.70 (2H), 2.22-2.41 (1H), 2.55 (3H), 3.05 (5H), 3.38 (2H), 3.50-3.83 (3H), 4.37 (3H), 7.15-7.29 (2H), 7.31-7.52 (4H), 7.55-7.73 (3H), 8.34 (1H), 8.53 (1H).

Example 399

2-{[1-(4-chlorobenzoyl)piperidin-4-yl]methyl}-N-(3-hydroxy-3-methylbutyl)-4-methyl-2H-indazole-5-carboxamide

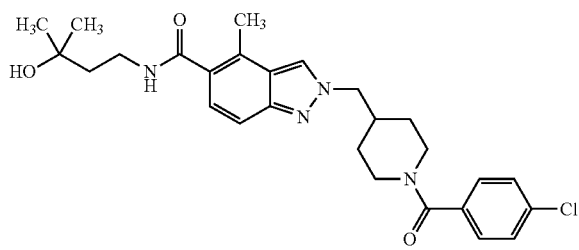 [SMILES: Cc1c(C(=O)NCCC(C)(C)O)ccc2nn(CC3CCN(C(=O)c4ccc(Cl)cc4)CC3)cc12]

Analogously to Example 1b, Version B, 37 mg of the title compound was obtained from 160 mg of 399b and 105 mg of 4-chlorobenzoic acid in DMF.

$^1$H-NMR (400 MHz, DMSO-$d_6$): δ [ppm], 1.14 (6H), 1.17-1.32 (2H), 1.33-1.71 (4H), 2.23-2.37 (1H), 2.51 (3H), 2.68-2.87 (1H), 2.87-3.13 (1H), 3.31 (2H), 3.47-3.55 (1H), 4.34 (s, 4H), 7.17 (1H), 7.33-7.45 (3H), 7.50 (2H), 7.97-8.09 (1H), 8.50 (1H).

The starting material was prepared as follows:

Example 399a

Tert-butyl 4-({5-[N-(3-hydroxy-3-methylbutyl)carbamoyl]-4-methyl-2H-indazol-2-yl}methyl)piperidin-1-carboxylate

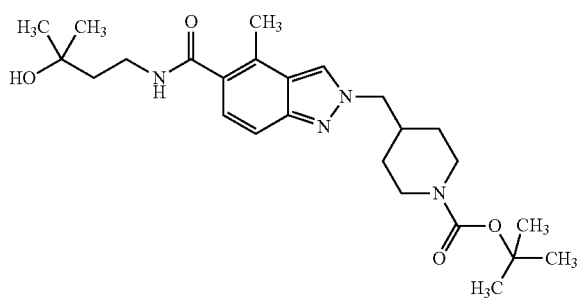 [SMILES: Cc1c(C(=O)NCCC(C)(C)O)ccc2nn(CC3CCN(C(=O)OC(C)(C)C)CC3)cc12]

Analogously to Example 1b, Version B, 150 mg of 1d and 69 mg of 4-amino-2-methylbutan-2-ol in DMF were reacted at 60° C. After phase separation and extraction, the combined organic phases were additionally washed with 0.1 N hydrochloric acid and saturated sodium hydrogen carbonate solution. This yielded 132 mg of the title compound, which was used in the next step without further purification.

Example 399b

N-(3-hydroxy-3-methylbutyl)-4-methyl-2-(4-piperidylmethyl)-2H-indazole-5-carboxamide

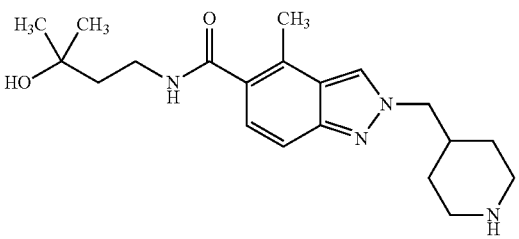 [SMILES: Cc1c(C(=O)NCCC(C)(C)O)ccc2nn(CC3CCNCC3)cc12]

Analogously to Example 258b, from 132 mg of 399a, 162 mg of the title compound was obtained, which was used in the next step without further purification.

Example 400

2-{[1-(4-chlorobenzoyl)piperidin-4-yl]methyl}-N-(2-cyanoethyl)-4-methyl-2H-indazole-5-carboxamide

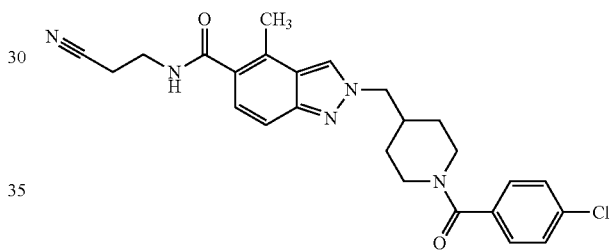

Analogously to Example 1b, Version B, 55 mg of the title compound was obtained from 177 mg of 400b and 128 mg of 4-chlorobenzoic acid in DMF.

$^1$H-NMR (400 MHz, DMSO-$d_6$): δ [ppm], 1.23 (2H), 1.33-1.70 (2H), 2.20-2.38 (1H), 2.56 (3H), 2.78 (3H), 2.90-3.11 (1H), 3.47 (3H), 4.35 (3H), 7.22 (1H), 7.34-7.56 (5H), 8.44-8.57 (2H).

The starting material was prepared as follows:

Example 400a

Tert-butyl 4-({5-[N-(2-cyanoethyl)carbamoyl]-4-methyl-2H-indazol-2-yl}-methyl)-piperidin-1-carboxylate

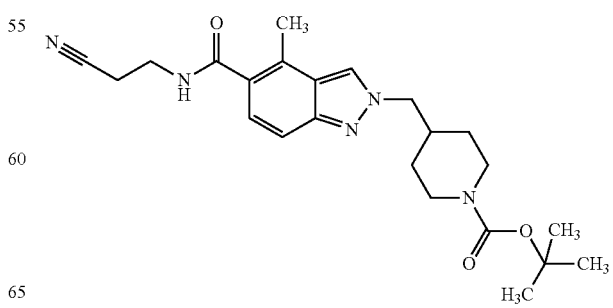

Analogously to Example 1b, Version B, 150 mg of 1d and 42 mg of 3-aminopropannitrile in DMF were reacted at 60° C. After phase separation and extraction, the combined organic phases were additionally washed with 0.1 N hydrochloric acid and saturated sodium hydrogen carbonate solution. This yielded 137 mg of the title compound, which was used in the next step without further purification.

Example 400b

N-(2-cyanoethyl)-4-methyl-2-(4-piperidylmethyl)-2H-indazole-5-carboxamide

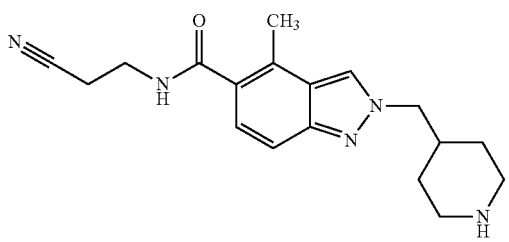 [SMILES: Cc1c(C(=O)NCCC#N)ccc2nn(CC3CCNCC3)cc12]

Analogously to Example 258b, from 137 mg of 400a 177 mg of the title compound was obtained, which was used in the next step without further purification.

Example 401

2-{[1-(4-chlorobenzoyl)piperidin-4-yl]methyl}-N-(cyanomethyl)-4-methyl-2H-indazole-5-carboxamide

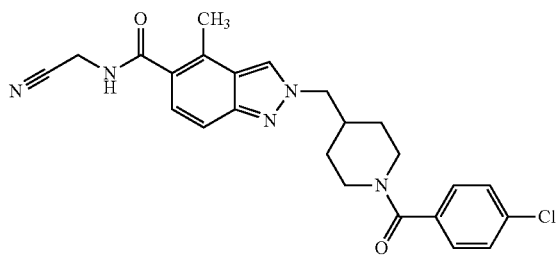 [SMILES: Cc1c(C(=O)NCC#N)ccc2nn(CC3CCN(C(=O)c4ccc(Cl)cc4)CC3)cc12]

Analogously to Example 1b, Version B, 75 mg of the title compound was obtained from 90 mg of 238c and 29 mg of aminoacetonitrile in DMF.

$^1$H-NMR (400 MHz, DMSO-d$_6$): δ [ppm], 1.21-1.33 (23H), 1.34-1.69 (2H), 2.15-2.41 (1H), 2.57 (3H), 2.75-2.86 (1H), 2.93-3.14 (1H), 3.39-3.69 (1H), 4.29 (2H), 4.33-4.55 (3H), 7.18-7.28 (1H), 7.39 (2H), 7.43-7.55 (3H), 8.57 (1H), 8.77-8.90 (1H).

Example 402

2-{[1-(4-chlorobenzoyl)piperidin-4-yl]methyl}-N-(cyclopropylmethyl)-4-methyl-2H-indazole-5-carboxamide

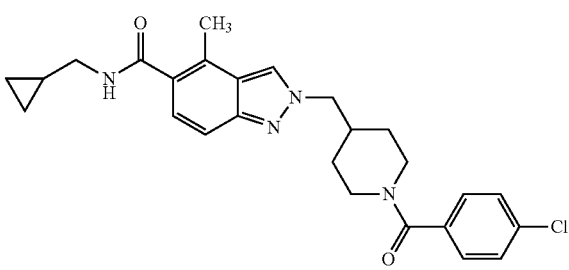 [SMILES: Cc1c(C(=O)NCC2CC2)ccc2nn(CC3CCN(C(=O)c4ccc(Cl)cc4)CC3)cc12]

Analogously to Example 1b, Version B, 44 mg of the title compound was obtained from 90 mg of 238c and 19 mg of cyclopropylmethylamine in DMF.

$^1$H-NMR (300 MHz, DMSO-d$_6$): δ [ppm], 0.23 (2H), 0.33-0.53 (2H), 0.94-1.11 (1H), 1.20-1.33 (2H), 1.34-1.68 (2H), 2.21-2.41 (1H), 2.54 (3H), 2.69-2.85 (1H), 2.93-3.08 (1H), 3.13 (2H), 3.44-3.68 (1H), 4.35 (3H), 7.18 (1H), 7.33-7.46 (3H), 7.47-7.60 (2H), 8.07-8.30 (1H), 8.51 (1H).

Example 403

N-(cyclobutylmethyl)-4-methyl-2-[(1-{4-[4-(trifluoromethyl)phenoxy]benzoyl}-piperidin-4-yl)methyl]-2H-indazole-5-carboxamide

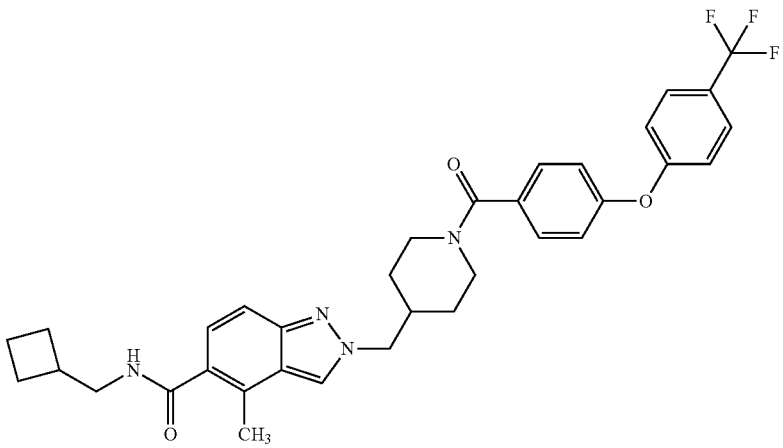 [SMILES: Cc1c(C(=O)NCC2CCC2)ccc2nn(CC3CCN(C(=O)c4ccc(Oc5ccc(C(F)(F)F)cc5)cc4)CC3)cc12]

Analogously to Example 1b, Version B, 48 mg of the title compound was obtained from 137 mg of 403b and 31 mg of (cyclobutylamino)methylamine hydrochloride.

$^1$H-NMR (400 MHz, DMSO-$d_6$): δ [ppm], 1.17-1.32 (2H), 1.35-1.64 (2H), 1.67-1.90 (4H), 1.93-2.08 (2H), 2.22-2.38 (1H), 2.51-2.52 (3H), 2.69-2.88 (1H), 2.90-3.13 (1H), 3.20-3.30 (2H), 3.51-3.83 (1H), 4.36 (3H), 7.09-7.27 (5H), 7.35-7.52 (3H), 7.76 (2H), 8.13 (1H), 8.51 (1H).

The starting material was prepared as follows:

Example 403a

Methyl 4-methyl-2-[(1-{4-[4-(trifluoromethyl)phenoxy]benzoyl}piperidin-4-yl)methyl]-2H-indazol-5-carboxylate

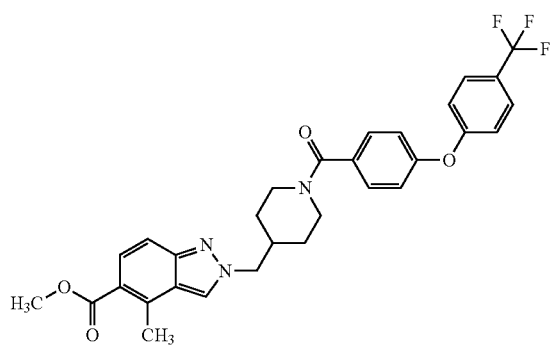 [SMILES: COC(=O)c1ccc2nn(CC3CCN(C(=O)c4ccc(Oc5ccc(C(F)(F)F)cc5)cc4)CC3)cc2c1C]

Analogously to Example 1b, Version B, 2.73 g of the title compound was obtained from 3.76 g of 238a and 3.28 g of 4-[4-(trifluoromethyl)phenoxy]benzoic acid.

$^1$H-NMR (400 MHz, DMSO-$d_6$): δ [ppm], 1.19-1.35 (2H), 1.38-1.74 (2H), 2.17-2.41 (1H), 2.76 (3H), 2.78-3.14 (2H), 3.44-3.76 (1H), 3.82 (3H), 4.37 (3H), 7.06-7.28 (4H), 7.38-7.50 (3H), 7.67 (1H), 7.76 (2H), 8.71 (1H).

Example 403b 4-methyl-2-[(1-{4-[4-(trifluoromethyl)phenoxy]benzoyl}piperidin-4-yl)-methyl]-2H-indazol-5-carboxylic acid

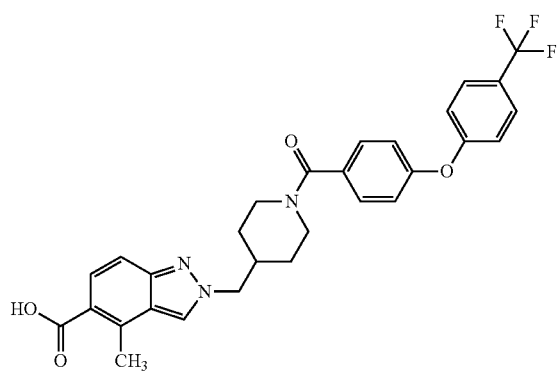 [SMILES: Cc1c(C(=O)O)ccc2nn(CC3CCN(C(=O)c4ccc(Oc5ccc(C(F)(F)F)cc5)cc4)CC3)cc12]

Analogously to Example 1d, from 1.05 g of 403a, 970 mg of the title compound was obtained, which was used in the next step without further purification.

Example 404

N-isobutyl-4-methyl-2-[(1-{4-[4-(trifluoromethyl)phenoxy]benzoyl}piperidin-4-yl)methyl]-2H-indazole-5-carboxamide

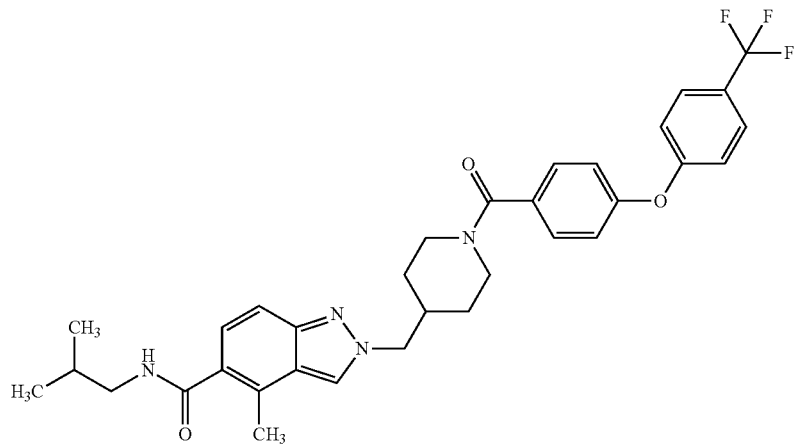 [SMILES: Cc1c(C(=O)NCC(C)C)ccc2nn(CC3CCN(C(=O)c4ccc(Oc5ccc(C(F)(F)F)cc5)cc4)CC3)cc12]

Analogously to Example 1b, Version B, 35 mg of the title compound was obtained from 100 mg of 403b and 14 mg of isobutylamine.

$^1$H-NMR (300 MHz, DMSO-$d_6$): δ [ppm], 0.91 (6H), 1.24 (2H), 1.34-1.69 (2H), 1.82 (1H), 2.19-2.42 (1H), 2.52 (3H), 2.71-2.90 (1H), 3.06 (3H), 3.51-3.85 (1H), 4.36 (3H), 7.05-7.27 (5H), 7.37-7.52 (3H), 7.76 (2H), 8.16 (1H), 8.51 (1H).

Example 405

4-methyl-N-neopentyl-2-[(1-{4-[4-(trifluoromethyl)phenoxy]benzoyl}piperidin-4-yl)methyl]-2H-indazole-5-carboxamide

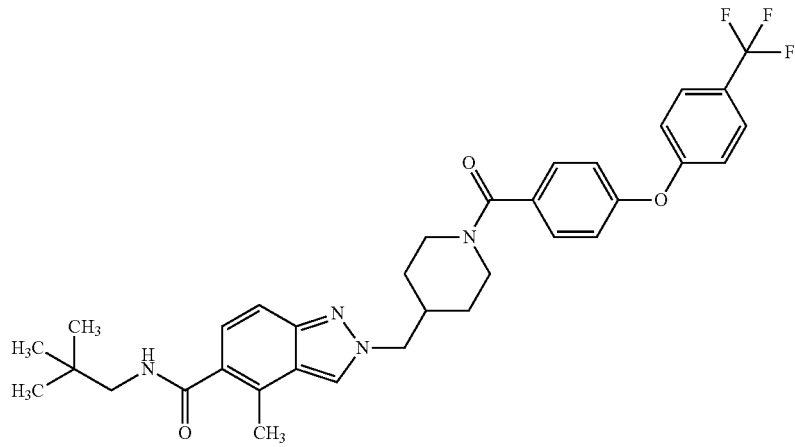 [SMILES: Cc1c(C(=O)NCC(C)(C)C)ccc2nn(CC3CCN(C(=O)c4ccc(Oc5ccc(C(F)(F)F)cc5)cc4)CC3)cc12]

Analogously to Example 1b, Version B, 36 mg of the title compound was obtained from 100 mg of 403b and 16 mg of neopentylamine.

$^1$H-NMR (400 MHz, DMSO-$d_6$): δ [ppm], 0.92 (9H), 1.17-1.32 (2H), 1.34-1.69 (2H), 2.21-2.38 (1H), 2.52-2.57 (3H), 2.70-2.88 (1H), 3.08 (3H), 3.53-3.85 (1H), 4.36 (3H), 7.04-7.28 (5H), 7.35-7.52 (3H), 7.76 (2H), 8.12 (1H), 8.51 (1H).

Example 406

N-(cyclopropylmethyl)-4-methyl-2-[(1-{4-[4-(trifluoromethyl)phenoxy]-benzoyl}piperidin-4-yl)methyl]-2H-indazole-5-carboxamide

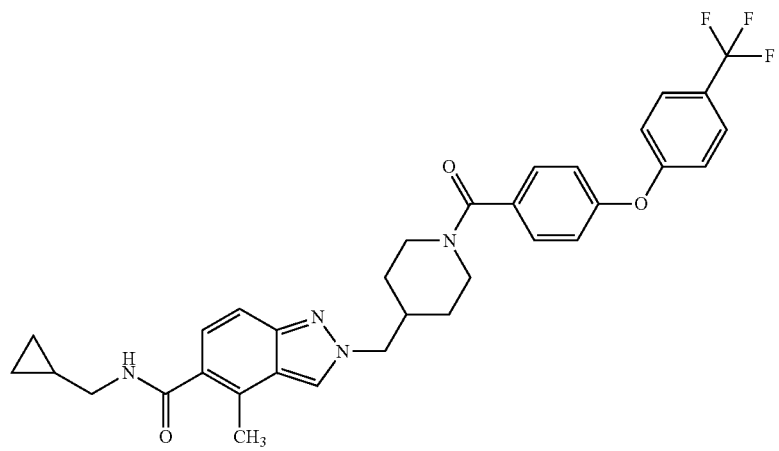 [SMILES: Cc1c(C(=O)NCC2CC2)ccc2nn(CC3CCN(C(=O)c4ccc(Oc5ccc(C(F)(F)F)cc5)cc4)CC3)cc12]

Analogously to Example 1b, Version B, 33 mg of the title compound was obtained from 100 mg of 403b and 26 mg of cyclopropylmethylamine.

$^1$H-NMR (300 MHz, DMSO-$d_6$): δ [ppm], 0.23 (2H), 0.35-0.54 (2H), 0.93-1.11 (1H), 1.23 (2H), 1.36-1.67 (2H), 2.18-2.41 (1H), 2.54 (3H), 2.66-3.22 (4H), 3.47-3.85 (1H), 4.36 (3H), 7.03-7.29 (5H), 7.35-7.53 (3H), 7.76 (2H), 8.22 (1H), 8.52 (1H).

Example 407

N-(2-cyanoethyl)-2-({1-[(4'-fluorobiphenyl-4-yl)carbonyl]piperidin-4-yl}-methyl)-4-methyl-2H-indazole-5-carboxamide

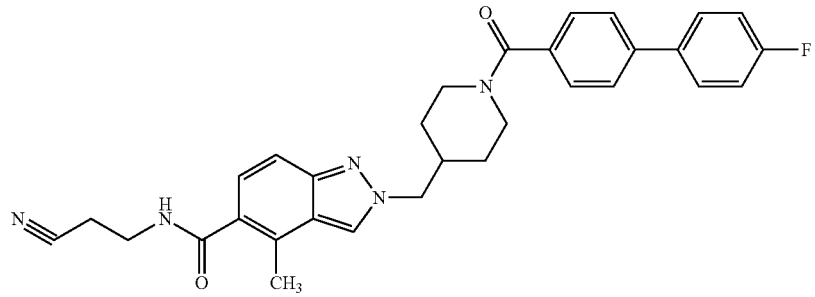 [SMILES: Cc1c(C(=O)NCCC#N)ccc2nn(CC3CCN(C(=O)c4ccc(-c5ccc(F)cc5)cc4)CC3)cc12]

Analogously to Example 1b, Version B, 37 mg of the title compound was obtained from 140 mg of 407a and 84 mg of 4'-fluorobiphenyl-4-carboxylic acid.

$^1$H-NMR (300 MHz, DMSO-$d_6$): δ [ppm], 1.18-1.37 (2H), 1.37-1.68 (2H), 2.22-2.41 (1H), 2.56 (3H), 2.78 (4H), 3.39-3.53 (2H), 3.56-3.82 (1H), 4.37 (3H), 7.14-7.37 (3H), 7.39-7.53 (3H), 7.63-7.83 (4H), 8.36-8.60 (2H).

The starting material was prepared as follows:

Example 407a

N-(2-cyanoethyl)-4-methyl-2-(4-piperidylmethyl)-2H-indazole-5-carboxamide hydrochloride

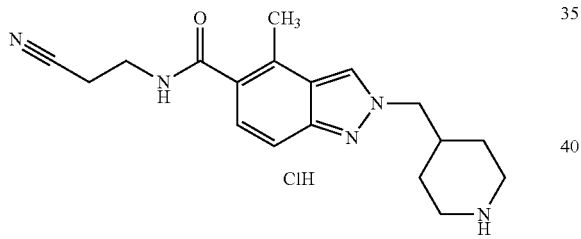

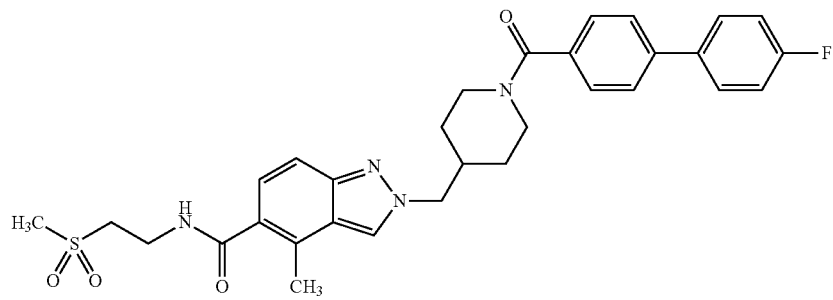 [SMILES: Cc1c(C(=O)NCCS(C)(=O)=O)ccc2nn(CC3CCN(C(=O)c4ccc(-c5ccc(F)cc5)cc4)CC3)cc12]

Analogously to Example 1b), Version B, 126 mg of the title compound was obtained from 300 mg of 408a) and 156 mg of 4'-fluorobiphenyl-4-carboxylic acid.

LC-MS: $R_t$=1.20 min, MS (ES+): m/z=577 (M+H)$^+$.

The starting material was prepared as follows:

Analogously to Example 1a, from 165 mg of 400a, 140 mg of the title compound was obtained, which was used in the next step without further purification.

Example 408

2-({1-[(4'-fluorobiphenyl-4-yl)carbonyl]piperidin-4-yl}methyl)-N-(2-mesylethyl)-4-methyl-2H-indazole-5-carboxamide

Example 408a

N-(2-mesylethyl)-4-methyl-2-(4-piperidylmethyl)-2H-indazole-5-carboxamide hydrochloride

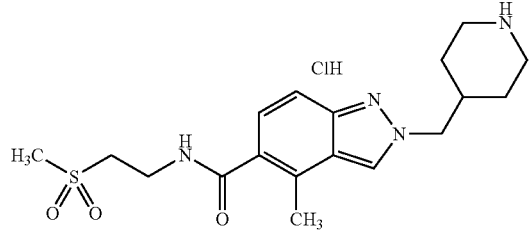 [SMILES: Cc1c(C(=O)NCCS(C)(=O)=O)ccc2nn(CC3CCNCC3)cc12 ; Cl]

Analogously to Example 1a, from 346 mg of 395a, 300 mg of the title compound was obtained, which was used in the next step without further purification.

Example 409

2-({1-[(4'-fluorobiphenyl-4-yl)carbonyl]piperidin-4-yl}methyl)-N-(3-hydroxypropyl)-4-methyl-2H-indazole-5-carboxamide

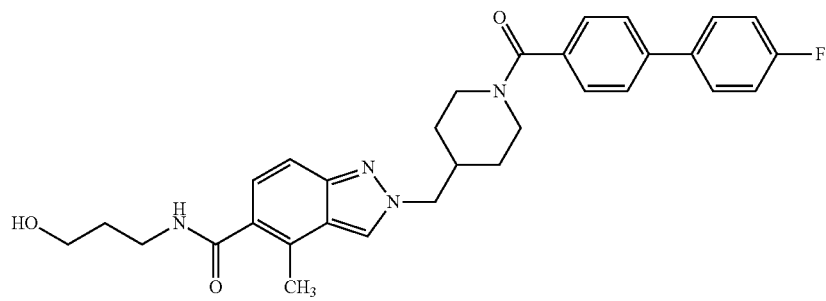 [SMILES: Cc1c(C(=O)NCCCO)ccc2nn(CC3CCN(C(=O)c4ccc(-c5ccc(F)cc5)cc4)CC3)cc12]

Analogously to Example 1b, Version B, 20 mg of the title compound was obtained from 124 mg of 409b) and 73 mg of 4'-fluorobiphenyl-4-carboxylic acid.

$^1$H-NMR (300 MHz, DMSO-d$_6$): δ [ppm], 1.26 (2H), 1.38-1.59 (2H), 1.67 (2H), 2.23-2.42 (1H), 2.52-2.57 (3H), 2.69-3.17 (2H), 3.19-3.94 (6H), 4.36 (3H), 7.18 (1H), 7.31 (2H), 7.38-7.51 (3H), 7.63-7.86 (4H), 8.08 (1H), 8.51 (1H).

The starting material was prepared as follows:

Example 409a

Tert-butyl 4-({5-[N-(3-hydroxypropyflcarbamoyl]-4-methyl-2H-indazol-2-yl}-methyl)piperidin-1-carboxylate

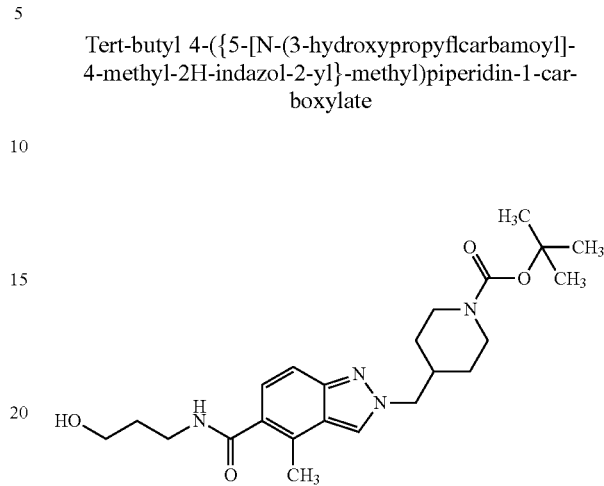

Analogously to Example 1b, Version B, 151 mg of the title compound was obtained from 150 mg of 1d and 30 mg of 3-amino-propan-1-ol.

$^1$H-NMR (400 MHz, DMSO-d$_6$): δ [ppm], 1.01-1.30 (3H), 1.32-1.49 (10H), 1.67 (2H), 2.08-2.27 (1H), 2.52 (3H), 2.57-2.80 (2H), 3.29 (2H), 3.41-3.54 (2H), 3.81-4.00 (2H), 4.32 (2H), 4.48 (1H), 7.18 (1H), 7.42 (1H), 8.10 (1H), 8.50 (1H).

Example 409b

N-(3-hydroxypropyl)-4-methyl-2-(4-piperidylmethyl)-2H-indazol-5-carboxamide

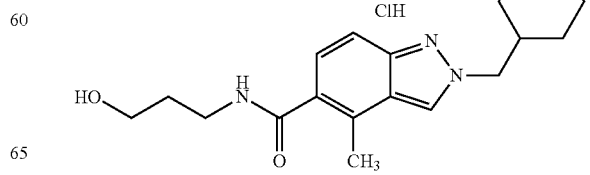

Analogously to Example 1a, from 246 mg of 409a, 124 mg of the title compound was obtained, which was used in the next step without further purification.

Example 410

2-({1-[(4'-fluorobiphenyl-4-yl)carbonyl]piperidin-4-yl}methyl)-N-(2-hydroxyethyl)-4-methyl-2H-indazole-5-carboxamide

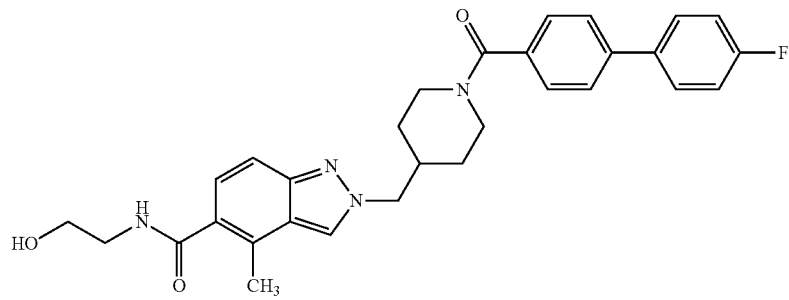 [SMILES: Cc1c(C(=O)NCCO)ccc2nn(CC3CCN(C(=O)c4ccc(-c5ccc(F)cc5)cc4)CC3)cc12]

Analogously to Example 1b, Version B, 36 mg of the title compound was obtained from 117 mg of 410b and 72 mg of 4'-fluorobiphenyl-4-carboxylic acid.

$^1$H-NMR (300 MHz, DMSO-d$_6$): δ [ppm], 1.26 (2H), 1.39-1.74 (2H), 2.21-2.40 (1H), 2.53 (3H), 2.75-3.16 (2H), 3.20-3.37 (2H), 3.43-3.74 (4H), 4.36 (3H), 7.21 (1H), 7.31 (2H), 7.38-7.52 (3H), 7.65-7.81 (4H), 8.03 (1H), 8.51 (1H).

The starting material was prepared as follows:

Example 410a

Tert-butyl 4-({5-[N-(2-hydroxyethyl)carbamoyl]-4-methyl-2H-indazol-2-yl}-methyl)piperidin-1-carboxylate

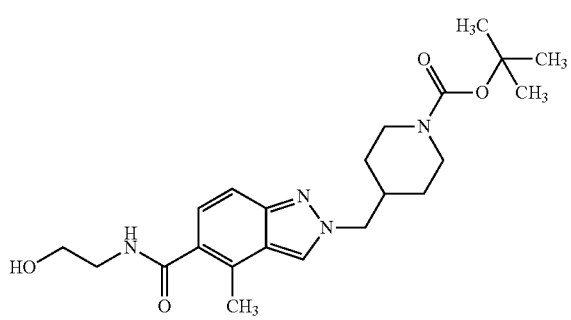 [SMILES: Cc1c(C(=O)NCCO)ccc2nn(CC3CCN(C(=O)OC(C)(C)C)CC3)cc12]

Analogously to Example 1b, Version B, 143 mg of the title compound was obtained from 150 mg of 1d) and 25 mg of 2-aminoethan-1-ol.

$^1$H-NMR (400 MHz, DMSO-d$_6$): δ [ppm], 1.01-1.30 (3H), 1.32-1.51 (10H), 2.07-2.26 (1H), 2.52-2.55 (3H), 2.58-2.82 (2H), 3.30 (2H), 3.45-3.58 (2H), 3.83-3.98 (2H), 4.32 (2H), 4.69 (1H), 7.21 (1H), 7.41 (1H), 8.05 (1H), 8.50 (1H).

Example 410b

N-(3-hydroxypropyl)-4-methyl-2-(4-piperidylmethyl)-2H-indazol-5-carboxamide hydrochloride

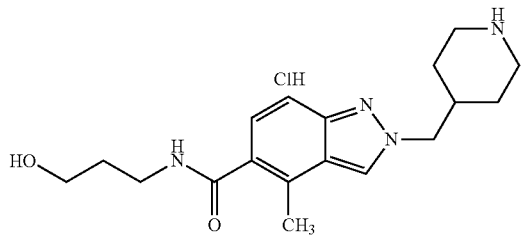 [SMILES: Cc1c(C(=O)NCCCO)ccc2nn(CC3CCNCC3)cc12 ; Cl]

Analogously to Example 1a) from 138 mg of 410a, 117 mg of the title compound was obtained, which was used in the next step without further purification.

Example 411

(+/−)-N-(1,4-dioxan-2-ylmethyl)-2-({1-[(4'-fluorobiphenyl-4-yl)carbonyl]-piperidin-4-yl}methyl)-4-methyl-2H-indazole-5-carboxamide

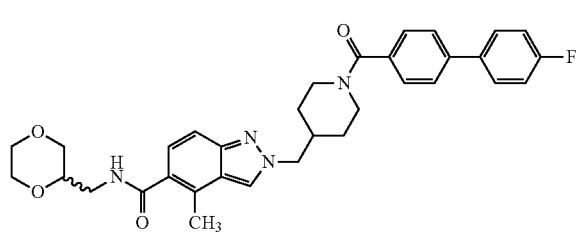 [SMILES: Cc1c(C(=O)NCC2COCCO2)ccc2nn(CC3CCN(C(=O)c4ccc(-c5ccc(F)cc5)cc4)CC3)cc12]

Analogously to Example 1b, Version B, 62 mg of the title compound was obtained from 226 mg of 411b) and 119 mg of 4'-fluorobiphenyl-4-carboxylic acid.

¹H-NMR (400 MHz, DMSO-d₆): δ [ppm], 1.19-1.34 (2H), 1.37-1.73 (2H), 2.23-2.42 (1H), 2.53 (3H), 2.69-2.90 (1H), 2.90-3.14 (1H), 3.17-3.30 (3H), 3.47 (1H), 3.58 (1H), 3.59-3.70 (3H), 3.71-3.82 (2H), 4.37 (3H), 7.19 (1H), 7.31 (2H), 7.38-7.53 (3H), 7.66-7.81 (4H), 8.18 (1H), 8.52 (1H).

The starting material was prepared as follows:

Example 411a (+/−)-tert-butyl 4-({5-[N-(1,4-dioxan-2-ylmethyl) carbamoyl]-4-methyl-2H-indazol-2-yl}methyl)piperidin-1-carboxylate

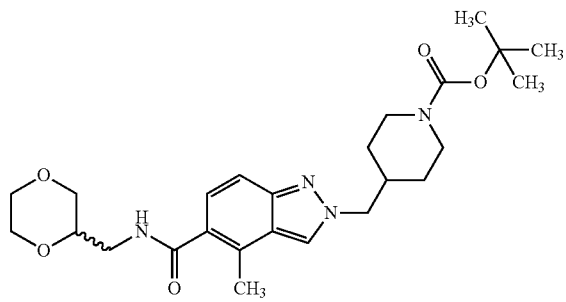 [SMILES: Cc1c(C(=O)NCC2COCCO2)ccc2nn(CC3CCN(C(=O)OC(C)(C)C)CC3)cc12]

Analogously to Example 1b, Version B, 267 mg of the title compound was obtained from 250 mg of 1d and 78 mg of (+/−)-1,4-dioxan-2-ylmethylamine.

¹H-NMR (400 MHz, DMSO-d₆): δ [ppm], 0.99-1.18 (2H), 1.38 (11H), 2.09-2.24 (1H), 2.53 (3H), 3.10-3.29 (4H), 3.41-3.52 (1H), 3.53-3.70 (4H), 3.70-3.81 (2H), 3.84-3.98 (2H), 4.32 (2H), 7.18 (1H), 7.41 (1H), 8.12-8.24 (1H), 8.51 (1H).

Example 411b (+/−)-N-(1,4-dioxan-2-ylmethyl)-4-methyl-2-(4-piperidylmethyl)-2H-indazole-5-carboxamide hydrochloride

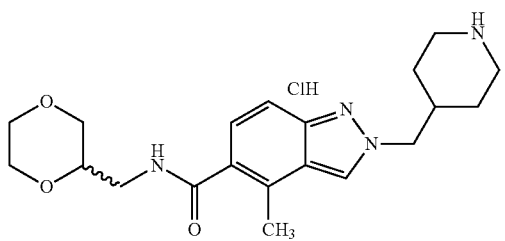 [SMILES: Cc1c(C(=O)NCC2COCCO2)ccc2nn(CC3CCNCC3)cc12 ; Cl]

Analogously to Example 1a, from 261 mg of 411a, 226 mg of the title compound was obtained, which was used in the next step without further purification.

Example 412

(+/−)-2-{[1-(4-chlorobenzoyl)piperidin-4-yl]methyl}-4-methyl-N-(oxetan-2-yl-methyl)-2H-indazole-5-carboxamide

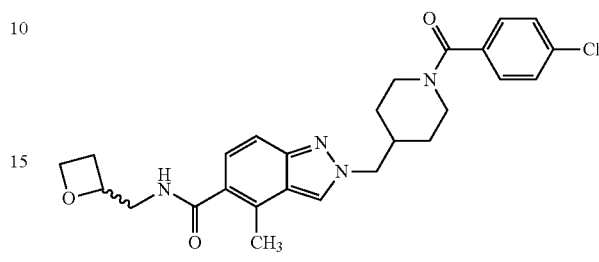

Analogously to Example 1b, Version B, 55 mg of the title compound was obtained from 350 mg of 238c) and 83 mg of (+/−)-oxetan-2-ylmethylamine.

¹H-NMR (300 MHz, DMSO-d₆): δ [ppm], 1.16-1.31 (2H), 1.33-1.69 (2H), 2.19-2.38 (2H), 2.53 (3H), 2.58-2.66 (1H), 2.66-2.86 (1H), 2.90-3.14 (1H), 3.38-3.64 (3H), 4.35 (5H), 4.71-4.96 (1H), 7.19 (1H), 7.33-7.45 (3H), 7.47-7.55 (2H), 8.21-8.37 (1H), 8.51 (1H).

Example 413

(+/−)-2-{[1-(4-chlorobenzoyl)piperidin-4-yl]methyl}-N-(1,4-dioxan-2-ylmethyl)-4-methyl-2H-indazole-5-carboxamide

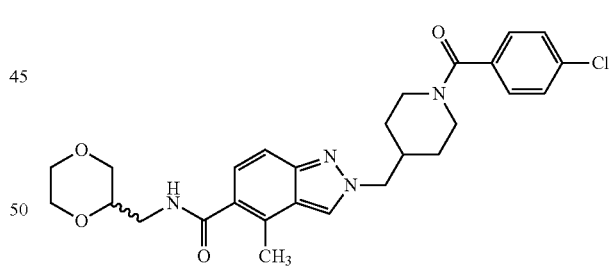

Analogously to Example 1b, Version B, 185 mg of the title compound was obtained from 376 mg of 238c and 111 mg of (+/−)-1,4-dioxan-2-ylmethylamine hydrochloride.

¹H-NMR (300 MHz, DMSO-d₆): δ [ppm], 1.19-1.32 (2H), 1.33-1.66 (2H), 2.20-2.40 (1H), 2.53 (3H), 2.71-2.86 (1H), 2.90-3.11 (1H), 3.16-3.32 (3H), 3.40-3.59 (3H), 3.60-3.70 (2H), 3.71-3.83 (2H), 4.35 (3H), 7.18 (1H), 7.31-7.46 (3H), 7.46-7.60 (2H), 8.21 (1H), 8.51 (1H).

Example 414

(R or S)-2-{[1-(4-chlorobenzoyl)piperidin-4-yl]methyl}-N-(1,4-dioxan-2-yl-methyl)-4-methyl-2H-indazole-5-carboxamide

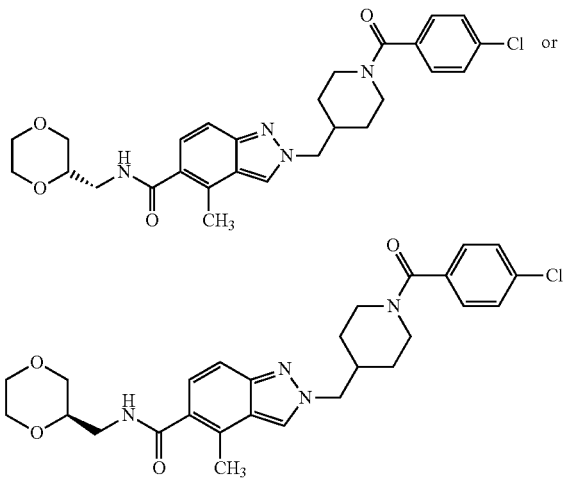

From 185 mg of the racemate prepared in Example 413, 51 mg of the title compound together with 58 mg of the slower-eluting enantiomer (Example 415) were obtained by racemate separation by means of preparative chiral HPLC (Method D).
Analytical chiral HPLC: 12.62 min

Example 415

(S or R)-2-{[1-(4-chlorobenzoyl)piperidin-4-yl]methyl}-N-(1,4-dioxan-2-yl-methyl)-4-methyl-2H-indazole-5-carboxamide

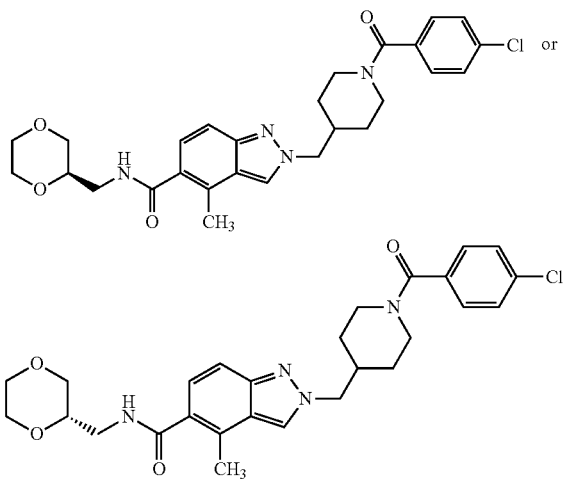

From 185 mg of the racemate prepared in Example 413, 58 mg of the title compound together with 51 mg of the faster-eluting enantiomer (Example 414) were obtained by racemate separation by means of preparative chiral HPLC (Method D).
Analytical chiral HPLC: 13.68 min

Example 416

(R or S)-4-methyl-N-(3,4,5,6-tetrahydro-2H-pyran-2-ylmethyl)-2-[(1-{4-[4-(trifluoromethyl)phenoxy]benzoyl}piperidin-4-yl)methyl]-2H-indazole-5-carboxamide

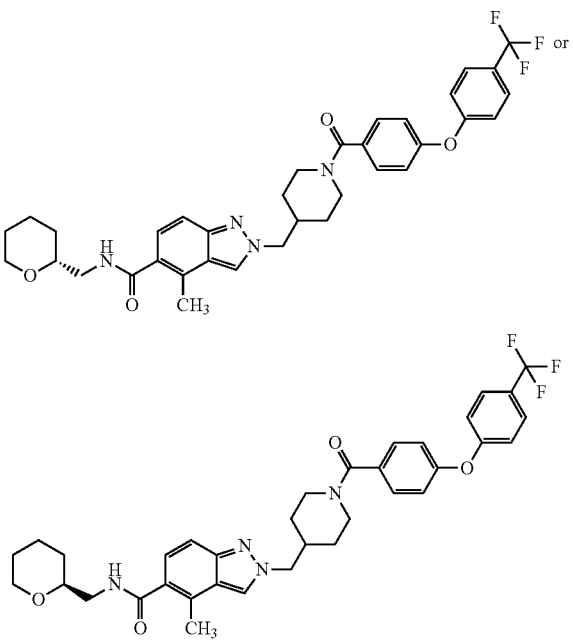

From 231 mg of the racemate prepared in Example 248, 24 mg of the title compound together with 24 mg of the slower-eluting enantiomer (Example 417) were obtained by racemate separation by means of preparative chiral HPLC (Method E).
Analytical chiral HPLC: 7.08 min.

Example 417

(S or R)-4-methyl-N-(3,4,5,6-tetrahydro-2H-pyran-2-ylmethyl)-2-[(1-{4-[4-(trifluoromethyl)phenoxy]benzoyl}piperidin-4-yl)methyl]-2H-indazole-5-carboxamide

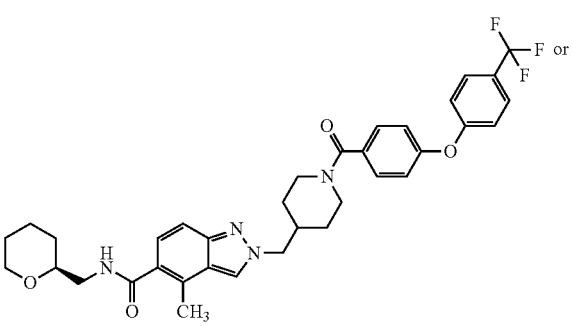

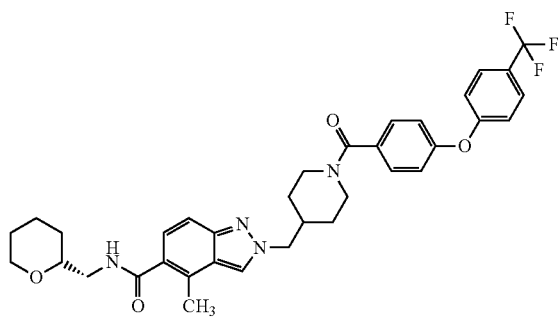

From 231 mg of the racemate prepared in Example 248, 24 mg of the title compound together with 24 mg of the faster-eluting enantiomer (Example 416) were obtained by racemate separation by means of preparative chiral HPLC (Method E).

Analytical chiral HPLC: 8.98 min.

Example 418

(R or S)—N-(1,4-dioxan-2-ylmethyl)-4-methyl-2-[(1-{4-[4-(trifluoromethyl)-phenoxy]benzoyl}piperidin-4-yl)methyl]-2H-indazole-5-carboxamide

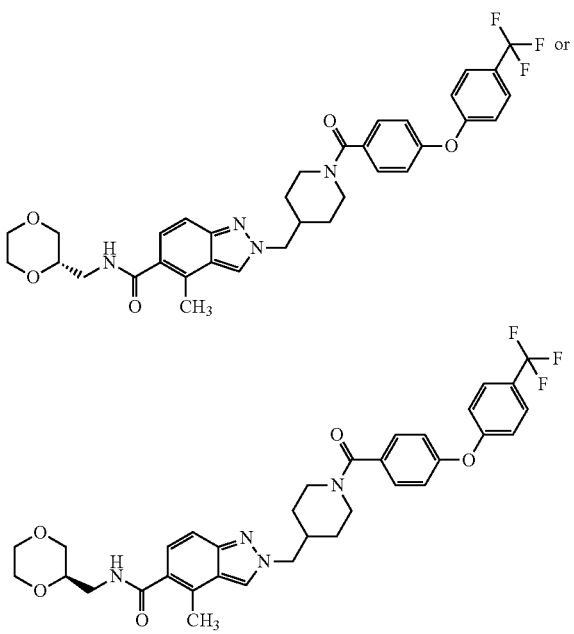

From 280 mg of the racemate prepared in Example 249, 65 mg of the title compound together with 75 mg of the slower-eluting enantiomer (Example 419) were obtained by racemate separation by means of preparative chiral HPLC (Method D (injection volume: 0.1 ml; detection: UV 210 nM)).

Analytical chiral HPLC: 13.66 min

Example 419

(R or S)—N-(1,4-dioxan-2-ylmethyl)-4-methyl-2-[(1-{4-[4-(trifluoromethyl)-phenoxy]benzoyl}piperidin-4-yl)methyl]-2H-indazole-5-carboxamide

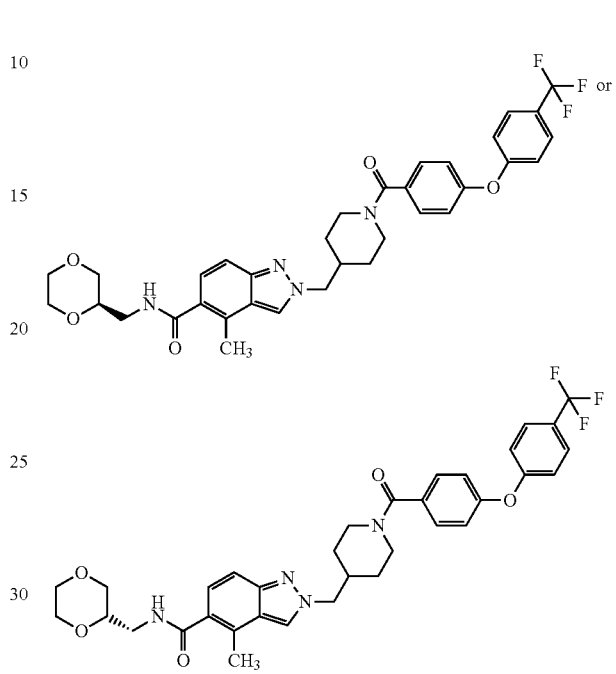

From 280 mg of the racemate prepared in Example 249, 75 mg of the title compound together with 65 mg of the faster-eluting enantiomer (Example 418) were obtained by racemate separation by means of preparative chiral HPLC (Method D (injection volume: 0.1 ml; Detection: UV 210 nM)).

Analytical chiral HPLC: 14.90 min

BIOLOGICAL EXAMPLES

The following biological examples which are described in sections 1-5 and have only been carried out using EP2 receptor antagonists are already contained in patent application PCT/EP2012/073556, unpublished at the priority date of the present specification.

1. Detection of Antagonism to the Human Prostaglandin E2 (Subtype EP2) Receptor Signal 1.1 Detection Principle The binding of $PGE_2$ to the EP2 subtype of the human $PGE_2$ receptor induces the activation of membrane-located adenylate cyclases and leads to the formation of cAMP. In the presence of the phosphodiesterase inhibitor IBMX, the cAMP accumulated owing to this stimulation and released by cell lysis is used in a competitive detection method. In this test, the cAMP present in the lysate competes with a fluorescence-labelled cAMP (cAMP-d2) for binding to an Eu cryptate-labelled anti-cAMP antibody.

In the absence of cellular cAMP, a maximal signal is produced, which is attributable to the binding of this cAMP-d2 molecule to the antibody. After excitation of the cAMP-d2 molecule at 337 nm, there is a fluorescence resonance energy transfer (FRET) to the Eu cryptate molecules of the anti-cAMP antibody (labelled therewith), followed by a long-lasting emission signal at 665 nm (and at 620 nM). Both signals are measured in a suitable measurement instrument with a time delay, i.e. after decay of the background fluorescence. Any increase in the low FRET signal caused by prostaglandin $E_2$ administration (measured as well ratio change=emission$_{665nm}$/emission$_{620nm}$*10000) indicates the action of antagonists.

1.2. Detection Method 1.2.1. Test for Antagonism (Data Per Well of a 384-Well Plate):

To a test plate with the substance solutions already added (0.05 µl; 100% DMSO, concentration range from 0.8 nM-16.5 nM) were added 4 µl of a cAMP-d2/cell suspension (625000 cells/ml). After a 20-minute preincubation at room temperature (RT), 2 µl of a 3×PGE2 solution (1.5 nM, in PBS-IBMX) were added and incubated in the presence of the agonist for a further 60 mins at RT (volume: ~6 n1). Next the reaction was stopped by addition of 2 µl of lysis buffer and incubated for a further 20 mins at RT before the actual measurement (volume: ~8 µl).

2. Detection of Antagonism to the Human Prostaglandin E2 (Subtype EP4) Receptor Signal 2.1 Detection Principle The binding of $PGE_2$ to the $EP_4$ subtype of the human $PGE_2$ receptor induces the activation of membrane-located adenylate cyclases and leads to the formation of cAMP. In the presence of the phosphodiesterase inhibitor IBMX, the cAMP accumulated owing to this stimulation and released by cell lysis is used in a competitive detection method. In this test, the cAMP present in the lysate competes with a fluorescence-labelled cAMP (cAMP-d2) for binding to an Eu cryptate-labelled anti-cAMP antibody.

In the absence of cellular cAMP a maximal signal is produced, which is attributable to the binding of this cAMP-d2 molecule to the antibody. After excitation of the cAMP-d2 molecule at 337 nm, there is a fluorescence resonance energy transfer (FRET) to the Eu cryptate molecules of the anti-cAMP antibody (labelled therewith), followed by a long-lasting emission signal at 665 nm (and at 620 nM). Both signals are measured in a suitable measurement instrument with a time delay, i.e. after decay of the background fluorescence. Any increase in the low FRET signal caused by prostaglandin $E_2$ administration (measured as well ratio change=emission$_{665nm}$/emission$_{620nm}$*10000) indicates the action of antagonists.

2.2. Detection Method 2.2.1. Test for Antagonism (Data Per Well of a 384-Well Plate):

To a test plate with the substance solutions already added (0.05 µl; 100% DMSO, concentration range from 0.8 nM-16.5 uM) were added 4 µl of a cAMP-d2/cell suspension (312500 cells/ml). After a 20-minute preincubation at room temperature (RT), 2 µl of a 3×PGE2 solution (0.3 nM, in PBS-IBMX) were added and incubated in the presence of the agonist for a further 60 mins at RT (volume: ~6 µl). Next the reaction was stopped by addition of 2 µl of lysis buffer and incubated for a further 20 mins at RT before the actual measurement (volume: ~8 µl).

3. Detection of Antagonism to the Human Prostaglandin D Receptor Signal 3.1 Detection Principle The binding of prostaglandin $D_2$ to the human PGD receptor induces the activation of membrane-located adenylate cyclases and leads to the formation of cAMP. In the presence of the phosphodiesterase inhibitor IBMX, the cAMP accumulated owing to this stimulation and released by cell lysis is used in a competitive detection method. In this test, the cAMP present in the lysate competes with a fluorescence-labelled cAMP (cAMP-d2) for binding to an Eu cryptate-labelled anti-cAMP antibody.

In the absence of cellular cAMP, a maximal signal is produced, which is attributable to the binding of this cAMP-d2 molecule to the antibody. After excitation of the cAMP-d2 molecule at 337 nm, there is a fluorescence resonance energy transfer (FRET) to the Eu cryptate molecules of the anti-cAMP antibody (labelled therewith), followed by a long-lasting emission signal at 665 nm (and at 620 nM). Both signals are measured in a suitable measurement instrument with a time delay, i.e. after decay of the background fluorescence. Any increase in the low FRET signal caused by prostaglandin E2 administration (measured as well ratio change=emission$_{665nm}$/emission$_{620nm}$*10000) indicates the action of antagonists.

3.2. Detection Method 3.2.1. Test for Antagonism (Data Per Well of a 384-Well Plate):

To a test plate with the substance solutions already added (0.05 µl; 100% DMSO, concentration range from 0.8 nM-16.5 nM) were added 4 µl of a cAMP-d2/cell suspension (625000 cells/ml). After a 20-minute preincubation at room temperature (RT), 2 µl of a 3×PGD2 solution (6 nM, in PBS-IBMX) were added and incubated in the presence of the agonist for a further 30 mins at RT (volume: ~6 µl). Next the reaction was stopped by addition of 2 µl of lysis buffer and incubated for a further 20 mins at RT before the actual measurement (volume: ~8 µl).

4. The EP2 Subtype of the PGE2 Receptor and the Pre-Ovulatory Cumulus Expansion 4.1. Background:

In the pre-ovulatory antral follicle, the oocyte is surrounded by cumulus cells, which form a dense cell crown around the oocyte. After the LH peak (luteinizing hormone), a series of processes is activated, which results in a marked morphological change in this cell crown of cumulus cells. During this, the cumulus cells form an extracellular matrix, which leads to the so-called cumulus expansion (Vanderhyden et al. Dev Biol.; (1990); 140(2): 307-317) This cumulus expansion is an important component of the ovulatory process and the subsequent possibility of fertilization.

During the cumulus expansion, prostaglandins and here prostaglandin $E_2$, synthesis whereof is induced by the LH peak, are of decisive importance. Prostanoid EP2 knockout mice (Hizaki et al., 1999, Proc Natl Acad Sci U.S.A; (1999) 96(18):10501-10506) show a markedly decreased cumulus expansion and severe subfertility, which demonstrates the importance of the prostanoid EP2 receptor for this process.

4.2. Cumulus Expansions Test In Vitro

In immature female mice (strain: B6D2F1 from Charles River), at an age of 14-18 days, the folliculogenesis was induced by a single administration (intraperitoneal) of 10 IU of PMSG (pregnant mare serum gonadotropin; Sigma G-4877, Lot 68H0909). 47-50 hours after the injection, the ovaries were removed and the cumulus-oocyte complexes removed. At this stage, the cumulus complex is not yet expanded.

The cumulus-oocyte complexes were now incubated for 20-24 hours with prostaglandin $E_2$ ($PGE_2$) (0.3 µM), vehicle control (ethanol) or test substances. Medium: alpha-MEM medium with 0.1 mM IBMX, pyruvate (0.23 mM), glutamine (2 mM), pen/strep 100 IU/ml pen. and 100 µg/ml strep.), HSA (8 mg/ml) and foetal bovine serum (FBS, 10%). The cumulus expansion was then established through the subdivision into four stages (after Vanderhyden et al. Dev Biol.; (1990); 140(2):307-317).

4.3 In-Vivo Action on Post-Ovulatory In-Vitro Fertilization:

Substances can exert an influence on fertility by decreasing the fertilizability of oocytes or cumulus-oocyte complexes. In order to study such effects, substances can be administered in vivo and subjected to in vitro fertilization after ovulation of cumulus-oocyte complexes has taken place. The in-vitro fertilization rate, where no test substance is any longer present, allows conclusions as to the in-vivo effects of the test substances.

Immature female mice (strain: B6D2F1, Charles River, Suelzfeld, age: 19-25 days) were kept in Macrolon cages in rooms with controlled illumination (12 hrs darkness: 12 hrs light), fed with a standard diet and provided with drinking water ad libitum.

The mice were primed with PMSG (pregnant mare serum gonadotropin) (10 IU/animal i.p.). After 48 hours, a stimulus triggering ovulation was created in the animals by one administration of 10 IU/animal i.p. (hCG, human chorionic gonadotropin). The test substances were dissolved in benzyl benzoate/castor oil (1+4 v/v) and administered in a volume of 0.1 ml s.c. 1 hour before hCG (n=5 animals per group). Fourteen hours after hCG administration, the animals were killed. Ovulated oocytes and cumulus-oocyte complexes were obtained from the bursa ovarii and/or oviduct and subjected to in-vitro fertilization, wherein for the fertilization a sperm count of 40000 sperms/0.5 ml was used for 1 hour. Twenty-four hours after the incubation with the sperms, the number of fertilized oocytes is established and the percentage fertilization rate determined The results in Table 4 show that Example 17 according to the invention has a dose-dependent influence on the fertilizability of ovulated cumulus-oocyte complexes.

4.4 In-Vivo Action on Fertility in Non-Human Primates (Cynomolgus):

In order to study the effect of substances on fertility, mating studies can be performed in monkeys (Jensen et al. Contraception 81; (2010) 82(2): 165-171). For this, the test substances are administered to female cynomolgus monkeys (*Macaca Fascicularis*) which are being kept in groups, then the animals are mated with a male animal. Matings are checked for by sperm detection in daily vaginal smears. Pregnancies resulting therefrom are identified by hormone determinations and ultrasound examinations. Through the changes in the serum oestradiol concentrations during the cycle, (rise before the midcycle LH peak), the fertile phase within a cycle of the individual animals can be determined. Matings in this fertile period are described as "timed matings" (matings in the fertile phase). Apart from the absolute number of pregnancies occurring, the effect on the fertility can also be expressed as pregnancies per "timed matings".

To test the action of EP2 receptor antagonists on fertility in monkeys, Examples 17 and 56 according to the invention were administered over 6 months, dissolved in 0.5 ml castor oil. Example 17 was administered once daily at a dosage of 10 mg/kg (n=10 animals), while Example 56 was administered twice daily at a dosage of 10 mg/kg (n=9 animals). Only the vehicle was administered to a control group (n=10 animals). In the first month of the treatment, no male animal was placed with the female animals. After this, female and male animals were kept together over 5 months, with detection of pregnancies and cycle monitoring.

Table 5 shows that both substances result in a marked reduction in the number of pregnancies occurring. These data for the first time show the strong contraceptive effect of EP2 receptor antagonists in the primate. Further results of the study show that the substances have no effects on hormone levels and cycle length. This confirms that the substances produce a contraceptive effect by non-hormonal mechanisms. The reversibility of the fertility was demonstrated on some animals after discontinuation of the treatment.

5. Determination of the Pharmacokinetic Parameters after Intravenous Administration 5.1. Intravenous Administration:

For this, the substances were administered in dissolved form, compatible solubilizers such as PEG400 and/or ethanol being used in tolerable quantity. The substances were administered at a dosage of 0.1-1 mg/kg. The administration was effected in the female rat as a bolus injection. Here, at various times after bolus injection ca. 100-150 µl blood samples were withdrawn from the jugular vein via a catheter. The blood samples were treated with lithium-heparin as anticoagulant and stored refrigerated until further work-up. After centrifugation of the samples for 15 mins at 3000 rpm, an aliquot of 100 µl was withdrawn from the supernatant (plasma) and precipitated by addition of 400 µl of cold acetonitrile or methanol (absolute). The precipitated samples were frozen overnight at −20° C., then centrifuged once again for 15 mins at 3000 rpm, before 150 µl of the clear supernatant was withdrawn for the concentration determination. The analysis was performed with an Agilent 1200 HPLC system with attached LCMS/MS detection.

5.2 Calculation of the PK Parameters

The calculation was performed by means of the PK calculation software WinNonLin®, where $t_{1/2}$ means half-life within a specified interval (here: terminal $t_{1/2}$, in hrs).

TABLE 1

Examples for the biological activity of the compounds according to the invention on the hEP2 receptor ($IC_{50}$ measured by cAMP antagonism test), selectivity towards hDP & $hEP_4$ ($IC_{50}$ measured by cAMP antagonism test): x: 1-10, xx: 10-100, xxx >100:

| Example | Antagonism hEP2 $IC_{50}$ [M] | Selectivity hEP2/hDP | Selectivity hEP2/hEP4 |
|---|---|---|---|
| 1 | 1.03E−07 | xxx | xxx |
| 2 | 2.17E−08 | xxx | xxx |
| 3 | 4.91E−09 | xxx | xxx |
| 4 | 6.81E−08 | xxx | xxx |
| 5 | 5.11E−09 | xxx | xxx |
| 6 | 3.13E−07 | xx | xx |
| 7 | 2.58E−08 | xxx | xxx |
| 8 | 9.37E−09 | xxx | xxx |
| 9 | 1.72E−08 | xxx | xxx |
| 10 | 8.67E−09 | xxx | xxx |
| 11 | 8.14E−09 | xxx | xxx |
| 12 | 2.03E−08 | xxx | xxx |
| 13 | 3.59E−08 | xxx | xxx |
| 14 | 3.67E−09 | xxx | xxx |
| 15 | 4.17E−09 | xxx | xxx |
| 16 | 5.85E−09 | xxx | xxx |
| 17 | 3.44E−09 | xxx | xxx |
| 18 | 7.66E−09 | xxx | xxx |
| 19 | 8.57E−09 | xxx | xxx |
| 20 | 7.33E−09 | xxx | xxx |
| 21 | 3.58E−08 | xxx | xxx |
| 22 | 3.03E−08 | xxx | xxx |
| 23 | 1.61E−08 | xxx | xxx |
| 24 | 6.01E−08 | xxx | xxx |
| 25 | 2.52E−08 | xxx | xxx |
| 26 | 2.42E−08 | xxx | xxx |
| 27 | 1.93E−08 | xxx | xxx |
| 28 | 3.39E−08 | xxx | xxx |
| 29 | 9.31E−09 | xxx | xxx |
| 30 | 6.43E−08 | xxx | xxx |
| 31 | 3.08E−09 | xxx | xxx |
| 32 | 1.04E−08 | xxx | xxx |
| 33 | 3.42E−08 | xxx | xxx |
| 34 | 1.34E−07 | xxx | xxx |

TABLE 1-continued

Examples for the biological activity of the compounds according to the invention on the hEP2 receptor ($IC_{50}$ measured by cAMP antagonism test), selectivity towards hDP & $hEP_4$ ($IC_{50}$ measured by cAMP antagonism test): x: 1-10, xx: 10-100, xxx >100:

| Example | Antagonism hEP2 $IC_{50}$ [M] | Selectivity hEP2/hDP | Selectivity hEP2/hEP4 |
|---|---|---|---|
| 35 | 6.92E−08 | xxx | xxx |
| 36 | 6.16E−08 | xxx | xxx |
| 37 | 1.04E−07 | xxx | xxx |
| 38 | 2.81E−08 | xxx | xxx |
| 39 | 1.13E−07 | xxx | xxx |
| 40 | 1.15E−08 | xxx | xxx |
| 41 | 5.62E−09 | xxx | xxx |
| 42 | 4.75E−09 | xxx | xxx |
| 43 | 4.82E−09 | xxx | xxx |
| 44 | 3.85E−09 | xxx | xxx |
| 45 | 5.51E−09 | xxx | xxx |
| 46 | 4.91E−09 | xxx | xxx |
| 47 | 5.61E−09 | xxx | xxx |
| 48 | 5.59E−09 | xxx | xxx |
| 49 | 6.44E−09 | xxx | xxx |
| 50 | 3.18E−09 | xxx | xxx |
| 51 | 6E−08 | xxx | xxx |
| 52 | 8.3E−07 | xx | xx |
| 53 | 4.42E−08 | xxx | xxx |
| 54 | 4.74E−09 | xxx | xxx |
| 55 | 9.67E−09 | xxx | xxx |
| 56 | 1.31E−08 | xxx | xxx |
| 57 | 5.29E−09 | xxx | xxx |
| 58 | 1.08E−06 | xx | xx |
| 59 | 7.58E−07 | xx | xx |
| 60 | 1.75E−07 | xx | xx |
| 61 | 1.5E−06 | xx | xx |
| 62 | 6.74E−07 | xx | xx |
| 63 | 1.44E−06 | xx | xx |
| 64 | 4.13E−06 | x | x |
| 65 | 2.79E−06 | x | x |
| 66 | 3.21E−07 | xx | xx |
| 67 | 4.05E−07 | xx | xx |
| 68 | 1.77E−08 | xxx | xxx |
| 69 | 2.9E−08 | xxx | |
| 70 | 4.9E−08 | xxx | |
| 71 | 8.29E−08 | xxx | xxx |
| 72 | 1.2E−07 | xxx | xxx |
| 73 | 7.78E−08 | xxx | xxx |
| 74 | 9.54E−08 | xxx | xxx |
| 75 | 6.7E−08 | xxx | xxx |
| 76 | 1.79E−07 | xx | xx |
| 77 | 5.39E−08 | xxx | xxx |
| 78 | 3.17E−08 | xxx | xxx |
| 79 | 1.25E−07 | xxx | xxx |
| 80 | 8.59E−08 | xxx | xxx |
| 81 | 5.13E−07 | xx | xx |
| 82 | 2.18E−07 | xx | xx |
| 83 | 3.26E−08 | xxx | xxx |
| 84 | 1.92E−08 | xxx | xxx |
| 85 | 3.55E−08 | xxx | xxx |
| 86 | 1.54E−08 | xxx | xxx |
| 87 | 2.4E−08 | xxx | xxx |
| 88 | 1.62E−08 | xxx | xxx |
| 89 | 9.4E−09 | xxx | xxx |
| 90 | 1.48E−08 | xxx | xxx |
| 91 | 2.03E−08 | xxx | xxx |
| 92 | 1.27E−08 | xxx | xxx |
| 93 | 1.15E−08 | xxx | xxx |
| 94 | 1.28E−08 | xxx | xxx |
| 95 | 6.18E−09 | xxx | xxx |
| 96 | 9.42E−09 | xxx | xxx |
| 97 | 1.27E−08 | xxx | xxx |
| 98 | 7.07E−09 | xxx | xxx |
| 99 | 1.04E−08 | xxx | xxx |
| 100 | 6.21E−09 | xxx | xxx |
| 101 | 6.58E−09 | xxx | xxx |
| 102 | 4.1E−07 | xx | xx |
| 103 | 5.95E−07 | xx | xx |
| 104 | 5.13E−07 | xx | xx |
| 105 | 2.85E−07 | xx | xx |
| 106 | 1.5E−07 | xxx | xxx |
| 107 | 1.14E−08 | xxx | xxx |
| 108 | 6.46E−09 | xxx | xxx |
| 109 | 9.53E−09 | xxx | xxx |
| 110 | 4.4E−09 | xxx | xxx |
| 111 | 1.37E−08 | xxx | xxx |
| 112 | 1.19E−08 | xxx | xxx |
| 113 | 1.39E−08 | xxx | xxx |
| 114 | 6.08E−09 | xxx | xxx |
| 115 | 9.05E−09 | xxx | xxx |
| 116 | 5.52E−09 | xxx | xxx |
| 117 | 1.78E−08 | xxx | xxx |
| 118 | 8.17E−09 | xxx | |
| 119 | 1.32E−08 | xxx | |
| 120 | 1.55E−08 | xxx | |
| 121 | 1.55E−08 | xxx | xxx |
| 122 | 2.86E−08 | xxx | xxx |
| 123 | 8.92E−09 | xxx | xxx |
| 124 | 7.99E−09 | xxx | xxx |
| 125 | 3.66E−09 | xxx | xxx |
| 126 | 2.12E−08 | xxx | xxx |
| 127 | 5.56E−08 | xxx | xxx |
| 128 | 4.71E−07 | xx | xx |
| 129 | 3.09E−07 | xx | xx |
| 130 | 2.41E−07 | xx | xx |
| 131 | 2.28E−07 | xx | xx |
| 132 | 1.09E−07 | xxx | xxx |
| 133 | 4.19E−08 | xxx | xxx |
| 134 | 5.65E−08 | xxx | xxx |
| 135 | 1.95E−08 | xxx | xxx |
| 136 | 6.59E−09 | xxx | xxx |
| 137 | 7.65E−09 | xxx | xxx |
| 138 | 1.6E−07 | xxx | xxx |
| 139 | 4.19E−07 | xx | xx |
| 140 | 5.53E−08 | xxx | xxx |
| 141 | 1.43E−07 | xxx | xxx |
| 142 | 7.13E−07 | xx | xx |
| 143 | 3.68E−08 | xxx | xxx |
| 144 | 5.08E−08 | xxx | xxx |
| 145 | 1.88E−08 | xxx | xxx |
| 146 | 5.26E−08 | xxx | xxx |
| 147 | 5.74E−08 | xxx | xxx |
| 148 | 2.74E−08 | xxx | xxx |
| 149 | 2.96E−08 | xxx | xxx |
| 150 | 1.28E−08 | xxx | xxx |
| 151 | 4.85E−08 | xxx | xxx |
| 152 | 3.33E−08 | xxx | xxx |
| 153 | 6.08E−08 | xxx | xxx |
| 154 | 8.08E−08 | xxx | xxx |
| 155 | 2.94E−08 | xxx | xxx |
| 156 | 1.84E−07 | xx | xx |
| 157 | 1.36E−08 | xxx | xxx |
| 158 | 6.21E−09 | xxx | xxx |
| 159 | 6.24E−09 | xxx | xxx |
| 160 | 8.29E−08 | xxx | xxx |
| 161 | 9.82E−08 | xxx | xxx |
| 162 | 9.33E−09 | xxx | xxx |
| 163 | 6.8E−09 | xxx | xxx |
| 164 | 1.09E−08 | xxx | xxx |
| 165 | 3.34E−08 | xxx | xxx |
| 166 | 2.87E−09 | xxx | xxx |
| 167 | 1.35E−08 | xxx | xxx |
| 168 | 2.93E−08 | xxx | xxx |
| 169 | 2.77E−08 | xxx | xxx |
| 170 | 4.25E−09 | xxx | xxx |
| 171 | 3.88E−09 | xxx | xxx |
| 172 | 3.16E−09 | xxx | xxx |
| 173 | 2.71E−09 | xxx | xxx |
| 174 | 6.58E−09 | xxx | xxx |
| 175 | 8.05E−09 | xxx | xxx |
| 176 | 7.77E−09 | xxx | xxx |
| 177 | 1.18E−07 | xxx | xxx |
| 178 | 6.83E−08 | xxx | xxx |

TABLE 1-continued

Examples for the biological activity of the compounds according to the invention on the hEP2 receptor (IC$_{50}$ measured by cAMP antagonism test), selectivity towards hDP & hEP$_4$ (IC$_{50}$ measured by cAMP antagonism test): x: 1-10, xx: 10-100, xxx >100:

| Example | Antagonism hEP2 IC$_{50}$ [M] | Selectivity hEP2/hDP | Selectivity hEP2/hEP4 |
|---|---|---|---|
| 179 | 2.61E−06 | x | x |
| 180 | 1.73E−08 | xxx | xxx |
| 181 | 3.52E−08 | xxx | xxx |
| 182 | 6.42E−08 | xxx | xxx |
| 183 | 4.66E−08 | xxx | xxx |
| 184 | 7.68E−08 | xxx | xxx |
| 185 | 2.48E−08 | xxx | xxx |
| 186 | 5.19E−08 | xxx | xxx |
| 187 | 2.35E−08 | xxx | xxx |
| 188 | 1.49E−07 | xxx | xxx |
| 189 | 3.36E−08 | xxx | xxx |
| 190 | 2.72E−07 | xx | xx |
| 191 | 4.71E−08 | xxx | xxx |
| 192 | 2.06E−07 | xx | xx |
| 193 | 1.45E−07 | xxx | xxx |
| 194 | 4.09E−08 | xxx | xxx |
| 195 | 2.27E−07 | xx | xx |
| 196 | 5.08E−08 | xxx | xxx |
| 197 | 6.32E−08 | xxx | xxx |
| 198 | 1.53E−07 | xxx | xxx |
| 199 | 9.71E−08 | xxx | xxx |
| 200 | 1.51E−08 | xxx | xxx |
| 201 | 2.49E−08 | xxx | xxx |
| 202 | 5.06E−09 | xxx | xxx |
| 203 | 8.57E−08 | xxx | xxx |
| 204 | 1E−08 | xxx | xxx |
| 205 | 4.33E−08 | xxx | xxx |
| 206 | 4.13E−08 | xxx | xxx |
| 207 | 3.03E−08 | xxx | xxx |
| 208 | 8.06E−08 | xxx | xxx |
| 209 | 2.51E−08 | xxx | xxx |
| 210 | 1.95E−08 | xxx | xxx |
| 211 | 5.01E−08 | xxx | xxx |
| 212 | 1.06E−07 | xxx | xxx |
| 213 | 8.24E−08 | xxx | xxx |
| 214 | 6.49E−08 | xxx | xxx |
| 215 | 3.9E−08 | xxx | xxx |
| 216 | 8.61E−08 | xxx | xxx |
| 217 | 1.14E−07 | xxx | xxx |
| 218 | 1.28E−07 | xxx | xxx |
| 219 | 2.73E−07 | xx | xx |
| 220 | 1.47E−07 | xxx | xxx |
| 221 | 2.35E−07 | xx | xx |
| 222 | 4.09E−08 | xxx | xxx |
| 223 | 2E−08 | xxx | xxx |
| 224 | 5.62E−09 | xxx | xxx |
| 225 | 1.43E−08 | xxx | xxx |
| 226 | 1.19E−08 | xxx | xxx |
| 227 | 9.89E−09 | xxx | xxx |
| 228 | 8.09E−09 | xxx | xxx |
| 229 | 1.02E−08 | xxx | xxx |
| 230 | 1.37E−08 | xxx | xxx |
| 231 | 1.32E−08 | xxx | xxx |
| 232 | 3.83E−08 | xxx | xxx |
| 233 | 3.97E−08 | xxx | xxx |
| 234 | 4.77E−08 | xxx | xxx |
| 235 | 1.67E−08 | xxx | xxx |
| 236 | 5.75E−08 | xxx | xxx |
| 237 | 3.1E−08 | xxx | xxx |
| 238 | 3.24E−08 | xxx | xxx |
| 239 | 2.7E−08 | xxx | xxx |
| 240 | 2.51E−08 | xxx | xxx |
| 241 | 9.03E−09 | xxx | xxx |
| 242 | 3.05E−07 | xx | xx |
| 243 | 3.35E−07 | xx | xx |
| 244 | 4.42E−08 | xxx | xxx |
| 245 | 7.79E−09 | xxx | xxx |
| 246 | 9.23E−09 | xxx | xxx |
| 247 | 1.26E−08 | xxx | xxx |
| 248 | 1.47E−08 | xxx | xxx |
| 249 | 1.12E−08 | xxx | xxx |
| 250 | 3.06E−08 | xxx | xxx |
| 251 | 3.81E−06 | x | x |
| 252 | 2.95E−07 | xx | xx |
| 253 | 1.68E−07 | xx | xx |
| 254 | 5.52E−08 | xxx | xxx |
| 255 | 8.35E−08 | xxx | xxx |
| 256 | 1.07E−07 | | xxx |
| 257 | 1.02E−07 | xxx | xxx |
| 258 | 1.09E−07 | xxx | xxx |
| 259 | 2.56E−08 | xxx | xxx |
| 260 | 8.02E−09 | xxx | xxx |
| 261 | 8.1E−08 | xxx | xxx |
| 262 | 3.34E−08 | xxx | xxx |
| 263 | 1.81E−07 | xx | xx |
| 264 | 1.37E−08 | xxx | xxx |
| 265 | 3.15E−08 | xxx | xxx |
| 266 | 1.89E−08 | xxx | xxx |
| 267 | 4.55E−08 | xxx | xxx |
| 268 | 2.29E−08 | xxx | xxx |
| 269 | 7.54E−09 | xxx | xxx |
| 270 | 5.31E−08 | xxx | xxx |
| 271 | 3.35E−08 | xxx | xxx |
| 272 | 2.37E−08 | xxx | xxx |
| 273 | 1.85E−08 | xxx | xxx |
| 274 | 4.46E−08 | xxx | xxx |
| 275 | 3.45E−08 | xxx | xxx |
| 276 | 2.26E−07 | xx | xx |
| 277 | 4.79E−08 | xxx | xxx |
| 278 | 1.04E−07 | xxx | xxx |
| 279 | 5.74E−08 | xxx | xxx |
| 280 | 3.07E−08 | xxx | xxx |
| 281 | 2.3E−08 | xxx | xxx |
| 282 | 2.01E−08 | xxx | xxx |
| 283 | 6.55E−08 | xxx | xxx |
| 284 | 5.64E−08 | xxx | xxx |
| 285 | 1E−07 | xxx | xxx |
| 286 | 1E−07 | xxx | xxx |
| 287 | 1.05E−06 | xx | xx |
| 288 | 4E−08 | xxx | xxx |
| 289 | 5.16E−08 | xxx | xxx |
| 290 | 4.26E−08 | xxx | xxx |
| 291 | 5.94E−09 | xxx | xxx |
| 292 | 2E−08 | xxx | xxx |
| 293 | 2.83E−08 | xxx | xxx |
| 294 | 1.32E−08 | xxx | xxx |
| 295 | 7.08E−08 | xxx | xxx |
| 296 | 2.97E−08 | xxx | xxx |
| 297 | 4.6E−07 | xx | xx |
| 298 | 3.45E−07 | xx | xx |
| 299 | 5.41E−07 | xx | xx |
| 300 | 7.98E−08 | xxx | xxx |
| 301 | 2.45E−08 | xxx | xxx |
| 302 | 1.31E−07 | xxx | xxx |
| 303 | 1.39E−08 | xxx | xxx |
| 304 | 9.98E−08 | xxx | xxx |
| 305 | 3.01E−07 | xx | xx |
| 306 | 7.66E−08 | xxx | xxx |
| 307 | 3.06E−08 | xxx | xxx |
| 308 | 2.22E−08 | xxx | xxx |
| 309 | 6.6E−08 | xxx | xxx |
| 310 | 8.06E−07 | xx | xx |
| 311 | 8.41E−08 | xxx | xxx |
| 312 | 1.58E−07 | xxx | xxx |
| 313 | 8.94E−08 | xxx | xxx |
| 314 | 2.78E−08 | xxx | xxx |
| 315 | 4.3E−08 | xxx | xxx |
| 316 | 7.9E−08 | xxx | xxx |
| 317 | 1.81E−07 | xx | xx |
| 318 | 2.63E−08 | xxx | xxx |
| 319 | 3.15E−07 | xx | xx |
| 320 | 1.56E−08 | xxx | xxx |
| 321 | 1.01E−07 | xxx | xxx |
| 322 | 7.62E−08 | xxx | xxx |

TABLE 1-continued

Examples for the biological activity of the compounds according to the invention on the hEP2 receptor ($IC_{50}$ measured by cAMP antagonism test), selectivity towards hDP & $hEP_4$ ($IC_{50}$ measured by cAMP antagonism test): x: 1-10, xx: 10-100, xxx >100:

| Example | Antagonism hEP2 $IC_{50}$ [M] | Selectivity hEP2/hDP | Selectivity hEP2/hEP4 |
|---|---|---|---|
| 323 | 1.28E−07 | xxx | xxx |
| 324 | 4.6E−07 | xx | xx |
| 325 | 3.21E−07 | xx | xx |
| 326 | 4.85E−07 | xx | xx |
| 327 | 1.21E−06 | xx | xx |
| 328 | 2.56E−07 | xx | xx |
| 329 | 2.32E−07 | xx | xx |
| 330 | 9.53E−09 | xxx | xxx |
| 331 | 9.47E−09 | xxx | xxx |
| 332 | 5.47E−09 | xxx | xxx |
| 333 | 6.42E−09 | xxx | xxx |
| 334 | 7.42E−08 | xxx | xxx |
| 335 | 5.09E−09 | xxx | xxx |
| 336 | 5.59E−09 | xxx | xxx |
| 337 | 1.81E−08 | xxx | xxx |
| 338 | 2.8E−08 | xxx | xxx |
| 339 | 7.15E−09 | xxx | xxx |
| 340 | 1.99E−08 | xxx | xxx |
| 341 | 5.53E−08 | xxx | xxx |
| 342 | 1.03E−07 | xxx | xxx |
| 343 | 4.24E−08 | xxx | xxx |
| 344 | 1.03E−08 | xxx | xxx |
| 345 | 6.26E−09 | xxx | xxx |
| 346 | 1.49E−08 | xxx | xxx |
| 347 | 7.88E−09 | xxx | xxx |
| 348 | 8.88E−09 | xxx | xxx |
| 349 | 4.82E−09 | xxx | xxx |
| 350 | 8.41E−09 | xxx | xxx |
| 351 | 6.84E−09 | xxx | xxx |
| 352 | 2.17E−08 | xxx | xxx |
| 353 | 5.02E−08 | xxx | xxx |
| 354 | 5.87E−09 | xxx | xxx |
| 355 | 5.39E−09 | xxx | xxx |
| 356 | 6.36E−08 | xxx | xxx |
| 357 | 7.36E−09 | xxx | xxx |
| 358 | 8.01E−09 | xxx | xxx |
| 359 | 6.99E−09 | xxx | xxx |
| 360 | 6.27E−09 | xxx | xxx |
| 361 | 5.11E−09 | xxx | xxx |
| 362 | 1.51E−08 | xxx | xxx |
| 363 | 5.48E−09 | xxx | xxx |
| 364 | 6.61E−09 | xxx | xxx |
| 365 | 5.3E−09 | xxx | xxx |
| 366 | 1.89E−08 | xxx | xxx |
| 367 | 5.84E−09 | xxx | xxx |
| 368 | 1.2E−08 | xxx | xxx |
| 369 | 5.66E−09 | xxx | xxx |
| 370 | 3.07E−09 | xxx | xxx |
| 371 | 6.11E−09 | xxx | xxx |
| 372 | 7.29E−09 | xxx | xxx |
| 373 | 4.07E−08 | xxx | xxx |
| 374 | 6.58E−09 | xxx | xxx |
| 375 | 5.8E−09 | xxx | xxx |
| 376 | 3.59E−09 | xxx | xxx |
| 377 | 2.73E−08 | xxx | xxx |
| 378 | 7.77E−09 | xxx | xxx |
| 379 | 6.26E−08 | xxx | xxx |
| 380 | 5.35E−09 | xxx | xxx |
| 381 | 5.84E−09 | xxx | xxx |
| 382 | 1.94E−08 | xxx | xxx |
| 383 | 5.78E−09 | xxx | xxx |
| 384 | 3.95E−09 | xxx | xxx |
| 385 | 1.31E−08 | xxx | xxx |
| 386 | 2.57E−08 | xxx | xxx |
| 387 | 1.32E−08 | xxx | xxx |
| 388 | 2.05E−08 | xxx | xxx |
| 389 | 4.51E−09 | xxx | xxx |
| 390 | 3.14E−09 | xxx | xxx |
| 391 | 6.07E−09 | xxx | xxx |
| 392 | 2.18E−08 | xxx | xxx |
| 393 | 5E−08 | xxx | xxx |
| 394 | 5.7E−09 | xxx | xxx |
| 395 | 3.04E−08 | xxx | xxx |
| 396 | 1.8E−08 | xxx | xxx |
| 397 | 1.25E−08 | xxx | xxx |
| 398 | 1.82E−08 | xxx | xxx |
| 399 | 5.93E−07 | xx | xx |
| 400 | 5.61E−08 | xxx | xxx |
| 401 | 1.55E−07 | xxx | xxx |
| 402 | 7.77E−08 | xxx | xxx |
| 403 | 9.59E−09 | xxx | xxx |
| 404 | 2.02E−08 | xxx | xxx |
| 405 | 2.14E−06 | x | x |
| 406 | 8.19E−09 | xxx | xxx |
| 407 | 1.16E−08 | xxx | xxx |
| 408 | 2.35E−08 | xxx | xxx |
| 409 | 3.18E−08 | xxx | xxx |
| 410 | 9.04E−08 | xxx | xxx |
| 411 | 1.65E−08 | xxx | xxx |
| 412 | 6.35E−08 | xxx | xxx |
| 413 | 3.78E−08 | xxx | xxx |
| 414 | 2.23E−07 | xx | xx |
| 415 | 2.13E−08 | xxx | xxx |
| 416 | 1.07E−08 | xxx | xxx |
| 417 | 9.75E−09 | xxx | xxx |
| 418 | 1.58E−08 | xxx | xxx |
| 419 | 1.09E−08 | xxx | xxx |

TABLE 2

Reduction in the cumulus expansion in percent with use of 0.3 µM PGE2 for stimulation, reference 1: example 62 from DE102009049662A1

| Example | % reduction at 1 µM | % reduction at 0.5 µm |
|---|---|---|
| Reference 1* | 79% (*reduction at 10 µM) | |
| Example 5 | 59 | 56 |
| Example 17 | 76 | 71 |
| Example 42 | 79 | 48 |
| Example 117 | 54 | 30 |
| Example 283 | 26 | 25 |
| Example 291 | 73 | 76 |
| Example 303 | 47 | 38 |
| Example 345 | 36 | 18 |

TABLE 3

Terminal half-life ($t_{1/2}$) after intravenous administration in the female rat, reference 1: example 62 from DE102009049662A1

| Example | $t_{1/2}$ [hr] |
|---|---|
| Reference 1 | 0.4 |
| Example 17 | 2.5 |
| Example 42 | 3.2 |
| Example 117 | 2.0 |
| Example 283 | 5.8 |

TABLE 4

Reduction in in-vitro fertilization rate after in-vivo administration of the test substance:

| Example | % fertilization with vehicle | % fertilization with 1 mg/kg | % fertilization with 5 mg/kg | % fertilization with 10 mg/kg |
|---|---|---|---|---|
| Example 17 | 30 ± 9 | 20 ± 10 | 9 ± 1 | 8 ± 4 |

TABLE 5

Reduction in the pregnancy rates in the non-human primate (Cynomolgus)

| Group | Animals per group | Number of "timed matings"* | Pregnancies | % Pregnancies/ "timed mating" |
|---|---|---|---|---|
| Control | 10 | 21 | 8 | 38 |
| Example 17 | 10 | 25 | 3 | 6 |
| Example 56 | 9 | 34 | 2 | 12 |

*Detection of vaginal sperms in the fertile phase of the cycle

6. Effect of a Single Administration of EP2 Receptor Antagonists and COX Inhibitors Alone or in Combination on the Fertility of the Rat The rat is a particularly suitable animal model for demonstrating the effect of substances on fertility, since the cycle can be observed easily by vaginal swabs and mating reliably leads to a high number of offspring.

In the experiments below, female Han Wistar rats having a weight of 200-270 g were used. The animals were kept in Makrolon cages in rooms with controlled lighting (12 hours of darkness; 12 hours of light), fed with a standard diet and provided with water ad libitum.

EP2 receptor antagonists were dissolved in benzyl benzoate/castor oil (1+4 v/v), and the dose was administered in a volume of 1 ml/kg of body weight s.c. Optionally, EP2 receptor antagonists were also administered orally in the same vehicle as the COX inhibitors (see below). Here, the oral administrations were divided to three points in time (12.30, 16.00 and 17.00 hours) (see Table 6.3).

The COX inhibitors were suspended in a carrier liquid (85 mg of Myrj®53 polyoxyl(50)stearate; CAS No. 9004-99-3) in 100 ml of 0.9% w/v NaCl solution), and the dose corresponding to the treatment group was administered in a volume of 2 ml/kg of body weight.

Prior to the start of the experiment, two cycles were observed using vaginal swabs. Only animals having a regular 4-day cycle were used in the experiment. The animals were randomized to the treatment groups.

The animals were treated once in the proestrus, the day in the cycle when the LH peak occurs in the evening, with the test substances either alone or in combination. On the evening of the proestrus, the female animals mated with a male rat. Successive mating was confirmed by detection of vaginal sperms in the vaginal swab the next morning. The effect on fertility was determined 9-15 days after mating by the number of implantation sites of the animals. The group size was n=6 per group.

As can be seen from Tables 6.1-6.6, in these experiments piroxicam, indomethacin and meloxicam in combination with various EP2 receptor antagonists had a strong antifertility effect. In particular, it should be noted that the individual administrations showed no or only a weak effect, whereas the combination showed a markedly increased contraceptive efficacy.

TABLE 6.1

Effect of a single administration of the EP2 receptor antagonist E16: N-(2-methoxyethyl)-4-methyl-2-[(1-{4-[4-(trifluoromethyl)phenoxy]benzoyl}piperidin-4-yl)methyl]-2H-indazole-5-carboxamide (Example 17) or piroxicam alone or in combination on the fertility of the female rat.

| Treatment group | Time of treatment (o'clock) | Absolute implantations number of 6 animals | Implantations per animal (mean ± SD) |
|---|---|---|---|
| Vehicle | 7:00 | 74 | 12.3 ± 0.8 |
| E16 4 mg/animal | 7:00 | 54 | 9.0 ± 3.4 |
| Piroxicam 2 mg/animal | 7:00 | 81 | 13.5 ± 1.0 |
| E16 4 mg/animal + Piroxicam 2 mg/animal | 7:00 | 22 | 3.7 ± 4.3 |
| E16 4 mg/animal | 13:00 | 49* | 8.2 ± 3.1 |
| Piroxicam 2 mg/animal | 13:00 | 68 | 11.3 ± 1.6 |
| E16 4 mg/animal + Piroxicam 2 mg/animal | 13:00 | 8* | 1.4 ± 1.1 |

*Data of n = 5 animals since one animal did not mate (no sperms detected in the vaginal swab)

TABLE 6.2

Effect of a single administration of the EP2 receptor antagonist E161: N-(2-methoxyethyl)-4-methyl-2-{[1-(4-{[5-(trifluoromethyl)pyridin-2-yl]oxy}benzoyl)piperidin-4-yl]methyl}-2H-indazole-5-carboxamide (Example 345) or piroxicam alone or in combination on the fertility of the female rat.

| Treatment group | Time of treatment (o'clock) | Absolute implantations number of 6 animals | Implantations per animal (mean ± SD) |
|---|---|---|---|
| Vehicle | 18:00 | 77 | 12.8 ± 2.2 |
| E161 2 mg/animal | 18:00 | 55 | 9.0 ± 3.4 |
| Piroxicam 2 mg/animal | 18:00 | 53* | 10.6 ± 1.5 |
| E161 2 mg/animal + Piroxicam 2 mg/animal | 18:00 | 24 | 4.0 ± 2.1 |

*Data of n = 5 animals since one animal did not mate (no sperms detected in the vaginal swab)

TABLE 6.3

Effect of an oral administration of EP2 receptor antagonist E16: N-(2-methoxyethyl)-4-methyl-2-[(1-{4-[4-(trifluoromethyl)phenoxy]benzoyl}piperidin-4-yl)methyl]-2H-indazole-5-carboxamide (Example 17) or E161: N-(2-methoxyethyl)-4-methyl-2-{[1-(4-{[5-(trifluoromethyl)pyridin-2-yl]oxy}benzoyl)piperidin-4-yl]methyl}-2H-indazole-5-carboxamide (Example 345) or piroxicam alone or in combination on the fertility of the female rat.

| Treatment group | Time of treatment (o'clock)# | Absolute implantations number of 6 animals | Implantations per animal (mean ± SD) |
|---|---|---|---|
| Vehicle | 12:30; 16:00 and 17:00 | 73 | 12.3 ± 1.2 |
| Piroxicam 2 mg/animal | 12:30 | 71 | 11.8 ± 3.7 |
| E16 2 mg/animal | 16:00 and 17:00 | 63 | 10.5 ± 1.5 |
| E161 2 mg/animal | 16:00 and 17:00 | 69 | 11.5 ± 3.1 |
| E16 2 mg/animal + Piroxicam 2 mg/animal | 12:30; 16:00 and 17:00 | 21 | 3.5 ± 2.9 |
| E161 2 mg/animal + Piroxicam 2 mg/animal | 12:30; 16:00 and 17:00 | 32 | 5.3 ± 4.1 |

Dosage of the EP2 receptor antagonists was divided to two points in time after administration of the COX inhibitor

TABLE 6.4

Effect of a single administration of the EP2 receptor antagonist E16: N-(2-methoxyethyl)-4-methyl-2-[(1-{4-[4-(trifluoromethyl)phenoxy]benzoyl}piperidin-4-yl)methyl]-2H-indazole-5-carboxamide (Example 17) or meloxicam in various dosages alone or in combination on the fertility of the female rat.

| Treatment group | Time of treatment (o'clock)# | Absolute implantations number of 6 animals | Implantations per animal (mean ± SD) |
|---|---|---|---|
| Vehicle | 17:00 | 31*** | 10.3 ± 0.6 |
| Meloxicam 0.25 mg/animal | 17:00 | 32* | 6.4 ± 5.9 |
| Meloxicam 0.5 mg/animal | 17:00 | 70 | 11.7 ± 6.4 |
| Meloxicam 1 mg/animal | 17:00 | 66 | 11 ± 5.5 |
| Meloxicam 2 mg/animal | 17:00 | 54* | 10.8 ± 4.4 |
| E16 4 mg/animal | 17:00 | 22** | 5.5 ± 5.4 |
| E16 4 mg/animal + Meloxicam 0.25 mg/animal | 17:00 | 31* | 6.2 ± 6.3 |
| E16 4 mg/animal + Meloxicam 0.5 mg/animal | 17:00 | 15*** | 5.0 ± 1.7 |
| E16 4 mg/animal + Meloxicam 1 mg/animal | 17:00 | 11* | 2.2 ± 3.3 |
| E16 4 mg/animal + Meloxicam 2 mg/animal | 17:00 | 7** | 1.8 ± 2.4 |

*Data of n = 5 animals since one animal did not mate (no sperms detected in the vaginal swab)
**Data of n = 4 animals since two animals did not mate (no sperms detected in the vaginal swab)
***Data of n = 3 animals since three animals did not mate (no sperms detected in the vaginal swab)

TABLE 6.5

Effect of a single dose-dependent administration of the EP2 receptor antagonist E16: N-(2-methoxyethyl)-4-methyl-2-[(1-{4-[4-(trifluoromethyl)phenoxy]benzoyl}piperidin-4-yl)methyl]-2H-indazole-5-carboxamide (Example 17) or meloxicam alone or in combination on the fertility of the female rat.

| Treatment group | Time of treatment (o'clock)# | Absolute implantations number of 6 animals | Implantations per animal (mean ± SD) |
|---|---|---|---|
| Vehicle | 17:00 | 61* | 12.2 ± 1.9 |
| E16 0.25 mg/animal | 17:00 | 78 | 13 ± 2.3 |
| E16 0.5 mg/animal | 17:00 | 60 | 10 ± 2.8 |
| E16 1 mg/animal | 17:00 | 42 | 7 ± 5.4 |
| E16 2 mg/animal | 17:00 | 30** | 7.5 ± 1.7 |
| E16 4 mg/animal | 17:00 | 32 | 5.3 ± 4.5 |
| Meloxicam 2 mg/animal | 17:00 | 63* | 12.6 ± 3.4 |
| E16 0.25 mg/animal + Meloxicam 2 mg/animal | 17:00 | 52 | 8.7 ± 2.5 |
| E16 0.5 mg/animal + Meloxicam 2 mg/animal | 17:00 | 36 | 6.0 ± 4.3 |
| E16 1 mg/animal + Meloxicam 2 mg/animal | 17:00 | 35 | 5.8 ± 3.4 |
| E16 2 mg/animal + Meloxicam 2 mg/animal | 17:00 | 19 | 3.2 ± 2.8 |
| E16 4 mg/animal + Meloxicam 2 mg/animal | 17:00 | 11*** | 3.7 ± 4.7 |

*Data of n = 5 animals since one animal did not mate (no sperms detected in the vaginal swab)
**Data of n = 4 animals since two animals did not mate (no sperms detected in the vaginal swab)
***Data of n = 3 animals since three animals did not mate (no sperms detected in the vaginal swab)

TABLE 6.6

Effect of a single dose-dependent administration of the EP2 receptor antagonist E16: N-(2-methoxyethyl)-4-methyl-2-[(1-{4-[4-(trifluoromethyl)phenoxy]benzoyl}piperidin-4-yl)methyl]-2H-indazole-5-carboxamide (Example 17) or indomethacin alone or in combination on the fertility of the female rat.

| Treatment group | Time of treatment (o'clock)# | Absolute implantations number of 6 animals | Implantations per animal (mean ± SD) |
|---|---|---|---|
| Vehicle | 16:00 | 67 | 11.2 ± 2.6 |
| E16 1 mg/animal | 16:00 | 62 | 10.3 ± 2.5 |
| E16 2 mg/animal | 16:00 | 71 | 11.8 ± 2.1 |
| E16 4 mg/animal | 16:00 | 50 | 8.3 ± 3.4 |
| E16 8 mg/animal | 16:00 | 43* | 8.6 ± 2.8 |
| Indomethacin 1 mg/animal | 16:00 | 67 | 11.2 ± 2.9 |
| E16 1 mg/animal + Indomethacin 1 mg/animal | 16:00 | 58 | 9.7 ± 1.9 |
| E16 2 mg/animal + Indomethacin 1 mg/animal | 16:00 | 38 | 6.3 ± 3.7 |
| E16 4 mg/animal + Indomethacin 1 mg/animal | 16:00 | 27 | 4.5 ± 1.6 |
| E16 8 mg/animal + Indomethacin 1 mg/animal | 16:00 | 26 | 4.3 ± 1.9 |

*Data of n = 5 animals since one animal did not mate (no sperms detected in the vaginal swab)

7. In-Vivo Effect on Postovulatory In-Vitro Fertilization in the Mouse

Substances can influence fertility by lowering fertilizability of oocytes or cumulus-oocyte complexes. To examine such effects, substances can be administered in vivo and, after ovulation of cumulus-oocyte complexes, the latter are subjected to in-vitro fertilization. The in-vitro fertilization rate in the absence of test substance allows conclusions to be drawn on the in-vivo effects of the test substances.

Immature female mice (strain: B6D2F1, Charles River, Suelzfeld, age: 19-25 days) were kept in Makrolon cages in rooms with controlled lighting (12 hours of darkness: 12 hours of light), fed with a standard diet and provided with water ad libitum.

The mice were primed with PMSG (Pregnant Mare Serum Gonadotropin) (10 IU/animal i.p.). After 48 hours, by administration of 10 IU/animal i.p., an ovulation-triggering stimulus (hCG, human Chorion Gonadotropin) was generated in the animals. EP2 receptor antagonists were dissolved in benzyl benzoate/castor oil (1+4 v/v) and administered in a volume of 0.1 ml s.c. 1 hour prior to hCG (n=5 animals per group). The COX inhibitor was suspended in a carrier liquid (85 mg of Myrj®53 polyoxyl(50)stearate; CAS No. 9004-99-3) in 100 ml of 0.9% w/v NaCl solution), and the appropriate dose was administered in a volume of 2 ml/kg of body weight orally 1 hour prior to hCG. Fourteen hours after administration of hCG, the animals were sacrificed. Ovulated oocytes and cumulus-oocyte complexes were obtained from the ovarii bursa and/or the oviduct and subjected to in-vitro fertilization, with a sperm number of 40 000 sperms/0.5 ml for 1 hour being used for fertilization. Twenty-four hours after incubation with the sperms, the number of fertilized oocytes and the number of 2-cell embryos per animal were determined.

TABLE 7.1

The results in this table show that the EP2 receptor antagonist according to the invention E126: 4-methyl-N-(2,2,2-trifluoroethyl)-2-[(1-{4-[4-(trifluoromethyl)phenoxy]benzoyl}piperidin-4-yl)methyl]-2H-indazole-5-carboxamide (Example 291) has a dose-dependent effect on the number of 2-cell embryos per animal.

| Treatment group | 2-Cell embryos per animal (mean ± SD) |
| --- | --- |
| Vehicle* | 36.3 ± 9.5 |
| Piroxicam 0.1 mg/animal | 10.8 ± 3.8 |
| E126 0.1 mg/animal | 30.8 ± 7.3 |
| Piroxicam 0.1 mg/animal + E126 0.1 mg/animal | 6.2 ± 4.5 |
| E126 0.5 mg/animal | 12.6 ± 3.6 |
| Piroxicam 0.1 mg/animal + E126 0.5 mg/animal* | 3.3 ± 2.1 |

*Data of n = 4 animals since there was no follicle maturation

Preparation Example 1

Combination tablets comprising 60 mg of piroxicam and 600 mg of N-(2-methoxyethyl)-4-methyl-2-[(1-{4-[4-(trifluoromethyl)phenoxy]benzoyl}piperidin-4-yl)methyl]-2H-indazole-5-carboxamide (E16)

In a fluidized-bed granulator, 1667 g of E16, 167 g of piroxicam, 444 g of microcrystalline cellulose and 125 g of croscarmellose sodium are initially charged. This powder mixture is granulated using a granulation liquid consisting of 75 g of hydroxypropylmethylcellulose 5 cP, 2.5 g of sodium lauryl sulphate and 1800 g of water. The granules are dried in the fluidized-bed granulator and then sieved and subsequently mixed with 20 g of magnesium stearate for 5 minutes. The powder mixture is then compressed on a rotary tablet press to oval tablets having a mass of 900 mg, a length of 18 mm and a width of 8 mm. The tablets are then coated with a dispersion of 55.6 g of ready-to-use film powder and 315 g of water. The ready-to-use film powder consists of 50.56% hypromellose 5 cP, 10.12% Macrogol 3350, 10.12% talc, 23.20% titanium dioxide and 6.00% yellow iron oxide.

Combination tablets comprising other EP2 receptor antagonists according to the invention and COX inhibitors can be prepared analogously. For alternative doses, the ratios can be adapted appropriately.

Alternatively, it is posible to formulate the EP2 receptor antagonist and COX inhibitor separately in separate tablets.

Preparation Example 2

Kit comprising 2 combination tablets comprising 60 mg of piroxicam and 600 mg of N-(2-methoxyethyl)-4-methyl-2-[(1-{4-[4-(trifluoromethyl)phenoxy]benzoyl}piperidin-4-yl)methyl]-2H-indazole-5-carboxamide (E16)

A folded box is manufactured which contains 3×2 combination tablets according to Preparation Example 1 and can thus be used for three expected sexual intercourses. The composition of the combination tablets is identical. The folded box furthermore contains a package insert which describes that the woman has to take one tablet orally 6 to 12 hours before sexual intercourse and a further tablet within 24 hours after sexual intercourse. Furthermore, the package insert indicates that intake of the second tablet can be dispensed with if there has been no sexual intercourse. If there has been no sexual intercourse after two administrations, the two tablets not used because of this may be used for a further administration.

The invention claimed is:

1. A pharmaceutical composition comprising (a) at least one EP2 receptor antagonist according to formula (I)

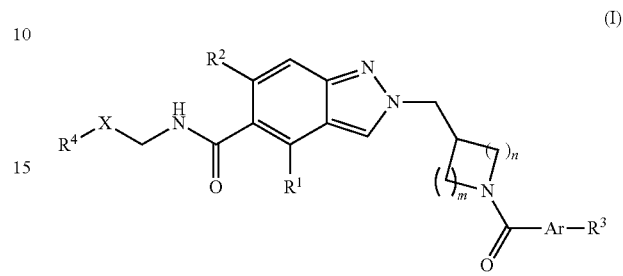

wherein
R$^1$ is H, C$_1$-C$_2$ alkyl or C$_1$-C$_2$ alkyloxy;
R$^2$ is H or methyl;
  subject to the proviso that one of R$^1$ or R$^2$ equals H;
X is —(CH$_2$)$_l$—, —(CH$_2$)$_k$—O—, —CH$_2$—S—, CH$_2$—S(O)$_2$—, —CH(CH$_3$)—, —CH(CH$_3$)—O— or —C(CH$_3$)$_2$—O—, wherein k is 1 or 2 and l is 0, 1 or 2;
R$^4$ is H, C$_1$-C$_4$ alkyl, C$_3$-C$_4$ cycloalkyl or CH$_2$-C$_3$-C$_4$ cycloalkyl and in the case that X is —(CH$_2$)$_l$— where is 0 or 1, or —CH(CH$_3$)—; R$^4$ additionally is a 4-6-membered heterocyclyl residue; and in the case that X is —(CH$_2$)$_l$— or —CH(CH$_3$)—; R$^4$ additionally means CN;
m is 1 or 2;
n is 1 or 2;
Ar is a 6-10-membered aryl or 5-10-membered hetaryl residue,
R$^3$ is halogen, CN, SF$_5$, C$_1$-C$_4$ alkyl, C$_3$-C$_6$ cycloalkyl, C$_4$-C$_6$ heterocyclyl, O—C$_1$-C$_4$ alkyl, O—C$_3$-C$_6$ cycloalkyl, O—C$_4$-C$_6$ heterocyclyl, S—C$_1$-C$_4$ alkyl, S(O)$_2$—C$_1$-C$_4$ alkyl, Ar', O—Ar', C(CH$_3$)$_2$—CN or C(CH$_3$)$_2$—OH; and
Ar' is an optionally singly or doubly substituted 6-membered aryl or 5-6-membered heteroaryl residue;
  wherein the substituents are selected from F, Cl, CN, C$_1$-C$_4$ alkyl, O—C$_1$-C$_4$ alkyl, C(CH$_3$)$_2$—CN, C(CH$_3$)$_2$—OH and C(O)NH$_2$;
wherein C$_1$-C$_2$ alkyl or C$_1$-C$_4$ alkyl is optionally singly or multiply substituted with fluorine;
and at least one COX inhibitor selected from a group consisting of:
  C1 indomethacin;
  C2 diclofenac;
  C4 naproxen;
  C5 ibuprofen;
  C6 meloxicam;
  C7 piroxicam;
  C8 nimesulide;
  C9 ketoprofen;
  C10 tenoxicam;
  C11 mefanemic acid;
  C12 ketorolac;
  C13 celecoxib (4-[5-(4-methylphenyl)-3-(trifluoromethyl)-1H-pyrazol-1-yl]benzenesulphonamide);
  C14 parecoxib(N-[4-(5-methyl-3-phenyl-4-isoxazolyl)phenyl]sulphonylpropionamide);

C15 rofecoxib (4-(4-mesylphenyl)-3-phenylfuran-2(5H)-one);
C16 valdecoxib (4-[5-methyl-3-phenyl-4-isoxazoyl)benzenesulphonamide); and
C17 etoricoxib
for on-demand contraception.

2. A pharmaceutical composition comprising (a) at least one EP2 receptor antagonist according to formula (Ia)

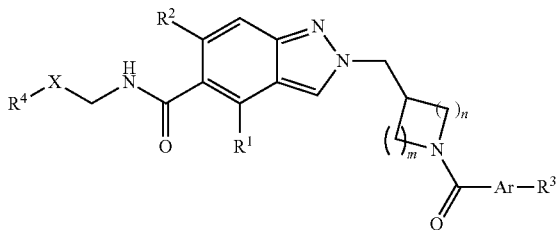

(Ia)

wherein
$R^1$, $R^2$ is H or methyl; subject to the proviso that one of $R^1$ or $R^2$ equals H;
X is —$(CH_2)_l$— or —$(CH_2)_k$—O—;
k is 1 or 2;
l is 0, 1 or 2;
$R^4$ is H, $C_1$-$C_4$ alkyl, $C_3$-$C_4$ cycloalkyl or $CH_2$—$C_3$-$C_4$ cycloalkyl;
m is 1 or 2;
n is 1 or 2;
Ar is a 6-10-membered aryl or 5-10-membered hetaryl residue,
$R^3$ is a halogen, CN, $SF_5$, $C_1$-$C_4$ alkyl, $C_3$-$C_6$ cycloalkyl, $C_4$-$C_6$ heterocyclyl, O—$C_1$-$C_4$ alkyl, O—$C_3$-$C_6$ cycloalkyl, O—$C_4$-$C_6$ heterocyclyl, S—$C_1$-$C_4$ alkyl, $S(O)_2$—$C_1$-$C_4$ alkyl, Ar', O—Ar', $C(CH_3)_2$—CN or $C(CH_3)_2$—OH; and
Ar' is an optionally singly or doubly substituted 6-membered aryl or 5-6-membered heteroaryl residue; wherein the substituents are selected from F, Cl, CN, $C_1$-$C_4$ alkyl, O—$C_1$-$C_4$ alkyl, $C(CH_3)_2$—CN, $C(CH_3)_2$—OH and $C(O)NH_2$;
wherein $C_1$-$C_2$ alkyl or $C_1$-$C_4$ alkyl is optionally singly or multiply substituted with fluorine,
and an isomer, diastereomer, enantiomer, salt or cyclodextrin clathrates thereof and
(b) at least one COX inhibitor selected from the list consisting essentially of:
C1 indomethacin;
C2 diclofenac;
C4 naproxen;
C5 ibuprofen;
C6 meloxicam;
C7 piroxicam;
C8 nimesulide;
C9 ketoprofen;
C10 tenoxicam;
C11 mefanemic acid;
C12 ketoralac;
C13 celecoxib (4-[5-(4-methylphenyl)-3-(trifluoromethyl)-1H-pyrazol-1-yl]benzenesulphonamide);
C14 parecoxib (N-[4-(5-methyl-3-phenyl-4-isoxazolyl) phenyl]sulphonylpropionamide);
C15 rofecoxib (4-(4-mesylphenyl)-3-phenylfuran-2(5H)-one);
C16 valdecoxib (4-[5-methyl-3-phenyl-4-isoxazoyl)benzenesulphonamide); and
C17 etoricoxib
as active compounds and at least one pharmaceutically acceptable carrier.

3. The pharmaceutical composition of claim 2, wherein
$R^1$ is a methyl group;
$R^2$ is H;
X is —$(CH_2)_l$— or —$(CH_2)_k$—O—;
k is 1;
l is 0 or 1;
$R^4$ is $C_1$-$C_4$ alkyl, $C_3$-$C_4$ cycloalkyl or $CH_2$—$C_3$-$C_4$ cycloalkyl;
m, n is 1; and
Ar is a phenyl residue;
or and isomer$_s$, diastereomer$_s$, enantiomer$_s$ salts or a cyclodextrin clathrate thereof and $R^3$ and Ar' have the meanings stated in claim 2.

4. The pharmaceutical composition of claim 2, wherein
$R^1$ is a methyl group;
$R^2$ is H;
X is —$(CH_2)_l$— or —$(CH_2)_k$—O—;
k is 1;
l is 0 or 1;
$R^4$ is $C_1$-$C_4$ alkyl, $C_3$-$C_4$ cycloalkyl or $CH_2$—$C_3$-$C_4$ cycloalkyl;
m, n is 2; and
Ar is a phenyl residue;
or diastereomer, an enantiomer, and salt or a cyclodextrin clathrate thereof and $R^3$ and Ar' have the meanings stated in claim 2.

5. The pharmaceutical composition according to claim 3 or 4, wherein the EP2 receptor antagonist is selected from the group consisting of:
E1  2-{[1-(4-cyano-2-fluorobenzoyl)piperidin-4-yl]methyl}-N-(2-methoxyethyl)-4-methyl-2H-indazole-5-carboxamide;
E2  2-{[1-(4-tert-butoxybenzoyl)piperidin-4-yl]methyl}-N-(2-methoxyethyl)-4-methyl-2H-indazole-5-carboxamide;
E3  2-({1-[4-(4-fluorophenoxy)benzoyl]piperidin-4-yl}methyl)-N-(2-methoxyethyl)-4-methyl-2H-indazole-5-carboxamide;
E4  N-(2-methoxyethyl)-4-methyl-2-{[1-(4-morpholinobenzoyl)piperidin-4-yl]methyl}-2H-indazole-5-carboxamide;
E5  2-({1-[(4'-fluorobiphenyl-4-yl)carbonyl]piperidin-4-yl}methyl)-N-(2-methoxyethyl)-4-methyl-2H-indazole-5-carboxamide;
E6  2-{[1-(2-fluoro-4-mesylbenzoyl)piperidin-4-yl]methyl}-N-(2-methoxyethyl)-4-methyl-2H-indazole-5-carboxamide;
E7  2-{[1-(2-fluoro-4-methoxybenzoyl)piperidin-4-yl]methyl}-N-(2-methoxyethyl)-4-methyl-2H-indazole-5-carboxamide;
E8  2-{[1-(4-bromo-2-fluorobenzoyl)piperidin-4-yl]methyl}-N-(2-methoxyethyl)-4-methyl-2H-indazole-5-carboxamide;
E9  2-{[1-(2-fluoro-4-methylbenzoyl)piperidin-4-yl]methyl}-N-(2-methoxyethyl)-4-methyl-2H-indazole-5-carboxamide;
E10  2-({1-[2-fluoro-4-(trifluoromethyl)benzoyl]piperidin-4-yl}methyl)-N-(2-methoxyethyl)-4-methyl-2H-indazole-5-carboxamide;
E11  N-(2-methoxyethyl)-4-methyl-2-({1-[4-(pentafluoro-$\lambda^6$-sulphanyl)benzoyl]piperidin-4-yl}methyl)-2H-indazole-5-carboxamide;

E12 N-(2-methoxyethyl)-4-methyl-2-{[1-(4-methylbenzoyl)piperidin-4-yl]methyl}-2H-indazole-5-carboxamide;

E13 2-({1-[4-(4-chlorophenoxy)benzoyl]piperidin-4-yl}methyl)-N-(2-methoxyethyl)-4-methyl-2H-indazole-5-carboxamide;

E14 N-(2-methoxyethyl)-4-methyl-2-({1-[4-(4-methylphenoxy)benzoyl]piperidin-4-yl}methyl)-2H-indazole-5-carboxamide;

E15 2-({1-[4-(4-tert-butylphenoxy)benzoyl]piperidin-4-yl}methyl)-N-(2-methoxyethyl)-4-methyl-2H-indazole-5-carboxamide;

E16 N-(2-methoxyethyl)-4-methyl-2-[(1-{4-[4-(trifluoromethyl)phenoxy]benzoyl}piperidin-4-yl)methyl]-2H-indazole-5-carboxamide;

E17 N-(2-methoxyethyl)-2-({1-[4-(4-methoxyphenoxy)benzoyl]piperidin-4-yl}methyl)-4-methyl-2H-indazole-5-carboxamide;

E18 N-(2-methoxyethyl)-4-methyl-2-{[1-(4-phenoxybenzoyl)piperidin-4-yl]methyl}-2H-indazole-5-carboxamide;

E19 2-{[1-(4-cyclopropylbenzoyl)piperidin-4-yl]methyl}-N-(2-methoxyethyl)-4-methyl-2H-indazole-5-carboxamide;

E20 2-{[1-(4-methoxybenzoyl)piperidin-4-yl]methyl}-N-(2-methoxyethyl)-4-methyl-2H-indazole-5-carboxamide;

E21 2-{[1-(4-fluorobenzoyl)piperidin-4-yl]methyl}-N-(2-methoxyethyl)-4-methyl-2H-indazole-5-carboxamide;

E22 N-(2-methoxyethyl)-4-methyl-2-({1-[4-(trifluoromethyl)benzoyl]piperidin-4-yl}methyl)-2H-indazole-5-carboxamide;

E23 2-{[1-(2-methoxybenzoyl)piperidin-4-yl]methyl}-N-(2-methoxyethyl)-4-methyl-2H-indazole-5-carboxamide;

E24 N-(2-methoxyethyl)-4-methyl-2-[(1-{4-[(trifluoromethyl)sulphonyl]benzoyl}piperidin-4-yl)methyl]-2H-indazole-5-carboxamide;

E25 N-(2-methoxyethyl)-4-methyl-2-({1-[3-(trifluoromethyl)benzoyl]piperidin-4-yl}methyl)-2H-indazole-5-carboxamide;

E26 N-(2-methoxyethyl)-4-methyl-2-{[1-(3-methylbenzoyl)piperidin-4-yl]methyl}-2H-indazole-5-carboxamide;

E27 2-{[1-(3-chlorobenzoyl)piperidin-4-yl]methyl}-N-(2-methoxyethyl)-4-methyl-2H-indazole-5-carboxamide;

E28 2-({1-[4-(4-carbamoylphenoxy)benzoyl]piperidin-4-yl}methyl)-N-(2-methoxyethyl)-4-methyl-2H-indazole-5-carboxamide;

E29 2-({1-[4-(cyclopentyloxy)benzoyl]piperidin-4-yl}methyl)-N-(2-methoxyethyl)-4-methyl-2H-indazole-5-carboxamide;

E30 2-({1-[4-(difluoromethyl)benzoyl]piperidin-4-yl}methyl)-N-(2-methoxyethyl)-4-methyl-2H-indazole-5-carboxamide;

E31 2-{[1-(4-cyanobenzoyl)piperidin-4-yl]methyl}-N-(2-methoxyethyl)-4-methyl-2H-indazole-5-carboxamide;

E32 2-({1-[4-(1H-imidazol-1-yl)benzoyl]piperidin-4-yl}methyl)-N-(2-methoxyethyl)-4-methyl-2H-indazole-5-carboxamide;

E33 N-(2-methoxyethyl)-4-methyl-2-({1-[4-(oxazol-2-yl)benzoyl]piperidin-4-yl}methyl)-2H-indazole-5-carboxamide;

E34 N-(2-methoxyethyl)-4-methyl-2-({1-[4-(oxazol-5-yl)benzoyl]piperidin-4-yl}methyl)-2H-indazole-5-carboxamide;

E35 N-(2-methoxyethyl)-4-methyl-2-({1-[4-(isoxazol-5-yl)benzoyl]piperidin-4-yl}methyl)-2H-indazole-5-carboxamide;

E36 N-(2-methoxyethyl)-4-methyl-2-({1-[4-(1H-pyrazol-1-yl)benzoyl]piperidin-4-yl}methyl)-2H-indazole-5-carboxamide;

E37 N-(2-methoxyethyl)-4-methyl-2-({1-[4-(1H-1,2,4-triazol-1-yl)benzoyl]piperidin-4-yl}-methyl)-2H-indazole-5-carboxamide;

E38 2-({1-[4-(difluoromethoxy)-2-fluorobenzoyl]piperidin-4-yl}methyl)-N-(2-methoxyethyl)-4-methyl-2H-indazole-5-carboxamide;

E39 2-({1-[2-fluoro-4-(pyrrolidin-1-yl)benzoyl]piperidin-4-yl}methyl)-N-(2-methoxyethyl)-4-methyl-2H-indazole-5-carboxamide;

E40 2-({1-[(3,4'-difluorobiphenyl-4-yl)carbonyl]piperidin-4-yl}methyl)-N-(2-methoxyethyl)-4-methyl-2H-indazole-5-carboxamide;

E41 2-({1-[(3-fluoro-4'-methoxybiphenyl-4-yl)carbonyl]piperidin-4-yl}methyl)-N-(2-methoxyethyl)-4-methyl-2H-indazole-5-carboxamide;

E42 2-({1-[(3-fluoro-4'-methylbiphenyl-4-yl)carbonyl]piperidin-4-yl}methyl)-N-(2-methoxy-ethyl)-4-methyl-2H-indazole-5-carboxamide;

E43 2-[(1-{[3-fluoro-3'-(trifluoromethyl)biphenyl-4-yl]carbonyl}piperidin-4-yl)methyl]-N-(2-methoxyethyl)-4-methyl-2H-indazole-5-carboxamide;

E44 2-[(1-{[3-fluoro-2'-(trifluoromethoxy)biphenyl-4-yl]carbonyl}piperidin-4-yl)methyl]-N-(2-methoxyethyl)-4-methyl-2H-indazole-5-carboxamide;

E45 2-({1-[(2'-fluorobiphenyl-4-yl)carbonyl]piperidin-4-yl}methyl)-N-(2-methoxyethyl)-4-methyl-2H-indazole-5-carboxamide;

E46 2-({1-[(2',4'-difluorobiphenyl-4-yl)carbonyl]piperidin-4-yl}methyl)-N-(2-methoxyethyl)-4-methyl-2H-indazole-5-carboxamide;

E47 2-({1-[(2-fluorobiphenyl-4-yl)carbonyl]piperidin-4-yl}methyl)-N-(2-methoxyethyl)-4-methyl-2H-indazole-5-carboxamide;

E48 N-(2-methoxyethyl)-4-methyl-2-({1-[(2'-methylbiphenyl-4-yl)carbonyl]piperidin-4-yl}-methyl)-2H-indazole-5-carboxamide;

E49 N-(2-methoxyethyl)-4-methyl-2-({1-[4-(4-pyridyloxy)benzoyl]piperidin-4-yl}methyl)-2H-indazole-5-carboxamide;

E50 N-(2-methoxyethyl)-4-methyl-2-({1-[4-(4H-1,2,4-triazol-4-yl)benzoyl]piperidin-4-yl}-methyl)-2H-indazole-5-carboxamide;

E51 2-({1-[2-fluoro-4-(morpholin-4-yl)benzoyl]piperidin-4-yl}methyl)-N-(2-methoxyethyl)-4-methyl-2H-indazole-5-carboxamide;

E52 2-{[1-(4-bromobenzoyl)piperidin-4-yl]methyl}-N-(2-methoxyethyl)-4-methyl-2H-indazole-5-carboxamide;

E53 N-(2-methoxyethyl)-4-methyl-2-({1-[4-(trifluoromethoxy)benzoyl]piperidin-4-yl}-methyl)-2H-indazole-5-carboxamide;

E54 2-{[1-(4-chlorobenzoyl)piperidin-4-yl]methyl}-N-(2-methoxyethyl)-4-methyl-2H-indazole-5-carboxamide;

E55 N-(2-methoxyethyl)-4-methyl-2-[(1-{4-[(trifluoromethyl)sulphanyl]benzoyl}piperidin-4-yl)methyl]-2H-indazole-5-carboxamide;

E56 4-methyl-2-({1-[4-(pentafluoro-$\lambda^6$-sulphanyl)benzoyl]piperidin-4-yl}methyl)-N-(2,2,2-trifluoroethyl)-2H-indazole-5-carboxamide;

E57 2-{[1-(4-chlorobenzoyl)piperidin-4-yl]methyl}-4-methyl-N-(2,2,2-trifluoroethyl)-2H-indazole-5-carboxamide;

E58 4-methyl-N-(2,2,2-trifluoroethyl)-2-({1-[4-(trifluoromethoxy)benzoyl]piperidin-4-yl}methyl)-2H-indazole-5-carboxamide;

E59 2-{[1-(4-chlorobenzoyl)piperidin-4-yl]methyl}-N-[2-(cyclopropylmethoxy)ethyl]-4-methyl-2H-indazole-5-carboxamide;

E60 N-[2-(cyclopropylmethoxy)ethyl]-4-methyl-2-{[1-(4-methylbenzoyl)piperidin-4-yl]-methyl}-2H-indazole-5-carboxamide;

E61 N-[2-(cyclopropylmethoxy)ethyl]-2-({1-[4-(4-fluorophenoxy)benzoyl]piperidin-4-yl]-methyl)-4-methyl-2H-indazole-5-carboxamide;

E62 N-[2-(cyclopropylmethoxy)ethyl]-4-methyl-2-({1-[4-(trifluoromethyl)benzoyl]piperidin-4-yl}methyl)-2H-indazole-5-carboxamide;

E63 N-[2-(cyclopropylmethoxy)ethyl]-2-({1-[(4'-fluorobiphenyl-4-yl)carbonyl]piperidin-4-yl}methyl)-4-methyl-2H-indazole-5-carboxamide;

E64 2-{[1-(4-cyclopropylbenzoyl)piperidin-4-yl]methyl}-N-[2-(cyclopropylmethoxy)ethyl]-4-methyl-2H-indazole-5-carboxamide;

E65 2-{[1-(4-chlorobenzoyl)piperidin-4-yl]methyl}-4-methyl-N-[2-(2,2,2-trifluoroethoxy)-ethyl]-2H-indazole-5-carboxamide;

E66 4-methyl-2-{[1-(4-methylbenzoyl)piperidin-4-yl]methyl}-N-[2-(2,2,2-trifluoroethoxy)-ethyl]-2H-indazole-5-carboxamide;

E67 2-({1-[4-(4-fluorophenoxy)benzoyl]piperidin-4-yl}methyl)-4-methyl-N-[2-(2,2,2-trifluoroethoxy)ethyl]-2H-indazole-5-carboxamide;

E68 4-methyl-N-[2-(2,2,2-trifluoroethoxy)ethyl]-2-({1-[4-(trifluoromethyl)benzoyl]piperidin-4-yl}methyl)-2H-indazole-5-carboxamide;

E69 2-({1-[(4'-fluorobiphenyl-4-yl)carbonyl]piperidin-4-yl}methyl)-4-methyl-N-[2-(2,2,2-trifluoroethoxy)ethyl]-2H-indazole-5-carboxamide;

E70 2-{[1-(4-cyclopropylbenzoyl)piperidin-4-yl]methyl}-4-methyl-N-[2-(2,2,2-trifluoro-ethoxy)ethyl]-2H-indazole-5-carboxamide;

E71 2-{[1-(4-chlorobenzoyl)piperidin-4-yl]methyl}-N-(2-isopropoxyethyl)-4-methyl-2H-indazole-5-carboxamide;

E72 N-(2-isopropoxyethyl)-4-methyl-2-{[1-(4-methylbenzoyl)piperidin-4-yl]methyl}-2H-indazole-5-carboxamide;

E73 2-({1-[4-(4-fluorophenoxy)benzoyl]piperidin-4-yl}methyl)-N-(2-isopropoxyethyl)-4-methyl-2H-indazole-5-carboxamide;

E74 N-(2-isopropoxyethyl)-4-methyl-2-({1-[4-(trifluoromethyl)benzoyl]piperidin-4-yl}-methyl)-2H-indazole-5-carboxamide;

E75 2-({1-[(4'-fluorobiphenyl-4-yl)carbonyl]piperidin-4-yl}methyl)-N-(2-isopropoxyethyl)-4-methyl-2H-indazole-5-carboxamide;

E76 2-{[1-(4-cyclopropylbenzoyl)piperidin-4-yl]methyl}-N-(2-isopropoxyethyl)-4-methyl-2H-indazole-5-carboxamide;

E77 2-{[1-(4-chlorobenzoyl)piperidin-4-yl]methyl}-4-methyl-N-[2-(trifluoromethoxy)ethyl]-2H-indazole-5-carboxamide;

E78 2-({1-[4-(4-fluorophenoxy)benzoyl]piperidin-4-yl}methyl)-4-methyl-N-[2-(trifluoro-methoxy)ethyl]-2H-indazole-5-carboxamide;

E79 2-({1-[(4'-fluorobiphenyl-4-yl)carbonyl]piperidin-4-yl}methyl)-4-methyl-N-[2-(trifluoro-methoxy)ethyl]-2H-indazole-5-carboxamide;

E80 4-methyl-N-[2-(trifluoromethoxy)ethyl]-2-[(1-{4-[4-(trifluoromethyl)phenoxy]benzoyl}-piperidin-4-yl)methyl]-2H-indazole-5-carboxamide;

E81 N-(2-tert-butoxyethyl)-2-{[1-(4-chlorobenzoyl)piperidin-4-yl]methyl}-4-methyl-2H-indazole-5-carboxamide;

E82 N-(2-tert-butoxyethyl)-2-({1-[4-(4-fluorophenoxy)benzoyl]piperidin-4-yl}methyl)-4-methyl-2H-indazole-5-carboxamide;

E83 N-(2-tert-butoxyethyl)-2-({1-[(4'-fluorobiphenyl-4-yl)carbonyl]piperidin-4-yl}methyl)-4-methyl-2H-indazole-5-carboxamide;

E84 N-(2-tert-butoxyethyl)-4-methyl-2-[(1-{4-[4-(trifluoromethyl)phenoxy]benzoyl}-piperidin-4-yl)methyl]-2H-indazole-5-carboxamide;

E85 2-{[1-(4-chlorobenzoyl)piperidin-4-yl]methyl}-4-methyl-N-{2-[($^2$H3)methyloxy]-($^2$H4)ethyl}-2H-indazole-5-carboxamide;

E86 2-({1-[4-(4-fluorophenoxy)benzoyl]piperidin-4-yl}methyl)-4-methyl-N-{2-[($^2$H3)methyloxy]($^2$H4)ethyl}-2H-indazole-5-carboxamide;

E87 2-{[1-(4-chlorobenzoyl)azetidin-3-yl]methyl}-N-(2-methoxyethyl)-4-methyl-2H-indazole-5-carboxamide;

E88 N-(2-methoxyethyl)-4-methyl-2-[(1-{4-[(trifluoromethyl)sulphanyl]benzoyl}azetidin-3-yl)methyl]-2H-indazole-5-carboxamide;

E89 N-(2-methoxyethyl)-4-methyl-2-({1-[4-(trifluoromethoxy)benzoyl]azetidin-3-yl}methyl)-2H-indazole-5-carboxamide;

E90 2-({1-[2-fluoro-4-(trifluoromethyl)benzoyl]azetidin-3-yl}methyl)-N-(2-methoxyethyl)-4-methyl-2H-indazole-5-carboxamide;

E91 2-{[1-(4-chloro-2-fluorobenzoyl)azetidin-3-yl]methyl}-N-(2-methoxyethyl)-4-methyl-2H-indazole-5-carboxamide;

E92 2-({1-[3-fluoro-4-(trifluoromethyl)benzoyl]azetidin-3-yl}methyl)-N-(2-methoxyethyl)-4-methyl-2H-indazole-5-carboxamide;

E93 2-({1-[4-chloro-3-(trifluoromethyl)benzoyl]azetidin-3-yl}methyl)-N-(2-methoxyethyl)-4-methyl-2H-indazole-5-carboxamide;

E94 2-{[1-(4-cyclopropylbenzoyl)azetidin-3-yl]methyl}-N-(2-methoxyethyl)-4-methyl-2H-indazole-5-carboxamide;

E95 N-(2-methoxyethyl)-4-methyl-2-[(1-{4-[4-(trifluoromethyl)phenoxy]benzoyl}azetidin-3-yl)methyl]-2H-indazole-5-carboxamide;

E96 2-{[1-(4-chlorobenzoyl)azetidin-3-yl]methyl}-4-methyl-N-(2,2,2-trifluoroethyl)-2H-indazole-5-carboxamide;

E97 4-methyl-N-(2,2,2-trifluoroethyl)-2-({1-[4-(trifluoromethoxy)benzoyl]azetidin-3-yl}-methyl)-2H-indazole-5-carboxamide;

E98 2-({1-[2-fluoro-4-(trifluoromethyl)benzoyl]azetidin-3-yl}methyl)-4-methyl-N-(2,2,2-trifluoroethyl)-2H-indazole-5-carboxamide;

E99 4-methyl-2-({1-[4-(pentafluoro-$\lambda^6$-sulphanyl)benzoyl]azetidin-3-yl}methyl)-N-(2,2,2-trifluoroethyl)-2H-indazole-5-carboxamide;

E100 N-[2-(cyclopropyloxy)ethyl]-4-methyl-2-({1-[4-(trifluoromethoxy)benzoyl]azetidin-3-yl}methyl)-2H-indazole-5-carboxamide;

E101 N-[2-(cyclobutyloxy)ethyl]-4-methyl-2-({1-[4-(trifluoromethoxy)benzoyl]azetidin-3-yl}methyl)-2H-indazole-5-carboxamide;

E102 2-{[1-(4-chlorobenzoyl)azetidin-3-yl]methyl}-N-[2-(cyclopropylmethoxy)ethyl]-4-methyl-2H-indazole-5-carboxamide;

E103 N-[2-(cyclopropylmethoxy)ethyl]-2-({1-[4-(4-fluorophenoxy)benzoyl]azetidin-3-yl}-methyl)-4-methyl-2H-indazole-5-carboxamide;

E104 N-[2-(cyclopropylmethoxy)ethyl]-4-methyl-2-{[1-(4-methylbenzoyl)azetidin-3-yl]-methyl}-2H-indazole-5-carboxamide;

E105 2-{[1-(4-chlorobenzoyl)azetidin-3-yl]methyl}-4-methyl-N-[2-(trifluoromethoxy)ethyl]-2H-indazole-5-carboxamide;

E106 N-(2-tert-butoxyethyl)-2-{[1-(4-chlorobenzoyl)azetidin-3-yl]methyl}-4-methyl-2H-indazole-5-carboxamide;

E107 N-[2-(cyclopropylmethoxy)ethyl]-2-({1-[(4'-fluorobiphenyl-4-yl)carbonyl]azetidin-3-yl}methyl)-4-methyl-2H-indazole-5-carboxamide;

E108 2-({1-[(4'-fluorobiphenyl-4-yl)carbonyl]azetidin-3-yl}methyl)-N-(2-methoxyethyl)-4-methyl-2H-indazole-5-carboxamide;

E109 2-({1-[4-(4-fluorophenoxy)benzoyl]azetidin-3-yl}methyl)-N-(2-methoxyethyl)-4-methyl-2H-indazole-5-carboxamide;

E110 2-({1-[4-(4-fluorophenoxy)benzoyl]azetidin-3-yl}methyl)-4-methyl-N-(2,2,2-trifluoroethyl)-2H-indazole-5-carboxamide;

E111 2-({1-[(4'-fluorobiphenyl-4-yl)carbonyl]azetidin-3-yl}methyl)-4-methyl-N-(2,2,2-trifluoroethyl)-2H-indazole-5-carboxamide;

E112 2-{[1-(4-chlorobenzoyl)azetidin-3-yl]methyl}-4-methyl-N-[2-(2,2,2-trifluoroethoxy)-ethyl]-2H-indazole-5-carboxamide;

E113 4-methyl-N-[2-(2,2,2-trifluoroethoxy)ethyl]-2-[(1-{4-[4-(trifluoromethyl)phenoxy]-benzoyl}azetidin-3-yl)methyl]-2H-indazole-5-carboxamide;

E114 4-methyl-N-(2,2,2-trifluoroethyl)-2-[(1-{4-[4-(trifluoromethyl)phenoxy]benzoyl}-azetidin-3-yl)methyl]-2H-indazole-5-carboxamide;

E115 2-({1-[4-(4-chlorophenoxy)benzoyl]azetidin-3-yl}methyl)-4-methyl-N-(2,2,2-trifluoro-ethyl)-2H-indazole-5-carboxamide;

E116 2-({1-[4-(4-chlorophenoxy)benzoyl]azetidin-3-yl}methyl)-N-(2-methoxyethyl)-4-methyl-2H-indazole-5-carboxamide;

E117 N-(2-methoxyethyl)-4-methyl-2-{[1-(4-{[5-(trifluoromethyl)pyridin-2-yl]oxy}benzoyl)-azetidin-3-yl]methyl}-2H-indazole-5-carboxamide;

E118 4-methyl-N-(2,2,2-trifluoroethyl)-2-{[1-(4-{[5-(trifluoromethyl)pyridin-2-yl]oxy}-benzoyl)azetidin-3-yl]methyl}-2H-indazole-5-carboxamide;

E119 2-{[1-(4-chlorobenzoyl)piperidin-4-yl]methyl}-N-ethyl-4-methyl-2H-indazole-5-carboxamide;

E120 2-({1-[4-(4-fluorophenoxy)benzoyl]piperidin-4-yl}methyl)-4-methyl-N-(2,2,2-trifluoroethyl)-2H-indazole-5-carboxamide;

E121 2-({1-[4-(4-chlorophenoxy)benzoyl]piperidin-4-yl}methyl)-4-methyl-N-(2,2,2-trifluoroethyl)-2H-indazole-5-carboxamide;

E122 4-methyl-2-({1-[4-(4-methylphenoxy)benzoyl]piperidin-4-yl}methyl)-N-(2,2,2-trifluoroethyl)-2H-indazole-5-carboxamide;

E123 2-({1-[(4'-fluorobiphenyl-4-yl)carbonyl]piperidin-4-yl}methyl)-4-methyl-N-(2,2,2-trifluoroethyl)-2H-indazole-5-carboxamide;

E124 4-methyl-2-{[1-(4-morpholinobenzoyl)piperidin-4-yl]methyl}-N-(2,2,2-trifluoroethyl)-2H-indazole-5-carboxamide;

E125 4-methyl-N-(2,2,2-trifluoroethyl)-2-[(1-{4-[(trifluoromethyl)sulphanyl]benzoyl}-piperidin-4-yl)methyl]-2H-indazole-5-carboxamide;

E126 4-methyl-N-(2,2,2-trifluoroethyl)-2-[(1-{4-[4-(trifluoromethyl)phenoxy]benzoyl}-piperidin-4-yl)methyl]-2H-indazole-5-carboxamide;

E127 4-methyl-N-(2,2,2-trifluoroethyl)-2-{[1-(4-{[5-(trifluoromethyl)pyridin-2-yl]oxy}-benzoyl)piperidin-4-yl]methyl}-2H-indazole-5-carboxamide;

E128 4-methyl-N-(2,2,2-trifluoroethyl)-2-{[1-(4-{[6-(trifluoromethyl)pyridin-3-yl]oxy}-benzoyl)piperidin-4-yl]methyl}-2H-indazole-5-carboxamide;

E129 4-methyl-N-(2,2,2-trifluoroethyl)-2-{[1-(4-{[6-(trifluoromethyl)pyridin-2-yl]oxy}-benzoyl)piperidin-4-yl]methyl}-2H-indazole-5-carboxamide;

E130 2-({1-[4-(4-cyanophenoxy)benzoyl]piperidin-4-yl}methyl)-4-methyl-N-(2,2,2-trifluoro-ethyl)-2H-indazole-5-carboxamide;

E131 2-({1-[4-(3-fluorophenoxy)benzoyl]piperidin-4-yl}methyl)-4-methyl-N-(2,2,2-trifluoro-ethyl)-2H-indazole-5-carboxamide;

E132 4-methyl-N-(2,2,2-trifluoroethyl)-2-[(1-{4-[3-(trifluoromethyl)phenoxy]benzoyl}-piperidin-4-yl)methyl]-2H-indazole-5-carboxamide;

E133 2-[(1-{4-[(5-cyanopyridin-2-yl)oxy]benzoyl}piperidin-4-yl)methyl]-4-methyl-N-(2,2,2-trifluoroethyl)-2H-indazole-5-carboxamide;

E134 2-[(1-{4-[(5-chloropyridin-2-yl)oxy]benzoyl}piperidin-4-yl)methyl]-4-methyl-N-(2,2,2-trifluoroethyl)-2H-indazole-5-carboxamide;

E135 4-methyl-N-(2,2,2-trifluoroethyl)-2-[(1-{4-[5-(trifluoromethyl)pyridin-2-yl]benzoyl}-piperidin-4-yl)methyl]-2H-indazole-5-carboxamide;

E136 2-({1-[4-(2,4-difluorophenoxy)benzoyl]piperidin-4-yl}methyl)-4-methyl-N-(2,2,2-trifluoroethyl)-2H-indazole-5-carboxamide;

E137 2-({1-[4-(3,4-difluorophenoxy)benzoyl]piperidin-4-yl}methyl)-4-methyl-N-(2,2,2-trifluoroethyl)-2H-indazole-5-carboxamide;

E138 4-methyl-N-(2,2,2-trifluoroethyl)-2-[(1-{[4'-(trifluoromethyl)biphenyl-4-yl]carbonyl}-piperidin-4-yl)methyl]-2H-indazole-5-carboxamide;

E139 2-{[1-(4-bromobenzoyl)piperidin-4-yl]methyl}-4-methyl-N-(2,2,2-trifluoroethyl)-2H-indazole-5-carboxamide;

E140 2-({1-[4-(5-chloropyridin-2-yl)benzoyl]piperidin-4-yl}methyl)-4-methyl-N-(2,2,2-trifluoroethyl)-2H-indazole-5-carboxamide;

E141 2-({1-[(4'-methoxy-2'-methylbiphenyl-4-yl)carbonyl]piperidin-4-yl}methyl)-4-methyl-N-(2,2,2-trifluoroethyl)-2H-indazole-5-carboxamide;

E142 4-methyl-2-({1-[4-(6-methylpyridin-3-yl)benzoyl]piperidin-4-yl}methyl)-N-(2,2,2-trifluoroethyl)-2H-indazole-5-carboxamide;

E143 2-({1-[(4'-fluoro-2'-methoxybiphenyl-4-yl)carbonyl]piperidin-4-yl}methyl)-4-methyl-N-(2,2,2-trifluoroethyl)-2H-indazole-5-carboxamide;

E144 4-methyl-N-(2,2,2-trifluoroethyl)-2-[(1-{4-[6-(trifluoromethyl)pyridin-3-yl]benzoyl}-piperidin-4-yl)methyl]-2H-indazole-5-carboxamide;

E145 2-({1-[4-(6-methoxypyridin-3-yl)benzoyl]piperidin-4-yl}methyl)-4-methyl-N-(2,2,2-trifluoroethyl)-2H-indazole-5-carboxamide;

E146 2-({1-[4-(6-methoxypyridin-2-yl)benzoyl]piperidin-4-yl}methyl)-4-methyl-N-(2,2,2-trifluoroethyl)-2H-indazole-5-carboxamide;

E147 4-methyl-2-({1-[4-(5-methylpyridin-2-yl)benzoyl]piperidin-4-yl}methyl)-N-(2,2,2-trifluoroethyl)-2H-indazole-5-carboxamide;

E148 2-({1-[4-(5-fluoropyridin-2-yl)benzoyl]piperidin-4-yl}methyl)-4-methyl-N-(2,2,2-trifluoroethyl)-2H-indazole-5-carboxamide;

E149 2-({1-[4-(5-methoxypyridin-2-yl)benzoyl]piperidin-4-yl}methyl)-4-methyl-N-(2,2,2-trifluoroethyl)-2H-indazole-5-carboxamide;

E150 4-methyl-2-({1-[4-(2-methylpyrimidin-5-yl)benzoyl]piperidin-4-yl}methyl)-N-(2,2,2-trifluoroethyl)-2H-indazole-5-carboxamide;

E151 4-methyl-N-(2,2,2-trifluoroethyl)-2-[(1-{4-[2-(trifluoromethyl)pyrimidin-5-yl]benzoyl}-piperidin-4-yl)methyl]-2H-indazole-5-carboxamide;

E152 4-methyl-N-(2,2,2-trifluoroethyl)-2-[(1-{4-[6-(trifluoromethyl)pyridin-2-yl]benzoyl}-piperidin-4-yl)methyl]-2H-indazole-5-carboxamide;

E153 2-({1-[4-(4-cyanophenoxy)benzoyl]piperidin-4-yl}methyl)-N-(2-methoxyethyl)-4-methyl-2H-indazole-5-carboxamide;

E154 2-{[1-(4-bromo-3-methylbenzoyl)piperidin-4-yl]methyl}-N-(2-methoxyethyl)-4-methyl-2H-indazole-5-carboxamide;

E155 2-{[1-(4-tert-butylbenzoyl)piperidin-4-yl]methyl}-N-(2-methoxyethyl)-4-methyl-2H-indazole-5-carboxamide;

E156 2-({1-[4-(1-hydroxy-1-methylethyl)benzoyl]piperidin-4-yl}methyl)-N-(2-methoxy-ethyl)-4-methyl-2H-indazole-5-carboxamide;

E157 2-{[1-(4-cyclohexylbenzoyl)piperidin-4-yl]methyl}-N-(2-methoxyethyl)-4-methyl-2H-indazole-5-carboxamide;

E158 2-({1-[4-(1-cyano-1-methylethyl)benzoyl]piperidin-4-yl}methyl)-N-(2-methoxyethyl)-4-methyl-2H-indazole-5-carboxamide;

E159 N-(2-methoxyethyl)-4-methyl-2-({1-[4-(pyrimidin-2-yloxy)benzoyl]piperidin-4-yl}-methyl)-2H-indazole-5-carboxamide;

E160 N-(2-methoxyethyl)-4-methyl-2-({1-[4-(pyridin-3-yloxy)benzoyl]piperidin-4-yl}methyl)-2H-indazole-5-carboxamide;

E161 N-(2-methoxyethyl)-4-methyl-2-{[1-(4-{[5-(trifluoromethyl)pyridin-2-yl]oxy}benzoyl)-piperidin-4-yl]methyl}-2H-indazole-5-carboxamide;

E162 N-(2-methoxyethyl)-4-methyl-2-({1-[4-(pyridin-2-yloxy)benzoyl]piperidin-4-yl}methyl)-2H-indazole-5-carboxamide;

E163 N-(2-methoxyethyl)-4-methyl-2-{[1-(4-{[4-(trifluoromethyl)pyrimidin-2-yl]oxy}-benzoyl)piperidin-4-yl]methyl}-2H-indazole-5-carboxamide;

E164 N-(2-methoxyethyl)-4-methyl-2-{[1-(4-{[6-(trifluoromethyl)pyridin-3-yl]oxy}benzoyl)-piperidin-4-yl]methyl}-2H-indazole-5-carboxamide;

E165 N-(2-methoxyethyl)-4-methyl-2-{[1-(4-{[6-(trifluoromethyl)pyridin-2-yl]oxy}benzoyl)-piperidin-4-yl]methyl}-2H-indazole-5-carboxamide;

E166 2-({1-[(4'-methoxybiphenyl-4-yl)carbonyl]piperidin-4-yl}methyl)-N-(2-methoxyethyl)-4-methyl-2H-indazole-5-carboxamide;

E167 N-(2-methoxyethyl)-4-methyl-2-({1-[4-(3,4,5,6-tetrahydro-2H-pyran-4-yloxy)benzoyl]-piperidin-4-yl}methyl)-2H-indazole-5-carboxamide;

E168 N-(2-methoxyethyl)-4-methyl-2-[(1-{4-[3-(trifluoromethyl)phenoxy]benzoyl}piperidin-4-yl)methyl]-2H-indazole-5-carboxamide;

E169 2-[(1-{4-[(5-cyanopyridin-2-yl)oxy]benzoyl}piperidin-4-yl)methyl]-N-(2-methoxy-ethyl)-4-methyl-2H-indazole-5-carboxamide;

E170 2-[(1-{4-[(5-chloropyridin-2-yl)oxy]benzoyl}piperidin-4-yl)methyl]-N-(2-methoxy-ethyl)-4-methyl-2H-indazole-5-carboxamide;

E171 2-({1-[4-(2,4-difluorophenoxy)benzoyl]piperidin-4-yl}methyl)-N-(2-methoxyethyl)-4-methyl-2H-indazole-5-carboxamide;

E172 2-({1-[4-(3,4-difluorophenoxy)benzoyl]piperidin-4-yl}methyl)-N-(2-methoxyethyl)-4-methyl-2H-indazole-5-carboxamide;

E173 N-(2-methoxyethyl)-4-methyl-2-[(1-{[4'-(trifluoromethyl)biphenyl-4-yl]carbonyl}-piperidin-4-yl)methyl]-2H-indazole-5-carboxamide;

E174 2-({1-[4-(3-fluorophenoxy)benzoyl]piperidin-4-yl}methyl)-N-(2-methoxyethyl)-4-methyl-2H-indazole-5-carboxamide;

E175 2-{[1-(2-fluoro-4-isopropoxybenzoyl)piperidin-4-yl]methyl}-N-(2-methoxyethyl)-4-methyl-2H-indazole-5-carboxamide;

E176 2-({1-[(3-fluoro-3',4'-dimethylbiphenyl-4-yl)carbonyl]piperidin-4-yl}methyl)-N-(2-methoxyethyl)-4-methyl-2H-indazole-5-carboxamide;

E177 2-({1-[(2',3-difluoro-4'-methoxybiphenyl-4-yl)carbonyl]piperidin-4-yl}methyl)-N-(2-methoxyethyl)-4-methyl-2H-indazole-5-carboxamide;

E178 2-({1-[4-(difluoromethoxy)benzoyl]piperidin-4-yl}methyl)-N-(2-methoxyethyl)-4-methyl-2H-indazole-5-carboxamide;

E179 2-({1-[4-(2-fluorophenoxy)benzoyl]piperidin-4-yl}methyl)-N-(2-methoxyethyl)-4-methyl-2H-indazole-5-carboxamide;

E180 2-({1-[(4'-cyano-2'-methylbiphenyl-4-yl)carbonyl]piperidin-4-yl}methyl)-N-(2-methoxyethyl)-4-methyl-2H-indazole-5-carboxamide;

E181 2-({1-[4-(5-chloropyridin-2-yl)benzoyl]piperidin-4-yl}methyl)-N-(2-methoxyethyl)-4-methyl-2H-indazole-5-carboxamide;

E182 N-(2-methoxyethyl)-4-methyl-2-[(1-{4-[6-(trifluoromethyl)pyridin-2-yl]benzoyl}-piperidin-4-yl)methyl]-2H-indazole-5-carboxamide;

E183 N-(2-methoxyethyl)-2-({1-[(4'-methoxy-2'-methylbiphenyl-4-yl)carbonyl]piperidin-4-yl}methyl)-4-methyl-2H-indazole-5-carboxamide;

E184 2-({1-[(4'-chloro-2'-methylbiphenyl-4-yl)carbonyl]piperidin-4-yl}methyl)-N-(2-methoxyethyl)-4-methyl-2H-indazole-5-carboxamide;

E185 2-[(1-{[4'-(2-cyanopropan-2-yl)biphenyl-4-yl]carbonyl}piperidin-4-yl)methyl]-N-(2-methoxyethyl)-4-methyl-2H-indazole-5-carboxamide;

E186 N-(2-methoxyethyl)-2-({1-[4-(5-methoxypyridin-2-yl)benzoyl]piperidin-4-yl}methyl)-4-methyl-2H-indazole-5-carboxamide;

E187 N-(2-methoxyethyl)-4-methyl-2-[(1-{4-[6-(trifluoromethyl)pyridin-3-yl]benzoyl}-piperidin-4-yl)methyl]-2H-indazole-5-carboxamide;

E188 N-(2-methoxyethyl)-2-({1-[4-(6-methoxypyridin-3-yl)benzoyl]piperidin-4-yl}methyl)-4-methyl-2H-indazole-5-carboxamide;

E189 2-({1-[(4'-fluoro-2'-methylbiphenyl-4-yl)carbonyl]piperidin-4-yl}methyl)-N-(2-methoxyethyl)-4-methyl-2H-indazole-5-carboxamide;

E190 N-(2-methoxyethyl)-4-methyl-2-({1-[4-(6-methylpyridin-3-yl)benzoyl]piperidin-4-yl}-methyl)-2H-indazole-5-carboxamide;

E191 N-(2-methoxyethyl)-2-({1-[4-(6-methoxypyridin-2-yl)benzoyl]piperidin-4-yl}methyl)-4-methyl-2H-indazole-5-carboxamide;

E192 N-(2-methoxyethyl)-4-methyl-2-({1-[4-(2-methylpyrimidin-5-yl)benzoyl]piperidin-4-yl}methyl)-2H-indazole-5-carboxamide;

E193 2-({1-[(4'-fluoro-2'-methoxybiphenyl-4-yl)carbonyl]piperidin-4-yl}methyl)-N-(2-methoxyethyl)-4-methyl-2H-indazole-5-carboxamide;

E194 2-({1-[(4'-chloro-2'-methoxybiphenyl-4-yl)carbonyl]piperidin-4-yl}methyl)-N-(2-methoxyethyl)-4-methyl-2H-indazole-5-carboxamide;

E195 N-(2-methoxyethyl)-4-methyl-2-[(1-{4-[2-(trifluoromethyl)pyrimidin-5-yl]benzoyl}-piperidin-4-yl)methyl]-2H-indazole-5-carboxamide;

E196 2-({1-[(4'-chloro-2'-fluorobiphenyl-4-yl)carbonyl]piperidin-4-yl}methyl)-N-(2-methoxy-ethyl)-4-methyl-2H-indazole-5-carboxamide;

E197 2-({1-[(2'-chloro-4'-fluorobiphenyl-4-yl)carbonyl]piperidin-4-yl}methyl)-N-(2-methoxy-ethyl)-4-methyl-2H-indazole-5-carboxamide;

E198 2-({1-[4-(5-chloropyridin-3-yl)benzoyl]piperidin-4-yl}methyl)-N-(2-methoxyethyl)-4-methyl-2H-indazole-5-carboxamide;

E199 2-({1-[4-(5-fluoropyridin-3-yl)benzoyl]piperidin-4-yl}methyl)-N-(2-methoxyethyl)-4-methyl-2H-indazole-5-carboxamide;

E200 N-(2-methoxyethyl)-4-methyl-2-[(1-{4-[5-(trifluoromethyl)pyridin-3-yl]benzoyl}-piperidin-4-yl)methyl]-2H-indazole-5-carboxamide;

E201 2-[(1{[4'-(2-hydroxypropan-2-yl)biphenyl-4-yl]carbonyl}piperidin-4-yl)methyl]-N-(2-methoxyethyl)-4-methyl-2H-indazole-5-carboxamide;

E202 2-({1-[(3',5'-difluorobiphenyl-4-yl)carbonyl]piperidin-4-yl}methyl)-N-(2-methoxy-ethyl)-4-methyl-2H-indazole-5-carboxamide;

E203 2-({1-[(4'-fluoro-2-methylbiphenyl-4-yl)carbonyl]piperidin-4-yl}methyl)-N-(2-methoxy-ethyl)-4-methyl-2H-indazole-5-carboxamide;

E204 2-({1-[(3',5'-difluoro-2-methylbiphenyl-4-yl)carbonyl]piperidin-4-yl}methyl)-N-(2-methoxyethyl)-4-methyl-2H-indazole-5-carboxamide;

E205 N-(2-methoxyethyl)-4-methyl-2-({1-[3-methyl-4-(3-pyridyl)benzoyl]piperidin-4-yl}-methyl)-2H-indazole-5-carboxamide;

E206 N-(2-methoxyethyl)-4-methyl-2-({1-[3-methyl-4-(4-pyridyl)benzoyl]piperidin-4-yl}-methyl)-2H-indazole-5-carboxamide; and E207 N-(2-methoxyethyl)-4-methyl-2-({1-[(2-methylbiphenyl-4-yl)carbonyl]piperidin-4-yl}-methyl)-2H-indazole-5-carboxamide.

6. The pharmaceutical composition of claim 5, where the EP2 receptor antagonist is selected from the group consisting of:

E2 2-{[1-(4-tert-butoxybenzoyl)piperidin-4-yl]methyl}-N-(2-methoxyethyl)-4-methyl-2H-indazole-5-carboxamide;

E3 2-({1-[4-(4-fluorophenoxy)benzoyl]piperidin-4-yl}methyl)-N-(2-methoxyethyl)-4-methyl-2H-indazole-5-carboxamide;

E5 2-({1-[(4'-fluorobiphenyl-4-yl)carbonyl]piperidin-4-yl}methyl)-N-(2-methoxyethyl)-4-methyl-2H-indazole-5-carboxamide;

E7 2-{[1-(2-fluoro-4-methoxybenzoyl)piperidin-4-yl]methyl}-N-(2-methoxyethyl)-4-methyl-2H-indazole-5-carboxamide;

E8 2-{[1-(4-bromo-2-fluorobenzoyl)piperidin-4-yl]methyl}-N-(2-methoxyethyl)-4-methyl-2H-indazole-5-carboxamide;

E9 2-{[1-(2-fluoro-4-methylbenzoyl)piperidin-4-yl]methyl}-N-(2-methoxyethyl)-4-methyl-2H-indazole-5-carboxamide;

E10 2-({1-[2-fluoro-4-(trifluoromethyl)benzoyl]piperidin-4-yl}methyl)-N-(2-methoxyethyl)-4-methyl-2H-indazole-5-carboxamide;

E11 N-(2-methoxyethyl)-4-methyl-2-({1-[4-(pentafluoro-$\lambda^6$-sulphanyl)benzoyl]piperidin-4-yl}methyl)-2H-indazole-5-carboxamide;

E12 N-(2-methoxyethyl)-4-methyl-2-{[1-(4-methylbenzoyl)piperidin-4-yl]methyl}-2H-indazole-5-carboxamide;

E13 2-({1-[4-(4-chlorophenoxy)benzoyl]piperidin-4-yl}methyl)-N-(2-methoxyethyl)-4-methyl-2H-indazole-5-carboxamide;

E14 N-(2-methoxyethyl)-4-methyl-2-({1-[4-(4-methylphenoxy)benzoyl]piperidin-4-yl}methyl)-2H-indazole-5-carboxamide;

E15 2-({1-[4-(4-tert-butylphenoxy)benzoyl]piperidin-4-yl}methyl)-N-(2-methoxyethyl)-4-methyl-2H-indazole-5-carboxamide;

E16 N-(2-methoxyethyl)-4-methyl-2-[(1-{4-[4-(trifluoromethyl)phenoxy]benzoyl}piperidin-4-yl)methyl]-2H-indazole-5-carboxamide;

E17 N-(2-methoxyethyl)-2-({1-[4-(4-methoxyphenoxy)benzoyl]piperidin-4-yl}methyl)-4-methyl-2H-indazole-5-carboxamide;

E18 N-(2-methoxyethyl)-4-methyl-2-{[1-(4-phenoxybenzoyl)piperidin-4-yl]methyl}-2H-indazole-5-carboxamide;

E19 2-{[1-(4-cyclopropylbenzoyl)piperidin-4-yl]methyl}-N-(2-methoxyethyl)-4-methyl-2H-indazole-5-carboxamide;

E20 2-{[1-(4-methoxybenzoyl)piperidin-4-yl]methyl}-N-(2-methoxyethyl)-4-methyl-2H-indazole-5-carboxamide;

E21 2-{[1-(4-fluorobenzoyl)piperidin-4-yl]methyl}-N-(2-methoxyethyl)-4-methyl-2H-indazole-5-carboxamide;

E22 N-(2-methoxyethyl)-4-methyl-2-({1-[4-(trifluoromethyl)benzoyl]piperidin-4-yl}methyl)-2H-indazole-5-carboxamide;

E24 N-(2-methoxyethyl)-4-methyl-2-[(1-{4-[(trifluoromethyl)sulphonyl]benzoyl}piperidin-4-yl)methyl]-2H-indazole-5-carboxamide;

E25 N-(2-methoxyethyl)-4-methyl-2-({1-[3-(trifluoromethyl)benzoyl]piperidin-4-yl}methyl)-2H-indazole-5-carboxamide;

E26 N-(2-methoxyethyl)-4-methyl-2-{[1-(3-methylbenzoyl)piperidin-4-yl]methyl}-2H-indazole-5-carboxamide;

E27 2-{[1-(3-chlorobenzoyl)piperidin-4-yl]methyl}-N-(2-methoxyethyl)-4-methyl-2H-indazole-5-carboxamide;

E29 2-({1-[4-(cyclopentyloxy)benzoyl]piperidin-4-yl}methyl)-N-(2-methoxyethyl)-4-methyl-2H-indazole-5-carboxamide;
E30 2-({1-[4-(difluoromethyl)benzoyl]piperidin-4-yl}methyl)-N-(2-methoxyethyl)-4-methyl-2H-indazole-5-carboxamide;
E31 2-{[1-(4-cyanobenzoyl)piperidin-4-yl]methyl}-N-(2-methoxyethyl)-4-methyl-2H-indazole-5-carboxamide;
E36 N-(2-methoxyethyl)-4-methyl-2-({1-[4-(1H-pyrazol-1-yl)benzoyl]piperidin-4-yl}methyl)-2H-indazole-5-carboxamide;
E38 2-({1-[4-(difluoromethoxy)-2-fluorobenzoyl]piperidin-4-yl}methyl)-N-(2-methoxyethyl)-4-methyl-2H-indazole-5-carboxamide;
E39 2-({1-[2-fluoro-4-(pyrrolidin-1-yl)benzoyl]piperidin-4-yl}methyl)-N-(2-methoxyethyl)-4-methyl-2H-indazole-5-carboxamide;
E40 2-({1-[(3,4'-difluorobiphenyl-4-yl)carbonyl]piperidin-4-yl}methyl)-N-(2-methoxyethyl)-4-methyl-2H-indazole-5-carboxamide;
E41 2-({1-[(3-fluoro-4'-methoxybiphenyl-4-yl)carbonyl]piperidin-4-yl}methyl)-N-(2-methoxyethyl)-4-methyl-2H-indazole-5-carboxamide;
E42 2-({1-[(3-fluoro-4'-methylbiphenyl-4-yl)carbonyl]piperidin-4-yl}methyl)-N-(2-methoxyethyl)-4-methyl-2H-indazole-5-carboxamide;
E43 2-[(1-{[3-fluoro-3'-(trifluoromethyl)biphenyl-4-yl]carbonyl}piperidin-4-yl)methyl]-N-(2-methoxyethyl)-4-methyl-2H-indazole-5-carboxamide;
E44 2-[(1-{[3-fluoro-2'-(trifluoromethoxy)biphenyl-4-yl]carbonyl}piperidin-4-yl)methyl]-N-(2-methoxyethyl)-4-methyl-2H-indazole-5-carboxamide;
E45 2-({1-[(2'-fluorobiphenyl-4-yl)carbonyl]piperidin-4-yl}methyl)-N-(2-methoxyethyl)-4-methyl-2H-indazole-5-carboxamide;
E46 2-({1-[(2',4'-difluorobiphenyl-4-yl)carbonyl]piperidin-4-yl}methyl)-N-(2-methoxyethyl)-4-methyl-2H-indazole-5-carboxamide;
E47 2-({1-[(2-fluorobiphenyl-4-yl)carbonyl]piperidin-4-yl}methyl)-N-(2-methoxyethyl)-4-methyl-2H-indazole-5-carboxamide;
E48 N-(2-methoxyethyl)-4-methyl-2-({1-[(2'-methylbiphenyl-4-yl)carbonyl]piperidin-4-yl}methyl)-2H-indazole-5-carboxamide;
E51 2-({1-[2-fluoro-4-(morpholin-4-yl)benzoyl]piperidin-4-yl}methyl)-N-(2-methoxyethyl)-4-methyl-2H-indazole-5-carboxamide;
E52 2-{[1-(4-bromobenzoyl)piperidin-4-yl]methyl}-N-(2-methoxyethyl)-4-methyl-2H-indazole-5-carboxamide;
E53 N-(2-methoxyethyl)-4-methyl-2-({1-[4-(trifluoromethoxy)benzoyl]piperidin-4-yl}methyl)-2H-indazole-5-carboxamide;
E54 2-{[1-(4-chlorobenzoyl)piperidin-4-yl]methyl}-N-(2-methoxyethyl)-4-methyl-2H-indazole-5-carboxamide;
E55 N-(2-methoxyethyl)-4-methyl-2-[(1-{4-[(trifluoromethyl)sulphanyl]benzoyl}piperidin-4-yl)methyl]-2H-indazole-5-carboxamide;
E59 2-{[1-(4-chlorobenzoyl)piperidin-4-yl]methyl}-N-[2-(cyclopropylmethoxy)ethyl]-4-methyl-2H-indazole-5-carboxamide;
E60 N-[2-(cyclopropylmethoxy)ethyl]-4-methyl-2-{[1-(4-methylbenzoyl)piperidin-4-yl]methyl}-2H-indazole-5-carboxamide;
E61 N-[2-(cyclopropylmethoxy)ethyl]-2-({1-[4-(4-fluorophenoxy)benzoyl]piperidin-4-yl}methyl)-4-methyl-2H-indazole-5-carboxamide;
E62 N-[2-(cyclopropylmethoxy)ethyl]-4-methyl-2-({1-[4-(trifluoromethyl)benzoyl]piperidin-4-yl}methyl)-2H-indazole-5-carboxamide;
E63 N-[2-(cyclopropylmethoxy)ethyl]-2-({1-[(4'-fluorobiphenyl-4-yl)carbonyl]piperidin-4-yl}methyl)-4-methyl-2H-indazole-5-carboxamide;
E64 2-{[1-(4-cyclopropylbenzoyl)piperidin-4-yl]methyl}-N-[2-(cyclopropylmethoxy)ethyl]-4-methyl-2H-indazole-5-carboxamide;
E65 2-{[1-(4-chlorobenzoyl)piperidin-4-yl]methyl}-4-methyl-N-[2-(2,2,2-trifluoroethoxy)ethyl]-2H-indazole-5-carboxamide;
E66 4-methyl-2-{[1-(4-methylbenzoyl)piperidin-4-yl]methyl}-N-[2-(2,2,2-trifluoroethoxy)ethyl]-2H-indazole-5-carboxamide;
E67 2-({1-[4-(4-fluorophenoxy)benzoyl]piperidin-4-yl}methyl)-4-methyl-N-[2-(2,2,2-trifluoroethoxy)ethyl]-2H-indazole-5-carboxamide;
E68 4-methyl-N-[2-(2,2,2-trifluoroethoxy)ethyl]-2-({1-[4-(trifluoromethyl)benzoyl]piperidin-4-yl}methyl)-2H-indazole-5-carboxamide;
E69 2-({1-[(4'-fluorobiphenyl-4-yl)carbonyl]piperidin-4-yl}methyl)-4-methyl-N-[2-(2,2,2-trifluoroethoxy)ethyl]-2H-indazole-5-carboxamide;
E70 2-{[1-(4-cyclopropylbenzoyl)piperidin-4-yl]methyl}-4-methyl-N-[2-(2,2,2-trifluoroethoxy)ethyl]-2H-indazole-5-carboxamide;
E71 2-{[1-(4-chlorobenzoyl)piperidin-4-yl]methyl}-N-(2-isopropoxyethyl)-4-methyl-2H-indazole-5-carboxamide;
E72 N-(2-isopropoxyethyl)-4-methyl-2-{[1-(4-methylbenzoyl)piperidin-4-yl]methyl}-2H-indazole-5-carboxamide;
E73 2-({1-[4-(4-fluorophenoxy)benzoyl]piperidin-4-yl}methyl)-N-(2-isopropoxyethyl)-4-methyl-2H-indazole-5-carboxamide;
E74 N-(2-isopropoxyethyl)-4-methyl-2-({1-[4-(trifluoromethyl)benzoyl]piperidin-4-yl}methyl)-2H-indazole-5-carboxamide;
E75 2-({1-[(4'-fluorobiphenyl-4-yl)carbonyl]piperidin-4-yl}methyl)-N-(2-isopropoxyethyl)-4-methyl-2H-indazole-5-carboxamide;
E76 2-{[1-(4-cyclopropylbenzoyl)piperidin-4-yl]methyl}-N-(2-isopropoxyethyl)-4-methyl-2H-indazole-5-carboxamide;
E77 2-{[1-(4-chlorobenzoyl)piperidin-4-yl]methyl}-4-methyl-N-[2-(trifluoromethoxy)ethyl]-2H-indazole-5-carboxamide;
E78 2-({1-[4-(4-fluorophenoxy)benzoyl]piperidin-4-yl}methyl)-4-methyl-N-[2-(trifluoromethoxy)ethyl]-2H-indazole-5-carboxamide;
E79 2-({1-[(4'-fluorobiphenyl-4-yl)carbonyl]piperidin-4-yl}methyl)-4-methyl-N-[2-(trifluoromethoxy)ethyl]-2H-indazole-5-carboxamide;
E80 4-methyl-N-[2-(trifluoromethoxy)ethyl]-2-[(1-{4-[4-(trifluoromethyl)phenoxy]benzoyl}piperidin-4-yl)methyl]-2H-indazole-5-carboxamide;
E81 N-(2-tert-butoxyethyl)-2-{[1-(4-chlorobenzoyl)piperidin-4-yl]methyl}-4-methyl-2H-indazole-5-carboxamide;
E82 N-(2-tert-butoxyethyl)-2-({1-[4-(4-fluorophenoxy)benzoyl]piperidin-4-yl}methyl)-4-methyl-2H-indazole-5-carboxamide;

E83 N-(2-tert-butoxyethyl)-2-({1-[(4'-fluorobiphenyl-4-yl)carbonyl]piperidin-4-yl}methyl)-4-methyl-2H-indazole-5-carboxamide;

E84 N-(2-tert-butoxyethyl)-4-methyl-2-[(1-{4-[4-(trifluoromethyl)phenoxy]benzoyl}piperidin-4-yl)methyl]-2H-indazole-5-carboxamide;

E85 2-{[1-(4-chlorobenzoyl)piperidin-4-yl]methyl}-4-methyl-N-{2-[(2H3)methyloxy](2H4)ethyl}-2H-indazole-5-carboxamide;

E86 2-({1-[4-(4-fluorophenoxy)benzoyl]piperidin-4-yl}methyl)-4-methyl-N-{2-[(2H3)methyloxy](2H4)ethyl}-2H-indazole-5-carboxamide;

E87 2-{[1-(4-chlorobenzoyl)azetidin-3-yl]methyl}-N-(2-methoxyethyl)-4-methyl-2H-indazole-5-carboxamide;

E88 N-(2-methoxyethyl)-4-methyl-2-[(1-{4-[(trifluoromethyl)sulphanyl]benzoyl}azetidin-3-yl)methyl]-2H-indazole-5-carboxamide;

E89 N-(2-methoxyethyl)-4-methyl-2-({1-[4-(trifluoromethoxy)benzoyl]azetidin-3-yl}methyl)-2H-indazole-5-carboxamide;

E90 2-({1-[2-fluoro-4-(trifluoromethyl)benzoyl]azetidin-3-yl}methyl)-N-(2-methoxyethyl)-4-methyl-2H-indazole-5-carboxamide;

E91 2-{[1-(4-chloro-2-fluorobenzoyl)azetidin-3-yl]methyl}-N-(2-methoxyethyl)-4-methyl-2H-indazole-5-carboxamide;

E92 2-({1-[3-fluoro-4-(trifluoromethyl)benzoyl]azetidin-3-yl}methyl)-N-(2-methoxyethyl)-4-methyl-2H-indazole-5-carboxamide;

E93 2-({1-[4-chloro-3-(trifluoromethyl)benzoyl]azetidin-3-yl}methyl)-N-(2-methoxyethyl)-4-methyl-2H-indazole-5-carboxamide;

E94 2-{[1-(4-cyclopropylbenzoyl)azetidin-3-yl]methyl}-N-(2-methoxyethyl)-4-methyl-2H-indazole-5-carboxamide;

E95 N-(2-methoxyethyl)-4-methyl-2-[(1-{4-[4-(trifluoromethyl)phenoxy]benzoyl}azetidin-3-yl)methyl]-2H-indazole-5-carboxamide;

E100 N-[2-(cyclopropyloxy)ethyl]-4-methyl-2-({1-[4-(trifluoromethoxy)benzoyl]azetidin-3-yl}methyl)-2H-indazole-5-carboxamide;

E101 N-[2-(cyclobutyloxy)ethyl]-4-methyl-2-({1-[4-(trifluoromethoxy)benzoyl]azetidin-3-yl}methyl)-2H-indazole-5-carboxamide;

E102 2-{[1-(4-chlorobenzoyl)azetidin-3-yl]methyl}-N-[2-(cyclopropylmethoxy)ethyl]-4-methyl-2H-indazole-5-carboxamide;

E103 N-[2-(cyclopropylmethoxy)ethyl]-2-({1-[4-(4-fluorophenoxy)benzoyl]azetidin-3-yl}methyl)-4-methyl-2H-indazole-5-carboxamide;

E104 N-[2-(cyclopropylmethoxy)ethyl]-4-methyl-2-{[1-(4-methylbenzoyl)azetidin-3-yl]methyl}-2H-indazole-5-carboxamide;

E105 2-{[1-(4-chlorobenzoyl)azetidin-3-yl]methyl}-4-methyl-N-[2-(trifluoromethoxy)ethyl]-2H-indazole-5-carboxamide;

E107 N-[2-(cyclopropylmethoxy)ethyl]-2-({1-[(4'-fluorobiphenyl-4-yl)carbonyl]azetidin-3-yl}methyl)-4-methyl-2H-indazole-5-carboxamide;

E108 2-({1-[(4'-fluorobiphenyl-4-yl)carbonyl]azetidin-3-yl}methyl)-N-(2-methoxyethyl)-4-methyl-2H-indazole-5-carboxamide;

E109 2-({1-[4-(4-fluorophenoxy)benzoyl]azetidin-3-yl}methyl)-N-(2-methoxyethyl)-4-methyl-2H-indazole-5-carboxamide;

E112 2-{[1-(4-chlorobenzoyl)azetidin-3-yl]methyl}-4-methyl-N-[2-(2,2,2-trifluoroethoxy)ethyl]-2H-indazole-5-carboxamide;

E113 4-methyl-N-[2-(2,2,2-trifluoroethoxy)ethyl]-2-[(1-{4-[4-(trifluoromethyl)phenoxy]benzoyl}azetidin-3-yl)methyl]-2H-indazole-5-carboxamide;

E114 4-methyl-N-(2,2,2-trifluoroethyl)-2-[(1-{4-[4-(trifluoromethyl)phenoxy]benzoyl}azetidin-3-yl)methyl]-2H-indazole-5-carboxamide;

E115 2-({1-[4-(4-chlorophenoxy)benzoyl]azetidin-3-yl}methyl)-4-methyl-N-(2,2,2-trifluoroethyl)-2H-indazole-5-carboxamide;

E116 2-({1-[4-(4-chlorophenoxy)benzoyl]azetidin-3-yl}methyl)-N-(2-methoxyethyl)-4-methyl-2H-indazole-5-carboxamide;

E117 N-(2-methoxyethyl)-4-methyl-2-{[1-(4-{[5-(trifluoromethyl)pyridin-2-yl]oxy}benzoyl)azetidin-3-yl]methyl}-2H-indazole-5-carboxamide;

E125 4-methyl-N-(2,2,2-trifluoroethyl)-2-[(1-{4-[(trifluoromethyl)sulphanyl]benzoyl}piperidin-4-yl)methyl]-2H-indazole-5-carboxamide;

E126 4-methyl-N-(2,2,2-trifluoroethyl)-2-[(1-{4-[4-(trifluoromethyl)phenoxy]benzoyl}piperidin-4-yl)methyl]-2H-indazole-5-carboxamide;

E127 4-methyl-N-(2,2,2-trifluoroethyl)-2-{[1-(4-{[5-(trifluoromethyl)pyridin-2-yl]oxy}benzoyl)piperidin-4-yl]methyl}-2H-indazole-5-carboxamide;

E128 4-methyl-N-(2,2,2-trifluoroethyl)-2-{[1-(4-{[6-(trifluoromethyl)pyridin-3-yl]oxy}benzoyl)piperidin-4-yl]methyl}-2H-indazole-5-carboxamide;

E131 2-({1-[4-(3-fluorophenoxy)benzoyl]piperidin-4-yl}methyl)-4-methyl-N-(2,2,2-trifluoroethyl)-2H-indazole-5-carboxamide;

E132 4-methyl-N-(2,2,2-trifluoroethyl)-2-[(1-{4-[3-(trifluoromethyl)phenoxy]benzoyl}piperidin-4-yl)methyl]-2H-indazole-5-carboxamide;

E137 2-({1-[4-(3,4-difluorophenoxy)benzoyl]piperidin-4-yl}methyl)-4-methyl-N-(2,2,2-trifluoroethyl)-2H-indazole-5-carboxamide;

E138 4-methyl-N-(2,2,2-trifluoroethyl)-2-[(1-{[4'-(trifluoromethyl)biphenyl-4-yl]carbonyl}piperidin-4-yl)methyl]-2H-indazole-5-carboxamide;

E141 2-({1-[(4'-methoxy-2'-methylbiphenyl-4-yl)carbonyl]piperidin-4-yl}methyl)-4-methyl-N-(2,2,2-trifluoroethyl)-2H-indazole-5-carboxamide;

E143 2-({1-[(4'-fluoro-2'-methoxybiphenyl-4-yl)carbonyl]piperidin-4-yl}methyl)-4-methyl-N-(2,2,2-trifluoroethyl)-2H-indazole-5-carboxamide;

E153 2-({1-[4-(4-cyanophenoxy)benzoyl]piperidin-4-yl}methyl)-N-(2-methoxyethyl)-4-methyl-2H-indazole-5-carboxamide;

E154 2-{[1-(4-bromo-3-methylbenzoyl)piperidin-4-yl]methyl}-N-(2-methoxyethyl)-4-methyl-2H-indazole-5-carboxamide;

E155 2-{[1-(4-tert-butylbenzoyl)piperidin-4-yl]methyl}-N-(2-methoxyethyl)-4-methyl-2H-indazole-5-carboxamide;

E157 2-{[1-(4-cyclohexylbenzoyl)piperidin-4-yl]methyl}-N-(2-methoxyethyl)-4-methyl-2H-indazole-5-carboxamide;

E160 N-(2-methoxyethyl)-4-methyl-2-({1-[4-(pyridin-3-yloxy)benzoyl]piperidin-4-yl}methyl)-2H-indazole-5-carboxamide;

E161 N-(2-methoxyethyl)-4-methyl-2-{[1-(4-{[5-(trifluoromethyl)pyridin-2-yl]oxy}benzoyl)piperidin-4-yl]methyl}-2H-indazole-5-carboxamide;

E162 N-(2-methoxyethyl)-4-methyl-2-({1-[4-(pyridin-2-yloxy)benzoyl]piperidin-4-yl}methyl)-2H-indazole-5-carboxamide;

E163 N-(2-methoxyethyl)-4-methyl-2-{[1-(4-{[4-(trifluoromethyl)pyrimidin-2-yl]oxy}benzoyl)piperidin-4-yl]methyl}-2H-indazole-5-carboxamide;

E164 N-(2-methoxyethyl)-4-methyl-2-{[1-(4-{[6-(trifluoromethyl)pyridin-3-yl]oxy}benzoyl)piperidin-4-yl]methyl}-2H-indazole-5-carboxamide;

E165 N-(2-methoxyethyl)-4-methyl-2-{[1-(4-{[6-(trifluormethyl)pyridin-2-yl]oxy}benzoyl)piperidin-4-yl]methyl}-2H-indazole-5-carboxamide;

E166 2-({1-[(4'-methoxybiphenyl-4-yl)carbonyl]piperidin-4-yl}methyl)-N-(2-methoxyethyl)-4-methyl-2H-indazole-5-carboxamide;

E168 N-(2-methoxyethyl)-4-methyl-2-[(1-{4-[3-(trifluoromethyl)phenoxy]benzoyl}piperidin-4-yl)methyl]-2H-indazole-5-carboxamide;

E170 2-[(1-{4-[(5-chloropyridin-2-yl)oxy]benzoyl}piperidin-4-yl)methyl]-N-(2-methoxyethyl)-4-methyl-2H-indazole-5-carboxamide;

E171 2-({1-[4-(2,4-difluorophenoxy)benzoyl]piperidin-4-yl}methyl)-N-(2-methoxyethyl)-4-methyl-2H-indazole-5-carboxamide;

E172 2-({1-[4-(3,4-difluorophenoxy)benzoyl]piperidin-4-yl}methyl)-N-(2-methoxyethyl)-4-methyl-2H-indazole-5-carboxamide;

E173 N-(2-methoxyethyl)-4-methyl-2-[(1-{[4'-(trifluoromethyl)biphenyl-4-yl]carbonyl}piperidin-4-yl)methyl]-2H-indazole-5-carboxamide;

E174 2-({1-[4-(3-fluorophenoxy)benzoyl]piperidin-4-yl}methyl)-N-(2-methoxyethyl)-4-methyl-2H-indazole-5-carboxamide;

E175 2-{[1-(2-fluoro-4-isopropoxybenzoyl)piperidin-4-yl]methyl}-N-(2-methoxyethyl)-4-methyl-2H-indazole-5-carboxamide;

E176 2-({1-[(3-fluoro-3',4'-dimethylbiphenyl-4-yl)carbonyl]piperidin-4-yl}methyl)-N-(2-methoxyethyl)-4-methyl-2H-indazole-5-carboxamide;

E177 2-({1-[(2',3-difluoro-4'-methoxybiphenyl-4-yl)carbonyl]piperidin-4-yl}methyl)-N-(2-methoxyethyl)-4-methyl-2H-indazole-5-carboxamide;

E178 2-({1-[4-(difluoromethoxy)benzoyl]piperidin-4-yl}methyl)-N-(2-methoxyethyl)-4-methyl-2H-indazole-5-carboxamide;

E179 2-({1-[4-(2-fluorophenoxy)benzoyl]piperidin-4-yl}methyl)-N-(2-methoxyethyl)-4-methyl-2H-indazole-5-carboxamide;

E180 2-({1-[(4'-cyano-2'-methylbiphenyl-4-yl)carbonyl]piperidin-4-yl}methyl)-N-(2-methoxyethyl)-4-methyl-2H-indazole-5-carboxamide;

E181 2-({1-[4-(5-chloropyridin-2-yl)benzoyl]piperidin-4-yl}methyl)-N-(2-methoxyethyl)-4-methyl-2H-indazole-5-carboxamide;

E182 N-(2-methoxyethyl)-4-methyl-2-[(1-{4-[6-(trifluoromethyl)pyridin-2-yl]benzoyl}piperidin-4-yl)methyl]-2H-indazole-5-carboxamide;

E183 N-(2-methoxyethyl)-2-({1-[(4'-methoxy-2'-methylbiphenyl-4-yl)carbonyl]piperidin-4-yl}methyl)-4-methyl-2H-indazole-5-carboxamide;

E184 2-({1-[(4'-chloro-2'-methylbiphenyl-4-yl)carbonyl]piperidin-4-yl}methyl)-N-(2-methoxyethyl)-4-methyl-2H-indazole-5-carboxamide;

E185 2-[(1-{[4'-(2-cyanopropan-2-yl)biphenyl-4-yl]carbonyl}piperidin-4-yl)methyl]-N-(2-methoxyethyl)-4-methyl-2H-indazole-5-carboxamide;

E186 N-(2-methoxyethyl)-2-({1-[4-(5-methoxypyridin-2-yl)benzoyl]piperidin-4-yl}methyl)-4-methyl-2H-indazole-5-carboxamide;

E187 N-(2-methoxyethyl)-4-methyl-2-[(1-{4-[6-(trifluoromethyl)pyridin-3-yl]benzoyl}piperidin-4-yl)methyl]-2H-indazole-5-carboxamide;

E188 N-(2-methoxyethyl)-2-({1-[4-(6-methoxypyridin-3-yl)benzoyl]piperidin-4-yl}methyl)-4-methyl-2H-indazole-5-carboxamide;

E189 2-({1-[(4'-fluoro-2'-methylbiphenyl-4-yl)carbonyl]piperidin-4-yl}methyl)-N-(2-methoxyethyl)-4-methyl-2H-indazole-5-carboxamide;

E190 N-(2-methoxyethyl)-4-methyl-2-({1-[4-(6-methylpyridin-3-yl)benzoyl]piperidin-4-yl}methyl)-2H-indazole-5-carboxamide;

E191 N-(2-methoxyethyl)-2-({1-[4-(6-methoxypyridin-2-yl)benzoyl]piperidin-4-yl}methyl)-4-methyl-2H-indazole-5-carboxamide;

E193 2-({1-[(4'-fluoro-2'-methoxybiphenyl-4-yl)carbonyl]piperidin-4-yl}methyl)-N-(2-methoxyethyl)-4-methyl-2H-indazole-5-carboxamide;

E194 2-({1-[(4'-chloro-2'-methoxybiphenyl-4-yl)carbonyl]piperidin-4-yl}methyl)-N-(2-methoxyethyl)-4-methyl-2H-indazole-5-carboxamide;

E195 N-(2-methoxyethyl)-4-methyl-2-[(1-{4-[2-(trifluoromethyl)pyrimidin-5-yl]benzoyl}piperidin-4-yl)methyl]-2H-indazole-5-carboxamide;

E196 2-({1-[(4'-chloro-2'-fluorobiphenyl-4-yl)carbonyl]piperidin-4-yl}methyl)-N-(2-methoxyethyl)-4-methyl-2H-indazole-5-carboxamide;

E197 2-({1-[(2'-chloro-4'-fluorobiphenyl-4-yl)carbonyl]piperidin-4-yl}methyl)-N-(2-methoxyethyl)-4-methyl-2H-indazole-5-carboxamide;

E198 2-({1-[4-(5-chloropyridin-3-yl)benzoyl]piperidin-4-yl}methyl)-N-(2-methoxyethyl)-4-methyl-2H-indazole-5-carboxamide;

E199 2-({1-[4-(5-fluoropyridin-3-yl)benzoyl]piperidin-4-yl}methyl)-N-(2-methoxyethyl)-4-methyl-2H-indazole-5-carboxamide;

E200 N-(2-methoxyethyl)-4-methyl-2-[(1-{4-[5-(trifluoromethyl)pyridin-3-yl]benzoyl}piperidin-4-yl)methyl]-2H-indazole-5-carboxamide;

E201 2-[(1-{[4'-(2-hydroxypropan-2-yl)biphenyl-4-yl]carbonyl}piperidin-4-yl)methyl]-N-(2-methoxyethyl)-4-methyl-2H-indazole-5-carboxamide;

E202 2-({1-[(3',5'-difluorobiphenyl-4-yl)carbonyl]piperidin-4-yl}methyl)-N-(2-methoxyethyl)-4-methyl-2H-indazole-5-carboxamide;

E203 2-({1-[(4'-fluoro-2-methylbiphenyl-4-yl)carbonyl]piperidin-4-yl}methyl)-N-(2-methoxyethyl)-4-methyl-2H-indazole-5-carboxamide;

E204 2-({1-[(3',5'-difluoro-2-methylbiphenyl-4-yl)carbonyl]piperidin-4-yl}methyl)-N-(2-methoxyethyl)-4-methyl-2H-indazole-5-carboxamide;

E205 N-(2-methoxyethyl)-4-methyl-2-({1-[3-methyl-4-(3-pyridyl)benzoyl]piperidin-4-yl}methyl)-2H-indazole-5-carboxamide;

E206 N-(2-methoxyethyl)-4-methyl-2-({1-[3-methyl-4-(4-pyridyl)benzoyl]piperidin-4-yl}methyl)-2H-indazole-5-carboxamide; and E207 N-(2-methoxyethyl)-4-methyl-2-({1-[(2-methylbiphenyl-4-yl)carbonyl]piperidin-4-yl}methyl)-2H-indazole-5-carboxamide.

7. The pharmaceutical composition off claim 6, where the EP2 receptor antagonist is selected from the group consisting of:

E16 N-(2-methoxyethyl)-4-methyl-2-[(1-{4-[4-(trifluoromethyl)phenoxy]benzoyl}piperidin-4-yl)methyl]-2H-indazole-5-carboxamide;

E126 4-methyl-N-(2,2,2-trifluoroethyl)-2-[(1-{4-[4-(trifluoromethyl)phenoxy]benzoyl}piperidin-4-yl)methyl]-2H-indazole-5-carboxamide; and E161 N-(2-methoxyethyl)-4-methyl-2-{[1-(4-{[5-(trifluoromethyl)pyridin-2-yl]oxy}benzoyl)piperidin-4-yl]methyl}-2H-indazole-5-carboxamide.

8. The pharmaceutical composition of claim 2, wherein the COX inhibitor is in a dose range selected from:
C1 indomethacin: 19-800 mg/day;
C2 diclofenac: 37.5-800 mg/day;
C4 naproxen: 125-4000 mg/day;
C5 ibuprofen: 200-4800 mg/day;
C6 meloxicam: 2-60 mg/day;
C7 piroxicam: 5-80 mg/day;
C8 nimesulide: 25-800 mg/day;
C9 ketoprofen: 25-1200 mg/day;
C10 tenoxicam: 10-160 mg/day;
C11 mefanemic acid: 125-2000 mg/day;
C12 ketoralac: 2.5-160 mg/day;
C13 celecoxib: 25-800 mg/day;
C14 parecoxib 12.5-200 mg/day;
C15 rofecoxib: 6-200 mg/day;
C16 valdecoxib: 10-160 mg/day; and
C17 etoricoxib: 15-360 mg/day.

9. Pharmaceutical composition according to any of claims 2-7, where the COX inhibitor is
C1 indomethacin;
C2 diclofenac;
C4 naproxen;
C5 ibuprofen;
C6 meloxicam;
C7 piroxicam; or
C8 nimesulide.

10. The pharmaceutical composition of claim 9, where the COX inhibitor is:
C1 indomethacin;
C2 diclofenac;
C6 meloxicam; or
C7 piroxicam.

11. A method of contraception comprising administering the pharmaceutical composition of claim 1 to a woman in a single administration dose in a period of up to 24 hours, preferably 6-12 hours, before expected sexual intercourse or up to 2 hours after sexual intercourse.

12. A method of on-demand contraception, comprising administering the pharmaceutical composition according to claim 2 to a woman on demand and once in a period of 0-24, preferably 6-12, hours prior to expected sexual intercourse or up to 2 hours after sexual intercourse.

13. A method of on-demand contraception, comprising initially taking a first pharmaceutical composition according to claim 2 in a period of up to 24 hours, prior to expected sexual intercourse, and taking a second pharmaceutical composition according to claim 2 in a period of up to 48 hours after sexual intercourse, where the preparations taken before and after intercourse are identical.

14. A method of on-demand contraception, comprising initially taking a first pharmaceutical composition according to claim 2 in a period of up to 24 hours, prior to expected sexual intercourse, and taking a second pharmaceutical composition according to claim 2 in a period of up to 48 hours after sexual intercourse, where the preparations taken before and after intercourse are not identical.

15. An administration protocol for on-demand contraception, characterized in that a pharmaceutical composition according to claim 2 is taken in a period of up to 24 hours, preferably 6-12 hours, prior to expected sexual intercourse and a further pharmaceutical composition according to claim 2 is taken in a period of up to 48 hours after sexual intercourse.

16. A kit for providing an administration protocol according to claim 15 or for carrying out the method of claim 13 of on-demand contraception, comprising at least one tablet comprising a pharmaceutical composition according to claim 2, for administration before, and at least one tablet comprising a pharmaceutical composition according to claim 2, for administration after expected sexual intercourse.

17. The pharmaceutical composition of claim 2, wherein the pharmaceutical composition is in the form of a pharmaceutical preparation for oral, pulmonary, nasal, dermal or transdermal administration.

18. The pharmaceutical composition of claim 1, wherein X is —(CH$_2$)$_l$— where l is; and
R$^4$ is additionally a 4-6-membered heterocyclyl radical linked via a ring carbon atom.

19. A kit for carrying out the method of claim 14 of on-demand contraception, comprising at least one tablet comprising a pharmaceutical composition according to claim 2, for administration before, and at least one tablet comprising a pharmaceutical composition according to claim 2, for administration after expected sexual intercourse.

\* \* \* \* \*